(12) United States Patent
Liotta et al.

(10) Patent No.: US 10,149,859 B2
(45) Date of Patent: Dec. 11, 2018

(54) NUCLEOTIDE AND NUCLEOSIDE THERAPEUTIC COMPOSITIONS AND USES RELATED THERETO

(71) Applicant: Emory University, Atlanta, GA (US)

(72) Inventors: Dennis C. Liotta, Atlanta, GA (US); George R. Painter, Atlanta, GA (US); Gregory R. Bluemling, Lithonia, GA (US); Abel de la Rosa, Alpharetta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/917,681

(22) PCT Filed: Sep. 10, 2014

(86) PCT No.: PCT/US2014/054930
§ 371 (c)(1),
(2) Date: Mar. 9, 2016

(87) PCT Pub. No.: WO2015/038596
PCT Pub. Date: Mar. 19, 2015

(65) Prior Publication Data
US 2016/0220595 A1    Aug. 4, 2016

Related U.S. Application Data

(60) Provisional application No. 61/876,473, filed on Sep. 11, 2013, provisional application No. 61/923,317, filed on Jan. 3, 2014, provisional application No. 61/986,577, filed on Apr. 30, 2014.

(51) Int. Cl.
| | |
|---|---|
| *A61K 31/7068* | (2006.01) |
| *C07H 19/06* | (2006.01) |
| *A61K 45/06* | (2006.01) |
| *A61K 9/127* | (2006.01) |
| *C07H 19/10* | (2006.01) |

(52) U.S. Cl.
CPC ......... *A61K 31/7068* (2013.01); *A61K 9/127* (2013.01); *A61K 45/06* (2013.01); *C07H 19/06* (2013.01); *C07H 19/10* (2013.01)

(58) Field of Classification Search
CPC .................................................... C07H 19/10
See application file for complete search history.

(56) References Cited

U.S. PATENT DOCUMENTS

| | | | |
|---|---|---|---|
| 3,975,374 A | 8/1976 | Hunter et al. | |
| 6,432,501 B1 * | 8/2002 | Yang ..................... | B32B 7/04 |
| | | | 106/287.35 |
| 2004/0063651 A1 | 4/2004 | Morioka et al. | |
| 2004/0063658 A1 | 4/2004 | Roberts et al. | |
| 2011/0286962 A1 | 11/2011 | Sommadossi et al. | |

FOREIGN PATENT DOCUMENTS

| | | | |
|---|---|---|---|
| GB | 2211185 | 6/1989 | |
| JP | S4947379 | 5/1974 | |
| WO | WO 01/90121 | 11/2001 | |
| WO | WO 01/92282 | 12/2001 | |
| WO | WO 02/18404 | 3/2002 | |
| WO | WO 2006121820 A1 * | 11/2006 | ............. C07H 19/04 |
| WO | WO 2007/083173 | 7/2007 | |
| WO | WO-2016099982 A2 * | 6/2016 | ......... A61K 31/7072 |

OTHER PUBLICATIONS

International Search Report for PCT/US2014/054932, dated Jan. 15, 2015.
Extended European Search Report for European Patent Application No. 14844012.6, dated Feb. 10, 2017.
Silvia Meneghesso et al: "Synthesis and Biological Evaluation of Pyrimidine Nucleoside Monophosphate Prodrugs Targeted Against Influenza Virus", Antiviral Research, Elsevier BV, NL, vol. 94, No. 1, Jan. 18, 2012 (Jan. 18, 2012), pp. 35-43.
Reimer K et al: "Inhibition of Hepatitis B Virus DNA Polymerase by Thymidine Triphosphate Analogs in Vitro", Antiviral Chemistry & Chemotherapy, International Medical Press, GB, vol. 2, No. 4, Jan. 1, 1991 (Jan. 1, 1991), pp. 249-253.
Poopeiko et al: "Synthesis, Confirmation and Biological Properties of 2', 3'-Dideoxy-3'-fluoro-5-chloro-4-thiouridine, Potential Anti-HIV Agent", Collection Symposium Series (XIIIth Symposium on Chemistry of Nucleic Acid Components Spindlerv Mlyn, Czech Republic; Sep. 3-9, 2005); {Collection Symposium Series}, XX, XX, vol. 61, Jan. 1, 1996 (Jan. 1, 1996), pp. S16-S19.
Ko H et al: "Synthesis and Potency of Novel Uracil Nucleotides and Derivatives as P2Y"2 and P2Y"6 Receptor Agonists", Bioorganic & Medicinal Chemistry, Pergamon, GB, vol. 16, No. 12, Jun. 15, 2008 (Jun. 15, 2008), pp. 6319-6332.

* cited by examiner

*Primary Examiner* — Alexander R Pagano
(74) *Attorney, Agent, or Firm* — King & Spalding

(57) ABSTRACT

This disclosure relates to nucleotide and nucleoside therapeutic compositions and uses in treating infectious diseases, viral infections, and cancer, where the base of the nucleotide or nucleoside contains at least one thiol, thione or thioether.

14 Claims, 10 Drawing Sheets

FIG. 8

NUCLEOTIDE AND NUCLEOSIDE THERAPEUTIC COMPOSITIONS AND USES RELATED THERETO

CROSS-REFERENCE TO RELATED APPLICATIONS

This application is a national phase application of PCT/US2012/054930, filed Sep. 10, 2014, which claims priority to U.S. Provisional Application No. 61/876,473, filed Sep. 11, 2013; U.S. Provisional Application No. 61/923,317, filed Jan. 3, 2014; and U.S. Provisional Application No. 61/986,577, filed Apr. 30, 2014; the disclosures of which are incorporated herein by reference.

FIELD OF THE INVENTION

This disclosure relates to nucleotide and nucleoside therapeutic compositions and uses related thereto. In certain embodiments, the disclosure relates to sulfur-containing nucleosides optionally conjugated to a phosphorus oxide or salts thereof. In certain embodiments, the disclosure relates to conjugate compounds or salts thereof comprising an amino acid ester, a lipid or a sphingolipid or derivative linked by a phosphorus oxide to a nucleotide or nucleoside. In certain embodiments, the disclosure contemplates pharmaceutical compositions comprising these compounds for uses in treating infectious diseases, viral infections, and cancer.

BACKGROUND

Nucleoside and nucleotide phosphates and phosphonates are clinically useful as antiviral agents. Two examples are tenofovir disoproxil fumarate for the treatment of human immunodeficiency virus and adefovir dipivoxil for the treatment of hepatitis B virus infections. Administration of three or more antiretroviral agents in combination, e.g., Highly Active Antiretroviral Therapy (HAART), has significantly reduced the morbidity and mortality associated with HIV infection. However, there is a growing need for new antiviral agents to address the critical issues of resistance and penetration into viral sanctuaries (commonly referred to as privileged compartments). Permeability into privileged compartments may be partially responsible for the current inability of chemotherapy to totally clear a patient of HIV infection and the emergence of resistance.

Anti-viral agents that are unphosphorylated nucleotides and nucleotide derivatives need to be phosphorylated to actively inhibit viral replication. Nucleoside analogues enter a cell via two types of broad-specificity transporters, concentrative nucleoside transporters (CNTs) and equilibrative nucleoside transporters (ENTs). Once inside, they utilize the host's nucleoside salvage pathway for sequential phosphorylation by deoxynucleoside kinases (dNKs), deoxynucleoside monophosphate kinases (dNMPKs) and nucleoside diphosphate kinase (NDPK). However, intracellular activation of these compounds is often compromised by the high substrate specificity of the host's endogenous kinases. In vitro and in vivo studies have demonstrated that the first and/or second phosphorylation, catalyzed by dNKs and dNMPKs, often represent the rate-limiting steps in nucleoside analogue activation. Thus, there is a need to identifying improved antiviral nucleoside analogues with structural features that are sufficiently activated by cellular kinases.

McGuigan et al., J Med Chem, 2005, 48(10), 3504-3515, report phenylmethoxyalaninyl phosphoramidate of abacavir as a prodrug leads to enhancement of antiviral potency. Painter et al., Antimicrob Agents Chemother, 2007, 51(10), 3505-3509, report promoting the oral availability of tenofovir with a hexadecyloxypropyl prodrug ester, designated CMX157.

Sphingolipids play roles in cell-cell and cell-substratum interactions, and help regulate growth and differentiation by a variety of mechanisms, such as inhibition of growth factor receptor kinases and effects on numerous cellular signal transduction systems. U.S. Pat. No. 6,610,835 discloses sphingosine analogues. It also discloses methods of treating infections and cancer. Pruett et al., J. Lipid Res. 2008, 49(8), 1621-1639, report on sphingosine and derivatives. Bushnev et al., ARKIVOC, 2010, (viii): 263-277, report an asymmetric synthetic method for preparing sphingolipid derivatives. Dougherty et al., Org. Lett. 2006, 8(4), 649-652, report the synthesis of 1-deoxysphingosine derivatives. Wiseman et al., Org. Lett. 2005, 7(15), 3155-3157, report 1-deoxy-5-hydroxysphingolipids in anticancer and stereoselective syntheses of 2-amino-3,5-diols.

References cited herein are not an admission of prior art.

SUMMARY OF THE INVENTION

This disclosure relates to nucleotide and nucleoside therapeutic compositions and uses related thereto. Included are sulfur-containing nucleosides optionally conjugated to a phosphorus oxide or salts thereof, prodrugs or conjugate compounds or salts thereof comprising an amino acid ester, lipid or a sphingolipid or derivative linked by a phosphorus oxide to a nucleotide or nucleoside.

BRIEF DESCRIPTION OF THE FIGURES

FIGS. 7, 8, 9, and 10 are graphs of the results of Venezuelan equine encephalitis virus (VEEV) replicon assays of various exemplary compounds.

DETAILED DESCRIPTION OF THE INVENTION

Figure 1:
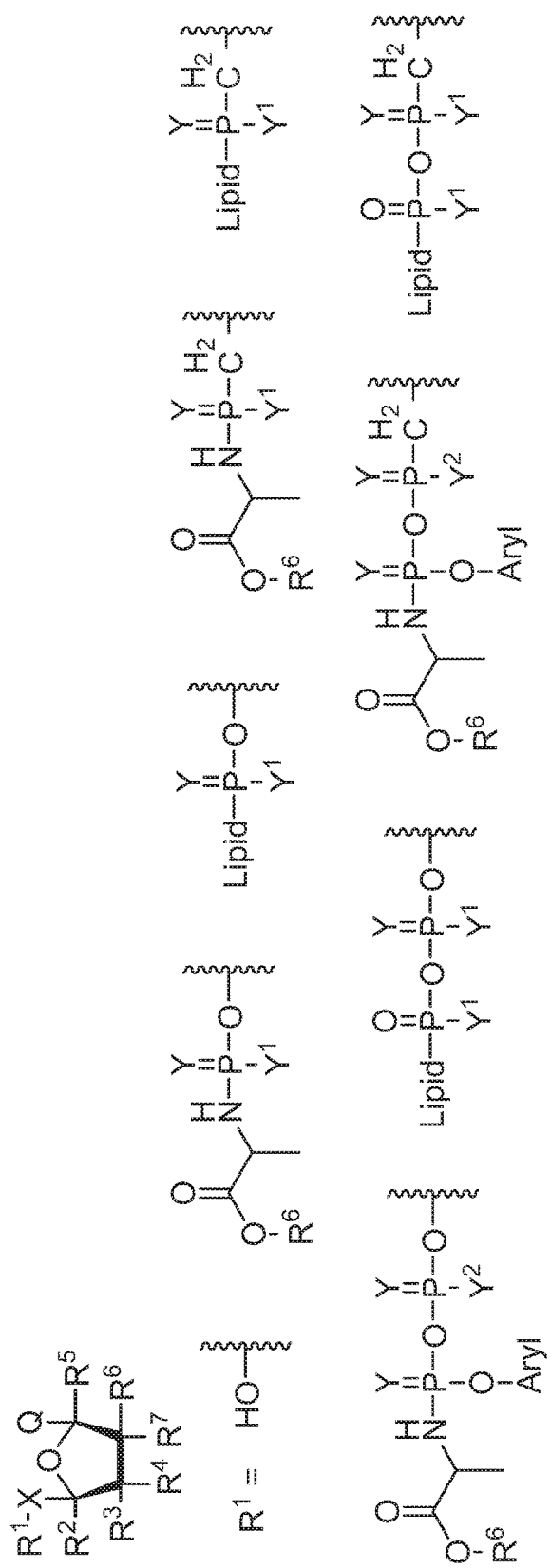
FIG. 1 illustrates certain embodiments of the disclosure.
Figure 2:
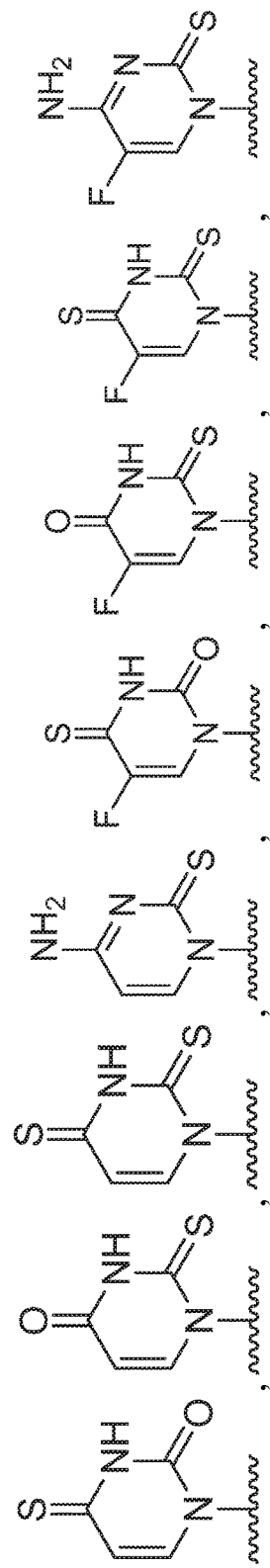
FIG. 2 illustrates exemplary thio-containing bases for certain embodiments provided herein.
Figure 3:
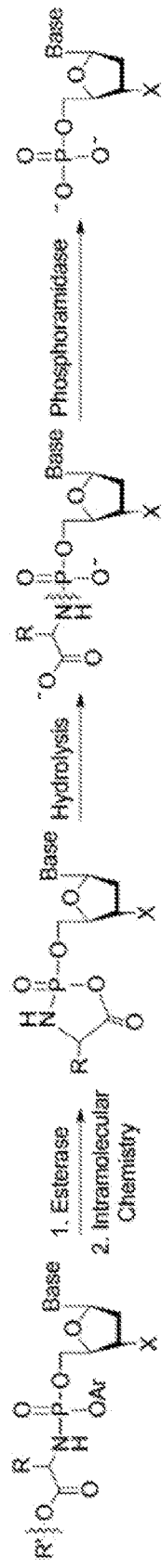
FIG. 3 illustrates the unraveling of McGuigan prodrugs in vivo. The metabolic unraveling of these prodrugs begins with an esterase-catalyzed cleavage of the carboxylic ester, followed by several chemical rearrangement steps resulting in an amino acid phosphoramidate. The final cleavage is carried out by one of several endogenous phosphoramidases, one of which has been identified to be the histidine triad nucleotide binding protein 1 (hINT1)
Figure 4:
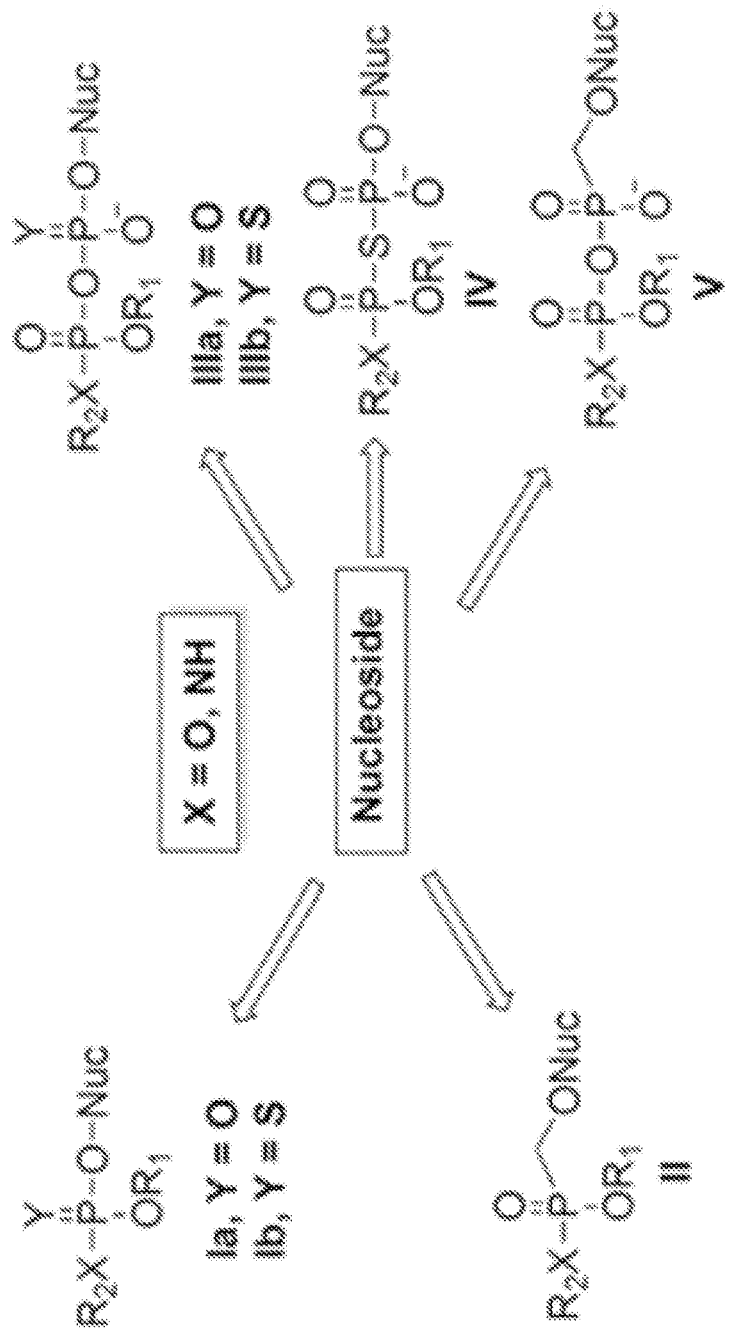
FIG. 4 illustrates embodiments of mono- and diphosphate structural types.

This disclosure relates to nucleotide and nucleoside therapeutic compositions and uses related thereto. In certain embodiments, the disclosure relates to sulfur containing nucleosides optionally conjugated to a phosphorus oxide or salts thereof. In certain embodiments, the disclosure relates to conjugate compounds or salts thereof comprising an amino acid ester, a lipid or a sphingolipid or derivative linked by a phosphorus oxide to a nucleotide or nucleoside. In certain embodiments, the disclosure contemplates pharmaceutical compositions comprising these compounds for uses in treating infectious diseases, viral infections, and cancer.

In certain embodiments, the disclosure relates to phosphorus oxide prodrugs of 2'-fluoronucleosides containing sulfur-containing bases for the treatment of positive-sense and negative-sense RNA viral infections through targeting of the virally encoded RNA-dependent RNA polymerase (RdRp). This disclosure also provides the general use of lipids and sphingolipids to deliver nucleoside analogs for the treatment of infectious disease and cancer.

In certain embodiments, the disclosure relates to conjugate compounds or salts thereof comprising a sphingolipid or derivative linked by a phosphorus oxide to a nucleotide or nucleoside, wherein the nucleotide or nucleoside contains a sulfur-containing base. In certain embodiments, the phosphorus oxide is a phosphate, phosphonate, polyphosphate, or polyphosphonate, wherein the phosphate, phosphonate or a phosphate in the polyphosphate or polyphosphonate is optionally a phosphorothioate or phosphoroamidate. In certain embodiments, the lipid or sphingolipid is covalently bonded to the phosphorus oxide through an amino group or a hydroxyl group.

The nucleotide or nucleoside comprises a heterocycle comprising two or more nitrogen heteroatoms substituted with at least one thione, thiol or thioether, wherein the substituted heterocycle is optionally substituted with one or more, the same or different alkyl, halogen, or cycloalkyl.

In certain embodiments, the heterocycle comprising two or more nitrogen heteroatoms substituted with at least one thione, thiol or thioether or selected from pyrimidin-2-one-4-thione, pyrimidine-2-thione-4-one, pyrimidine-2,4-dithione, 4-aminopyrimidine-2-thione, 5-fluoropyrimidin-2-one-4-thione, 5-fluoropyrimidine-2-thione-4-one, 5-fluoropyrimidine-2,4-dithione or 4-amino-5-fluoropyrimidine-2-thione.

In certain embodiments, the sphingolipid is saturated or unsaturated 2-aminoalkyl or 2-aminooctadecane optionally substituted with one or more substituents. In certain embodiments, the sphingolipid derivative is saturated or unsaturated 2-aminooctadecane-3-ol optionally substituted with one or more substituents. In certain embodiments, the sphingolipid derivative is saturated or unsaturated 2-aminooctadecane-3,5-diol optionally substituted with one or more substituents.

In certain embodiments, the disclosure contemplates pharmaceutical compositions comprising any of the compounds disclosed herein and a pharmaceutically acceptable excipient. In certain embodiments, the pharmaceutical composition is in the form of a pill, capsule, tablet, or saline buffer comprising a saccharide. In certain embodiments, the composition may contain a second active agent such as a pain reliever, anti-inflammatory agent, non-steroidal anti-inflammatory agent, anti-viral agent, anti-biotic, or anti-cancer agent.

In certain embodiments, the disclosure relates to methods of treating or preventing an infection comprising administering an effective amount of a compound disclosed herein to a subject in need thereof. Typically, the subject is diagnosed with or at risk of an infection from a virus, bacteria, fungi, protozoa, or parasite.

In certain embodiments, the disclosure relates the methods of treating a viral infection comprising administering an effective amount of a pharmaceutical composition disclosed herein to a subject in need thereof. In certain embodiments, the subject is a mammal, for example, a human. In certain embodiments, the subject is diagnosed with a chronic viral infection. In certain embodiments, administration is under conditions such that the viral infection is no longer detected. In certain embodiments, the subject is diagnosed with a RNA virus, DNA virus, or retroviruses. In certain embodiments, the subject is diagnosed with a virus that is a double stranded DNA virus, sense single stranded DNA virus, double stranded RNA virus, sense single stranded RNA virus, antisense single stranded RNA virus, sense single stranded RNA retrovirus or a double stranded DNA retrovirus.

In certain embodiments, the subject is diagnosed with influenza A virus including subtype H1N1, H3N2, H7N9, or H5N1, influenza B virus, influenza C virus, rotavirus A, rotavirus B, rotavirus C, rotavirus D, rotavirus E, human coronavirus, SARS coronavirus, MERS coronavirus, human adenovirus types (HAdV-1 to 55), human papillomavirus (HPV) Types 16, 18, 31, 33, 35, 39, 45, 51, 52, 56, 58, and 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), Dengue virus, chikungunya, Eastern equine encephalitis virus (EEEV), Western equine encephalitis virus (WEEV), Venezuelan equine encephalitis virus (VEEV), yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, or Kaposi's sarcoma-associated herpesvirus, hepatitis A, hepatitis B, hepatitis C, hepatitis D, hepatitis E or human immunodeficiency virus (HIV).

In certain embodiments, the subject is diagnosed with influenza A virus including subtypes H1N1, H3N2, H7N9, H5N1 (low path), and H5N1 (high path) influenza B virus, influenza C virus, rotavirus A, rotavirus B, rotavirus C, rotavirus D, rotavirus E, SARS coronavirus, MERS-CoV, human adenovirus types (HAdV-1 to 55), human papillomavirus (HPV) Types 16, 18, 31, 33, 35, 39, 45, 51, 52, 56, 58, and 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, parainfluenza viruses 1 and 3, rinderpest virus, chikungunya, eastern equine encephalitis virus (EEEV), Venezuelan equine encephalitis virus (VEEV), western equine encephalitis virus (WEEV), California encephalitis virus, Japanese encephalitis virus, Rift Valley fever virus (RVFV), hantavirus, Dengue virus serotypes 1, 2, 3 and 4, West Nile virus, Tacaribe virus, Junin, rabies virus, ebola virus, marburg virus, adenovirus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, or Kaposi's sarcoma-associated herpesvirus, hepatitis A, hepatitis B, hepatitis C, hepatitis D, hepatitis E or human immunodeficiency virus (HIV).

In certain embodiments, the subject is diagnosed with gastroenteritis, acute respiratory disease, severe acute respiratory syndrome, post-viral fatigue syndrome, viral hemorrhagic fevers, acquired immunodeficiency syndrome or hepatitis.

In certain embodiments, pharmaceutical compositions disclosed herein are administered in combination with a second antiviral agent, such as abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, sofosbuvir, stavudine, telaprevir, tenofovir, tenofovir disoproxil, tipranavir, trifluridine, trizivir, tromantadine, truvada, valaciclovir, valganciclovir, vicriviroc, vidarabine, viramidine zalcitabine, zanamivir, or zidovudine and combinations thereof.

In certain embodiments, the disclosure relates to methods of treating a cancer comprising administering an effective amount of a pharmaceutical composition disclosed herein to subject in need thereof. In certain embodiments, the cancer is selected from bladder cancer, lung cancer, breast cancer, melanoma, colon and rectal cancer, non-Hodgkins lymphoma, endometrial cancer, pancreatic cancer, kidney cancer, prostate cancer, leukemia, thyroid cancer, and brain cancer.

In certain embodiments, the compositions are administered in combination with a second anti-cancer agent, such as temozolamide, bevacizumab, procarbazine, lomustine, vincristine, gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vinblastine, vindesine, vinorelbine, taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, combretastatin, thalidomide, and/or lenalidomide or combinations thereof.

In certain embodiment, the disclosure relates to uses of compounds disclosed herein in the production or manufacture of a medicament for the treatment or prevention of an infectious disease, viral infection, or cancer.

In certain embodiments, the disclosure relates to derivatives of compounds disclosed herein or any of the formula.

Additional advantages of the disclosure will be set forth in part in the description which follows. It is to be understood that both the foregoing general description and the following detailed description are exemplary and explanatory only and are not restrictive of the disclosure, as claimed.

It is to be understood that this disclosure is not limited to the particular embodiments described. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, the term "phosphorus oxide" refers to any variety of chemical moieties that contain a phosphorus-oxygen (P—O or P=O) bond. When used as linking groups herein, the joined molecules may bond to oxygen or directly to the phosphorus atoms. The term is intended to include, but are not limited to phosphates, in which the phosphorus is typically bonded to four oxygens and phosphonates, in which the phosphorus is typically bonded to one carbon and three oxygens. A "polyphosphate" generally refers to phosphates linked together by at least one phosphorus-oxygen-phosphorus (P—O—P) bond. A "polyphosphonate" refers to a polyphosphate that contains at least one phosphorus-carbon (C—P—O—P) bond. In addition to containing phosphorus-oxygen bond, phosphorus oxides may contain a phosphorus-thiol (P—S or P=S) bond and/or a phosphorus-amine (P—N) bond, respectively referred to as phosphorothioate or phosphoroamidate. In phosphorus oxides, the oxygen atom may form a double or single bond to the phosphorus or combinations, and the oxygen may further bond with other atoms such as carbon or may exist as an anion which is counter balanced with a cation, e.g., metal or quaternary amine.

As used herein, "alkyl" means a noncyclic, cyclic, linear or branched, unsaturated or saturated hydrocarbon such as those containing from 1 to 22 carbon atoms, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Alkyl groups can be optionally substituted with one or more moieties selected from, for example, hydroxyl, amino, halo, deutero, alkylamino, arylamino, alkoxy, aryloxy, nitro, cyano, sulfonic acid, sulfate, phosphonic acid, phosphate, or phosphonate, or any other viable functional group that does not inhibit the pharmacological activity of this compound, either unprotected, or protected, as necessary, as known to those skilled in the art, for example, as taught in T. W. Greene and P. G. M. Wuts, "Protective Groups in Organic Synthesis," 3ed., John Wiley & Sons, 1999, hereby incorporated by reference.

The term "lower alkyl," as used herein, and unless otherwise specified, refers to a C1 to C4 saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred.

The term "halo" or "halogen," as used herein, includes chloro, bromo, iodo and fluoro.

Non-aromatic mono or polycyclic alkyls are referred to herein as "carbocycles" or "carbocyclyl" groups that contain 3 to 30 carbon atoms. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring that contains 6 to 32 carbon atoms, such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-ylsubstituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—$CH_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, and t-butoxy.

"Alkylamino" refers an alkyl group as defined above attached through an amino bridge. An example of an alkylamino is methylamino, (i.e., —NH—$CH_3$).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfinyl" refers to an alkyl as defined above attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In typical embodiments, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, rodent, monkey or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted with one or more substituents, a salt, in different hydration/oxidation states, e.g., substituting a single or double bond, substituting a hydroxy group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative. The derivative may be a prodrug. Derivatives may be prepared by any variety of synthetic methods or appropriate adaptations presented in the chemical literature or as in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the terms "prevent" and "preventing" include the full or partial inhibition of the recurrence, spread or onset of a referenced pathological condition or disease. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

Nucleoside Analogues as Antiviral Agents

Nucleoside analogs utilize the host's nucleoside salvage pathway for sequential phosphorylation by deoxynucleoside kinases (dNKs), deoxynucleoside monophosphate kinases (dNMPKs) and nucleoside diphosphate kinase (NDPK). However, intracellular activation of these compounds is often compromised by the high substrate specificity of the host's endogenous kinases. In vitro and in vivo studies have demonstrated that the first and/or second phosphorylation, catalyzed by dNKs and dNMPKs, often represent the rate-limiting steps in nucleoside analog activation. These significant blockades in the phosphorylation cascade of a given nucleoside analog will result in the lack of any observable activity in cellular assays. To circumvent these blockades, several kinase bypass strategies have been developed. For example, McGuigan phosphoramidates are chemical conjugates used for kinase bypass. See Serpi et al., J Med Chem, 2012, 55(10):4629-4639. The metabolism of these prodrugs begins with an esterase-catalyzed cleavage of the carboxylic ester, followed by several chemical rearrangement steps resulting in an amino acid phosphoramidate. The final cleavage is carried out by one of several endogenous phosphoramidases, one of which has been identified to be the histidine triad nucleotide binding protein 1 (hINT1).

An alternative prodrug strategy to circumvent these blockades is to utilize sphingoid bases to mask nucleotide analog phosphates. Sphingoid bases have the potential for delivering nucleotide analog phosphates to critical tissues such as the brain. The design concept driving the use of sphingoid bases to form nucleoside-lipid conjugates is based on observations that the sphingoid base analogs are: (a) well absorbed after oral administration, (b) resistant to oxidative catabolism in enterocytes, and (c) achieve high concentrations in the brain. Based on data for intestinal uptake of traditional phospholipid drug conjugates in mice and our data for sphingoid base oral absorption in rats, our sphingoid base conjugates should be well absorbed and resist first pass metabolism. After absorption, sphingoid bases, including sphingosine-1-phosphate, are transported in blood via both lipoproteins and free plasma proteins like albumin. Active epithelial cell uptake of sphingoid base phosphates has been demonstrated to occur via the ABC transporter, CFTR, but passive protein transport and endocytotic uptake are also possible; it is believed that extracellularly delivered drug conjugates would be processed similarly by target cells in the central nervous system (CNS) and the gut-associated lymphoid tissue (GALT). The rat sphingolipid PK studies mentioned above resulted in 24 hour tissue concentrations exceeding plasma Cmax concentrations by 10 to 300+ fold, with lung and brain levels being particularly high and without evidence of toxicity. This approach has significant potential for conjugate delivery of high drug concentrations to critical tissues.

Compounds

In certain embodiments, the disclosure relates to nucleosides having sulfur containing bases conjugated to a phosphorus moiety or pharmaceutically acceptable salts thereof.

In certain embodiments, the present invention relates to compounds of the following formula:

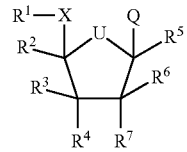

Formula I or pharmaceutically acceptable salts thereof wherein,

U is O or S;

X is O, $CH_2$, or $CD_2$;

$R^1$ is a phosphonate, phosphonophosphate, phosphonodiphosphate or phosphate, including monophosphate, diphosphate, triphosphate, and polyphosphate, or polyphosphonate;

wherein the phosphonate or a phosphate in the polyphosphate is optionally a phosphoroborate, phosphorothioate, or phosphoroamidate;

wherein the phosphonate or a phosphate in the polyphosphate, phosphoroborate, phosphorothiolate, or phosphoroamidate is optionally substituted with one or more, the same or different $R^8$;

wherein the phosphonate or a phosphate in the polyphosphate, phosphoroborate, phosphorothiolate, or phosphoroamidate optionally forms a phosphorus containing heterocyclic ring;

wherein the phosphonate, phosphonophosphate, phosphonodiphosphate, phosphate, polyphosphate, polyphosphonate, phosphorothiolate, or phosphoroamidate optionally forms a phosphorus containing heterocyclic ring with the $R^3$ or $R^4$ carbon;

$R^2$, $R^3$, $R^4$, $R^6$, $R^7$, and $R^8$ are independently H, D, $C_{1-22}$ alkyl, $C_{2-22}$ alkenyl, $C_{2-22}$ alkynyl, allyl, ethynyl, vinyl, $C_{1-22}$ alkoxy, $CH_3$, $CD_3$, $CF_3$, $CF_2H$, $CFH_2$, OH, SH, $NH_2$, $N_3$, CHO, CN, Cl, Br, F, I, $NO_2$, $C(O)O(C_{1-22}$ alkyl), $C(O)O(C_{1-22}$ alkyl), $C(O)O(C_{1-22}$ alkynyl), $C(O)O(C_{1-22}$ alkenyl), $O(C_{1-22}$ acyl), $O(C_{1-22}$ alkyl), $O(C_{1-22}$ alkenyl), $S(C_{1-22}$ acyl), $S(C_{1-22}$ alkyl), $S(C_{1-22}$ alkynyl), $S(C_{1-22}$ alkenyl), $SO(C_{1-22}$ acyl), $SO(C_{1-22}$ alkyl), $SO(C_{1-22}$ alkynyl), $SO(C_{1-22}$ alkenyl), $SO_2(C_{1-22}$ acyl), $SO_2(C_{1-22}$ alkyl), $SO_2(C_{1-22}$ alkynyl), $SO_2(C_{1-22}$ alkenyl), $O_3S(C_{1-22}$ acyl), $O_3S(C_{1-22}$ alkyl), $O_3S(C_{1-22}$ alkenyl), $NH_2$, $NH(C_{1-22}^{alkyl})$, $NH(C_{1-22}$ alkenyl), $NH(C_{1-22}$ alkynyl), $NH(C_{1-22}$ acyl), $N(C_{1-22}$ alkyl$)_2$, $N(C_{1-22}$ acyl$)_2$, sulfamoyl, N-methylcarbamoyl, N-ethylcarbamoyl, N,N-dimethylcarbamoyl, N,N-diethylcarbamoyl, N-methyl-N-ethylcarbamoyl, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, or carbocyclyl;

wherein alkyl, alkynyl, alkenyl and vinyl are optionally substituted by $N_3$, CN, one to three halogen (Cl, Br, F, I), deuterium, $NO_2$, $C(O)O(C_{1-22}$ alkyl), $C(O)O(C_{1-22}$ alkyl), $C(O)O(C_{1-22}$ alkynyl), $C(O)O(C_{1-22}$ alkenyl), $O(C_{1-22}$ acyl), $O(C_{1-22}$ alkyl), $O(C_{1-22}$ alkenyl), $S(C_{1-22}$ acyl), $S(C_{1-22}$ alkyl), $S(C_{1-22}$ alkynyl), $S(C_{1-22}$ alkenyl), $SO(C_{1-22}$ acyl), $SO(C_{1-22}$ alkyl), $SO(C_{1-22}$ alkynyl), $SO(C_{1-22}$ alkenyl), $SO_2(C_{1-22}$ acyl), $SO_2(C_{1-22}$ alkyl), $SO_2(C_{1-22}$ alkynyl), $SO_2(C_{1-22}$ alkenyl), $O_3S(C_{1-22}$ acyl), $O_3S(C_{1-22}$ alkyl), $O_3S(C_{1-22}$ alkenyl), $NH_2$, $NH(C_{1-22}$ alkyl), $NH(C_{1-22}$ alkenyl), $NH(C_{1-22}$ alkynyl), $NH(C_{1-22}$ acyl), $N(C_{1-22}$ alkyl$)_2$, $N(C_{1-22}$ acyl$)_2$, sulfamoyl, N-methylcarbamoyl, N-ethylcarbamoyl, N,N-dimethylcarbamoyl, N,N-diethylcarbamoyl, N-methyl-N-ethylcarbamoyl, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, or carbocyclyl;

$R^5$ is H or D; and

Q is a heterocyclyl comprising two or more nitrogen heteroatoms substituted with at least one thione, thiol or thioether, wherein Q is optionally substituted with one or more, the same or different alkyl, halogen, cycloalkyl.

In certain embodiments, the Q heterocyclyl is selected from pyrimidin-2-one-4-thione, pyrimidine-2-thione-4-one, pyrimidine-2,4-dithione, 4-aminopyrimidine-2-thione, 5-fluoropyrimidin-2-one-4-thione, 5-fluoropyrimidine-2-thione-4-one, 5-fluoropyrimidine-2,4-dithione, 4-amino-5-fluoropyrimidine-2-thione, 2-amino-purin-6-thione, 2-amino-7-deaza-purin-6-thione or 2-amino-7-deaza-7-substituted-purin-6-thione.

In preferred embodiments, U is O and Q is a pyrimidine with at least one thione, thiol or thioether at the 2 and/or 4-position of said pyrimidine. In other preferred embodiments, U is S and Q is a pyrimidine with at least one thione, thiol or thioether at the 2 and/or 4 position of said pyrimidine.

In preferred embodiments, the nucleoside conjugated to a phosphorus moiety or pharmaceutically acceptable salt thereof has the following structure:

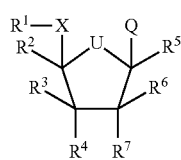

Formula Ia or pharmaceutically acceptable salts thereof wherein,

U is O or S;

X is $CH_2$ or $CD_2$;

$R^1$ is OH, monophosphate, diphosphate, or triphosphate;

$R^2$, $R^3$, $R^4$, $R^6$ and $R^7$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^9$;

each $R^9$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

$R^5$ is H or D; and

Q is one of the following bases:

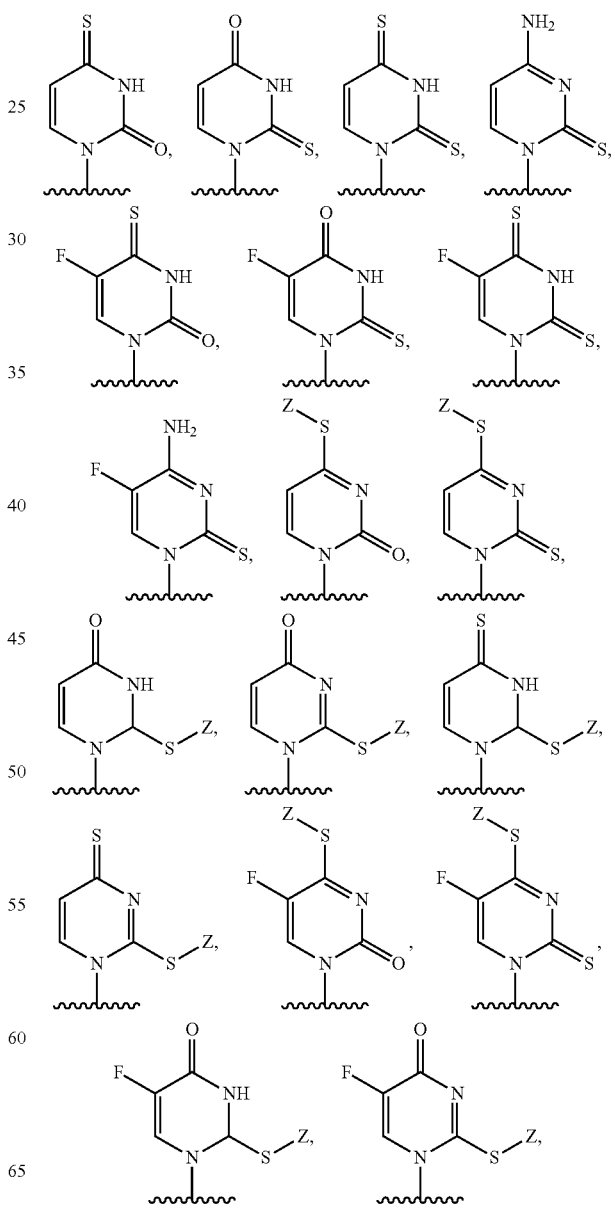

wherein Z is alkyl, alkyenyl, acyl, lipid, or geranyl.

In a particular embodiment, $R^2$ is selected from the group consisting of H, D, $CH_3$, $CD_3$, $CF_3$, $CF_2H$, $CFH_2$, $CH_2OH$, $CH_2Cl$, CCH, OH, SH, $NH_2$, $N_3$, CHO, CN, Cl, Br, F or I.

In one embodiment, $R^2$ is H.

In another particular embodiment, $R^3$ is selected from the group consisting of H, D, $CH_3$, $CD_3$, $CF_3$, $CF_2H$, $CFH_2$, $CH_2OH$, $CH_2Cl$, CCH, OH, SH, $NH_2$, $N_3$, CHO, CN, Cl, Br, F or I.

In still another particular embodiment, $R^4$ is selected from the group consisting of H, D, $CH_3$, $CD_3$, $CF_3$, $CF_2H$, $CFH_2$, $CH_2OH$, $CH_2Cl$, CCH, OH, SH, $NH_2$, $N_3$, CHO, CN, Cl, Br, F or I.

In a further particular embodiment, $R^6$ is selected from the group consisting of H, D, $CH_3$, $CD_3$, $CF_3$, $CF_2H$, $CFH_2$, $CH_2OH$, $CH_2Cl$, CCH, OH, SH, $NH_2$, $N_3$, CHO, CN, Cl, Br, F or I.

In yet another particular embodiment, $R^7$ is selected from the group consisting of H, D, $CH_3$, $CD_3$, $CF_3$, $CF_2H$, $CFH_2$, $CH_2OH$, $CH_2Cl$, CCH, OH, SH, $NH_2$, $N_3$, CHO, CN, Cl, Br, F or I.

Lipid, as used herein, is a $C_{6-22}$ alkyl, alkoxy, polyethylene glycol, or aryl substituted with an alkyl group.

In certain embodiments, the lipid is a fatty alcohol, fatty amine, or fatty thiol derived from essential and non-essential fatty acids.

In certain embodiments, the lipid is an unsaturated, polyunsaturated, omega unsaturated, or omega polyunsaturated fatty alcohol, fatty amine, or fatty thiol derived from essential and non-essential fatty acids.

In certain embodiments, the lipid is a fatty alcohol, fatty amine, or fatty thiol derived from essential and non-essential fatty acids that have one or more of its carbon units substituted with an oxygen, nitrogen, or sulfur.

In certain embodiments, the lipid is an unsaturated, polyunsaturated, omega unsaturated, or omega polyunsaturated fatty alcohol, fatty amine, or fatty thiol derived from essential and non-essential fatty acids that have one or more of its carbon units substituted with an oxygen, nitrogen, or sulfur.

In certain embodiments, the lipid is a fatty alcohol, fatty amine, or fatty thiol derived from essential and non-essential fatty acids that is optionally substituted.

In certain embodiments, the lipid is an unsaturated, polyunsaturated, omega unsaturated, or omega polyunsaturated fatty alcohol, fatty amine, or fatty thiol derived from essential and non-essential fatty acids that is optionally substituted.

In certain embodiments, the lipid is a fatty alcohol, fatty amine, or fatty thiol derived from essential and non-essential fatty acids that have one or more of its carbon units substituted with an oxygen, nitrogen, or sulfur that is optionally substituted.

In certain embodiments, the lipid is an unsaturated, polyunsaturated, omega unsaturated, or omega polyunsaturated fatty alcohol, fatty amine, or fatty thiol derived from essential and non-essential fatty acids that have one or more of its carbon units substituted with an oxygen, nitrogen, or sulfur that is also optionally substituted.

In certain embodiments, the lipid is hexadecyloxypropyl.

In certain embodiments, the lipid is 2-aminohexadecyloxypropyl.

In certain embodiments, the lipid is 2-aminoarachidyl.

In certain embodiments, the lipid is 2-benzyloxyhexadecyloxypropyl.

In certain embodiments, the lipid is lauryl, myristyl, palmityl, stearyl, arachidyl, behenyl, or lignoceryl.

In certain embodiments, the lipid is a sphingolipid having the formula:

wherein, $R^8$ of the sphingolipid is hydrogen, alkyl, $C(=O)R^{12}$, $C(=O)OR^{12}$, or $C(=O)NHR^{12}$;

$R^9$ of the sphingolipid is hydrogen, fluoro, $OR^{12}$, $OC(=O)R^{12}$, $OC(=O)OR^{12}$, or $OC(=O)NHR^{12}$;

$R^{10}$ of the sphingolipid is a saturated or unsaturated alkyl chain of greater than 6 and less than 22 carbons optionally substituted with one or more halogen or hydroxy or a structure of the following formula:

n is 8 to 14 or less than or equal to 8 to less than or equal to 14, o is 9 to 15 or less than or equal to 9 to less than or equal to 15, the total or m and n is 8 to 14 or less than or equal to 8 to less than or equal to 14, the total of m and o is 9 to 15 or less than or equal to 9 to less than or equal to 15; or

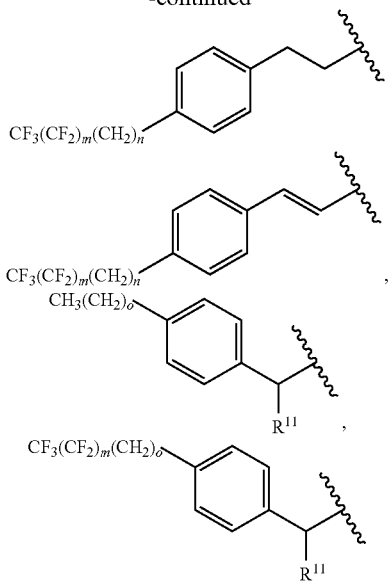

n is 4 to 10 or less than or equal to 4 to less than or equal to 10, o is 5 to 11 or less than or equal to 5 to less than or equal to 11, the total of m and n is 4 to 10 or less than or equal to 4 to less than or equal to 10, and the total of m and o is 5 to 11 or less than or equal to 5 to less than or equal to 11; or

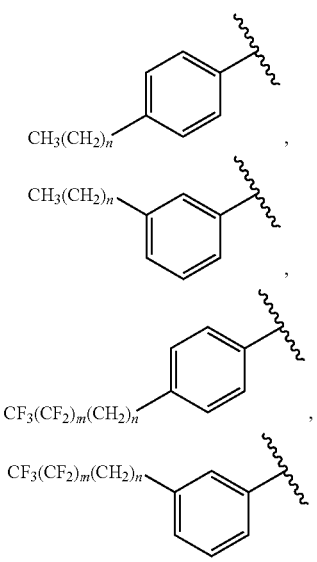

n is 6 to 12 or n is less than or equal to 6 to less than or equal to 12, the total of m and n is 6 to 12 or n is less than or equal to 6 to less than or equal to 12;

$R^{11}$ of the sphingolipid is $OR^{12}$, $OC(=O)R^{12}$, $OC(=O)OR^{12}$, or $OC(=O)NHR^{12}$;

$R^{12}$ of the sphingolipid is hydrogen, a branched or strait chain $C_{1-12}$alkyl, $C_{13-22}$alkyl, cycloalkyl, or aryl selected from benzyl or phenyl, wherein the aryl is optionally substituted with one or more, the same or different $R^{13}$; and $R^{13}$ of the sphingolipid is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfonyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^{12}$ of the sphingolipid is H, alkyl, methyl, ethyl, propyl, n-butyl, branched alkyl, isopropyl, 2-butyl, 1-ethylpropyl,1-propylbutyl, cycloalkyl, cyclopropyl, cyclobutyl, cyclopentyl, cyclohexyl, benzyl, phenyl, monosubstituted phenyl, disubstituted phenyl, trisubstituted phenyl, or saturated or unsaturated C12-C19 long chain alkyl.

In certain embodiments, the sphingolipid has the formula:

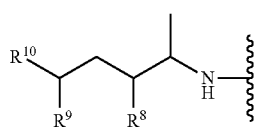

wherein, $R^8$ of the sphingolipid is hydrogen, hydroxy, fluoro, $OR^{12}$, $OC(=O)R^{12}$, $OC(=O)OR^{12}$, or $OC(=O)NHR^{12}$;

$R^9$ of the sphingolipid is hydrogen, hydroxy, fluoro, $OR^{12}$, $OC(=O)R^{12}$, $OC(=O)OR^{12}$, or $OC(=O)NHR^{12}$;

$R^{10}$ of the sphingolipid is a saturated or unsaturated alkyl chain of greater than 6 and less than 22 carbons optionally substituted with one or more halogens or a structure of the following formula:

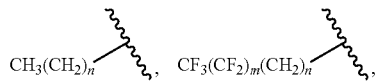

n is 8 to 14 or less than or equal to 8 to less than or equal to 14, the total or m and n is 8 to 14 or less than or equal to 8 to less than or equal to 14;

$R^{12}$ of the sphingolipid is hydrogen, a branched or strait chain $C_{1-12}$alkyl, $C_{13-22}$alkyl, cycloalkyl, or aryl selected from benzyl or phenyl, wherein the aryl is optionally substituted with one or more, the same or different $R^{13}$; and $R^{13}$ of the sphingolipid is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^{12}$ of the sphingolipid is H, alkyl, methyl, ethyl, propyl, n-butyl, branched alkyl, isopropyl, 2-butyl, 1-ethylpropyl,1-propylbutyl, cycloalkyl, cyclopropyl, cyclobutyl, cyclopentyl, cyclohexyl, benzyl, phenyl, monosubstituted phenyl, disubstituted phenyl, trisubstituted phenyl, or saturated or unsaturated $C_{12}$-$C_{19}$ long chain alkyl.

Suitable sphingolipids include, but are not limited to, sphingosine, ceramide, or sphingomyelin, or 2-aminoalkyl optionally substituted with one or more substituents.

Other suitable sphingolipids include, but are not limited to, 2-aminooctadecane-3,5-diol; (2S,3S,5S)-2-aminooctadecane-3,5-diol; (2S,3R,5S)-2-aminooctadecane-3,5-diol; 2-(methylamino)octadecane-3,5-diol; (2S,3R,5S)-2-(methylamino)octadecane-3,5-diol; 2-(dimethylamino)octadecane-3,5-diol; (2R,3S,5S)-2-(dimethylamino)octadecane-3,5-diol; 1-(pyrrolidin-2-yl)hexadecane-1,3-diol; (1S,3S)-1-((S)-pyrrolidin-2-yl)hexadecane-1,3-diol; 2-amino-11,11-difluorooctadecane-3,5-diol; (2S,3S,5S)-2-amino-11,11-difluorooctadecane-3,5-diol; 11,11-difluoro-2-(methylamino)octadecane-3,5-diol; (2S,3S,5S)-11,11-difluoro-2-(methylamino)octadecane-3,5-diol; N-((2S,3S,5S)-3,5-dihydroxyoctadecan-2-yl)acetamide; N-((2S,3S,5S)-3,5-dihydroxyoctadecan-2-yl)palmitamide; 1-(1-aminocyclopropyl)hexadecane-1,3-diol; (1S,3R)-1-(1-aminocyclopropyl)hexadecane-1,3-diol; (1S,3S)-1-(1-aminocyclopropyl)hexadecane-1,3-diol; 2-amino-2-methyloctadecane-3,5-diol; (3S,5S)-2-amino-2-methyloctadecane-3,5-diol; (3S,5R)-2-amino-2-methyloctadecane-3,5-diol; (3S,5S)-2-methyl-2-(methylamino)octadecane-3,5-diol; 2-amino-5-hydroxy-2-methyloctadecan-3-one; (Z)-2-amino-5-hydroxy-2-methyloctadecan-3-one oxime; (2S,3R,5R)-2-amino-6,6-difluorooctadecane-3,5-diol; (2S,3S,5R)-2-amino-6,6-difluorooctadecane-3,5-diol; (2S,3S,5S)-2-amino-6,6-difluorooctadecane-3,5-diol; (2S,3R,5S)-2-amino-6,6-difluorooctadecane-3,5-diol; and (2S,3S,5S)-2-amino-18,18,18-trifluorooctadecane-3,5-diol; which may be optionally substituted with one or more substituents.

In certain embodiments, the disclosure relates to compounds of the following formula:

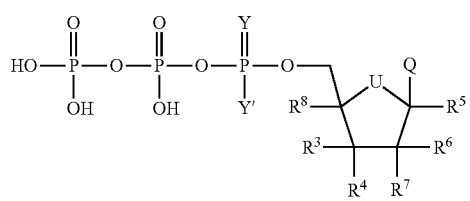

Formula Ib or a pharmaceutically acceptable salt thereof wherein,
U is O or S;
Y is O or S;
Y' is OH or $BH_3^-M^+$;
Q is a heterocyclyl comprising two or more nitrogen heteroatoms substituted with at least one thione, thiol or thioether, wherein Q is optionally substituted with one or more, the same or different alkyl, halogen, or cycloalkyl;
$R^3$, $R^4$, $R^6$, $R^7$ and $R^8$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^9$;
each $R^9$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl; and
$R^5$ is H or D.

In particular embodiments, Q is a heterocycle selected from the group consisting of pyrimidin-2-one-4-thione, pyrimidine-2-thione-4-one, pyrimidine-2,4-dithione, 4-aminopyrimidine-2-thione, 5-fluoropyrimidin-2-one-4-thione, 5-fluoropyrimidine-2-thione-4-one, 5-fluoropyrimidine-2,4-dithione, 4-amino-5-fluoropyrimidine-2-thione, 2-amino-purin-6-thione, 2-amino-7-deaza-purin-6-thione or 2-amino-7-deaza-7-substituted-purin-6-thione.

In preferred embodiments, U is O and Q is a pyrimidine with at least one thione, thiol or thioether at the 2 and/or 4-position of said pyrimidine. In other preferred embodiments, U is S and Q is a pyrimidine with at least one thione, thiol or thioether at the 2 and/or 4 position of said pyrimidine.

In one embodiment, $R^3$ is selected from the group consisting of H, D, $CH_3$, $CD_3$, $CF_3$, $CF_2H$, $CFH_2$, $CH_2OH$, $CH_2Cl$, CCH, OH, SH, $NH_2$, $N_3$, CHO, CN, Cl, Br, F or I.

In another embodiment, $R^4$ is selected from the group consisting of H, $CH_3$, $CD_3$, $CF_3$, $CF_2H$, $CFH_2$, $CH_2OH$, $CH_2Cl$, CCH, OH, SH, $NH_2$, $N_3$, CHO, CN, Cl, Br, F or I.

In still another embodiment, $R^6$ is selected from the group consisting of H, $CH_3$, $CD_3$, $CF_3$, $CF_2H$, $CFH_2$, $CH_2OH$, $CH_2Cl$, CCH, OH, SH, $NH_2$, $N_3$, CHO, CN, Cl, Br, F or I.

In yet another embodiment, $R^7$ is selected from the group consisting of H, $CH_3$, $CD_3$, $CF_3$, $CF_2H$, $CFH_2$, $CH_2OH$, $CH_2Cl$, CCH, OH, SH, $NH_2$, $N_3$, CHO, CN, Cl, Br, F or I.

In yet a further embodiment, $R^8$ is selected from the group consisting of H, $CH_3$, $CD_3$, $CF_3$, $CF_2H$, $CFH_2$, $CH_2OH$, $CH_2Cl$, CCH, OH, SH, $NH_2$, $N_3$, CHO, CN, Cl, Br, F or I.
In one embodiment, $R^8$ is H.

In certain embodiments, the disclosure relates to compounds of one of the following formulae:

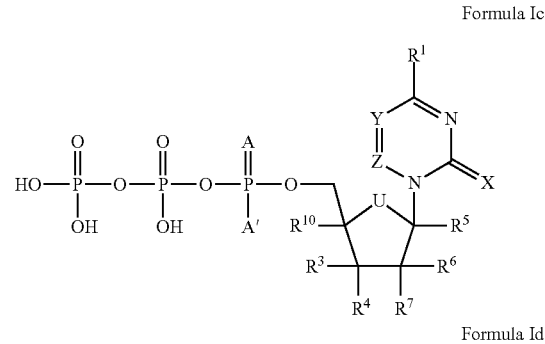

Formula Ic

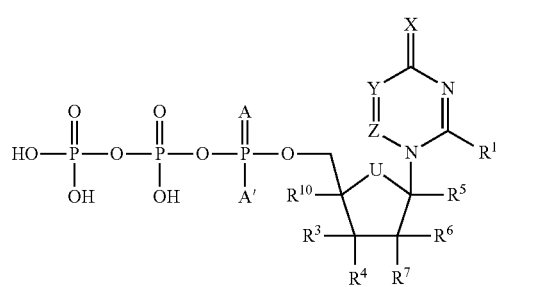

Formula Id

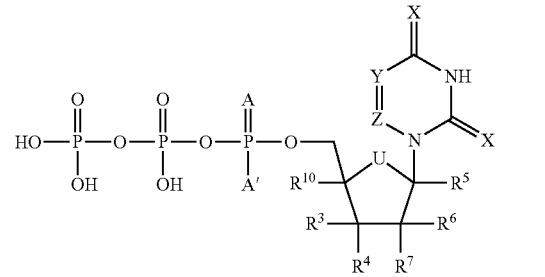

Formula Ie or a pharmaceutically acceptable salt thereof, wherein
A is O or S;
A' is OH or $BH_3^-M^+$;
$R^5$ is H or D;
U is O or S;
each X is independently O, S, NH, $NR^8$, NHOH, $NR^8OH$, $NHOR^8$, or $NR^8OR^8$;
$R^1$ is OH, SH, $NH_2$, $OR^8$, $SR^8$, $NHR^8$, NHOH, $NR^8OH$, $NHOR^8$, or $NR^8OR^8$;
  wherein in Formula Ic and Id, either X is S or R' is $SR^8$, or both X is S and R' is $SR^8$;
  wherein in Formula Ie, at least one X is S;
Y is CH, N, or $CR^2$;
Z is CH, N, or $CR^2$;
$R^3$, $R^4$, $R^6$, $R^7$ and $R^{10}$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^9$;
$R^8$ is methyl, alkenyl, alkynyl, vinyl, allyl, halogen, halogentated alkyl, hydroxyl alkyl, acyl, lipid, geranyl, $C_{1-22}$ alkyl optionally substituted with one or more, the same or different, $R^9$;
  each $R^9$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;
$R^2$ is methyl, trifluoromethyl, fluoro, iodo, alkenyl, alkynyl, vinyl, allyl, halogen, halogentated alkyl, hydroxyl alkyl, acyl, $C_{1-22}$ alkyl optionally substituted with one or more, the same or different, $R^9$.

In one embodiment, $R^3$ is selected from the group consisting of H, D, $CH_3$, $CD_3$, $CF_3$, $CF_2H$, $CFH_2$, $CH_2OH$, $CH_2Cl$, CCH, OH, SH, $NH_2$, $N_3$, CHO, CN, Cl, Br, F or I.

In another embodiment, $R^4$ is selected from the group consisting of H, D, $CH_3$, $CD_3$, $CF_3$, $CF_2H$, $CFH_2$, $CH_2OH$, $CH_2Cl$, CCH, OH, SH, $NH_2$, $N_3$, CHO, CN, Cl, Br, F or I.

In still another embodiment, $R^6$ is selected from the group consisting of H, D, $CH_3$, $CD_3$, $CF_3$, $CF_2H$, $CFH_2$, $CH_2OH$, $CH_2Cl$, CCH, OH, SH, $NH_2$, $N_3$, CHO, CN, Cl, Br, F or I.

In yet another embodiment, $R^7$ is selected from the group consisting of H, D, $CH_3$, $CD_3$, $CF_3$, $CF_2H$, $CFH_2$, $CH_2OH$, $CH_2Cl$, CCH, OH, SH, $NH_2$, $N_3$, CHO, CN, Cl, Br, F or I.

In yet a further embodiment, $R^{10}$ is selected from the group consisting of H, D, $CH_3$, $CD_3$, $CF_3$, $CF_2H$, $CFH_2$, $CH_2OH$, $CH_2Cl$, CCH, OH, SH, $NH_2$, $N_3$, CHO, CN, Cl, Br, F or I. In one embodiment, $R^8$ is H.

In certain embodiments, U is S and Y and Z are CH.
In other embodiments, U is O and Y and Z are CH.
In one embodiment, $R^3$ is H. In another embodiment, $R^4$ is hydroxyl. In a further embodiment, $R^5$ is H. In still another embodiment, $R^6$ is methyl. In yet another embodiment, $R^7$ is fluoro. In an still further embodiment, $R^{10}$ is H. In exemplary embodiments, the compound is selected from the group consisting of:

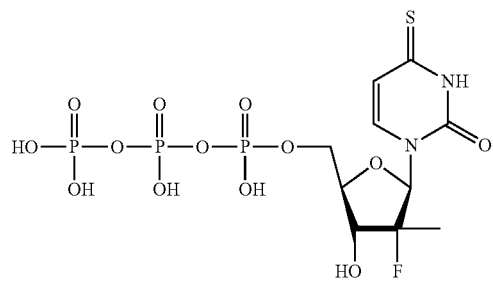

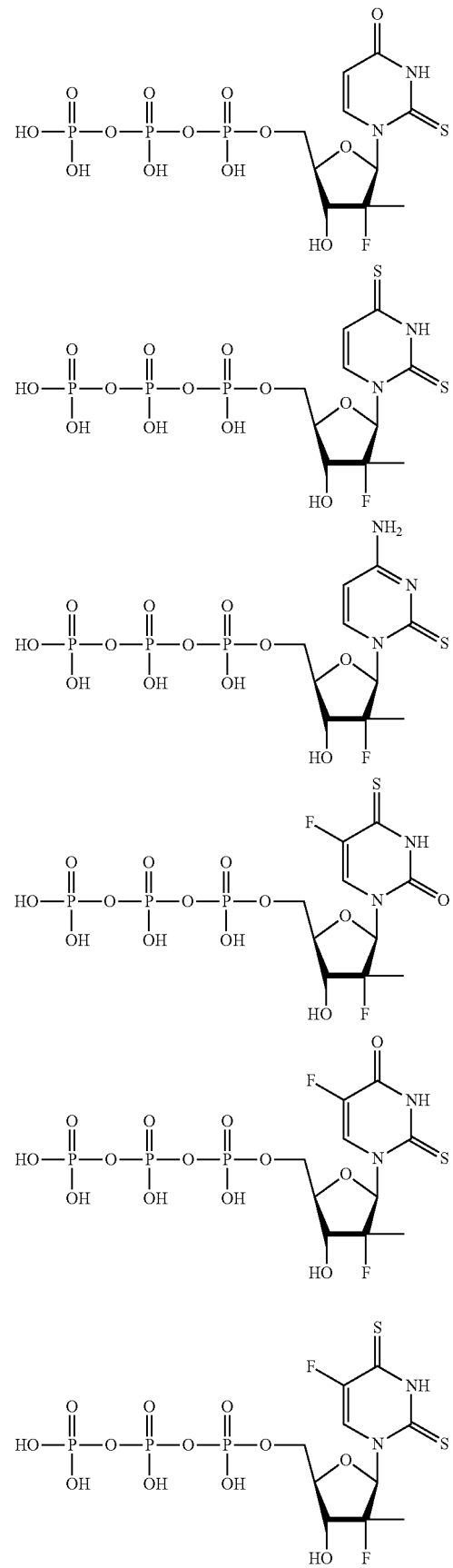

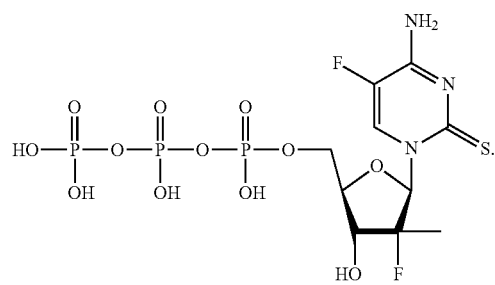

In one embodiment, $R^3$ is H. In another embodiment, $R^4$ is hydroxyl. In a further embodiment, $R^5$ is H. In still another embodiment, $R^6$ is trifluoromethyl. In yet another embodiment, $R^7$ is fluoro. In a still further embodiment, $R^{10}$ is H. In exemplary embodiments, the compound is selected from the group consisting of:

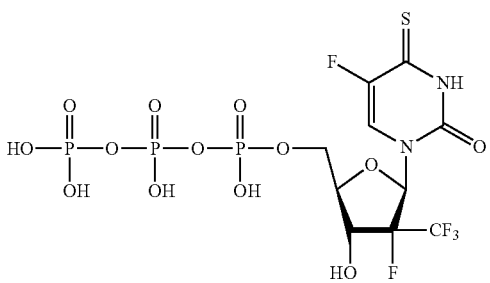

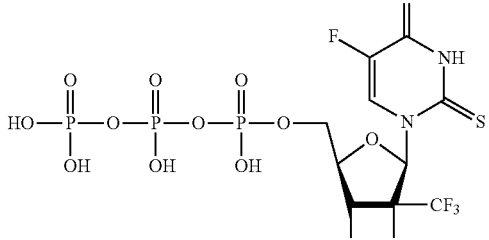

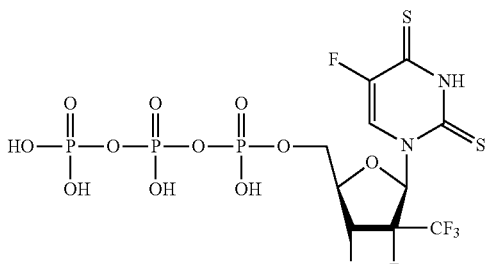

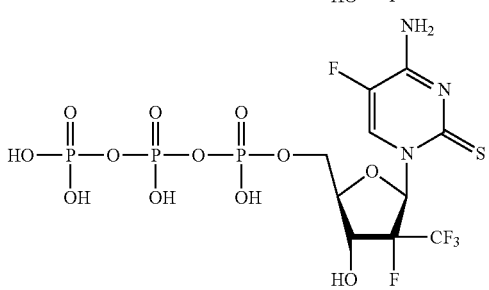

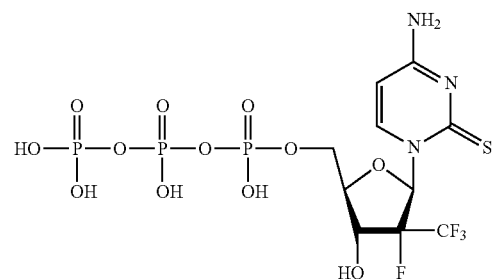

In one embodiment, $R^3$ is H. In another embodiment, $R^4$ is hydroxyl. In a further embodiment, $R^5$ is H. In still another embodiment, $R^6$ is C≡CH. In yet another embodiment, $R^7$ is fluoro. In a still further embodiment, $R^{10}$ is H. In exemplary embodiments, the compound is selected from the group consisting of:

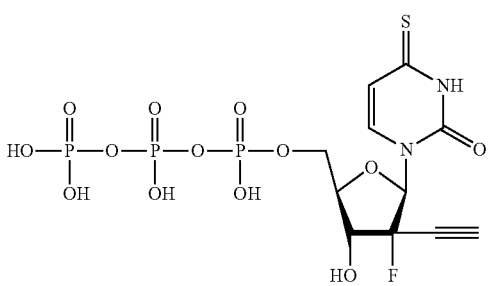

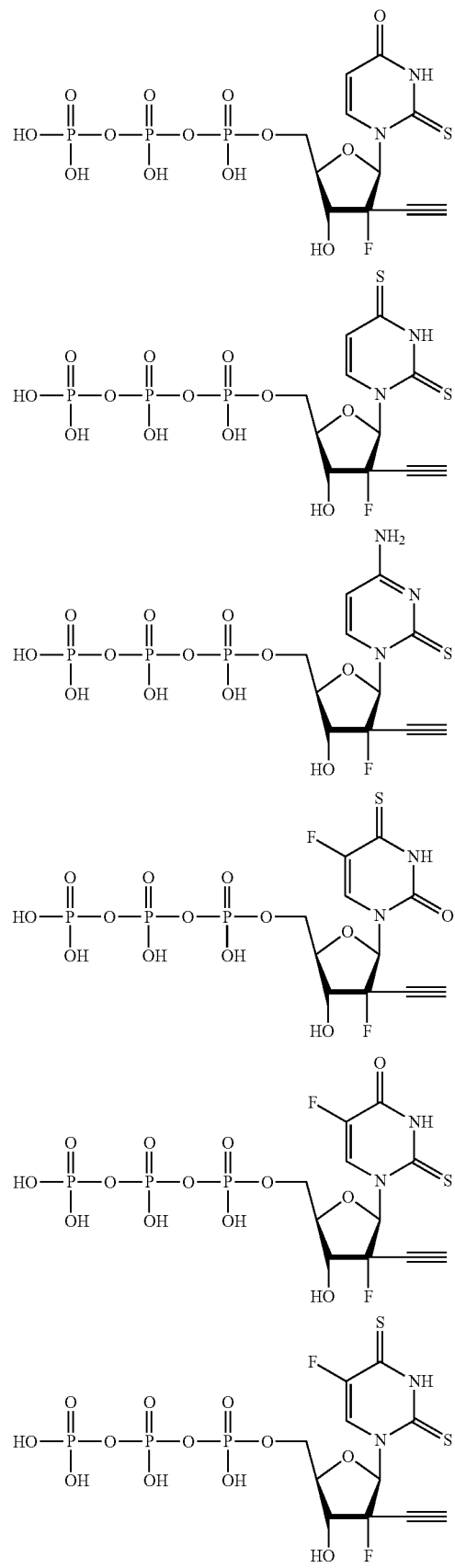
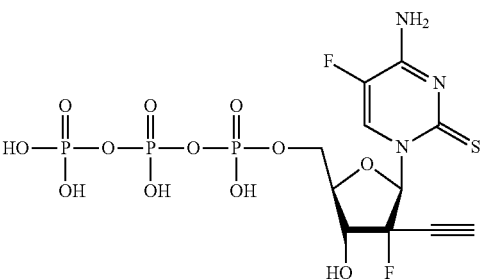
In one embodiment, $R^3$ is H. In another embodiment, $R^4$ is hydroxyl. In a further embodiment, $R^5$ is H. In still another embodiment, $R^6$ is $CH_2F$. In yet another embodiment, $R^7$ is fluoro. In a still further embodiment, $R^{10}$ is H. In exemplary embodiments, the compound is selected from the group consisting of:
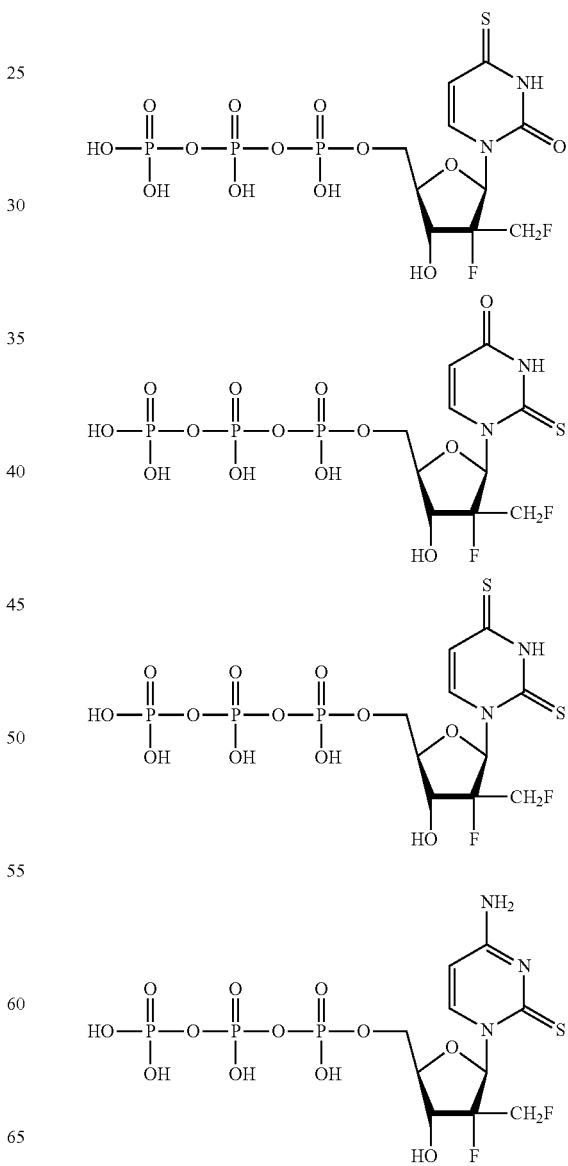

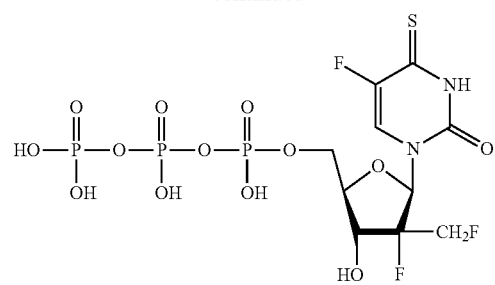
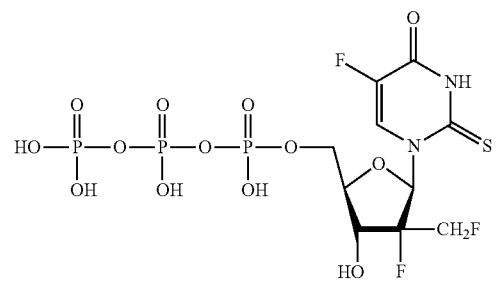
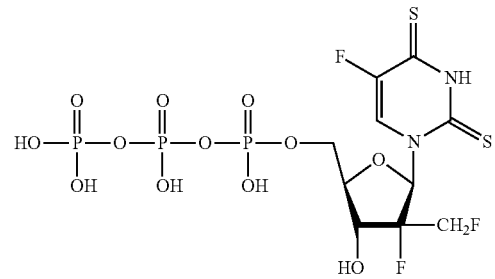
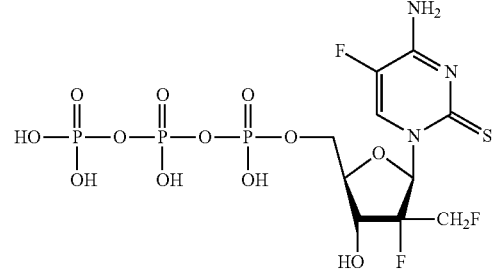
In one embodiment, R³ is H. In another embodiment, R⁴ is H. In a further embodiment, R⁵ is H. In still another embodiment, R⁶ is H. In yet another embodiment, R⁷ is fluoro. In a still further embodiment, R¹⁰ is H. In exemplary embodiments, the compound is selected from the group consisting of:
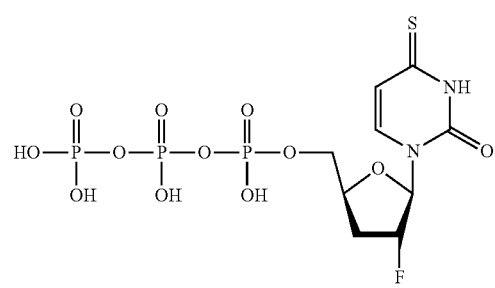
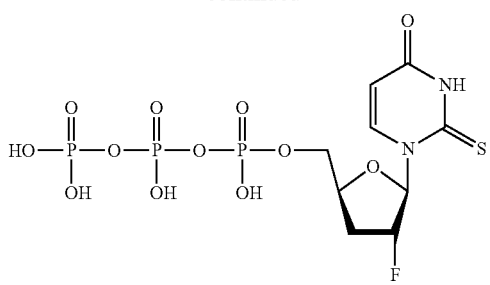
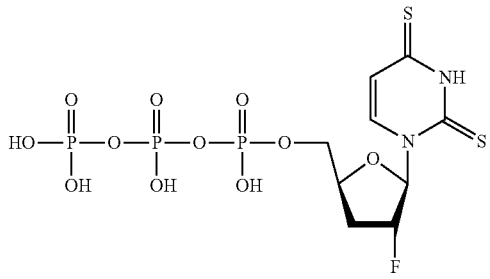
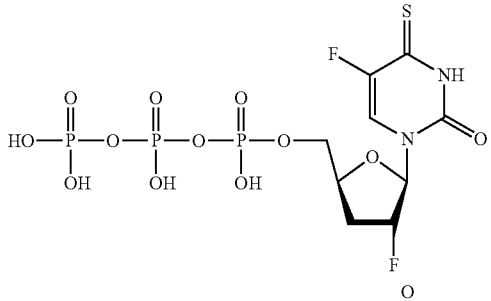
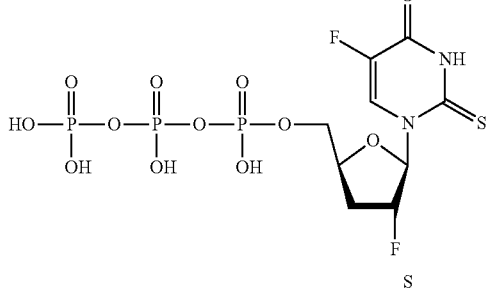
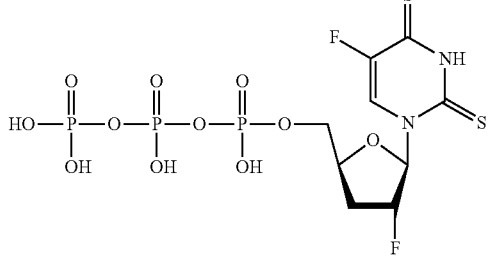
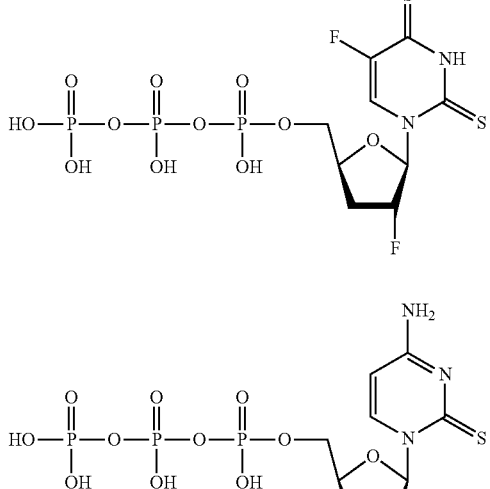

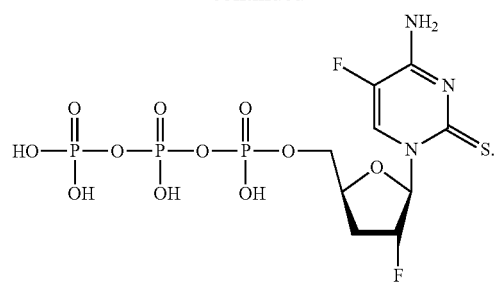

In one embodiment, $R^3$ is H. In another embodiment, $R^4$ is H. In a further embodiment, $R^5$ is H. In still another embodiment, $R^6$ is methyl. In yet another embodiment, $R^7$ is fluoro. In a still further embodiment, $R^{10}$ is H. In exemplary embodiments, the compound is selected from the group consisting of:

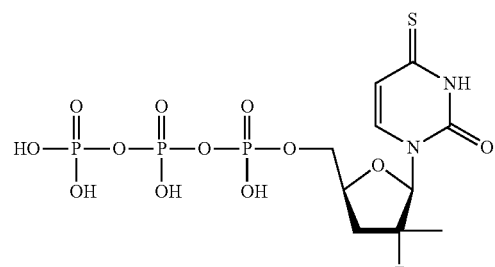

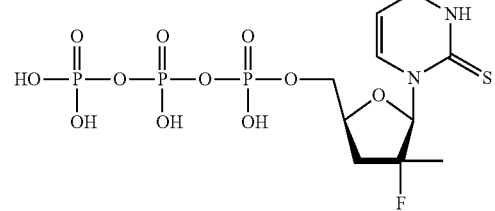

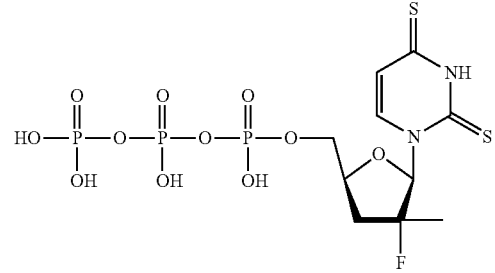

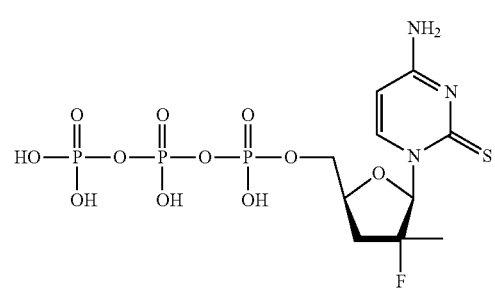

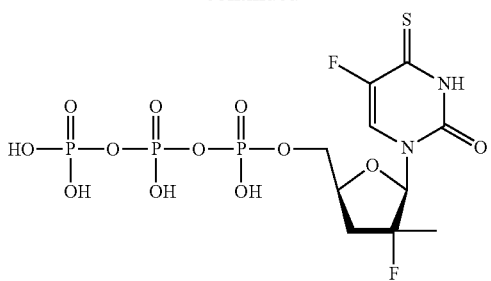

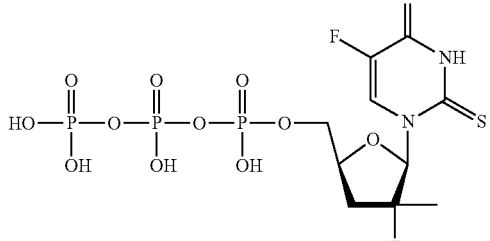

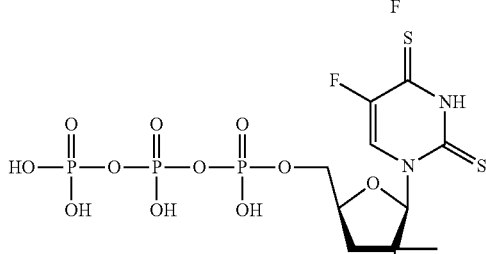

In one embodiment, $R^3$ is H. In another embodiment, $R^4$ is H. In a further embodiment, $R^5$ is H. In still another embodiment, $R^6$ is trifluoromethyl. In yet another embodiment, $R^7$ is fluoro. In a still further embodiment, $R^{10}$ is H. In exemplary embodiments, the compound is selected from the group consisting of:

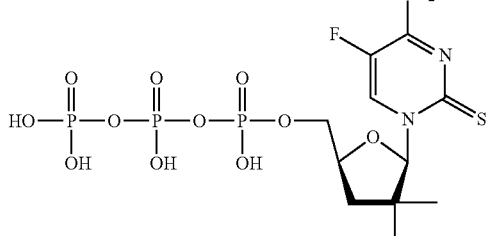

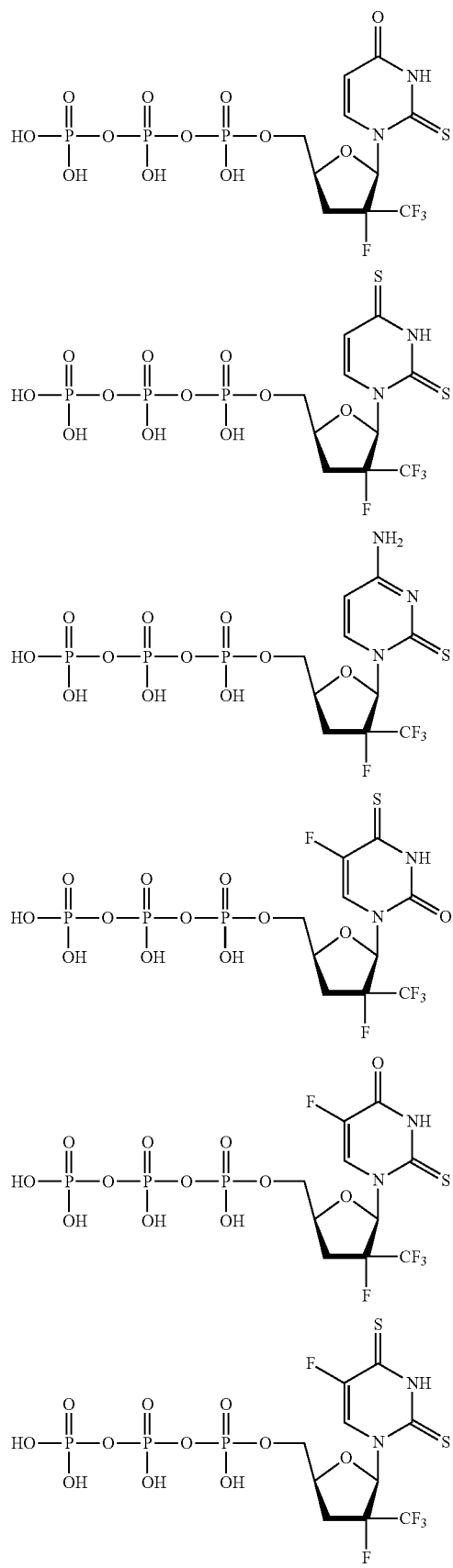
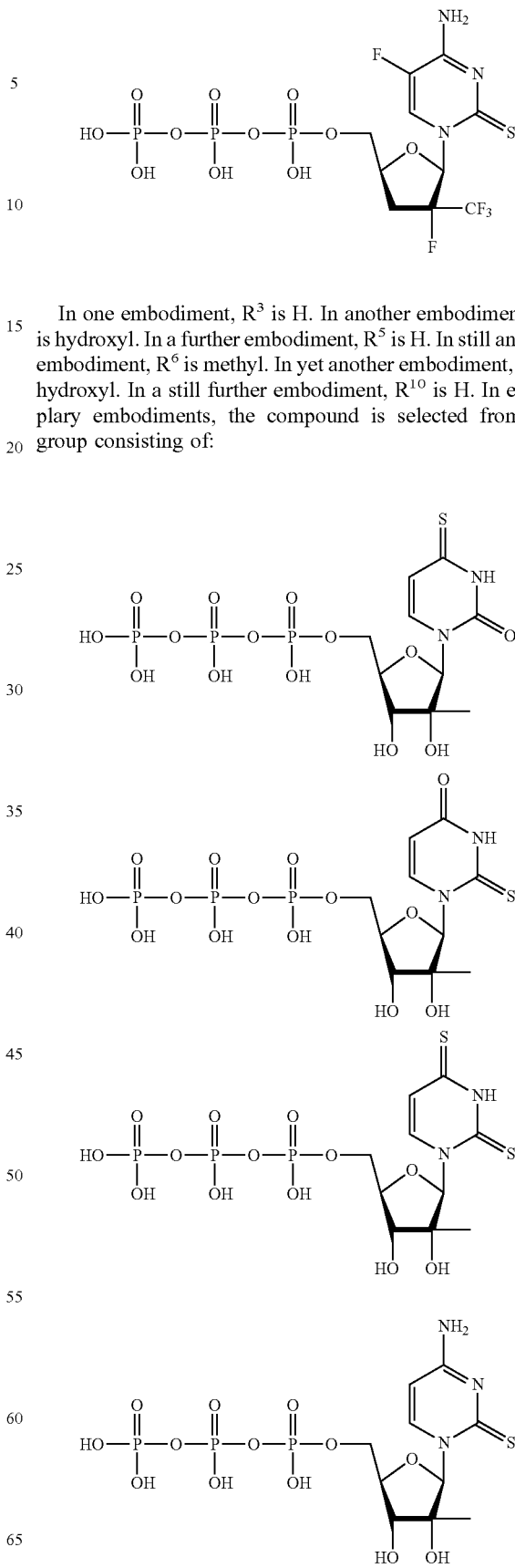
In one embodiment, R³ is H. In another embodiment, R⁴ is hydroxyl. In a further embodiment, R⁵ is H. In still another embodiment, R⁶ is methyl. In yet another embodiment, R⁷ is hydroxyl. In a still further embodiment, R¹⁰ is H. In exemplary embodiments, the compound is selected from the group consisting of:

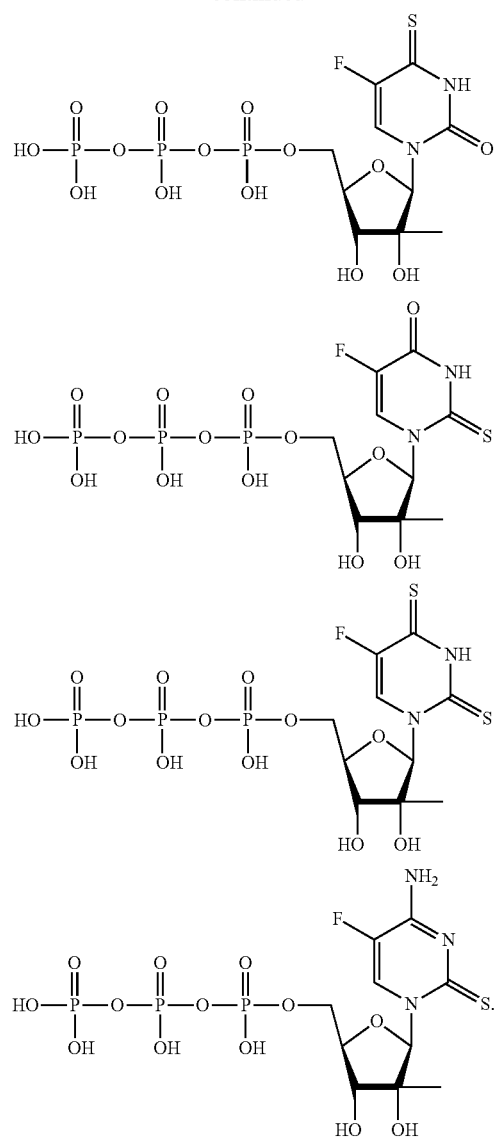
In one embodiment, R³ is H. In another embodiment, R⁴ is hydroxyl. In a further embodiment, R⁵ is H. In still another embodiment, R⁶ is trifluoromethyl. In yet another embodiment, R⁷ is hydroxyl. In a still further embodiment, R¹⁰ is H. In exemplary embodiments, the compound is selected from the group consisting of:
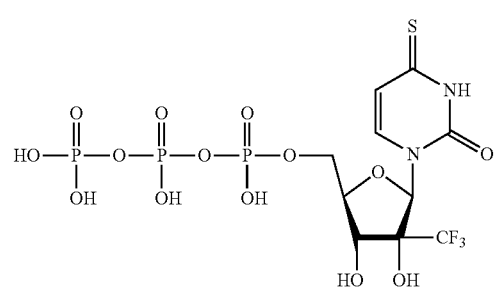
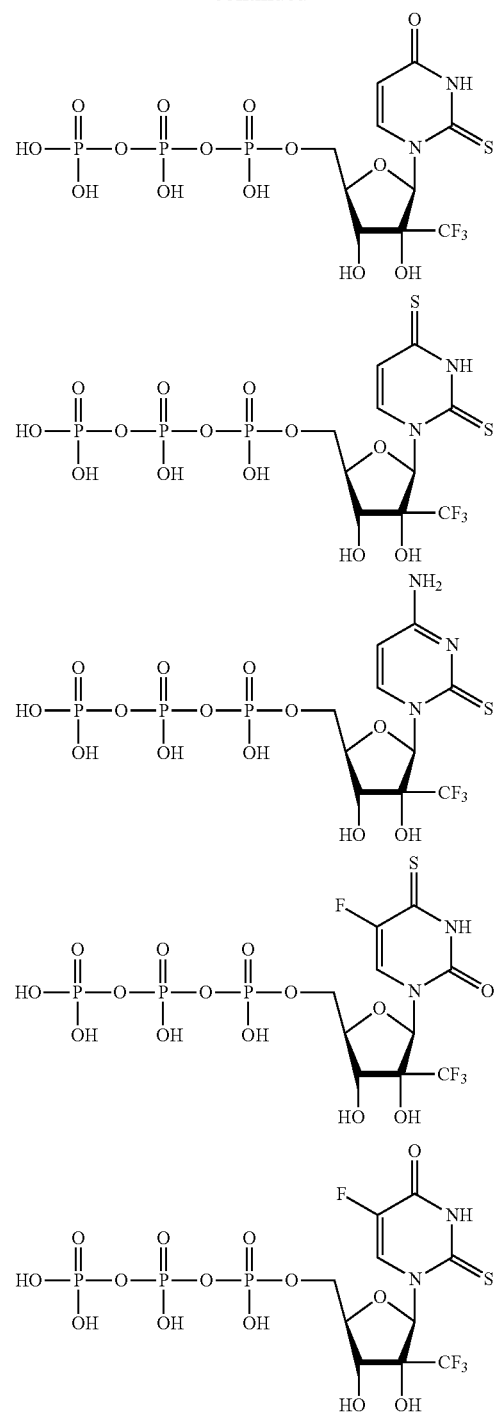
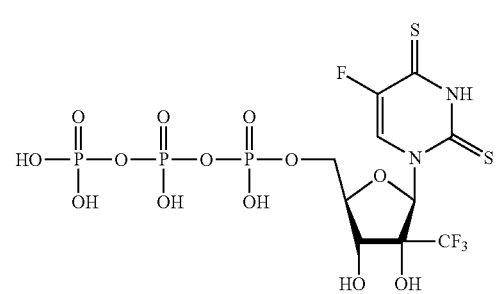

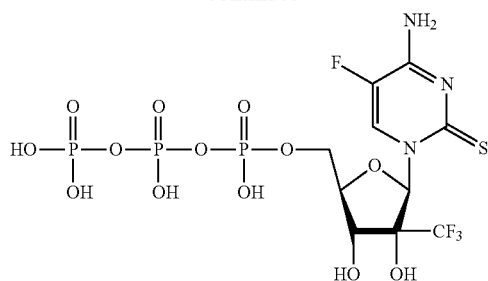

In one embodiment, $R^3$ is H. In another embodiment, $R^4$ is hydroxyl. In a further embodiment, $R^5$ is H. In still another embodiment, $R^6$ is C≡CH. In yet another embodiment, $R^7$ is hydroxyl. In a still further embodiment, $R^{10}$ is H. In exemplary embodiments, the compound is selected from the group consisting of:

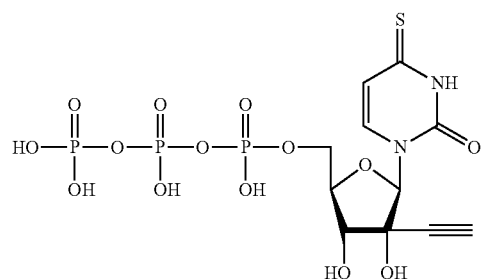

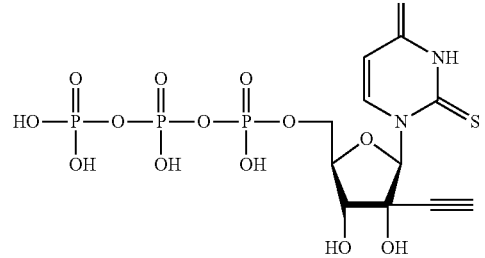

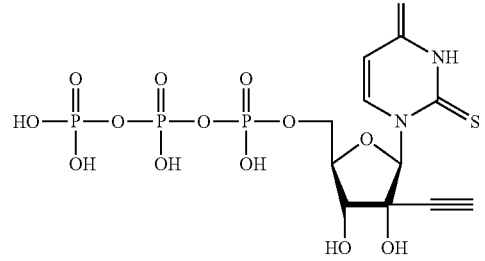

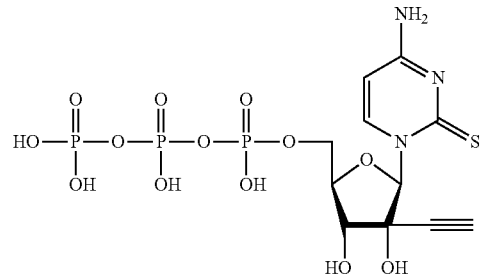

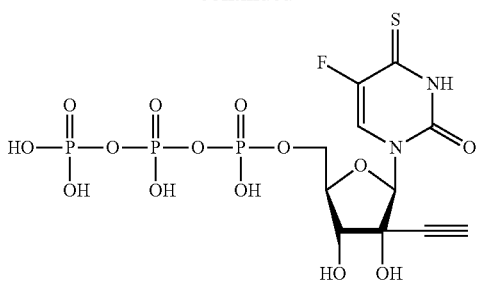

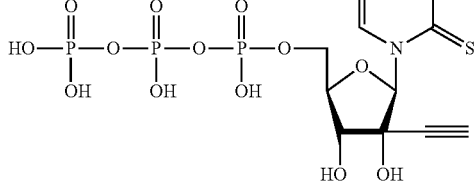

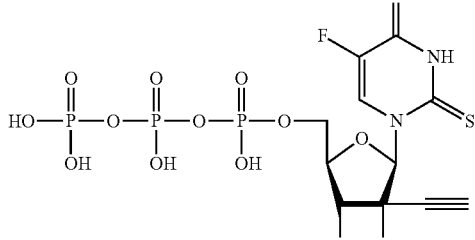

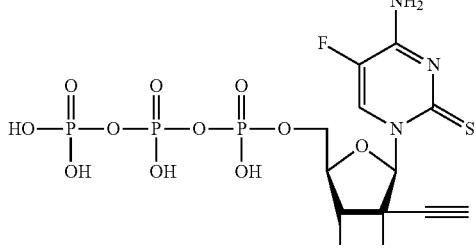

In one embodiment, $R^3$ is H. In another embodiment, $R^4$ is hydroxyl. In a further embodiment, $R^5$ is H. In still another embodiment, $R^6$ is $CH_2F$. In yet another embodiment, $R^7$ is hydroxyl. In a still further embodiment, $R^{10}$ is H. In exemplary embodiments, the compound is selected from the group consisting of:

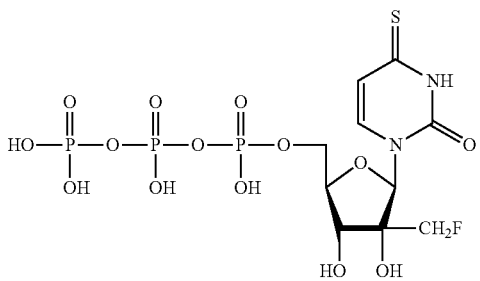

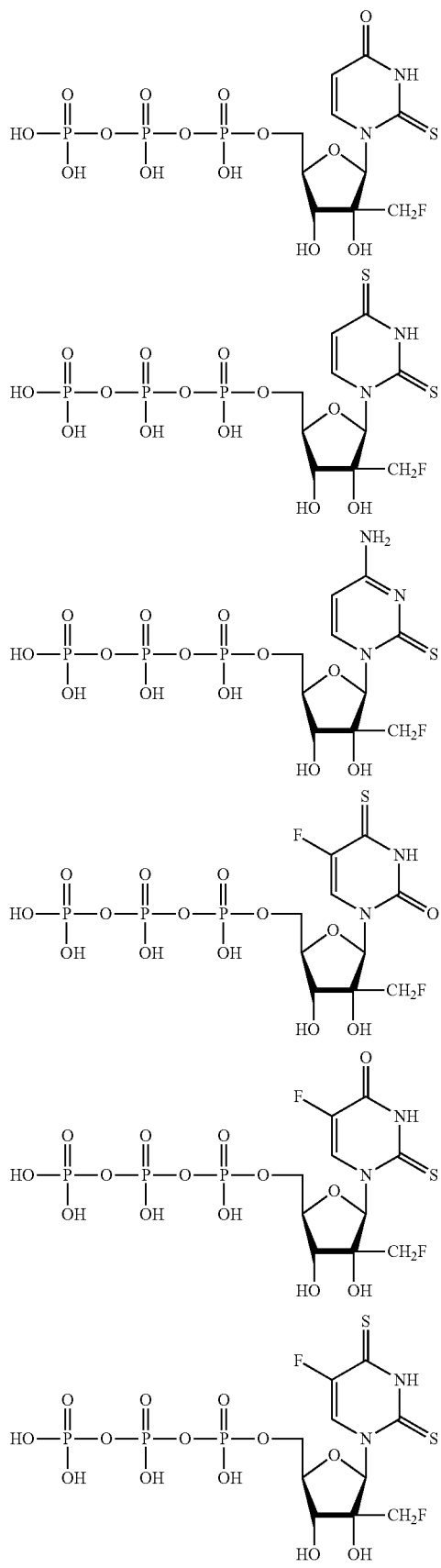
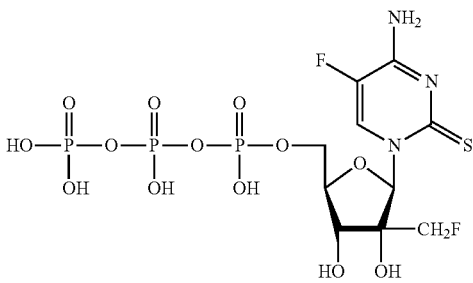
In one embodiment, $R^3$ is H. In another embodiment, $R^4$ is hydroxyl. In a further embodiment, $R^5$ is H. In still another embodiment, $R^6$ is methyl. In yet another embodiment, $R^7$ is H. In a still further embodiment, $R^{10}$ is H. In exemplary embodiments, the compound is selected from the group consisting of:
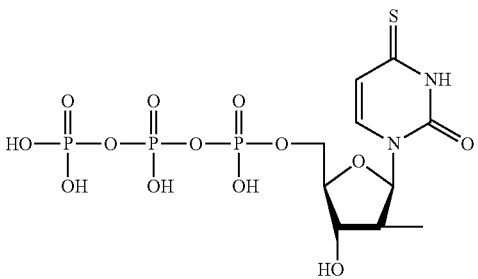
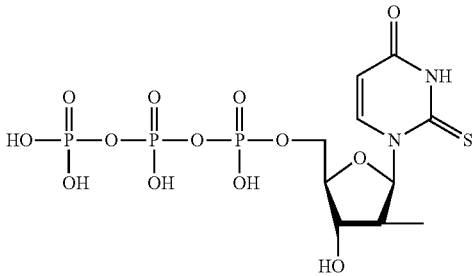
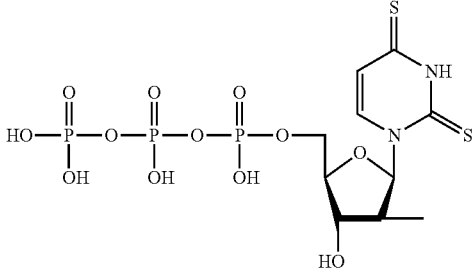
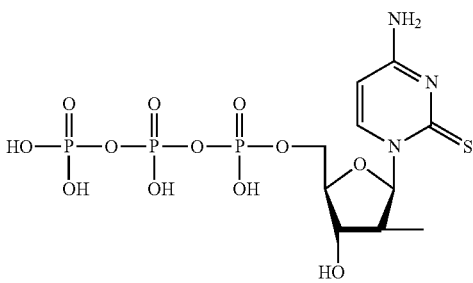

-continued
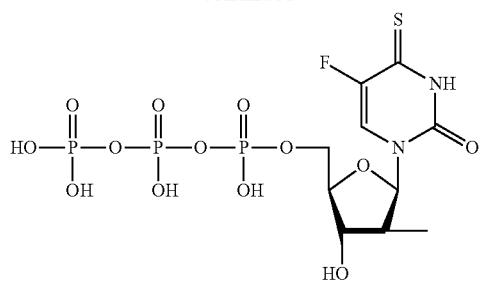
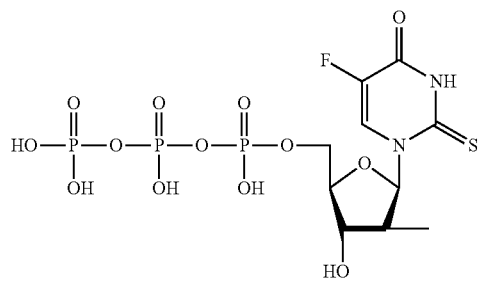
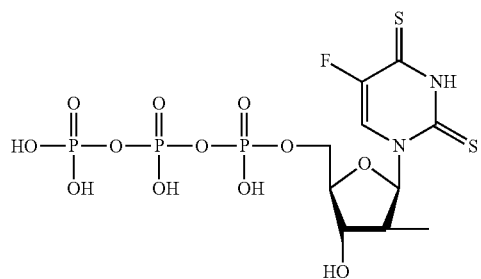
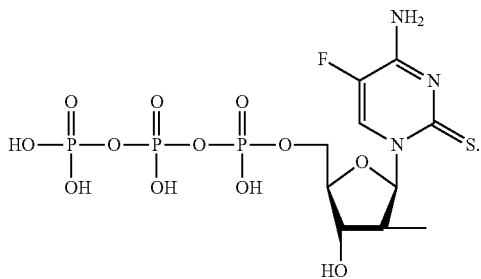
In one embodiment, $R^3$ is H. In another embodiment, $R^4$ is hydroxyl. In a further embodiment, $R^5$ is H. In still another embodiment, $R^6$ is trifluoromethyl. In yet another embodiment, $R^7$ is H. In a still further embodiment, $R^{10}$ is H. In exemplary embodiments, the compound is selected from the group consisting of:
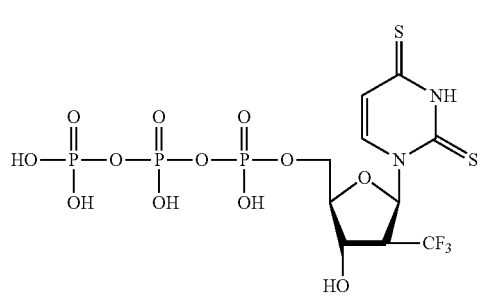
-continued
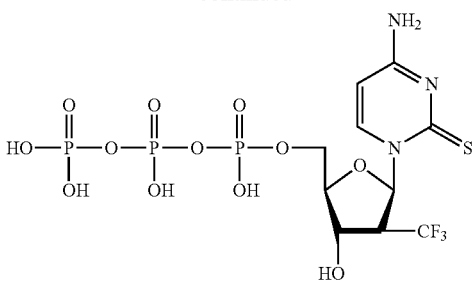
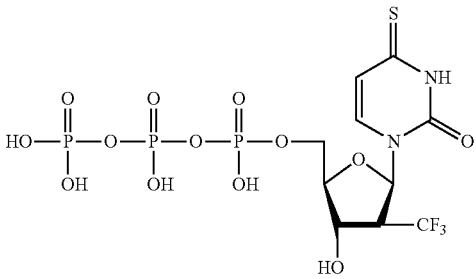
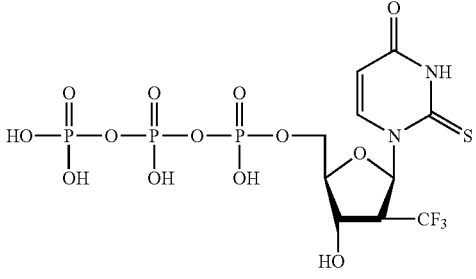
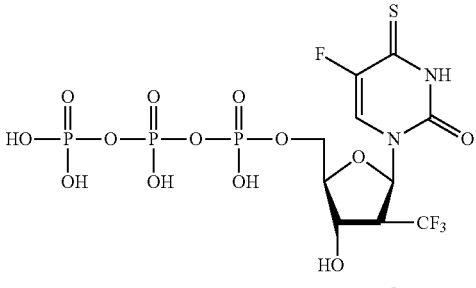
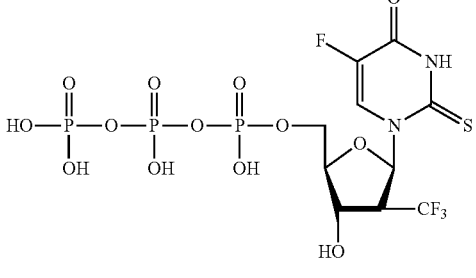
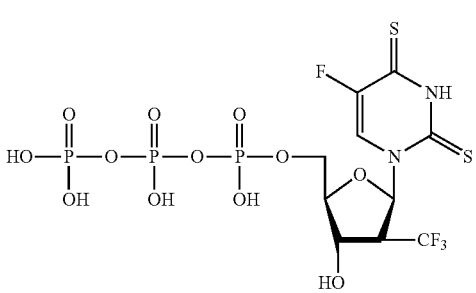

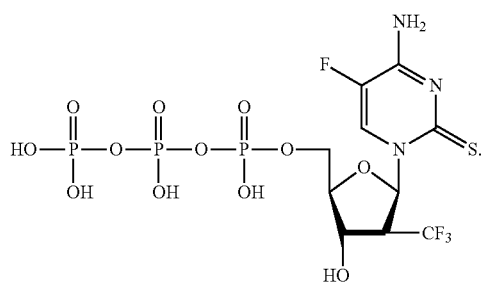

In one embodiment, $R^3$ is H. In another embodiment, $R^4$ is hydroxyl. In a further embodiment, $R^5$ is H. In another embodiment, $R^{10}$ is $N_3$. In still another embodiment, $R^6$ is H. In yet another embodiment, $R^7$ is hydroxyl. In exemplary embodiments, the compound is selected from the group consisting of:

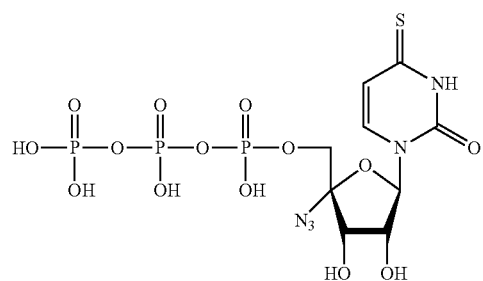

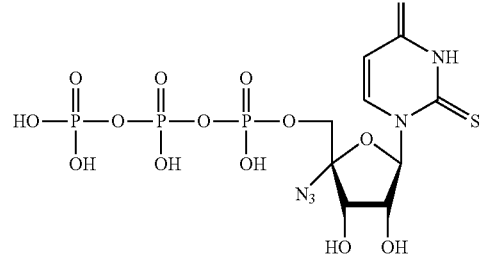

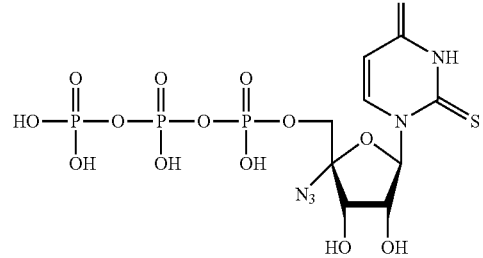

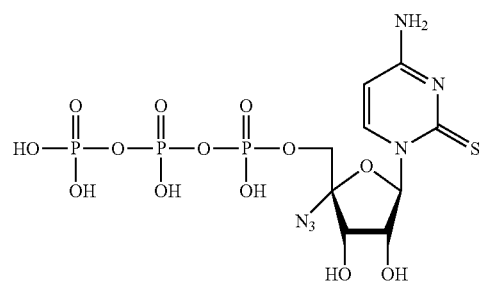

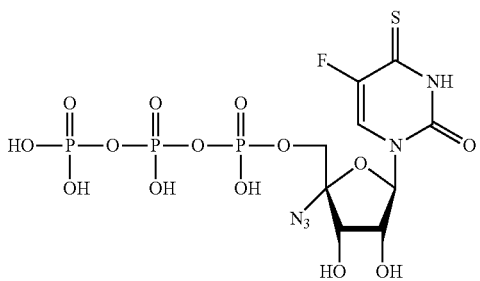

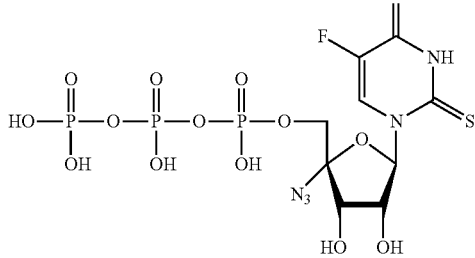

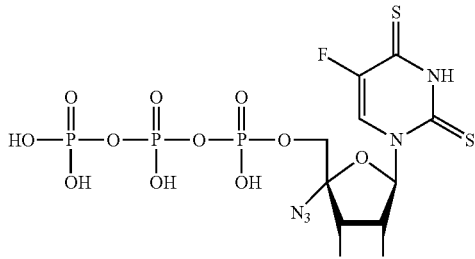

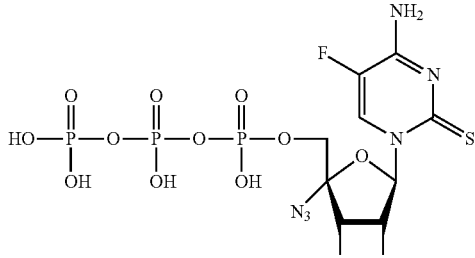

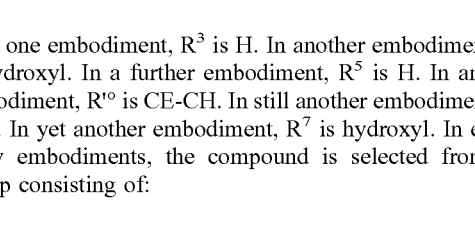

In one embodiment, $R^3$ is H. In another embodiment, $R^4$ is hydroxyl. In a further embodiment, $R^5$ is H. In another embodiment, $R^{10}$ is CE-CH. In still another embodiment, $R^6$ is H. In yet another embodiment, $R^7$ is hydroxyl. In exemplary embodiments, the compound is selected from the group consisting of:

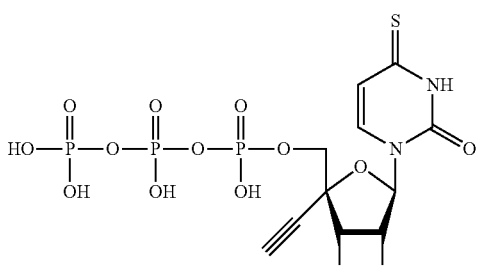

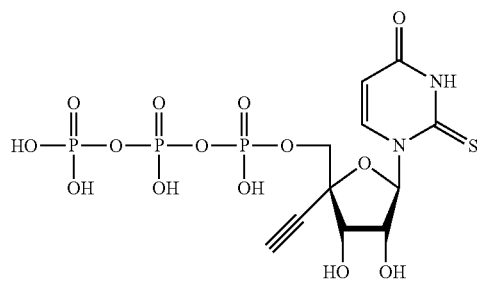
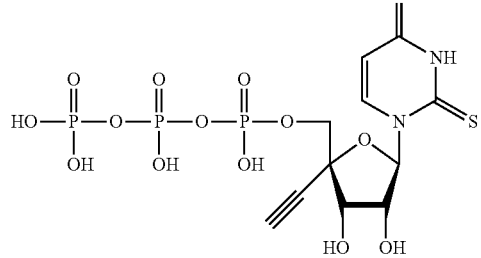
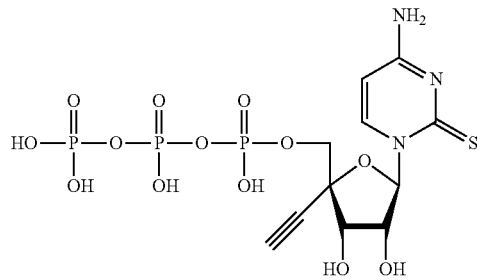
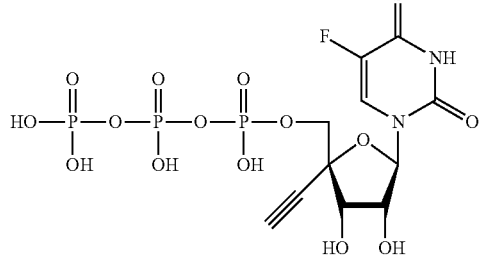
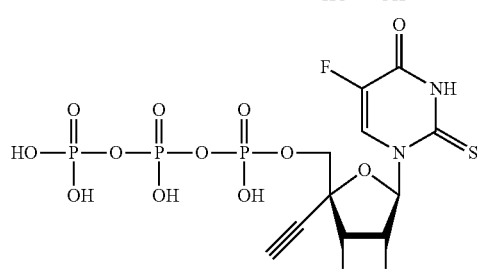
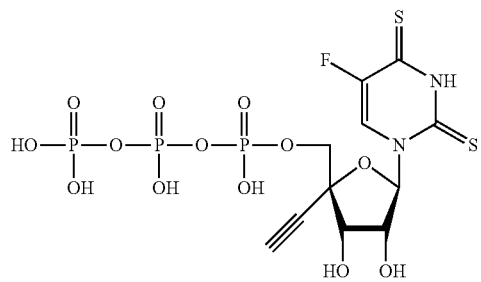
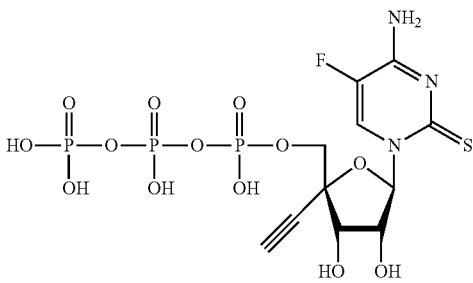
In one embodiment, $R^3$ is H. In another embodiment, $R^4$ is hydroxyl. In a further embodiment, $R^5$ is H. In another embodiment, $R^{10}$ is $CH_2F$. In still another embodiment, $R^6$ is H. In yet another embodiment, $R^7$ is hydroxyl. In exemplary embodiments, the compound is selected from the group consisting of:
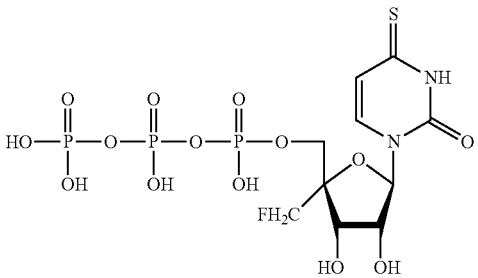
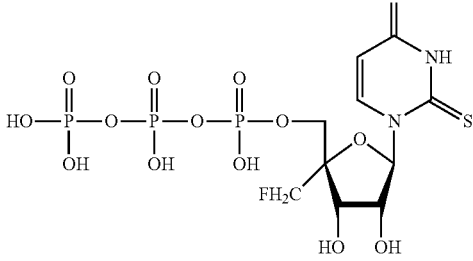
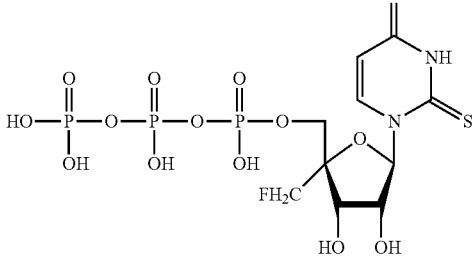
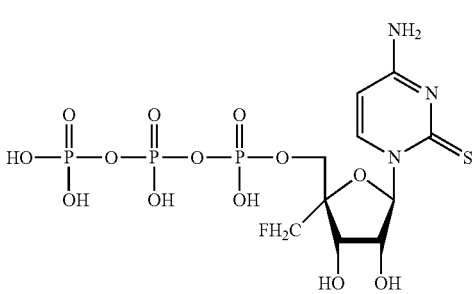

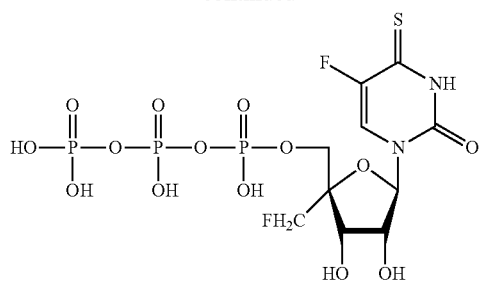
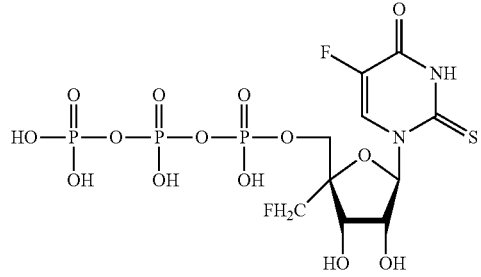
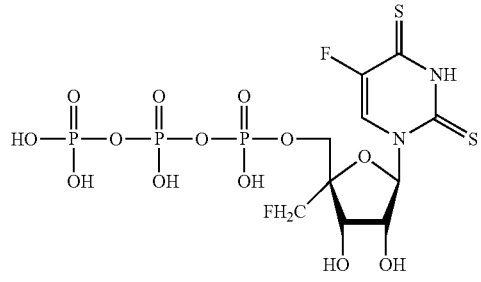
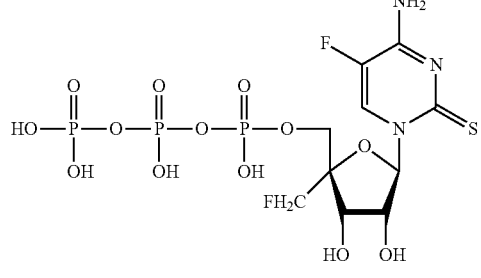
In one embodiment, $R^3$ is H. In another embodiment, $R^4$ is hydroxyl. In a further embodiment, $R^5$ is H. In another embodiment, $R^{10}$ is $N_3$. In still another embodiment, $R^6$ is H. In yet another embodiment, $R^7$ is fluoro. In exemplary embodiments, the compound is selected from the group consisting of:
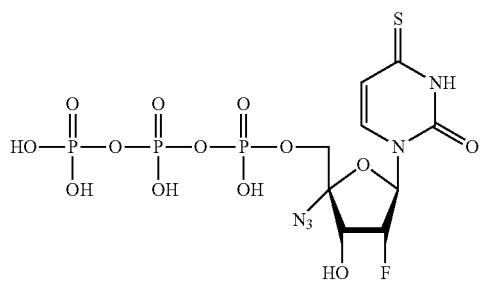
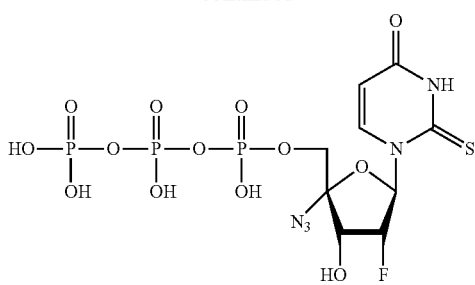
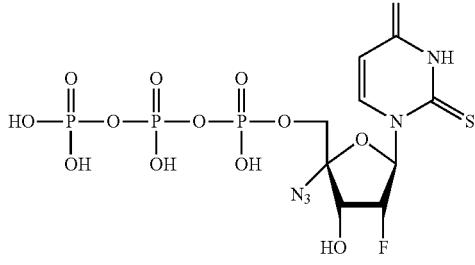
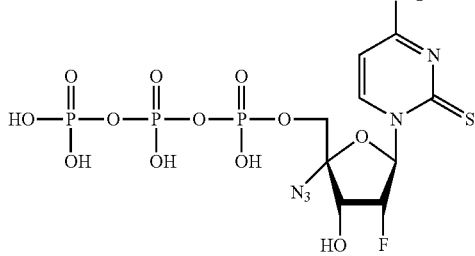
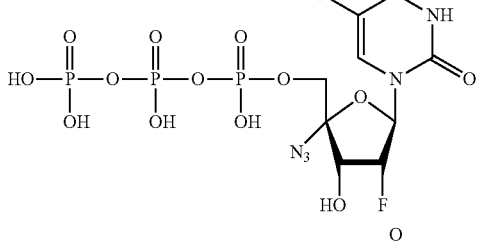
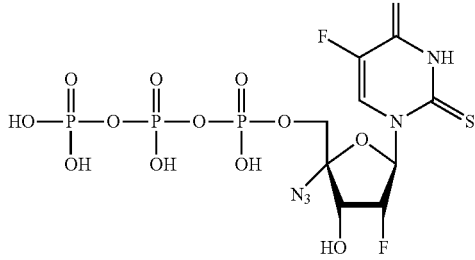
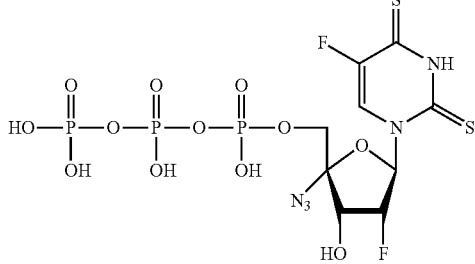

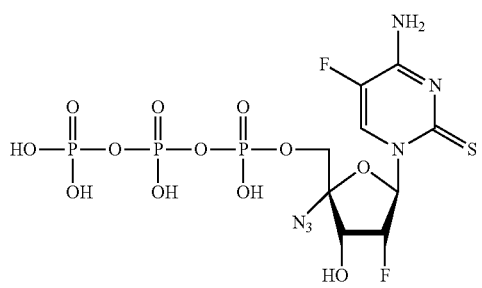

In one embodiment, R³ is H. In another embodiment, R⁴ is hydroxyl. In a further embodiment, R⁵ is H. In another embodiment, R¹⁰ is C≡CH. In still another embodiment, R⁶ is H. In yet another embodiment, R⁷ is fluoro. In exemplary embodiments, the compound is selected from the group consisting of:

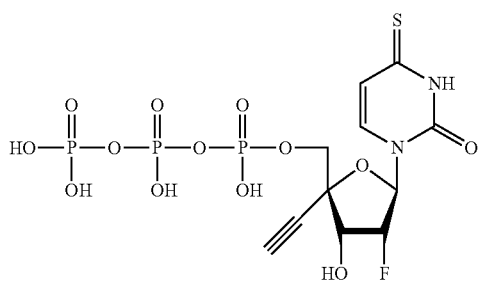

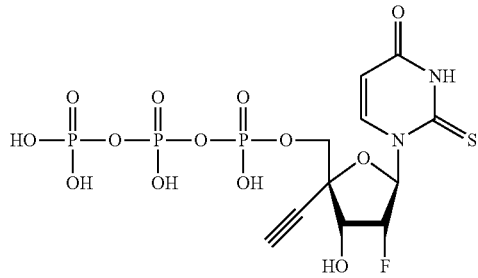

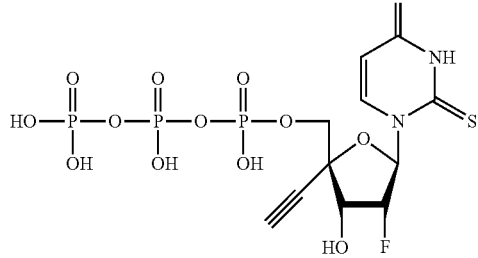

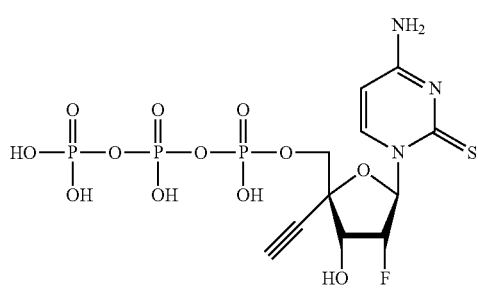

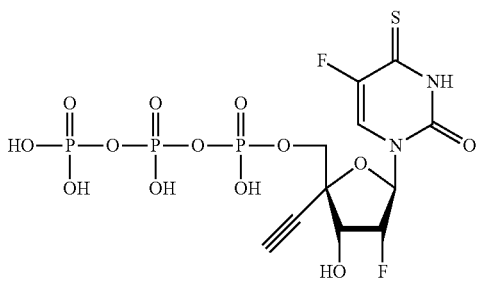

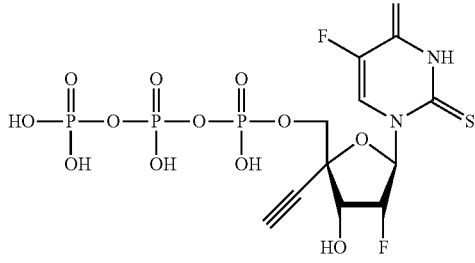

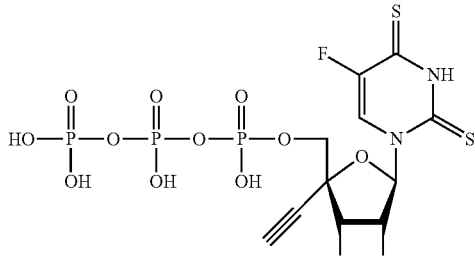

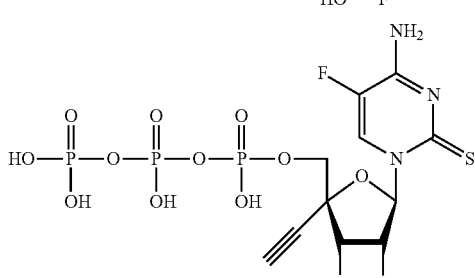

In one embodiment, R³ is H. In another embodiment, R⁴ is hydroxyl. In a further embodiment, R⁵ is H. In another embodiment, R¹⁰ is CH₂F. In still another embodiment, R⁶ is H. In yet another embodiment, R⁷ is fluoro. In exemplary embodiments, the compound is selected from the group consisting of:

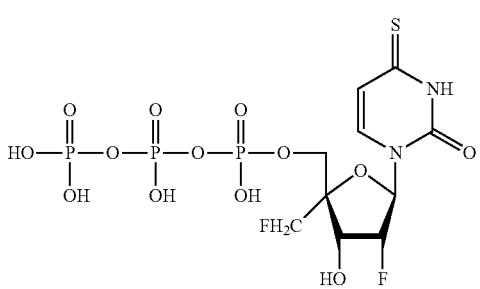

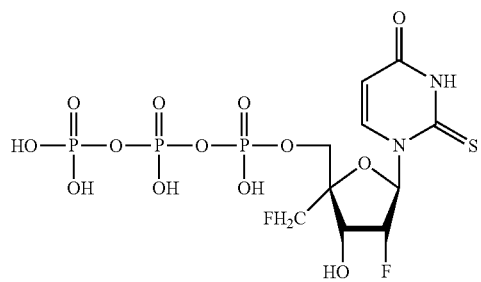
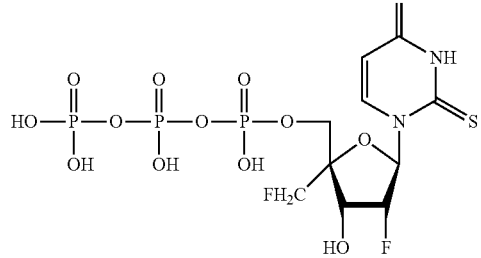
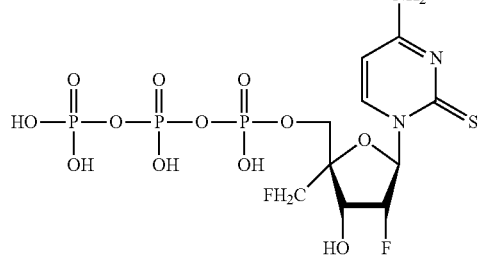
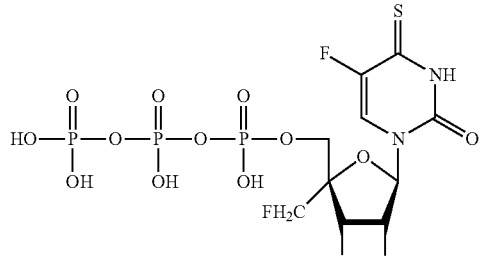
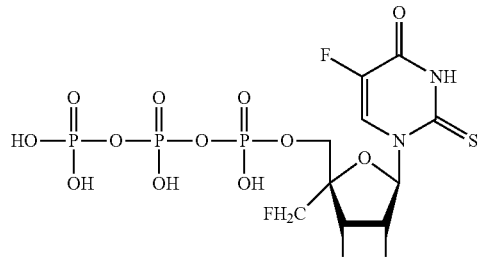
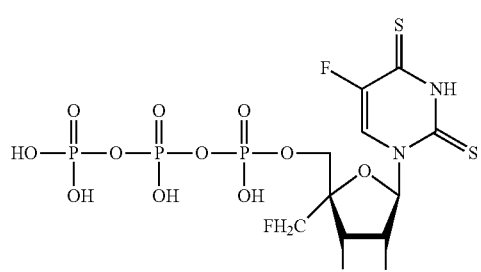
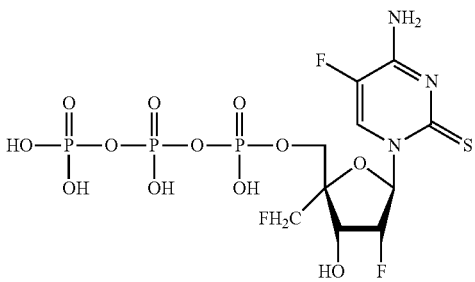
In one embodiment, $R^3$ is H. In another embodiment, $R^4$ is fluoro. In a further embodiment, $R^5$ is H. In another embodiment, $R^{10}$ is H. In still another embodiment, $R^6$ is H. In yet another embodiment, $R^7$ is hydroxyl. In exemplary embodiments, the compound is selected from the group consisting of:
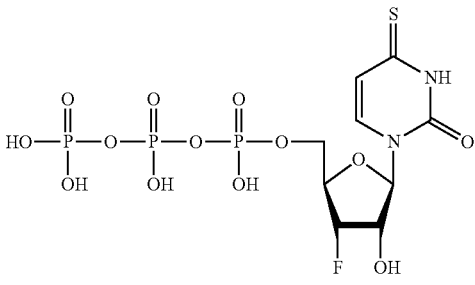
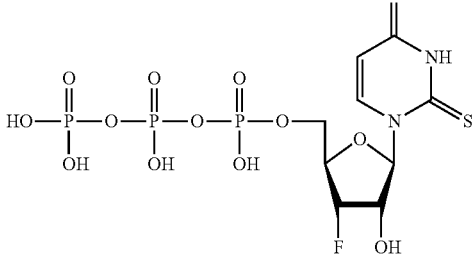
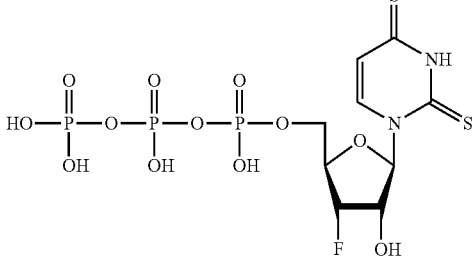
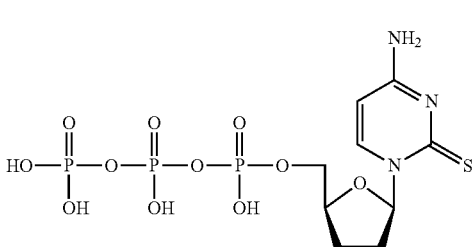

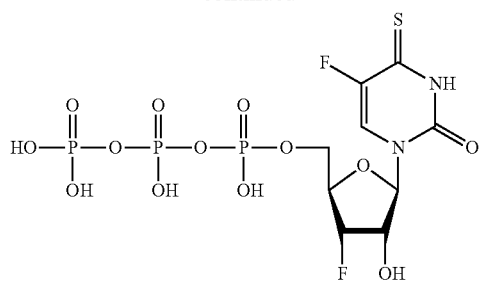
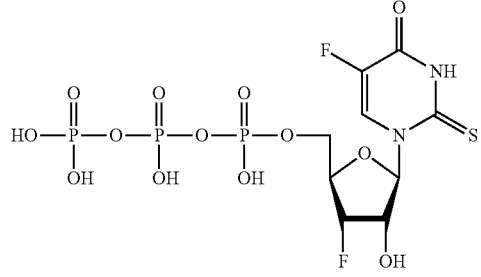
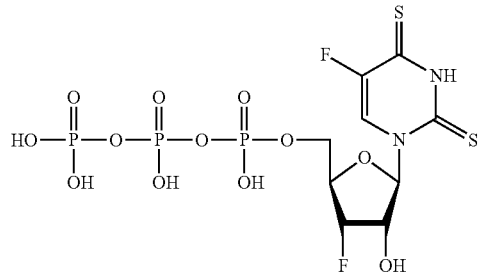
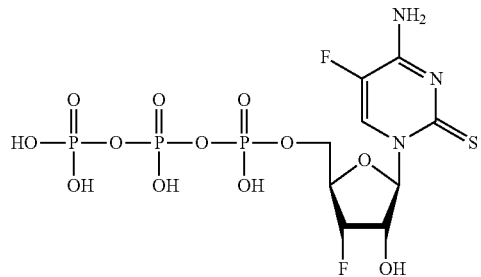
In one embodiment, $R^3$ is H. In another embodiment, $R^4$ is fluoro. In a further embodiment, $R^5$ is H. In another embodiment, $R^{10}$ is H. In still another embodiment, $R^6$ is methyl. In yet another embodiment, $R^7$ is hydroxyl. In exemplary embodiments, the compound is selected from the group consisting of:
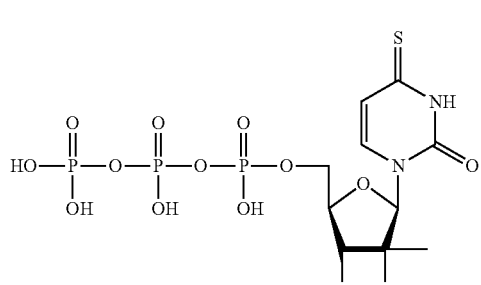
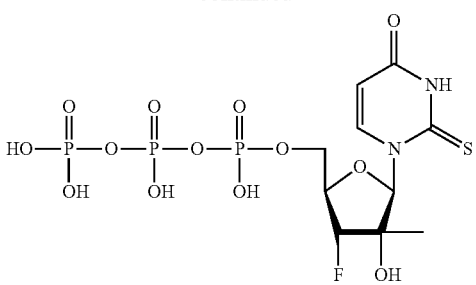
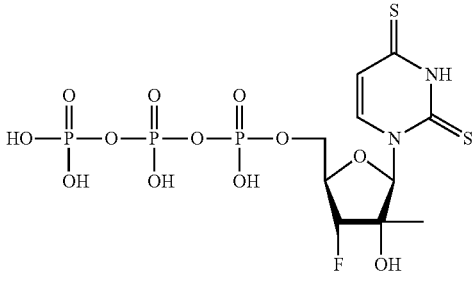
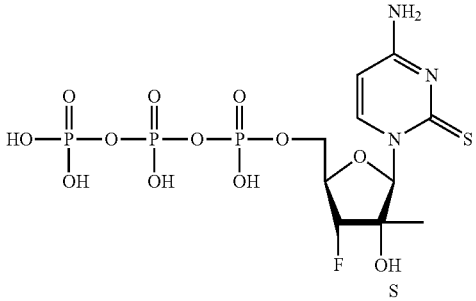
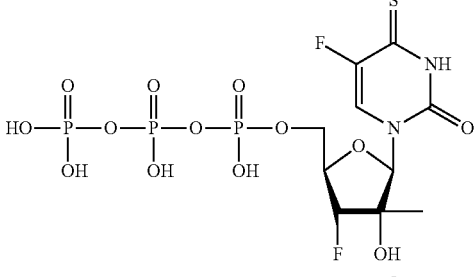
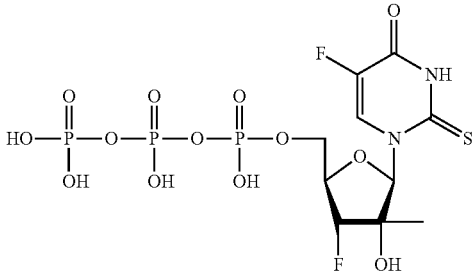
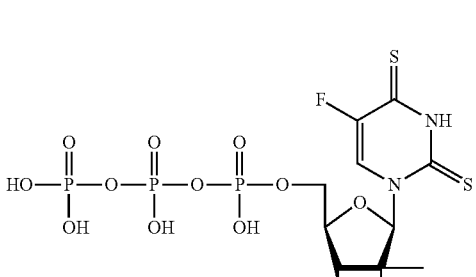

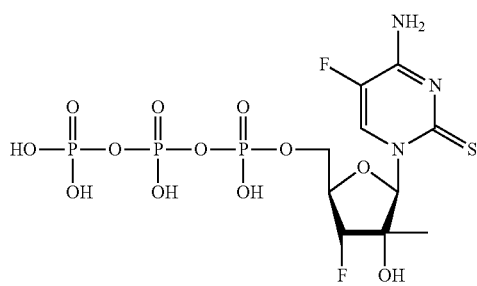

In one embodiment, $R^3$ is H. In another embodiment, $R^4$ is fluoro. In a further embodiment, $R^5$ is H. In another embodiment, $R^{10}$ is H. In still another embodiment, $R^6$ is C≡CH. In yet another embodiment, $R^7$ is hydroxyl. In exemplary embodiments, the compound is selected from the group consisting of:

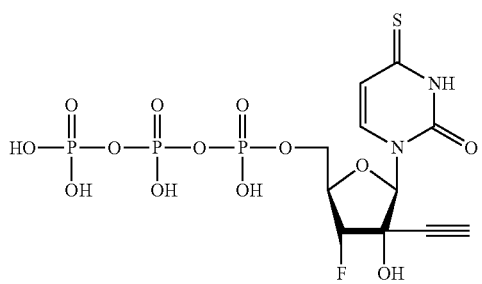

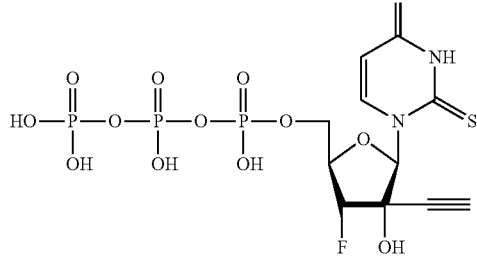

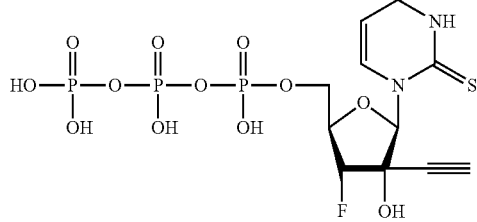

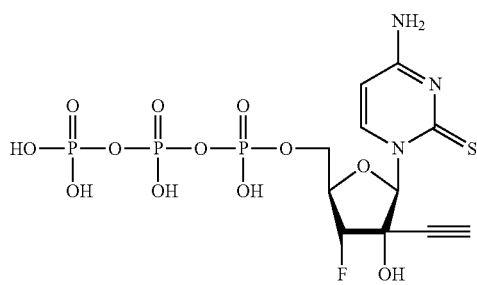

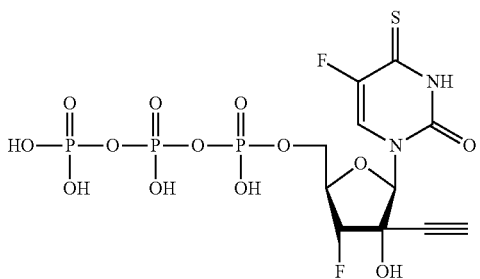

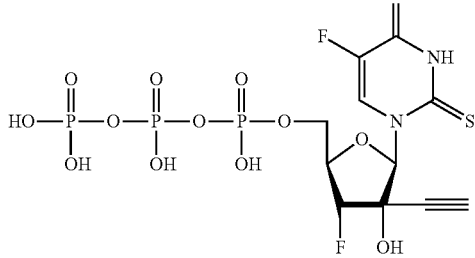

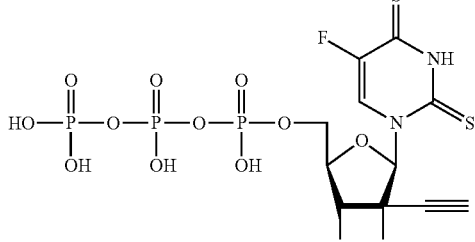

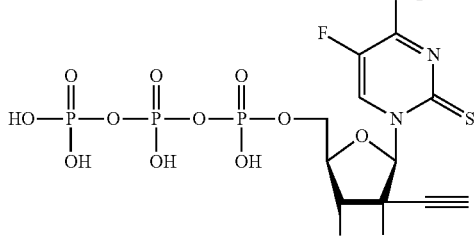

In one embodiment, $R^3$ is H. In another embodiment, $R^4$ is fluoro. In a further embodiment, $R^5$ is H. In another embodiment, $R^{10}$ is H. In still another embodiment, $R^6$ is $CH_2F$. In yet another embodiment, $R^7$ is hydroxyl. In exemplary embodiments, the compound is selected from the group consisting of:

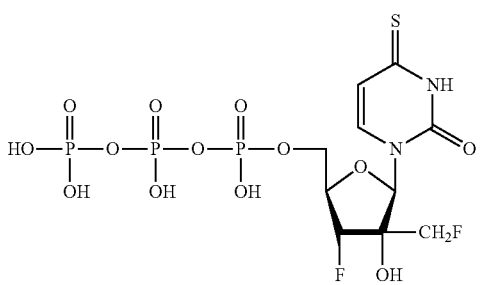

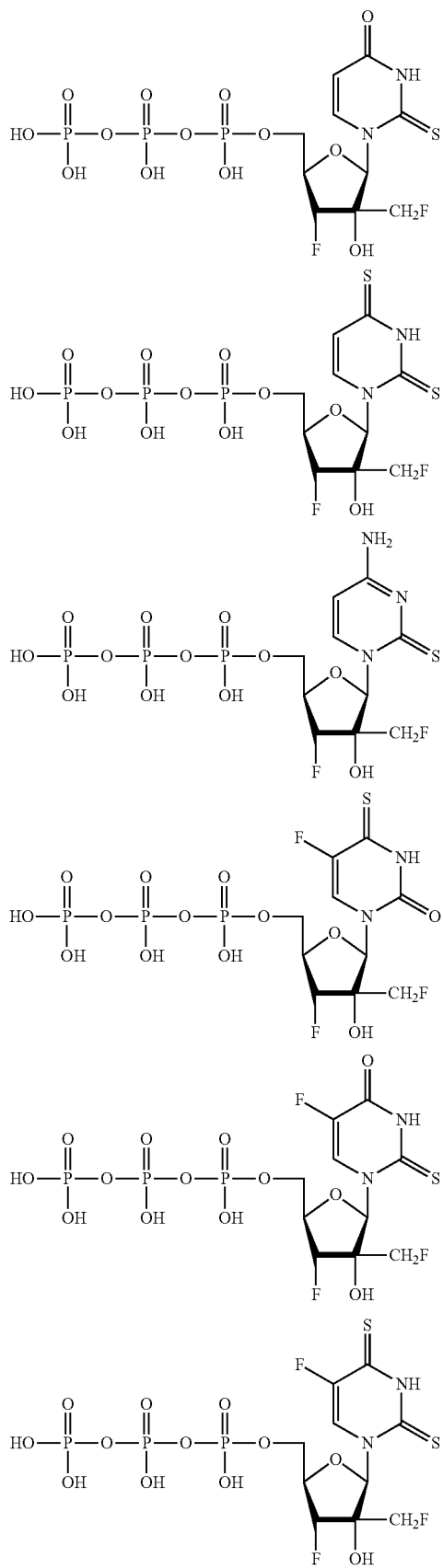
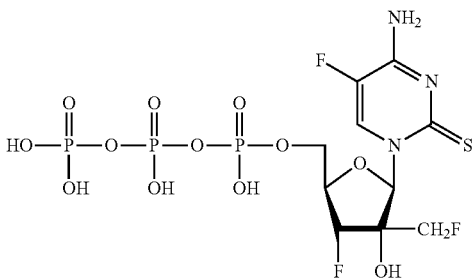
In one embodiment, $R^3$ is H. In another embodiment, $R^4$ is hydroxyl. In a further embodiment, $R^5$ is H. In another embodiment, $R^{10}$ is fluoro. In still another embodiment, $R^6$ is methyl. In yet another embodiment, $R^7$ is hydroxyl. In exemplary embodiments, the compound is selected from the group consisting of:
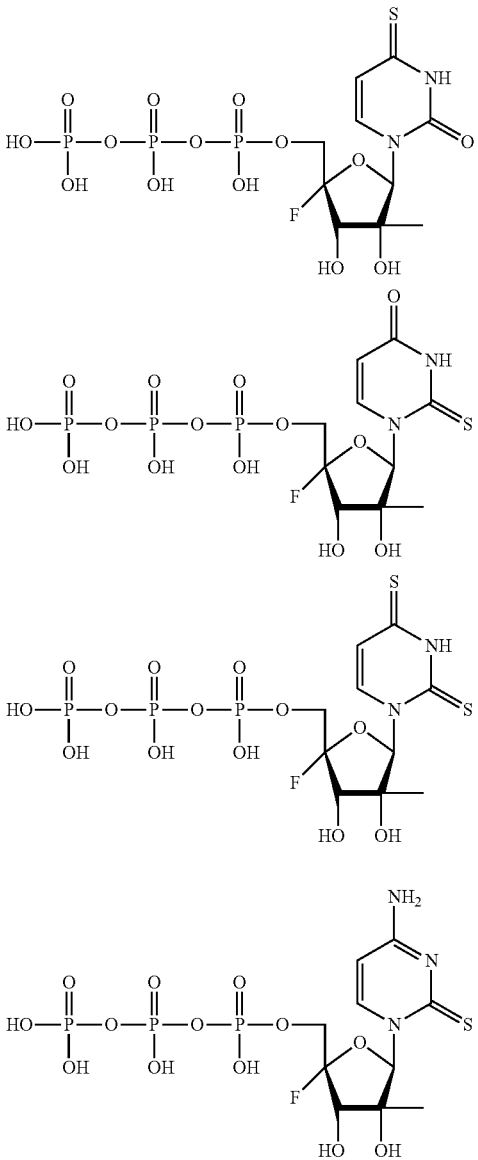

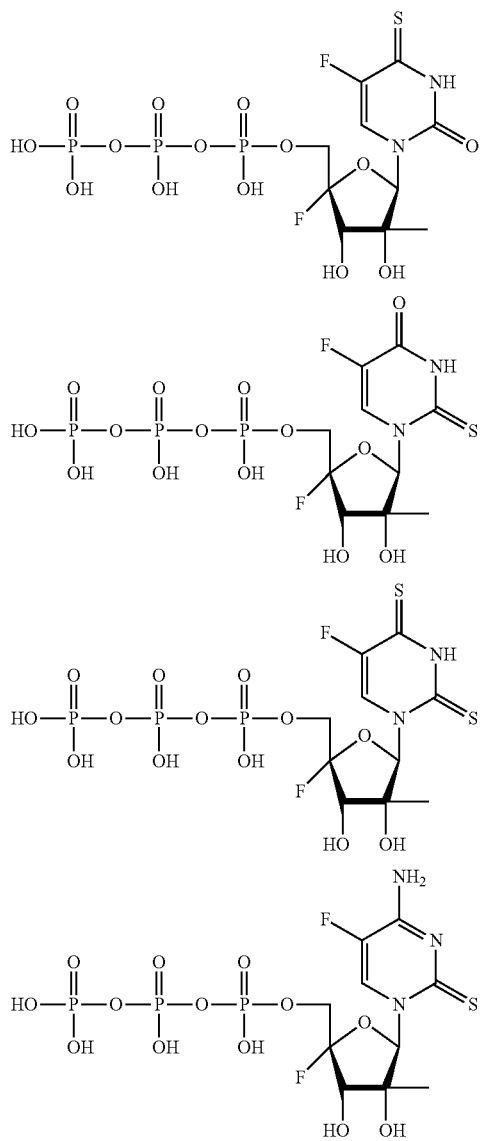
In one embodiment, $R^3$ is H. In another embodiment, $R^4$ is hydroxyl. In a further embodiment, $R^5$ is H. In another embodiment, $R^{10}$ is fluoro. In still another embodiment, $R^6$ is C≡CH. In yet another embodiment, $R^7$ is hydroxyl. In exemplary embodiments, the compound is selected from the group consisting of:
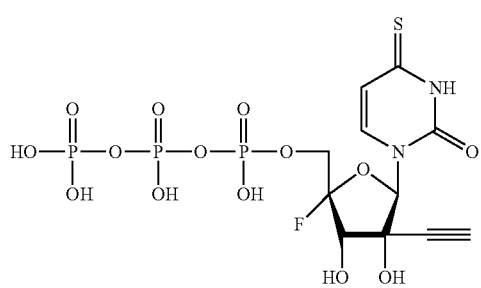
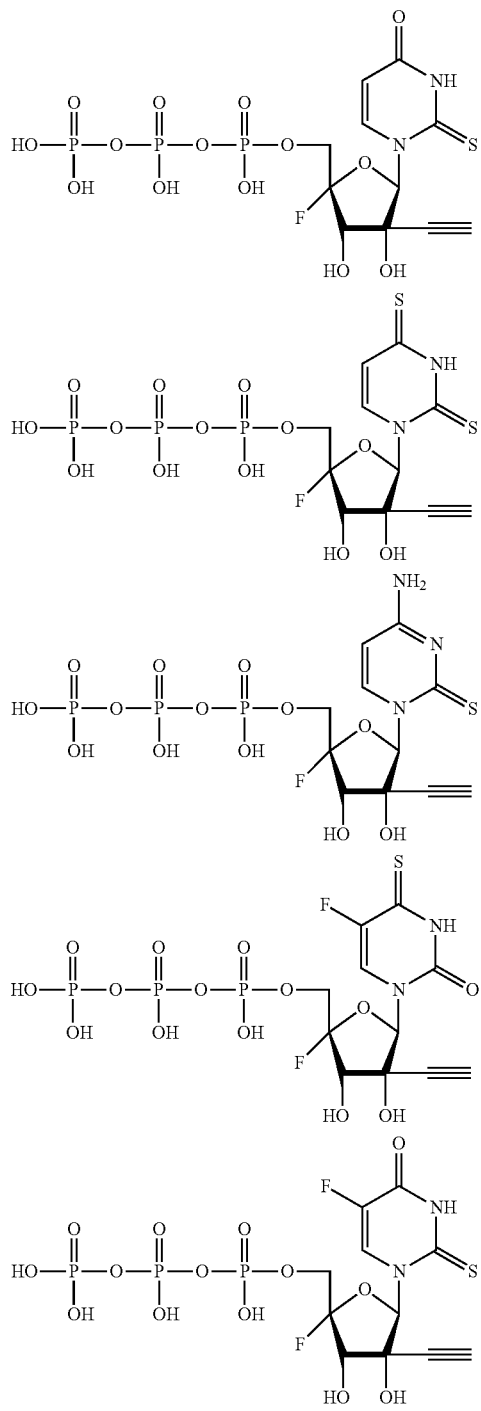
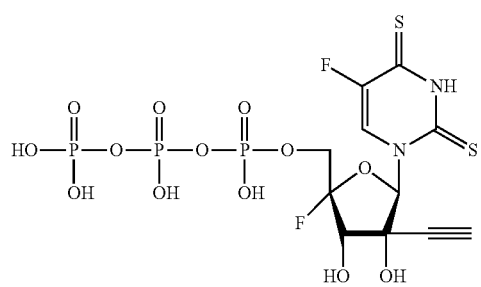

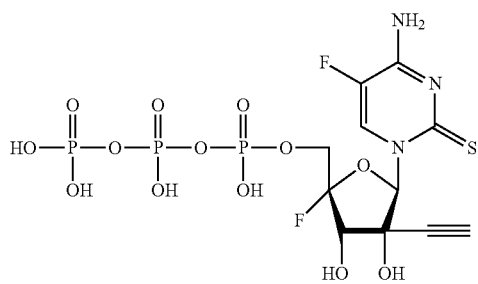

In one embodiment, $R^3$ is H. In another embodiment, $R^4$ is hydroxyl. In a further embodiment, $R^5$ is H. In another embodiment, $R^{10}$ is fluoro. In still another embodiment, $R^6$ is $CH_2F$. In yet another embodiment, $R^7$ is hydroxyl. In exemplary embodiments, the compound is selected from the group consisting of:

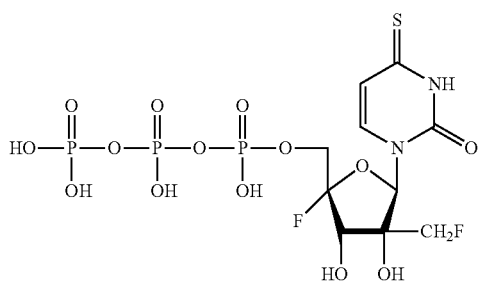

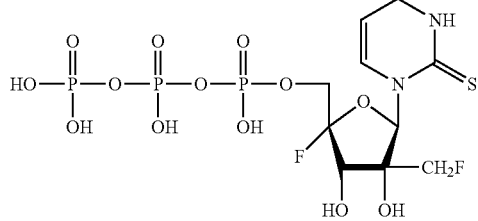

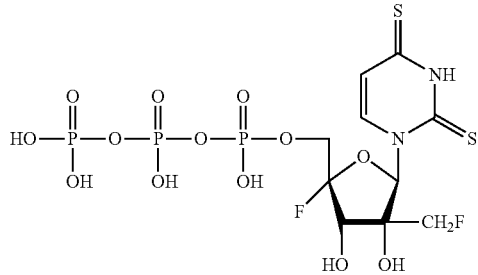

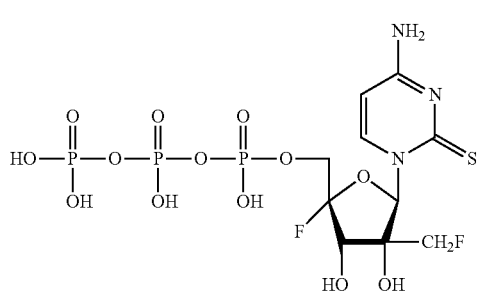

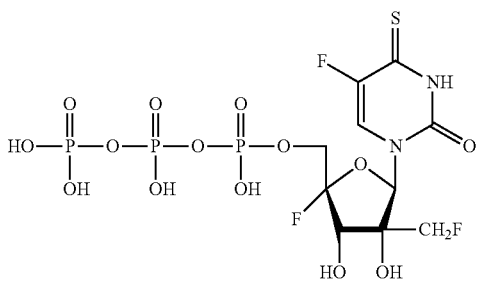

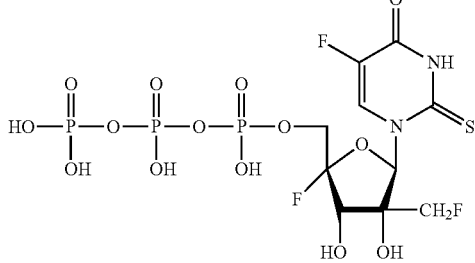

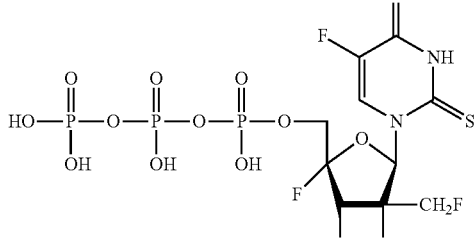

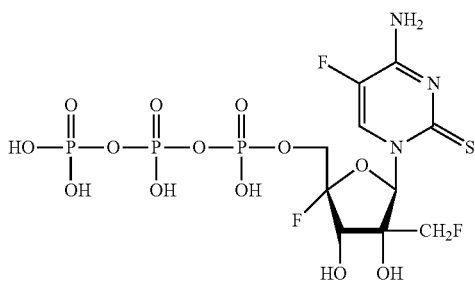

In one embodiment, $R^3$ is H. In another embodiment, $R^4$ is hydroxyl. In a further embodiment, $R^5$ is H. In another embodiment, $R^{10}$ is fluoro. In still another embodiment, $R^6$ is methyl. In yet another embodiment, $R^7$ is fluoro. In exemplary embodiments, the compound is selected from the group consisting of:

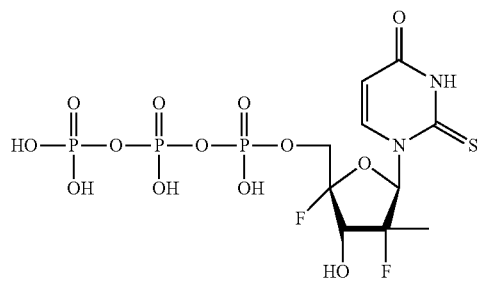
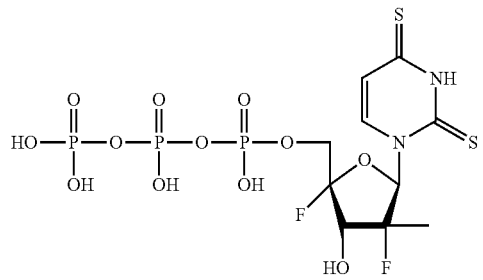
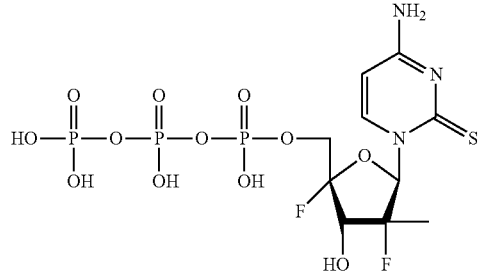
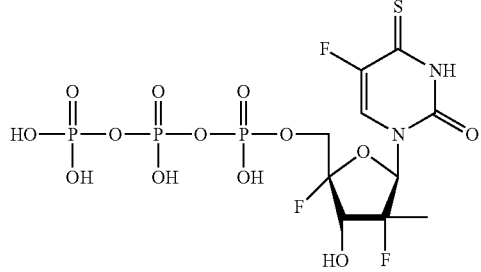
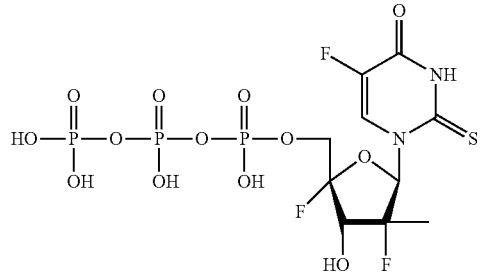
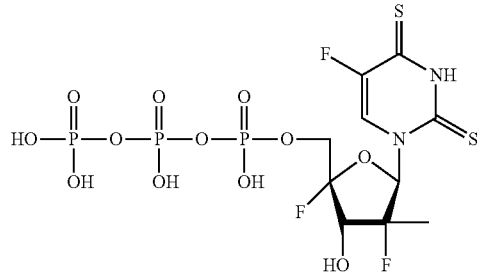
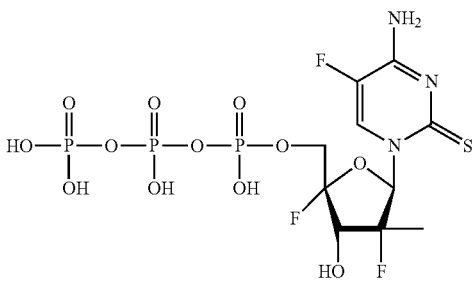
In one embodiment, $R^3$ is H. In another embodiment, $R^4$ is hydroxyl. In a further embodiment, $R^5$ is H. In another embodiment, $R^{10}$ is fluoro. In still another embodiment, $R^6$ is C≡CH. In yet another embodiment, $R^7$ is fluoro. In exemplary embodiments, the compound is selected from the group consisting of:
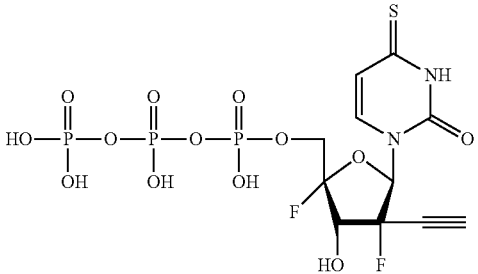
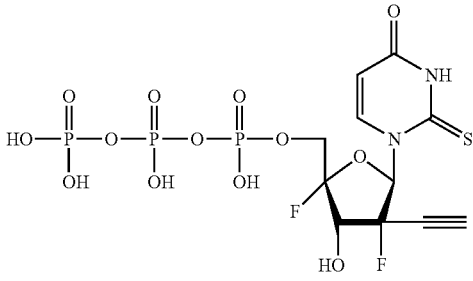
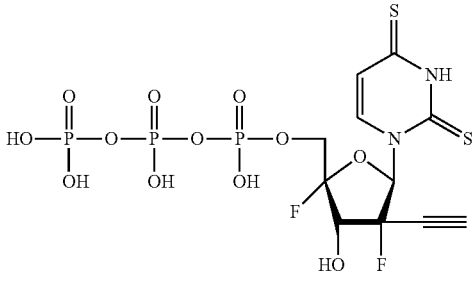
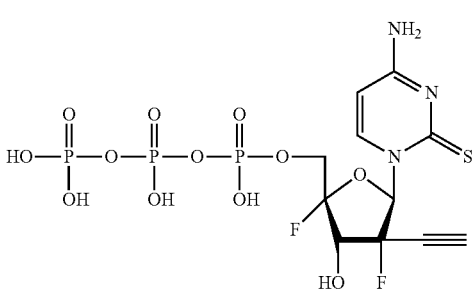

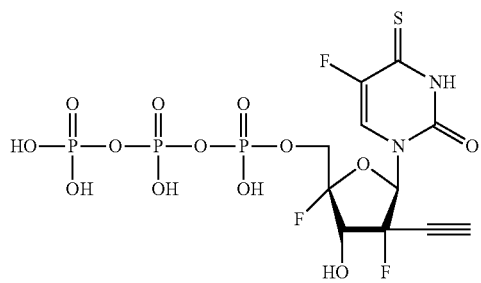
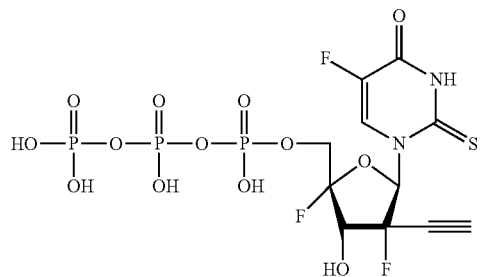
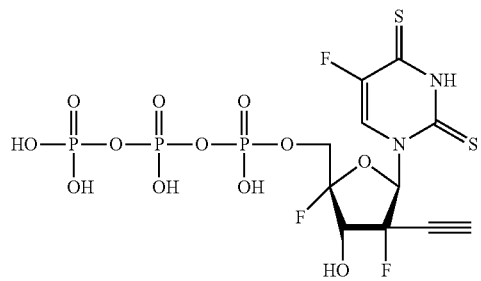
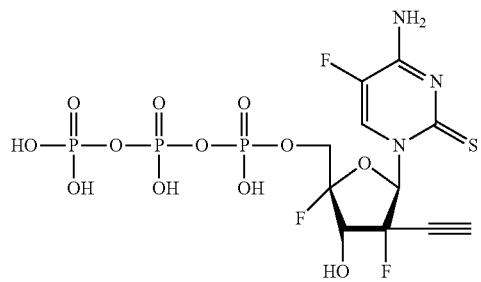
In one embodiment, R³ is H. In another embodiment, R⁴ is hydroxyl. In a further embodiment, R⁵ is H. In another embodiment, R¹⁰ is fluoro. In still another embodiment, R⁶ is CH₂F. In yet another embodiment, R⁷ is fluoro. In exemplary embodiments, the compound is selected from the group consisting of:
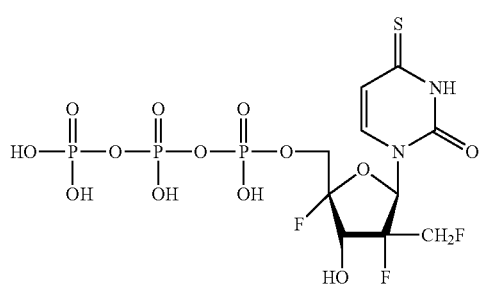

-continued

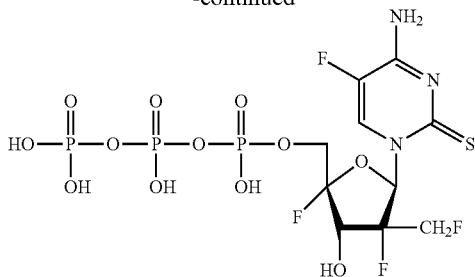

In certain embodiments, the disclosure relates to a compound of the following formula:

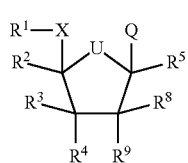

Formula If or pharmaceutically acceptable salts thereof, wherein
U is O or S;
X is O, $CH_2$ or $CD_2$;
$R^5$ is H or D;
$R^2$, $R^3$, $R^4$, $R^8$ and $R^9$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^{19}$;
$R^1$ is one of the formula:

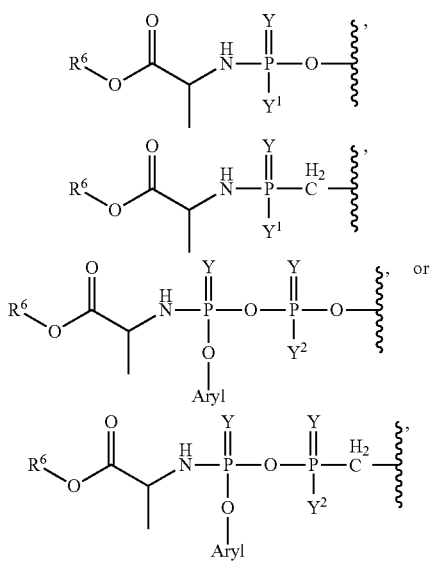

Y is O or S;
$Y^1$ is OAryl or $BH_3^-M^+$;
$Y^2$ is OH or $BH_3^-M^+$;
Aryl is phenyl, 1-naphthyl, 2-naphthyl, aromatic, heteroaromatic, 4-substituted phenyl, 4-chlorophenyl, 4-bromophenyl;
Q is a heterocyclyl comprising two or more nitrogen heteroatoms substituted with at least one thione, thiol or thioether, wherein Q is optionally substituted with one or more, the same or different alkyl, halogen, cycloalkyl;

each $R^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

$R^6$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^6$ is optionally substituted with one or more, the same or different, $R^{10}$.

In preferred embodiments, U is O and Q is a pyrimidine with at least one thione, thiol or thioether at the 2 and/or 4-position of said pyrimidine. In other preferred embodiments, U is S and Q is a pyrimidine with at least one thione, thiol or thioether at the 2 and/or 4 position of said pyrimidine.

In certain embodiment, $R^2$, $R^3$, $R^4$, $R^8$ and $R^9$ are each independently selected from H, D, $CH_3$, $CD_3$, $CF_3$, $CF_2H$, $CFH_2$, $CH_2OH$, $CH_2Cl$, CCH, OH, SH, $NH_2$, $N_3$, CHO, CN, Cl, Br, F or I.

In certain embodiments, the disclosure relates to a compound of the following formulae:

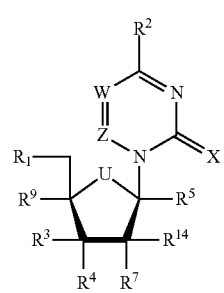

Formula Ig

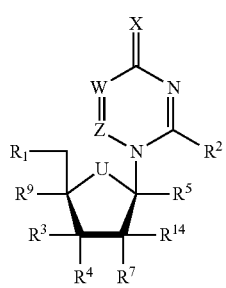

Formula Ih

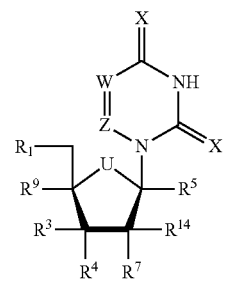

Formula Ii or a pharmaceutically acceptable salt thereof wherein,
U is O or S;
$R^5$ is H or D;

$R^1$ is one of the formula:

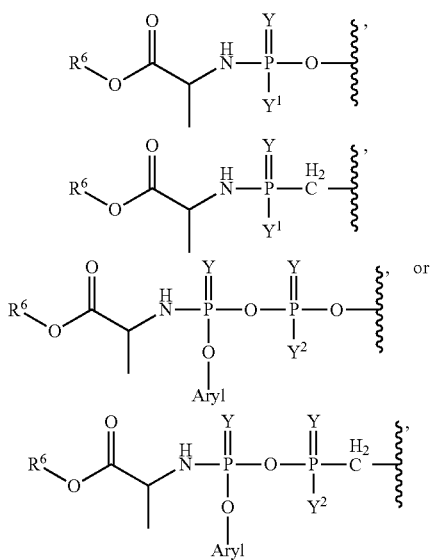

Y is O or S;
$Y^1$ is OAryl or $BH_3^-M^+$
$Y^2$ is OH or $BH_3^-M^+$
each X is independently O, S, NH, $NR^8$, NHOH, $NR^8OH$, $NHOR^8$, or $NR^8OR^8$;
$R^2$ is OH, SH, $NH_2$, $OR^8$, $SR^8$, $NHR^8$, NHOH, $NR^8OH$, $NHOR^8$, or $NR^8OR^8$;
    wherein in Formula Ig and Ih, one of X is S or $R^2$ is $SR^8$, or both X is S and $R^2$ is $SR^8$;
    wherein in Formula Ii, at least one X is S;
    W is CH, N, or $CR^8$;
    Z is CH, N, or $CR^8$;
    $R^3$, $R^4$, $R^7$, $R^9$ and $R^{14}$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^{10}$;
    each $R^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;
    Aryl is phenyl, 1-naphthyl, 2-naphthyl, aromatic, heteroaromatic, 4-substituted phenyl, 4-chlorophenyl, 4-bromophenyl;
    $R^8$ is methyl, trifluoromethyl, fluoro, iodo, alkenyl, alkynyl, vinyl, allyl, halogen, halogentated alkyl, hydroxyl alkyl, acyl, lipid, geranyl, $C_{1-22}$ alkyl optionally substituted with one or more, the same or different, $R^{10}$;
    $R^6$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^6$ is optionally substituted with one or more, the same or different, $R^{10}$.
    In certain embodiments, U is S and Y and Z are CH.
    In other embodiments, U is O and Y and Z are CH.
    In one embodiment, $R^5$ is H. In another embodiment, $R^3$ is H. In still another embodiment, $R^4$ is H. In yet another embodiment, Ie is F and $R^{14}$ is H. In a further embodiment, $R^1$ is

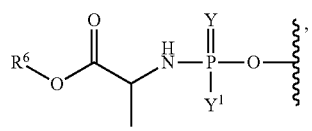

wherein Y is O, $Y^1$ is phenoxy and $R^6$ is iso-propyl.

In exemplary embodiments, the compound is selected from:

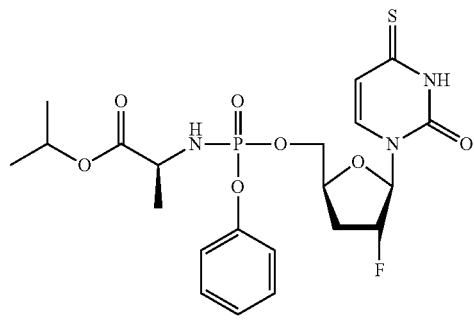

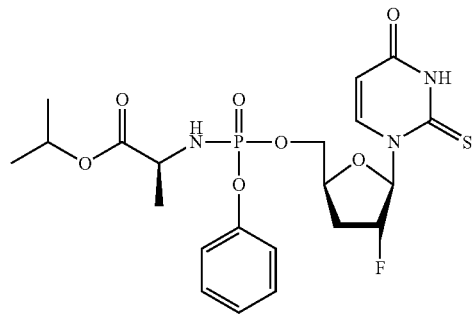

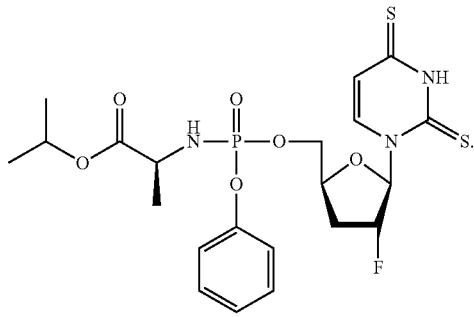

In one embodiment, $R^5$ is H. In another embodiment, $R^3$ is H. In yet another embodiment, $R^4$ is H. In yet another embodiment, $R^7$ is F and $R^{14}$ is methyl. In a further embodiment, $R^1$ is

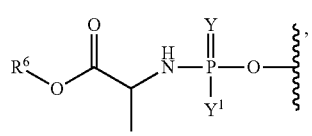

wherein Y is O, $Y^1$ is phenoxy, and $R^6$ is iso-propyl.

In exemplary embodiments, the compound is selected from:

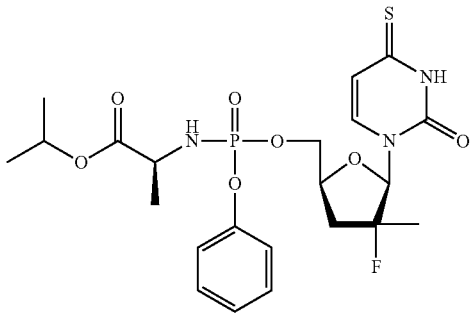

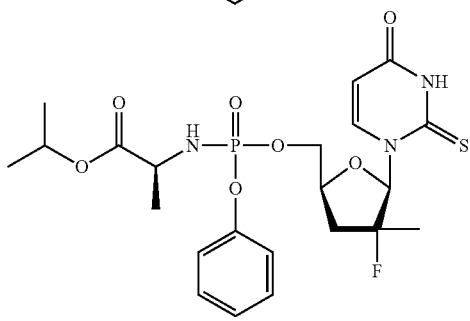

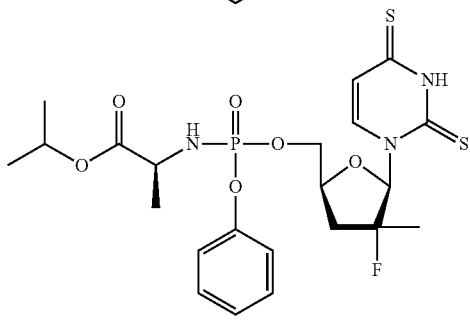

In one embodiment, $R^5$ is H. In another embodiment, $R^3$ is H. In yet another embodiment, $R^4$ is H. In yet another embodiment, $R^7$ is F and $R^{14}$ is trifluoromethyl. In a further embodiment, $R^1$ is

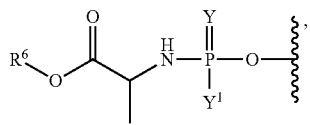

wherein Y is O, $Y^1$ is phenoxy, and $R^6$ is iso-propyl.

In exemplary embodiments, the compound is selected from:

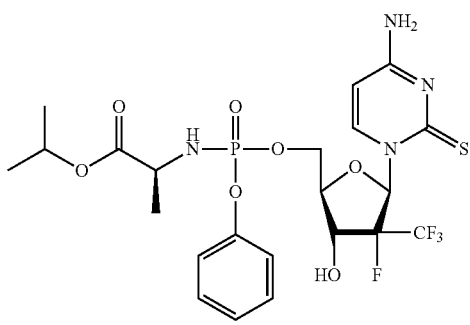

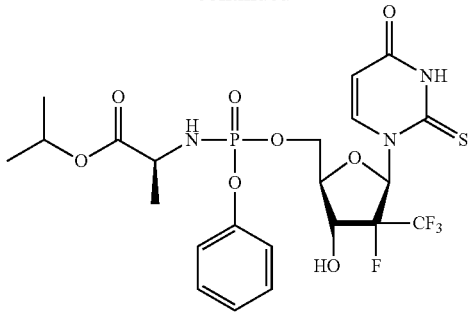

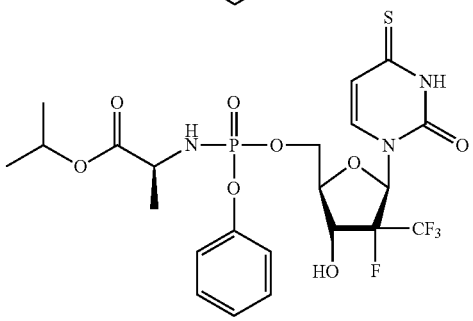

In one embodiment, $R^5$ is H. In another embodiment, $R^3$ is H. In yet another embodiment, $R^4$ is hydroxyl. In yet another embodiment, $R^7$ is F. In another embodiment, $R^{14}$ is trifluoromethyl. In a further embodiment, $R^1$ is

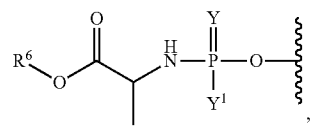

wherein Y is O, $Y^1$ is phenoxy, and $R^6$ is iso-propyl.

In exemplary embodiments, the compound is selected from:

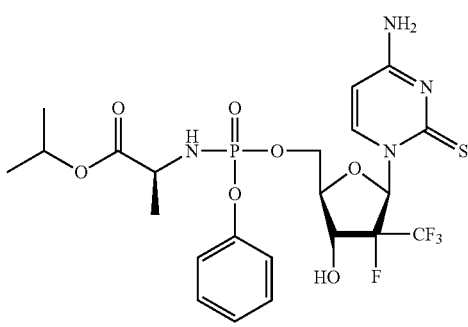

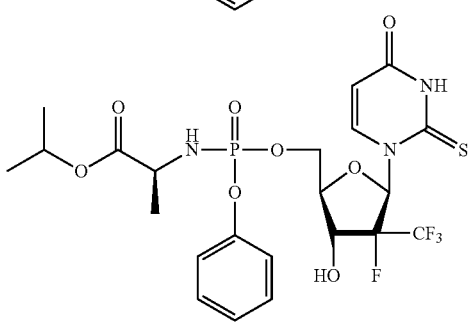

-continued

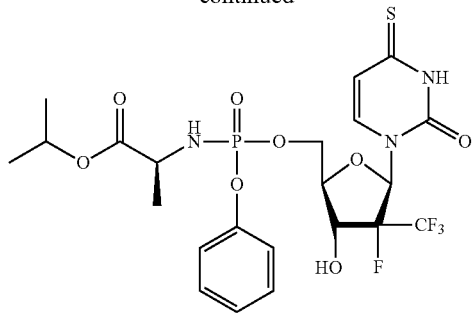

In one embodiment, R⁵ is H. In another embodiment, R³ is H. In yet another embodiment, R⁴ is hydroxyl. In yet another embodiment, R⁷ is F. In another embodiment, R¹⁴ is methyl. In a further embodiment, R¹ is

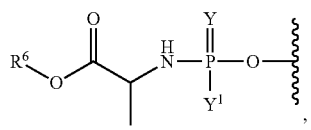

wherein Y is O, Y¹ is phenoxy, and R⁶ is iso-propyl.

In exemplary embodiments, the compound is selected from:

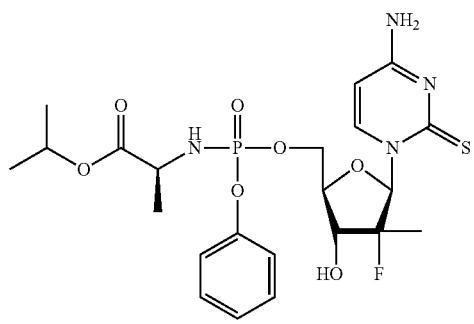

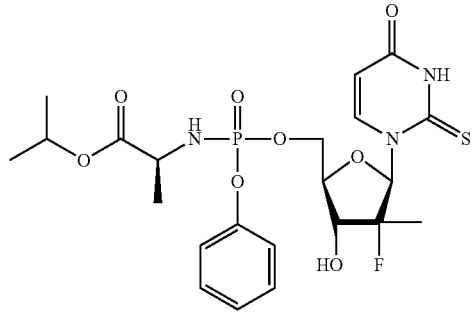

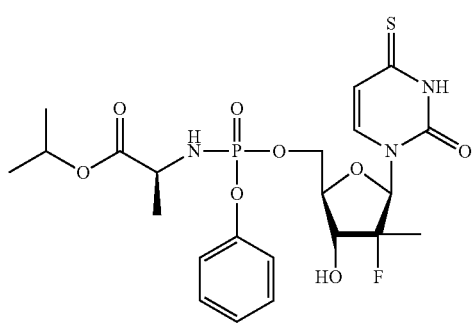

In one embodiment, R⁵ is H. In another embodiment, R³ is H. In yet another embodiment, R⁴ is OH. In yet another embodiment, R⁷ is F and R¹⁴ is ethynyl. In a further embodiment, R¹ is

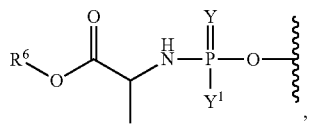

wherein Y is O, Y¹ is phenoxy, and R⁶ is iso-propyl.

In exemplary embodiments, the compound is selected from:

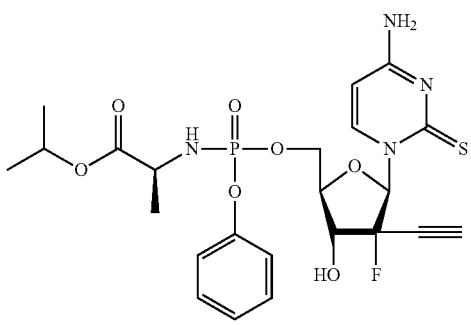

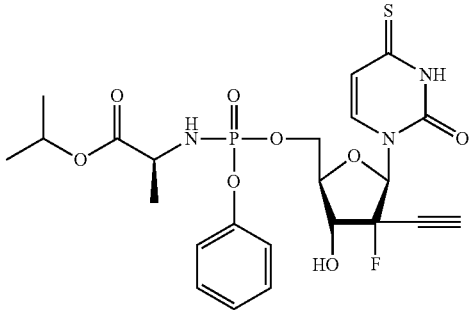

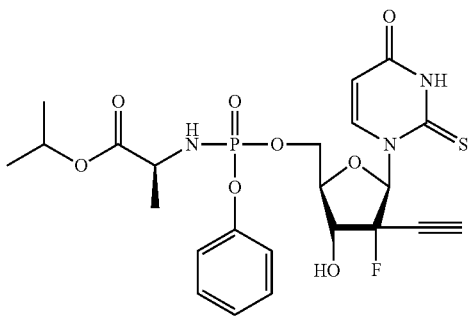

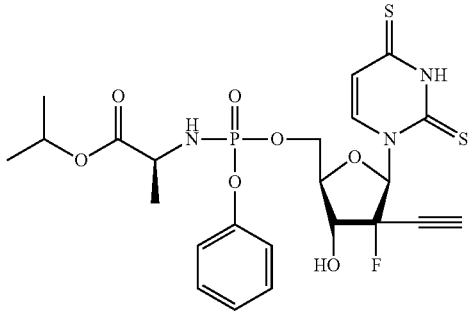

In one embodiment, R⁵ is H. In another embodiment, R³ is H. In yet another embodiment, R⁴ is OH. In yet another embodiment, $R^7$ is F and $R^{14}$ is monofluoromethyl. In a further embodiment, $R^1$ is

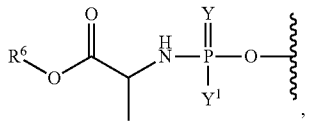

wherein Y is O, $Y^1$ is phenoxy, and $R^6$ is iso-propyl.

In exemplary embodiments, the compound is selected from:

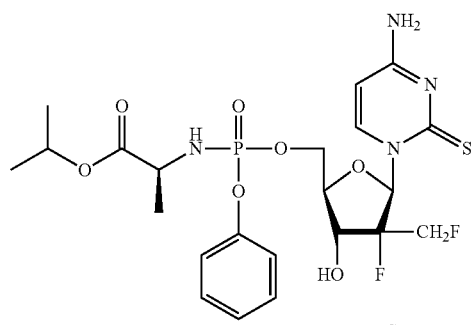

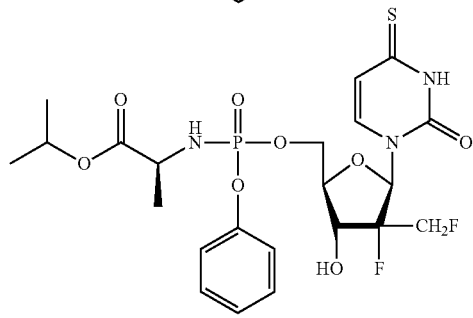

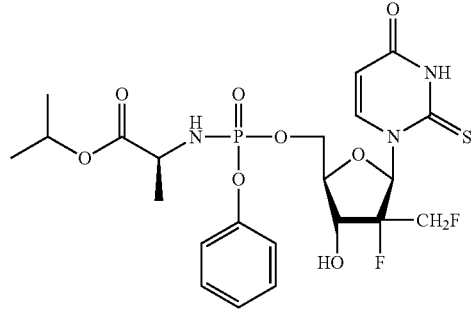

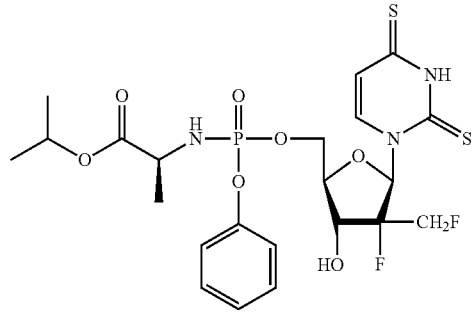

another embodiment, $R^7$ is H. In another embodiment, $R^{14}$ is methyl. In a further embodiment, $R^1$ is

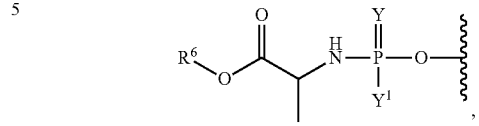

wherein Y is O, $Y^1$ is phenoxy, and $R^6$ is iso-propyl.

In exemplary embodiments, the compound is selected from:

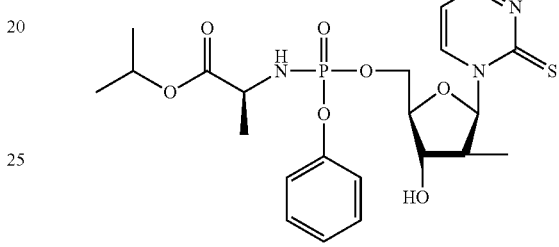

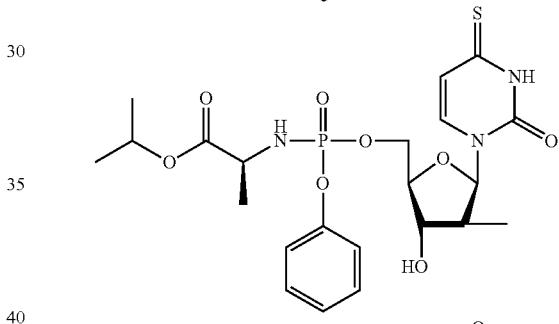

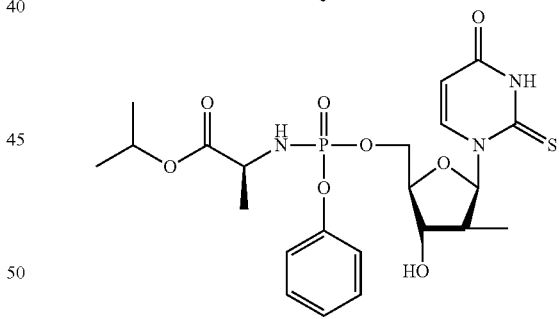

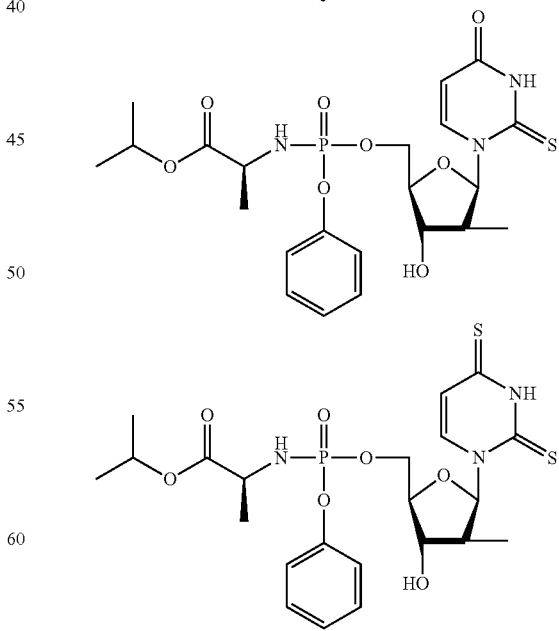

In one embodiment, $R^5$ is H. In another embodiment, $R^3$ is H. In yet another embodiment, $R^4$ is hydroxyl. In yet In one embodiment, $R^5$ is H. In another embodiment, $R^3$ is H. In yet another embodiment, $R^4$ is OH. In yet another embodiment, $R^7$ is H and $R^{14}$ is trifluoromethyl. In a further embodiment, $R^1$ is

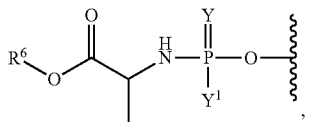

wherein Y is O, $Y^1$ is phenoxy, and $R^6$ is iso-propyl.

In exemplary embodiments, the compound is selected from:

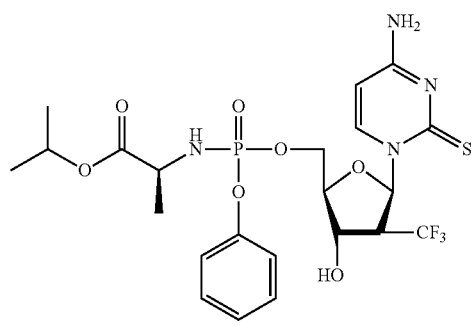

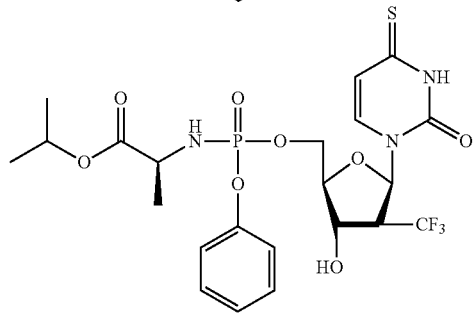

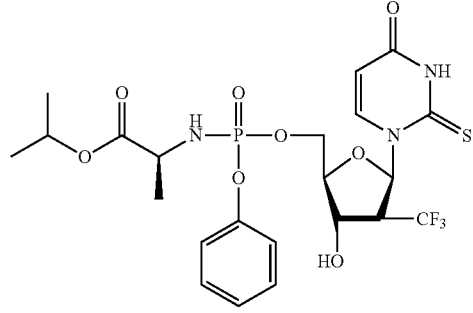

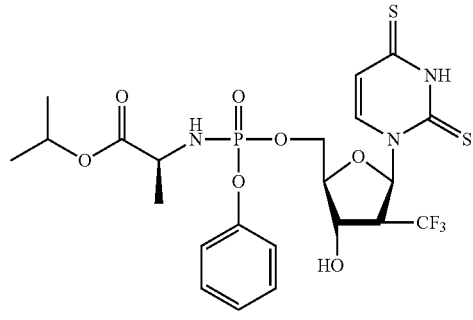

In one embodiment, $R^5$ is H. In another embodiment, $R^3$ is H. In yet another embodiment, $R^4$ is hydroxyl. In yet another embodiment, $R^7$ is hydroxyl. In another embodiment, $R^{14}$ is trifluoromethyl. In a further embodiment, $R^1$ is

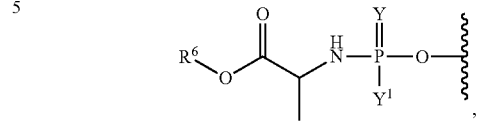

wherein Y is O, $Y^1$ is phenoxy, and $R^6$ is iso-propyl.

In exemplary embodiments, the compound is selected from:

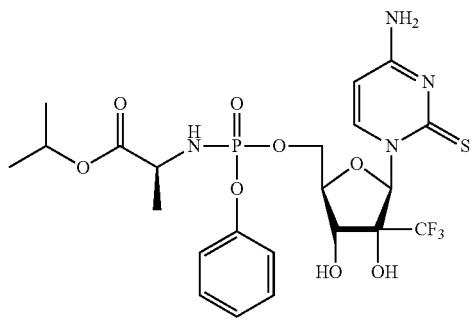

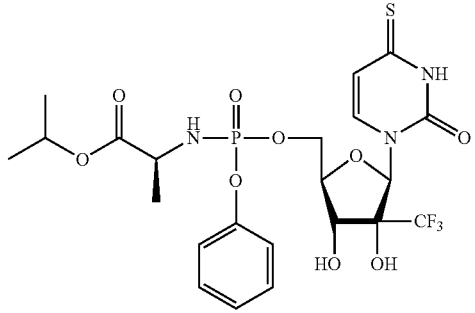

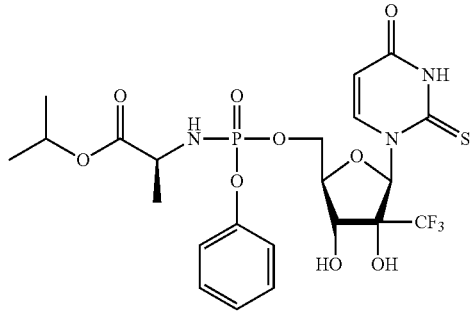

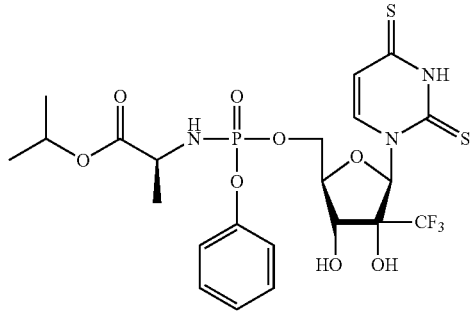

In one embodiment, $R^5$ is H. In another embodiment, $R^3$ is H. In yet another embodiment, $R^4$ is hydroxyl. In yet another embodiment, R⁷ is hydroxyl. In another embodiment, R¹⁴ is methyl. In a further embodiment, R¹ is

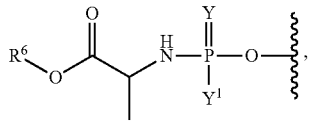

wherein Y is O, Y¹ is phenoxy, and R⁶ is iso-propyl.

In exemplary embodiments, the compound is selected from:

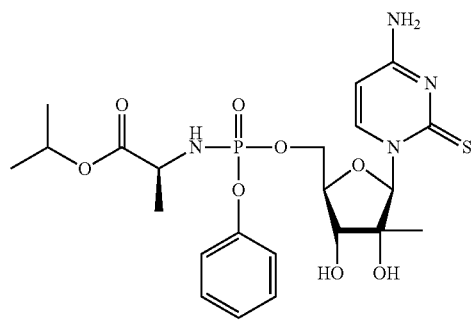

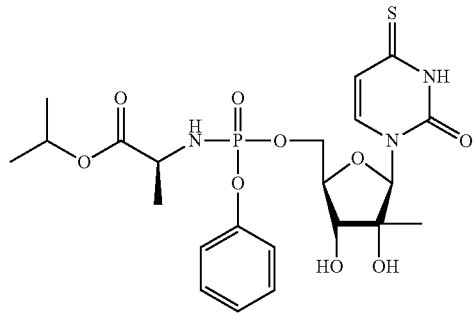

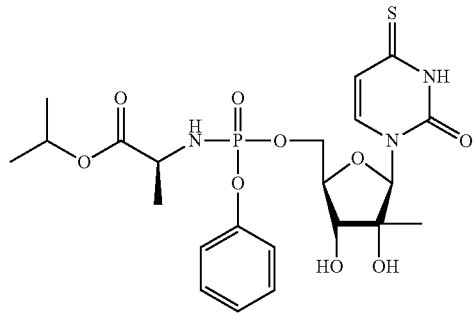

In one embodiment, R⁵ is H. In another embodiment, R³ is H. In yet another embodiment, R⁴ is hydroxyl. In yet another embodiment, R⁷ is hydroxyl. In another embodiment, R¹⁴ is methyl. In a further embodiment, R¹ is

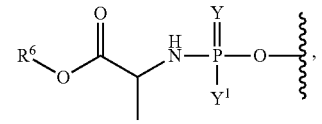

wherein Y is O.

In exemplary embodiments, the compound is selected from:

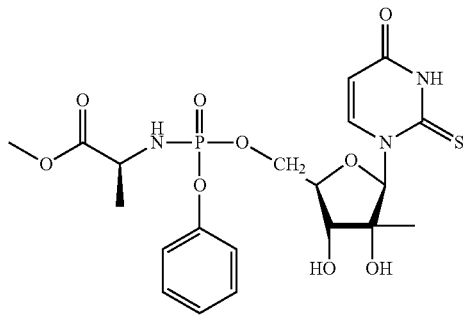

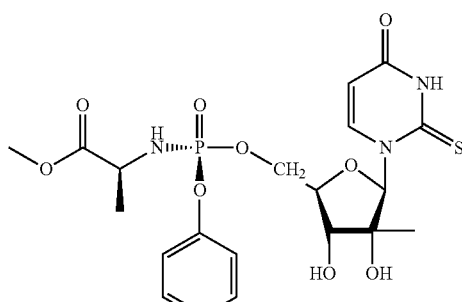

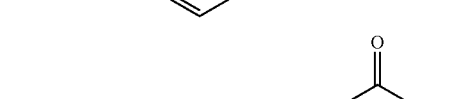

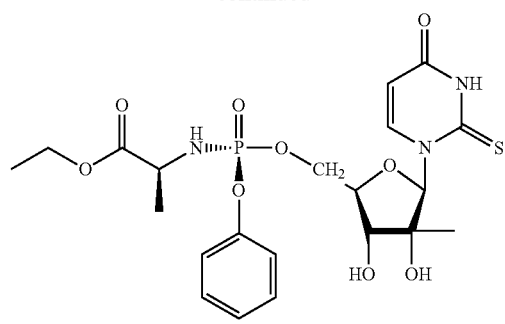
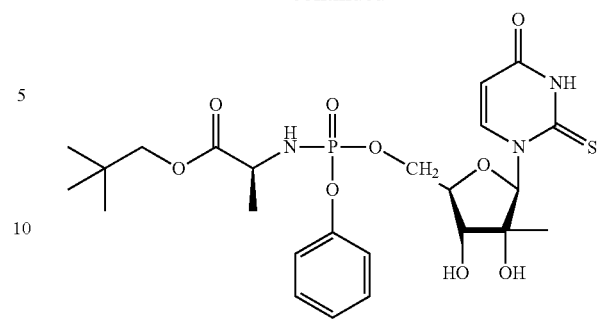
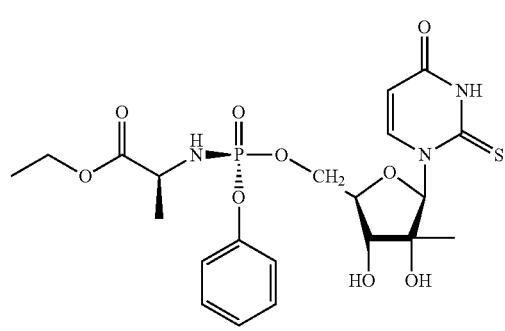
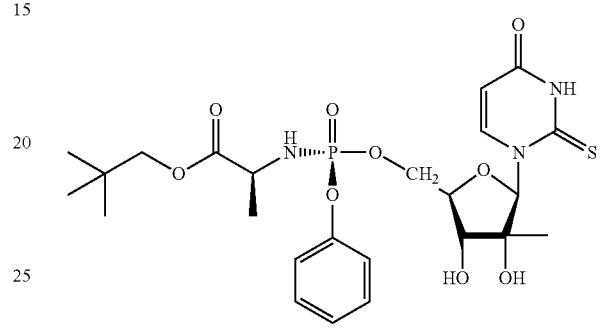
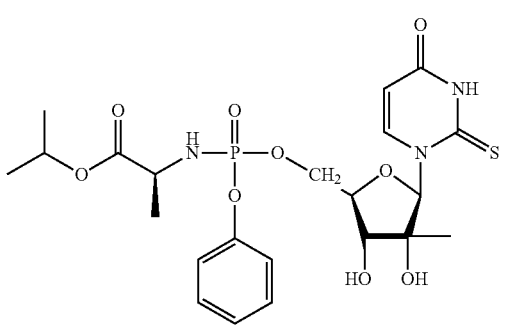
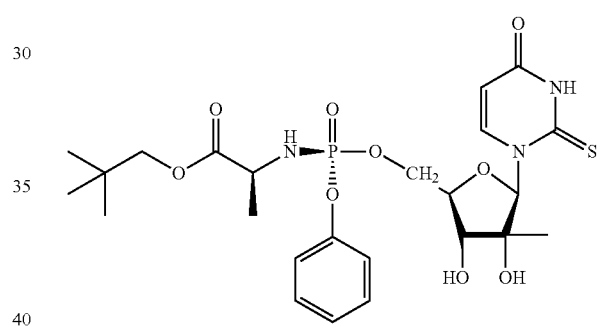
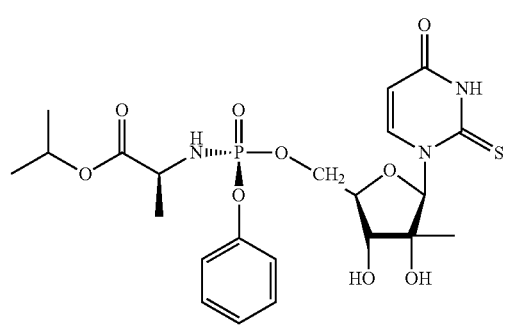
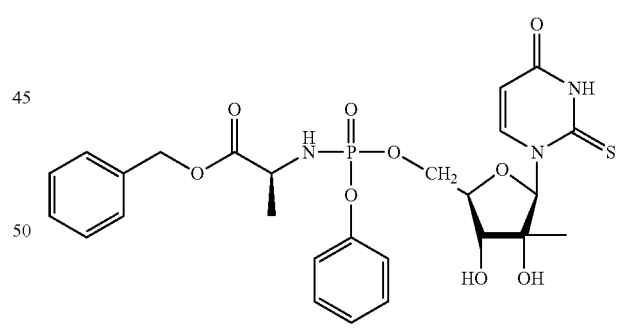
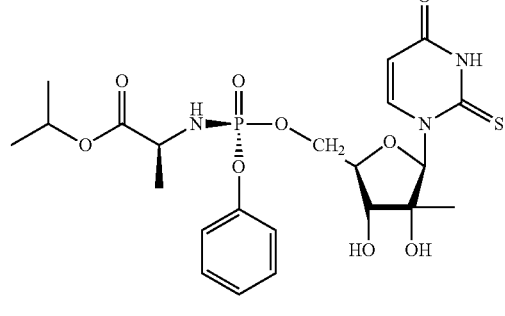
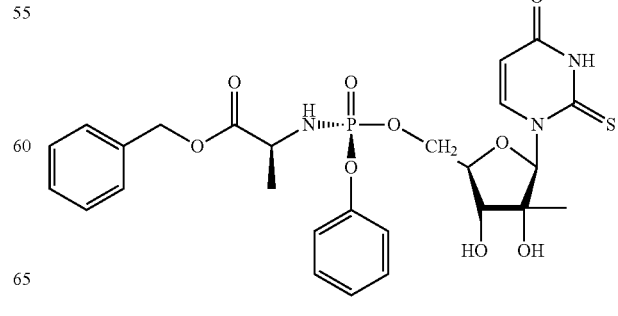

79
-continued
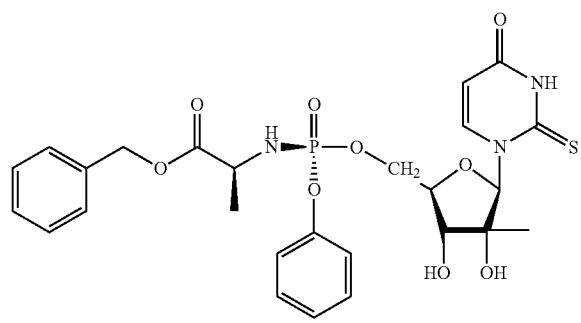
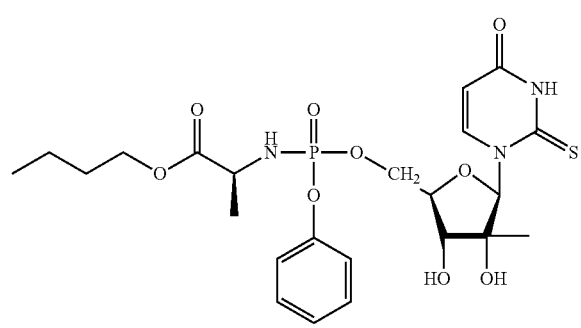
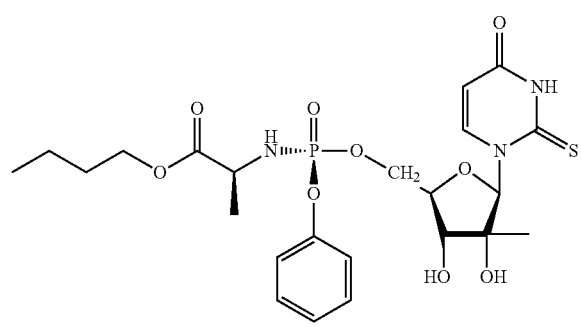
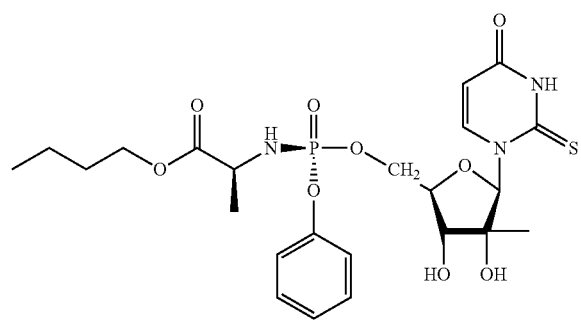
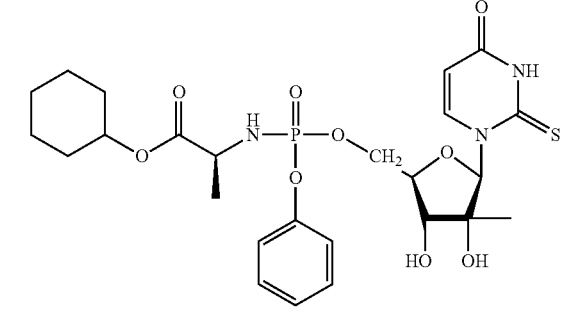
80
-continued
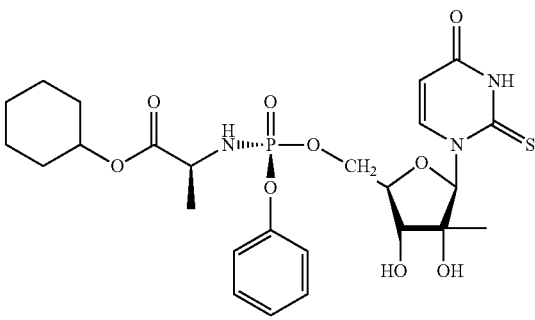
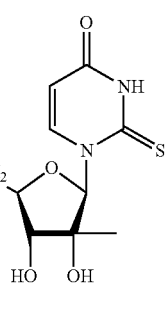
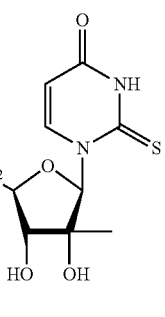
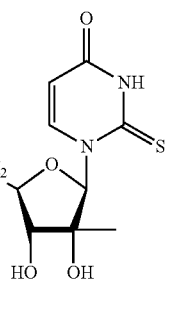
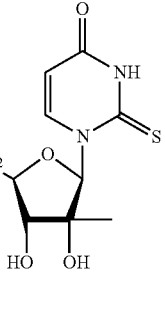

81
-continued
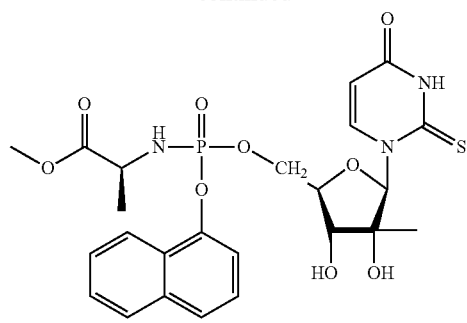
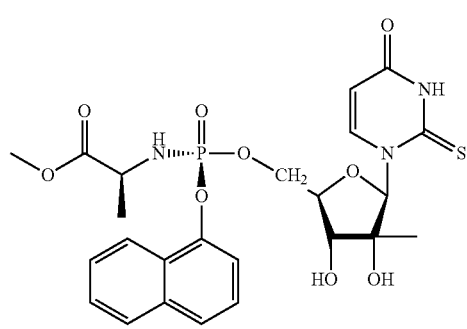
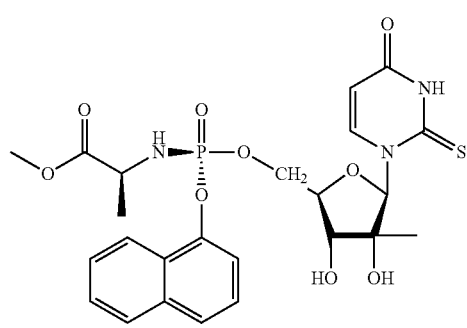
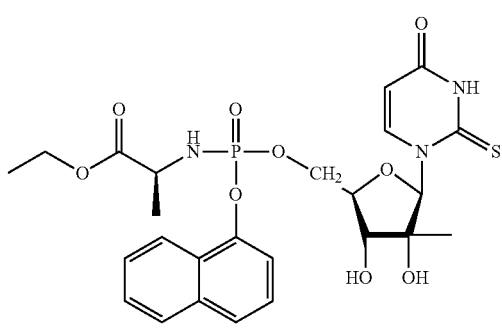
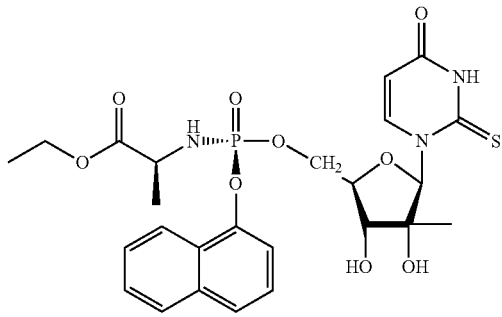
82
-continued
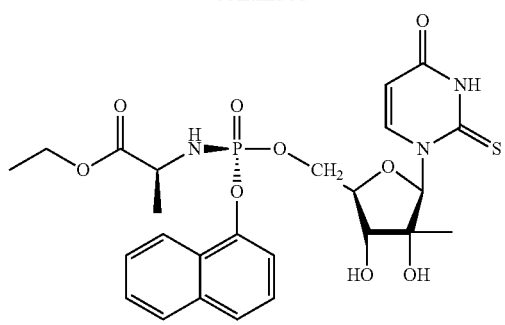
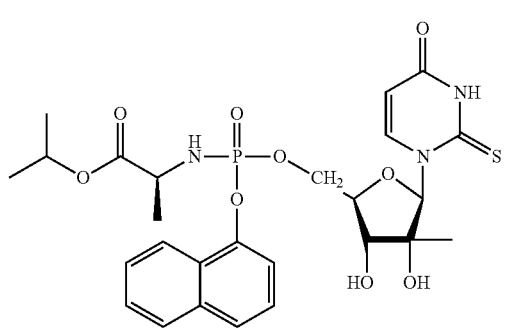
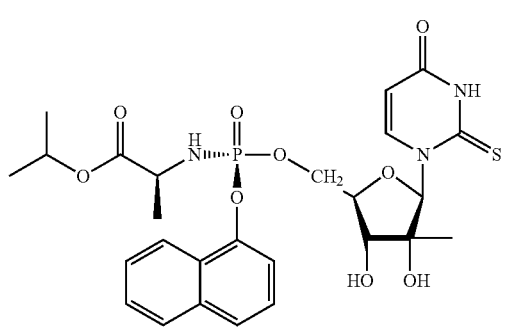
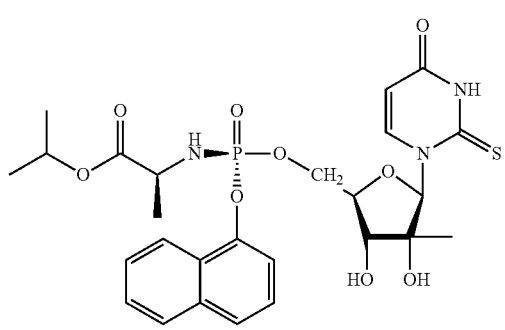
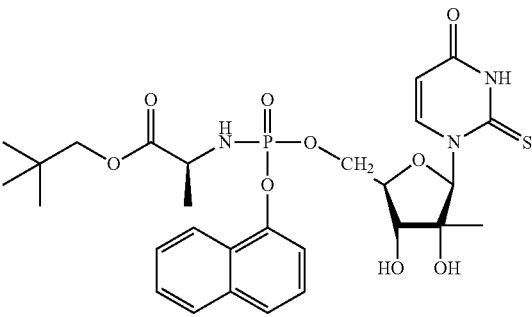

83
-continued
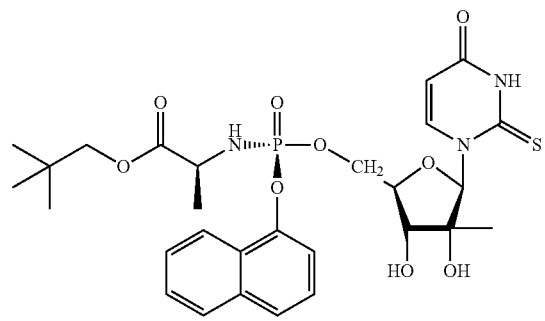
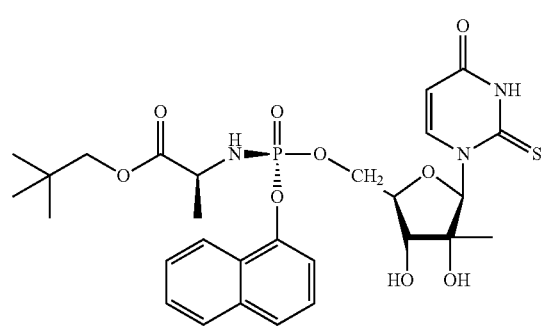
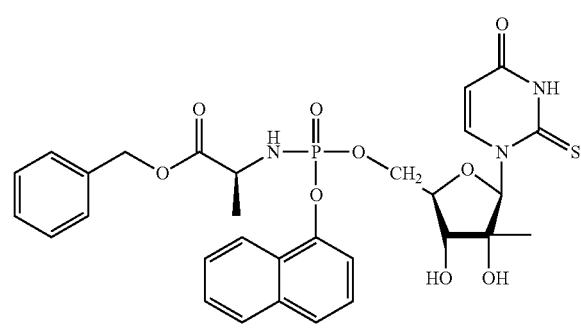
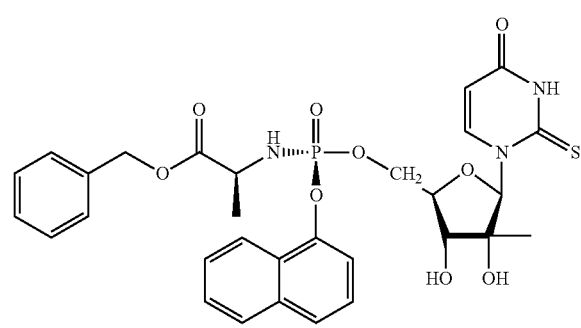
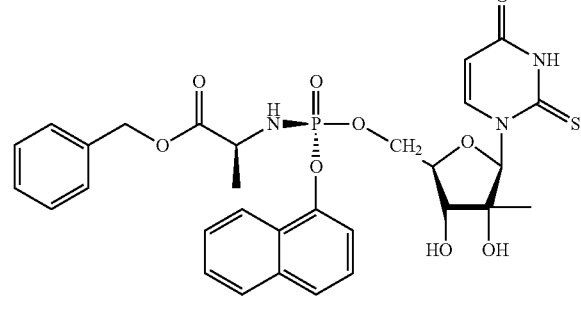
84
-continued
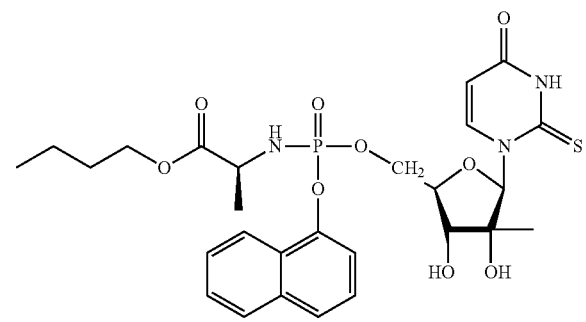
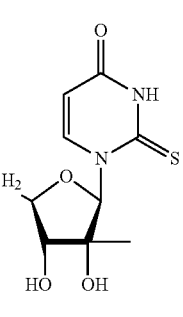
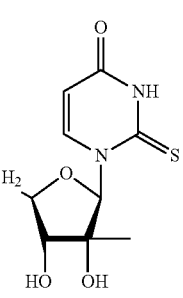
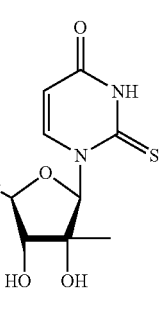
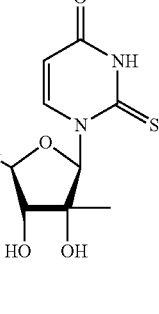

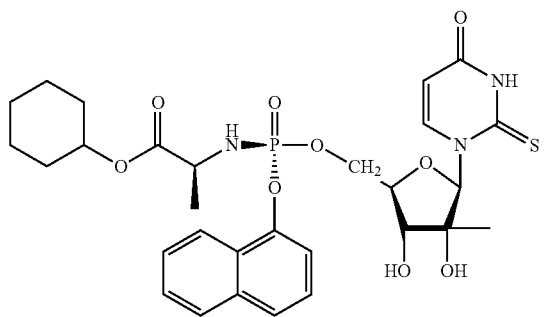
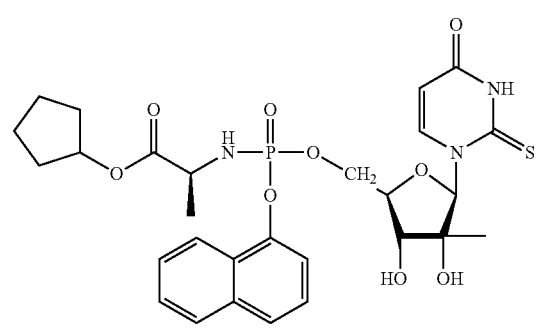
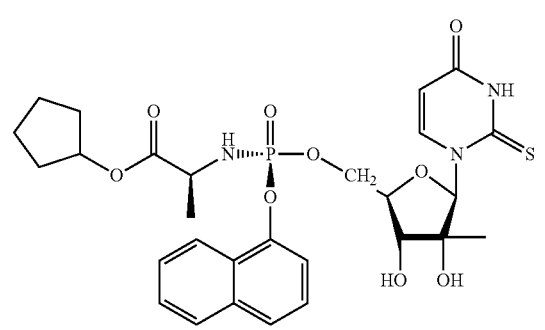
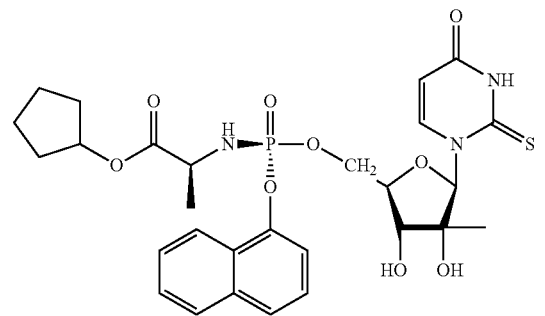
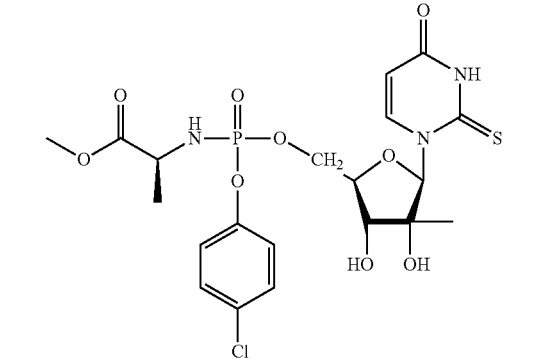
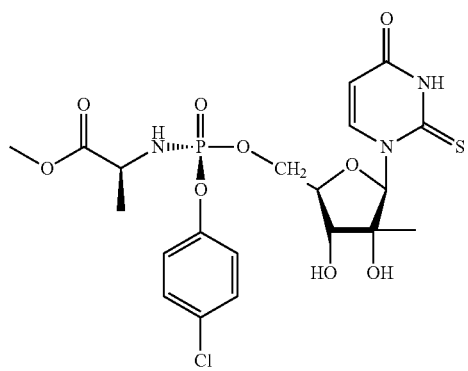
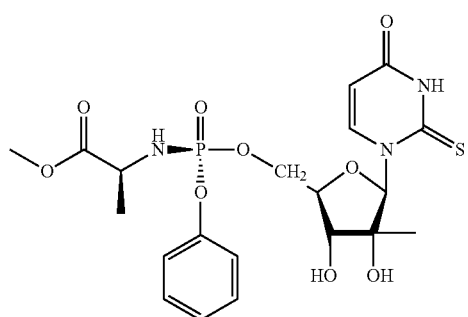
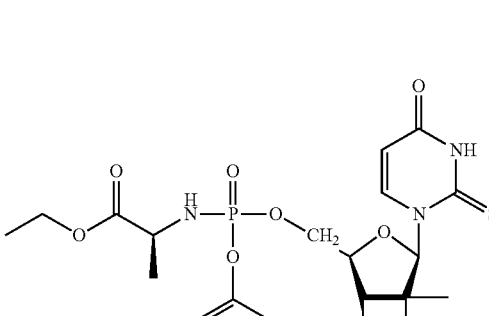
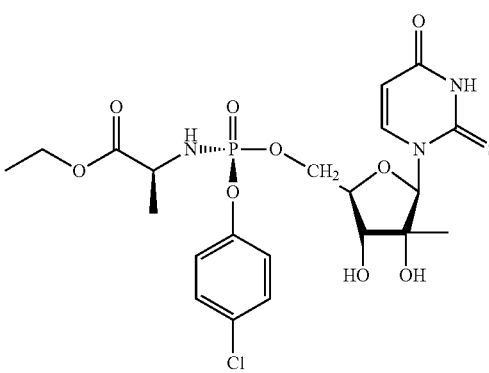

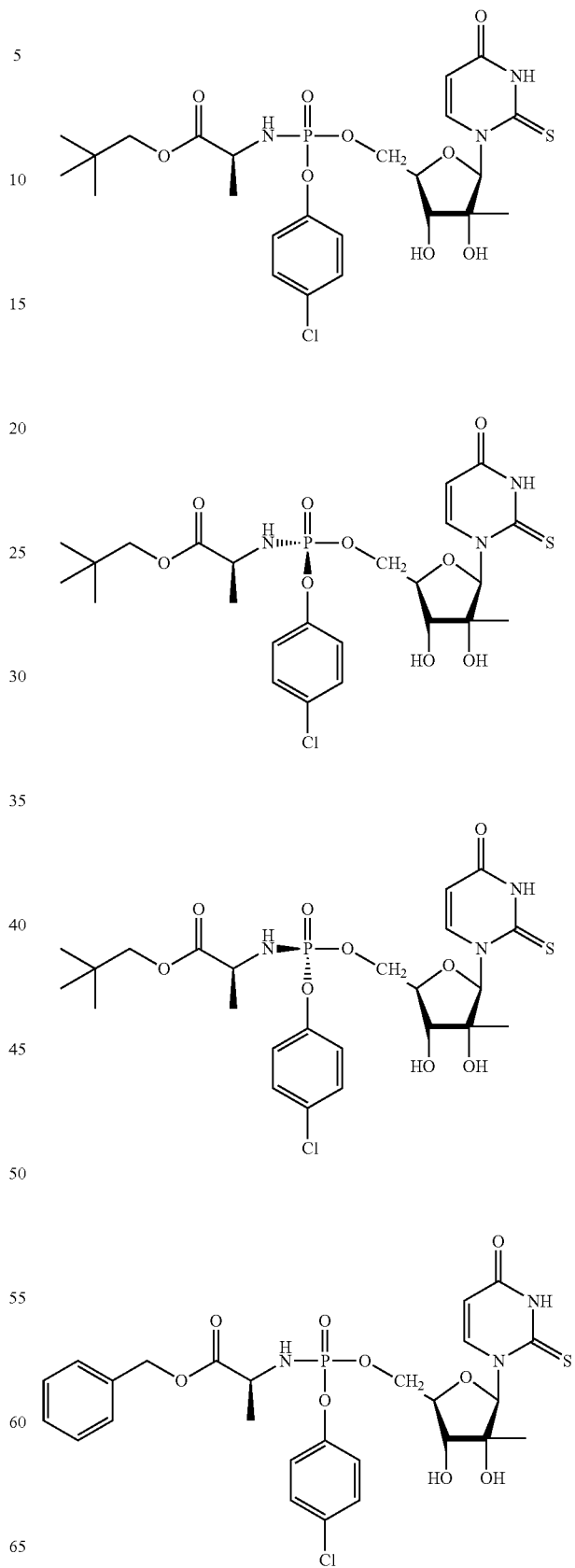

89
-continued
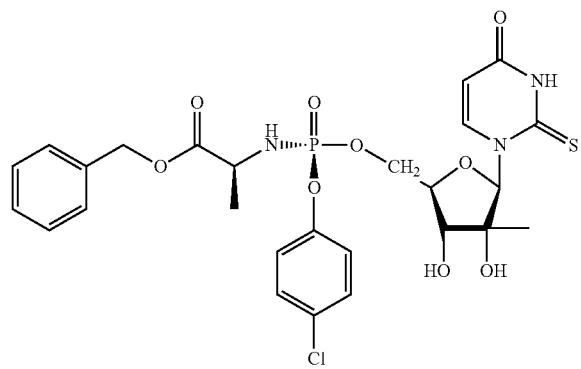
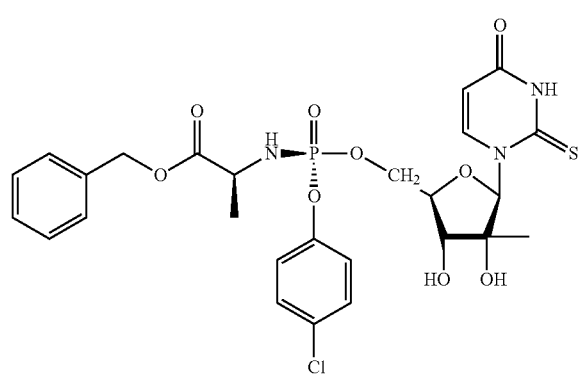
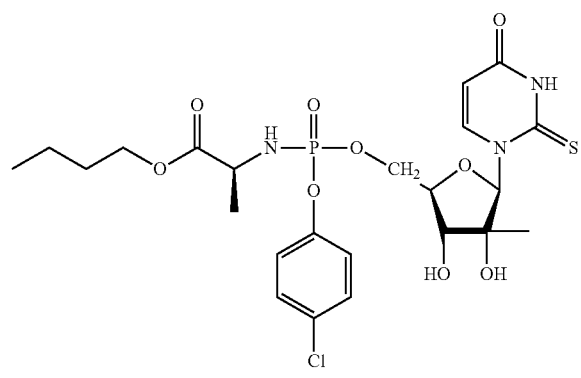
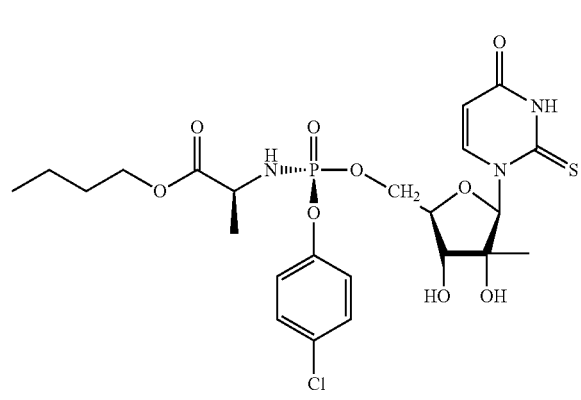
90
-continued
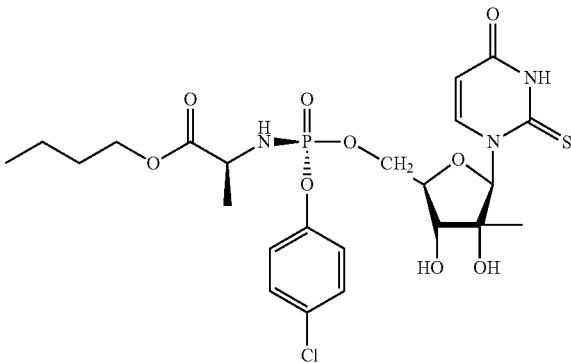
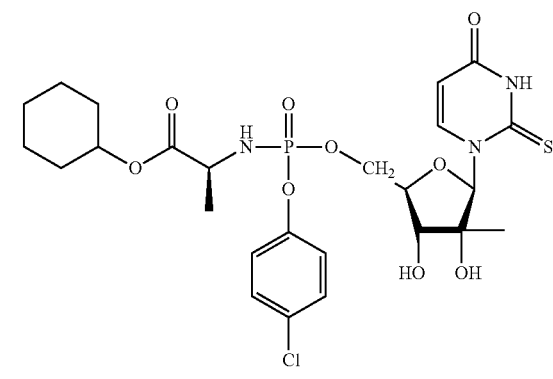
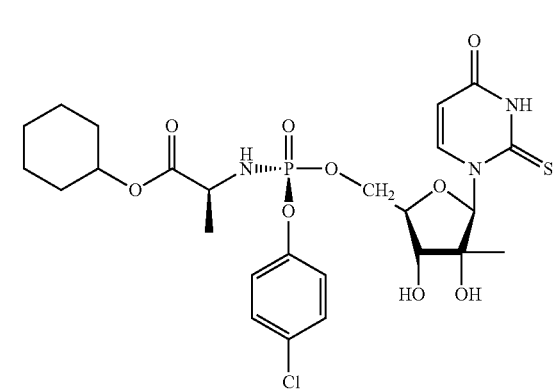
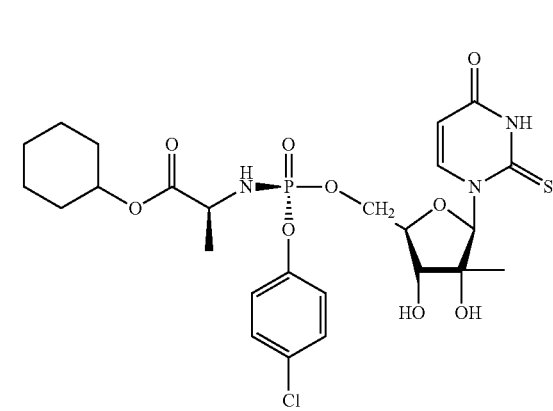

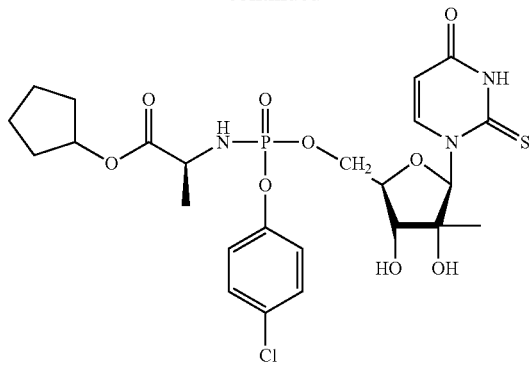

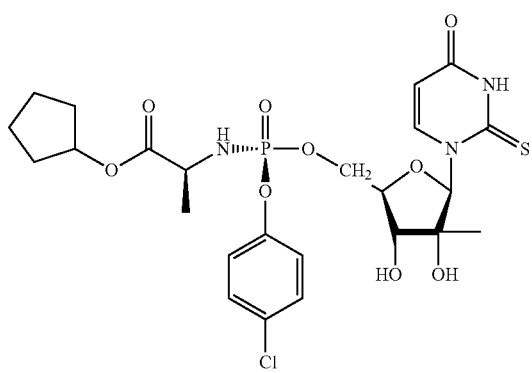

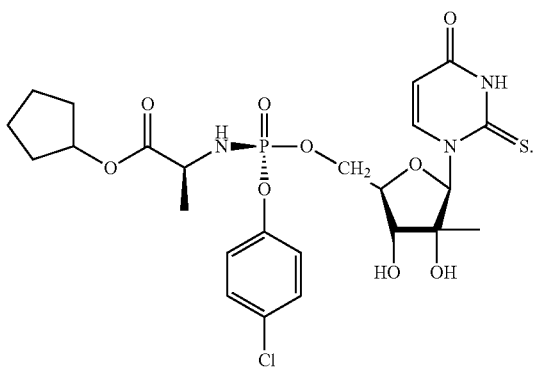

In a more preferred embodiment, a compound of the present invention is selected from one or more of the following:

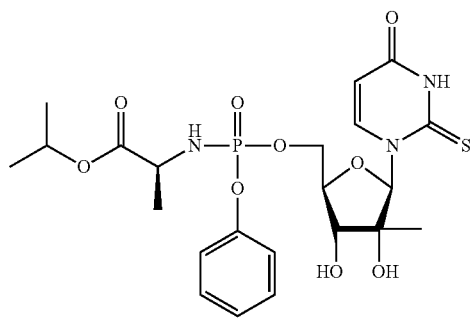

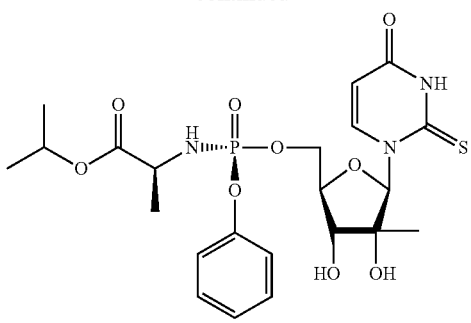

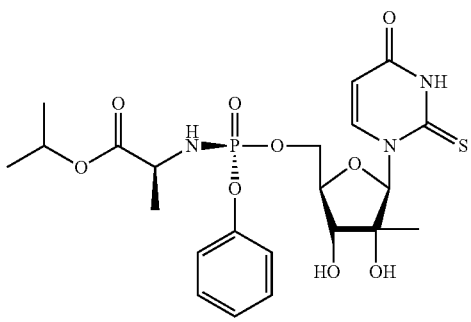

In one embodiment, $R^5$ is H. In another embodiment, $R^3$ is H. In yet another embodiment, $R^4$ is hydroxyl. In yet another embodiment, $R^7$ is hydroxyl. In another embodiment, $R^{14}$ is ethynyl. In a further embodiment, $R^1$ is

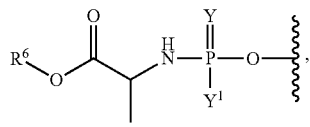

wherein Y is O, $Y^1$ is phenoxy, and $R^6$ is iso-propyl.

In exemplary embodiments, the compound is selected from:

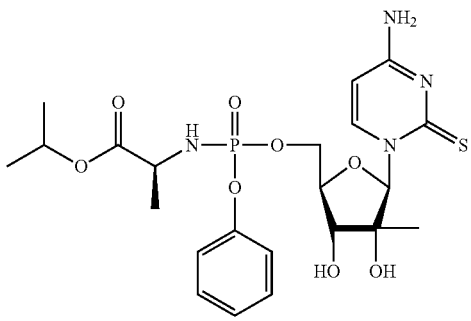

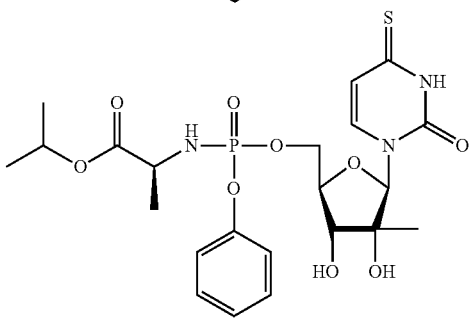

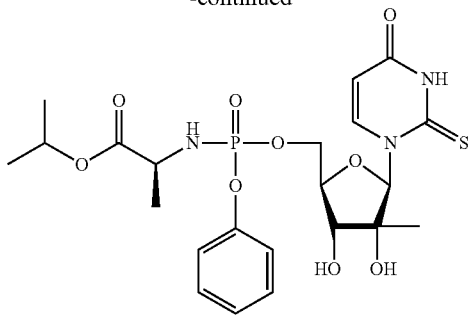

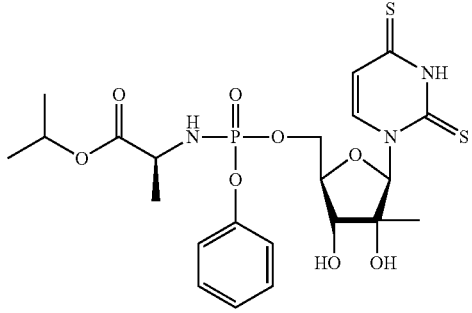

In one embodiment, $R^5$ is H. In another embodiment, $R^3$ is H. In yet another embodiment, $R^4$ is hydroxyl. In yet another embodiment, $R^7$ is hydroxyl. In another embodiment, $R^{14}$ is monofluoromethyl. In a further embodiment, $R^1$ is

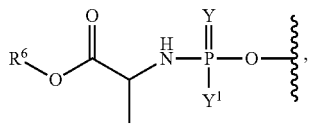

wherein Y is O, $Y^1$ is phenoxy, and $R^6$ is iso-propyl.

In exemplary embodiments, the compound is selected from:

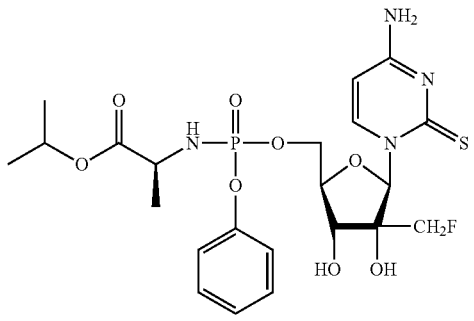

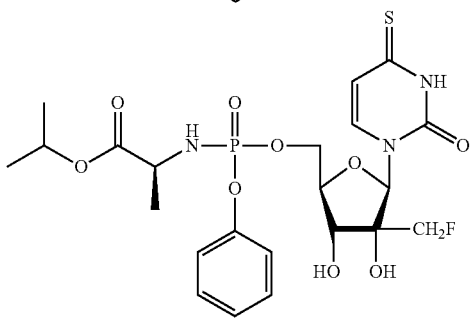

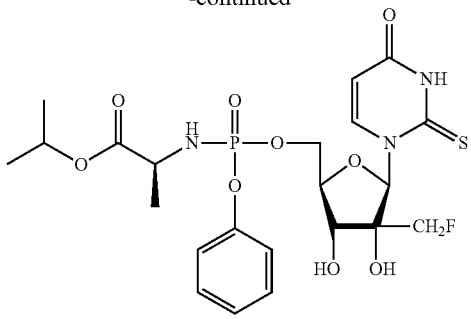

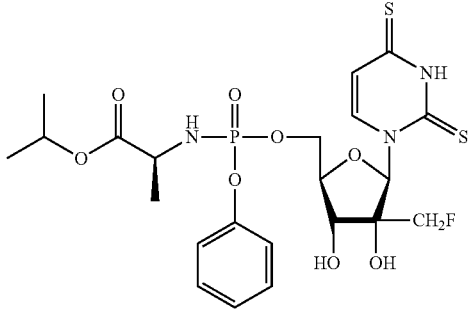

In one embodiment, $R^5$ is H. In another embodiment, $R^3$ is H. In yet another embodiment, $R^4$ is fluoro. In yet another embodiment, $R^7$ is hydroxyl. In another embodiment, $R^{14}$ is H. In a further embodiment, $R^1$ is

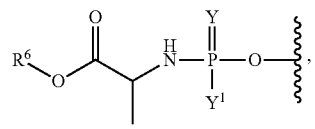

wherein Y is O, $Y^1$ is phenoxy, and $R^6$ is iso-propyl.

In exemplary embodiments, the compound is selected from:

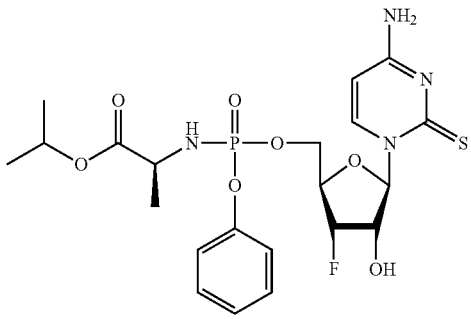

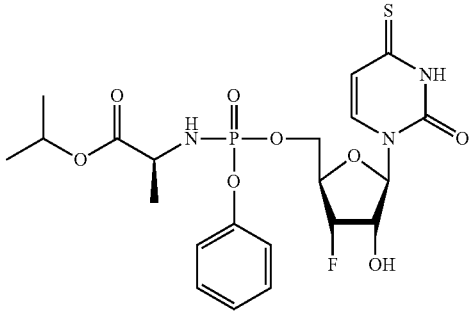

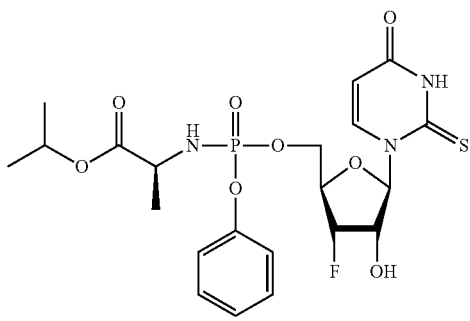

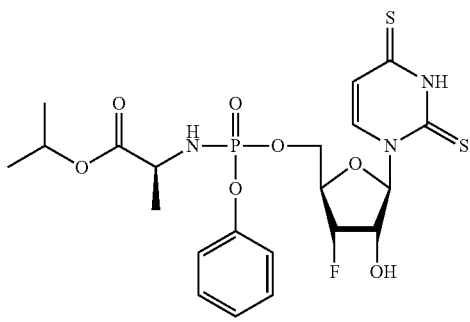

In one embodiment, $R^5$ is H. In another embodiment, $R^3$ is H. In yet another embodiment, $R^4$ is fluoro. In yet another embodiment, $R^7$ is hydroxyl. In another embodiment, $R^{14}$ is methyl. In a further embodiment, $R^1$ is

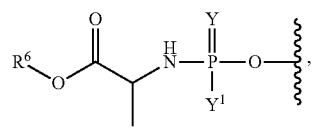

wherein Y is O, $Y^1$ is phenoxy, and $R^6$ is iso-propyl.

In exemplary embodiments, the compound is selected from:

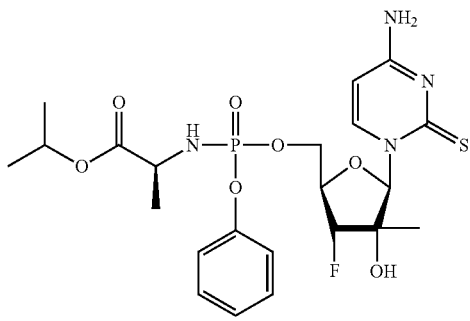

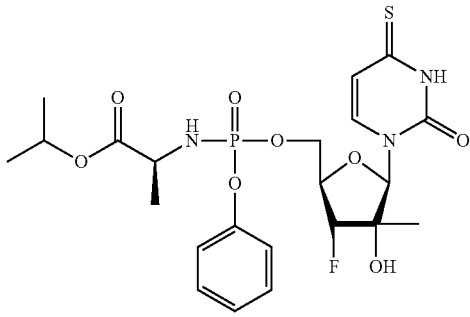

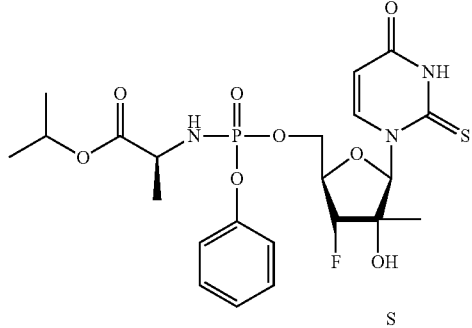

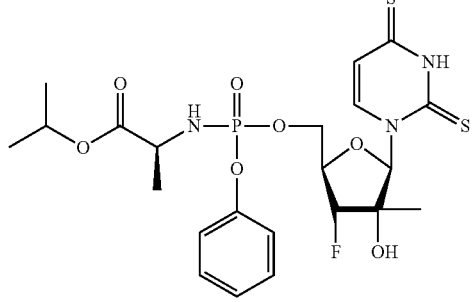

In one embodiment, $R^5$ is H. In another embodiment, $R^3$ is H. In yet another embodiment, $R^4$ is fluoro. In yet another embodiment, $R^7$ is hydroxyl. In another embodiment, $R^{14}$ is ethynyl. In a further embodiment, $R^1$ is wherein Y is O, $Y^1$ is phenoxy, and $R^6$ is iso-propyl.

In exemplary embodiments, the compound is selected from:

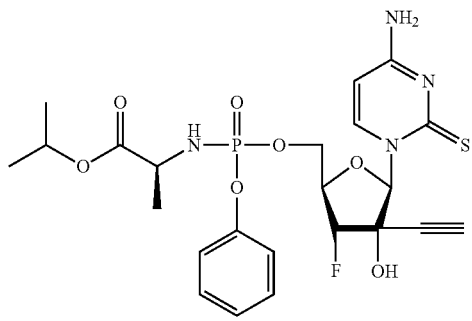

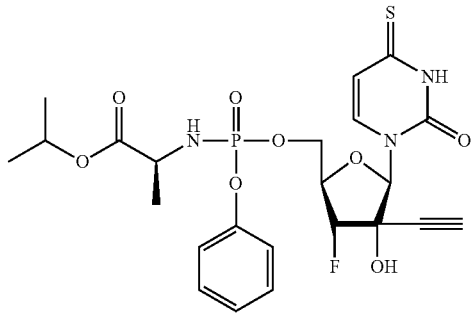

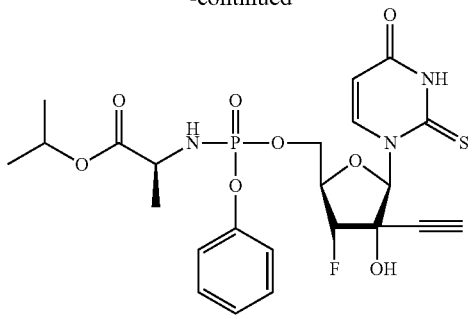

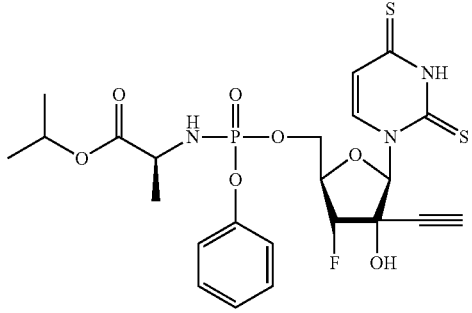

In one embodiment, R⁵ is H. In another embodiment, R³ is H. In yet another embodiment, R⁴ is fluoro. In yet another embodiment, R⁷ is hydroxyl. In another embodiment, R¹⁴ is monofluoromethyl. In a further embodiment, R¹ is

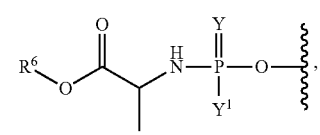

wherein Y is O, Y¹ is phenoxy, and R⁶ is iso-propyl.

In exemplary embodiments, the compound is selected from:

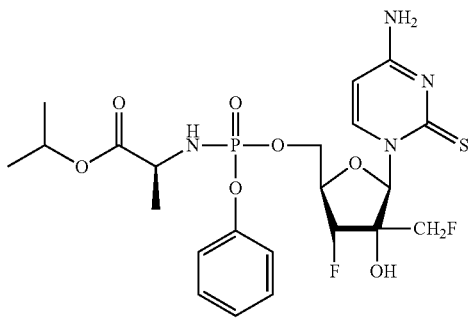

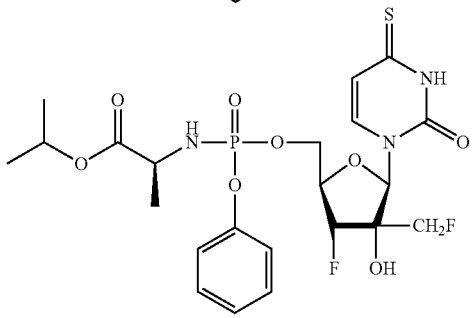

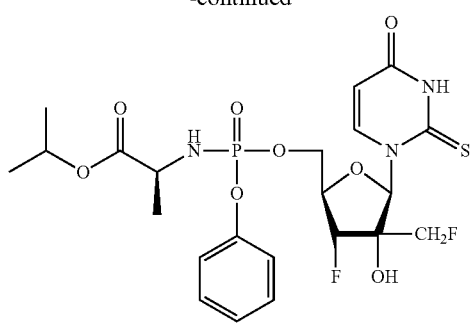

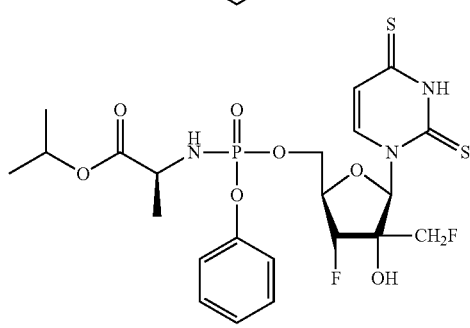

In exemplary embodiments, the compound is selected from:

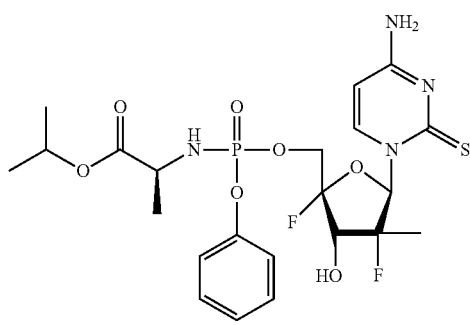

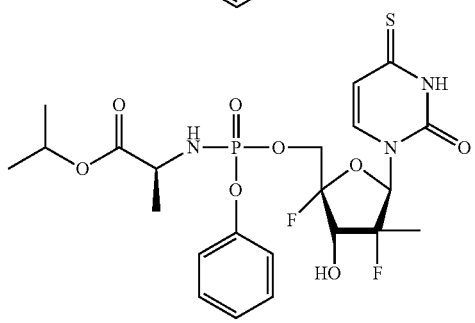

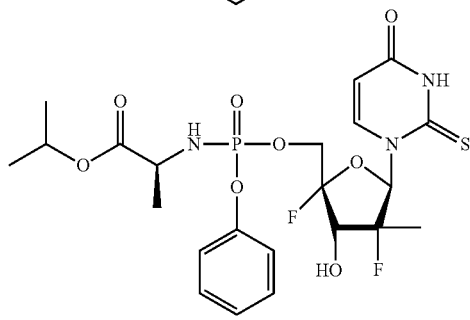

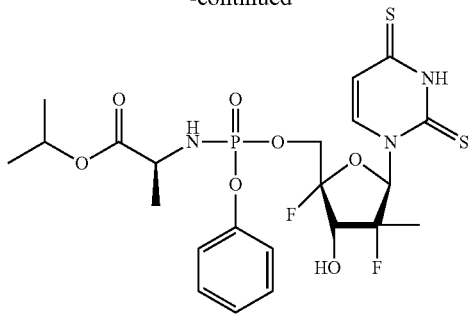
In exemplary embodiments, the compound is selected from:
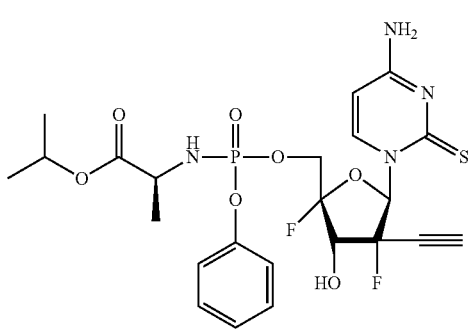
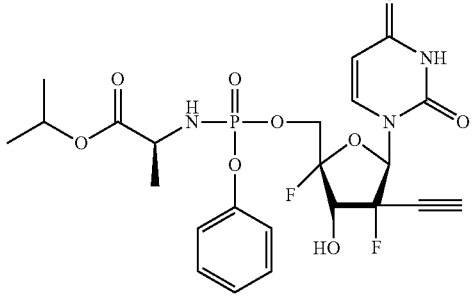
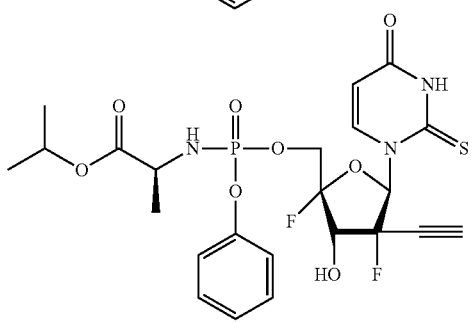
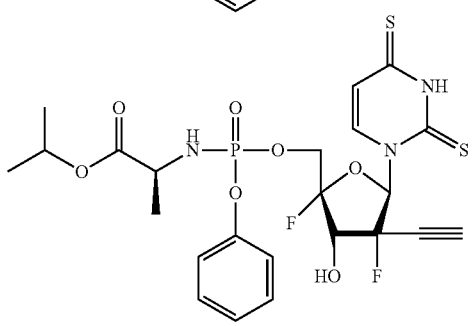
In exemplary embodiments, the compound is selected from:
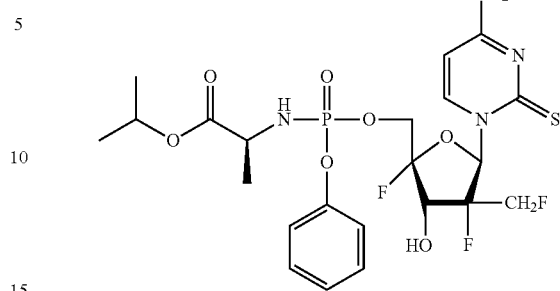
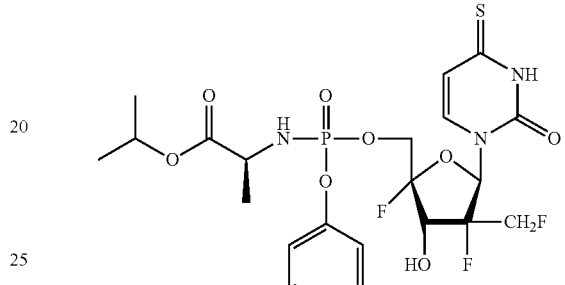
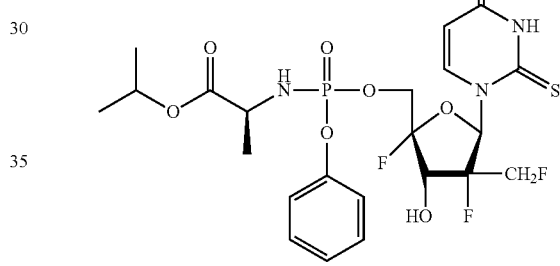
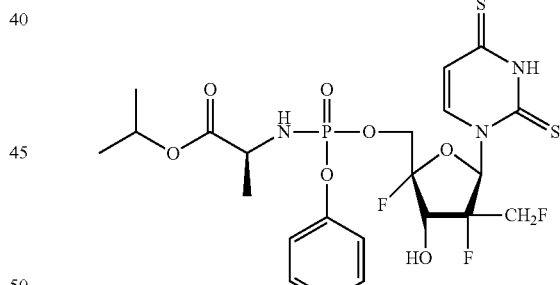
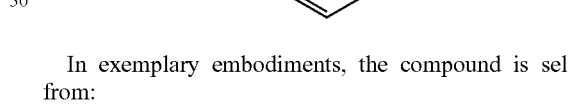
In exemplary embodiments, the compound is selected from:
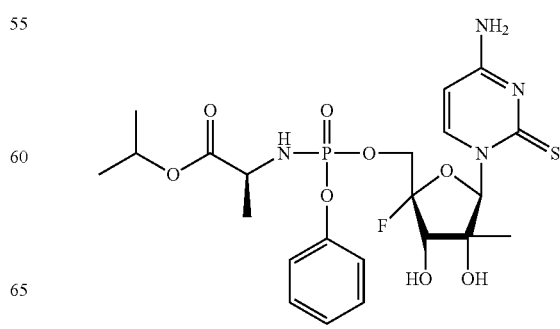

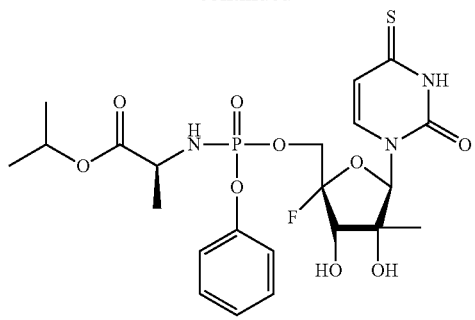
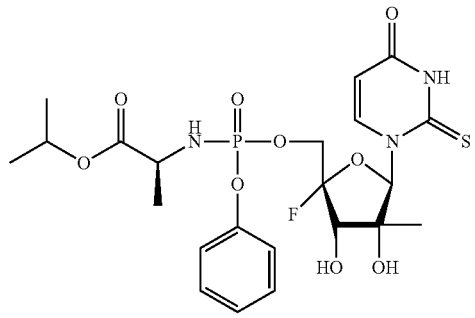
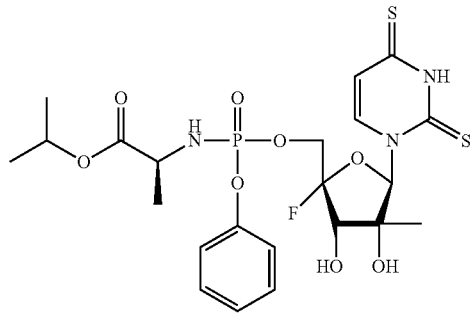
In exemplary embodiments, the compound is selected from:
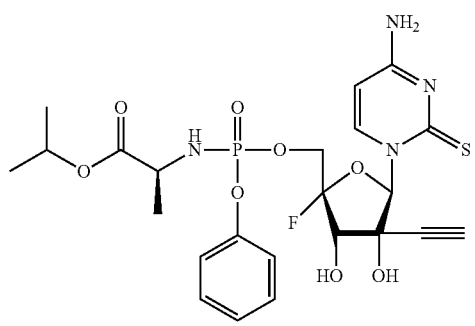
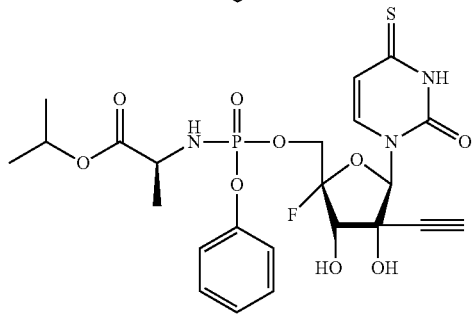
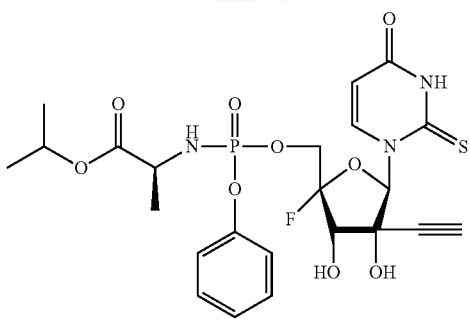
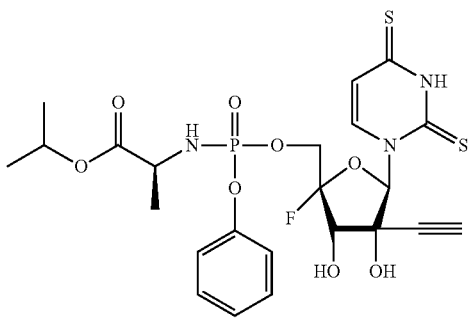
In exemplary embodiments, the compound is selected from:
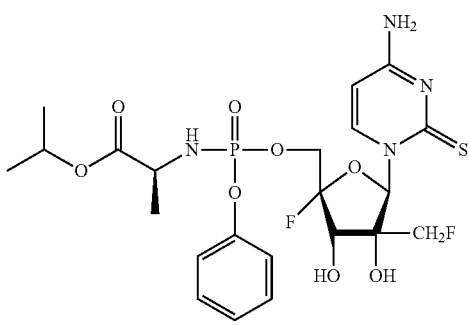
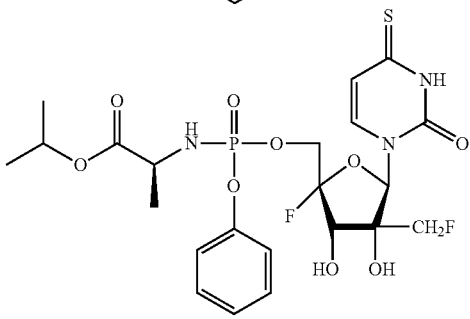
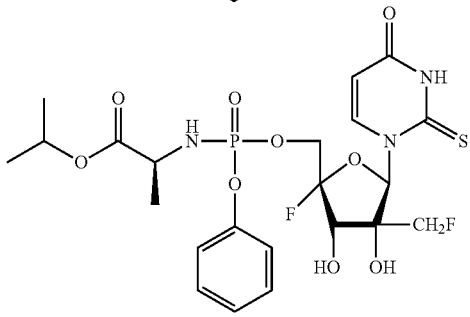

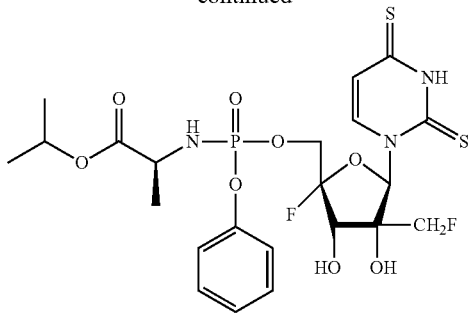
In exemplary embodiments, the compound is selected from:
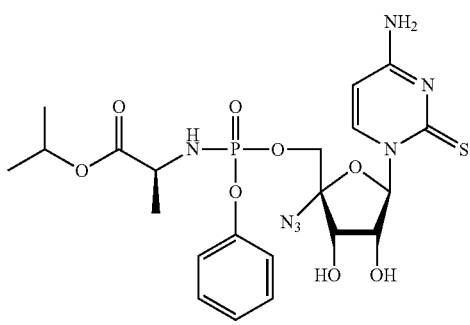
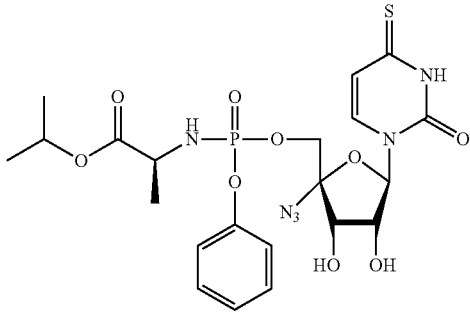
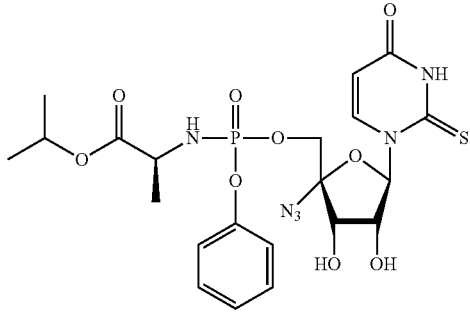
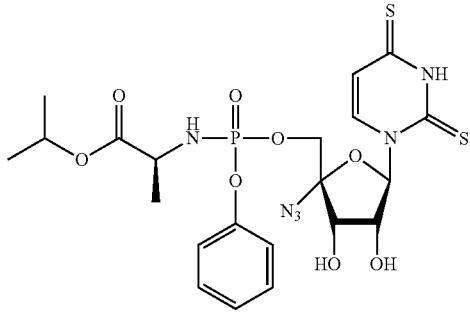
In exemplary embodiments, the compound is selected from:
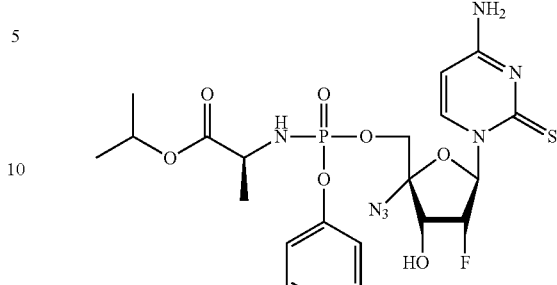
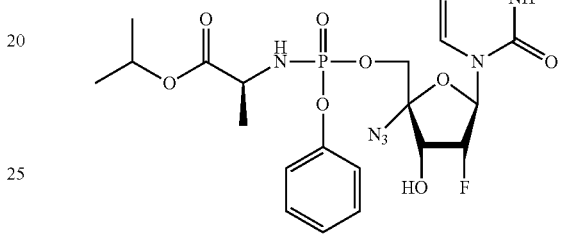
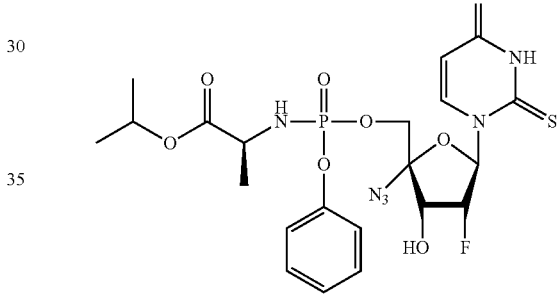
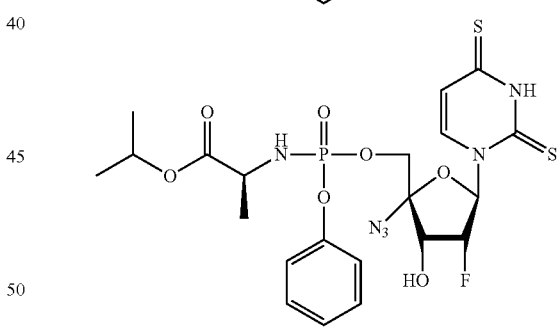
In exemplary embodiments, the compound is selected from:
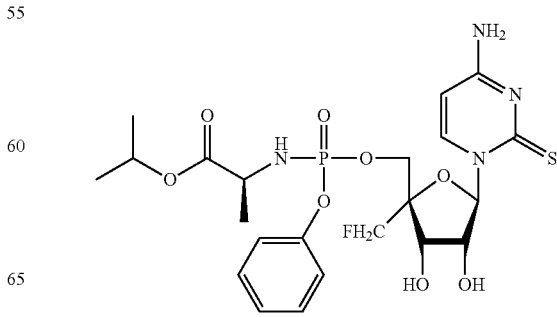

-continued
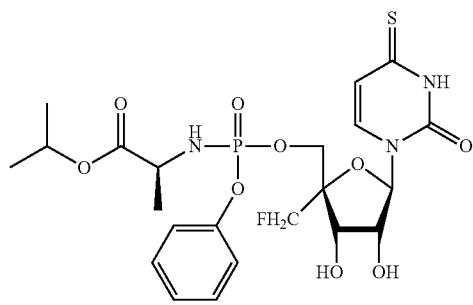
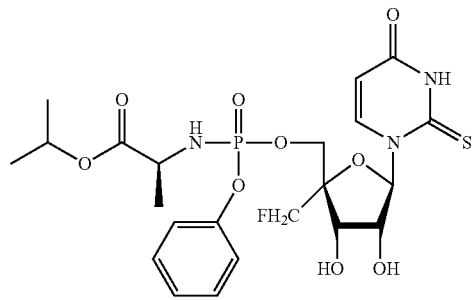
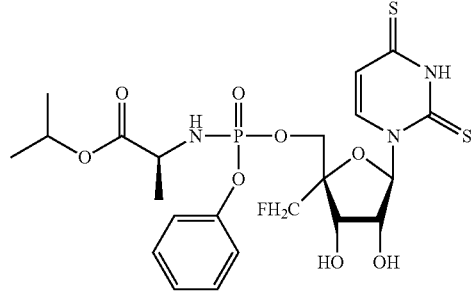
In exemplary embodiments, the compound is selected from:
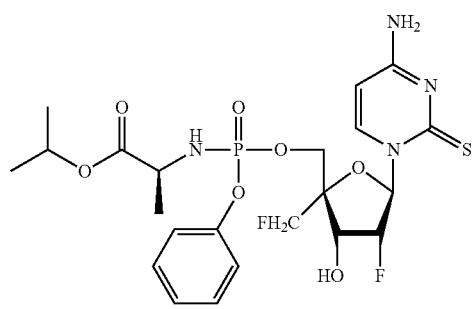
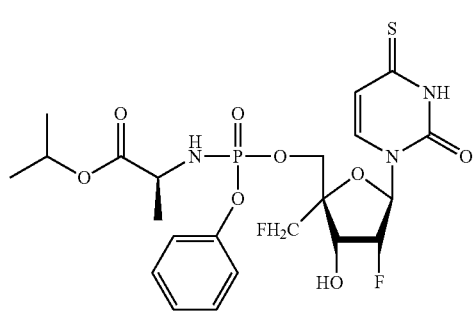
-continued
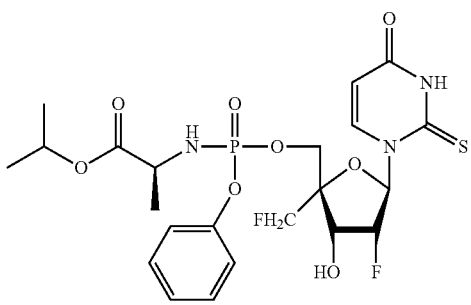
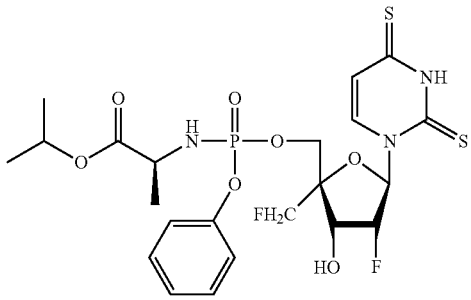
In exemplary embodiments, the compound is selected from:
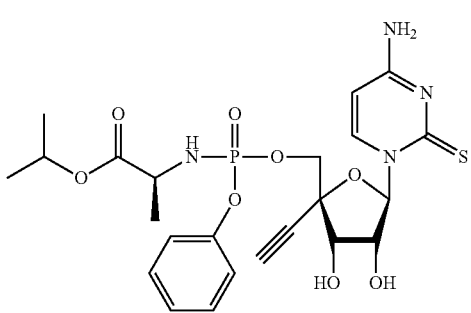
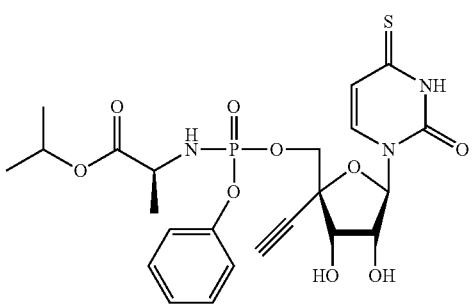
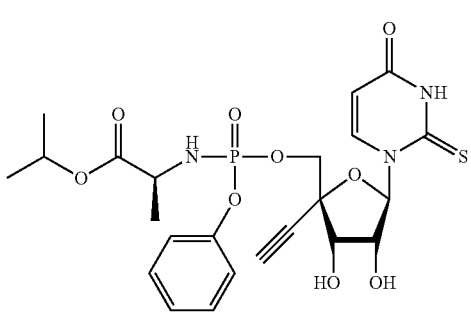

-continued
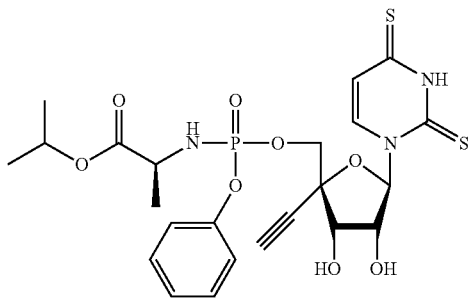
In exemplary embodiments, the compound is selected from:
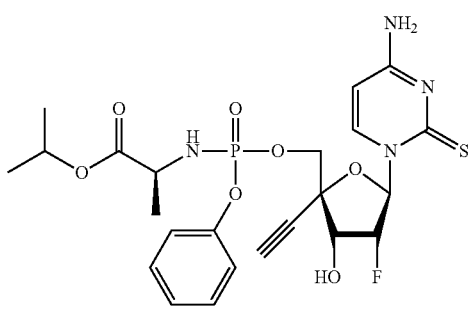
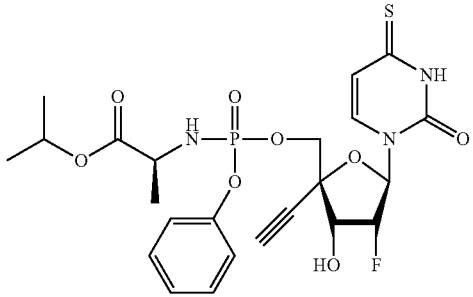
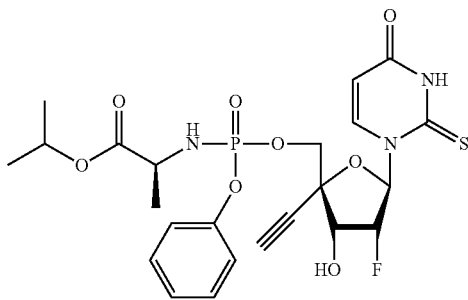
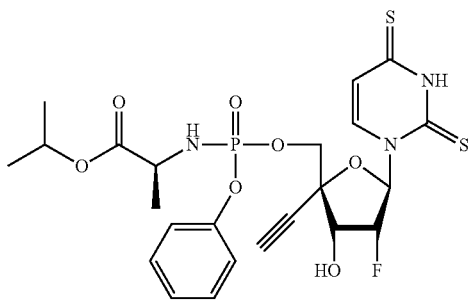
In certain embodiments, the disclosure relates to a compound of the following formulae:
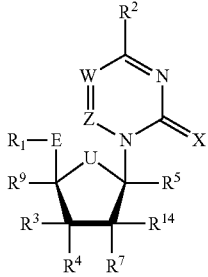
Formula Ij
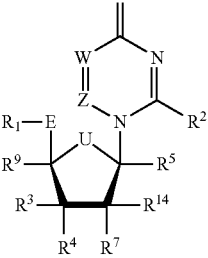
Formula Ik
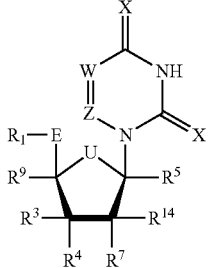
Formula Il
or a pharmaceutically acceptable salt thereof, wherein
E is $CD_2$;
U is O or S;
$R^5$ is H or D;
$R^1$ is one of the formula:
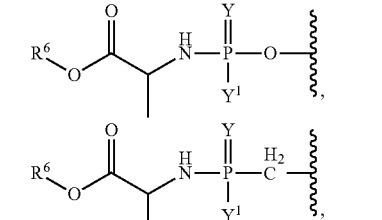
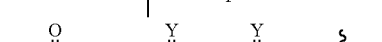
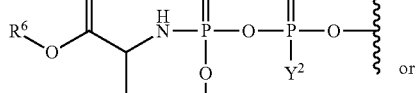 or
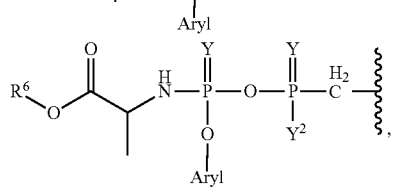
Y is O or S;
$Y^1$ is OAryl or $BH_3^-M^+$;

$Y^2$ is OH or $BH_3^-M^+$;

each X is independently O, S, NH, $NR^8$, NHOH, $NR^8OH$, $NHOR^8$, or $NR^8OR^8$;

$R^2$ is OH, SH, $NH_2$, $OR^8$, $SR^8$, $NHR^8$, NHOH, $NR^8OH$, $NHOR^8$, or $NR^8OR^8$;

wherein in Formula Ij and Ik, one of X is S or $R^2$ is $SR^8$, or both X is S and $R^2$ is $SR^8$;

wherein in Formula Il, at least one X is S;

W is CH, N, or $CR^8$;

Z is CH, N, or $CR^8$;

$R^3$, $R^4$, $R^7$, $R^9$ and $R^{14}$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different $R^{10}$;

each $R^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

Aryl is phenyl, 1-naphthyl, 2-naphthyl, aromatic, heteroaromatic, 4-substituted phenyl, 4-chlorophenyl, 4-bromophenyl;

$R^8$ is methyl, trifluoromethyl, fluoro, iodo, alkenyl, alkynyl, vinyl, allyl, halogen, halogentated alkyl, hydroxyl alkyl, acyl, lipid, geranyl, $C_{1-22}$ alkyl optionally substituted with one or more, the same or different, $R^{10}$;

$R^6$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^6$ is optionally substituted with one or more, the same or different, $R^{10}$.

In certain embodiments, U is S and Y and Z are CH.

In other embodiments, U is O and Y and Z are CH.

In one embodiment, $R^5$ is H. In another embodiment, $R^3$ is H. In yet another embodiment, $R^4$ is hydroxyl. In yet another embodiment, $R^7$ is hydroxyl. In another embodiment, $R^{14}$ is methyl. In a further embodiment, $R^1$ is

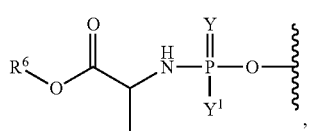

wherein Y is O, $Y^1$ is phenoxy, and $R^6$ is iso-propyl.

In exemplary embodiments, the compound is selected from:

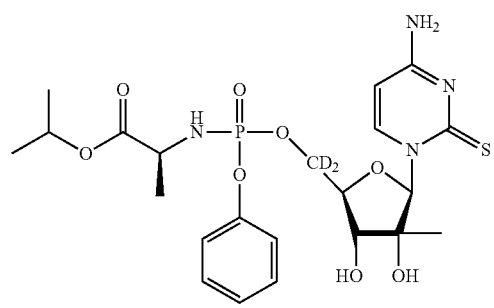

-continued

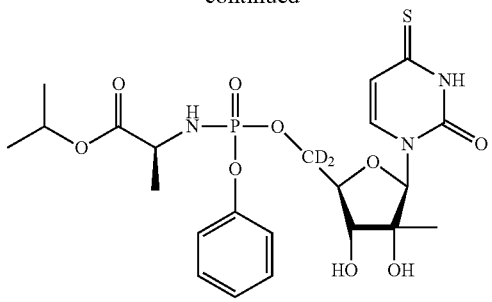

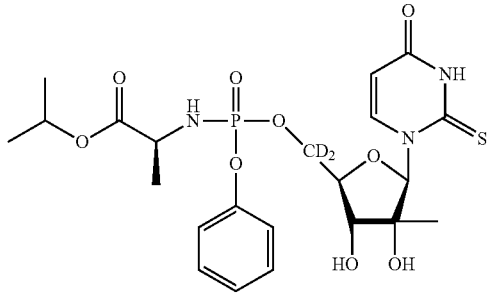

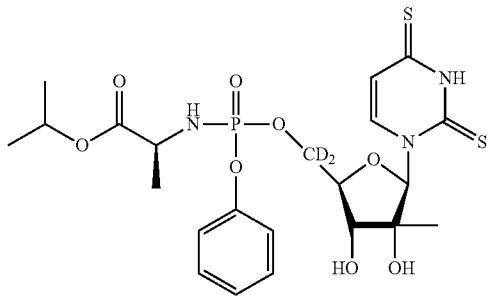

In one embodiment, $R^5$ is H. In another embodiment, $R^3$ is H. In yet another embodiment, $R^4$ is hydroxyl. In yet another embodiment, $R^7$ is hydroxyl. In another embodiment, $R^{14}$ is methyl. In a further embodiment, $R^1$ is

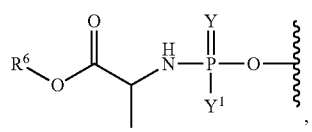

wherein Y is O and $Y^1$ is O-aryl.

In exemplary embodiments, the compound is selected from:

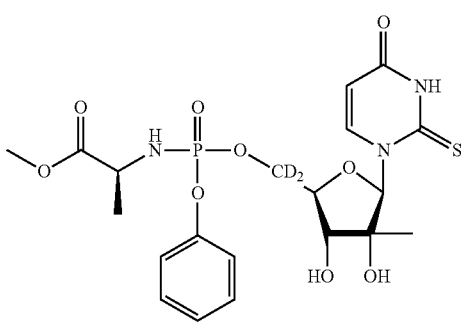

111
-continued
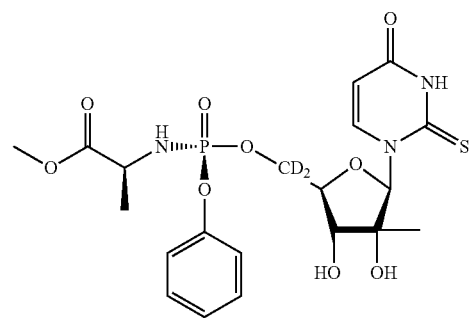
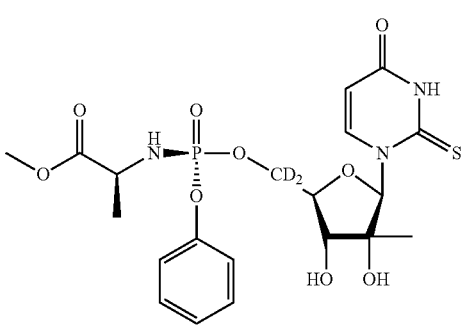
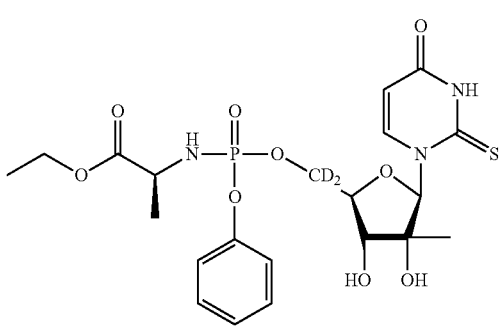
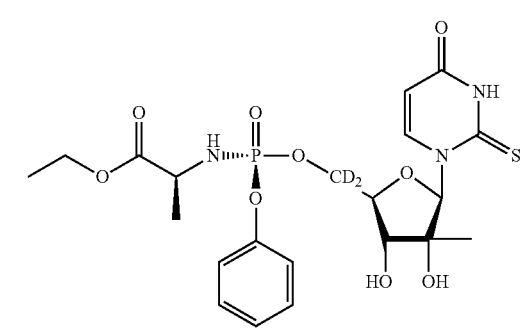
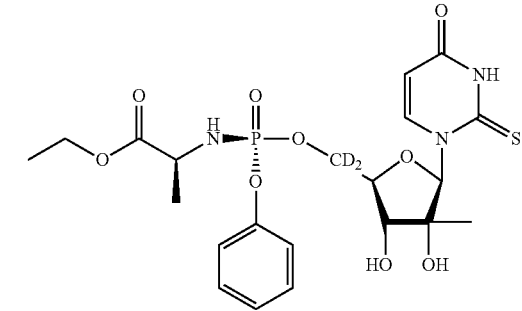
112
-continued
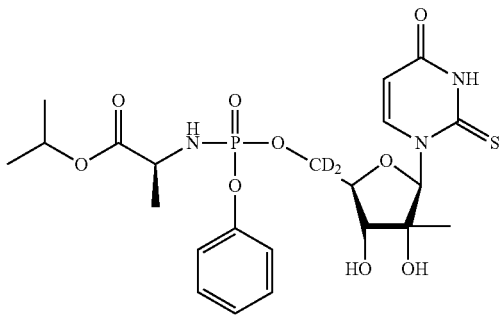
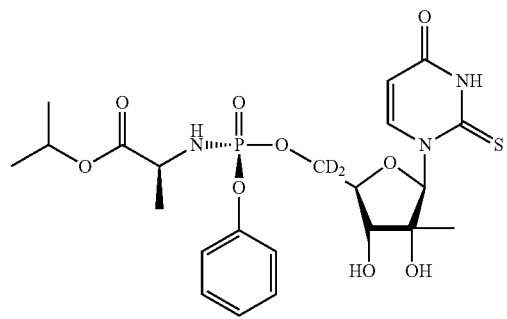
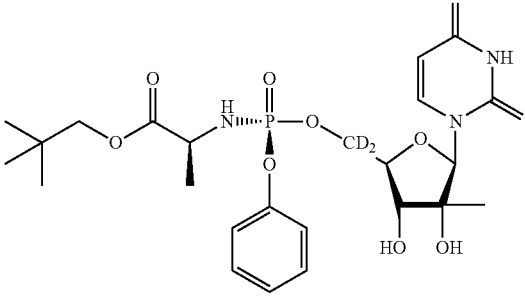

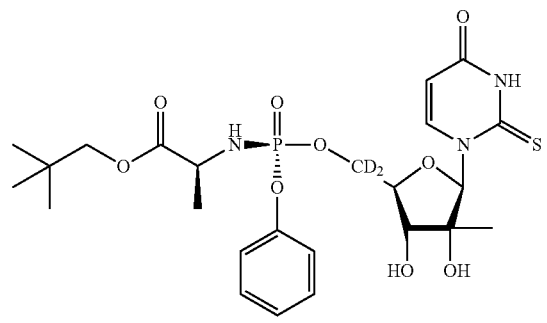
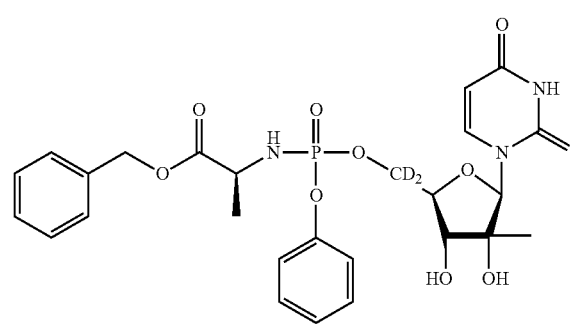
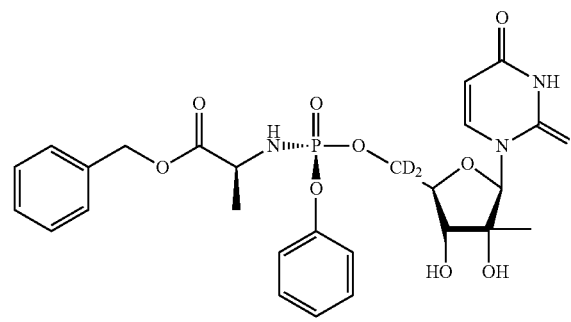
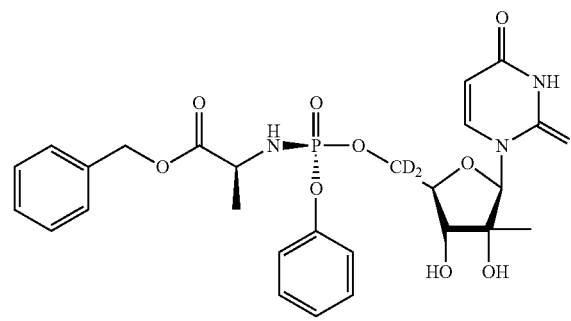
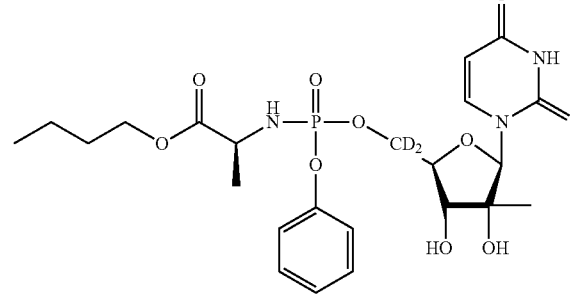
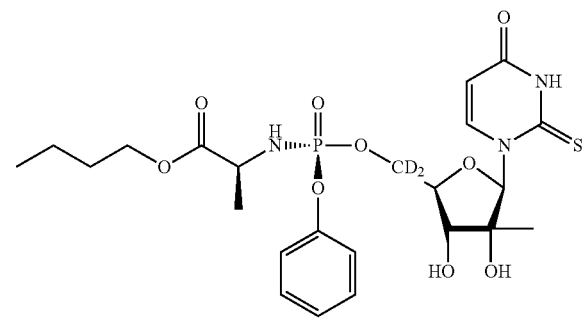
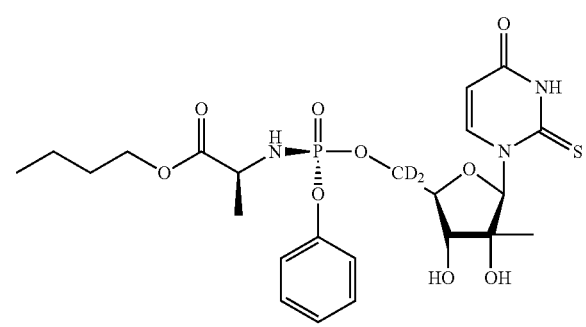
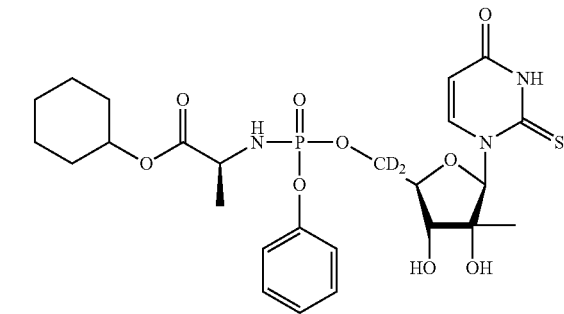
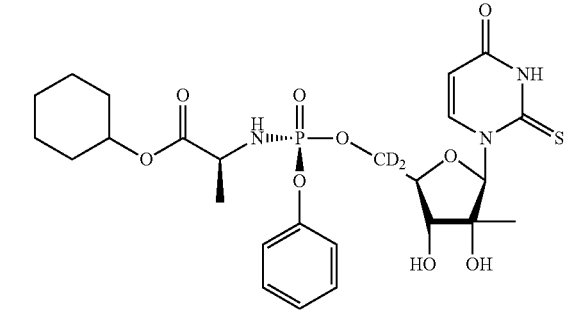
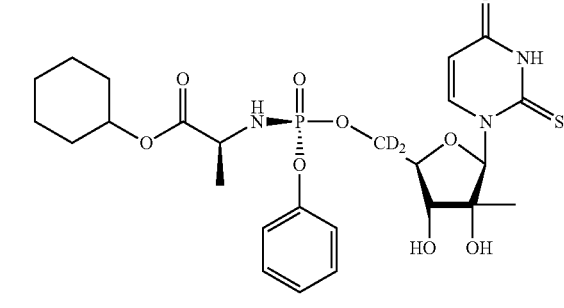

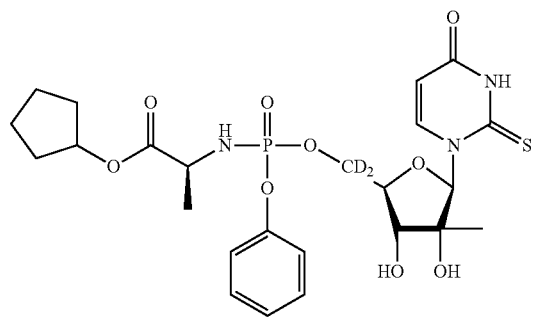
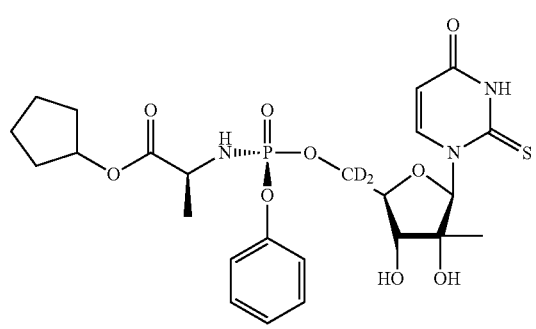
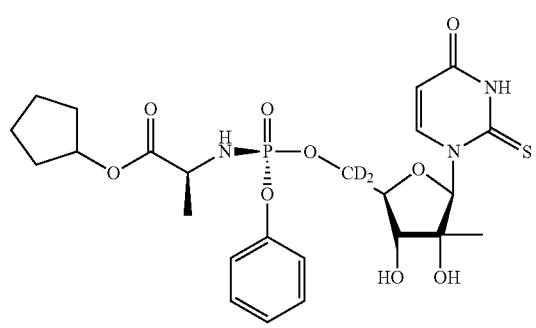
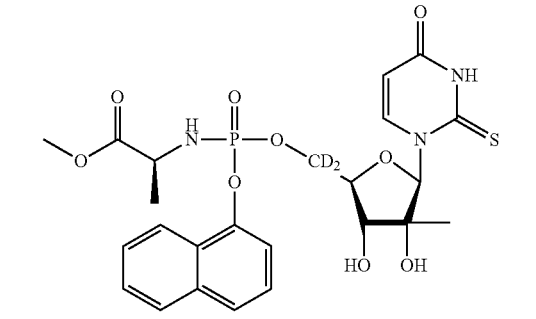
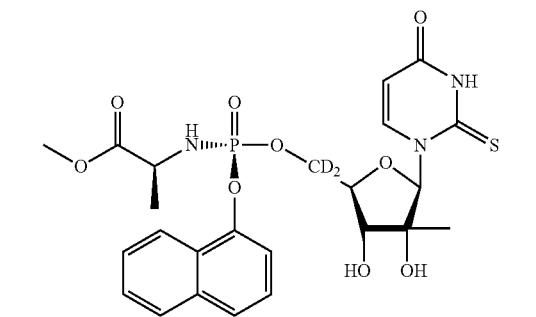
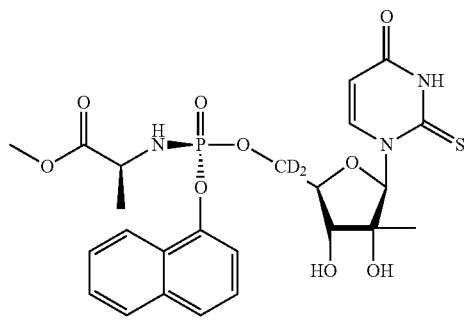
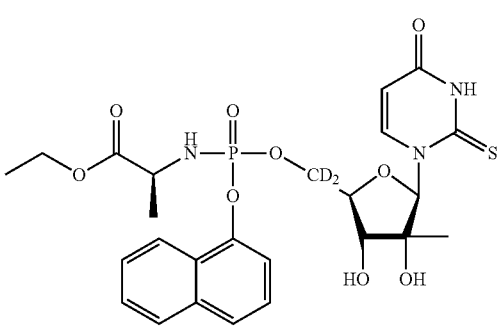
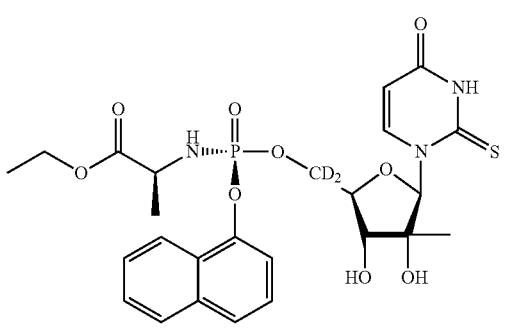
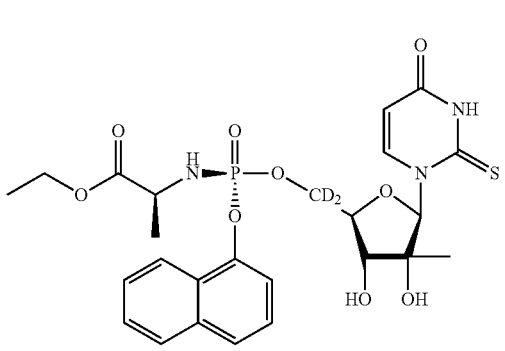
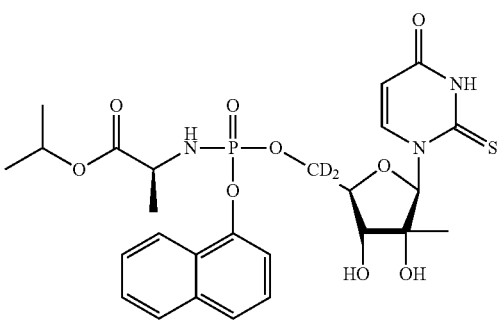

117
-continued
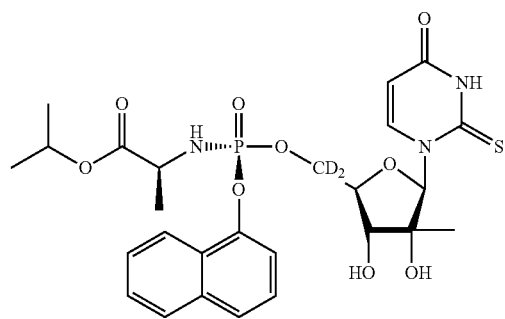
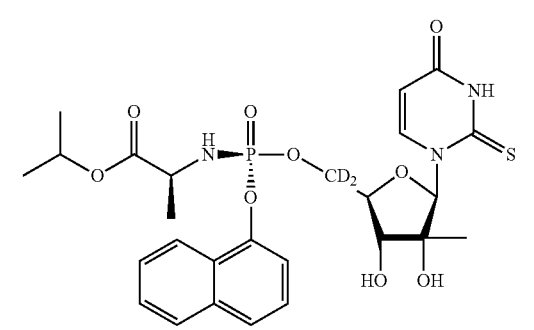
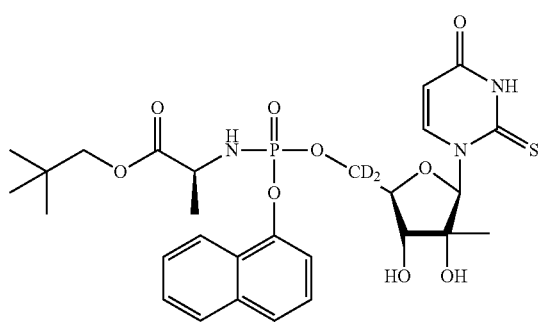
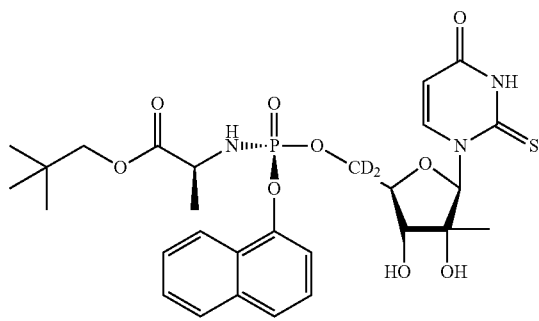
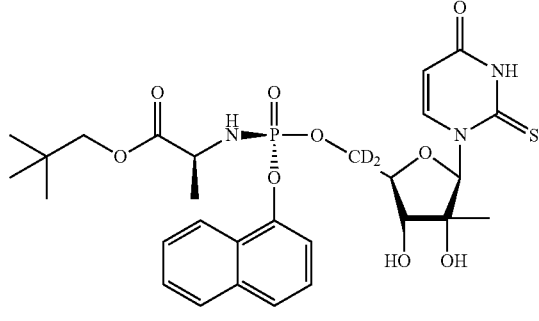
118
-continued
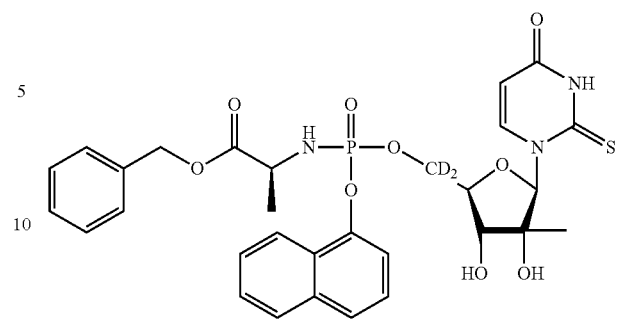
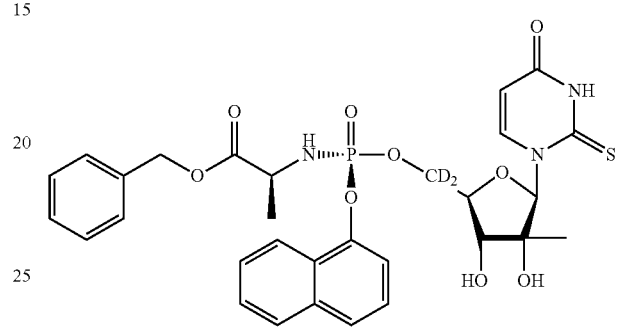
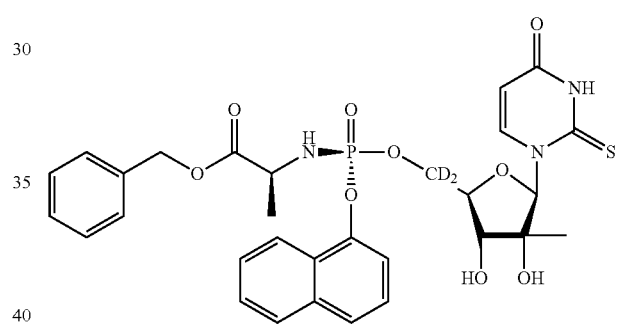
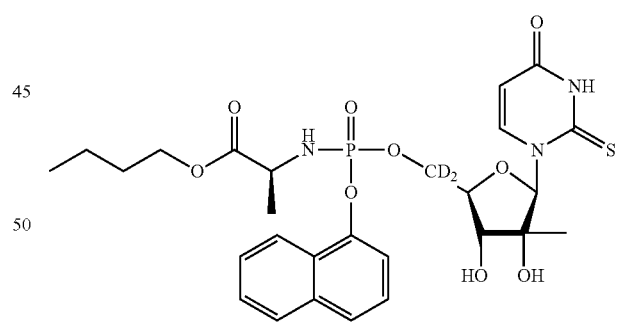
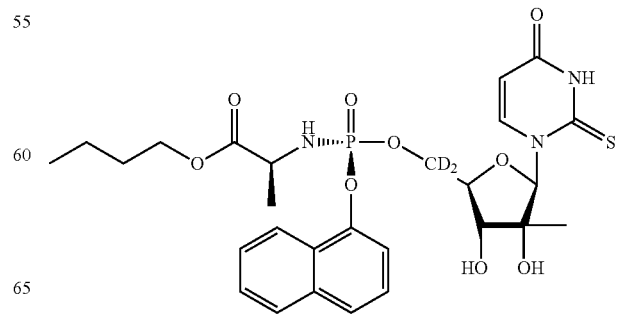

119
-continued
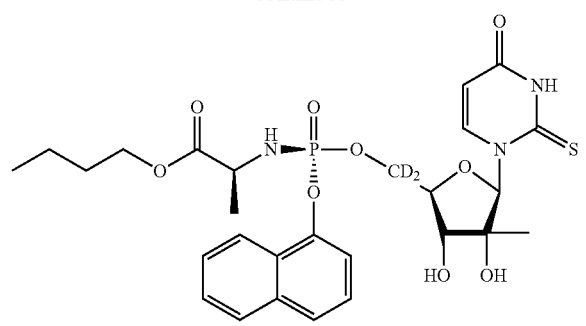
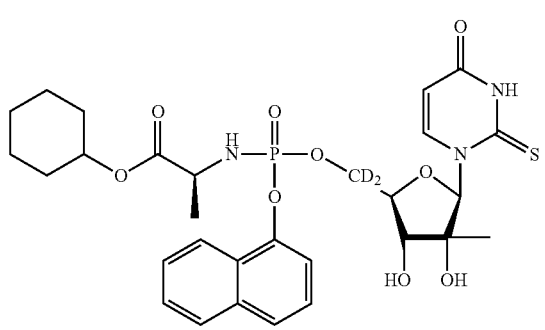
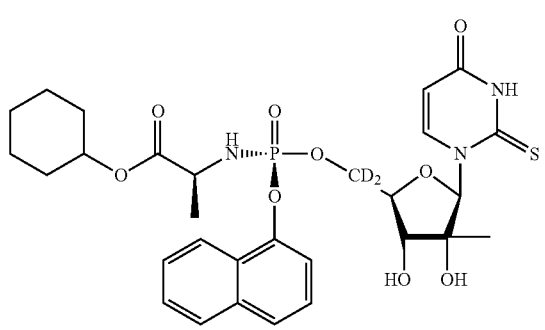
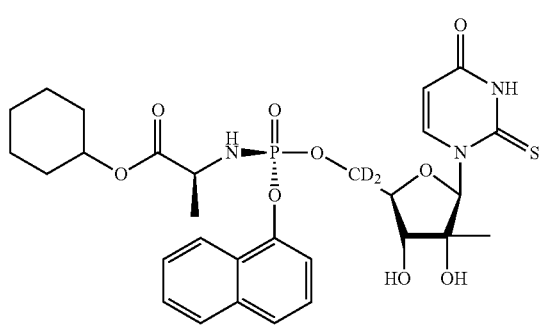
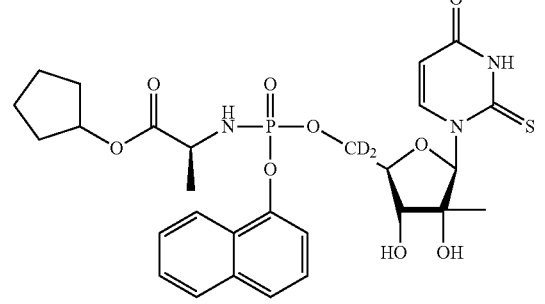
120
-continued
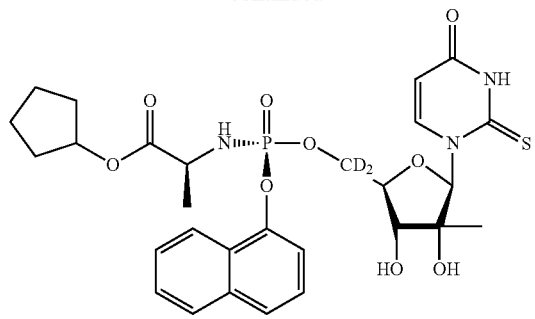
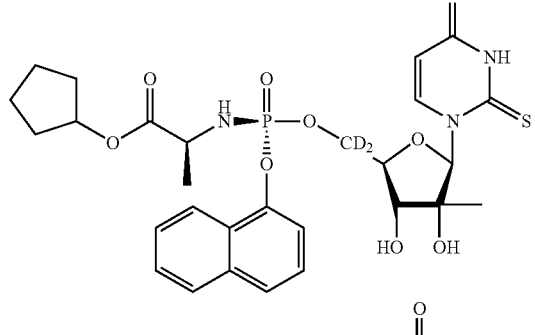
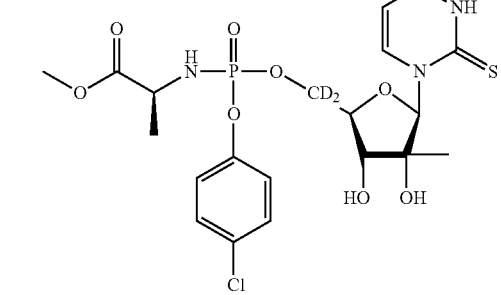
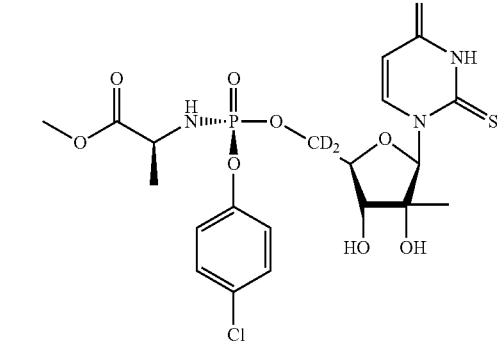
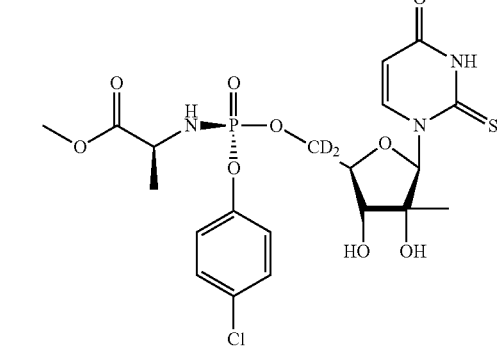

121
-continued

122
-continued

123
-continued
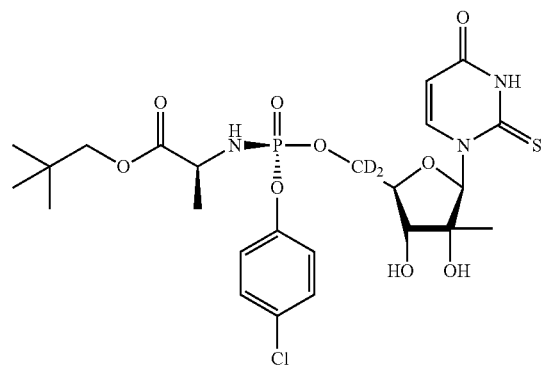
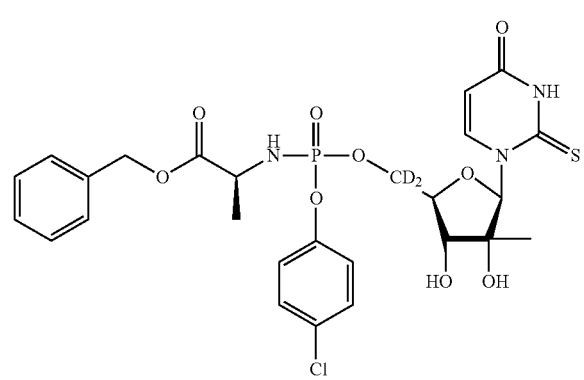
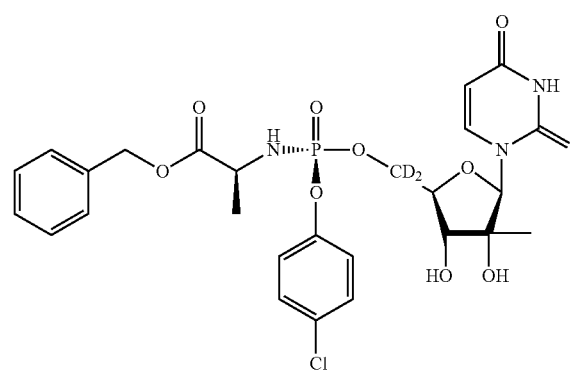
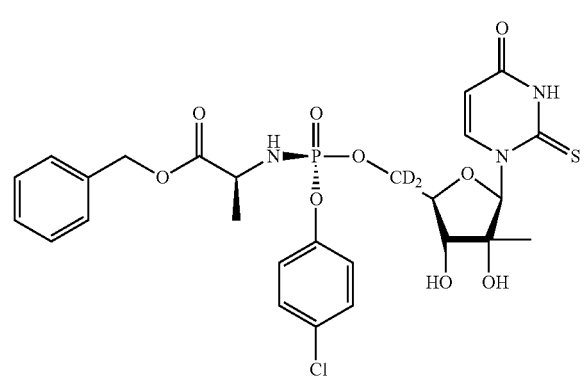
124
-continued
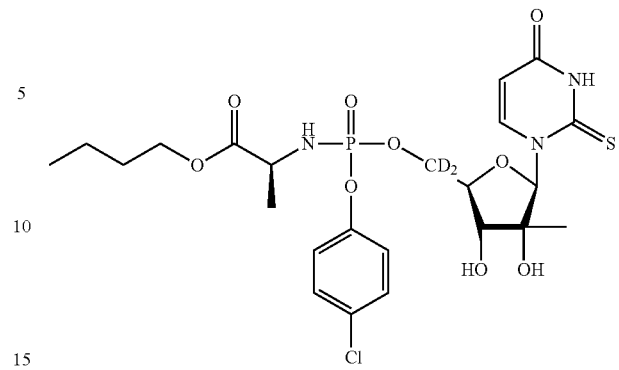
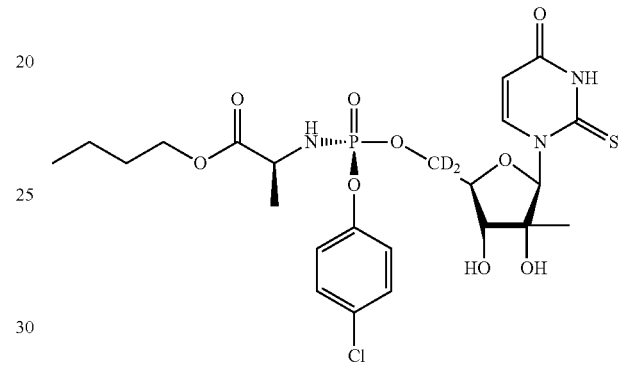
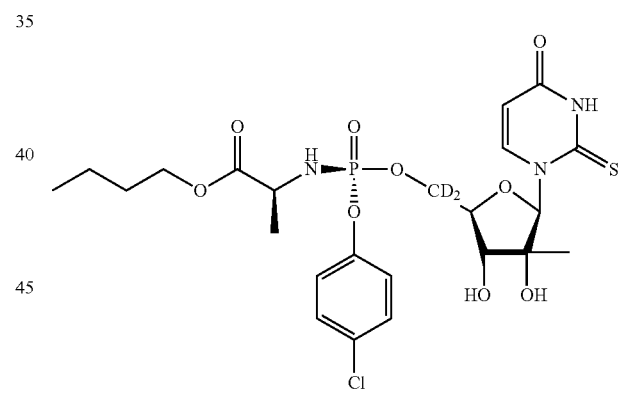
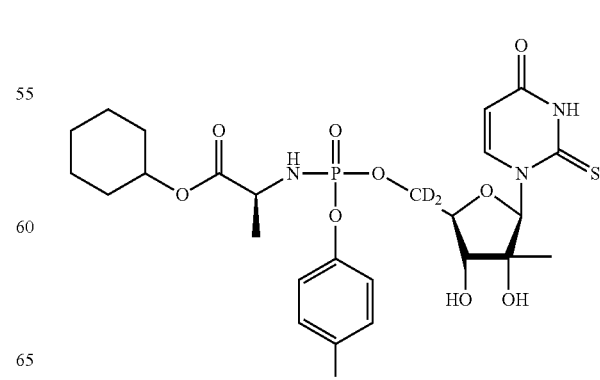

125
-continued
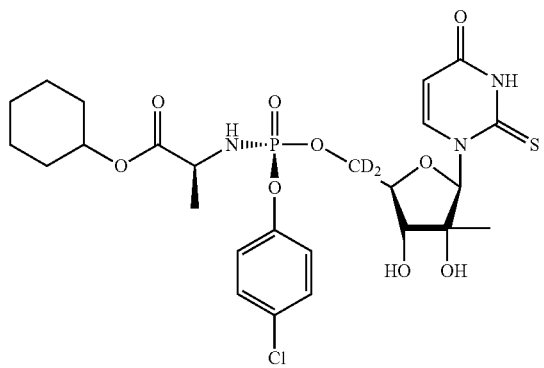
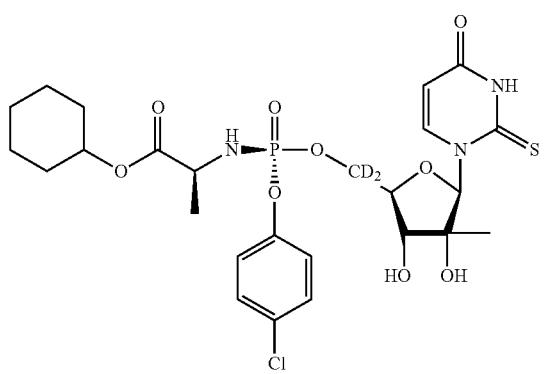
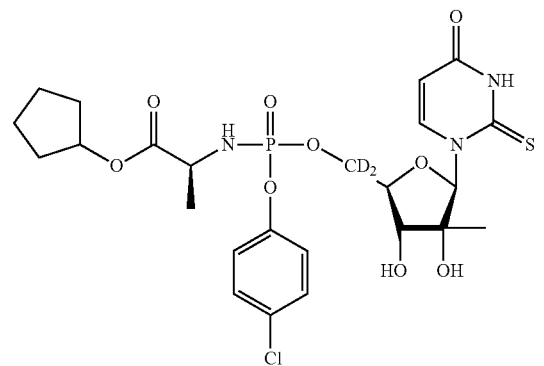
126
-continued
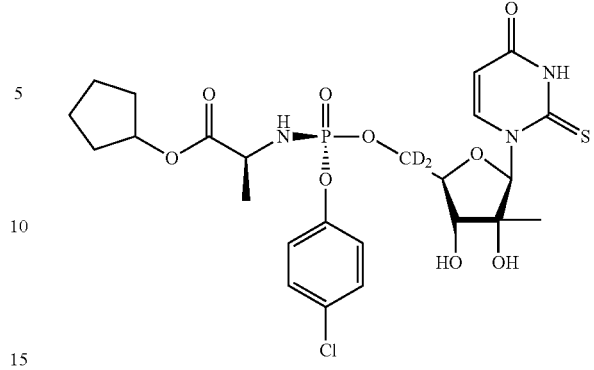
In preferred embodiments, the nucleoside conjugated to a phosphorus moiety has the following structure:
Formula Im
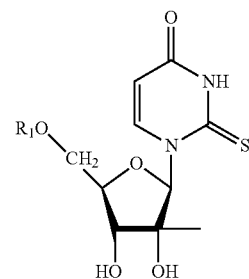
Formula In
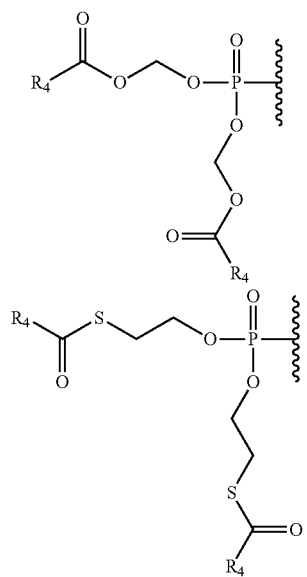
or a pharmaceutically acceptable salt thereof, wherein $R_1$ is selected from one of the following:

127
-continued

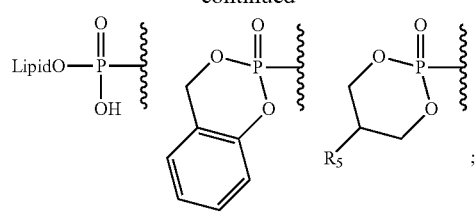

$R_4$ is $C_{1-22}$ alkoxy, or $C_{1-22}$ alkyl, alkyl, branched alkyl, cycloalkyl, or alkyoxy;

$R_5$ is aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl.

In exemplified embodiments, the nucleoside conjugated to a phosphorus moiety or pharmaceutically acceptable salt thereof has the following structure:

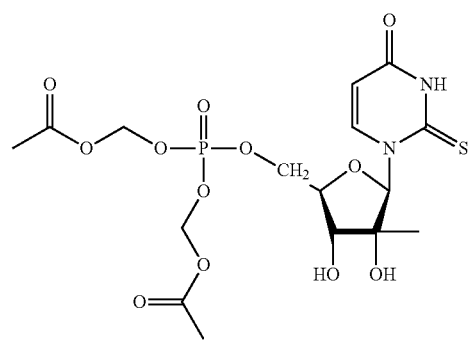

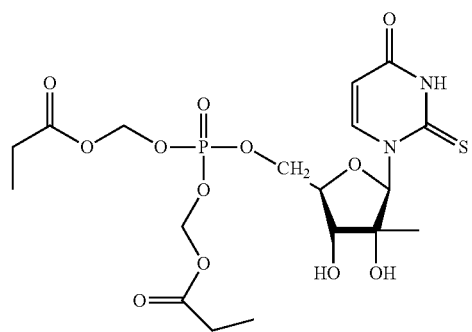

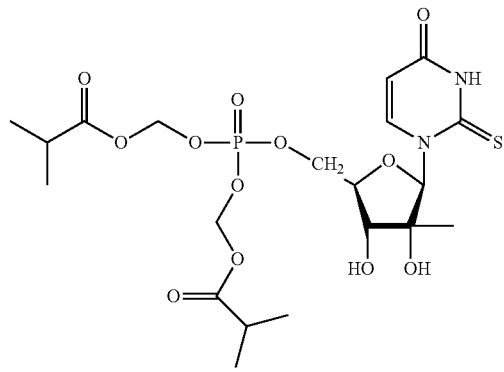

128
-continued

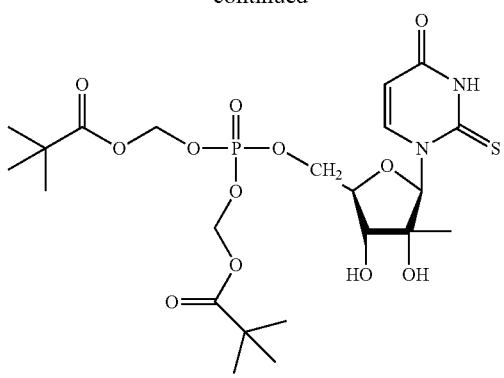

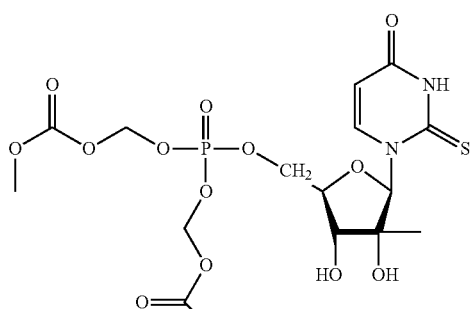

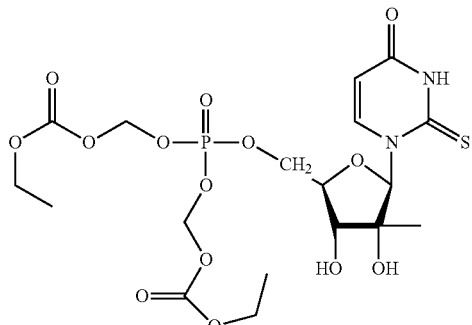

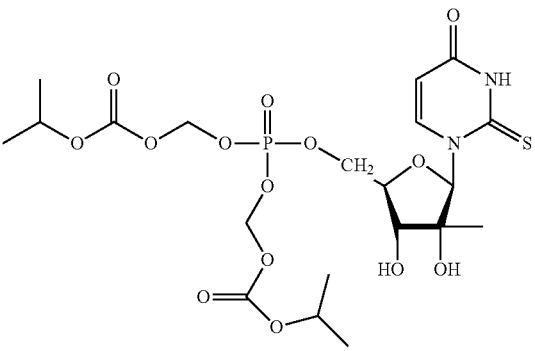

129
-continued
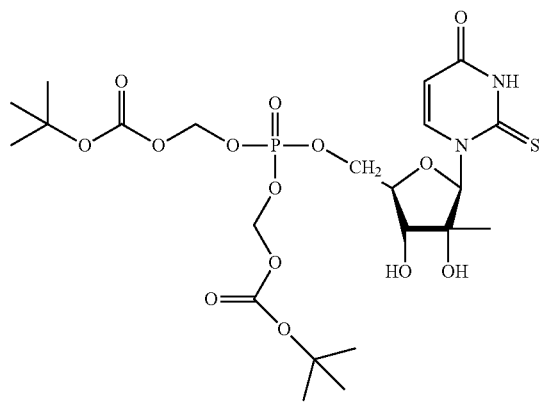
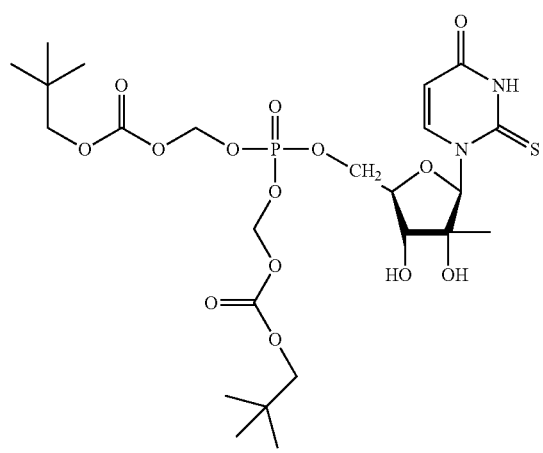
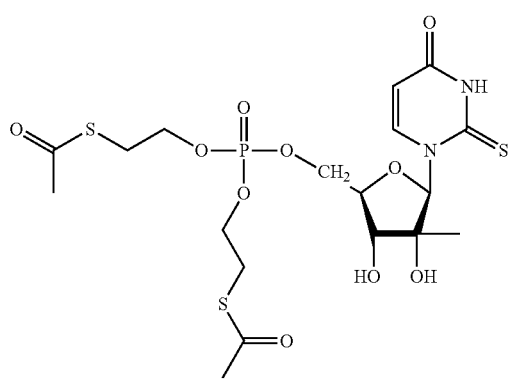
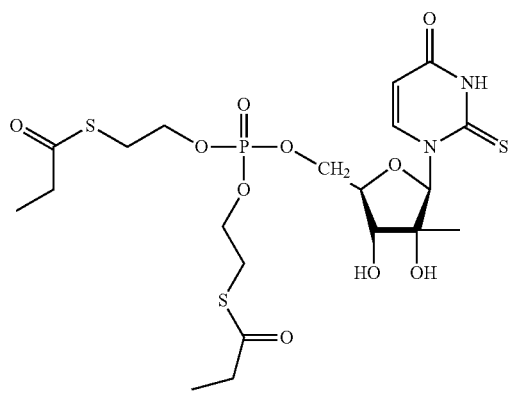
130
-continued
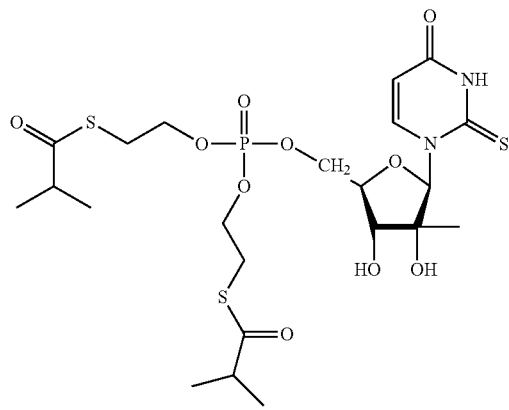
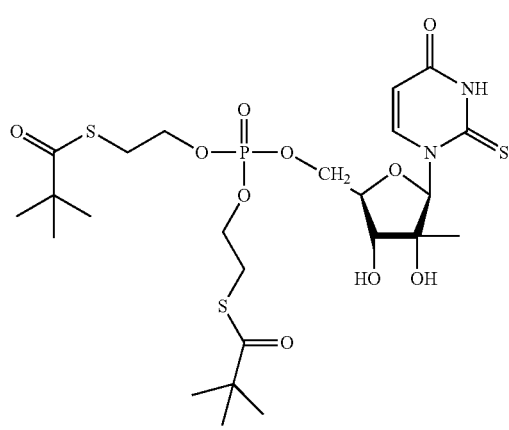
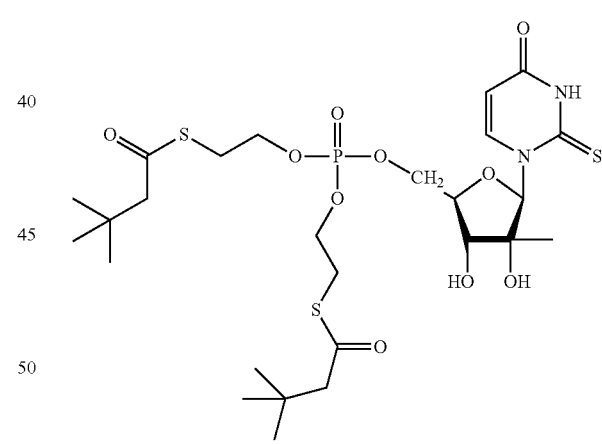
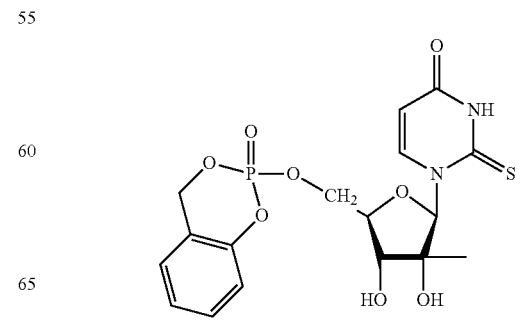

131
-continued
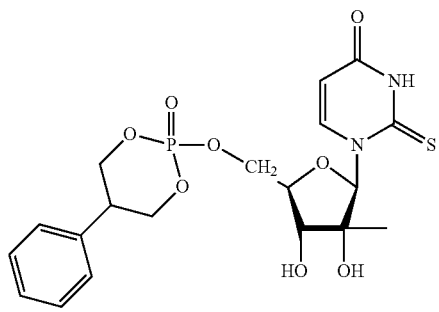
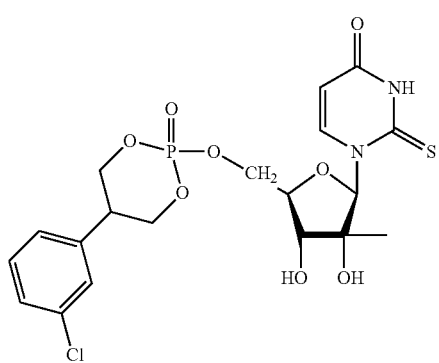
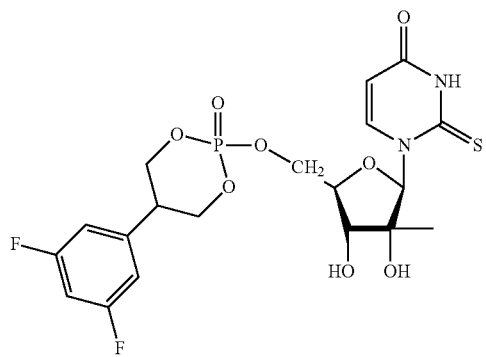
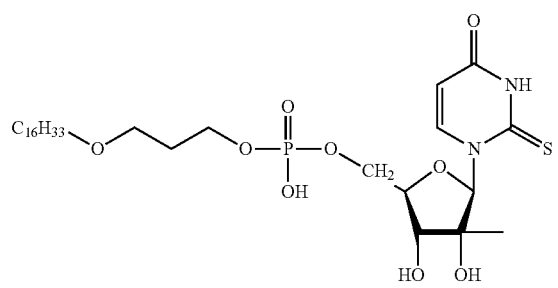
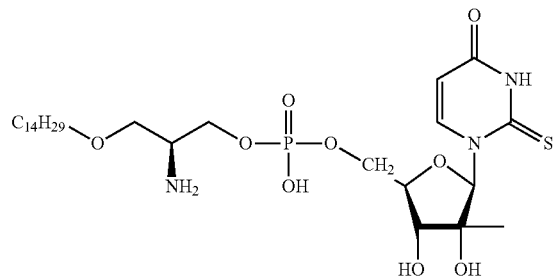
132
-continued
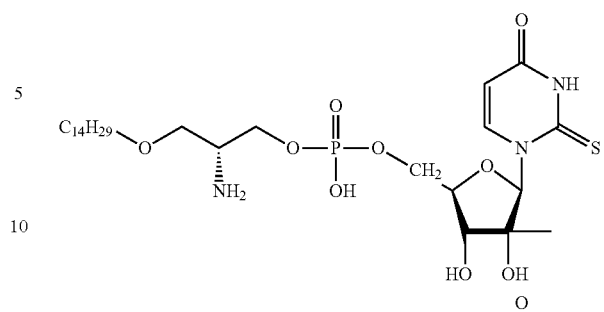
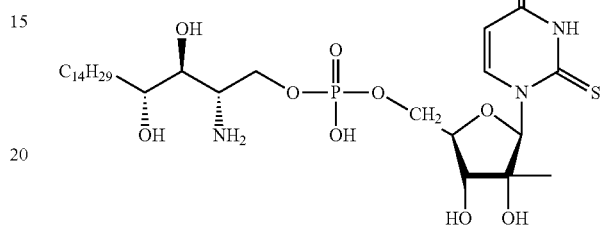
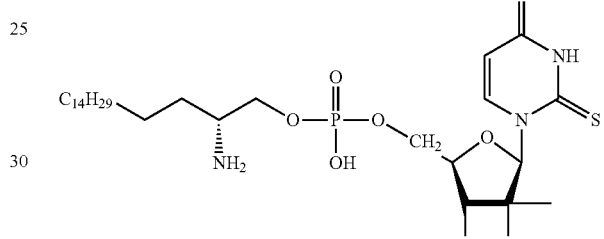
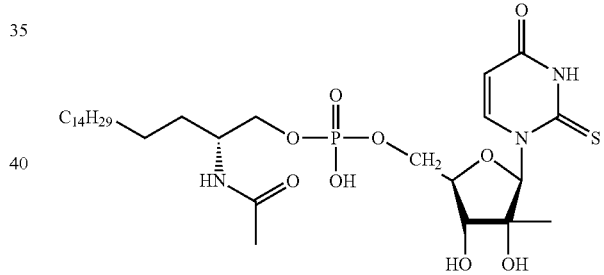
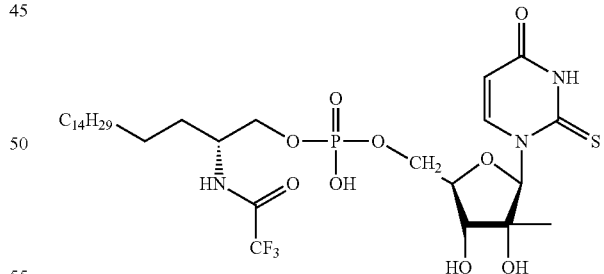
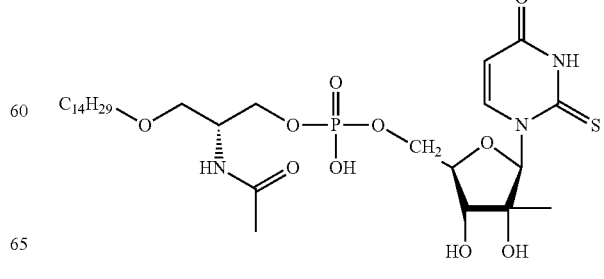

133
-continued
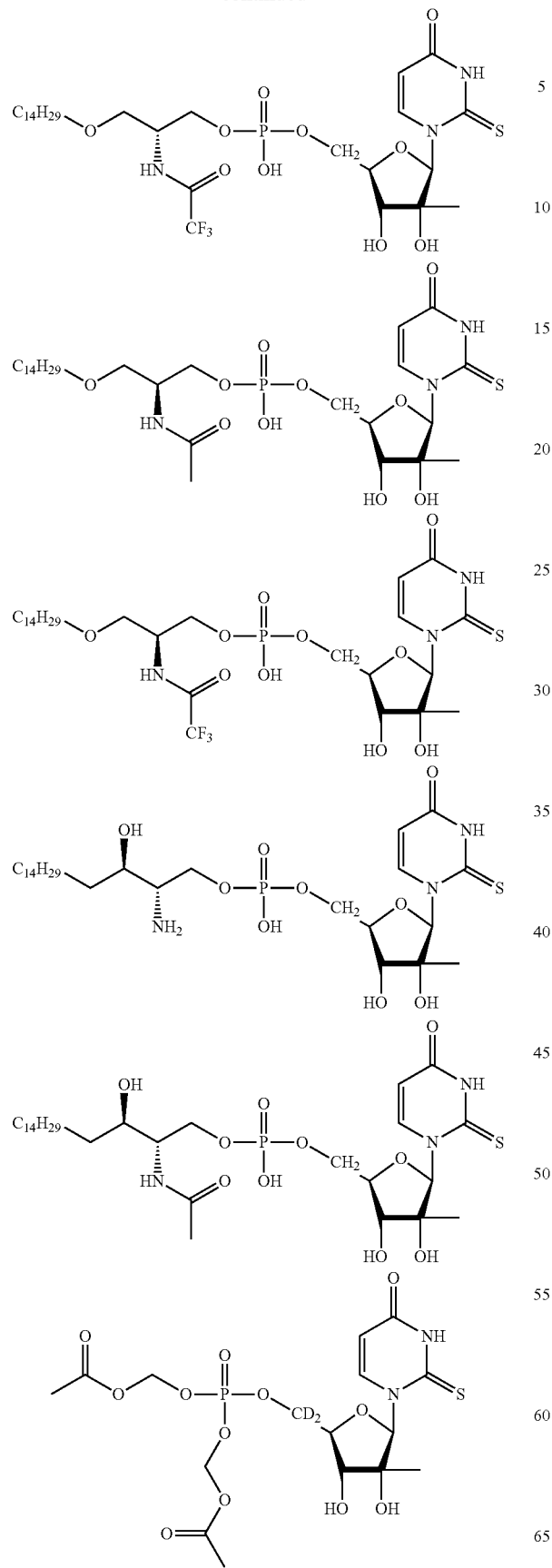
134
-continued
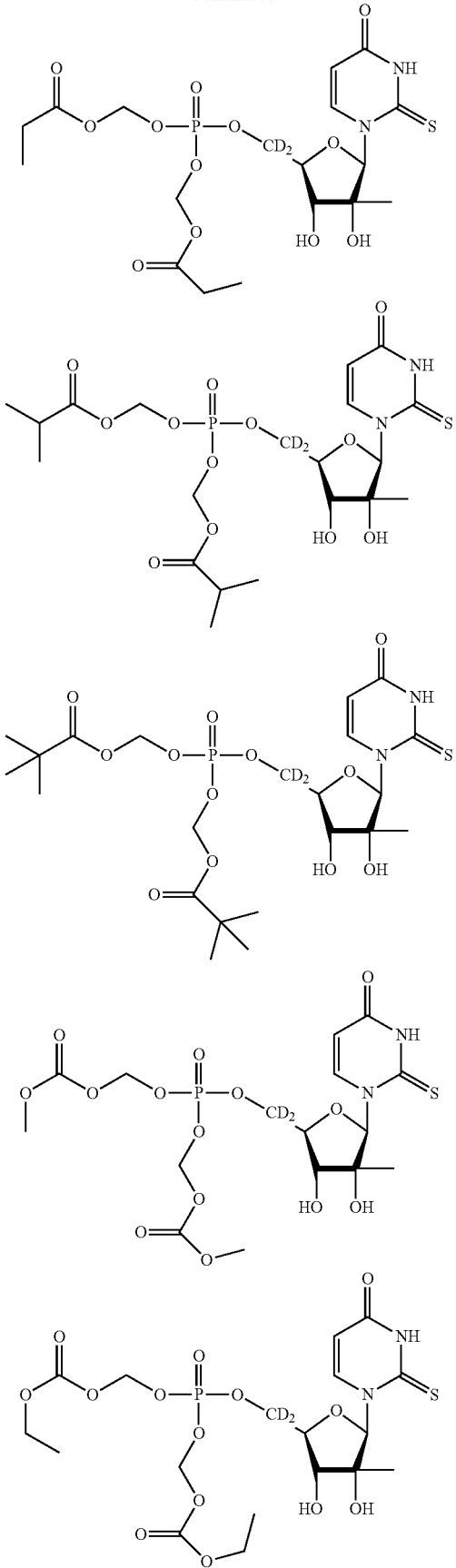

135
-continued
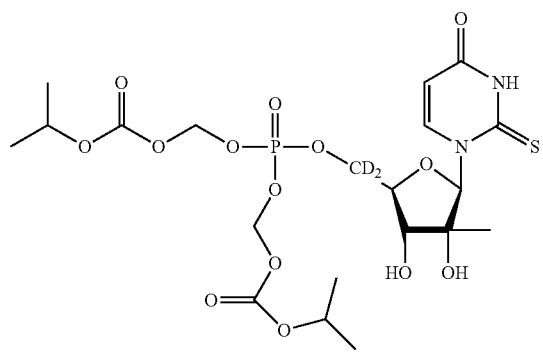
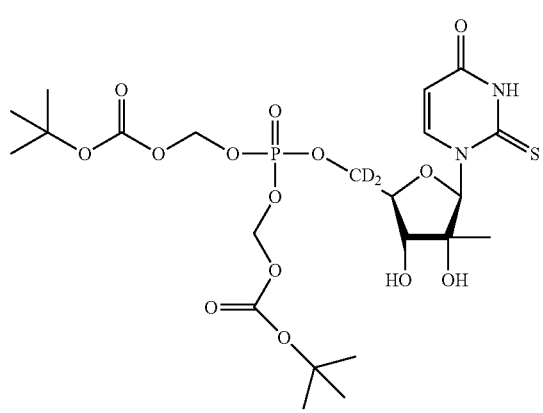
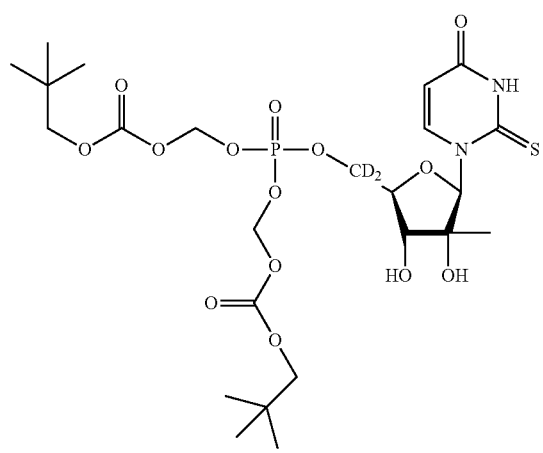
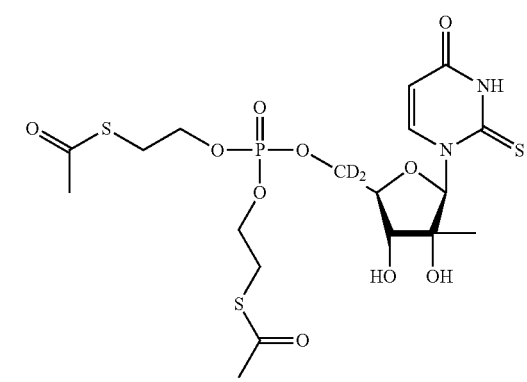
136
-continued
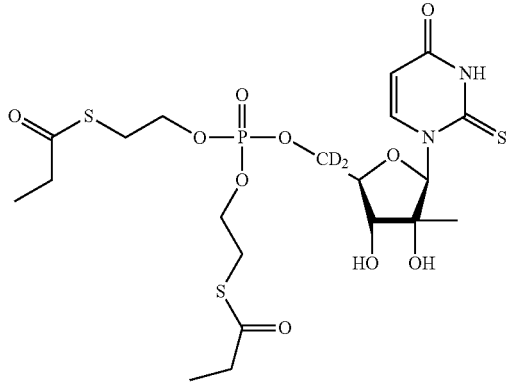
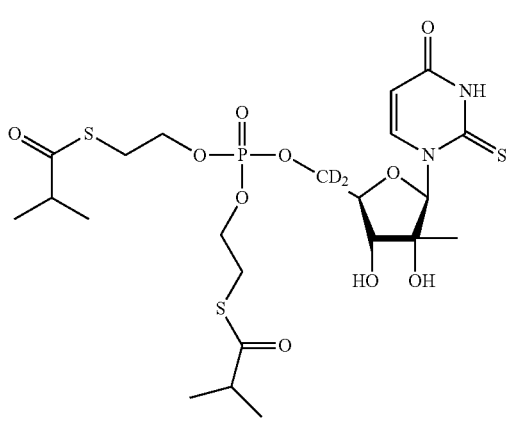
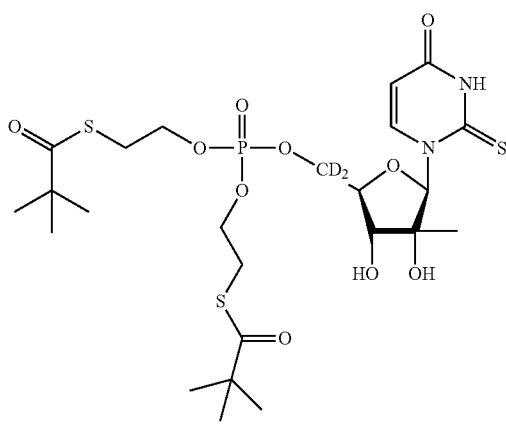
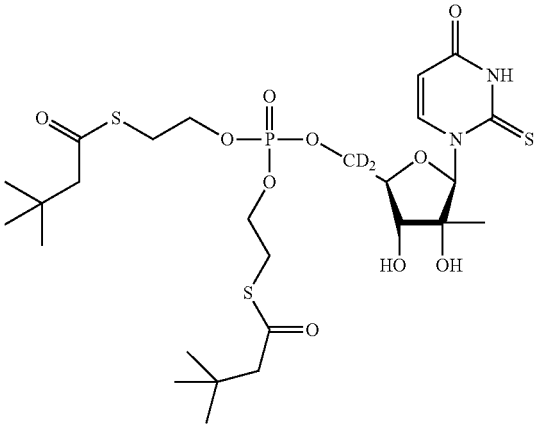

137
-continued
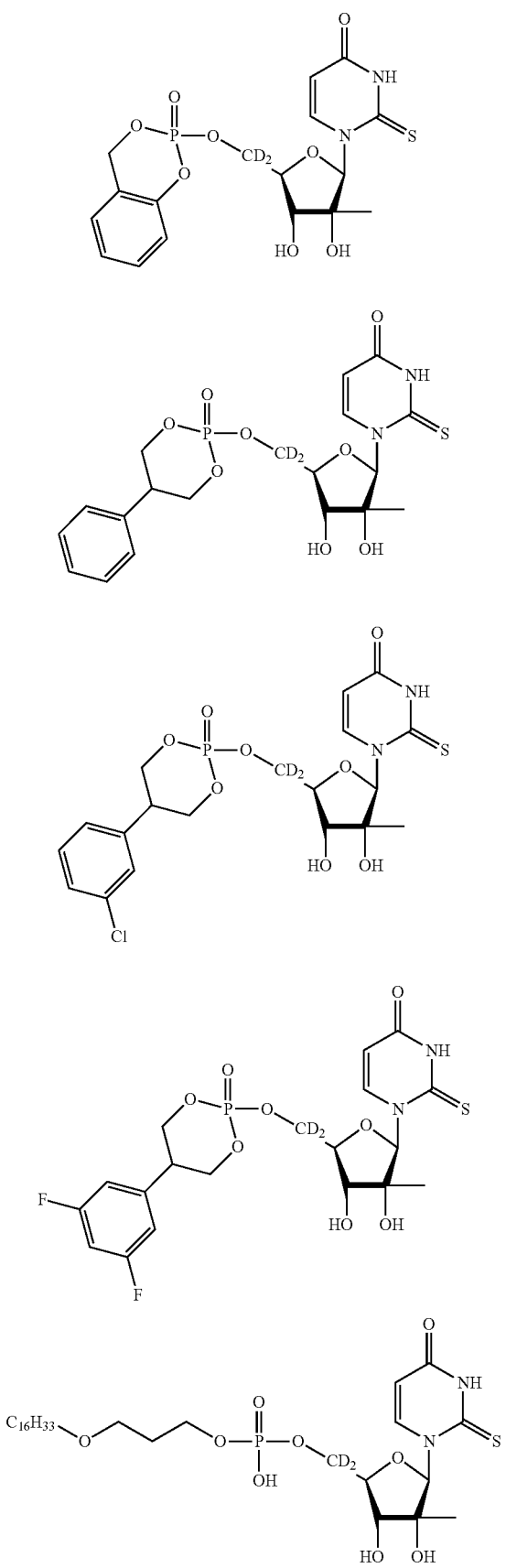
138
-continued
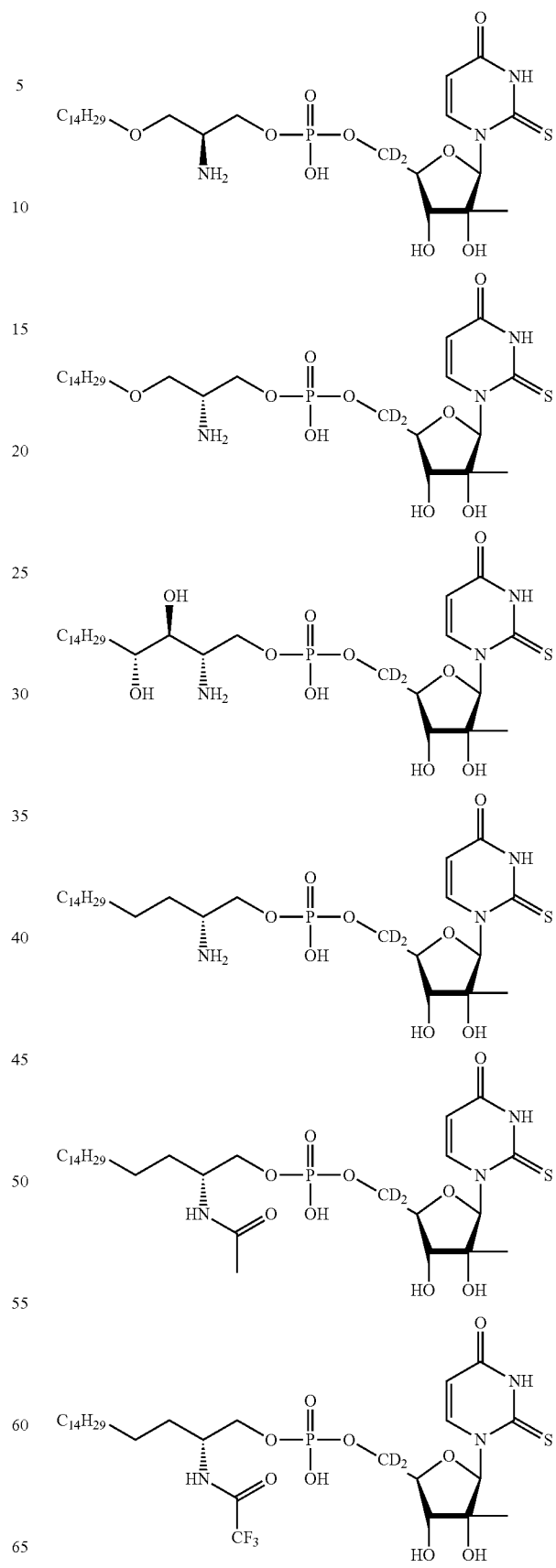

-continued

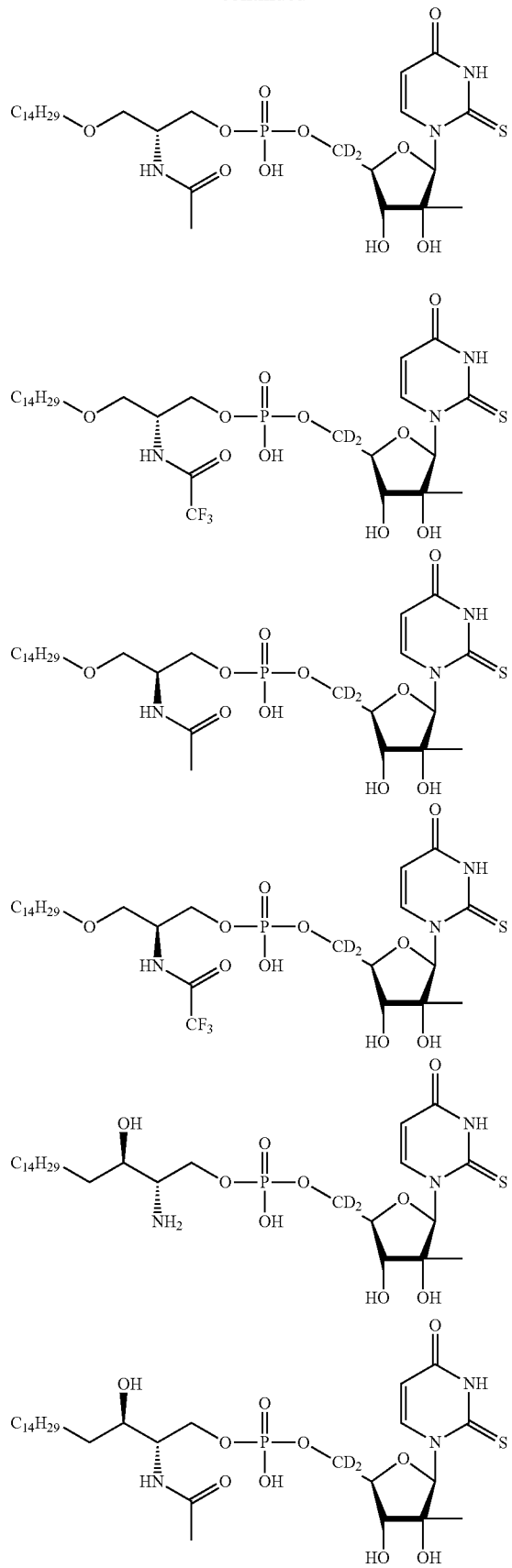

In other embodiments, $R_1$ of Formula Im or In is selected from one of the following:

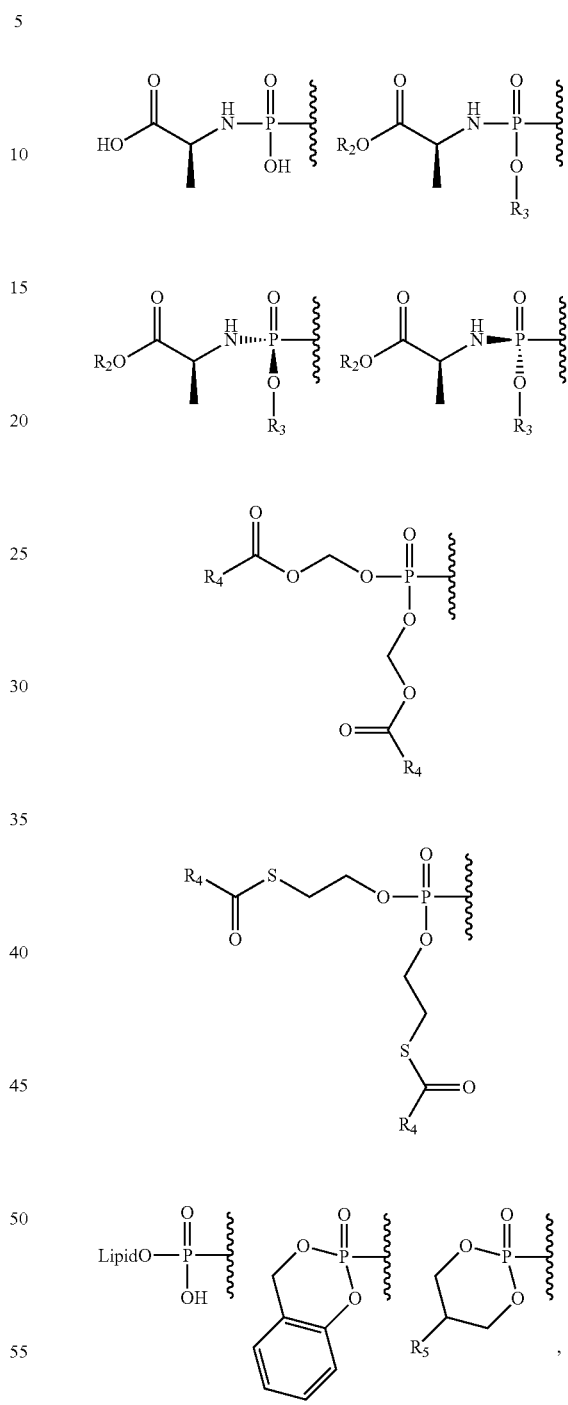

wherein
$R_2$ is alkyl, branched alkyl, or cycloalkyl;
$R_3$ is aryl, biaryl, or substituted aryl;
$R_4$ is $C_{1-22}$ alkoxy, or $C_{1-22}$ alkyl, alkyl, branched alkyl, cycloalkyl, or alkyoxy;
$R_5$ is aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl.

In preferred embodiments, the nucleoside conjugated to a phosphorus moiety or pharmaceutically acceptable salt thereof has the following structure:

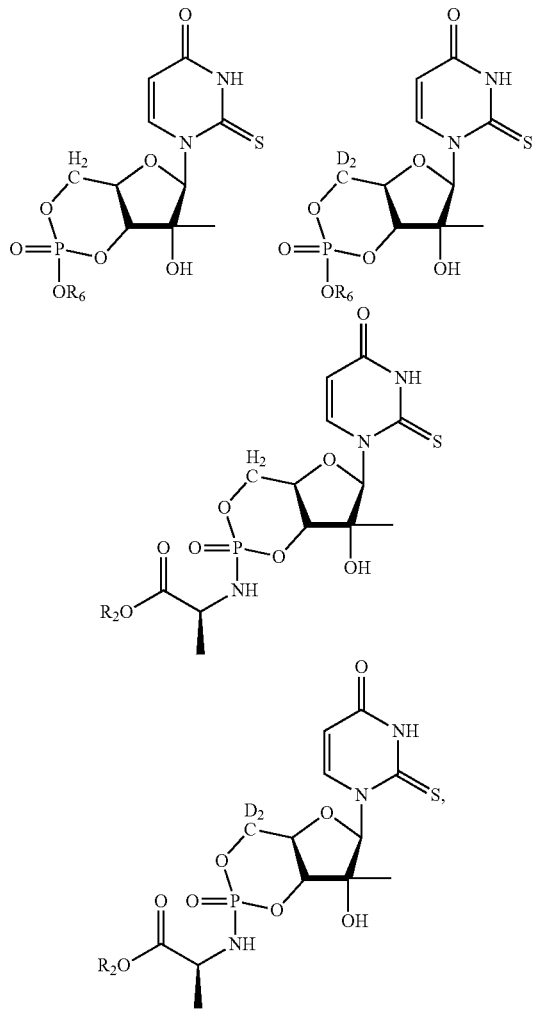

$R_2$ is selected from $C_{1-22}$ alkyl, $C_{2-22}$ alkenyl, $C_{2-22}$ alkynyl, branched alkyl, or cycloalkyl;

$R_6$ is lipid, $C_{1-22}$ alkyl, $C_{2-22}$ alkenyl, $C_{2-22}$ alkynyl, branched alkyl, pivaloyloxymethyl, cycloalkyl, or selected from

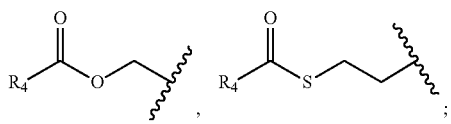

wherein $R_4$ is $C_{1-22}$ alkoxy, or $C_{1-22}$ alkyl, alkyl, branched alkyl, cycloalkyl, or alkyoxy.

In certain embodiments, the disclosure relates to a compound of the following formula:

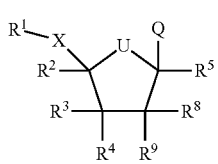

Formula Io or pharmaceutically acceptable salts thereof wherein,
U is O or S;
X is O, $CH_2$ or $CD_2$;
$R^5$ is H or D;

Q is a heterocyclyl comprising two or more nitrogen heteroatoms substituted with at least one thione, thiol or thioether, wherein Q is optionally substituted with one or more, the same or different alkyl, halogen, or cycloalkyl;

$R^2$, $R^3$, $R^4$, $R^8$ and $R^9$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^{10}$;

each $R^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

$R^1$ is one of the formula:

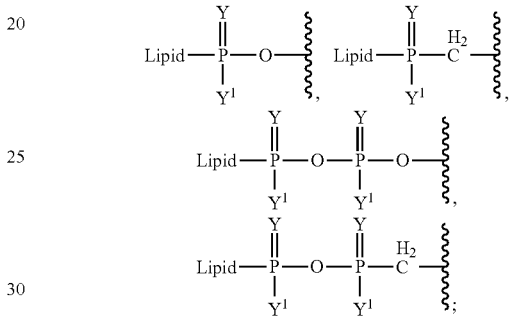

Y is O or S;
$Y^1$ is OH or $BH_3$-$M^+$; and
Lipid is as described herein.

In certain embodiments, the Q heterocyclyl is selected from pyrimidin-2-one-4-thione, pyrimidine-2-thione-4-one, pyrimidine-2,4-dithione, 4-aminopyrimidine-2-thione, 5-fluoropyrimidin-2-one-4-thione, 5-fluoropyrimidine-2-thione-4-one, 5-fluoropyrimidine-2,4-dithione, 4-amino-5-fluoropyrimidine-2-thione, 2-amino-purin-6-thione, 2-amino-7-deaza-purin-6-thione or 2-amino-7-deaza-7-substituted-purin-6-thione.

In preferred embodiments, U is O and Q is a pyrimidine with at least one thione, thiol or thioether at the 2 and/or 4-position of said pyrimidine. In other preferred embodiments, U is S and Q is a pyrimidine with at least one thione, thiol or thioether at the 2 and/or 4 position of said pyrimidine.

In certain embodiments, the disclosure relates to a compound of the following formulae:

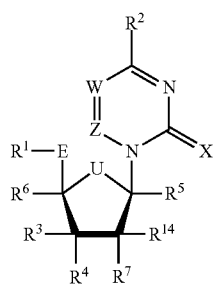

Formula Ip

-continued

Formula Iq

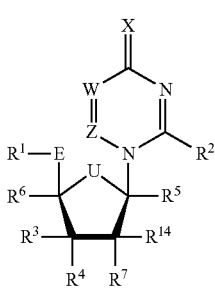

Formula Ir

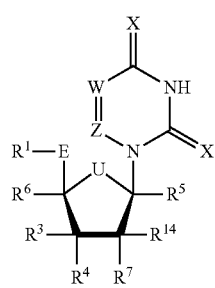

or pharmaceutically acceptable salts thereof, wherein
$R^5$ is H or D;
U is O or S;
E is $CH_2$ or $CD_2$;
$R^1$ is one of the formula:

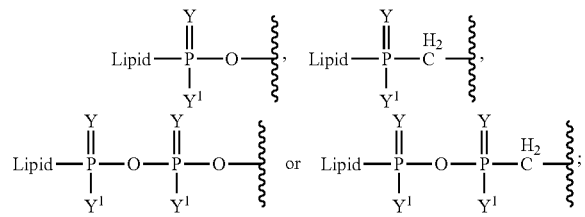

Y is O or S;
$Y^1$ is OH or $BH_3\text{-}M^+$;
Lipid is as described herein;
each X is independently O, S, NH, $NR^8$, NHOH, $NR^8OH$, $NHOR^8$, or $NR^8OR^8$;
$R^2$ is OH, SH, $NH_2$, $OR^8$, $SR^8$, $NHR^8$, NHOH, $NR^8OH$, $NHOR^8$, or $NR^8OR^8$;
 wherein in Formula Ip and Iq, one of X is S or $R^2$ is $SR^8$, or both X is S and $R^2$ is $SR^8$;
 wherein in Formula Ir, at least one X is S;
W is CH, N, or $CR^8$;
Z is CH, N, or $CR^8$;
$R^8$ is methyl, trifluoromethyl, fluoro, iodo, alkenyl, alkynyl, vinyl, allyl, halogen, halogentated alkyl, hydroxyl alkyl, acyl, lipid, geranyl, $C_{1-22}$ alkyl optionally substituted with one or more, the same or different, $R^{10}$;
$R^3$, $R^4$, $R^6$, $R^7$ and $R^{14}$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^{10}$;
each $R^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl.

In certain embodiments, U is S and Y and Z are CH.
In other embodiments, U is O and Y and Z are CH.
In certain embodiments, the lipid is a sphingolipid having the formula:

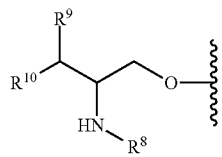

wherein,
$R^8$ of the sphingolipid is hydrogen, alkyl, $C(=O)R^{12}$, $C(=O)OR^{12}$, or $C(=O)NHR^{12}$;
$R^9$ of the sphingolipid is hydrogen, fluoro, $OR^{12}$, $OC(=O)R^{12}$, $OC(=O)OR^{12}$, or $OC(=O)NHR^{12}$;
$R^{10}$ of the sphingolipid is a saturated or unsaturated alkyl chain of greater than 6 and less than 22 carbons optionally substituted with one or more halogen or hydroxy or a structure of the following formula:

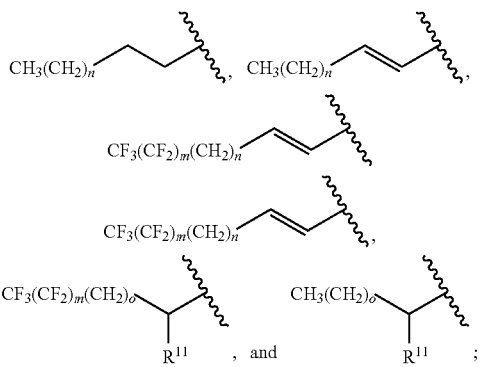

n is 8 to 14 or less than or equal to 8 to less than or equal to 14, o is 9 to 15 or less than or equal to 9 to less than or equal to 15, the total or m and n is 8 to 14 or less than or equal to 8 to less than or equal to 14, the total of m and o is 9 to 15 or less than or equal to 9 to less than or equal to 15; or

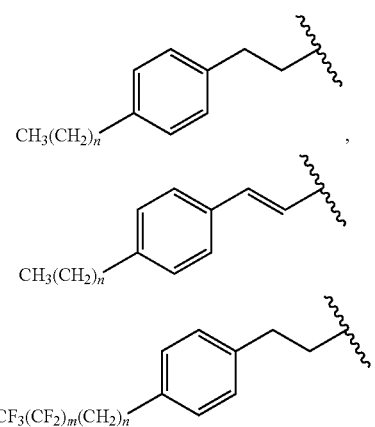

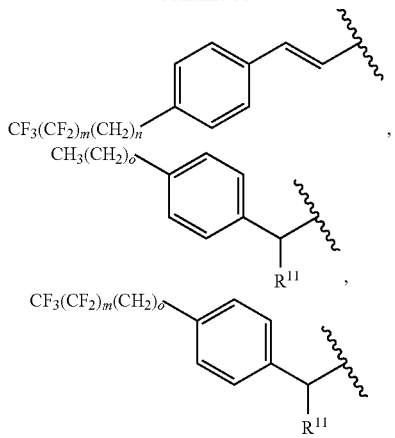

n is 4 to 10 or less than or equal to 4 to less than or equal to 10, o is 5 to 11 or less than or equal to 5 to less than or equal to 11, the total of m and n is 4 to 10 or less than or equal to 4 to less than or equal to 10, and the total of m and o is 5 to 11 or less than or equal to 5 to less than or equal to 11; or

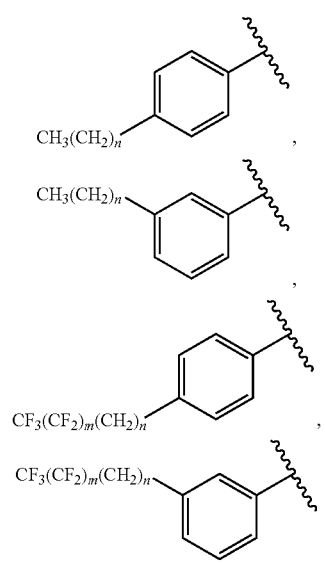

n is 6 to 12 or n is less than or equal to 6 to less than or equal to 12, the total of m and n is 6 to 12 or n is less than or equal to 6 to less than or equal to 12;

$R^{11}$ of the sphingolipid is $OR^{12}$, $OC(=O)R^{12}$, $OC(=O)OR^{12}$, or $OC(=O)NHR^{12}$;

$R^{12}$ of the sphingolipid is hydrogen, a branched or strait chain $C_{1-12}$alkyl, $C_{13-22}$alkyl, cycloalkyl, or aryl selected from benzyl or phenyl, wherein the aryl is optionally substituted with one or more, the same or different $R^{13}$; and $R^{13}$ of the sphingolipid is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^{12}$ of the sphingolipid is H, alkyl, methyl, ethyl, propyl, n-butyl, branched alkyl, isopropyl, 2-butyl, 1-ethylpropyl,1-propylbutyl, cycloalkyl, cyclopropyl, cyclobutyl, cyclopentyl, cyclohexyl, benzyl, phenyl, monosubstituted phenyl, disubstituted phenyl, trisubstituted phenyl, or saturated or unsaturated C12-C19 long chain alkyl.

In certain embodiments, the sphingolipid has the formula:

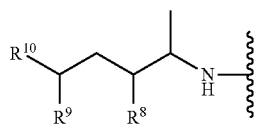

wherein, $R^8$ of the sphingolipid is hydrogen, hydroxy, fluoro, $OR^{12}$, $OC(=O)R^{12}$, $OC(=O)OR^{12}$, or $OC(=O)NHR^{12}$;

$R^9$ of the sphingolipid is hydrogen, hydroxy, fluoro, $OR^{12}$, $OC(=O)R^{12}$, $OC(=O)OR^{12}$, or $OC(=O)NHR^{12}$;

$R^{10}$ of the sphingolipid is a saturated or unsaturated alkyl chain of greater than 6 and less than 22 carbons optionally substituted with one or more halogens or a structure of the following formula:

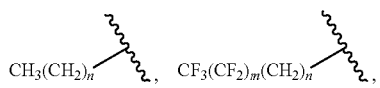

n is 8 to 14 or less than or equal to 8 to less than or equal to 14, the total or m and n is 8 to 14 or less than or equal to 8 to less than or equal to 14;

$R^{12}$ of the sphingolipid is hydrogen, a branched or strait chain $C_{1-12}$alkyl, $C_{13-22}$alkyl, cycloalkyl, or aryl selected from benzyl or phenyl, wherein the aryl is optionally substituted with one or more, the same or different $R^{13}$; and $R^{13}$ of the sphingolipid is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^{12}$ of the sphingolipid is H, alkyl, methyl, ethyl, propyl, n-butyl, branched alkyl, isopropyl, 2-butyl, 1-ethylpropyl,1-propylbutyl, cycloalkyl, cyclopropyl, cyclobutyl, cyclopentyl, cyclohexyl, benzyl, phenyl, monosubstituted phenyl, disubstituted phenyl, trisubstituted phenyl, or saturated or unsaturated $C_{12}$-$C_{19}$ long chain alkyl.

In one embodiment, $R^5$ is H. In another embodiment, $R^4$ is hydroxyl. In still another embodiment, $R^7$ is hydroxyl. In yet another embodiment, $R^{14}$ is methyl. In a further embodiment, $R^3$ is hydrogen. In another embodiment, $R^1$ is

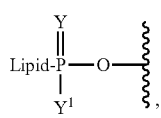
wherein Y is O, Y¹ is —OH and lipid is a sphingolipid. In another embodiment, E is CH₂. In exemplary embodiments, the compound is selected from:
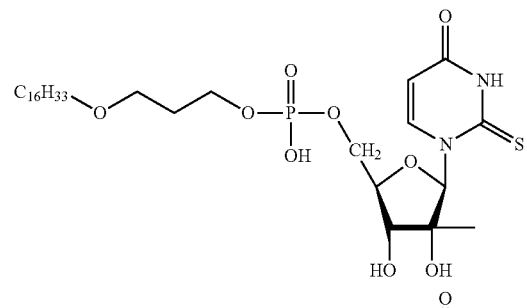
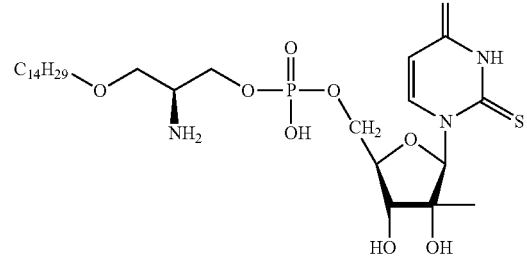
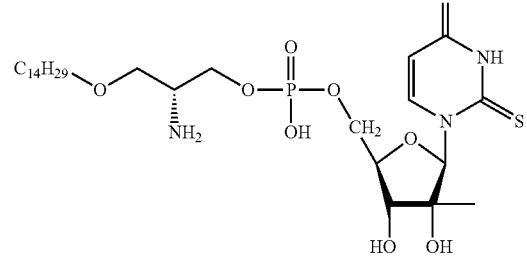
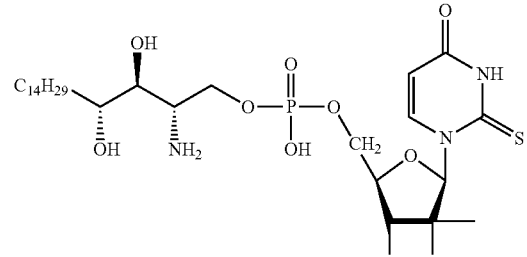
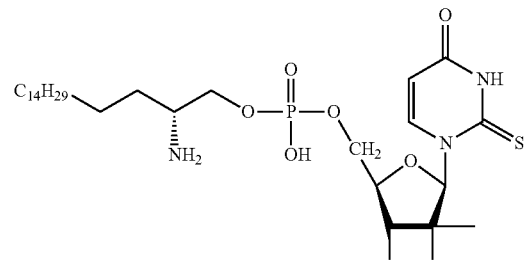
-continued
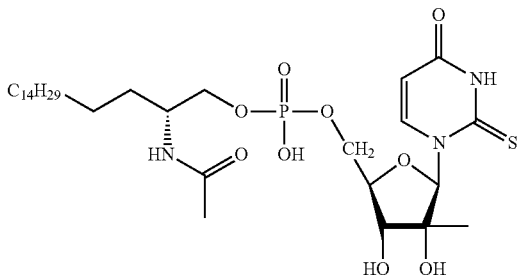
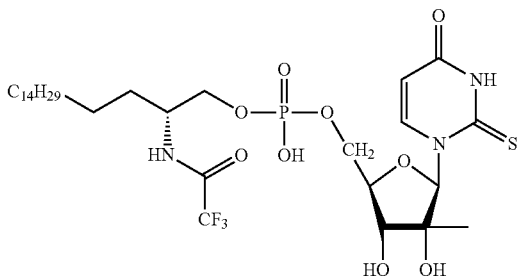
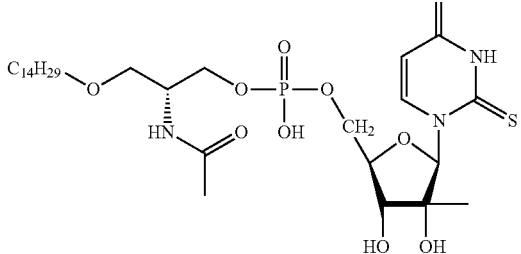
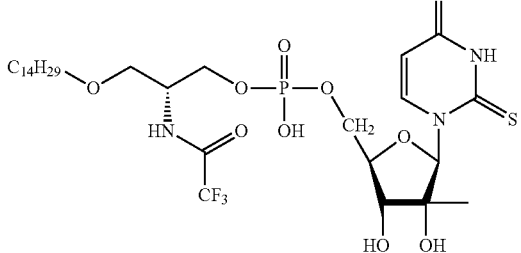
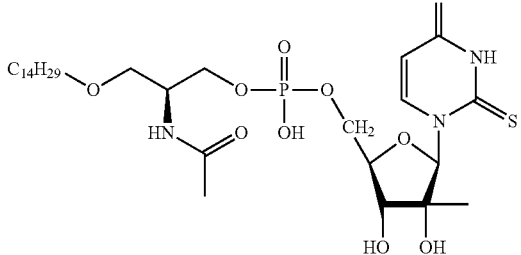
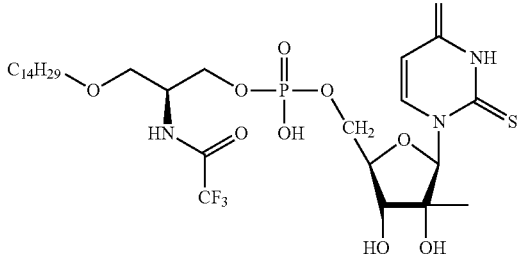

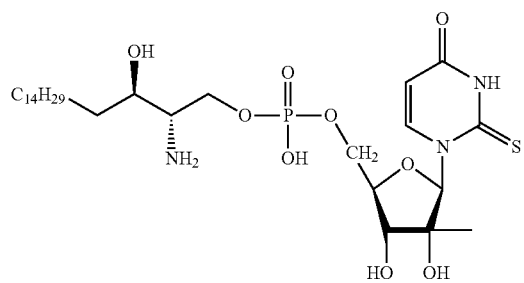


In one embodiment, $R^5$ is H. In another embodiment, $R^4$ is hydroxyl. In still another embodiment, $R^7$ is hydroxyl. In yet another embodiment, $R^{14}$ is methyl. In a further embodiment, $R^3$ is hydrogen. In another embodiment, $R^1$ is

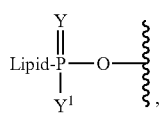

wherein Y is O, $Y^1$ is —OH and lipid is a sphingolipid. In another embodiment, E is $CD_2$. In exemplary embodiments, the compound is selected from:

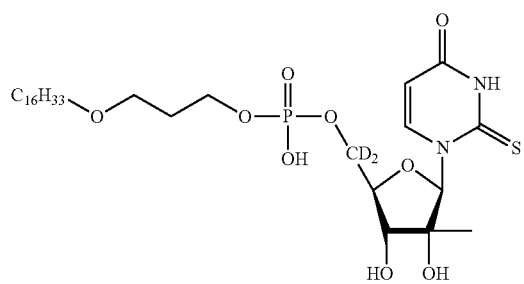


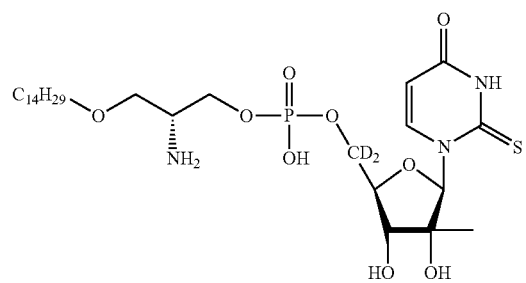

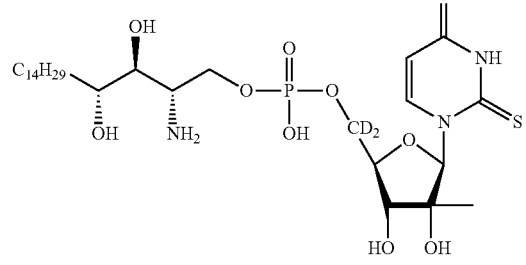

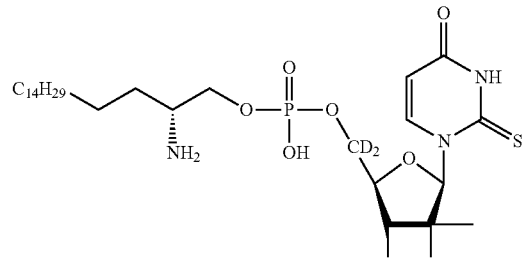

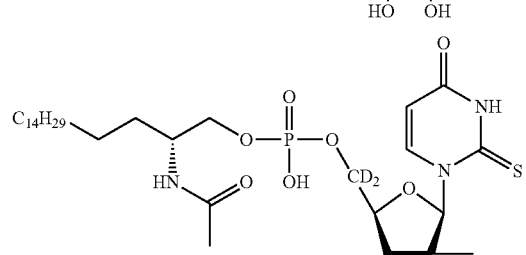

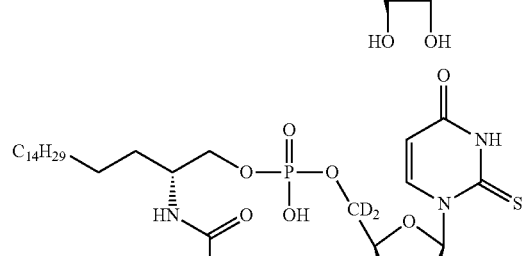

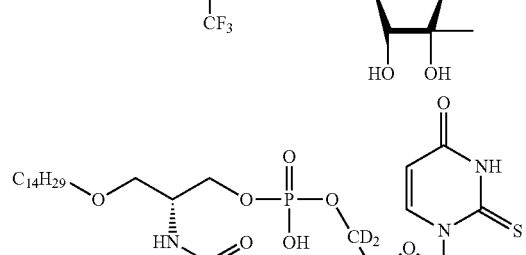

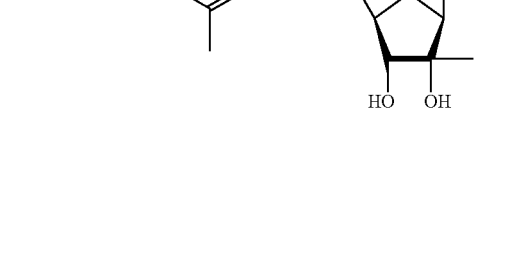

-continued

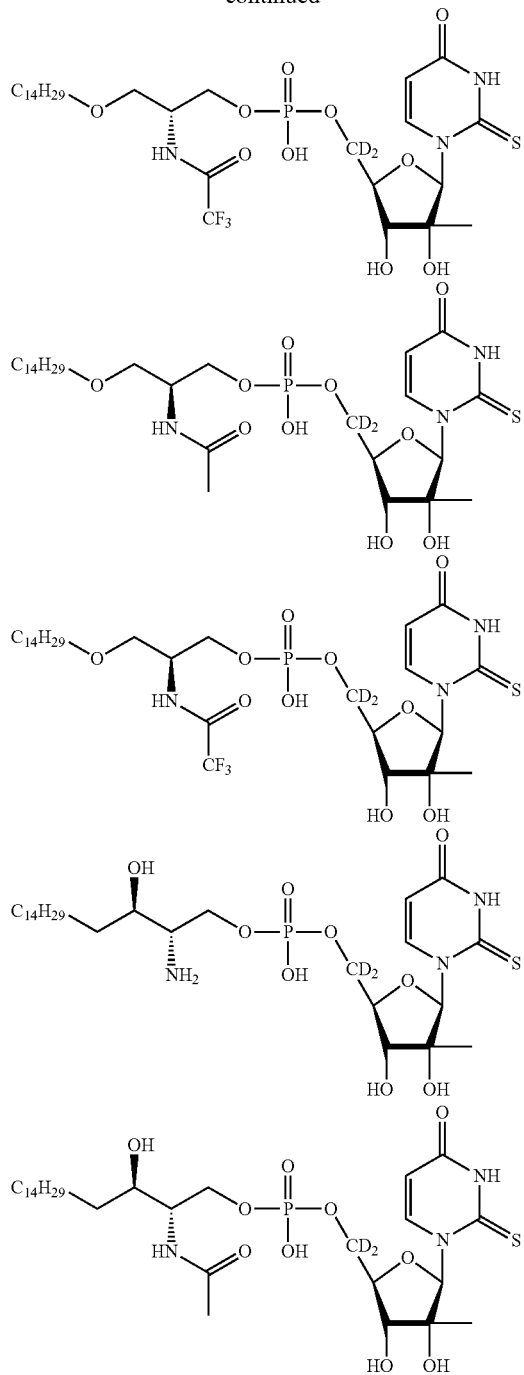

In certain embodiments, the disclosure relates to a compound of the following formula:

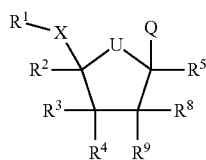

Formula Is or pharmaceutically acceptable salts thereof, wherein

U is O or S;

X is $CH_2$ or $CD_2$;

$R^5$ is H or D;

$R^1$ is hydroxyl;

Q is a heterocyclyl comprising two or more nitrogen heteroatoms substituted with at least one thione, thiol or thioether, wherein Q is optionally substituted with one or more, the same or different alkyl, halogen, or cycloalkyl;

$R^2$, $R^3$, $R^4$, $R^8$ and $R^9$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^m$;

each $R^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl.

In certain embodiments, the Q heterocyclyl is selected from pyrimidin-2-one-4-thione, pyrimidine-2-thione-4-one, pyrimidine-2,4-dithione, 4-aminopyrimidine-2-thione, 5-fluoropyrimidin-2-one-4-thione, 5-fluoropyrimidine-2-thione-4-one, 5-fluoropyrimidine-2,4-dithione, 4-amino-5-fluoropyrimidine-2-thione, 2-amino-purin-6-thione, 2-amino-7-deaza-purin-6-thione or 2-amino-7-deaza-7-substituted-purin-6-thione.

In preferred embodiments, U is O and Q is a pyrimidine with at least one thione, thiol or thioether at the 2 and/or 4-position of said pyrimidine. In other preferred embodiments, U is S and Q is a pyrimidine with at least one thione, thiol or thioether at the 2 and/or 4 position of said pyrimidine.

In certain embodiments, $R^8$ and $R^9$ are selected from H, fluoro, methyl, fluoromethyl, hydroxymethyl, difluoromethyl, trifluoromethyl, acetylenyl, ethyl, vinyl and cyano.

In certain embodiments, the disclosure relates to compounds of the following formulae:

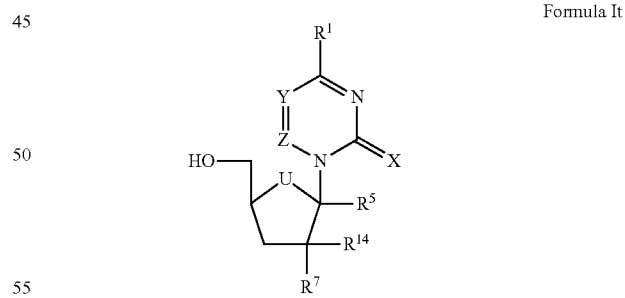

Formula It

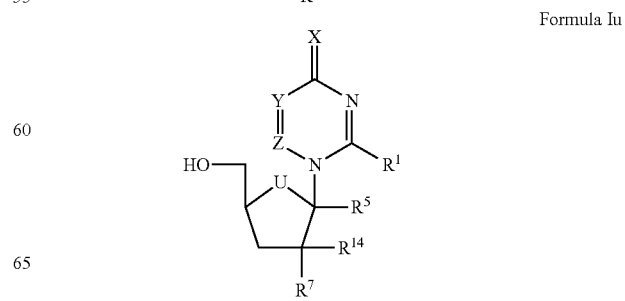

Formula Iu

Formula Iv

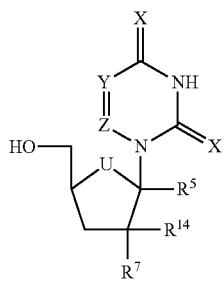

or a pharmaceutically acceptable salt thereof wherein, $R^5$ is H or D;

U is O or S;

each X is independently O, S, NH, $NR^8$, NHOH, $NR^8OH$, $NHOR^8$, or $NR^8OR^8$;

$R^1$ is OH, SH, $NH_2$, $OR^8$, $SR^8$, $NHR^8$, NHOH, $NR^8OH$, $NHOR^8$, or $NR^8OR^8$;

wherein in Formula It and Iu, one of X is S or $R^1$ is $SR^8$, or both X is S and $R^1$ is $SR^8$;

wherein in Formula Iv, at least one X is S;

Y is CH, N, or $CR^8$;

Z is CH, N, or $CR^8$;

$R^7$ and $R^{14}$ are each independently selected from are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^{10}$;

each $R^8$ is independently selected from methyl, trifluoromethyl, fluoro, iodo, alkenyl, alkynyl, vinyl, allyl, halogen, halogentated alkyl, hydroxyl alkyl, acyl, lipid, geranyl, $C_{1-22}$ alkyl optionally substituted with one or more, the same or different, $R^{10}$;

each $R^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl.

In certain embodiments, U is S and Y and Z are CH.

In other embodiments, U is O and Y and Z are CH.

In certain embodiments, $R^5$ is H. In other embodiments, $R^7$ is F and $R^{14}$ is H. In exemplary embodiments, the compound is selected from:

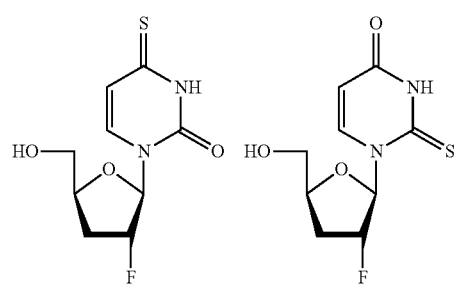

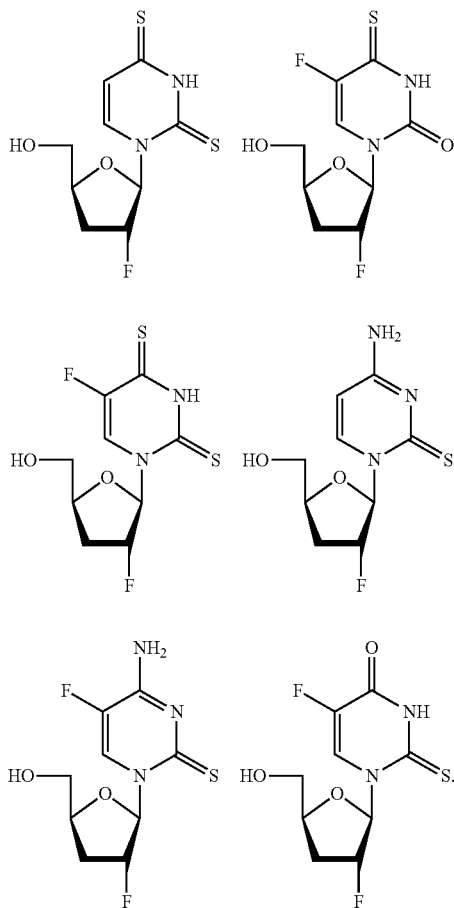

In certain embodiments, $R^5$ is H. In other embodiments, $R^7$ is F and $R^{14}$ is methyl. In exemplary embodiments, the compound is selected from:

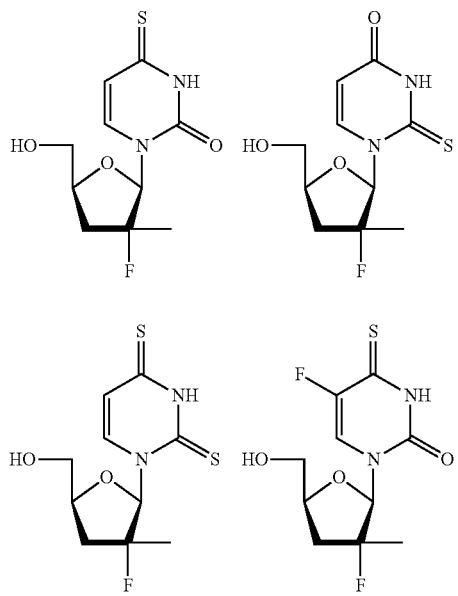

-continued

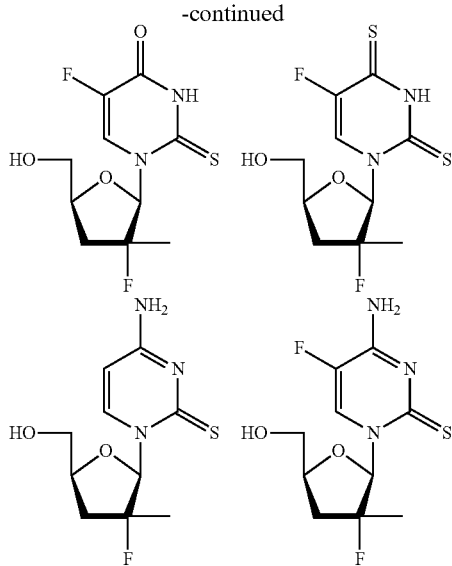

In certain embodiments, the disclosure relates to compounds of the following formula:

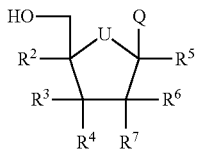

Formula Iw or a pharmaceutically acceptable salt thereof wherein,
U is O or S;
Q is a heterocyclyl comprising two or more nitrogen heteroatoms substituted with at least one thione, thiol or thioether, wherein Q is optionally substituted with one or more, the same or different alkyl, halogen, cycloalkyl;
$R^2$, $R^3$, $R^4$, $R^6$ and $R^7$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^9$;
each $R^9$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;
and $R^5$ is H or D.

In certain embodiments, the Q heterocyclyl is selected from pyrimidin-2-one-4-thione, pyrimidine-2-thione-4-one, pyrimidine-2,4-dithione, 4-aminopyrimidine-2-thione, 5-fluoropyrimidin-2-one-4-thione, 5-fluoropyrimidine-2-thione-4-one, 5-fluoropyrimidine-2,4-dithione, 4-amino-5-fluoropyrimidine-2-thione, 2-amino-purin-6-thione, 2-amino-7-deaza-purin-6-thione or 2-amino-7-deaza-7-substituted-purin-6-thione.

In preferred embodiments, U is O and Q is a pyrimidine with at least one thione, thiol or thioether at the 2 and/or 4-position of said pyrimidine. In other preferred embodiments, U is S and Q is a pyrimidine with at least one thione, thiol or thioether at the 2 and/or 4 position of said pyrimidine.

In certain embodiments, the disclosure relates to compounds of one of the following formulae:

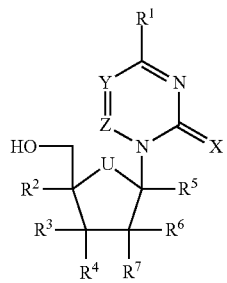

Formula Ix

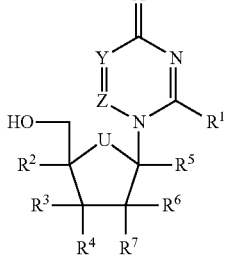

Formula Iy

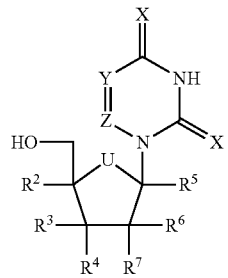

Formula Iz or a pharmaceutically acceptable salt thereof, wherein
U is O or S;
$R^5$ is H or D;
each X is independently O, S, NH, $NR^8$, NHOH, $NR^8OH$, $NHOR^8$, or $NR^8OR^8$;
$R^1$ is OH, SH, $NH_2$, $OR^8$, $SR^8$, $NHR^8$, NHOH, $NR^8OH$, $NHOR^8$, or $NR^8OR^8$;
wherein in Formula Ix and Iy, one of X is S or R' is $SR^8$, or both X is S and $R^1$ is $SR^8$;
wherein in Formula Iz, at least one X is S;
Y is CH, N, or $CR^8$;
Z is CH, N, or $CR^8$;
$R^2$, $R^3$, $R^4$, $R^6$ and $R^7$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^9$;
each $R^8$ is independently selected from methyl, trifluoromethyl, fluoro, iodo, alkenyl, alkynyl, vinyl, allyl, halogen, halogentated alkyl, hydroxyl alkyl, acyl, lipid, geranyl, $C_{1-22}$ alkyl optionally substituted with one or more, the same or different, $R^9$;
each $R^9$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl.

In certain embodiments, U is S and Y and Z are CH.
In other embodiments, U is O and Y and Z are CH.
In one embodiment, $R^2$ is H. In another embodiment, $R^3$ is H. In still another embodiment, $R^4$ is hydroxyl. In a further embodiment, $R^5$ is H. In yet another embodiment, $R^6$ is methyl. In a still further embodiment, $R^7$ is fluoro. In exemplary embodiments, the compound is selected from the group consisting of:

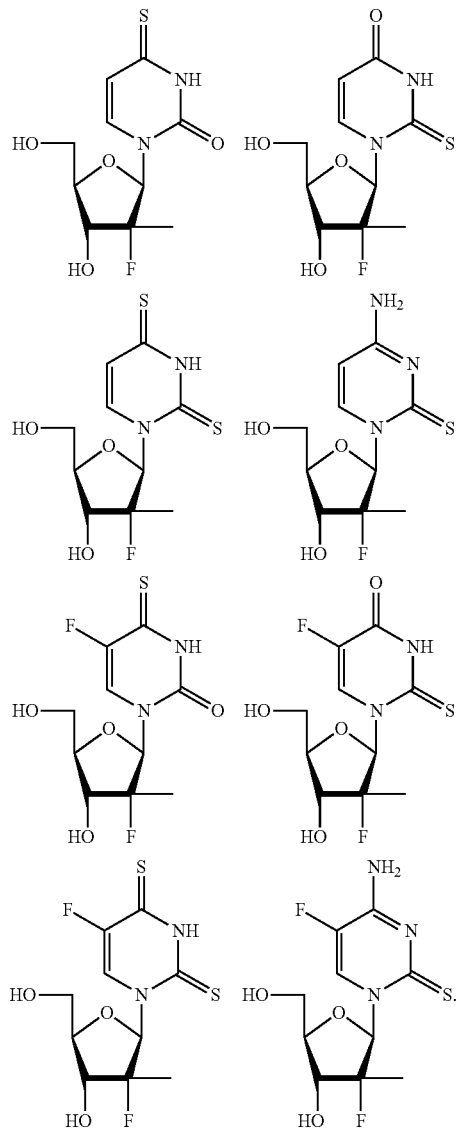

In one embodiment, $R^2$ is H. In another embodiment, $R^3$ is H. In still another embodiment, $R^4$ is hydroxyl. In a further embodiment, $R^5$ is H. In yet another embodiment, $R^6$ is trifluoromethyl. In a still further embodiment, $R^7$ is fluoro. In exemplary embodiments, the compound is selected from the group consisting of:

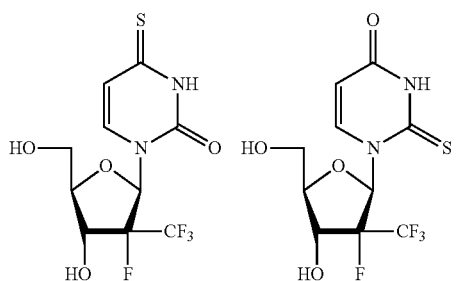

-continued

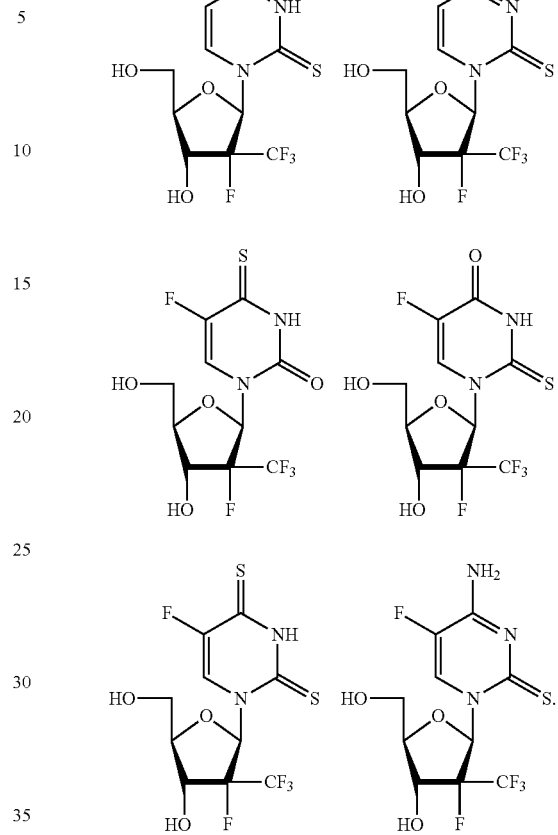

In one embodiment, $R^2$ is H. In another embodiment, $R^3$ is H. In still another embodiment, $R^4$ is hydroxyl. In a further embodiment, $R^5$ is H. In yet another embodiment, $R^6$ is C≡CH. In a still further embodiment, $R^7$ is fluoro. In exemplary embodiments, the compound is selected from the group consisting of:

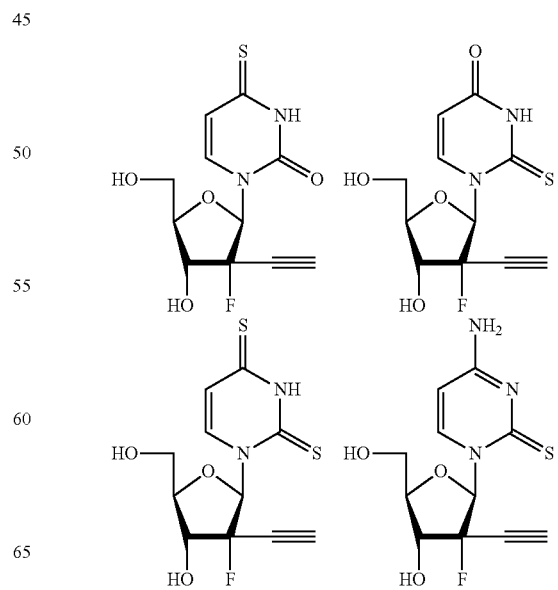

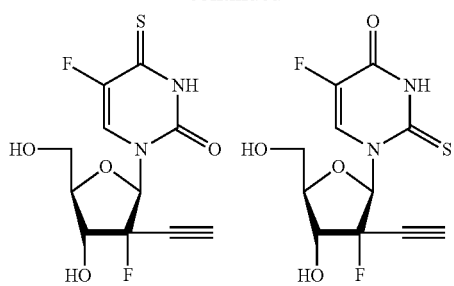

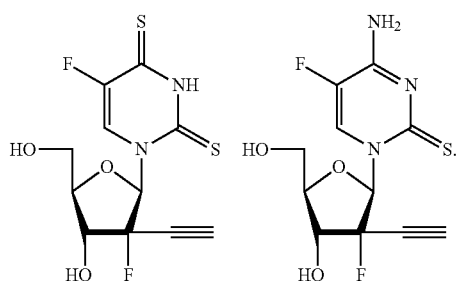

In one embodiment, $R^2$ is H. In another embodiment, $R^3$ is H. In still another embodiment, $R^4$ is hydroxyl. In a further embodiment, $R^5$ is H. In yet another embodiment, $R^6$ is $CH_2F$. In a still further another embodiment, $R^7$ is fluoro. In exemplary embodiments, the compound is selected from the group consisting of:

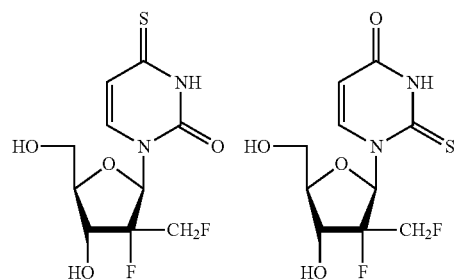

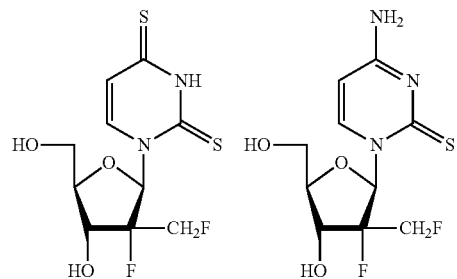

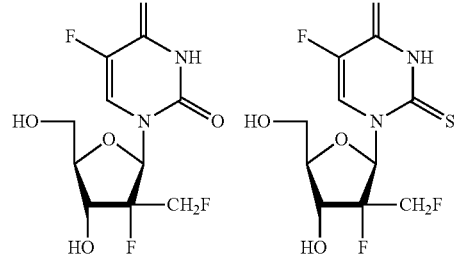

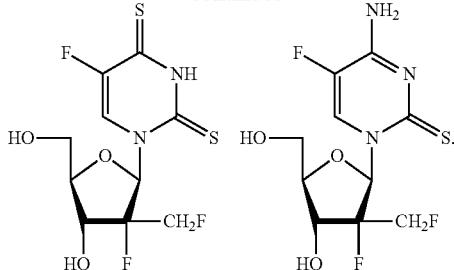

In one embodiment, $R^2$ is H. In another embodiment, $R^3$ is H. In still another embodiment, $R^4$ is H. In a further embodiment, $R^5$ is H. In yet another embodiment, $R^6$ is H. In a still further embodiment, $R^7$ is fluoro. In exemplary embodiments, the compound is selected from the group consisting of:

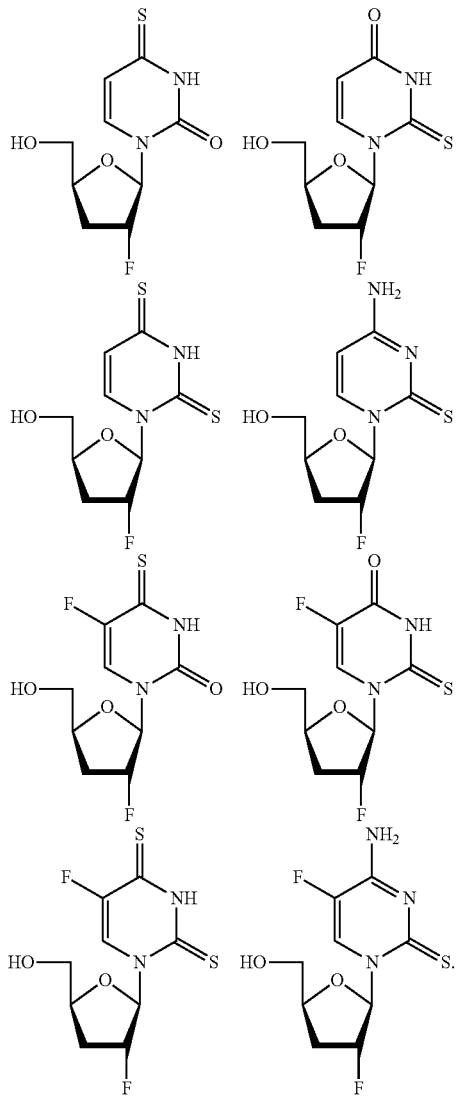

In one embodiment, $R^2$ is H. In another embodiment, $R^3$ is H. In still another embodiment, $R^4$ is H. In a further embodiment, $R^5$ is H. In yet another embodiment, $R^6$ is methyl. In a still further embodiment, $R^7$ is fluoro. In exemplary embodiments, the compound is selected from the group consisting of:

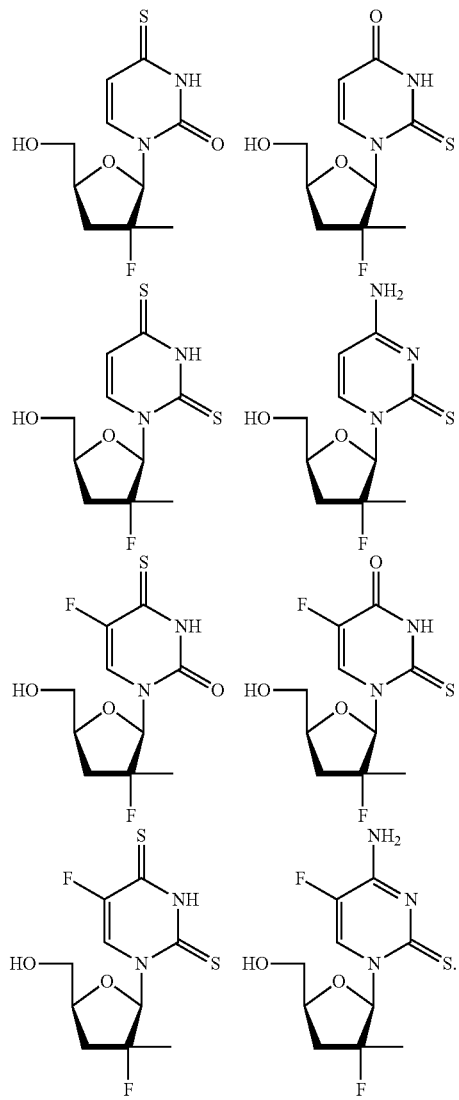

In one embodiment, $R^2$ is H. In another embodiment, $R^3$ is H. In still another embodiment, $R^4$ is H. In a further embodiment, $R^5$ is H. In yet another embodiment, $R^6$ is trifluoromethyl. In a still further embodiment, $R^7$ is fluoro. In exemplary embodiments, the compound is selected from the group consisting of:

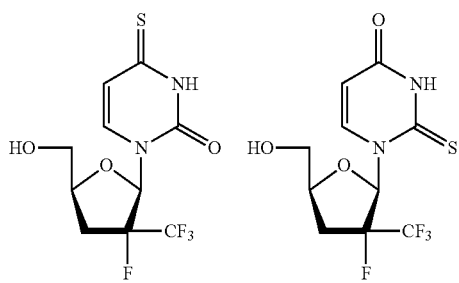

-continued

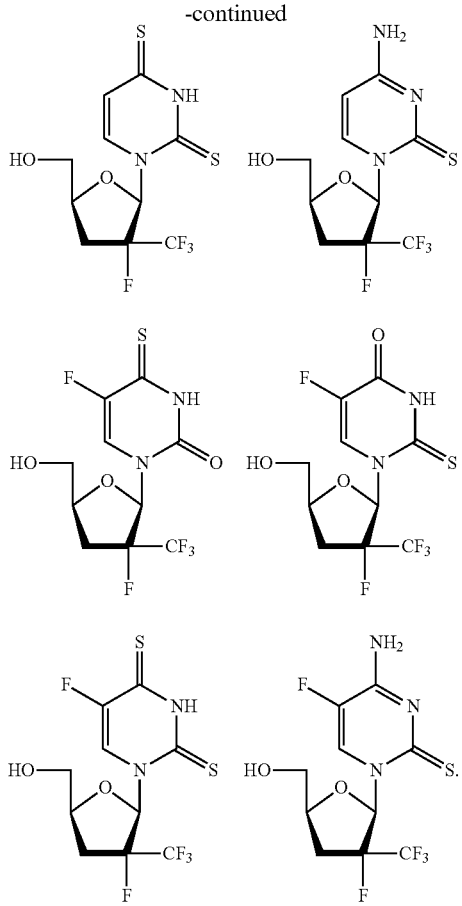

In one embodiment, $R^2$ is H. In another embodiment, $R^3$ is H. In still another embodiment, $R^4$ is hydroxyl. In a further embodiment, $R^5$ is H. In yet another embodiment, $R^6$ is methyl. In a still further embodiment, $R^7$ is hydroxyl. In exemplary embodiments, the compound is selected from the group consisting of:

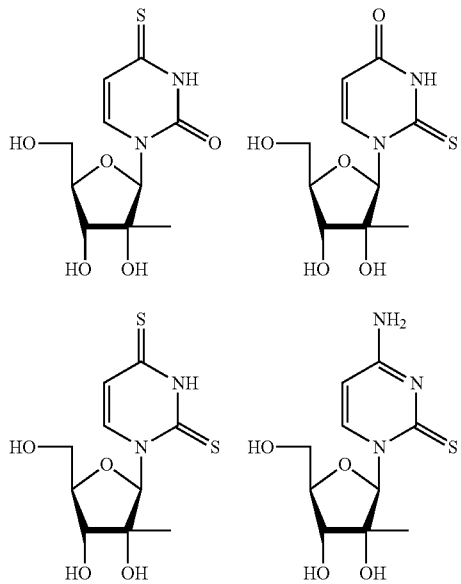

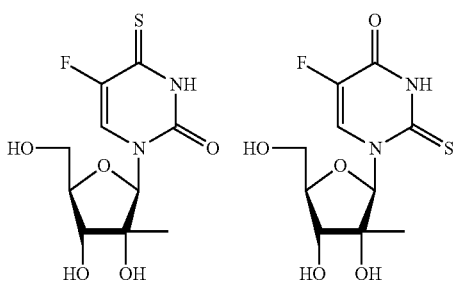

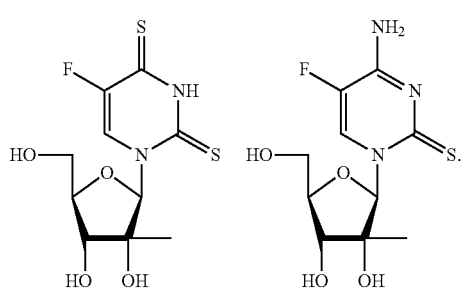

In one embodiment, $R^2$ is H. In another embodiment, $R^3$ is H. In still another embodiment, $R^4$ is hydroxyl. In a further embodiment, $R^5$ is H. In yet another embodiment, $R^6$ is trifluoromethyl. In a still further embodiment, $R^7$ is hydroxyl. In exemplary embodiments, the compound is selected from the group consisting of:

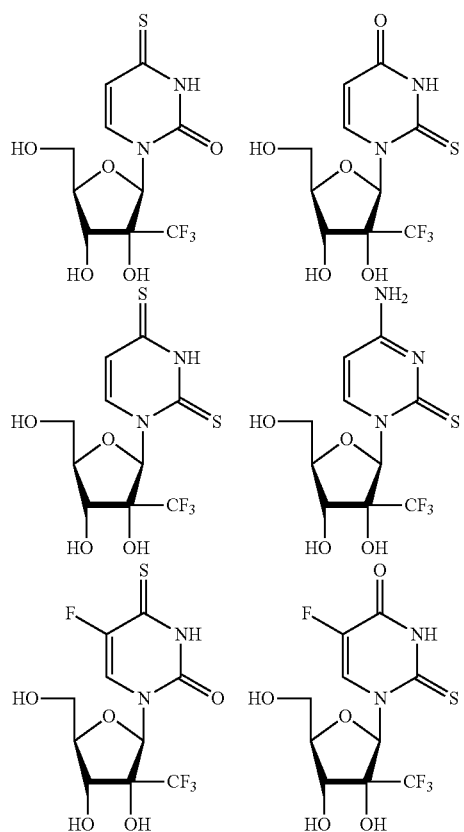

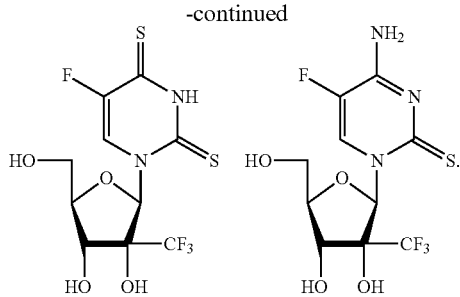

In one embodiment, $R^2$ is H. In another embodiment, $R^3$ is H. In still another embodiment, $R^4$ is hydroxyl. In a further embodiment, $R^5$ is H. In yet another embodiment, $R^6$ is C≡CH. In a still further embodiment, $R^7$ is hydroxyl. In exemplary embodiments, the compound is selected from the group consisting of:

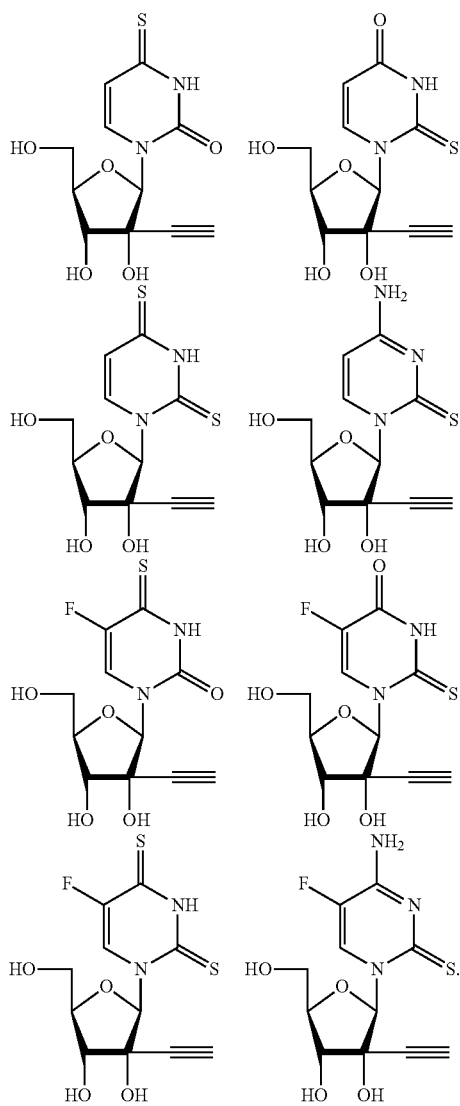

In one embodiment, $R^2$ is H. In another embodiment, $R^3$ is H. In still another embodiment, $R^4$ is hydroxyl. In a further embodiment, $R^5$ is H. In yet another embodiment, $R^6$ is CH$_2$F. In a still further embodiment, R$^7$ is hydroxyl. In exemplary embodiments, the compound is selected from the group consisting of:

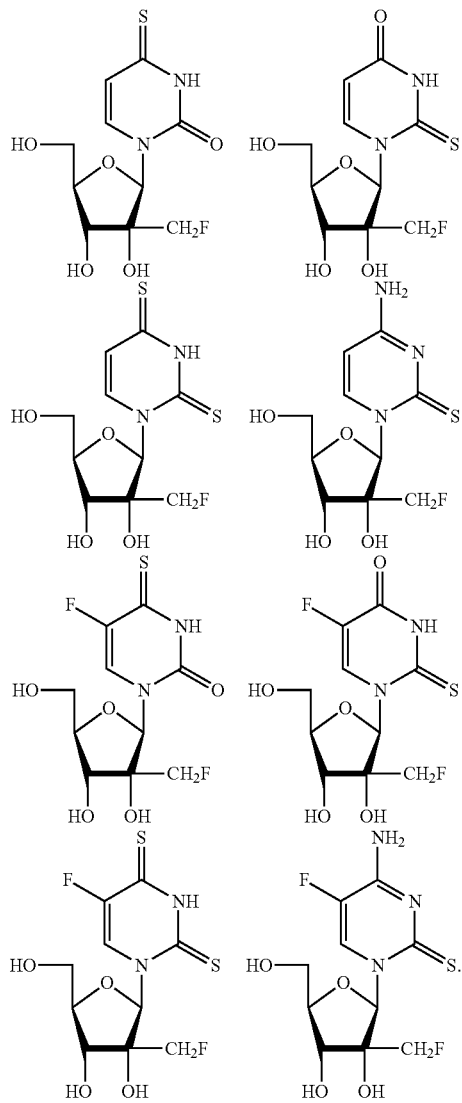

In one embodiment, R$^2$ is H. In another embodiment, R$^3$ is H. In still another embodiment, R$^4$ is hydroxyl. In a further embodiment, R$^5$ is H. In yet another embodiment, R$^6$ is methyl. In a still further embodiment, R$^7$ is H. In exemplary embodiments, the compound is selected from the group consisting of:

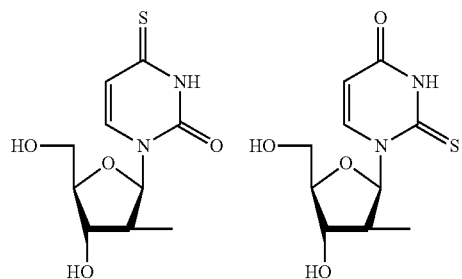

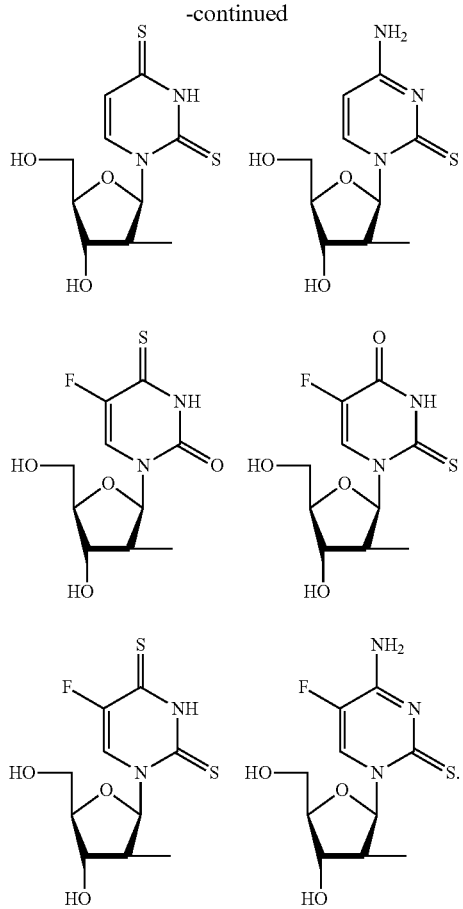

In one embodiment, R$^2$ is H. In another embodiment, R$^3$ is H. In still another embodiment, R$^4$ is hydroxyl. In a further embodiment, R$^5$ is H. In yet another embodiment, R$^6$ is trifluoromethyl. In a still further embodiment, R$^7$ is H. In exemplary embodiments, the compound is selected from the group consisting of:

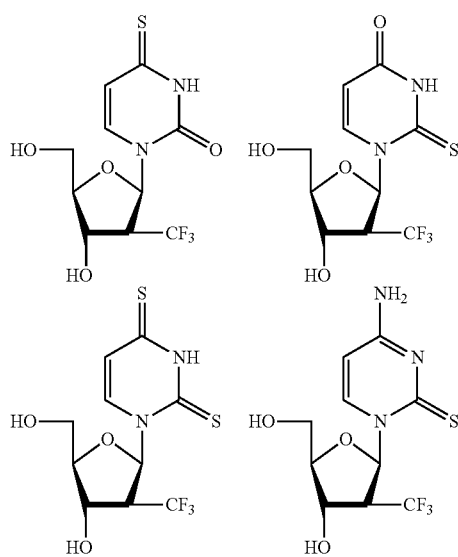

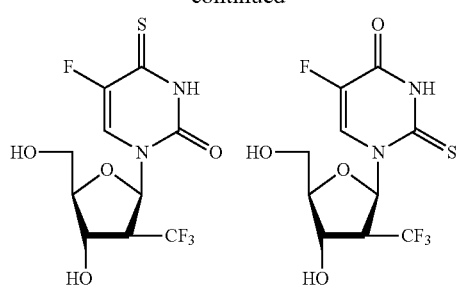

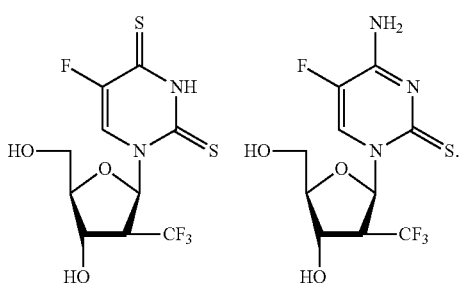

In one embodiment, $R^2$ is $N_3$. In another embodiment, $R^3$ is H. In still another embodiment, $R^4$ is hydroxyl. In a further embodiment, $R^5$ is H. In yet another embodiment, $R^6$ is H. In a still further embodiment, $R^7$ is hydroxyl. In exemplary embodiments, the compound is selected from the group consisting of:

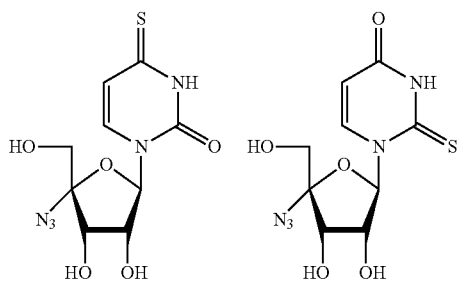

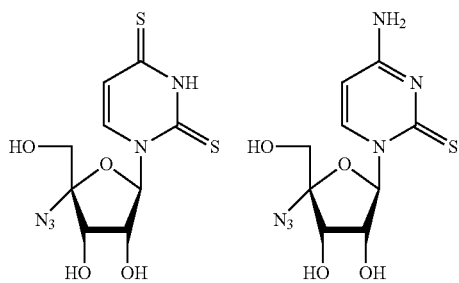

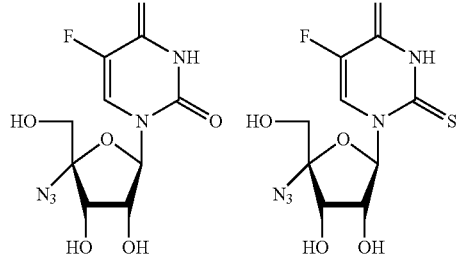

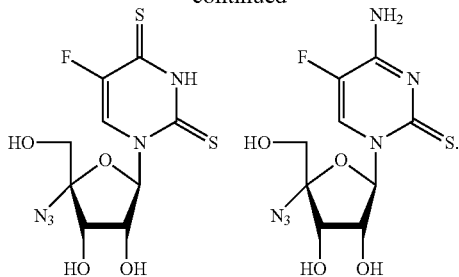

In one embodiment, $R^2$ is C≡CH. In another embodiment, $R^3$ is H. In still another embodiment, $R^4$ is hydroxyl. In a further embodiment, $R^5$ is H. In yet another embodiment, $R^6$ is H. In a still further embodiment, $R^7$ is hydroxyl. In exemplary embodiments, the compound is selected from the group consisting of:

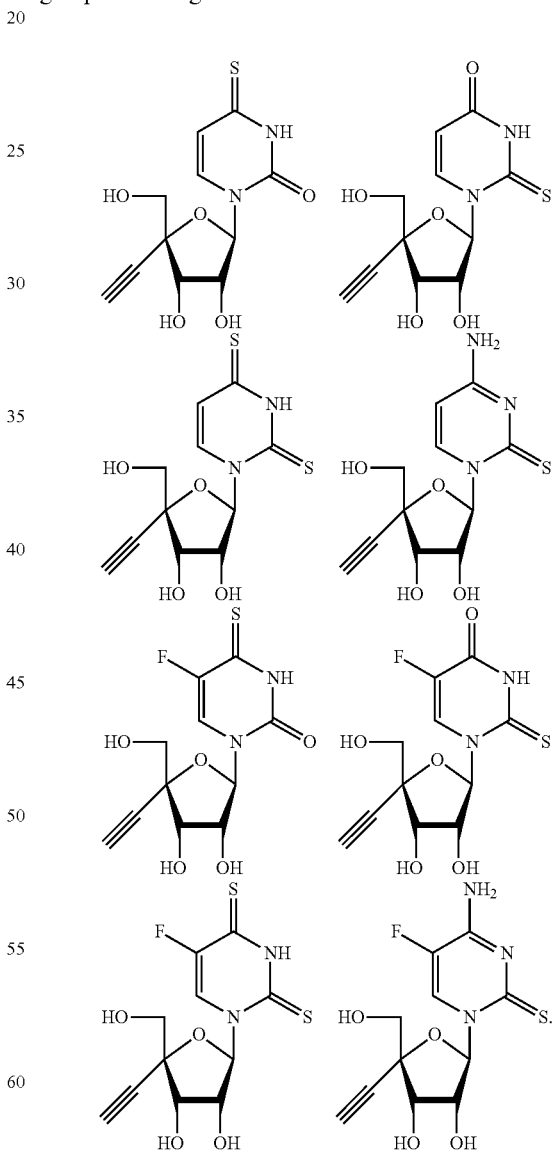

In one embodiment, $R^2$ is $CH_2F$. In another embodiment, $R^3$ is H. In still another embodiment, $R^4$ is hydroxyl. In a further embodiment, $R^5$ is H. In yet another embodiment, $R^6$ is H. In a still further embodiment, R⁷ is hydroxyl. In exemplary embodiments, the compound is selected from the group consisting of:

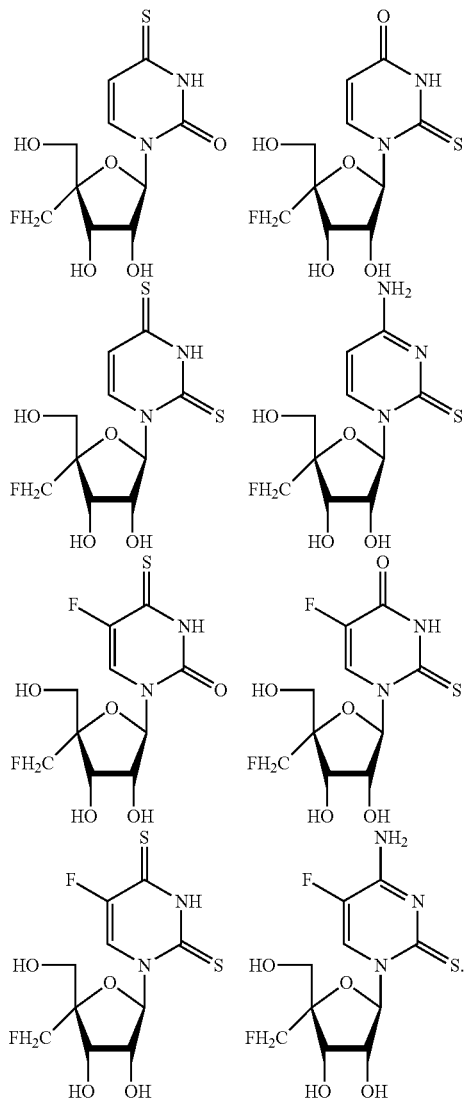

In one embodiment, R² is N₃. In another embodiment, R³ is H. In still another embodiment, R⁴ is hydroxyl. In a further embodiment, R⁵ is H. In yet another embodiment, R⁶ is H. In a still further embodiment, R⁷ is fluoro. In exemplary embodiments, the compound is selected from the group consisting of:

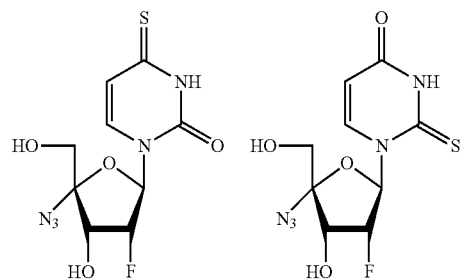

-continued

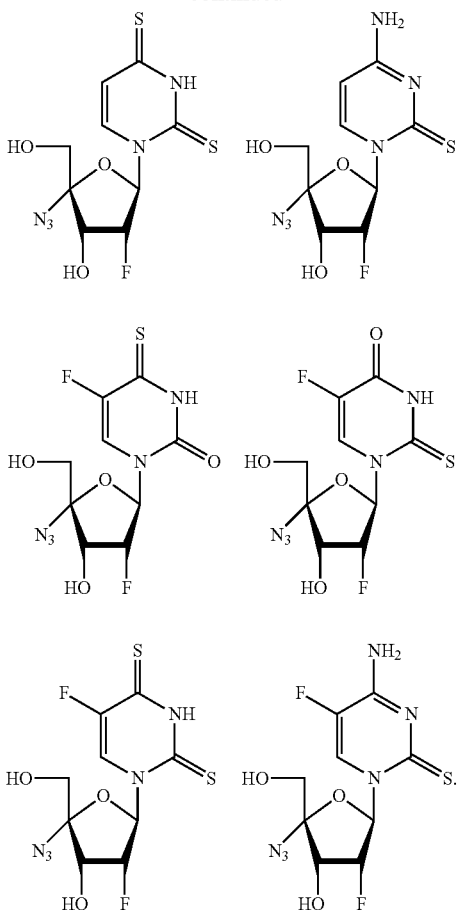

In one embodiment, R² is C≡CH. In another embodiment, R³ is H. In still another embodiment, R⁴ is hydroxyl. In a further embodiment, R⁵ is H. In yet another embodiment, R⁶ is H. In a still further embodiment, R⁷ is fluoro. In exemplary embodiments, the compound is selected from the group consisting of:

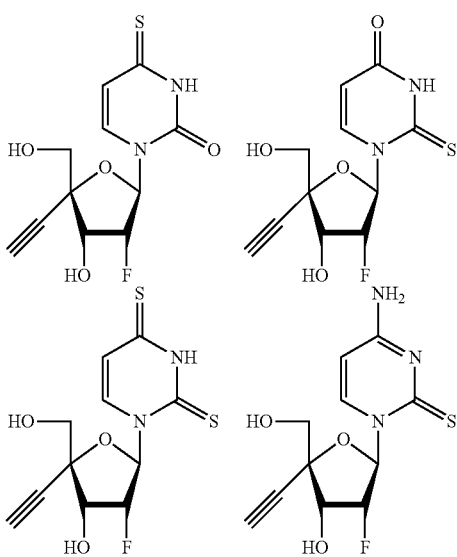

-continued

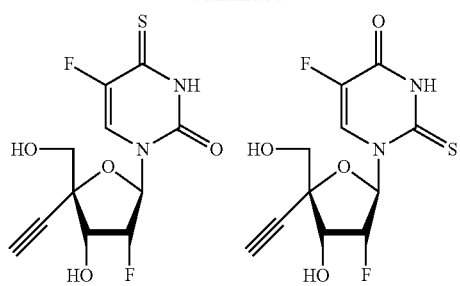

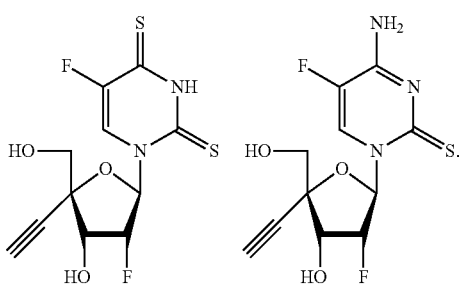

In one embodiment, $R^2$ is $CH_2F$. In another embodiment, $R^3$ is H. In still another embodiment, $R^4$ is hydroxyl. In a further embodiment, $R^5$ is H. In yet another embodiment, $R^6$ is H. In a still further embodiment, $R^7$ is fluoro. In exemplary embodiments, the compound is selected from the group consisting of:

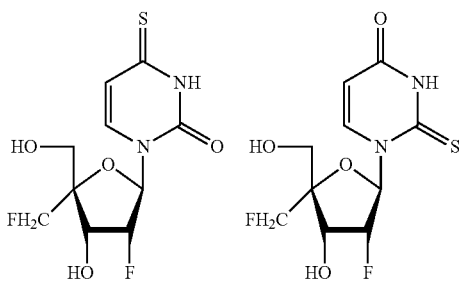

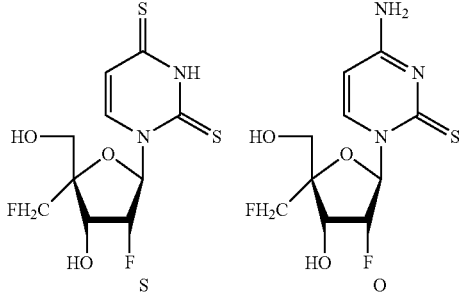

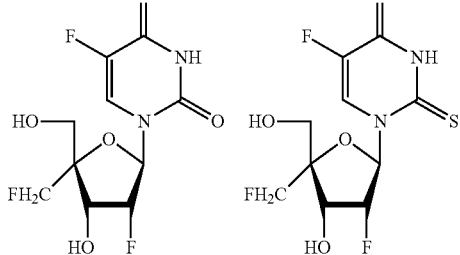

-continued

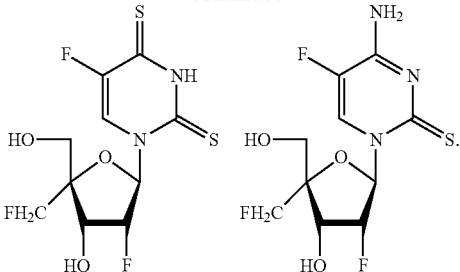

In one embodiment, $R^2$ is H. In another embodiment, $R^3$ is H. In still another embodiment, $R^4$ is fluoro. In a further embodiment, $R^5$ is H. In yet another embodiment, $R^6$ is H. In a still further embodiment, $R^7$ is hydroxyl. In exemplary embodiments, the compound is selected from the group consisting of:

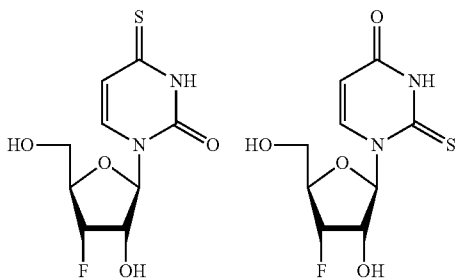

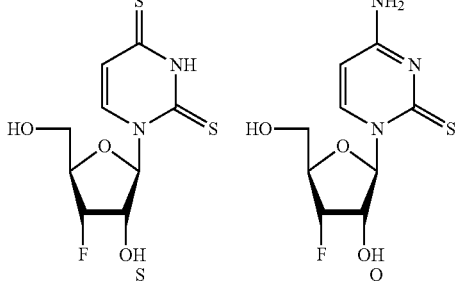

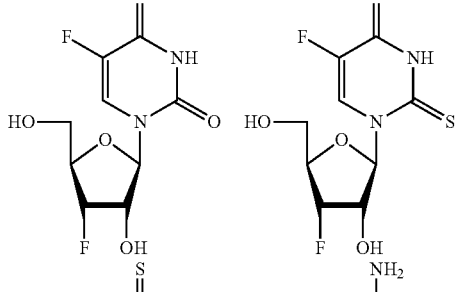

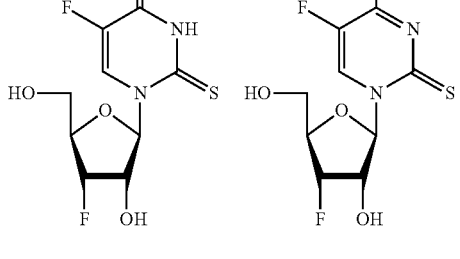

In one embodiment, $R^2$ is H. In another embodiment, $R^3$ is H. In still another embodiment, $R^4$ is fluoro. In a further embodiment, $R^5$ is H. In yet another embodiment, $R^6$ is methyl. In a still further embodiment, $R^7$ is hydroxyl. In exemplary embodiments, the compound is selected from the group consisting of:

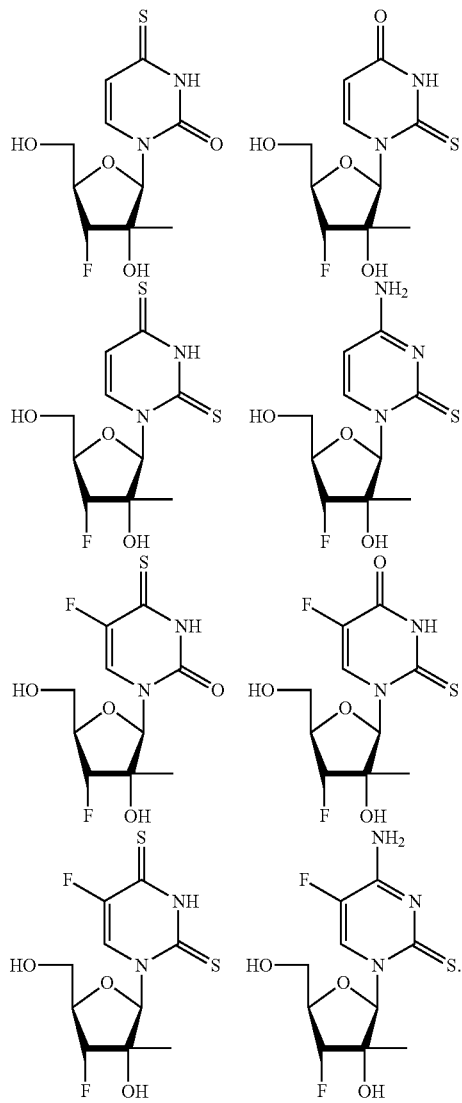

In one embodiment, $R^2$ is H. In another embodiment, $R^3$ is H. In still another embodiment, $R^4$ is fluoro. In a further embodiment, $R^5$ is H. In yet another embodiment, $R^6$ is C≡CH. In a still further embodiment, $R^7$ is hydroxyl. In exemplary embodiments, the compound is selected from the group consisting of:

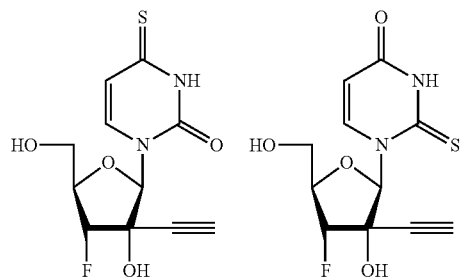

-continued

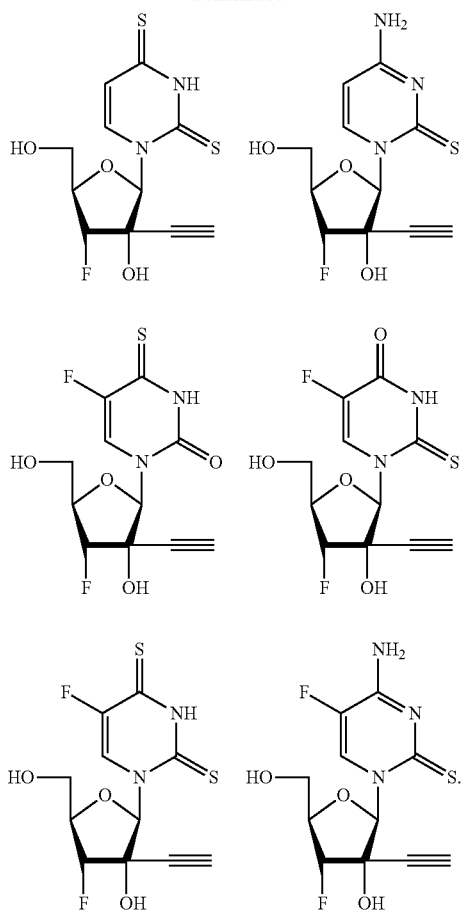

In one embodiment, $R^2$ is H. In another embodiment, $R^3$ is H. In still another embodiment, $R^4$ is fluoro. In a further embodiment, $R^5$ is H. In yet another embodiment, $R^6$ is $CH_2F$. In a still further embodiment, $R^7$ is hydroxyl. In exemplary embodiments, the compound is selected from the group consisting of:

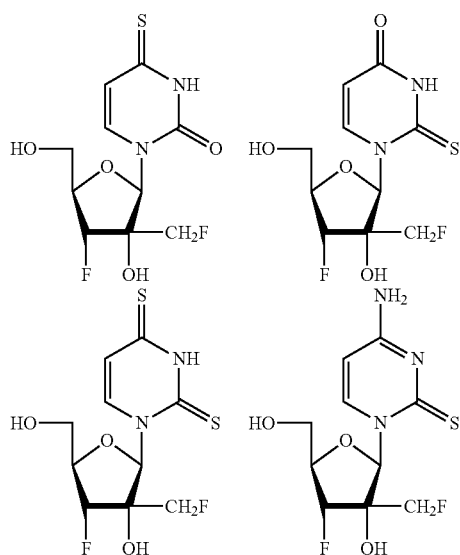

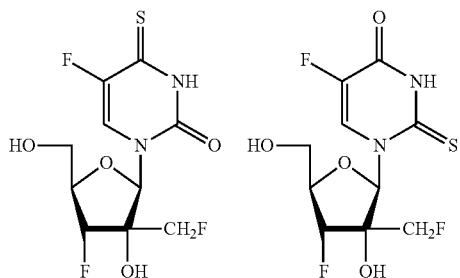

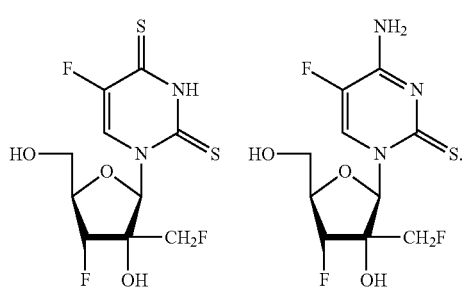

In one embodiment, R² is fluoro. In another embodiment, R³ is H. In still another embodiment, R⁴ is hydroxyl. In a further embodiment, R⁵ is H. In yet another embodiment, R⁶ is methyl. In a still further another embodiment, R⁷ is hydroxyl. In exemplary embodiments, the compound is selected from the group consisting of:

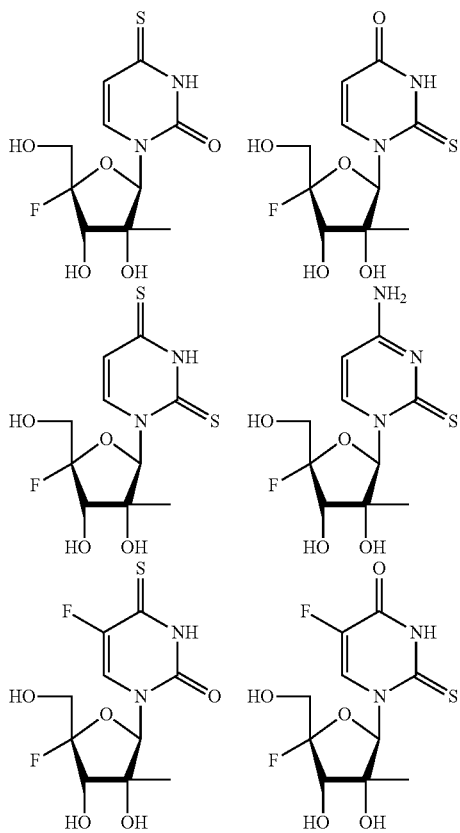

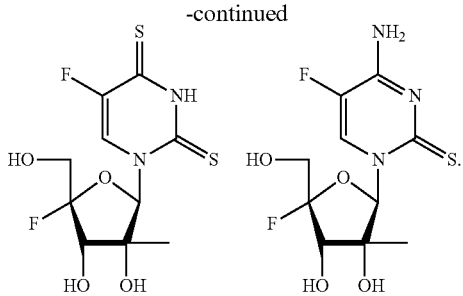

In one embodiment, R² is fluoro. In another embodiment, R³ is H. In still another embodiment, R⁴ is hydroxyl. In a further embodiment, R⁵ is H. In yet another embodiment, R⁶ is C≡CH. In a still further embodiment, R⁷ is hydroxyl. In exemplary embodiments, the compound is selected from the group consisting of:

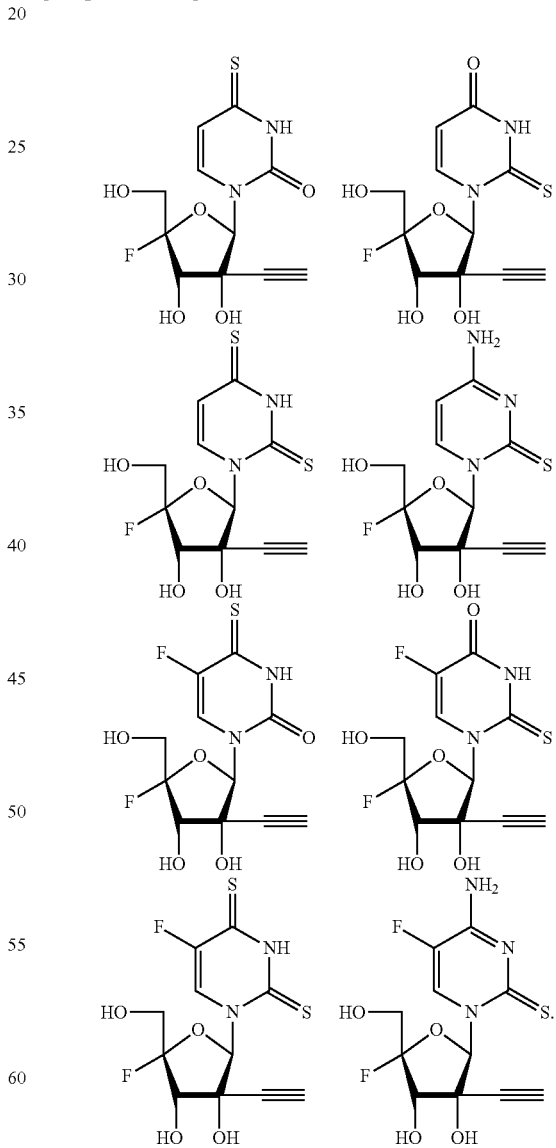

In one embodiment, R² is fluoro. In another embodiment, R³ is H. In still another embodiment, R⁴ is hydroxyl. In a further embodiment, R⁵ is H. In yet another embodiment, R⁶ is CH$_2$F. In a still further embodiment, R$^7$ is hydroxyl. In exemplary embodiments, the compound is selected from the group consisting of:

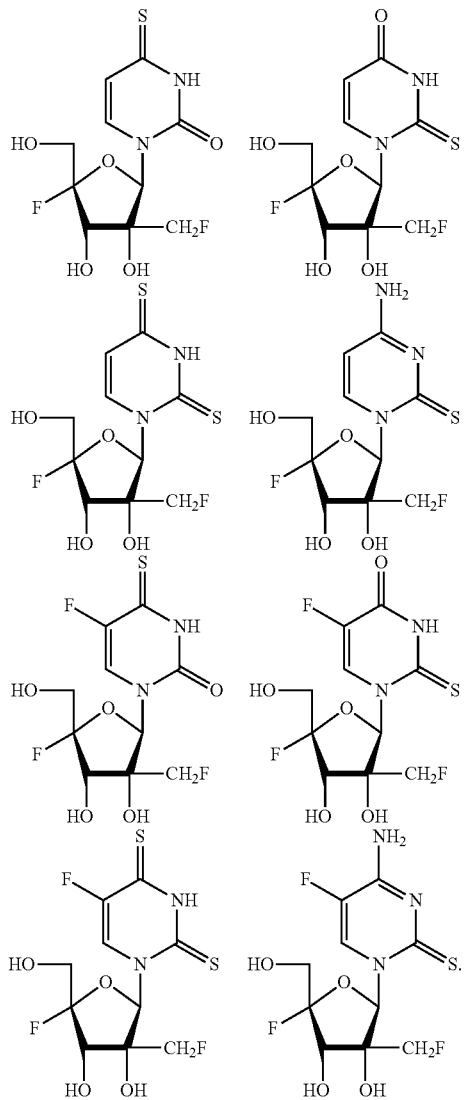

In one embodiment, R$^2$ is fluoro. In another embodiment, R$^3$ is H. In still another embodiment, R$^4$ is hydroxyl. In a further embodiment, R$^5$ is H. In yet another embodiment, R$^6$ is methyl. In a still further embodiment, R$^7$ is fluoro. In exemplary embodiments, the compound is selected from the group consisting of:

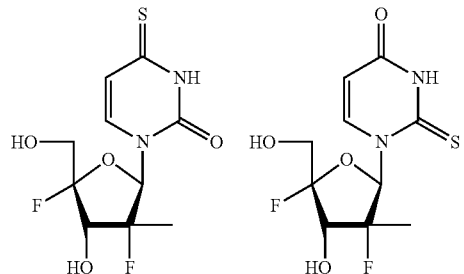

-continued

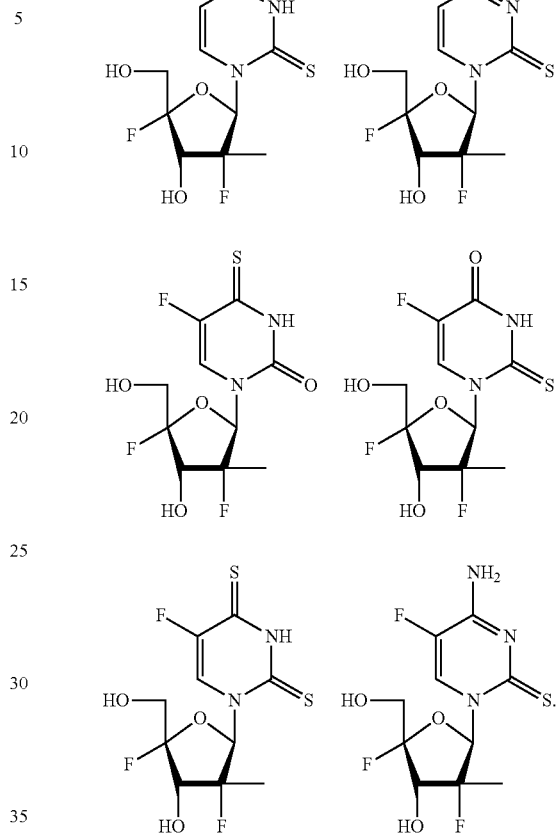

In one embodiment, R$^2$ is fluoro. In another embodiment, R$^3$ is H. In still another embodiment, R$^4$ is hydroxyl. In a further embodiment, R$^5$ is H. In yet another embodiment, R$^6$ is C≡CH. In a still further embodiment, R$^7$ is fluoro. In exemplary embodiments, the compound is selected from the group consisting of:

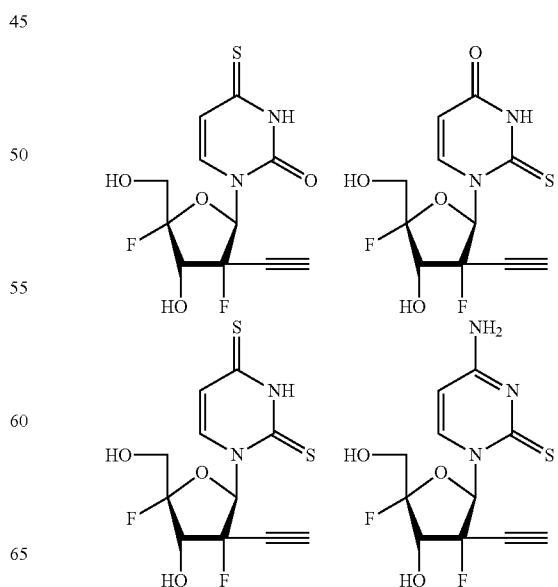

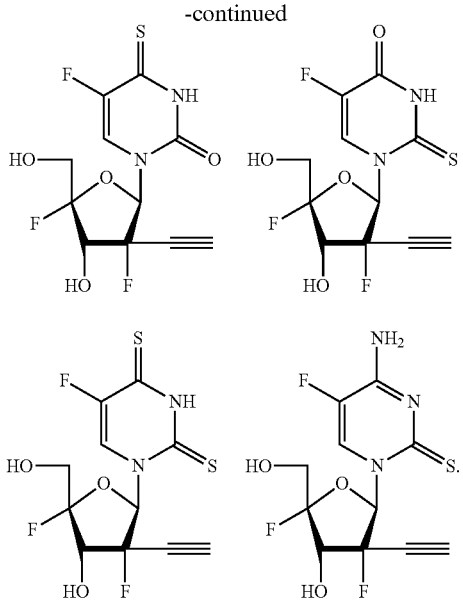

In one embodiment, $R^2$ is fluoro. In another embodiment, $R^3$ is H. In still another embodiment, $R^4$ is hydroxyl. In a further embodiment, $R^5$ is H. In yet another embodiment, $R^6$ is $CH_2F$. In a still further embodiment, $R^7$ is fluoro. In exemplary embodiments, the compound is selected from the group consisting of:

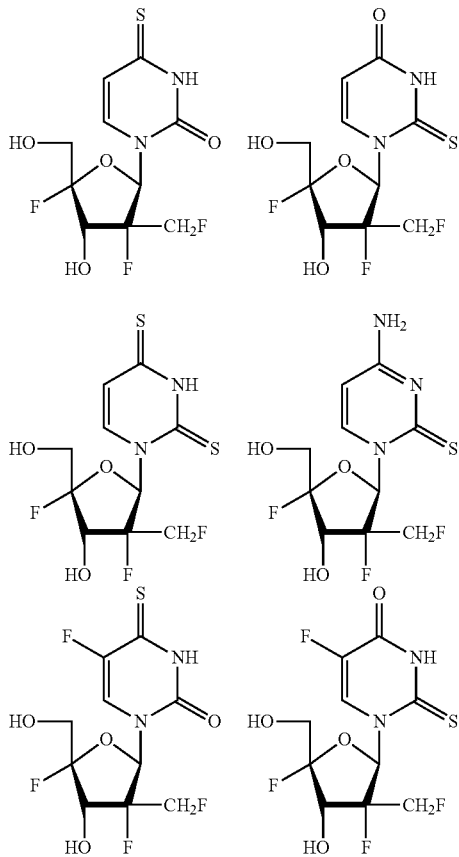

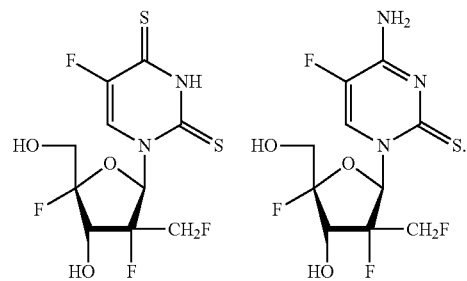

In one embodiment, the nucleoside conjugated to a phosphorus moiety is of the following formulae:

Formula Iaa

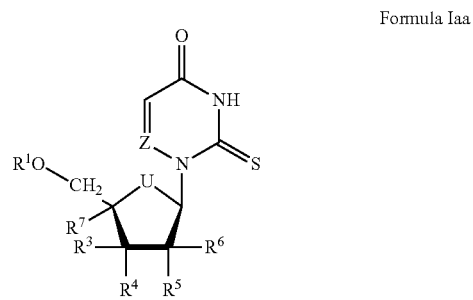

Formula Iab

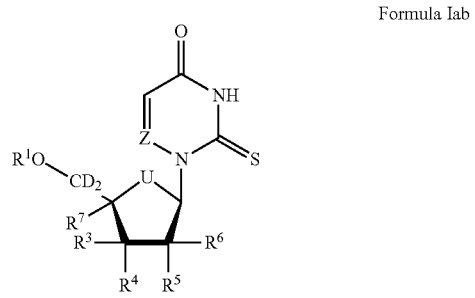

Formula Iac

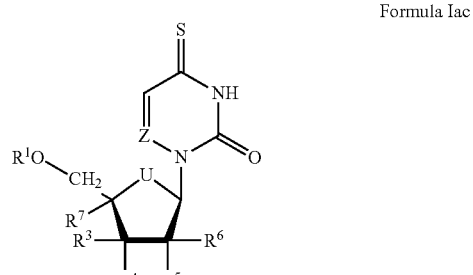

Formula Iad

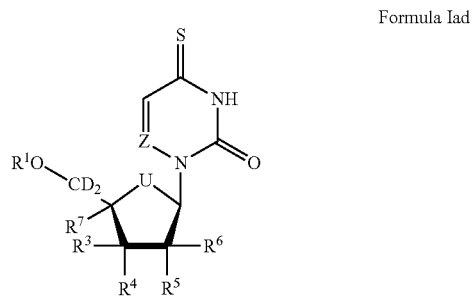

Formula ae

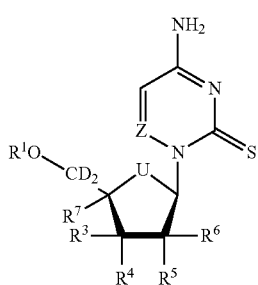

or a pharmaceutically acceptable salt thereof, wherein
R$^1$ is H, monophosphate, diphosphate, triphosphate, or selected from one of the following:

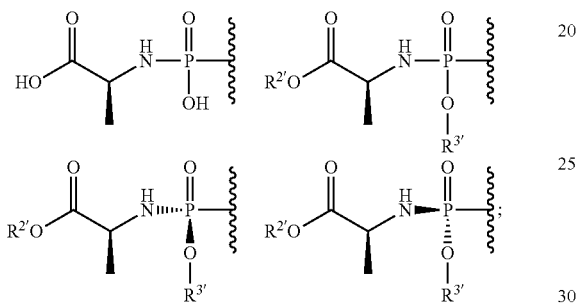

U is O or S;
R$^{2'}$ is alkyl, branched alkyl, or cycloalkyl;
R$^{3'}$ is aryl, biaryl, or substituted aryl;
Z is CH or N;
R$^7$ is H, D, N$_3$, ethynyl, vinyl, fluoro, fluoromethyl, difluoromethyl, trifluoromethyl,
methyl, CD$_3$, hydroxymethyl or cyano;
R$^3$ is H, D, methyl, CD$_3$, ethynyl, cyano, fluoro, fluoromethyl, difluoromethyl, trifluoromethyl, hydroxymethyl or vinyl;
R$^4$ is H, D, hydroxyl, methoxy, azido, amino, fluoro, chloro or SH;
R$^5$ is H, D, hydroxyl, methoxy, azido, amino, fluoro, chloro or SH;
R$^6$ is H, D, methyl, CD$_3$, ethynyl, cyano, fluoro, fluoromethyl, difluoromethyl, trifluoromethyl, hydroxymethyl or vinyl.
In certain embodiments, U is S and Z is CH.
In other embodiments, U is O and Z is CH.
In one embodiment, the nucleoside conjugated to a phosphorus moiety is of the following formulae:

Formula Iaf

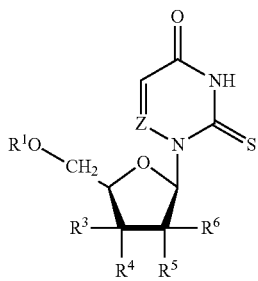

Formula Iag

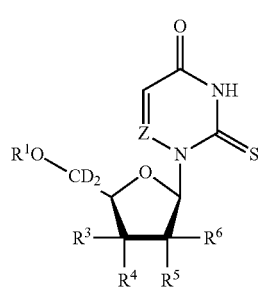

Formula Iah

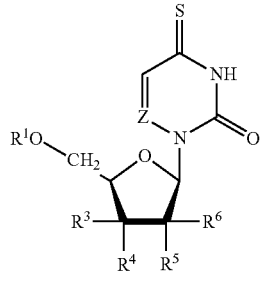

Formula Iai

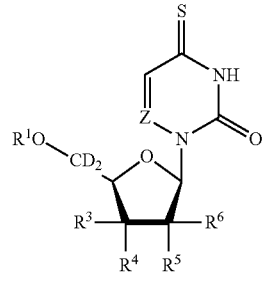

Formula Iaj

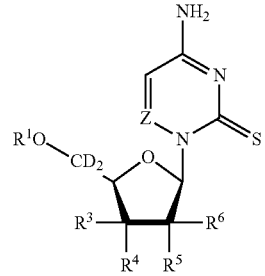

or a pharmaceutically acceptable salt thereof, wherein
R$^1$ is H, monophosphate, diphosphate, triphosphate, or selected from one of the following:

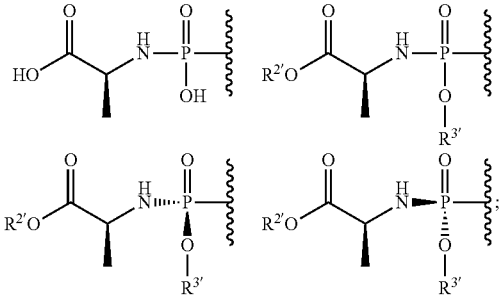

R$^{2'}$ is alkyl, branched alkyl, or cycloalkyl;
R$^{3'}$ is aryl, biaryl, or substituted aryl;

Z is CH or N;

R³ is H, D, methyl, CD₃, ethynyl, cyano, fluoro, chloro, fluoromethyl, difluoromethyl, trifluoromethyl, hydroxymethyl, vinyl or allyl;

R⁴ is H, D, hydroxyl, methoxy, azido, amino, fluoro, chloro or SH;

R⁵ is H, D, hydroxyl, methoxy, azido, amino, fluoro, chloro or SH;

R⁶ is H, D, methyl, CD₃, ethynyl, cyano, fluoro, chloro, fluoromethyl, difluoromethyl, trifluoromethyl, hydroxymethyl, vinyl or allyl.

In certain embodiments, Z is CH.

In one embodiment, the nucleoside conjugated to a phosphorus moiety is of the following formula:

Formula Iak

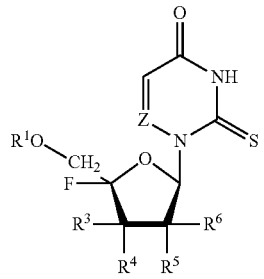

Formula Ial

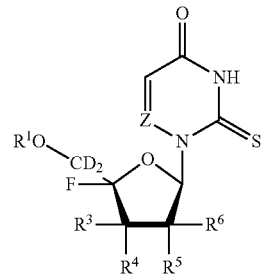

Formula Iam

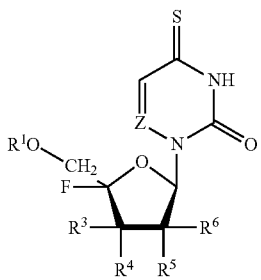

Formula Ian

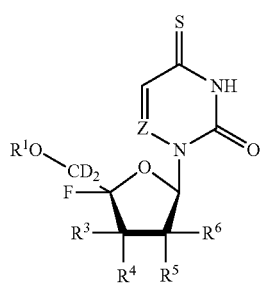

Formula Iao

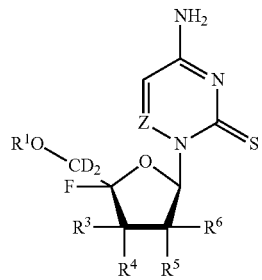

or a pharmaceutically acceptable salt thereof, wherein $R^1$ is H, monophosphate, diphosphate, triphosphate, or selected from one of the following:

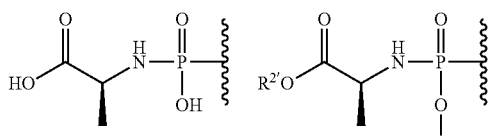

$R^{2'}$ is alkyl, branched alkyl, or cycloalkyl;

$R^{3'}$ is aryl, biaryl, or substituted aryl;

Z is CH or N;

R³ is H, D, methyl, CD₃, ethynyl, cyano, fluoro, chloro, fluoromethyl, difluoromethyl, trifluoromethyl, hydroxymethyl, vinyl or allyl;

R⁴ is H, D, hydroxyl, methoxy, azido, amino, fluoro, chloro or SH;

R⁵ is H, D, hydroxyl, methoxy, azido, amino, fluoro, chloro or SH;

R⁶ is H, D, methyl, CD₃, ethynyl, cyano, fluoro, chloro, fluoromethyl, difluoromethyl, trifluoromethyl, hydroxymethyl, vinyl or allyl.

In certain embodiments, Z is CH.

In preferred embodiments, the nucleoside conjugated to a phosphorus moiety is of the following formulae:

Formula Iap

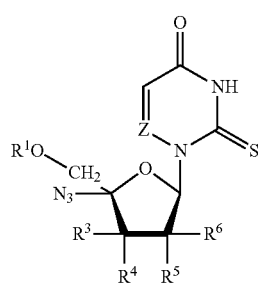

Formula Iaq
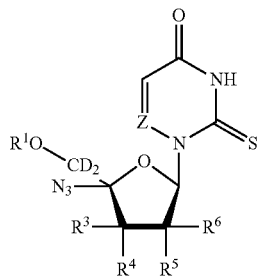

Formula Iar
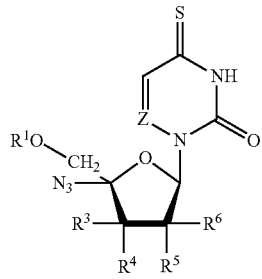

Formula Ias
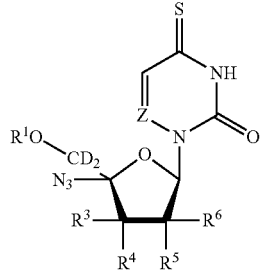

Formula Iat
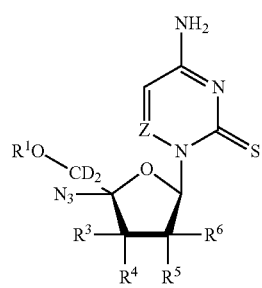

or a pharmaceutically acceptable salt thereof, wherein $R^1$ is H, monophosphate, diphosphate, triphosphate, or selected from one of the following:

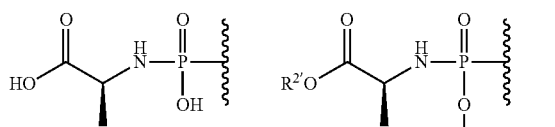
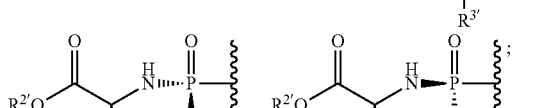

$R^{2'}$ is alkyl, branched alkyl, or cycloalkyl;
$R^{3'}$ is aryl, biaryl, or substituted aryl;

Z is CH or N;

$R^3$ is H, D, methyl, $CD_3$, ethynyl, cyano, fluoro, chloro, fluoromethyl, difluoromethyl, trifluoromethyl, hydroxymethyl, vinyl or allyl;

$R^4$ is H, D, hydroxyl, methoxy, azido, amino, fluoro, chloro or SH;

$R^5$ is H, D, hydroxyl, methoxy, azido, amino, fluoro, chloro or SH;

$R^6$ is H, D, methyl, $CD_3$, ethynyl, cyano, fluoro, chloro, fluoromethyl, difluoromethyl, trifluoromethyl, hydroxymethyl, vinyl or allyl.

In certain embodiments, Z is CH.

In one embodiment, the nucleoside conjugated to a phosphorus moiety is of the following formulae:

Formula Iau
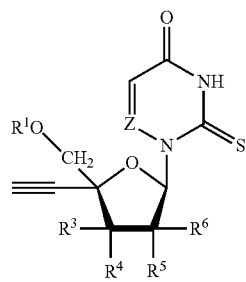

Formula Iav
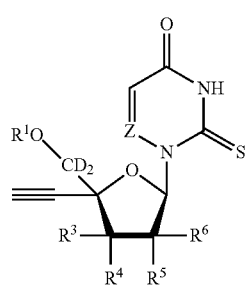

Formula Iaw
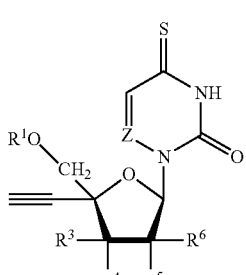

Formula Iax
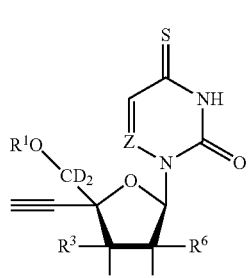

Formula Iay

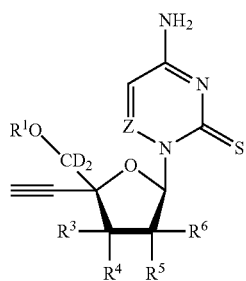

or a pharmaceutically acceptable salt thereof, wherein $R^1$ is H, monophosphate, diphosphate, triphosphate, or selected from one of the following:

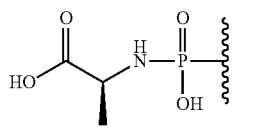 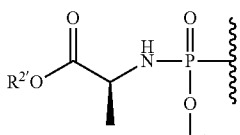

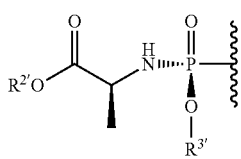 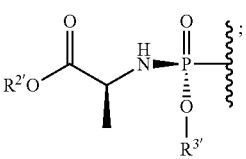

$R^{2'}$ is alkyl, branched alkyl, or cycloalkyl;

$R^{3'}$ is aryl, biaryl, or substituted aryl;

Z is CH or N;

$R^3$ is H, D, methyl, $CD_3$, ethynyl, cyano, fluoro, chloro, fluoromethyl, difluoromethyl, trifluoromethyl, hydroxymethyl, vinyl or allyl;

$R^4$ is H, D, hydroxyl, methoxy, azido, amino, fluoro, chloro or SH;

$R^5$ is H, D, hydroxyl, methoxy, azido, amino, fluoro, chloro or SH;

$R^6$ is H, D, methyl, $CD_3$, ethynyl, cyano, fluoro, chloro, fluoromethyl, difluoromethyl, trifluoromethyl, hydroxymethyl, vinyl or allyl.

In certain embodiments, Z is CH.

In one embodiment, the nucleoside conjugated to a phosphorus moiety is of the following formulae:

Formula Iaz

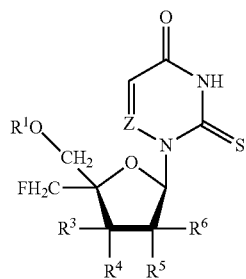

Formula Iba

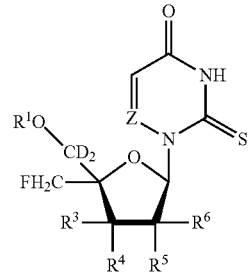

Formula Ibb

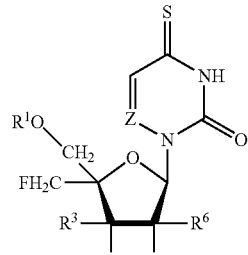

Formula Ibc

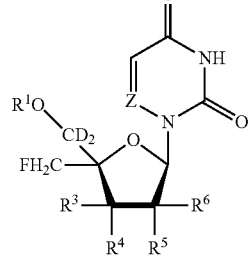

Formula Ibd

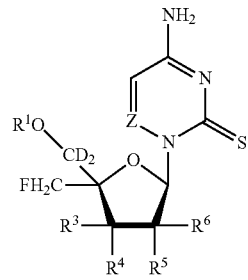

or a pharmaceutically acceptable salt thereof, wherein $R^1$ is H, monophosphate, diphosphate, triphosphate, or selected from one of the following:

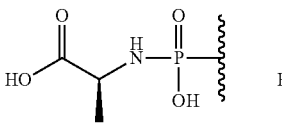 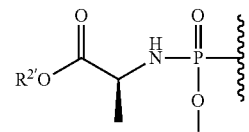

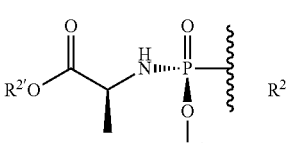 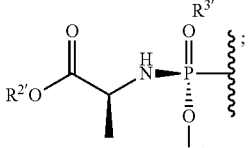

$R^{2'}$ is alkyl, branched alkyl, or cycloalkyl;

$R^{3'}$ is aryl, biaryl, or substituted aryl;

Z is CH or N;

R³ is H, D, methyl, CD₃, ethynyl, cyano, fluoro, chloro, fluoromethyl, difluoromethyl, trifluoromethyl, hydroxymethyl, vinyl or allyl;

R⁴ is H, D, hydroxyl, methoxy, azido, amino, fluoro, chloro or SH;

R⁵ is H, D, hydroxyl, methoxy, azido, amino, fluoro, chloro or SH;

R⁶ is H, D, methyl, CD₃, ethynyl, cyano, fluoro, chloro, fluoromethyl, difluoromethyl, trifluoromethyl, hydroxymethyl, vinyl or allyl.

In certain embodiments, Z is CH.

In one embodiment, the nucleoside conjugated to a phosphorus moiety is of the following formulae:

Formula Ibe

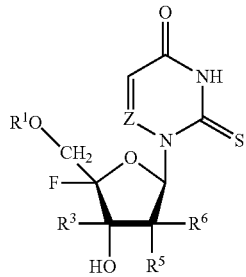

Formula Ibf

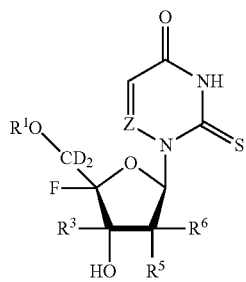

Formula Ibg

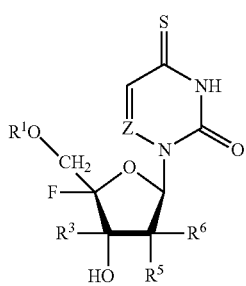

Formula Ibh

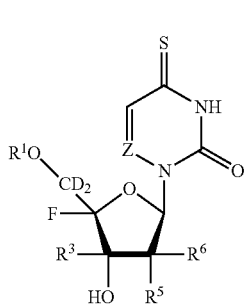

Formula Ibi

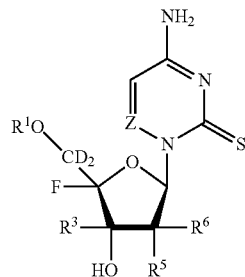

or a pharmaceutically acceptable salt thereof, wherein

R¹ is H, monophosphate, diphosphate, triphosphate, or selected from one of the following:

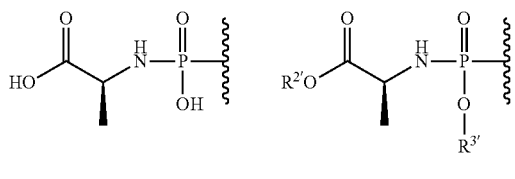

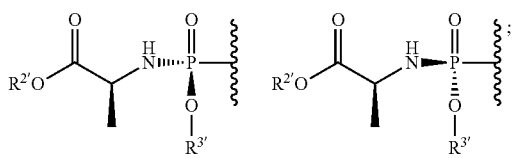

R²' is alkyl, branched alkyl, or cycloalkyl;

R³' is aryl, biaryl, or substituted aryl;

Z is CH or N;

R³ is H, D, methyl, CD₃, ethynyl, cyano, fluoro, chloro, fluoromethyl, difluoromethyl, trifluoromethyl, hydroxymethyl, vinyl or allyl;

R⁵ is H, D, hydroxyl, methoxy, azido, amino, fluoro, chloro or SH;

R⁶ is H, D, methyl, CD₃, ethynyl, cyano, fluoro, chloro, fluoromethyl, difluoromethyl, trifluoromethyl, hydroxymethyl, vinyl or allyl.

In certain embodiments, Z is CH.

In one embodiment, the nucleoside conjugated to a phosphorus moiety is of the following formulae:

Formula Ibj

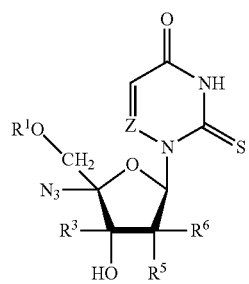

-continued

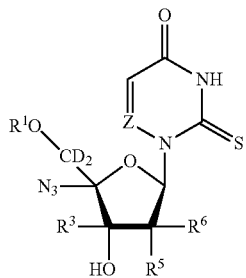
Formula Ibk

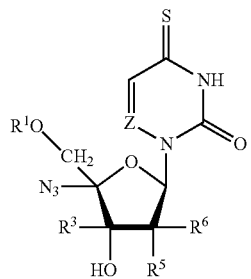
Formula Ibl

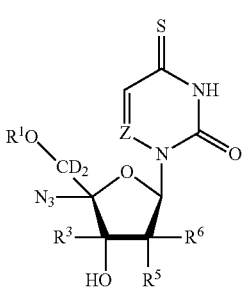
Formula Ibm

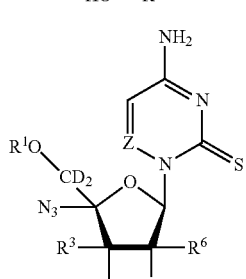
Formula Ibn or a pharmaceutically acceptable salt thereof, wherein
$R^1$ is H, monophosphate, diphosphate, triphosphate, or selected from one of the following:

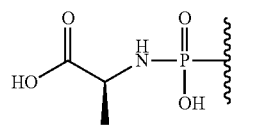 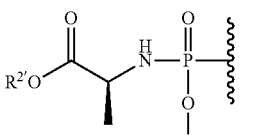
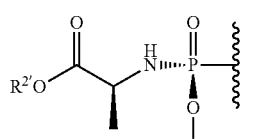 

$R^{2'}$ is alkyl, branched alkyl, or cycloalkyl;
$R^{3'}$ is aryl, biaryl, or substituted aryl;

Z is CH or N;
$R^3$ is H, D, methyl, $CD_3$, ethynyl, cyano, fluoro, chloro, fluoromethyl, difluoromethyl, trifluoromethyl, hydroxymethyl, vinyl or allyl;
$R^5$ is H, D, hydroxyl, methoxy, azido, amino, fluoro, chloro or SH;
$R^6$ is H, D, methyl, $CD_3$, ethynyl, cyano, fluoro, chloro, fluoromethyl, difluoromethyl, trifluoromethyl, hydroxymethyl, vinyl or allyl.

In certain embodiments, Z is CH.

In one embodiment, the nucleoside conjugated to a phosphorus moiety is of the following formuale:

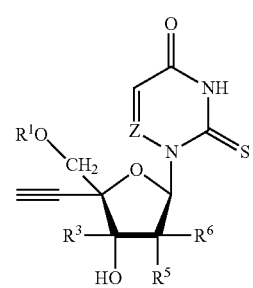
Formula Ibo

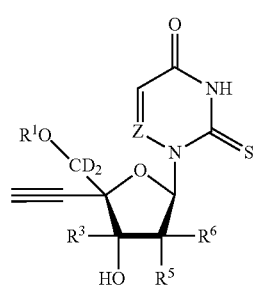
Formula Ibp

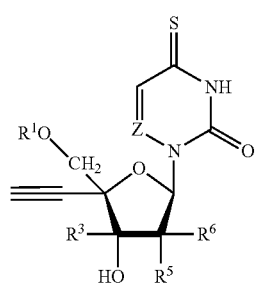
Formula Ibq

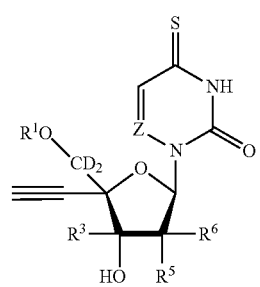
Formula Ibr

Formula Ibs

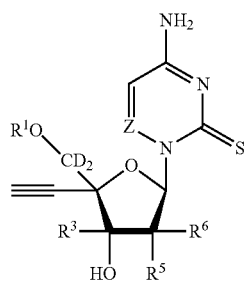

or a pharmaceutically acceptable salt thereof, wherein $R^1$ is H, monophosphate, diphosphate, triphosphate, or selected from one of the following:

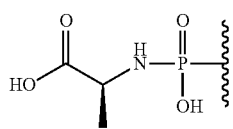 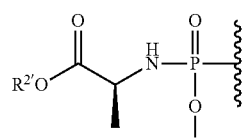

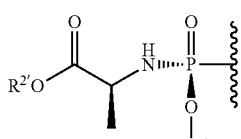 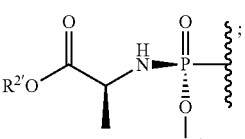

$R^{2'}$ is alkyl, branched alkyl, or cycloalkyl;

$R^{3'}$ is aryl, biaryl, or substituted aryl;

Z is CH or N;

$R^3$ is H, D, methyl, $CD_3$, ethynyl, cyano, fluoro, chloro, fluoromethyl, difluoromethyl, trifluoromethyl, hydroxymethyl, vinyl or allyl;

$R^5$ is H, D, hydroxyl, methoxy, azido, amino, fluoro, chloro or SH;

$R^6$ is H, D, methyl, $CD_3$, ethynyl, cyano, fluoro, chloro, fluoromethyl, difluoromethyl, trifluoromethyl, hydroxymethyl, vinyl or allyl.

In certain embodiments, Z is CH.

In one embodiment, the nucleoside conjugated to a phosphorus moiety is of the following formulae:

Formula Ibt

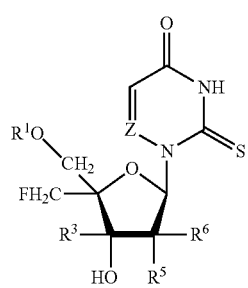

Formula Ibu

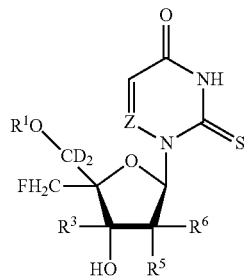

Formula Ibv

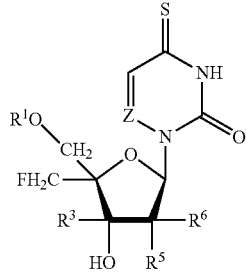

Formula Ibw

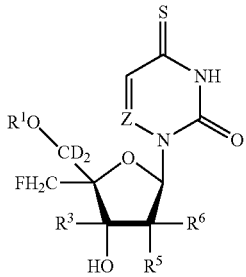

Formula Ibx

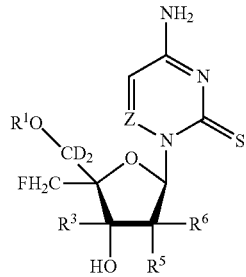

or a pharmaceutically acceptable salt thereof, wherein $R^1$ is H, monophosphate, diphosphate, triphosphate, or selected from one of the following:

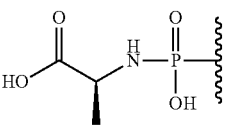 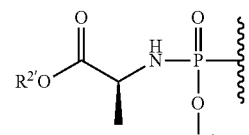

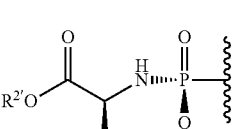 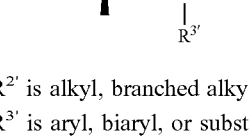

$R^{2'}$ is alkyl, branched alkyl, or cycloalkyl;

$R^{3'}$ is aryl, biaryl, or substituted aryl;

Z is CH or N;

$R^3$ is H, D, methyl, $CD_3$, ethynyl, cyano, fluoro, chloro, fluoromethyl, difluoromethyl, trifluoromethyl, hydroxymethyl, vinyl or allyl;

$R^5$ is H, D, hydroxyl, methoxy, azido, amino, fluoro, chloro or SH;

$R^6$ is H, D, methyl, $CD_3$, ethynyl, cyano, fluoro, chloro, fluoromethyl, difluoromethyl, trifluoromethyl, hydroxymethyl, vinyl or allyl.

In certain embodiments, Z is CH.

In one embodiment, the nucleoside conjugated to a phosphorus moiety is of the following formulae:

Formula Iby

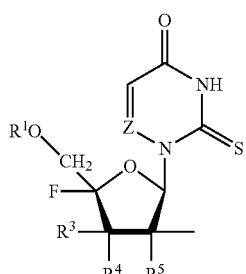

Formula Ibz

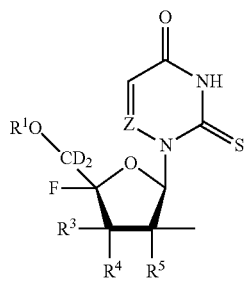

Formula Ica

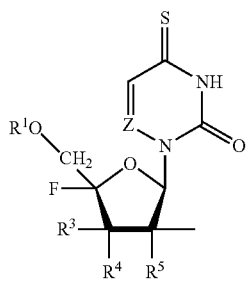

Formula Icb

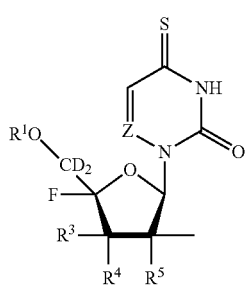

Formula Icc

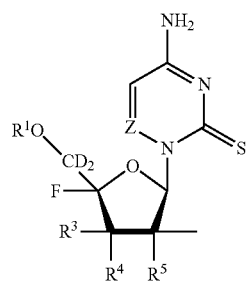

or a pharmaceutically acceptable salt thereof, wherein $R^1$ is H, monophosphate, diphosphate, triphosphate, or selected from one of the following:

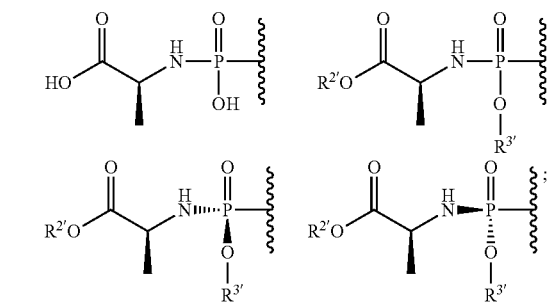

$R^{2'}$ is alkyl, branched alkyl, or cycloalkyl;

$R^{3'}$ is aryl, biaryl, or substituted aryl;

Z is CH or N;

$R^3$ is H, D, methyl, $CD_3$, ethynyl, cyano, fluoro, chloro, fluoromethyl, difluoromethyl, trifluoromethyl, hydroxymethyl, vinyl or allyl;

$R^4$ is H, D, hydroxyl, methoxy, azido, amino, fluoro, chloro or SH;

$R^5$ is H, D, hydroxyl, methoxy, azido, amino, fluoro, chloro or SH.

In certain embodiments, Z is CH.

In one embodiment, the nucleoside conjugated to a phosphorus moiety is of the following formulae:

Formula Icd

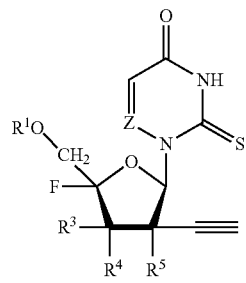

Formula Ice

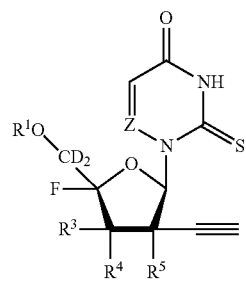

-continued

Formula Icf

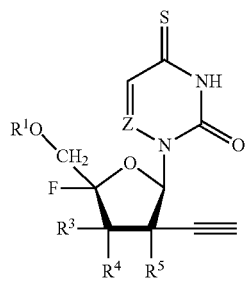

Formula Icg

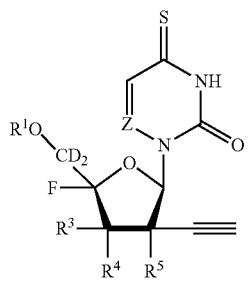

Formula Ich

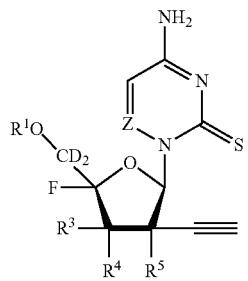

or a pharmaceutically acceptable salt thereof, wherein $R^1$ is H, monophosphate, diphosphate, triphosphate, or selected from one of the following:

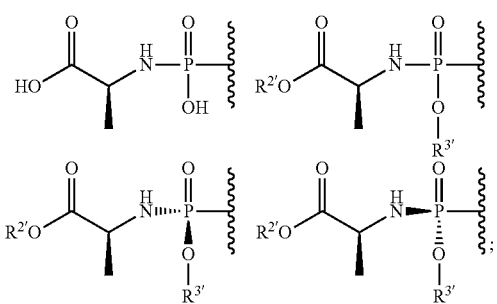

$R^{2'}$ is alkyl, branched alkyl, or cycloalkyl;

$R^{3'}$ is aryl, biaryl, or substituted aryl;

Z is CH or N;

$R^3$ is H, D, methyl, $CD_3$, ethynyl, cyano, fluoro, chloro, fluoromethyl, difluoromethyl, trifluoromethyl, hydroxymethyl, vinyl or allyl;

$R^4$ is H, D, hydroxyl, methoxy, azido, amino, fluoro, chloro or SH;

$R^5$ is H, D, hydroxyl, methoxy, azido, amino, fluoro, chloro or SH.

In certain embodiments, Z is CH.

In one embodiment, the nucleoside conjugated to a phosphorus moiety is of the following formuale:

Formula Ici

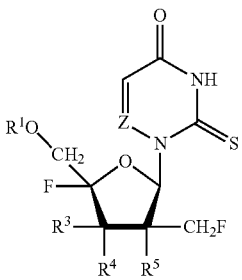

Formula Icj

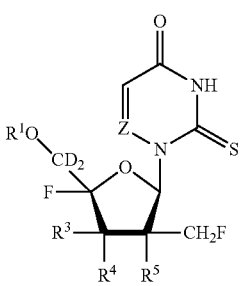

Formula Ick

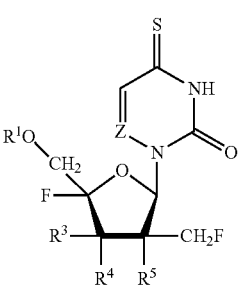

Formula Icl

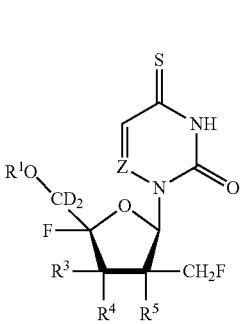

Formula Icm

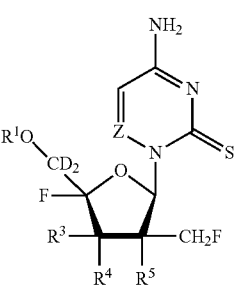

or a pharmaceutically acceptable salt thereof, wherein
$R^1$ is H, monophosphate, diphosphate, triphosphate, or selected from one of the following:

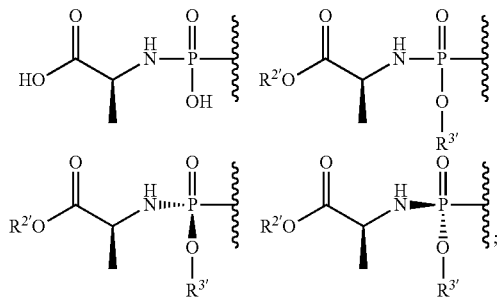

$R^{2'}$ is alkyl, branched alkyl, or cycloalkyl;
$R^{3'}$ is aryl, biaryl, or substituted aryl;
Z is CH or N;
$R^3$ is H, D, methyl, $CD_3$, ethynyl, cyano, fluoro, chloro, fluoromethyl, difluoromethyl, trifluoromethyl, hydroxymethyl, vinyl or allyl;
$R^4$ is H, D, hydroxyl, methoxy, azido, amino, fluoro, chloro or SH;
$R^5$ is H, D, hydroxyl, methoxy, azido, amino, fluoro, chloro or SH.

In certain embodiments, Z is CH.
In one embodiment, the nucleoside conjugated to a phosphorus moiety is of the following formulae:

Formula Icn

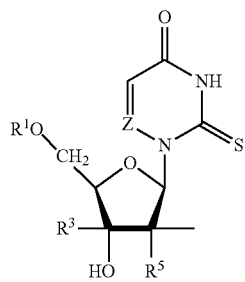

Formula Ico

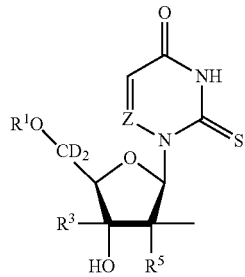

Formula Icp

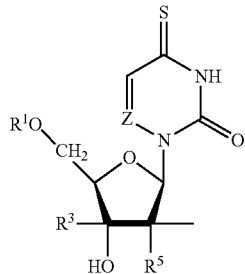

Formula Icq

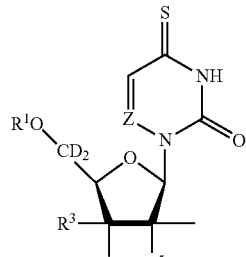

Formula Icr

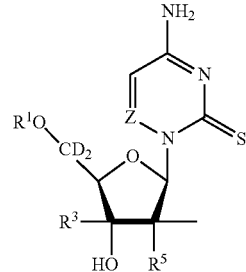

or a pharmaceutically acceptable salt thereof, wherein
$R^1$ is H, monophosphate, diphosphate, triphosphate, or selected from one of the following:

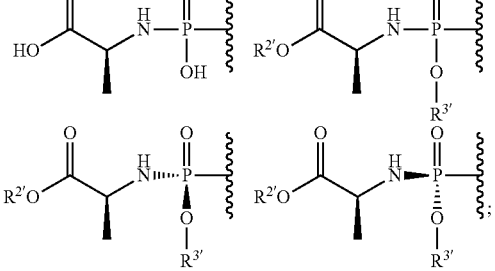

$R^{2'}$ is alkyl, branched alkyl, or cycloalkyl;
$R^{3'}$ is aryl, biaryl, or substituted aryl;
Z is CH or N;
$R^3$ is H, D, methyl, $CD_3$, ethynyl, cyano, fluoro, chloro, fluoromethyl, difluoromethyl, trifluoromethyl, hydroxymethyl, vinyl or allyl;
$R^5$ is H, D, hydroxyl, methoxy, azido, amino, fluoro, chloro or SH.

In certain embodiments, Z is CH.
In one embodiment, the nucleoside conjugated to a phosphorus moiety is of the following formulae:

Formula Ics

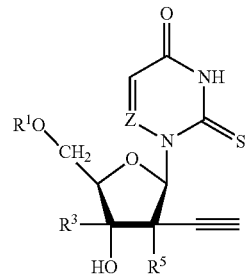

-continued

Formula Ict
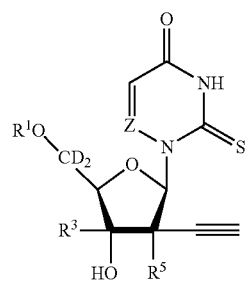

Formula Icu
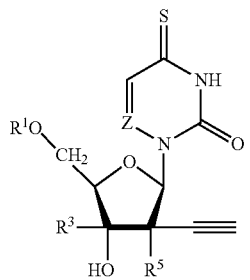

Formula Icv
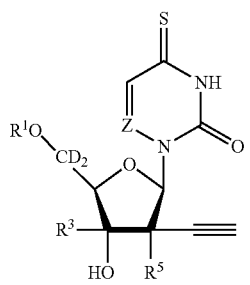

Formula Icw
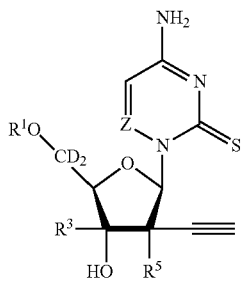

or a pharmaceutically acceptable salt thereof, wherein $R^1$ is H, monophosphate, diphosphate, triphosphate, or selected from one of the following:

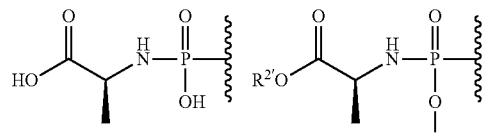

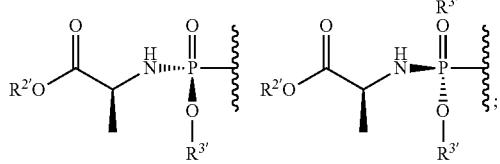

$R^{2'}$ is alkyl, branched alkyl, or cycloalkyl;
$R^{3'}$ is aryl, biaryl, or substituted aryl;
Z is CH or N;
$R^3$ is H, D, methyl, $CD_3$, ethynyl, cyano, fluoro, chloro, fluoromethyl, difluoromethyl, trifluoromethyl, hydroxymethyl, vinyl or allyl;
$R^5$ is H, D, hydroxyl, methoxy, azido, amino, fluoro, chloro or SH.

In certain embodiments, Z is CH.

In one embodiment, the nucleoside conjugated to a phosphorus moiety is of the following formulae:

Formula Icx
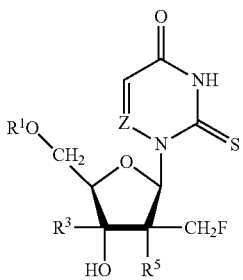

Formula Icy
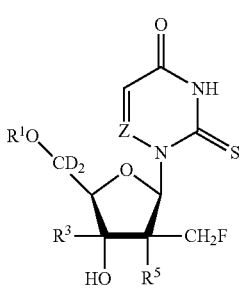

Formula Icz
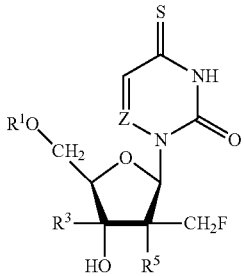

Formula Ida
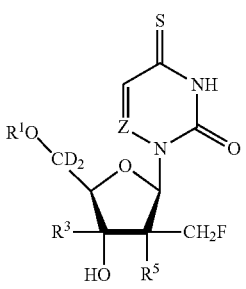

Formula Idb
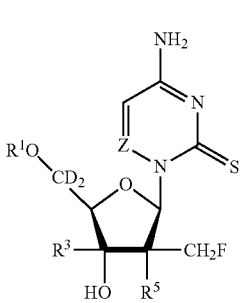

or a pharmaceutically acceptable salt thereof, wherein $R^1$ is H, monophosphate, diphosphate, triphosphate, or selected from one of the following:

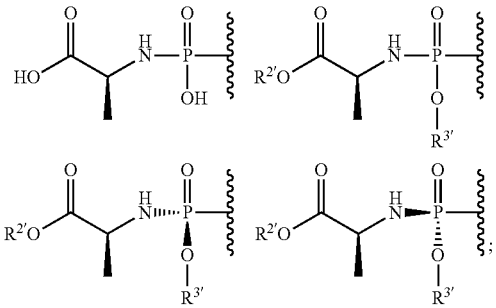

$R^{2'}$ is alkyl, branched alkyl, or cycloalkyl;

$R^{3'}$ is aryl, biaryl, or substituted aryl;

Z is CH or N;

$R^3$ is H, D, methyl, $CD_3$, ethynyl, cyano, fluoro, chloro, fluoromethyl, difluoromethyl, trifluoromethyl, hydroxymethyl, vinyl or allyl;

$R^5$ is H, D, hydroxyl, methoxy, azido, amino, fluoro, chloro or SH.

In certain embodiments, Z is CH.

In one embodiment, the nucleoside conjugated to a phosphorus moiety is of the following formulae:

Formula Idc

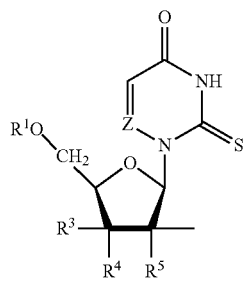

Formula Idd

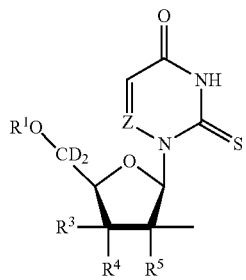

Formula Ide

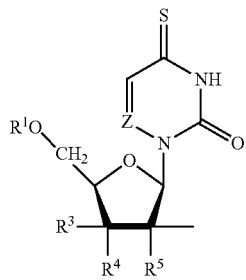

-continued

Formula Idf

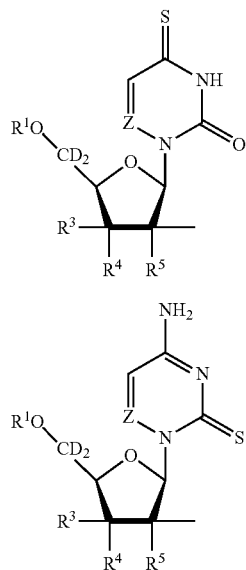

Formula Idg

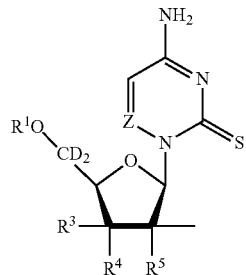

or a pharmaceutically acceptable salt thereof, wherein $R^1$ is H, monophosphate, diphosphate, triphosphate, or selected from one of the following:

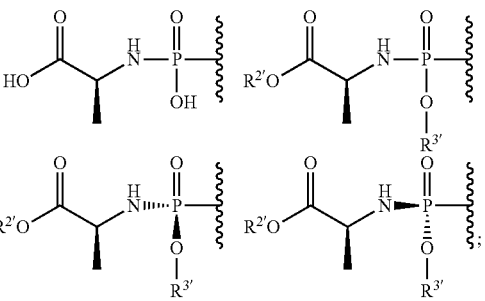

$R^{2'}$ is alkyl, branched alkyl, or cycloalkyl;

$R^{3'}$ is aryl, biaryl, or substituted aryl;

Z is CH or N;

$R^3$ is H, D, methyl, $CD_3$, ethynyl, cyano, fluoro, chloro, fluoromethyl, difluoromethyl, trifluoromethyl, hydroxymethyl, vinyl or allyl;

$R^4$ is H, D, hydroxyl, methoxy, azido, amino, fluoro, chloro or SH;

$R^5$ is H, D, hydroxyl, methoxy, azido, amino, fluoro, chloro or SH.

In certain embodiments, Z is CH.

In one embodiment, the nucleoside conjugated to a phosphorus moiety is of the following formulae:

Formula Idh

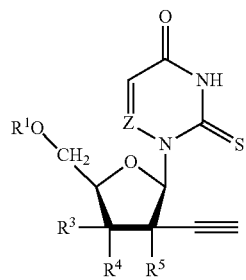

-continued

Formula Idi

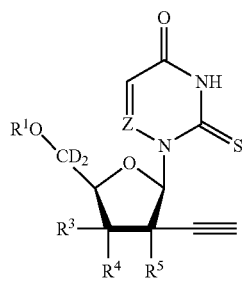

Formula Idj

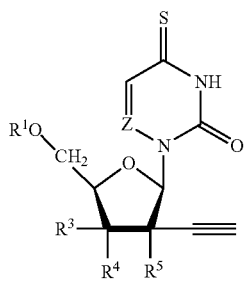

Formula Idk

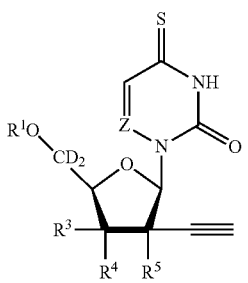

Formula Idl

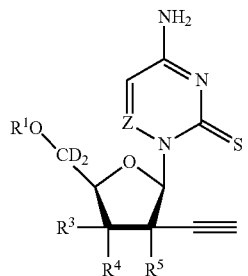

or a pharmaceutically acceptable salt thereof, wherein
$R^1$ is H, monophosphate, diphosphate, triphosphate, or selected from one of the following:

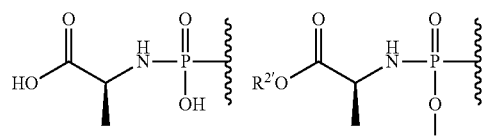

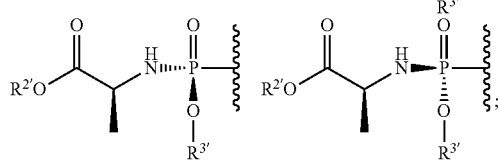

$R^{2'}$ is alkyl, branched alkyl, or cycloalkyl;
$R^{3'}$ is aryl, biaryl, or substituted aryl;
Z is CH or N;
$R^3$ is H, D, methyl, $CD_3$, ethynyl, cyano, fluoro, chloro, fluoromethyl, difluoromethyl, trifluoromethyl, hydroxymethyl, vinyl or allyl;

$R^4$ is H, D, hydroxyl, methoxy, azido, amino, fluoro, chloro or SH;
$R^5$ is H, D, hydroxyl, methoxy, azido, amino, fluoro, chloro or SH.

In certain embodiments, Z is CH.

In one embodiment, the nucleoside conjugated to a phosphorus moiety is a compound of the following formulae:

Formula Idm

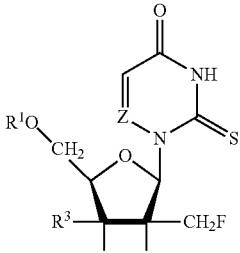

Formula Idn

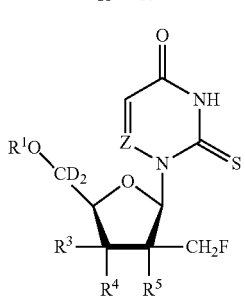

Formula Ido

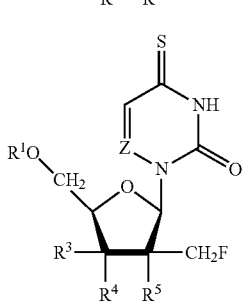

Formula Idp

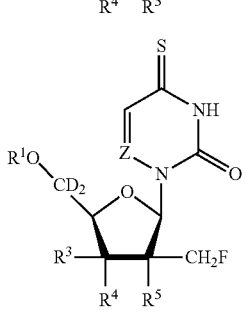

Formula Idq

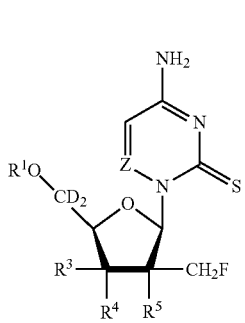

or a pharmaceutically acceptable salt thereof, wherein
R$^1$ is H, monophosphate, diphosphate, triphosphate, or selected from one of the following:

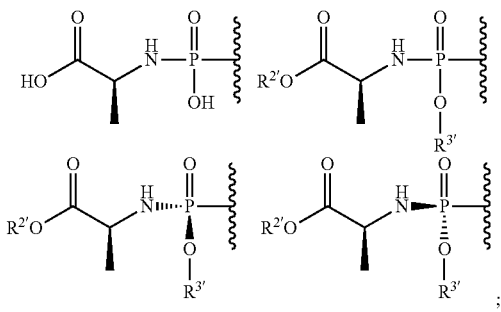

R$^{2'}$ is alkyl, branched alkyl, or cycloalkyl;
R$^{3'}$ is aryl, biaryl, or substituted aryl;
Z is CH or N;
R$^3$ is H, D, methyl, CD$_3$, ethynyl, cyano, fluoro, chloro, fluoromethyl, difluoromethyl, trifluoromethyl, hydroxymethyl, vinyl or allyl;
R$^4$ is H, D, hydroxyl, methoxy, azido, amino, fluoro, chloro or SH;
R$^5$ is H, D, hydroxyl, methoxy, azido, amino, fluoro, chloro or SH.

In certain embodiments, Z is CH.

In one embodiment, the nucleoside conjugated to a phosphorus moiety is a compound of the following formulae:

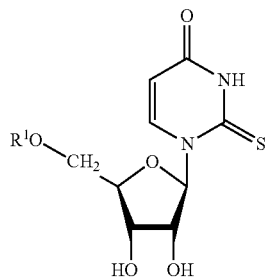

Formula Idr

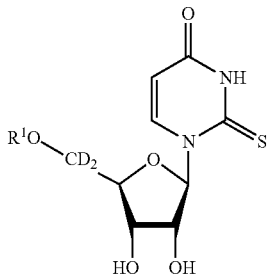

Formula Ids or a pharmaceutically acceptable salt thereof, wherein
R$^1$ is H, monophosphate, diphosphate, triphosphate, or selected from one of the following:

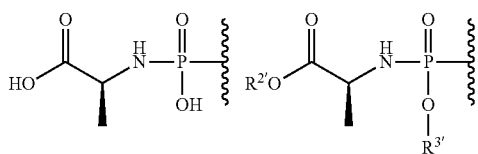

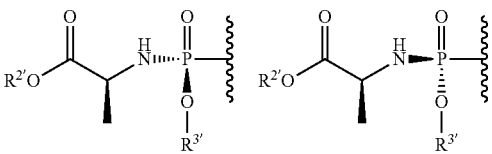

R$^{2'}$ is alkyl, branched alkyl, or cycloalkyl and
R$^{3'}$ is aryl, biaryl, or substituted aryl.

In another embodiment, R$^1$ is selected from one of the following:

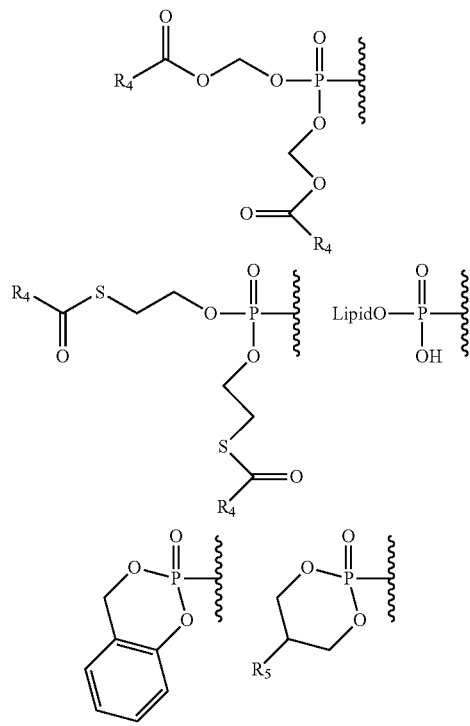

R$_4$ is alkyl, branched alkyl, cycloalkyl, or alkyoxy;
R$_5$ is aryl, heteroaryl, substituted aryl, or substituted heteroaryl.

In certain embodiments of Formula I, X is methylene (CH$_2$) and R$^1$ is one of the following:

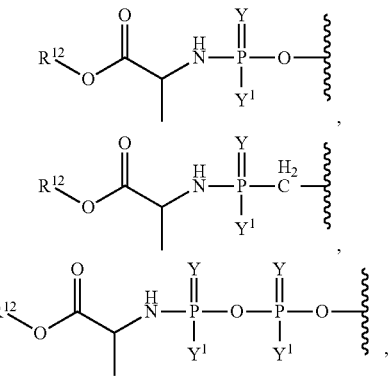

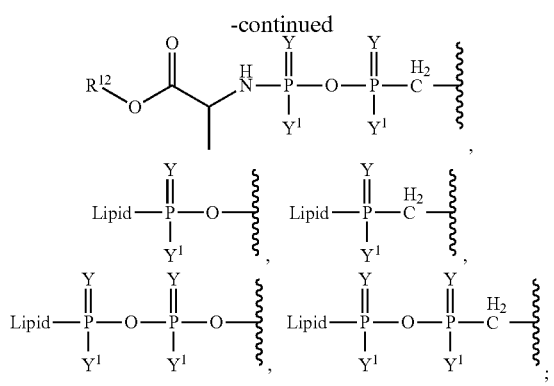

wherein $R^{12}$ $C_{1-22}$ alkyl, $C_{2-22}$ alkenyl, $C_{2-22}$ alkynyl, branched alkyl, or cycloalkyl; Y is O or S;

$Y^1$ is OH, OAryl, or $BH_3^-M^+$; and

Aryl is phenyl, 1-naphthyl, 2-naphthyl, aromatic, heteroaromatic, 4-substituted phenyl, 4-chlorophenyl, 4-bromophenyl.

In certain embodiments, X is methylene ($CH_2$) and $R^1$ is one of the following:

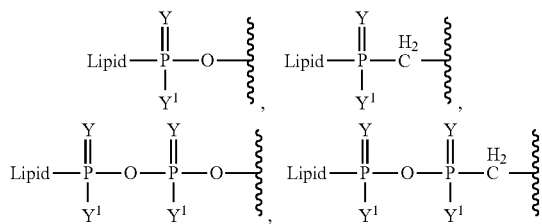

wherein
Y is O or S;
$Y^1$ is OH, OAryl, or $BH_3^-M^+$; and
Aryl is phenyl, 1-naphthyl, 2-naphthyl, aromatic, heteroaromatic, 4-substituted phenyl, 4-chlorophenyl, 4-bromophenyl.

In certain embodiments, the present invention relates to a compound of the following formula:

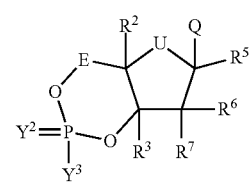

Formula II or a pharmaceutically acceptable salt thereof, wherein
U is O or S;
$Y^2$ is O or S;
$Y^3$ is $OR^{10}$, lipid, $BH_3^-M^+$ or selected from

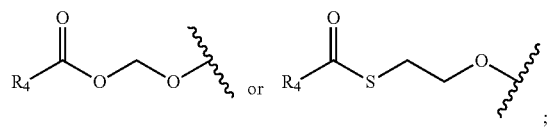

E is $CH_2$ or $CD_2$;
$R^5$ is H or D;
Q is a heterocyclyl comprising two or more nitrogen heteroatoms substituted with at least one thione, thiol or thioether, wherein Q is optionally substituted with one or more, the same or different alkyl, halogen, cycloalkyl;

$R^2$, $R^3$, $R^6$ and $R^7$ are independently selected from are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^{11}$;

$R^{10}$ is $C_{1-22}$ alkyl, $C_{2-22}$ alkenyl, $C_{2-22}$ alkynyl, branched alkyl, or cycloalkyl;

$R^4$ is $C_{1-22}$ alkyl, $C_{1-22}$ alkoxy, $C_{2-22}$ alkenyl, $C_{2-22}$ alkynyl, branched alkyl, or cycloalkyl; and each $R^{11}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl.

In certain embodiments, the Q heterocyclyl is selected from pyrimidin-2-one-4-thione, pyrimidine-2-thione-4-one, pyrimidine-2,4-dithione, 4-aminopyrimidine-2-thione, 5-fluoropyrimidin-2-one-4-thione, 5-fluoropyrimidine-2-thione-4-one, 5-fluoropyrimidine-2,4-dithione, 4-amino-5-fluoropyrimidine-2-thione, 2-amino-purin-6-thione, 2-amino-7-deaza-purin-6-thione or 2-amino-7-deaza-7-substituted-purin-6-thione.

In preferred embodiments, U is O and Q is a pyrimidine with at least one thione, thiol or thioether at the 2 and/or 4-position of said pyrimidine. In other preferred embodiments, U is S and Q is a pyrimidine with at least one thione, thiol or thioether at the 2 and/or 4 position of said pyrimidine.

In other certain embodiments, $R^2$, $R^3$, $R^6$ and $R^7$ are independently selected from the group consisting of H, D, $CH_3$, $CD_3$, $CF_3$, $CF_2H$, $CFH_2$, OH, SH, $NH_2$, $N_3$, CHO, CN, Cl, Br, F or I.

In still other certain embodiments, $R^{10}$ is alkyl, methyl, ethyl, propyl, n-butyl, branched alkyl, isopropyl, 2-butyl, 1-ethylpropyl, 1-propylbutyl, cycloalkyl, cyclopropyl, cyclobutyl, cyclopentyl, cyclohexyl, benzyl, or 2-butyl.

In certain embodiments, the disclosure relates to compounds of the following formula:

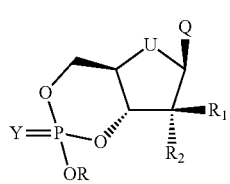

Formula IIa

U is O or S;

wherein $R_1$ and $R_2$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^8$;

each $R^8$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

Q is selected from

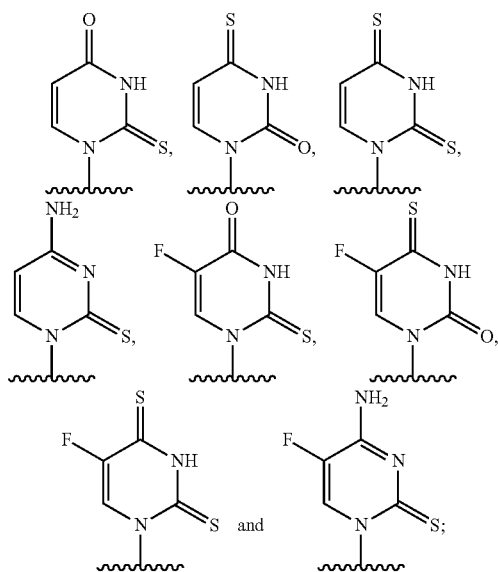

Y is O or S; and

R is straight or branched alkyl, e.g. methyl, ethyl, propyl, n-butyl, isopropyl, 2-butyl, 1-ethylpropyl, 1-propylbutyl, or a $C_{12-19}$ long chain alkyl; cycloalkyl, e.g. cyclopropyl, cyclobutyl, cyclopentyl, or cyclohexyl; or benzyl.

In certain embodiments, the disclosure relates to compounds of the formula:

Formula IIb

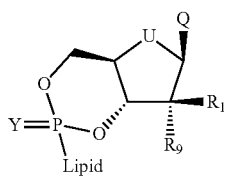

or a pharmaceutically acceptable salt thereof, wherein
U is O or S;
wherein $R_1$ and $R_9$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^{10}$;
each $R^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;
Q is selected from

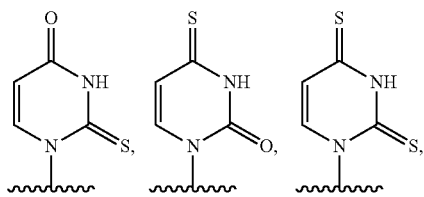

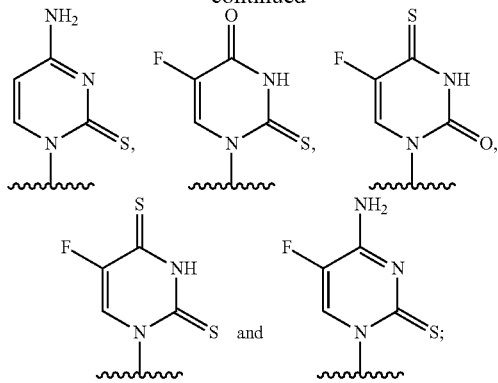

Y is O or S;
Lipid is

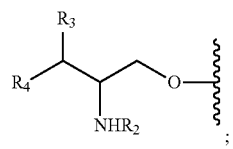

wherein $R_2$ is H; alkyl, e.g. methyl; C(O)R'; C(O)OR'; or C(O)NHR';
$R_3$ is H; hydroxyl; fluoro; OR'; OC(O)R'; OC(O)OR'; OC(O)NHR';
R' is H; straight or branched alkyl, e.g. methyl, ethyl, propyl, n-butyl, isopropyl, 2-butyl, 1-ethylpropyl, 1-propylbutyl, or a $C_{12-19}$ long chain alkyl; cycloalkyl, e.g. cyclopropyl, cyclobutyl, cyclopentyl, or cyclohexyl; benzyl; phenyl; monosubstituted phenyl; disubstituted phenyl or trisubstituted phenyl;
$R^4$ is a $C_{11-17}$ long alkyl chain, e.g.

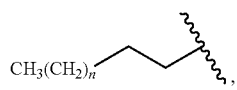

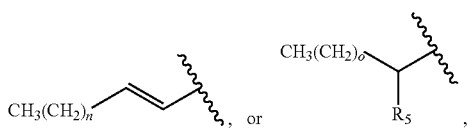

wherein n is 8-14 and o is 9-15; or

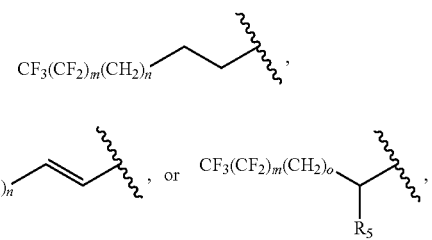

wherein "m+n" is 8-14 and "m+o" is 9-15; or

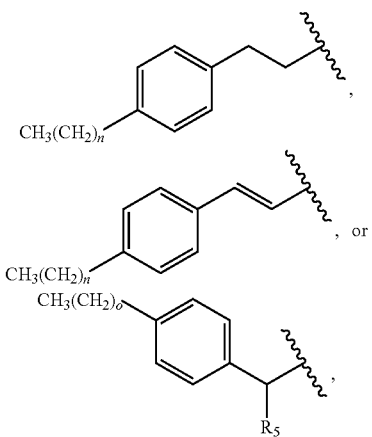

wherein n is 4-10 and o is 5-11; or

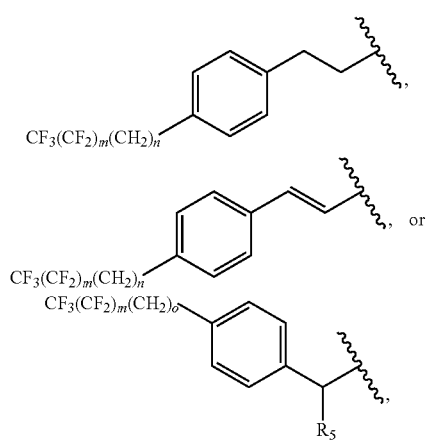

wherein "m+n" is 4-10 and "m+o" is 5-11; or

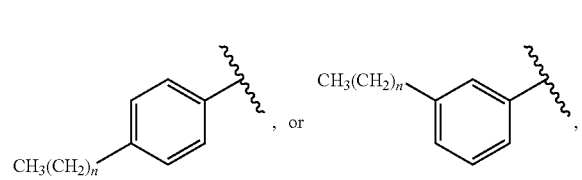

wherein n is 6-12; or

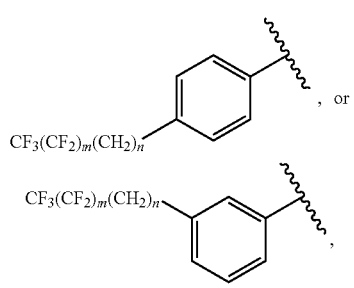

wherein "m+n" is 6-12; and $R_5$ is H, hydroxyl, fluoro, OR', OC(O)R', OC(O)OR', or OC(O)NHR'.

In an alternative embodiment, Lipid is

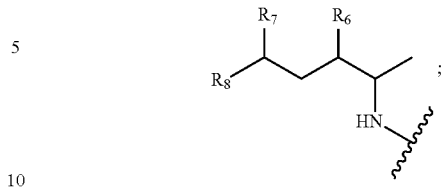

wherein $R_6$ is H; hydroxyl; fluoro; OR'; OC(O)R'; OC(O)OR'; or OC(O)NHR';

$R_7$ is H; hydroxyl; fluoro; OR'; OC(O)R'; OC(O)OR'; or OC(O)NHR';

R' is H; straight or branched alkyl, e.g. methyl, ethyl, propyl, n-butyl, isopropyl, 2-butyl, 1-ethylpropyl, 1-propylbutyl, or a $C_{12-19}$ long chain alkyl; cycloalkyl, e.g. cyclopropyl, cyclobutyl, cyclopentyl, or cyclohexyl; benzyl; phenyl; monosubstituted phenyl; disubstituted phenyl; trisubstituted phenyl;

$R_8$ is a $C_{9-15}$ alkyl chain, e.g.

wherein n is 8-14 or

wherein "m+n" is 8-14.

In certain embodiments, the disclosure relates to compounds of the formulae:

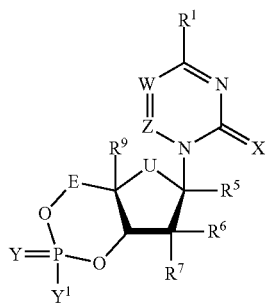

Formula IIc

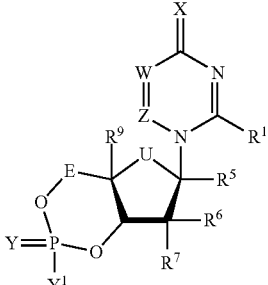

Formula IId

Formula IIe

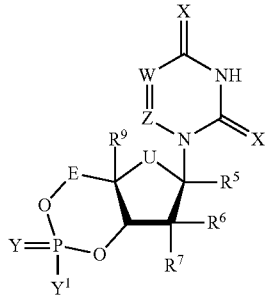

or a pharmaceutically salt thereof, wherein
$R^5$ is H or D;
E is $CH_2$ or $CD_2$;
U is O or S;
Y is O or S;
$Y^1$ is $OR^{40}$, lipid, $BH_3\text{-}M^+$ or selected from

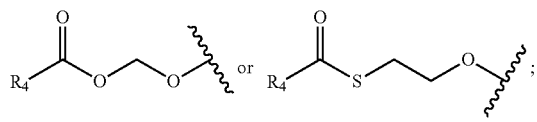

each X is independently O, S, NH, $NR^8$, NHOH, $NR^8OH$, $NHOR^8$, or $NR^8OR^8$;
$R^1$ is OH, SH, $NH_2$, $OR^8$, $SR^8$, $NHR^8$, NHOH, $NR^8OH$, $NHOR^8$, or $NR^8OR^8$;
  wherein in Formula IIc and IId, one of X is S or $R^1$ is $SR^8$, or both X is S and $R^1$ is $SR^8$;
  wherein in Formula IIe at least one X is S;
W is CH, N, or $CR^8$;
Z is CH, N, or $CR^8$;
$R^6$, $R^7$, and $R^9$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different $R^8$;
  each $R^8$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;
$R^{40}$ is $C_{1-22}$ alkyl, $C_{2-22}$ alkenyl, $C_{2-22}$ alkynyl, branched alkyl, or cycloalkyl;
$R^4$ is $C_{1-22}$ alkyl, $C_{1-22}$ alkoxy, $C_{2-22}$ alkenyl, $C_{2-22}$ alkynyl, branched alkyl, or cycloalkyl.
In certain embodiments, U is S and Y and Z are CH.
In other embodiments, U is O and Y and Z are CH.
In exemplary embodiments, the compound is selected from:

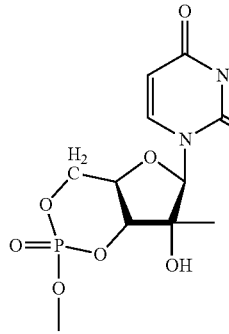
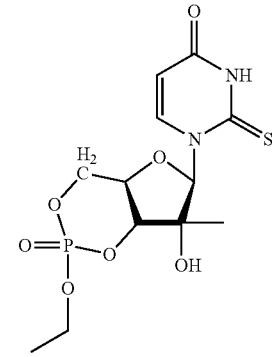

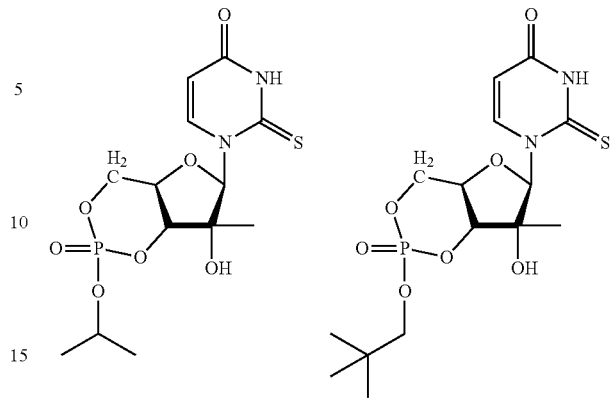

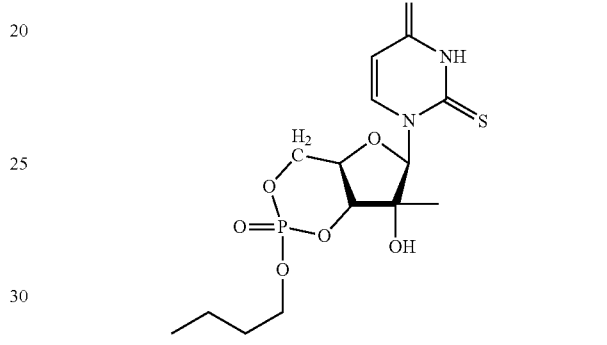

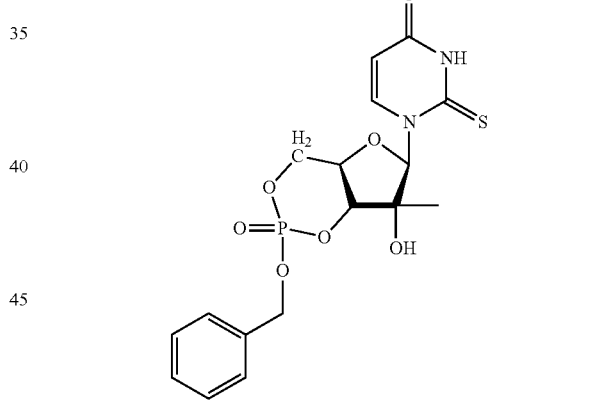

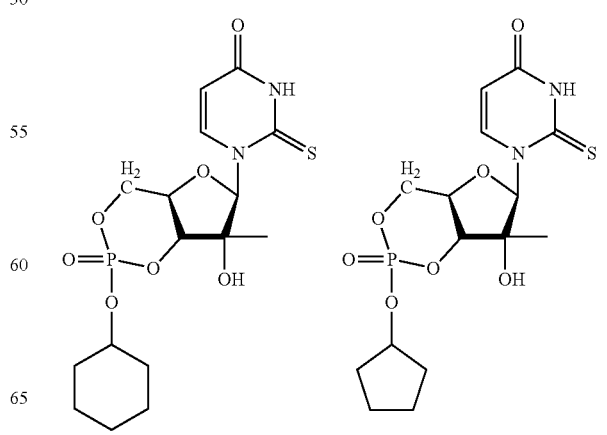

217
-continued
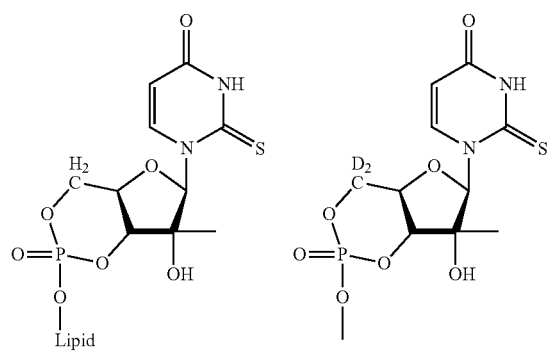
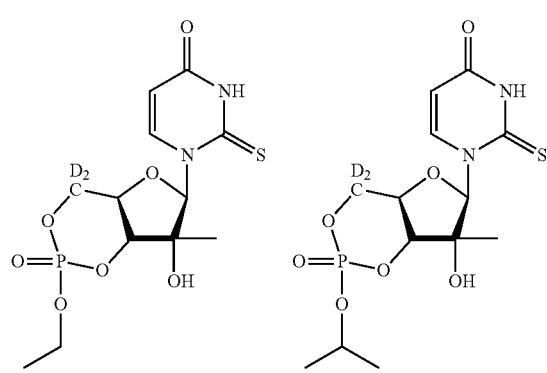
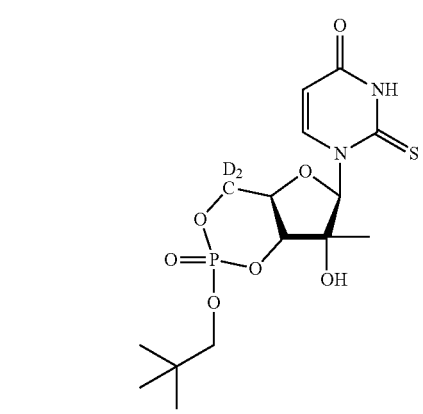
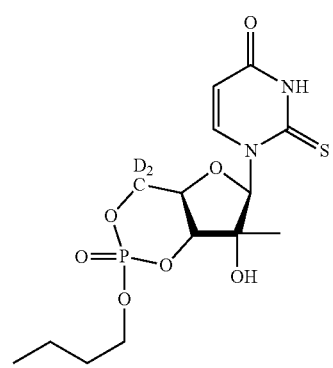
218
-continued
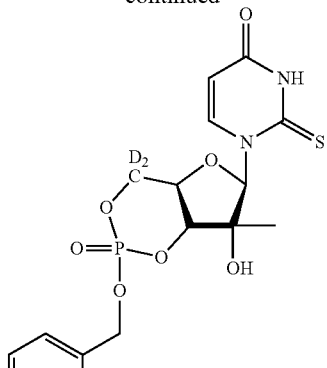
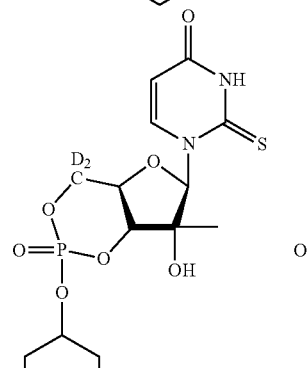
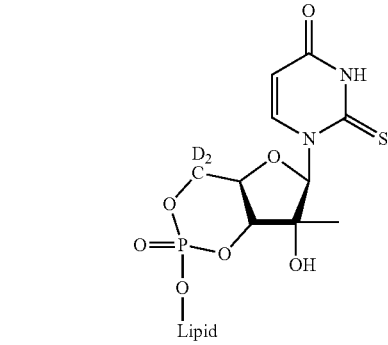
In certain embodiments, the present invention relates to a compound of the following formula:
Formula III
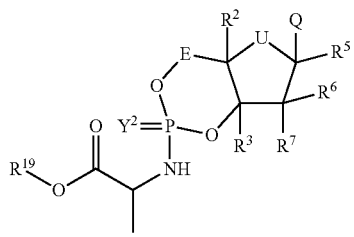
or pharmaceutically acceptable salts thereof wherein,
$R^5$ is H or D;
U is O or S;
E is $CH_2$ or $CD_2$;
$Y^2$ is O or S;

$R^2$, $R^3$, $R^6$ and $R^7$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^8$;

Q is a heterocyclyl comprising two or more nitrogen heteroatoms substituted with at least one thione, thiol or thioether, wherein Q is optionally substituted with one or more, the same or different alkyl, halogen, or cycloalkyl;

each $R^8$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)2amino, alkylsulfinyl, alkylsulfonyl, arylsulfonyl, carbocyclyl, aryl, or heterocyclyl;

$R^{19}$ is $C_{1-22}$ alkyl, $C_{2-22}$ alkenyl, $C_{2-22}$ alkynyl, branched alkyl, or cycloalkyl.

In preferred embodiments, U is O and Q is a pyrimidine with at least one thione, thiol or thioether at the 2 and/or 4-position of said pyrimidine. In other preferred embodiments, U is S and Q is a pyrimidine with at least one thione, thiol or thioether at the 2 and/or 4 position of said pyrimidine.

In certain embodiments, $R^6$ is selected from hydrogen, methyl, fluoromethyl, hydroxymethyl, difluoromethyl, trifluoromethyl, acetylenyl, ethyl, vinyl, or cyano.

In certain embodiments, $R^{19}$ is selected from is alkyl, methyl, ethyl, propyl, n-butyl, branched alkyl, isopropyl, 2-butyl, 1-ethylpropyl, 1-propylbutyl, cycloalkyl, cyclopropyl, cyclobutyl, cyclopentyl, cyclohexyl, benzyl, or 2-butyl.

In certain embodiments, the disclosure relates to compounds of formula:

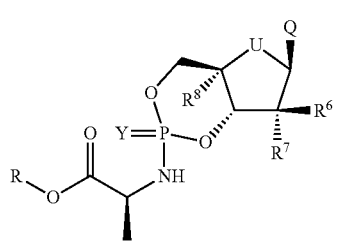

Formula IIIa or a pharmaceutically acceptable salt thereof, wherein U is O or S;

$R^6$ and $R^7$ are each independently selected from are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^{10}$;

each $R^{11}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

Q is selected from

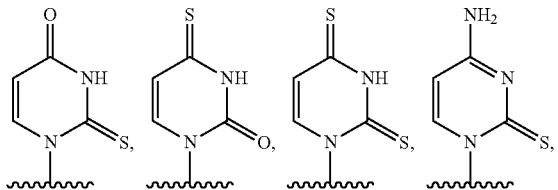

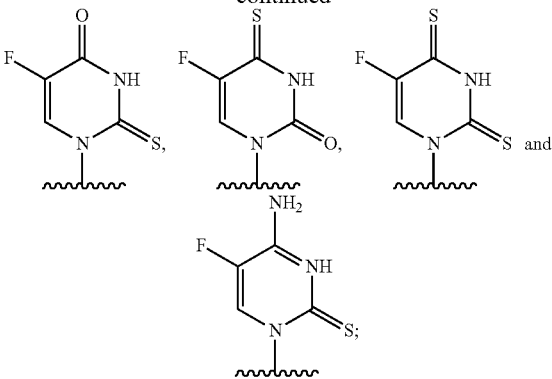

Y is O or S;

R is straight or branched alkyl, e.g. methyl, ethyl, propyl, n-butyl, isopropyl, 2-butyl, 1-ethylpropyl, 1-propylbutyl, or a $C_{12-19}$ long chain alkyl; cycloalkyl, e.g. cyclopropyl, cyclobutyl, cyclopentyl, or cyclohexyl; or benzyl.

In certain embodiments, the disclosure relates to a compound of the following formulae:

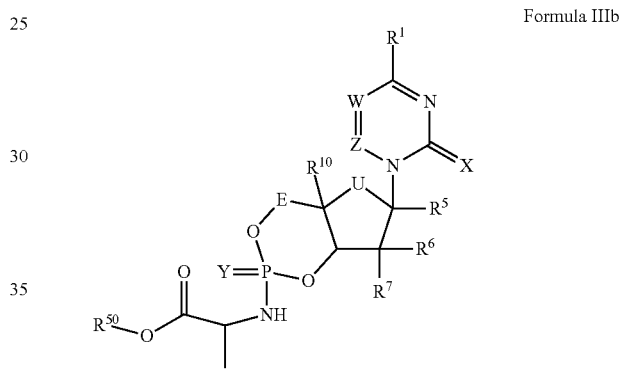

Formula IIIb

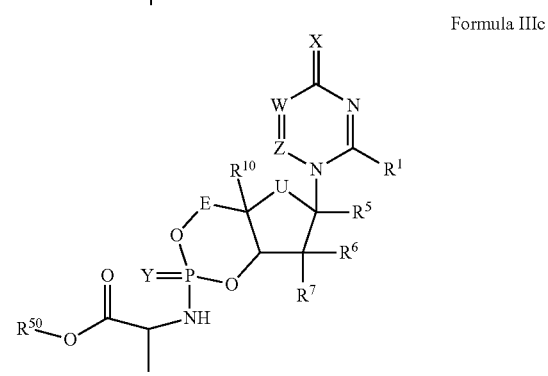

Formula IIIc

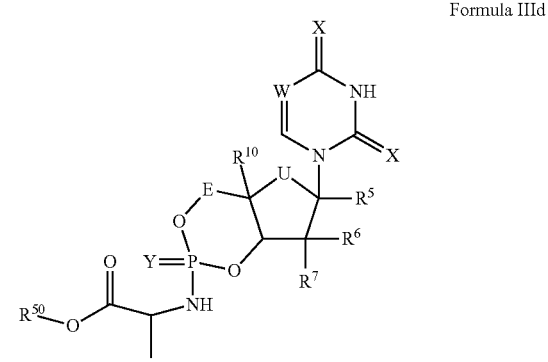

Formula IIId or a pharmaceutically acceptable salt thereof, wherein $R^5$ is H or D;

E is $CH_2$ or $CD_2$;

U is O or S;

Y is O or S;

each X is independently O, S, NH, $NR^8$, NHOH, $NR^8OH$, $NHOR^8$, or $NR^8OR^8$;

$R^1$ is OH, SH, $NH_2$, $OR^8$, $SR^8$, $NHR^8$, NHOH, $NR^8OH$, $NHOR^8$, or $NR^8OR^8$;

wherein in Formula IIIb and IIIc, one of X is S or $R^1$ is $SR^8$, or both X is S and $R^1$ is $SR^8$;

wherein in Formula IIId at least one X is S;

W is CH, N, or $CR^8$;

Z is CH, N, or $CR^8$;

wherein $R^6$, $R^7$ and $R^{10}$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^9$;

$R^8$ is methyl, trifluoromethyl, fluoro, iodo, alkenyl, alkynyl, vinyl, allyl, halogen, halogentated alkyl, hydroxyl alkyl, acyl, lipid, geranyl, $C_{1-22}$ alkyl optionally substituted with one or more, the same or different, $R^9$;

each $R^9$ is independently selected from alkyl, deutero, halogen, nitro, cyano, hydroxy, amino, mercapto, formyl, carboxy, alkanoyl, carbamoyl, alkoxy, alkylthio, alkylamino, $(alkyl)_2amino$, alkylsulfinyl, alkylsulfonyl, arylsulfonyl, carbocyclyl, aryl, or heterocyclyl;

$R^{50}$ is $C_{1-22}$ alkyl, $C_{2-22}$ alkenyl, $C_{2-22}$ alkynyl, branched alkyl, or cycloalkyl.

In certain embodiments U is S and W and Z are CH. In other embodiments, U is O and W and Z are CH.

In certain embodiments, $R^5$ is H. In other embodiments, $R^6$ is methyl. In still other embodiments, $R^7$ is hydroxyl. In a preferred embodiment, $R^5$ is H, $R^6$ is methyl and $R^7$ is hydroxyl.

In certain embodiments, $R^{50}$ is alkyl, methyl, ethyl, propyl, n-butyl, branched alkyl, isopropyl, 2-butyl, 1-ethylpropyl, 1-propylbutyl, cycloalkyl, cyclopropyl, cyclobutyl, cyclopentyl, cyclohexyl, benzyl, or 2-butyl.

In exemplary embodiments, the compound is selected from:

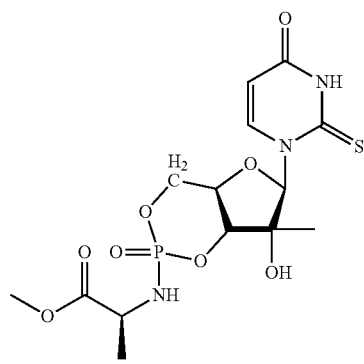

-continued

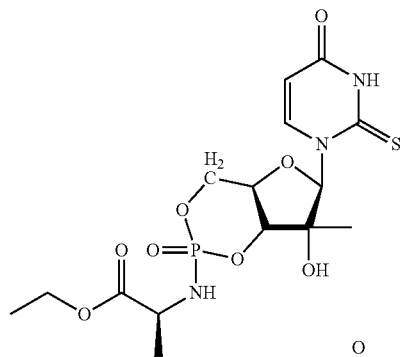

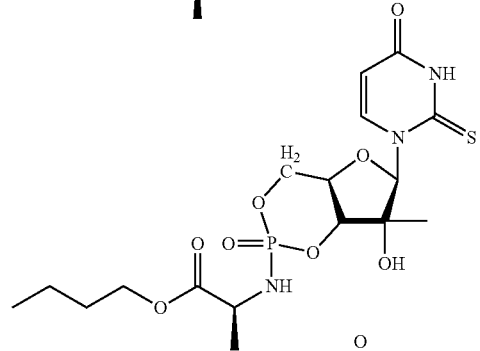

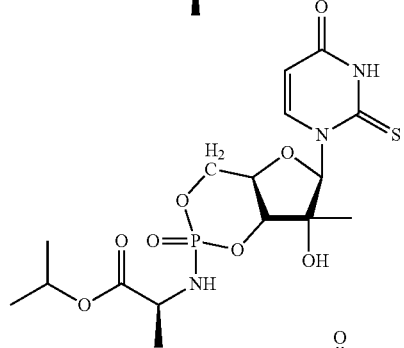

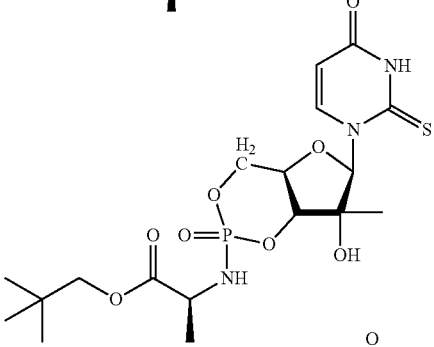

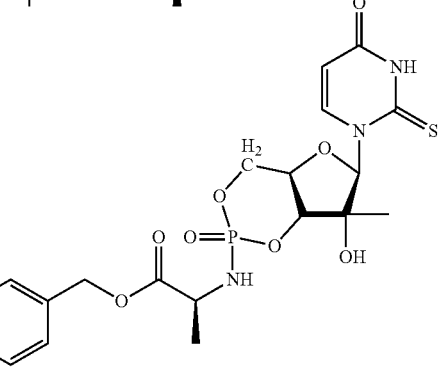

223
-continued
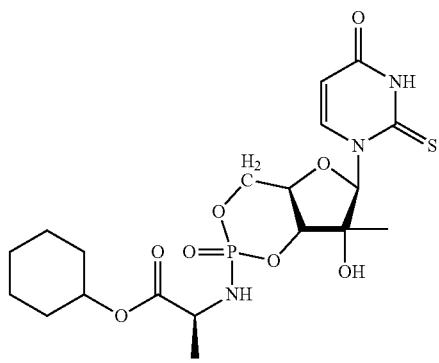
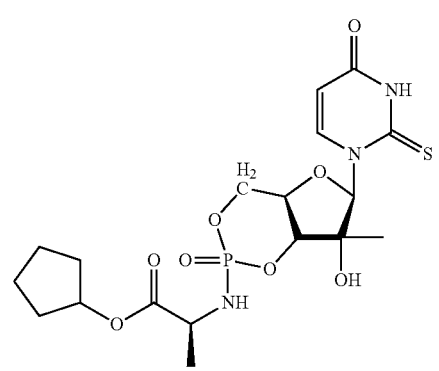
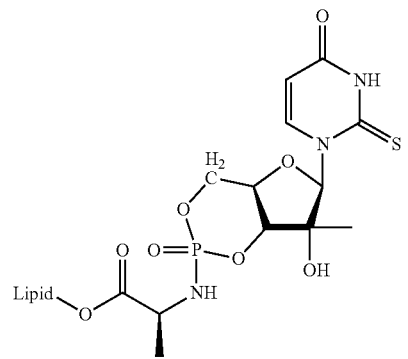
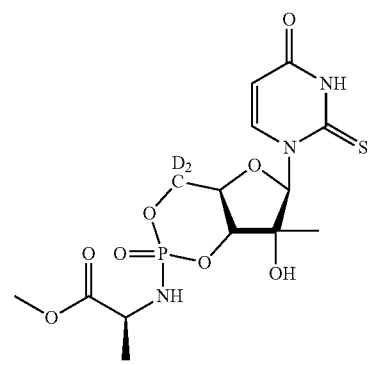
224
-continued
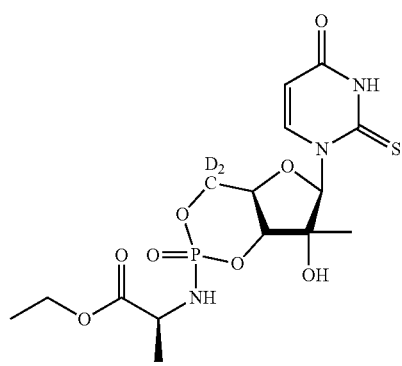
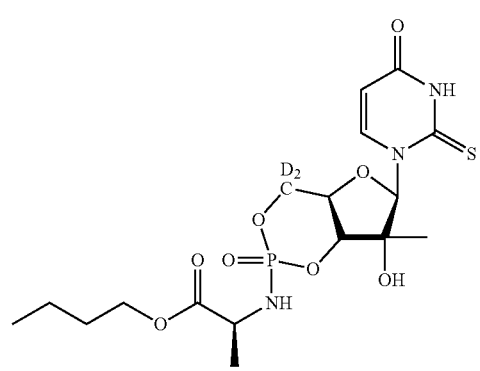
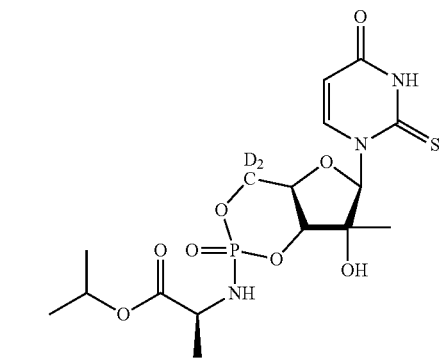
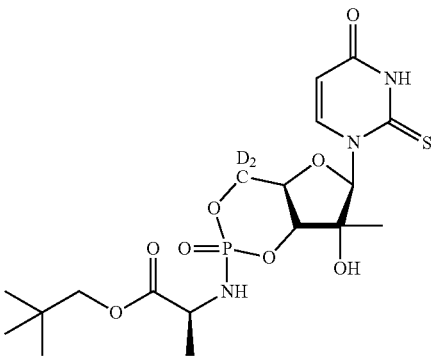

-continued

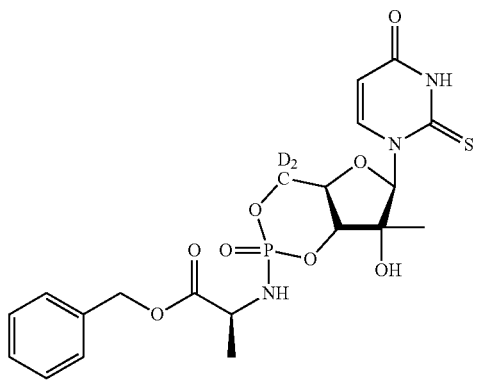

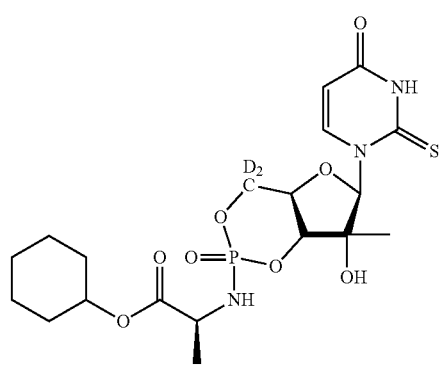

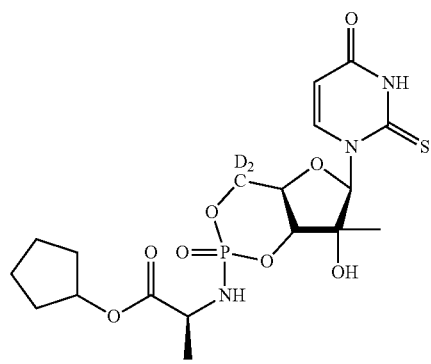

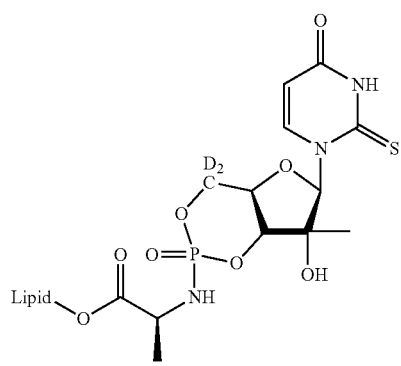

In certain embodiments, the present invention relates to compounds of the following formula:

Formula IV

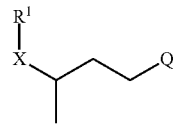

or a pharmaceutically acceptable salt thereof, wherein X is O, $CH_2$ or $CD_2$;

$R^1$ is a phosphate, phosphonate, polyphosphate, polyphosphonate substituent wherein the phosphate or a phosphate in the polyphosphate or polyphosphonate is optionally a phosphoroborate, phosphorothioate, or phosphoroamidate, and the substituent is further substituted with an amino acid ester or lipid or derivative optionally substituted with one or more, the same or different, $R^6$;

Q is a heterocyclyl comprising two or more nitrogen heteroatoms substituted with at least one thione, thiol or thioether, wherein Q is optionally substituted with one or more, the same or different alkyl, halogen, or cycloalkyl;

$R^6$ is the same or different alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^6$ is optionally substituted with one or more, the same or different, $R^7$; and $R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the Q heterocyclyl is pyrimidin-2-one-4-thione, pyrimidine-2-thione-4-one, pyrimidine-2,4-dithione, 4-aminopyrimidine-2-thione, 5-fluoropyrimidin-2-one-4-thione, 5-fluoropyrimidine-2-thione-4-one, 5-fluoropyrimidine-2,4-dithione, 4-amino-5-fluoropyrimidine-2-thione, 2-amino-purin-6-thione, 2-amino-7-deaza-purin-6-thione or 2-amino-7-deaza-7-substituted-purin-6-thione.

In preferred embodiments, U is O and Q is a pyrimidine with at least one thione, thiol or thioether at the 2 and/or 4-position of said pyrimidine. In other preferred embodiments, U is S and Q is a pyrimidine with at least one thione, thiol or thioether at the 2 and/or 4 position of said pyrimidine.

In certain embodiments, the lipid is a sphingolipid of any of the formula described above or herein.

In certain embodiments, the present invention relates to a compound of the following formula Formula V

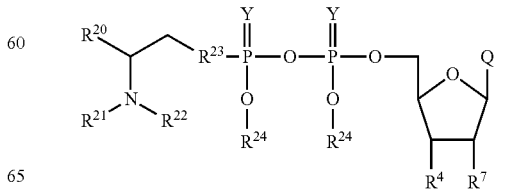

or a pharmaceutically acceptable salt thereof wherein,
each Y is independently O or S;
$R^{23}$ is O or NH;
$R^4$ and $R^7$ are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^9$.

Q is a heterocyclyl comprising two or more nitrogen heteroatoms substituted with at least one thione, thiol or thioether, wherein Q is optionally substituted with one or more, the same or different alkyl, halogen, or cycloalkyl;

each $R^9$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

$R^{20}$ is an alkyl of 6 to 22 carbons optionally substituted with one or more, the same or different $R^{26}$;

$R^{21}$ and $R^{22}$ are each independently selected from hydrogen, alkyl, or alkanoyl, wherein $R^{21}$ and $R^{22}$ are each optionally substituted with one or more, the same or different $R^{26}$;

$R^{24}$ and $R^{25}$ are each independently selected from hydrogen, alkyl, or aryl, wherein $R^{24}$ and $R^{25}$ are each optionally substituted with one or more, the same or different $R^{26}$;

each $R^{26}$ is independently selected from alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl.

In certain embodiments, $R^4$ and $R^7$ are independently hydrogen, hydroxy, alkoxy, azide, or halogen.

In certain embodiments, the present invention relates to compounds of the following formula

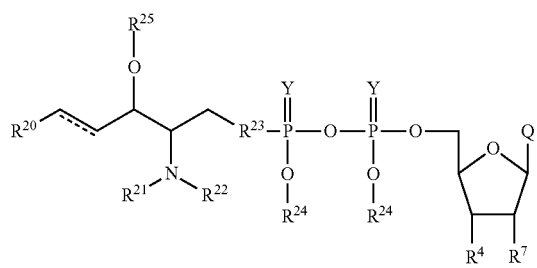

Formula VI or a pharmaceutically acceptable salt thereof wherein,
the dotted line represents the presence of a single or double bond;

Q is a heterocyclyl comprising two or more nitrogen heteroatoms substituted with at least one thione, thiol or thioether, wherein Q is optionally substituted with one or more, the same or different alkyl, halogen, cycloalkyl;

$R^{23}$ is O or NH;

$R^4$ and $R^7$ are each independently selected from are each independently selected from H, D, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^{26}$;

$R^{20}$ is an alkyl of 6 to 22 carbons optionally substituted with one or more, the same or different $R^{26}$;

$R^{21}$, $R^{22}$, and $R^{25}$ are independently selected from hydrogen, alkyl, or alkanoyl, wherein $R^{21}$, $R^{22}$, and $R^{25}$ are each optionally substituted with one or more, the same or different $R^{26}$;

each $R^{24}$ is independently selected from hydrogen, alkyl, or aryl, wherein each $R^{24}$ is optionally substituted with one or more, the same or different $R^{26}$;

each $R^{26}$ is independently selected from alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl In certain embodiments, the Q heterocyclyl is pyrimidin-2-one-4-thione, pyrimidine-2-thione-4-one, pyrimidine-2,4-dithione, 4-aminopyrimidine-2-thione, 5-fluoropyrimidin-2-one-4-thione, 5-fluoropyrimidine-2-thione-4-one, 5-fluoropyrimidine-2,4-dithione, 4-amino-5-fluoropyrimidine-2-thione, 2-amino-purin-6-thione, 2-amino-7-deazapurin-6-thione or 2-amino-7-deaza-7-substituted-purin-6-thione.

In certain embodiments, the present invention relates to a compound having the following formula:

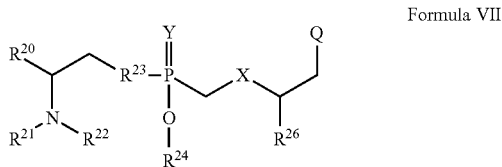

Formula VII or a pharmaceutically acceptable salt thereof wherein,
X is O or NH or $CD_2$;
Y is O or S;
$R^{23}$ is O or NH;

Q is a heterocyclyl comprising two or more nitrogen heteroatoms substituted with at least one thione, thiol or thioether, wherein Q is optionally substituted with one or more, the same or different alkyl, halogen, or cycloalkyl;

$R^{20}$ is an alkyl of 6 to 22 carbons optionally substituted with one or more, the same or different $R^{37}$;

$R^{21}$ and $R^{22}$ are each independently selected from hydrogen, alkyl, or alkanoyl, wherein $R^{21}$ and $R^{22}$ are each optionally substituted with one or more, the same or different $R^{37}$;

$R^{24}$ is hydrogen, alkyl, or aryl wherein $R^{24}$ is optionally substituted with one or more, the same or different $R^{37}$;

$R^{26}$ is alkyl;

each $R^{37}$ is independently selected from alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl.

In certain embodiments, the Q heterocyclyl is pyrimidin-2-one-4-thione, pyrimidine-2-thione-4-one, pyrimidine-2,4-dithione, 4-aminopyrimidine-2-thione, 5-fluoropyrimidin-2-one-4-thione, 5-fluoropyrimidine-2-thione-4-one, 5-fluoropyrimidine-2,4-dithione, 4-amino-5-fluoropyrimidine-2-thione, 2-amino-purin-6-thione, 2-amino-7-deazapurin-6-thione or 2-amino-7-deaza-7-substituted-purin-6-thione.

In certain embodiment, the present invention relates to compounds having the following formula:

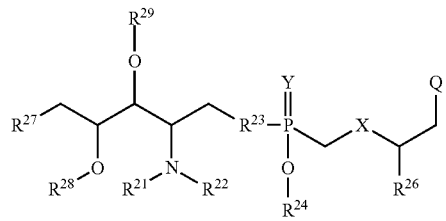

Formula VIII or a pharmaceutically acceptable salt thereof wherein,
X is O or NH or $CD_2$;
Y is O or S;
$R^{23}$ is O or NH;
Q is a heterocyclyl comprising two or more nitrogen heteroatoms substituted with at least one thione, thiol or thioether wherein Q is optionally substituted with one or more, the same or different alkyl, halogen, or cycloalkyl;
$R^{27}$ is an alkyl of 6 to 22 carbons optionally substituted with one or more, the same or different $R^{37}$;
$R^{21}$, $R^{22}$, $R^{28}$, and $R^{29}$ are each independently selected from hydrogen, alkyl, or alkanoyl, wherein $R^{21}$, $R^{22}$, $R^{28}$, and $R^{29}$ are each optionally substituted with one or more, the same or different $R^{37}$;
$R^{24}$ is hydrogen, alkyl, or aryl wherein $R^{24}$ is optionally substituted with one or more, the same or different $R^{37}$;
$R^{26}$ is alkyl;
each $R^{37}$ is independently selected from alkyl, halogen, nitro, cyano, hydroxy, amino, mercapto, formyl, carboxy, alkanoyl, carbamoyl, alkoxy, alkylthio, alkylamino, (alkyl)$_2$ amino, alkylsulfinyl, alkylsulfonyl, arylsulfonyl, carbocyclyl, aryl, or heterocyclyl.

In certain embodiments, the Q heterocyclyl is pyrimidin-2-one-4-thione, pyrimidine-2-thione-4-one, pyrimidine-2,4-dithione, 4-aminopyrimidine-2-thione, 5-fluoropyrimidin-2-one-4-thione, 5-fluoropyrimidine-2-thione-4-one, 5-fluoropyrimidine-2,4-dithione, 4-amino-5-fluoropyrimidine-2-thione, 2-amino-purin-6-thione, 2-amino-7-deazapurin-6-thione or 2-amino-7-deaza-7-substituted-purin-6-thione.

In preferred embodiments, U is O and Q is a pyrimidine with at least one thione, thiol or thioether at the 2 and/or 4-position of said pyrimidine. In other preferred embodiments, U is S and Q is a pyrimidine with at least one thione, thiol or thioether at the 2 and/or 4 position of said pyrimidine.

In certain embodiments, the fragment defined by $R^{23}$-$R^{27}$ is a sphingolipid. Suitable sphingolipids include, but are not limited to, 2-aminooctadecane-3,5-diol; (2S,3S,5S)-2-aminooctadecane-3,5-diol; (2S,3R,5S)-2-aminooctadecane-3,5-diol; 2-(methylamino)octadecane-3,5-diol; (2S,3R,5S)-2-(methylamino)octadecane-3,5-diol; 2-(dimethylamino)octadecane-3,5-diol; (2R,3S,5S)-2-(dimethylamino)octadecane-3,5-diol; 1-(pyrrolidin-2-yl)hexadecane-1,3-diol; (1S,3S)-1-((S)-pyrrolidin-2-yl)hexadecane-1,3-diol; 2-amino-11,11-difluorooctadecane-3,5-diol; (2S,3S,5S)-2-amino-11,11-difluorooctadecane-3,5-diol; 11,11-difluoro-2-(methylamino)octadecane-3,5-diol; (2S,3S,5S)-11,11-difluoro-2-(methylamino)octadecane-3,5-diol; N-((2S,3S,5S)-3,5-dihydroxyoctadecan-2-yl)acetamide; N-((2S,3S,5S)-3,5-dihydroxyoctadecan-2-yl)palmitamide; 1-(1-aminocyclopropyl)hexadecane-1,3-diol; (1S,3R)-1-(1-aminocyclopropyl)hexadecane-1,3-diol; (1S,3S)-1-(1-aminocyclopropyl)hexadecane-1,3-diol; 2-amino-2-methyloctadecane-3,5-diol; (3S,5S)-2-amino-2-methyloctadecane-3,5-diol; (3S,5R)-2-amino-2-methyloctadecane-3,5-diol; (3S,5S)-2-methyl-2-(methylamino)octadecane-3,5-diol; 2-amino-5-hydroxy-2-methyloctadecan-3-one; (Z)-2-amino-5-hydroxy-2-methyloctadecan-3-one oxime; (2S,3R,5R)-2-amino-6,6-difluorooctadecane-3,5-diol; (2S,3S,5R)-2-amino-6,6-difluorooctadecane-3,5-diol; (2S,3S,5S)-2-amino-6,6-difluorooctadecane-3,5-diol; (2S,3R,5S)-2-amino-6,6-difluorooctadecane-3,5-diol; and (2S,3S,5S)-2-amino-18,18,18-trifluorooctadecane-3,5-diol; which may be optionally substituted with one or more substituents.

In preferred embodiments, the nucleoside conjugate has the following structure:

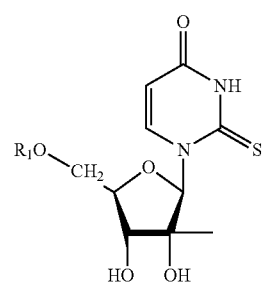

Formula IXa

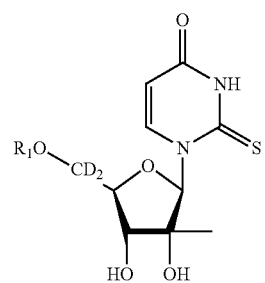

Formula IXb or a pharmaceutically acceptable salt thereof, wherein $R_1$ is H, monophosphate, diphosphate, triphosphate, or selected from one of the following:

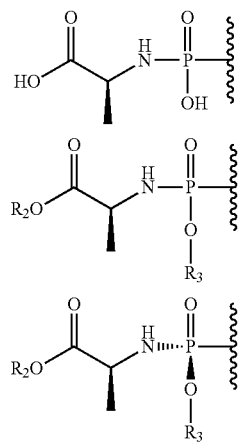

-continued

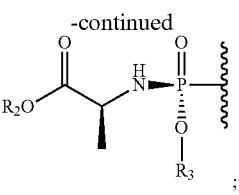

$R_2$ is alkyl, branched alkyl, or cycloalkyl;

$R_3$ is aryl, biaryl, or substituted aryl;

In exemplified embodiments, the nucleoside conjugated to a phosphorus moiety or pharmaceutically acceptable salt thereof has the following structure:

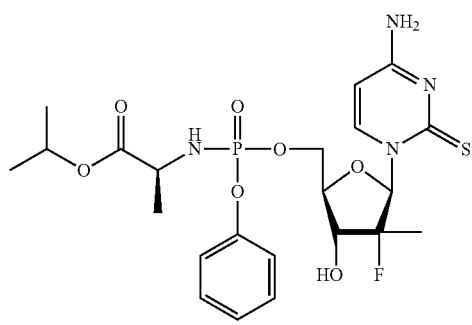

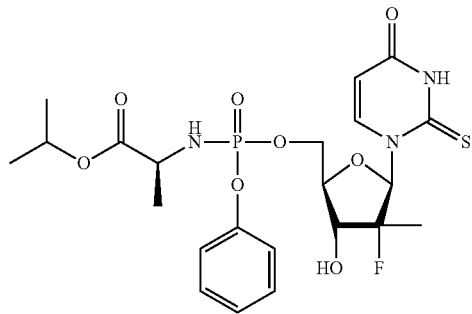

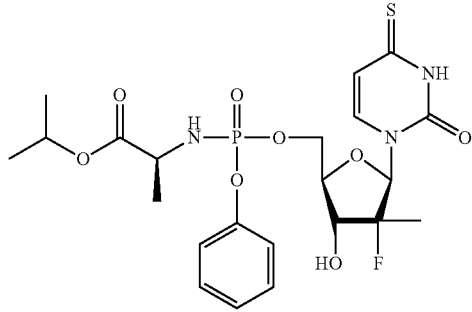

In certain embodiments, the disclosure relates to a compound of the following formulae:

Formula Xa

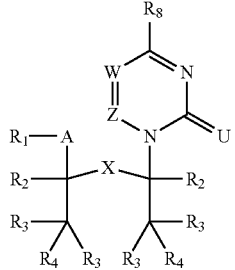

Formula Xb

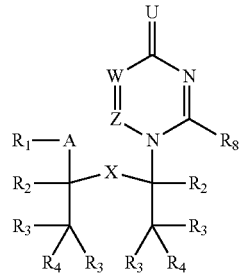

Formula Xc

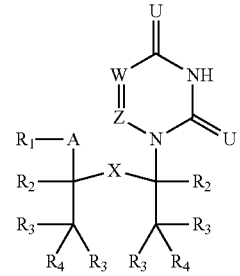

or a pharmaceutically acceptable salt thereof, wherein

A is absent or selected from $CH_2$, $CD_2$, $0$, $CH_2O$, $CD_2O$, $OCH_2$, or $OCD_2$;

$R_1$ is selected from one of the following:

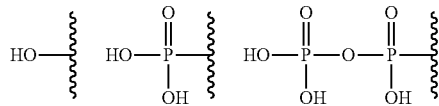

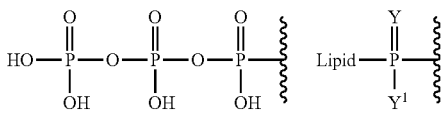

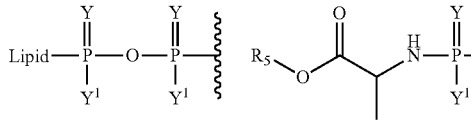

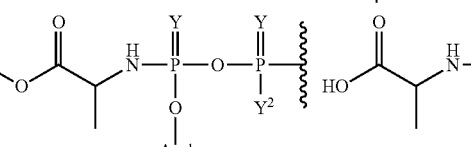

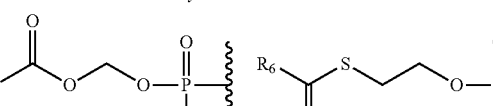

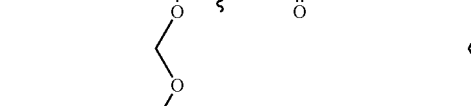

-continued

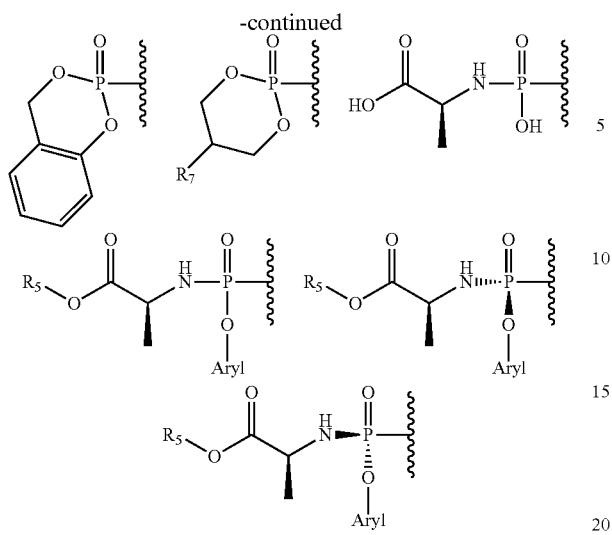

X is O, S, NH, $CH_2$, $CD_2$, CHF, $CF_2$, $CCH_2$, or $CCF_2$;
each U is independently O, S, NH, $NR^9$, NHOH, $NR^9OH$, $NHOR^9$, or $NR^9OR^9$;

each $R^8$ is independently OH, SH, $NH_2$, $OR^9$, $SR^9$, $NHR^9$, NHOH, $NR^9OH$, $NHOR^9$, or $NR^9OR^9$;

wherein in Formula Xa and Xb, one of U is S or $R^8$ is $SR^9$, or both U is S and $R^8$ is $SR^9$;

wherein in Formula Xc at least one U is S;

W is CH, N, or $CR^9$;

Z is CH, N, or $CR^9$;

each $R^9$ is independently methyl, trifluoromethyl, fluoro, iodo, alkenyl, alkynyl, vinyl, allyl, halogen, halogentated alkyl, hydroxyl alkyl, acyl, lipid, geranyl, $C_{1-22}$ alkyl optionally substituted with one or more, the same or different, $R^{10}$;

each $R^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

each $R_2$ is independently selected from hydrogen, deuterium, hydroxyl, cyano, halogen, fluoro, methyl, ethynyl, vinyl, allyl, monofluoromethyl, difluoromethyl, trifluoromethyl, trideuteromethyl, azido, methoxy, or amino;

each $R_3$ is independently selected from hydrogen, deuterium, hydroxyl, cyano, halogen, fluoro, methyl, ethynyl, vinyl, allyl, monofluoromethyl, difluoromethyl, trifluoromethyl, trideuteromethyl, or azido;

each $R_4$ is independently selected from hydrogen, deuterium, hydroxyl, halogen, fluoro, azido, methoxy, or amino;

Lipid is as described herein;

Y is O or S;

$Y^1$ is OAryl or $BH_3^-M^+$;

$Y^2$ is OH or $BH_3^-M^+$;

$R_5$ is alkyl, branched alkyl, or cycloalkyl;

Aryl is as described herein;

$R_6$ is $C_{1-22}$ alkoxy, or $C_{1-22}$ alkyl, alkyl, branched alkyl, cycloalkyl, or alkyoxy;

$R_7$ is aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl.

In certain embodiments, the disclosure relates to a compound of the following formulae:

Formula Xd

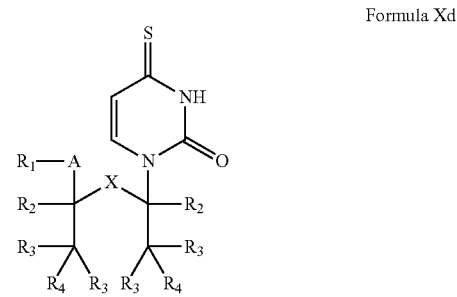

Formula Xe

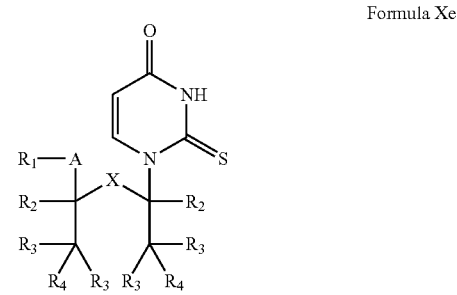

Formula Xf

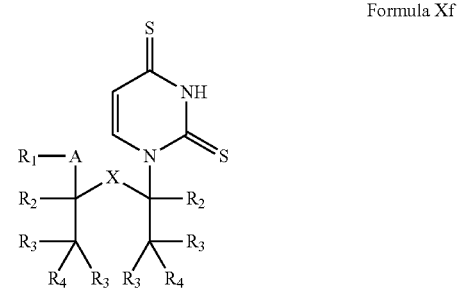

Formula Xg

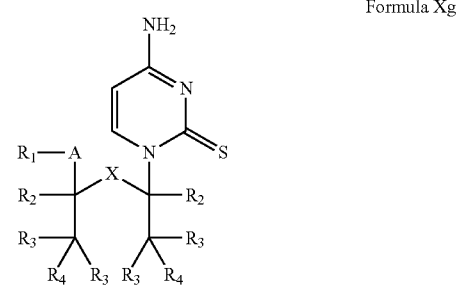

or a pharmaceutically acceptable salt thereof, wherein

A is absent or selected from $CH_2$, $CD_2$, O, $CH_2O$, $CD_2O$, $OCH_2$, or $OCD_2$;

$R_1$ is selected from one of the following:

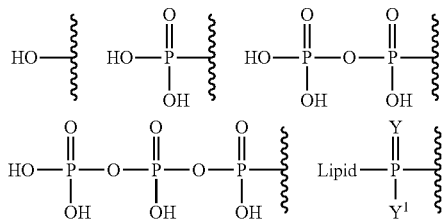

235
-continued

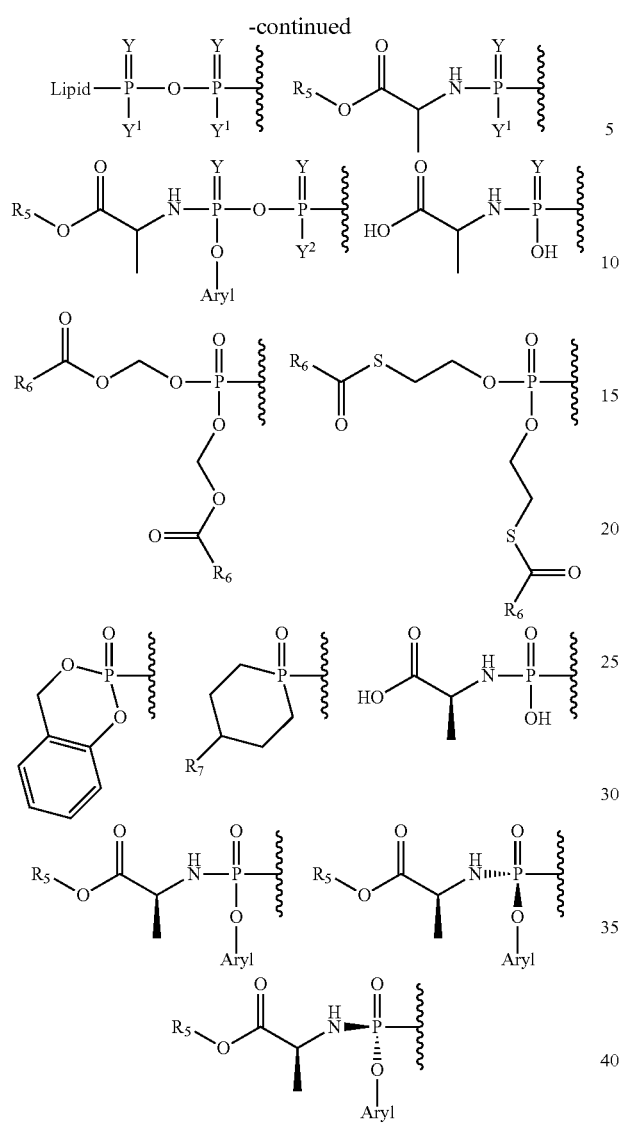

X is O, S, NH, CH$_2$, CD$_2$, CHF, CF$_2$, CCH$_2$, or CCF$_2$;

each R$_2$ is independently hydrogen, deuterium, hydroxyl, cyano, halogen, fluoro, methyl, ethynyl, vinyl, allyl, monofluoromethyl, difluoromethyl, trifluoromethyl, trideuteromethyl, azido, methoxy, or amino;

each R$_3$ is independently hydrogen, deuterium, hydroxyl, cyano, halogen, fluoro, methyl, ethynyl, vinyl, allyl, monofluoromethyl, difluoromethyl, trifluoromethyl, trideuteromethyl, or azido;

each R$_4$ is independently hydrogen, deuterium, hydroxyl, halogen, fluoro, azido, methoxy, or amino;

Lipid is as described herein;
Y is O or S;
Y$^1$ is OAryl or BH$_3^-$M$^+$;
Y$^2$ is OH or BH$_3^-$M$^+$;
R$_5$ is alkyl, branched alkyl, or cycloalkyl;
Aryl is as described herein;
R$_6$ is C$_{1-22}$ alkoxy, or C$_{1-22}$ alkyl, alkyl, branched alkyl, cycloalkyl, or alkyoxy;
R$_7$ is aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl.

236

In certain embodiments, the disclosure relates to a compound of the following formulae:

Formula XIa

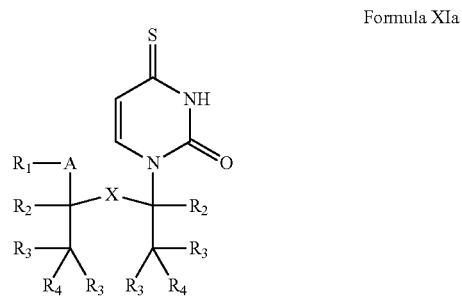

Formula XIb

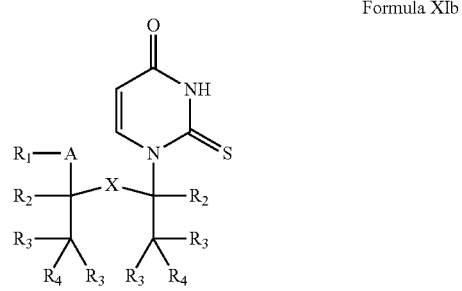

Formula XIc

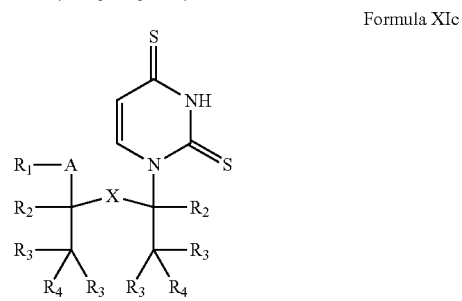

Formula XId

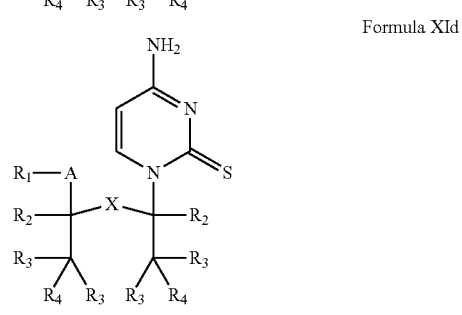

or a pharmaceutically acceptable salt thereof, wherein
A is absent or selected from CH$_2$, CD$_2$, O, CH$_2$O, CD$_2$O, OCH$_2$, or OCD$_2$;
R$_1$ is selected from one of the following:

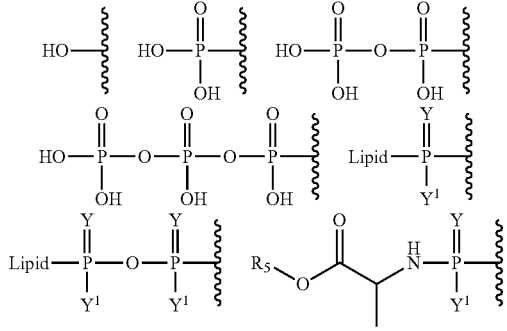

-continued

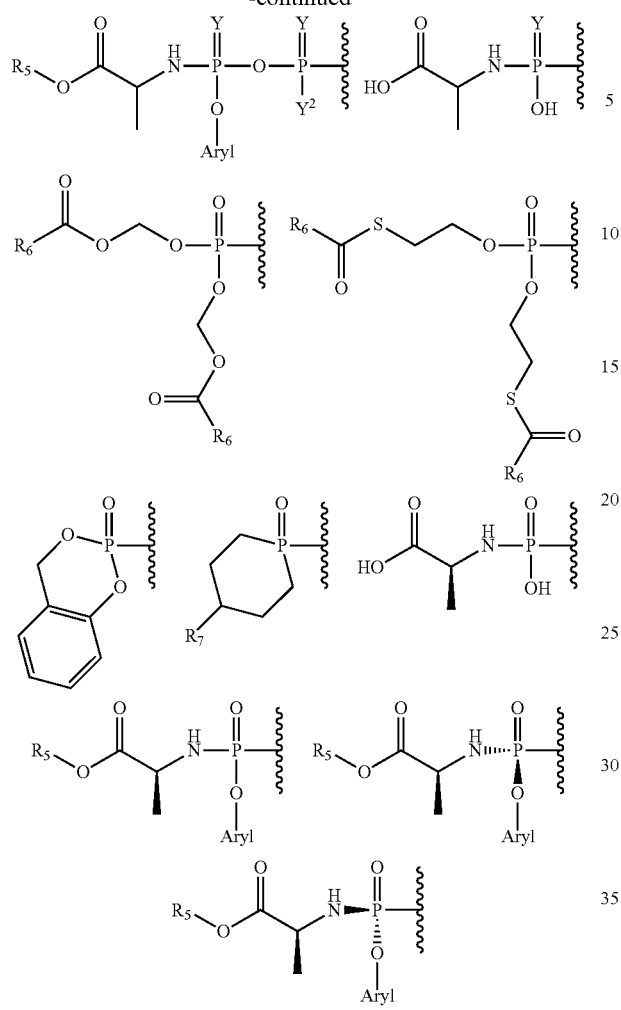

X is O, S, NH, CH$_2$, CD$_2$, CHF, CF$_2$, CCH$_2$, or CCF$_2$;

each R$_2$ is independently hydrogen, deuterium, hydroxyl, cyano, halogen, fluoro, methyl, ethynyl, vinyl, allyl, monofluoromethyl, difluoromethyl, trifluoromethyl, trideuteromethyl, azido, methoxy, or amino;

each R$_3$ is independently hydrogen, deuterium, hydroxyl, cyano, halogen, fluoro, methyl, ethynyl, vinyl, allyl, monofluoromethyl, difluoromethyl, trifluoromethyl, trideuteromethyl, or azido;

each R$_4$ is independently hydrogen, deuterium, hydroxyl, halogen, fluoro, azido, methoxy, or amino;

Lipid is as described herein;

Y is O or S;

Y$^1$ is OAryl or BH$_3^-$M$^+$;

Y$^2$ is OH or BH$_3^-$M$^+$;

R$_5$ is alkyl, branched alkyl, or cycloalkyl;

Aryl is as described herein;

R$_6$ is C$_{1-22}$ alkoxy, or C$_{1-22}$ alkyl, alkyl, branched alkyl, cycloalkyl, or alkyoxy;

R$_7$ is aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl.

In certain embodiments, the disclosure relates to a compound of the following formulae:

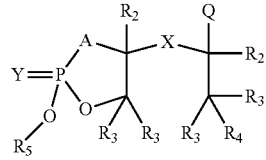

Formula XIIa

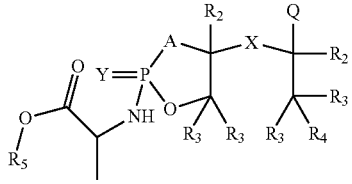

Formula XIIb or a pharmaceutically acceptable salt thereof, wherein

A is absent or selected from CH$_2$, CD$_2$, O, CH$_2$O, CD$_2$O, OCH$_2$, or OCD$_2$;

X is O, S, NH, CH$_2$, CD$_2$, CHF, CF$_2$, CCH$_2$, or CCF$_2$;

Q is a heterocyclyl comprising two or more nitrogen heteroatoms substituted with at least one thione, thiol or thioether, wherein Q is optionally substituted with one or more, the same or different alkyl, halogen, cycloalkyl;

each R$_2$ is independently hydrogen, deuterium, hydroxyl, cyano, halogen, fluoro, methyl, ethynyl, vinyl, allyl, monofluoromethyl, difluoromethyl, trifluoromethyl, trideuteromethyl, azido, methoxy, or amino;

each R$_3$ is independently hydrogen, deuterium, hydroxyl, cyano, halogen, fluoro, methyl, ethynyl, vinyl, allyl, monofluoromethyl, difluoromethyl, trifluoromethyl, trideuteromethyl, or azido;

each R$_4$ is independently hydrogen, deuterium, hydroxyl, halogen, fluoro, azido, methoxy, or amino;

Y is O or S;

R$_5$ is aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl.

In certain embodiments, the disclosure relates to a compound of the following formulae:

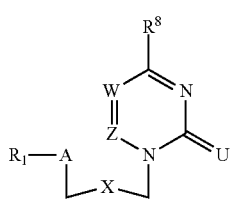

Formula XIIIa

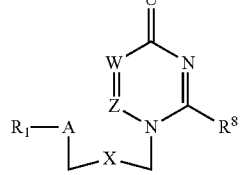

Formula XIIIb

239
-continued

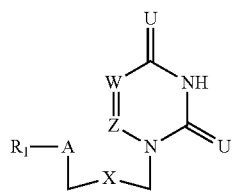
Formula XIIIc or a pharmaceutically acceptable salt thereof, wherein A is absent or selected from $CH_2$, $CD_2$, O, $CH_2O$, $CD_2O$, $OCH_2$, or $OCD_2$;

$R_1$ is selected from one of the following:

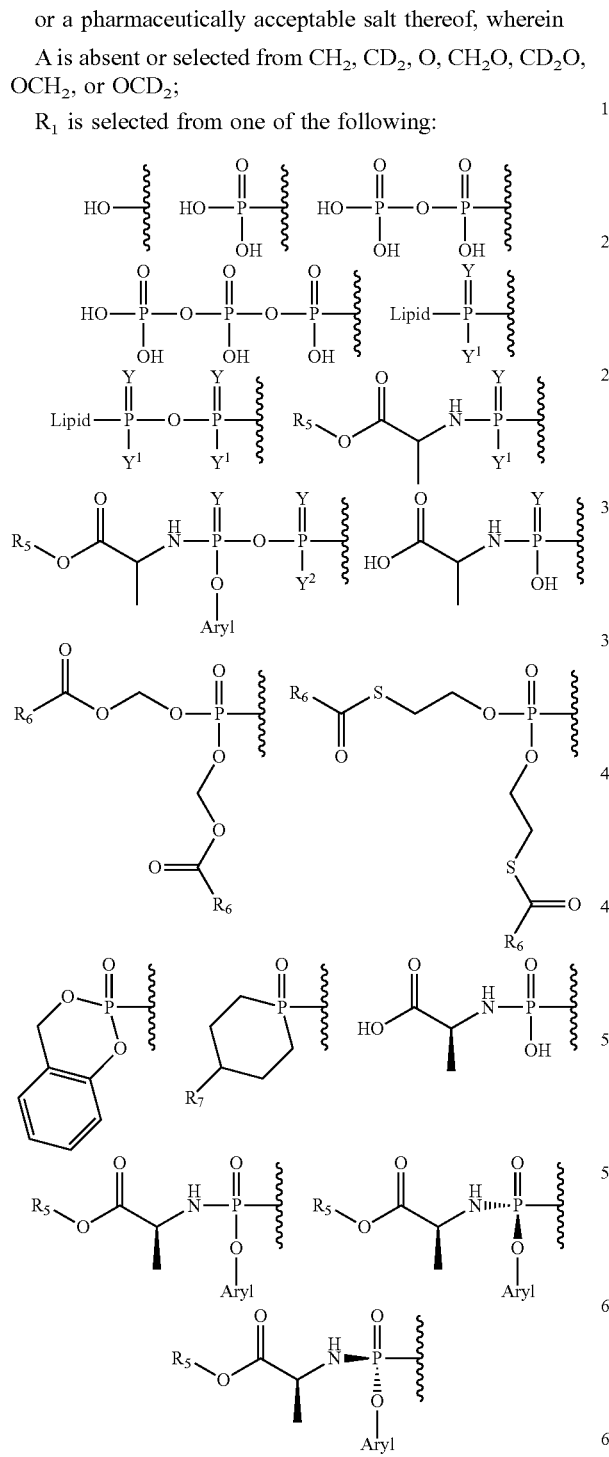

240

X is O, S, NH, $CH_2$, $CD_2$, CHF, $CF_2$, $CCH_2$, or $CCF_2$;

each U is independently O, S, NH, $NR^9$, NHOH, $NR^9OH$, $NHOR^9$, or $NR^9OR^9$;

$R^8$ is OH, SH, $NH_2$, $OR^9$, $SR^9$, $NHR^9$, NHOH, $NR^9OH$, $NHOR^9$, or $NR^9OR^9$;

wherein in Formula XIIIa and XIIIb, one of U is S or $R^8$ is $SR^9$, or both U is S and $R^8$ is $SR^9$;

wherein in Formula XIIIc at least one U is S;

W is CH, N, or $CR^9$;

Z is CH, N, or $CR^9$;

each $R^9$ is independently methyl, trifluoromethyl, fluoro, iodo, alkenyl, alkynyl, vinyl, allyl, halogen, halogentated alkyl, hydroxyl alkyl, acyl, lipid, geranyl, $C_{1-22}$ alkyl optionally substituted with one or more, the same or different, $R^{10}$;

each $R^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

Lipid is as described herein;

Y is O or S;

$Y^1$ is OAryl or $BH_3^-M^+$;

$Y^2$ is OH or $BH_3^-M^+$;

$R_5$ is alkyl, branched alkyl, or cycloalkyl;

Aryl is as described herein;

$R_6$ is $C_{1-22}$ alkoxy, or $C_{1-22}$ alkyl, alkyl, branched alkyl, cycloalkyl, or alkyoxy;

$R_7$ is aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl.

In certain embodiments, the disclosure relates to a compound of the following formulae:

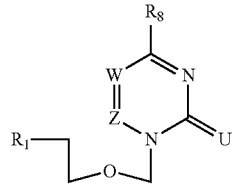
Formula XIVa

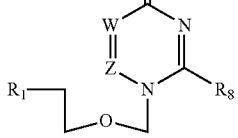
Formula XIVb

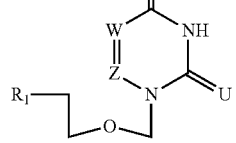
Formula XIVc or a pharmaceutically acceptable salt thereof, wherein
$R_1$ is selected from one of the following:

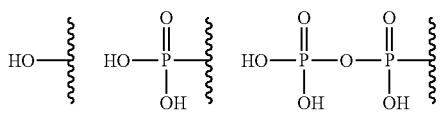

-continued

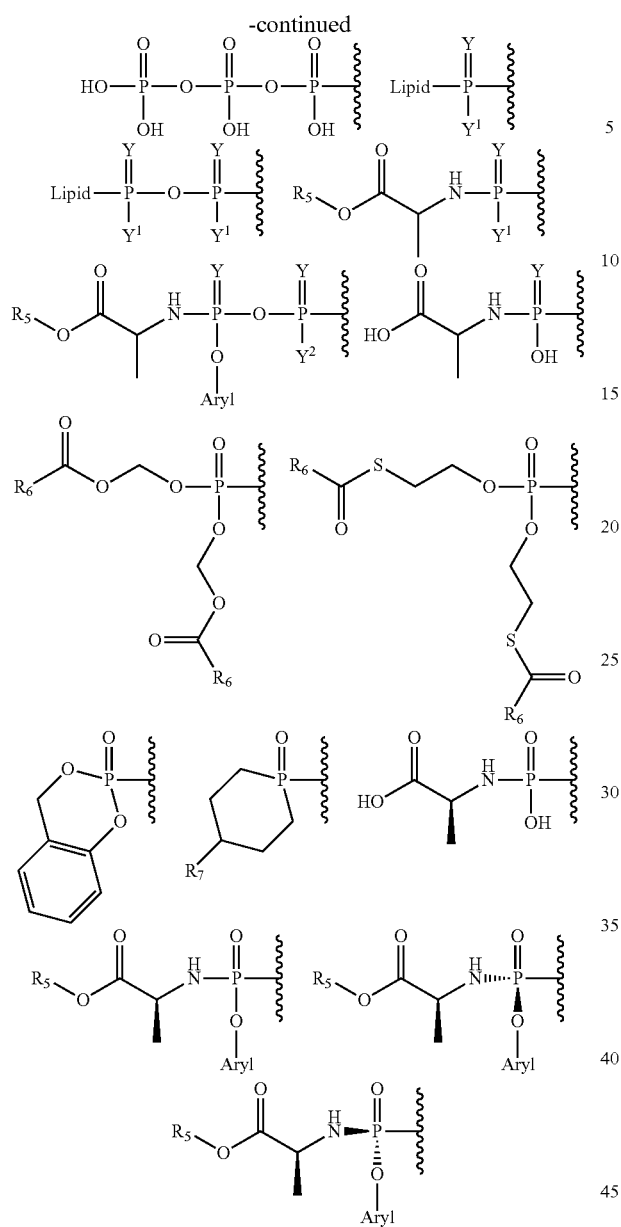

each U is independently O, S, NH, $NR^9$, NHOH, $NR^9OH$, $NHOR^9$, or $NR^9OR^9$;

$R^8$ is OH, SH, $NH_2$, $OR^9$, $SR^9$, $NHR^9$, NHOH, $NR^9OH$, $NHOR^9$, or $NR^9OR^9$;

wherein in Formula XIVa and XIVb, one of U is S or $R^8$ is $SR^9$, or both U is S and $R^8$ is $SR^9$;

wherein in Formula XIVc at least one U is S;

W is CH, N, or $CR^9$;

Z is CH, N, or $CR^9$;

each $R^9$ is independently methyl, trifluoromethyl, fluoro, iodo, alkenyl, alkynyl, vinyl, allyl, halogen, halogentated alkyl, hydroxyl alkyl, acyl, lipid, geranyl, $C_{1-22}$ alkyl optionally substituted with one or more, the same or different, $R^{10}$;

each $R^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

Lipid is as described herein;
Y is O or S;
$Y^1$ is OAryl or $BH_3^-M^+$;
$Y^2$ is OH or $BH_3^-M^+$;
$R_5$ is alkyl, branched alkyl, or cycloalkyl;
Aryl is as described herein;
$R_6$ is $C_{1-22}$ alkoxy, or $C_{1-22}$ alkyl, alkyl, branched alkyl, cycloalkyl, or alkyoxy;
$R_7$ is aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl.

In certain embodiments, the disclosure relates to a compound of the following formulae:

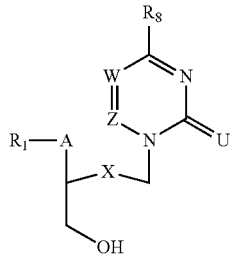

Formula XVa

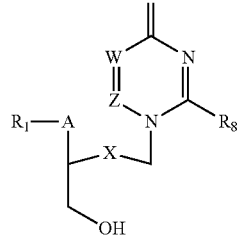

Formula XVa

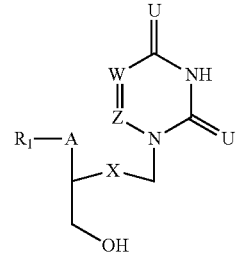

Formula XVc or a pharmaceutically acceptable salt thereof, wherein
A is absent or selected from $CH_2$, $CD_2$, 0, $CH_2O$, $CD_2O$, $OCH_2$, or $OCD_2$;
$R_1$ is selected from one of the following:

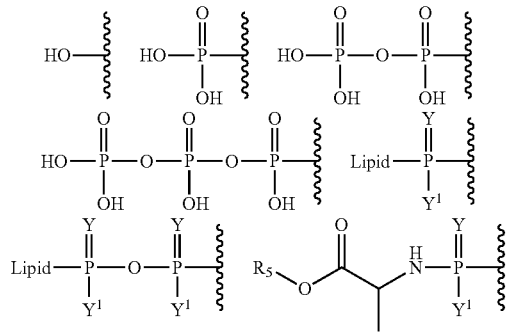

243

-continued

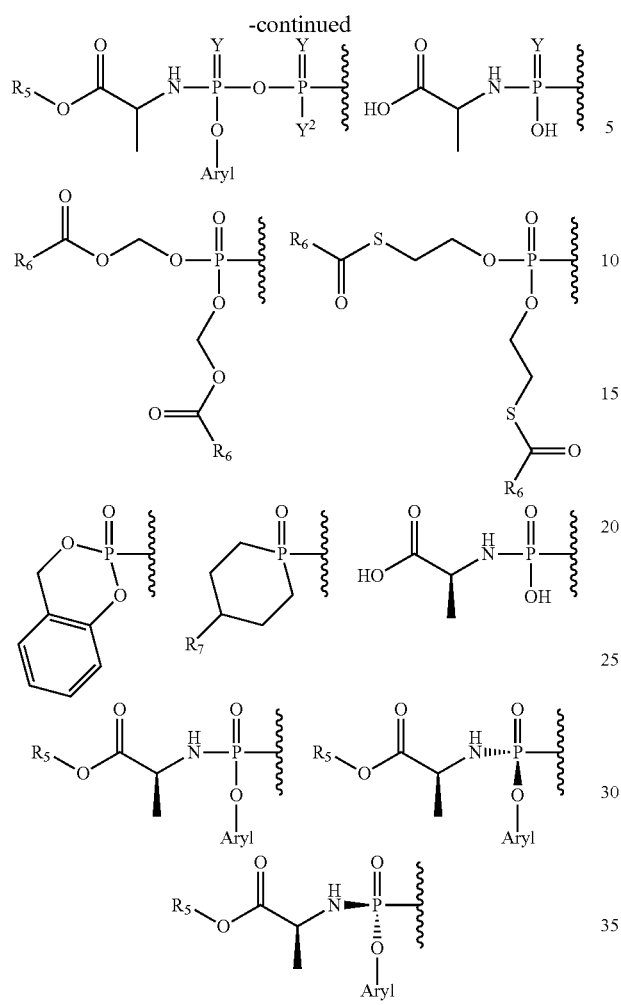

X is O, S, NH, CH$_2$, CD$_2$, CHF, CF$_2$, CCH$_2$, or CCF$_2$;

each U is independently O, S, NH, NR$^9$, NHOH, NR$^9$OH, NHOR$^9$, or NR$^9$OR$^9$;

R$^8$ is OH, SH, NH$_2$, OR$^9$, SR$^9$, NHR$^9$, NHOH, NR$^9$OH, NHOR$^9$, or NR$^9$OR$^9$;

wherein in Formula XVa and XVb, one of U is S or R$^8$ is SR$^9$, or both U is S and R$^8$ is SR$^9$;

wherein in Formula XVc at least one U is S;

W is CH, N, or CR$^9$;

Z is CH, N, or CR$^9$;

each R$^9$ is methyl, trifluoromethyl, fluoro, iodo, alkenyl, alkynyl, vinyl, allyl, halogen, halogentated alkyl, hydroxyl alkyl, acyl, lipid, geranyl, C$_{1-22}$ alkyl optionally substituted with one or more, the same or different, R$^{10}$;

each R$^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

Lipid is as described herein;

Y is O or S;

Y$^1$ is OAryl or BH$_3^-$M$^+$;

Y$^2$ is OH or BH$_3^-$M$^+$;

R$_5$ is alkyl, branched alkyl, or cycloalkyl;

Aryl is as described herein;

R$_6$ is C$_{1-22}$ alkoxy, or C$_{1-22}$ alkyl, alkyl, branched alkyl, cycloalkyl, or alkyoxy;

244

R$_7$ is aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl.

In certain embodiments, the disclosure relates to a compound of the following formulae:

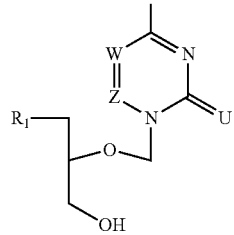

Formula XVIa

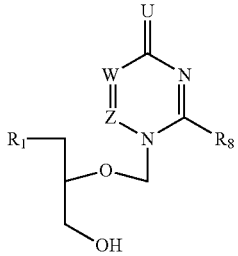

Formula XVIb

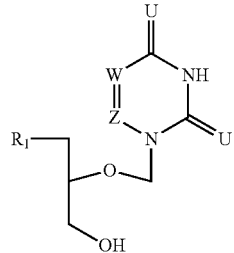

Formula XVIc or a pharmaceutically acceptable salt thereof, wherein R$_1$ is selected from one of the following:

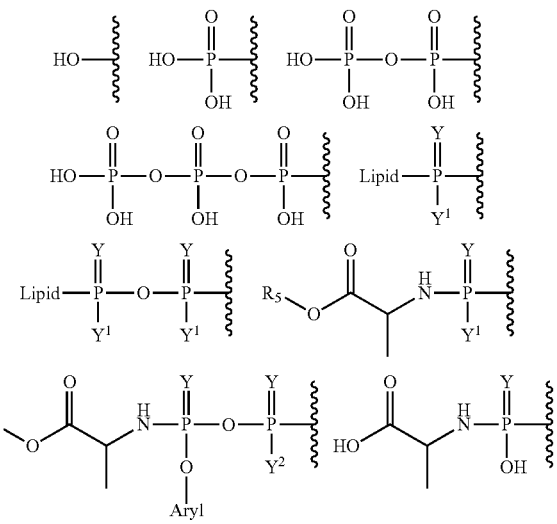

-continued

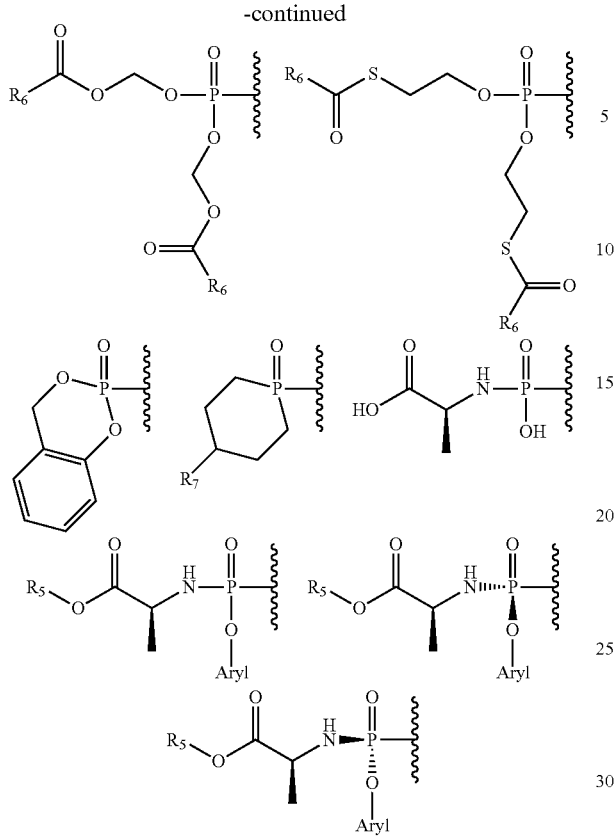

each U is independently O, S, NH, $NR^9$, NHOH, $NR^9OH$, $NHOR^9$, or $NR^9OR^9$;

$R^8$ is OH, SH, $NH_2$, $OR^9$, $SR^9$, $NHR^9$, NHOH, $NR^9OH$, $NHOR^9$, or $NR^9OR^9$;

wherein in Formula XVIa and XVIb, one of U is S or $R^8$ is $SR^9$, or both U is S and $R^8$ is $SR^9$;

wherein in Formula XVIc at least one U is S;

W is CH, N, or $CR^9$;

Z is CH, N, or $CR^9$;

each $R^9$ is independently methyl, trifluoromethyl, fluoro, iodo, alkenyl, alkynyl, vinyl, allyl, halogen, halogentated alkyl, hydroxyl alkyl, acyl, lipid, geranyl, $C_{1-22}$ alkyl optionally substituted with one or more, the same or different, $R^{10}$;

each $R^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

Lipid is as described herein;

Y is O or S;

$Y^1$ is OAryl or $BH_3M^+$;

$Y^2$ is OH or $BH_3^-M^+$;

$R_5$ is alkyl, branched alkyl, or cycloalkyl;

Aryl is as described herein;

$R_6$ is $C_{1-22}$ alkoxy, or $C_{1-22}$ alkyl, alkyl, branched alkyl, cycloalkyl, or alkyoxy;

$R_7$ is aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl.

In certain embodiments, the disclosure relates to a compound of the following formulae:

Formula XVIIa

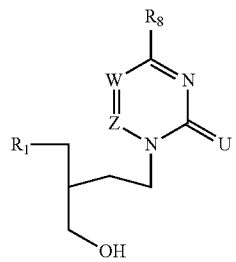

Formula XVIIb

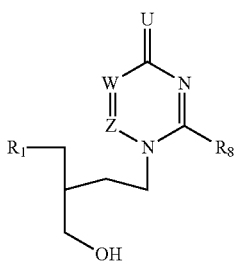

Formula XVIIc

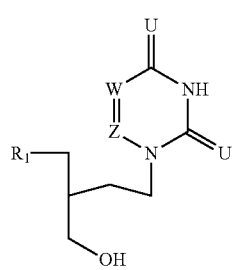

or a pharmaceutically acceptable salt thereof, wherein $R_1$ is selected from one of the following:

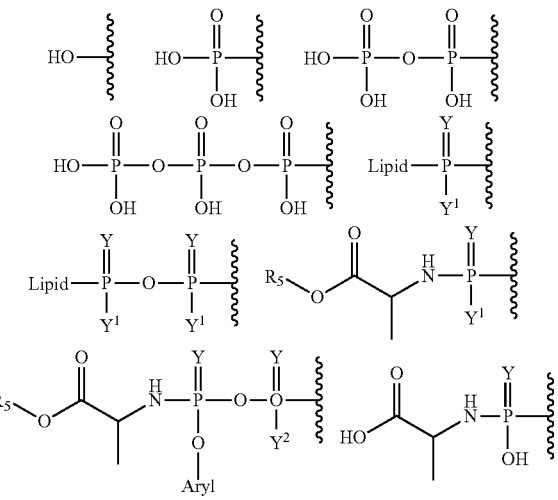

-continued

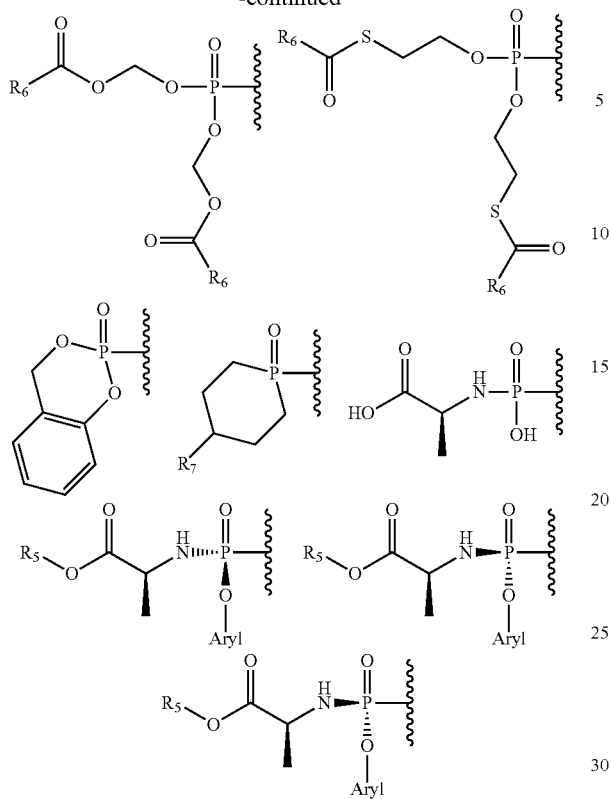

each U is independently O, S, NH, NR$^9$, NHOH, NR$^9$OH, NHOR$^9$, or NR$^9$OR$^9$;

R$^8$ is OH, SH, NH$_2$, OR$^9$, SR$^9$, NHR$^9$, NHOH, NR$^9$OH, NHOR$^9$, or NR$^9$OR$^9$;

wherein in Formula XVIIa and XVIIb, one of U is S or R$^8$ is SR$^9$, or both U is S and R$^8$ is SR$^9$;

wherein in Formula XVIIc at least one U is S;

W is CH, N, or CR$^9$;

Z is CH, N, or CR$^9$;

each R$^9$ is independently methyl, trifluoromethyl, fluoro, iodo, alkenyl, alkynyl, vinyl, allyl, halogen, halogentated alkyl, hydroxyl alkyl, acyl, lipid, geranyl, C$_{1-22}$ alkyl optionally substituted with one or more, the same or different, R$^{10}$;

each R$^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

Lipid is as described herein;

Y is O or S;

Y$^1$ is OAryl or BH$_3^-$M$^+$;

Y$^2$ is OH or BH$_3^-$M$^+$;

R$_5$ is alkyl, branched alkyl, or cycloalkyl;

Aryl is as described herein;

R$_6$ is C$_{1-22}$ alkoxy, or C$_{1-22}$ alkyl, alkyl, branched alkyl, cycloalkyl, or alkyoxy;

R$_7$ is aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl.

In certain embodiments, the disclosure relates to a compound of the following formulae:

Formula XVIIIa

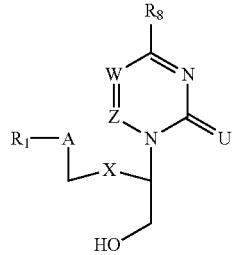

Formula XVIIIb

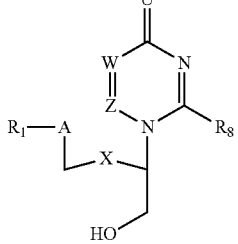

Formula XVIIIc

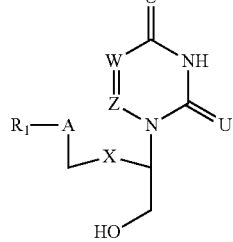

or a pharmaceutically acceptable salt thereof, wherein

A is absent or selected from CH$_2$, CD$_2$, O, CH$_2$O, CD$_2$O, OCH$_2$, or OCD$_2$;

R$_1$ is selected from one of the following:

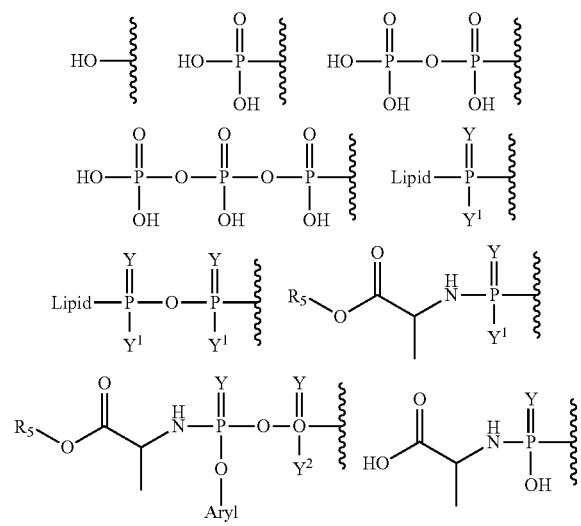

-continued

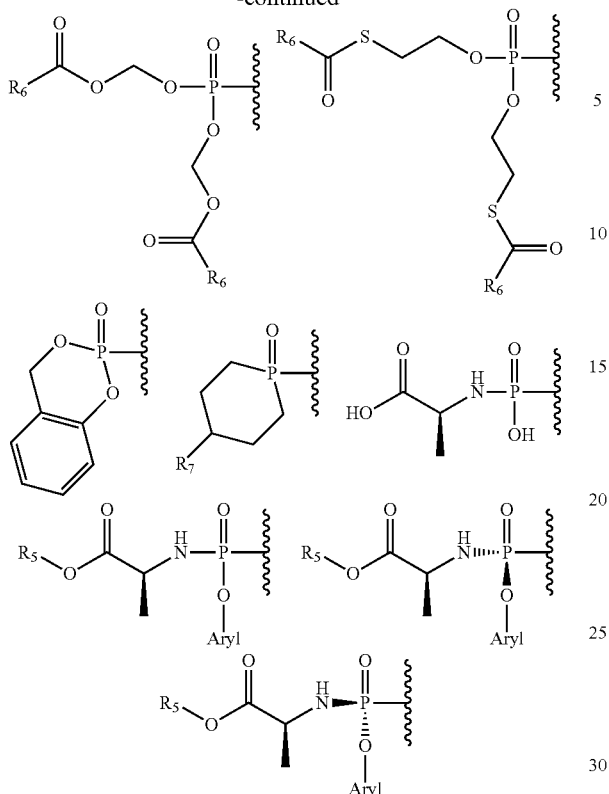

X is O, S, NH, CH$_2$, CD$_2$, CHF, CF$_2$, CCH$_2$, or CCF$_2$;

each U is independently O, S, NH, NR$^9$, NHOH, NR$^9$OH, NHOR$^9$, or NR$^9$OR$^9$;

R$^8$ is OH, SH, NH$_2$, OR$^9$, SR$^9$, NHR$^9$, NHOH, NR$^9$OH, NHOR$^9$, or NR$^9$OR$^9$;

wherein in Formula XVIIIa and XVIIIb, one of U is S or R$^8$ is SR$^9$, or both U is S and R$^8$ is SR$^9$;

wherein in Formula XVIIIc at least one U is S;

W is CH, N, or CR$^9$;

Z is CH, N, or CR$^9$;

each R$^9$ is independently methyl, trifluoromethyl, fluoro, iodo, alkenyl, alkynyl, vinyl, allyl, halogen, halogentated alkyl, hydroxyl alkyl, acyl, lipid, geranyl, C$_{1-22}$ alkyl optionally substituted with one or more, the same or different, R$^{10}$;

each R$^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

Lipid is as described herein;

Y is O or S;

Y' is OAryl or BH$_3^-$M$^+$;

Y$^2$ is OH or BH$_3^-$M$^+$;

R$_5$ is alkyl, branched alkyl, or cycloalkyl;

Aryl is as described herein;

R$_6$ is C$_{1-22}$ alkoxy, or C$_{1-22}$ alkyl, alkyl, branched alkyl, cycloalkyl, or alkyoxy;

R$_7$ is aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl.

In certain embodiments, the disclosure relates to a compound of the following formulae:

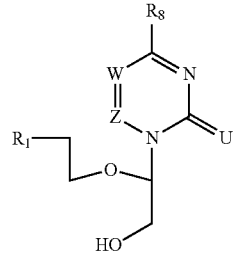

Formula XIXa

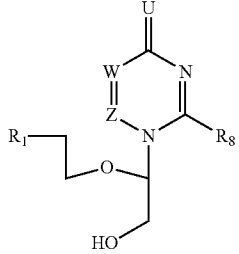

Formula XIXb

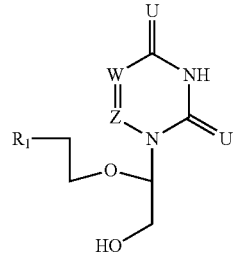

Formula XIXc or a pharmaceutically acceptable salt thereof, wherein R$_1$ is selected from one of the following:

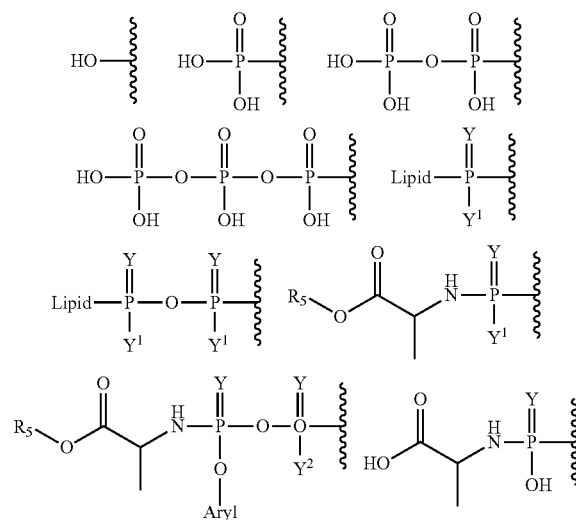

-continued

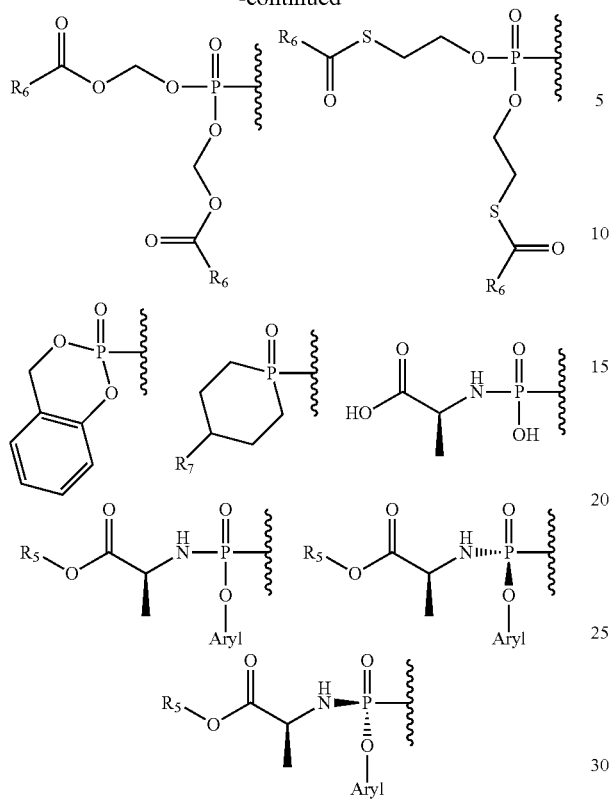

each U is independently O, S, NH, NR$^9$, NHOH, NR$^9$OH, NHOR$^9$, or NR$^9$OR$^9$;

R$^8$ is OH, SH, NH$_2$, OR$^9$, SR$^9$, NHR$^9$, NHOH, NR$^9$OH, NHOR$^9$, or NR$^9$OR$^9$;

wherein in Formula XIXa and XIXb, one of U is S or R$^8$ is SR$^9$, or both U is S and R$^8$ is SR$^9$;

wherein in Formula XIXc at least one U is S;

W is CH, N, or CR$^9$;

Z is CH, N, or CR$^9$;

R$^9$ is methyl, trifluoromethyl, fluoro, iodo, alkenyl, alkynyl, vinyl, allyl, halogen, halogentated alkyl, hydroxyl alkyl, acyl, lipid, geranyl, C$_{1-22}$ alkyl optionally substituted with one or more, the same or different, R$^{10}$;

each R$^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl; Lipid is as described herein;

Y is O or S;

Y$^1$ is OAryl or BH$_3^-$M$^+$;

Y$^2$ is OH or BH$_3^-$M$^+$;

R$_5$ is alkyl, branched alkyl, or cycloalkyl;

Aryl is as described herein;

R$_6$ is C$_{1-22}$ alkoxy, or C$_{1-22}$ alkyl, alkyl, branched alkyl, cycloalkyl, or alkyoxy;

R$_7$ is aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl.

In certain embodiments, the disclosure relates to a compound of the following formulae:

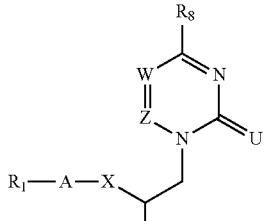

Formula XXa

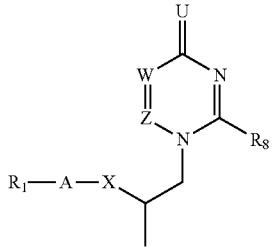

Formula XXb

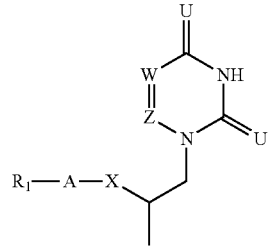

Formula XXc or a pharmaceutically acceptable salt thereof, wherein

A is absent or selected from CH$_2$, CD$_2$, O, CH$_2$O, CD$_2$O, OCH$_2$, or OCD$_2$;

R$_1$ is selected from one of the following:

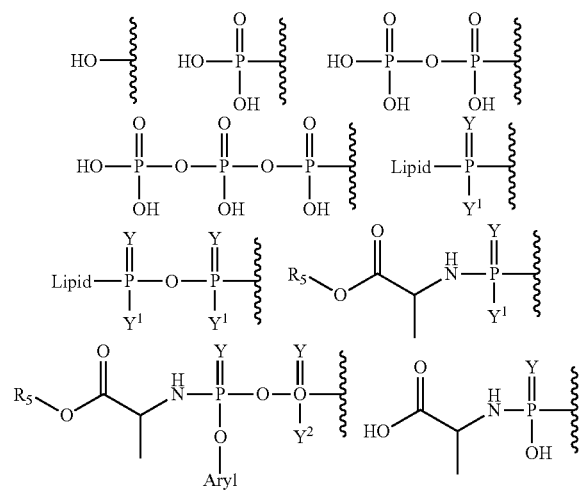

-continued

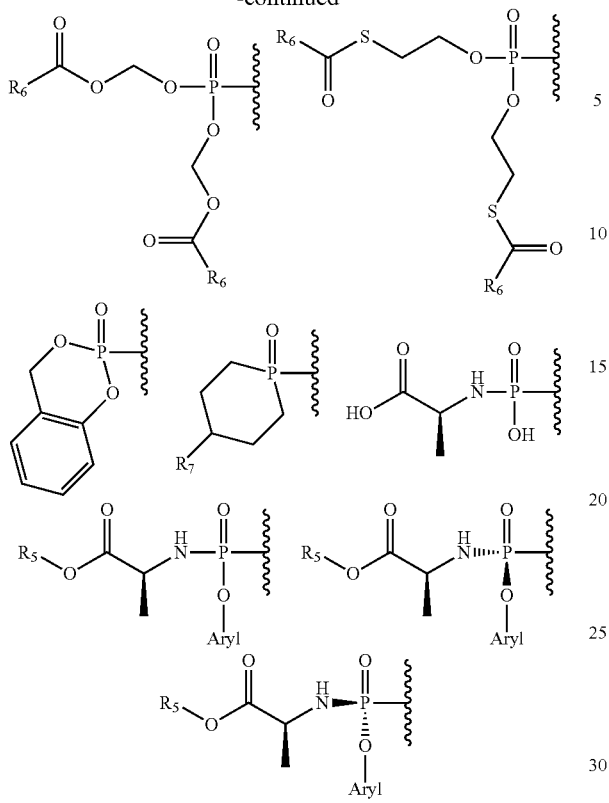

X is O, S, NH, CH$_2$, CD$_2$, CHF, CF$_2$, CCH$_2$, or CCF$_2$;

each U is independently O, S, NH, NR$^9$, NHOH, NR$^9$OH, NHOR$^9$, or NR$^9$OR$^9$;

R$^8$ is OH, SH, NH$_2$, OR$^9$, SR$^9$, NHR$^9$, NHOH, NR$^9$OH, NHOR$^9$, or NR$^9$OR$^9$;

wherein in Formula XXa and XXb, one of U is S or R$^8$ is SR$^9$, or both U is S and R$^8$ is SR$^9$;

wherein in Formula XXc at least one U is S;

W is CH, N, or CR$^9$;

Z is CH, N, or CR$^9$;

each R$^9$ is independently methyl, trifluoromethyl, fluoro, iodo, alkenyl, alkynyl, vinyl, allyl, halogen, halogentated alkyl, hydroxyl alkyl, acyl, lipid, geranyl, C$_{1-22}$ alkyl optionally substituted with one or more, the same or different, R$^{10}$;

each R$^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

Lipid is as described herein;

Y is O or S;

Y$^1$ is OAryl or BH$_3^-$M$^+$;

Y$^2$ is OH or BH$_3^-$M$^+$;

R$_5$ is alkyl, branched alkyl, or cycloalkyl;

Aryl is as described herein;

R$_6$ is C$_{1-22}$ alkoxy, or C$_{1-22}$ alkyl, alkyl, branched alkyl, cycloalkyl, or alkyoxy;

R$_7$ is aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl.

In certain embodiments, the disclosure relates to a compound of the following formulae:

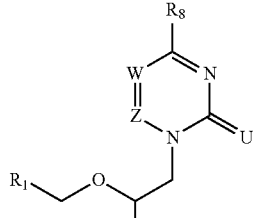

Formula XXIa

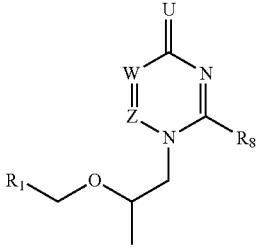

Formula XXIb

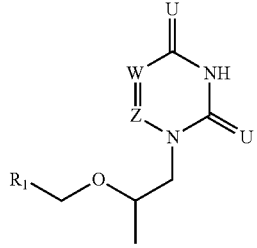

Formula XXIc or a pharmaceutically acceptable salt thereof, wherein R$_1$ is selected from one of the following:

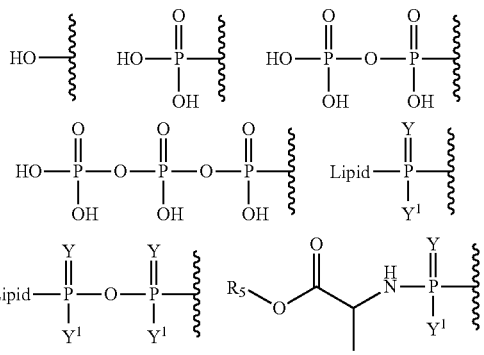

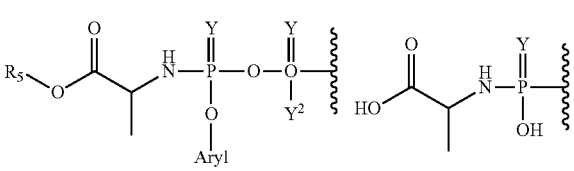

-continued

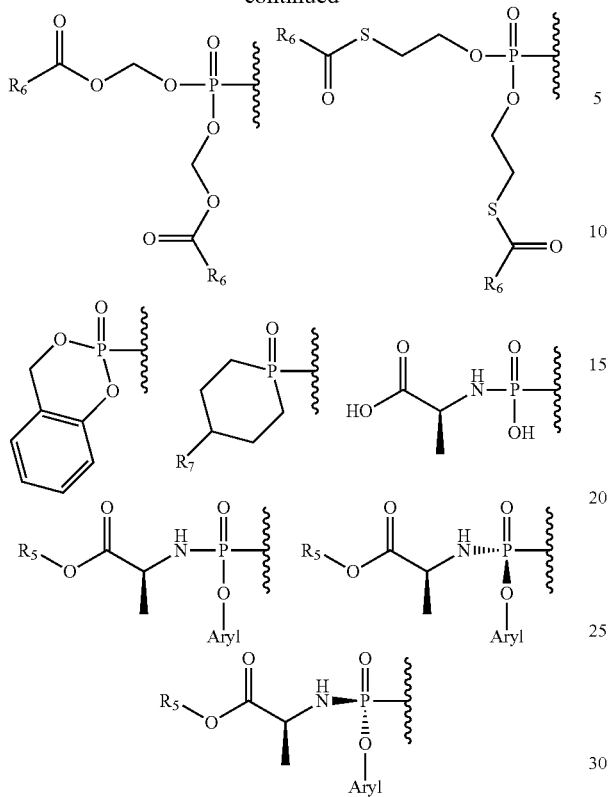

each U is independently O, S, NH, $NR^9$, $NHOH$, $NR^9OH$, $NHOR^9$, or $NR^9OR^9$;

$R^8$ is OH, SH, $NH_2$, $OR^9$, $SR^9$, $NHR^9$, NHOH, $NR^9OH$, $NHOR^9$, or $NR^9OR^9$;

wherein in Formula XXIa and XXIb, one of U is S or $R^8$ is $SR^9$, or both U is S and $R^8$ is $SR^9$;

wherein in Formula XXIc at least one U is S;

W is CH, N, or $CR^9$;

Z is CH, N, or $CR^9$;

each $R^9$ is independently methyl, trifluoromethyl, fluoro, iodo, alkenyl, alkynyl, vinyl, allyl, halogen, halogentated alkyl, hydroxyl alkyl, acyl, lipid, geranyl, $C_{1-22}$ alkyl optionally substituted with one or more, the same or different, $R^{10}$;

each $R^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

Lipid is as described herein;

Y is O or S;

$Y^1$ is OAryl or $BH_3^-M^+$;

$Y^2$ is OH or $BH_3^-M^+$;

$R_5$ is alkyl, branched alkyl, or cycloalkyl;

Aryl is as described herein;

$R_6$ is $C_{1-22}$ alkoxy, or $C_{1-22}$ alkyl, alkyl, branched alkyl, cycloalkyl, or alkyoxy;

$R_7$ is aryl, heteroaryl, substituted aryl, lipid, $C_{1-22}$ alkoxy, $C_{1-22}$ alkyl, $C_{2-22}$ alkenyl, $C_{2-22}$ alkynyl, or substituted heteroaryl.

In certain embodiments, the disclosure relates to a compound of the following formulae:

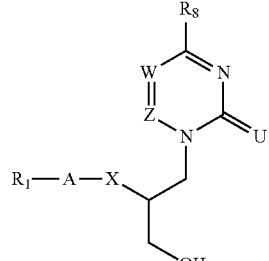

Formula XXIIa

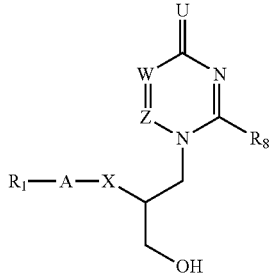

Formula XXIIb

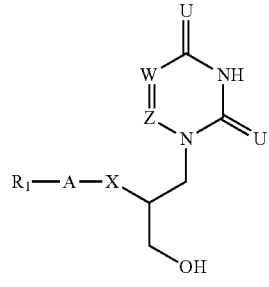

Formula XXIIc or a pharmaceutically acceptable salt thereof, wherein

A is absent or selected from $CH_2$, $CD_2$, O, $CH_2O$, $CD_2O$, $OCH_2$, or $OCD_2$;

$R_1$ is selected from one of the following:

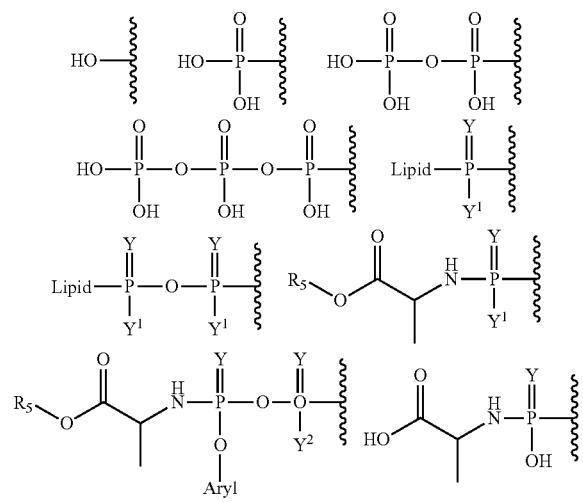

257

-continued

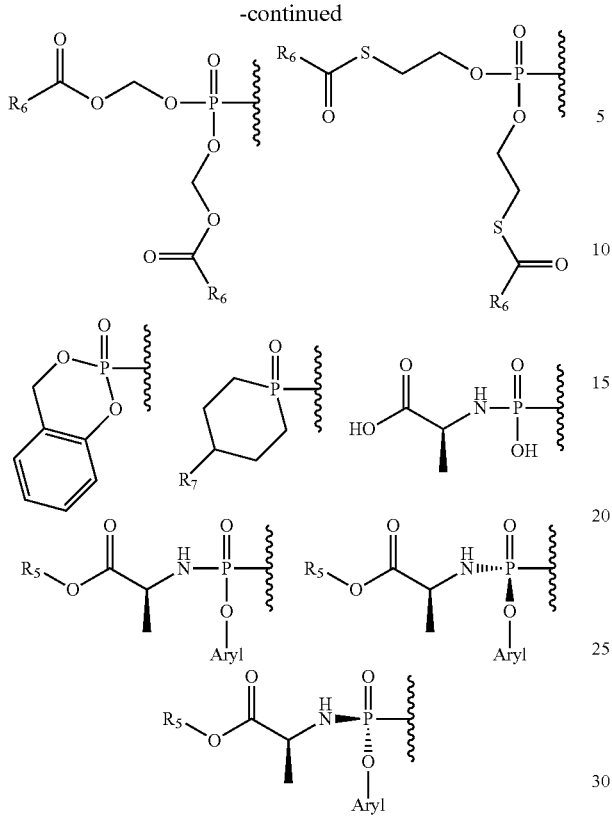

X is O, S, NH, CH$_2$, CD$_2$, CHF, CF$_2$, CCH$_2$, or CCF$_2$;

each U is independently O, S, NH, NR$^9$, NHOH, NR$^9$OH, NHOR$^9$, or NR$^9$OR$^9$;

R$^8$ is OH, SH, NH$_2$, OR$^9$, SR$^9$, NHR$^9$, NHOH, NR$^9$OH, NHOR$^9$, or NR$^9$OR$^9$;

wherein in Formula XXIIa and XXIIb, one of U is S or R$^8$ is SR$^9$, or both U is S and R$^8$ is SR$^9$;

wherein in Formula XXIIc at least one U is S;

W is CH, N, or CR$^9$;

Z is CH, N, or CR$^9$;

each R$^9$ is independently methyl, trifluoromethyl, fluoro, iodo, alkenyl, alkynyl, vinyl, allyl, halogen, halogentated alkyl, hydroxyl alkyl, acyl, lipid, geranyl, C$_{1-22}$ alkyl optionally substituted with one or more, the same or different, R$^{10}$;

each R$^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

Lipid is as described herein;

Y is O or S;

Y$^1$ is OAryl or BH$_3$$^-$M$^+$;

Y$^2$ is OH or BH$_3$M$^+$;

R$_5$ is alkyl, branched alkyl, or cycloalkyl;

Aryl is as described herein;

R$_6$ is C$_{1-22}$ alkoxy, or C$_{1-22}$ alkyl, alkyl, branched alkyl, cycloalkyl, or alkyoxy;

R$_7$ is aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl.

258

In certain embodiments, the disclosure relates to a compound of the following formulae:

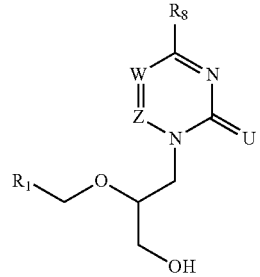

Formula XXIIIa

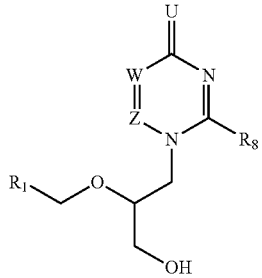

Formula XXIIIb

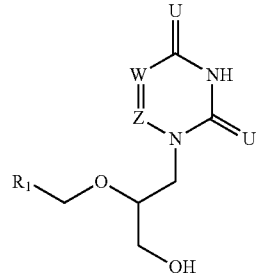

Formula XXIIIc or a pharmaceutically acceptable salt thereof, wherein R$_1$ is selected from one of the following:

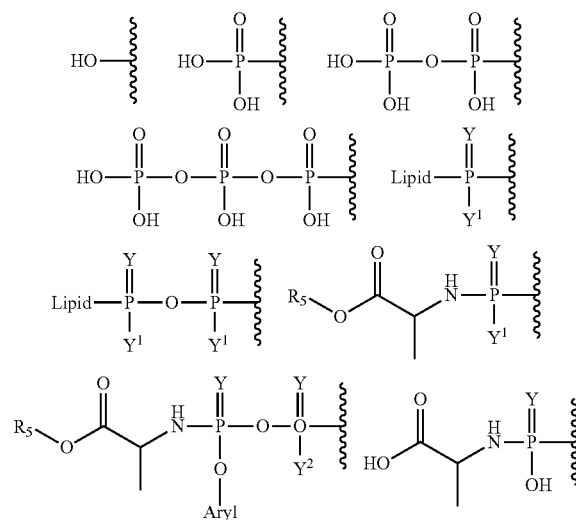

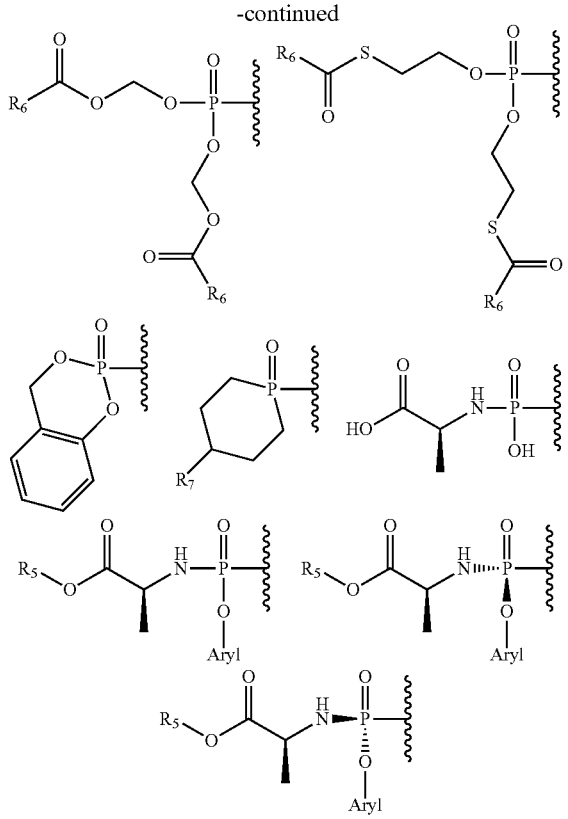

each U is independently O, S, NH, NR$^9$, NHOH, NR$^9$OH, NHOR$^9$, or NR$^9$OR$^9$;

R$^8$ is OH, SH, NH$_2$, OR$^9$, SR$^9$, NHR$^9$, NHOH, NR$^9$OH, NHOR$^9$, or NR$^9$OR$^9$;

wherein in Formula XXIIIa and XXIIIb, one of U is S or R$^8$ is SR$^9$, or both U is S and R$^8$ is SR$^9$;

wherein in Formula XXIIIc at least one U is S;

W is CH, N, or CR$^9$;

Z is CH, N, or CR$^9$;

each R$^9$ is independently methyl, trifluoromethyl, fluoro, iodo, alkenyl, alkynyl, vinyl, allyl, halogen, halogentated alkyl, hydroxyl alkyl, acyl, lipid, geranyl, C$_{1-22}$ alkyl optionally substituted with one or more, the same or different, R$^{10}$;

each R$^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl;

Lipid is as described herein;

Y is O or S;

Y$^1$ is OAryl or BH$_3^-$M$^+$;

Y$^2$ is OH or BH$_3^-$M$^+$;

R$_5$ is alkyl, branched alkyl, or cycloalkyl;

Aryl is as described herein;

R$_6$ is C$_{1-22}$ alkoxy, or C$_{1-22}$ alkyl, alkyl, branched alkyl, cycloalkyl, or alkyoxy;

R$_7$ is aryl, heteroaryl, substituted aryl, lipid, C$_{1-22}$ alkoxy, C$_{1-22}$ alkyl, C$_{2-22}$ alkenyl, C$_{2-22}$ alkynyl, or substituted heteroaryl.

Infectious Diseases

The compounds provided herein can be used to treat viral infectious diseases. Examples of viral infections include but are not limited to, infections caused by RNA viruses (including negative stranded RNA viruses, positive stranded RNA viruses, double stranded RNA viruses and retroviruses) or DNA viruses. All strains, types, and subtypes of RNA viruses and DNA viruses are contemplated herein.

Examples of RNA viruses include, but are not limited to picornaviruses, which include aphthoviruses (for example, foot and mouth disease virus O, A, C, Asia 1, SAT1, SAT2 and SAT3), cardioviruses (for example, encephalomycarditis virus and Theiller's murine encephalomyelitis virus), enteroviruses (for example polioviruses 1, 2 and 3, human enteroviruses A-D, bovine enteroviruses 1 and 2, human coxsackieviruses A1-A22 and A24, human coxsackieviruses B1-B5, human echoviruses 1-7, 9, 11-12, 24, 27, 29-33, human enteroviruses 68-71, porcine enteroviruses 8-10 and simian enteroviruses 1-18), erboviruses (for example, equine rhinitis virus), hepatovirus (for example human hepatitis A virus and simian hepatitis A virus), kobuviruses (for example, bovine kobuvirus and Aichi virus), parechoviruses (for example, human parechovirus 1 and human parechovirus 2), rhinovirus (for example, rhinovirus A, rhinovirus B, rhinovirus C, HRV$_{16}$, HRV$_{16}$(VR-11757), HRV$_{14}$ (VR-284), or HRV$_{14}$ (VR-1559), human rhinovirus 1-100 and bovine rhinoviruses 1-3) and teschoviruses (for example, porcine teschovirus).

Additional examples of RNA viruses include caliciviruses, which include noroviruses (for example, Norwalk virus), sapoviruses (for example, Sapporo virus), lagoviruses (for example, rabbit hemorrhagic disease virus and European brown hare syndrome) and vesiviruses (for example vesicular exanthema of swine virus and feline calicivirus). Other RNA viruses include astroviruses, which include mamastorviruses and avastroviruses. Togaviruses are also RNA viruses. Togaviruses include alphaviruses (for example, Chikungunya virus, Sindbis virus, Semliki Forest virus, Western equine encephalitis virus, Eastern Getah virus, Everglades virus, Venezuelan equine encephalitis virus and Aura virus) and rubella viruses. Additional examples of RNA viruses include the flaviviruses (for example, tick-borne encephalitis virus, Tyuleniy virus, Aroa virus, M virus (types 1 to 4), Kedougou virus, Japanese encephalitis virus (JEV), West Nile virus (WNV), Dengue Virus (including genotypes 1-4), Kokobera virus, Ntaya virus, Spondweni virus, Yellow fever virus, Entebbe bat virus, Modoc virus, Rio Bravo virus, Cell fusing agent virus, pestivirus, GB virus A, GBV-A like viruses, GB virus C, Hepatitis G virus, hepacivirus (hepatitis C virus (HCV)) all six genotypes), bovine viral diarrhea virus (BVDV) types 1 and 2, and GB virus B).

Other examples of RNA viruses are the coronaviruses, which include, human respiratory coronaviruses such as SARS-CoV, HCoV-229E, HCoV-NL63 and HCoV-OC43. Coronaviruses also include bat SARS-like CoV, Middle East Respiratory Syndrome coronavirus (MERS), turkey coronavirus, chicken coronavirus, feline coronavirus and canine coronavirus. Additional RNA viruses include arteriviruses (for example, equine arterivirus, porcine reproductive and respiratory syndrome virus, lactate dehydrogenase elevating virus of mice and simian hemorraghic fever virus). Other RNA viruses include the rhabdoviruses, which include lyssaviruses (for example, rabies, Lagos bat virus, Mokola virus, Duvenhage virus and European bat lyssavirus), vesiculoviruses (for example, VSV-Indiana, VSV-New Jersey, VSV-Alagoas, Piry virus, Cocal virus, Maraba virus, Isfahan virus and Chandipura virus), and ephemeroviruses (for example, bovine ephemeral fever virus, Adelaide River virus and Berrimah virus). Additional examples of RNA viruses include the filoviruses. These include the Marburg and Ebola viruses (for example, EBOV-Z, EBOV-S, EBOV-IC and EBOV-R).

The paramyxoviruses are also RNA viruses. Examples of these viruses are the rubulaviruses (for example, mumps, parainfluenza virus 5, human parainfluenza virus type 2, Mapuera virus and porcine rubulavirus), avulaviruses (for example, Newcastle disease virus), respoviruses (for example, Sendai virus, human parainfluenza virus type 1 and type 3, bovine parainfluenza virus type 3), henipaviruses (for example, Hendra virus and Nipah virus), morbilloviruses (for example, measles, Cetacean morvilliirus, Canine distemper virus, Peste des-petits-ruminants virus, Phocine distemper virus and Rinderpest virus), pneumoviruses (for example, human respiratory syncytial virus (RSV) A2, B1 and S2, bovine respiratory syncytial virus and pneumonia virus of mice), metapneumoviruses (for example, human metapneumovirus and avian metapneumovirus). Additional paramyxoviruses include Fer-de-Lance virus, Tupaia paramyxovirus, Menangle virus, Tioman virus, Beilong virus, J virus, Mossman virus, Salem virus and Nariva virus.

Additional RNA viruses include the orthomyxoviruses. These viruses include influenza viruses and strains (e.g., influenza A, influenza A strain A/Victoria/3/75, influenza A strain A/Puerto Rico/8/34, influenza A H1N1 (including but not limited to A/WS/33, A/NWS/33 and A/California/04/2009 strains), influenza B, influenza B strain Lee, and influenza C viruses) H2N2, H3N2, H5N1, H7N7, H1N2, H9N2, H7N2, H7N3 and H10N7), as well as avian influenza (for example, strains H5N1, H5N1 Duck/MN/1525/81, H5N2, H7N1, H7N7 and H9N2) thogotoviruses and isaviruses. Orthobunyaviruses (for example, Akabane virus, California encephalitis, Cache Valley virus, Snowshoe hare virus,) nairoviruses (for example, Nairobi sheep virus, Crimean-Congo hemorrhagic fever virus Group and Hughes virus), phleboviruses (for example, Candiru, Punta Toro, Rift Valley Fever, Sandfly Fever, Naples, Toscana, Sicilian and Chagres), and hantaviruses (for example, Hantaan, Dobrava, Seoul, Puumala, Sin Nombre, Bayou, Black Creek Canal, Andes and Thottapalayam) are also RNA viruses. Arenaviruses such as lymphocytic choriomeningitis virus, Lujo virus, Lassa fever virus, Argentine hemorrhagic fever virus, Bolivian hemorrhagic fever virus, Venezuelan hemorrhagic fever virus, SABV and WWAV are also RNA viruses. Borna disease virus is also an RNA virus. Hepatitis D (Delta) virus and hepatitis E are also RNA viruses.

Additional RNA viruses include reoviruses, rotaviruses, birnaviruses, chrysoviruses, cystoviruses, hypoviruses partitiviruses and totoviruses. Orbiviruses such as African horse sickness virus, Blue tongue virus, Changuinola virus, Chenuda virus, Chobar GorgeCorriparta virus, epizootic hemorraghic disease virus, equine encephalosis virus, Eubenangee virus, Ieri virus, Great Island virus, Lebombo virus, Orungo virus, Palyam virus, Peruvian Horse Sickness virus, St. Croix River virus, Umatilla virus, Wad Medani virus, Wallal virus, Warrego virus and Wongorr virus are also RNA viruses. Retroviruses include alpharetroviruses (for example, Rous sarcoma virus and avian leukemia virus), betaretroviruses (for example, mouse mammary tumor virus, Mason-Pfizer monkey virus and Jaagsiekte sheep retrovirus), gammaretroviruses (for example, murine leukemia virus and feline leukemia virus, deltraretroviruses (for example, human T cell leukemia viruses (HTLV-1, HTLV-2), bovine leukemia virus, STLV-1 and STLV-2), epsilonretriviruses (for example, Walleye dermal sarcoma virus and Walleye epidermal hyperplasia virus 1), reticuloendotheliosis virus (for example, chicken syncytial virus, lentiviruses (for example, human immunodeficiency virus (HIV) type 1, human immunodeficiency virus (HIV) type 2, human immunodeficiency virus (HIV) type 3, simian immunodeficiency virus, equine infectious anemia virus, feline immunodeficiency virus, caprine arthritis encephalitis virus and Visna maedi virus) and spumaviruses (for example, human foamy virus and feline syncytia-forming virus).

Examples of DNA viruses include polyomaviruses (for example, simian virus 40, simian agent 12, BK virus, JC virus, Merkel Cell polyoma virus, bovine polyoma virus and lymphotrophic papovavirus), papillomaviruses (for example, human papillomavirus, bovine papillomavirus, adenoviruses (for example, adenoviruses A-F, canine adenovirus type I, canined adeovirus type 2), circoviruses (for example, porcine circovirus and beak and feather disease virus (BFDV)), parvoviruses (for example, canine parvovirus), erythroviruses (for example, adeno-associated virus types 1-8), betaparvoviruses, amdoviruses, densoviruses, iteraviruses, brevidensoviruses, pefudensoviruses, herpes viruses 1, 2, 3, 4, 5, 6, 7 and 8 (for example, herpes simplex virus 1, herpes simplex virus 2, varicella-zoster virus, Epstein-Barr virus, cytomegalovirus, Kaposi's sarcoma associated herpes virus, human herpes virus-6 variant A, human herpes virus-6 variant B and cercophithecine herpes virus 1 (B virus)), poxviruses (for example, smallpox (variola), cowpox, monkeypox, vaccinia, Uasin Gishu, camelpox, psuedocowpox, pigeonpox, horsepox, fowlpox, turkeypox and swinepox), and hepadnaviruses (for example, hepatitis B and hepatitis B-like viruses). Chimeric viruses comprising portions of more than one viral genome are also contemplated herein.

In some embodiments, the disclosure relates to treating or preventing an infection by viruses, bacteria, fungi, protozoa, and parasites. In some embodiments, the disclosure relates to methods of treating a viral infection comprising administering a compound herein to a subject that is diagnosed with, suspected of, or exhibiting symptoms of a viral infection.

Viruses are infectious agents that can typically replicate inside the living cells of organisms. Virus particles (virions) usually consist of nucleic acids, a protein coat, and in some cases an envelope of lipids that surrounds the protein coat. The shapes of viruses range from simple helical and icosahedral forms to more complex structures. Virally coded protein subunits will self-assemble to form a capsid, generally requiring the presence of the virus genome. Complex viruses can code for proteins that assist in the construction of their capsid. Proteins associated with nucleic acid are known as nucleoproteins, and the association of viral capsid proteins with viral nucleic acid is called a nucleocapsid.

Viruses are transmitted by a variety of methods including direct or bodily fluid contact, e.g., blood, tears, semen, preseminal fluid, saliva, milk, vaginal secretions, lesions; droplet contact, fecal-oral contact, or as a result of an animal bite or birth. A virus has either DNA or RNA genes and is called a DNA virus or a RNA virus respectively. A viral genome is either single-stranded or double-stranded. Some viruses contain a genome that is partially double-stranded and partially single-stranded. For viruses with RNA or single-stranded DNA, the strands are said to be either positive-sense (called the plus-strand) or negative-sense (called the minus-strand), depending on whether it is complementary to the viral messenger RNA (mRNA). Positive-sense viral RNA is identical to viral mRNA and thus can be immediately translated by the host cell. Negative-sense viral RNA is complementary to mRNA and thus must be converted to positive-sense RNA by an RNA polymerase before translation. DNA nomenclature is similar to RNA nomenclature, in that the coding strand for the viral mRNA is complementary to it (negative), and the non-coding strand is a copy of it (positive).

Antigenic shift, or reassortment, can result in novel strains. Viruses undergo genetic change by several mechanisms. These include a process called genetic drift where individual bases in the DNA or RNA mutate to other bases. Antigenic shift occurs when there is a major change in the genome of the virus. This can be a result of recombination or reassortment. RNA viruses often exist as quasispecies or swarms of viruses of the same species but with slightly different genome nucleoside sequences.

The genetic material within viruses, and the method by which the material is replicated, vary between different types of viruses. The genome replication of most DNA viruses takes place in the nucleus of the cell. If the cell has the appropriate receptor on its surface, these viruses enter the cell by fusion with the cell membrane or by endocytosis. Most DNA viruses are entirely dependent on the host DNA and RNA synthesizing machinery, and RNA processing machinery. Replication usually takes place in the cytoplasm. RNA viruses typically use their own RNA replicase enzymes to create copies of their genomes.

The Baltimore classification of viruses is based on the mechanism of mRNA production. Viruses must generate mRNAs from their genomes to produce proteins and replicate themselves, but different mechanisms are used to achieve this. Viral genomes may be single-stranded (ss) or double-stranded (ds), RNA or DNA, and may or may not use reverse transcriptase (RT). Additionally, ssRNA viruses may be either sense (plus) or antisense (minus). This classification places viruses into seven groups: I, dsDNA viruses (e.g. adenoviruses, herpesviruses, poxviruses); II, ssDNA viruses (plus)sense DNA (e.g. parvoviruses); III, dsRNA viruses (e.g. reoviruses); IV, (plus)ssRNA viruses (plus)sense RNA (e.g. picornaviruses, togaviruses); V, (minus)ssRNA viruses (minus)sense RNA (e.g. orthomyxoviruses, Rhabdoviruses); VI, snRNA-RT viruses (plus)sense RNA with DNA intermediate in life-cycle (e.g. retroviruses); and VII, dsDNA-RT viruses (e.g. hepadnaviruses).

Human immunodeficiency virus (HIV) is a lentivirus (a member of the retrovirus family) that causes acquired immunodeficiency syndrome (AIDS). Lentiviruses are transmitted as single-stranded, positive-sense, enveloped RNA viruses. Upon entry of the target cell, the viral RNA genome is converted to double-stranded DNA by a virally encoded reverse transcriptase. This viral DNA is then integrated into the cellular DNA by a virally encoded integrase, along with host cellular co-factors. There are two species of HIV. HIV-1 is sometimes termed LAV or HTLV-III.

HIV infects primarily vital cells in the human immune system such as helper T cells (CD4+ T cells), macrophages, and dendritic cells. HIV infection leads to low levels of CD4+ T cells. When CD4+ T cell numbers decline below a critical level, cell-mediated immunity is lost, and the body becomes progressively more susceptible to other viral or bacterial infections. Subjects with HIV typically develop malignancies associated with the progressive failure of the immune system.

The viral envelope is composed of two layers of phospholipids taken from the membrane of a human cell when a newly formed virus particle buds from the cell. Embedded in the viral envelope are proteins from the host cell and a HIV protein known as Env. Env contains glycoproteinsgp120, and gp41. The RNA genome consists of at structural landmarks (LTR, TAR, RRE, PE, SLIP, CRS, and INS) and nine genes (gag, pol, and env, tat, rev, nef, vif, vpr, vpu, and sometimes a tenth tev, which is a fusion of tat env and rev) encoding 19 proteins. Three of these genes, gag, pol, and env, contain information needed to make the structural proteins for new virus particles. HIV-1 diagnosis is typically done with antibodies in an ELISA, Western blot, orimmunoaffinity assays or by nucleic acid testing (e.g., viral RNA or DNA amplification).

HIV is typically treated with a combination of antiviral agent, e.g., two nucleoside-analogue reverse transcription inhibitors and one non-nucleoside-analogue reverse transcription inhibitor or protease inhibitor. The three-drug combination is commonly known as a triple cocktail. In certain embodiments, the disclosure relates to treating a subject diagnosed with HIV by administering a pharmaceutical composition disclosed herein in combination with two nucleoside-analogue reverse transcription inhibitors and one non-nucleoside-analogue reverse transcription inhibitor or protease inhibitor.

In certain embodiments, the disclosure relates to treating a subject by administering a compound disclosed herein, emtricitabine, tenofovir, and efavirenz. In certain embodiments, the disclosure relates to treating a subject by administering a compound disclosed herein, emtricitabine, tenofovir and raltegravir. In certain embodiments, the disclosure relates to treating a subject by administering a compound disclosed herein, emtricitabine, tenofovir, ritonavir and darunavir. In certain embodiments, the disclosure relates to treating a subject by administering a compound disclosed herein, emtricitabine, tenofovir, ritonavir and atazanavir.

Banana lectin (BanLec or BanLec-1) is one of the predominant proteins in the pulp of ripe bananasand has binding specificity for mannose and mannose-containing oligosaccharides. BanLec binds to the HIV-1 envelope protein gp120. In certain embodiments, the disclosure relates to treating viral infections, such as HIV, by administering a compound disclosed herein in combination with a banana lectin.

The hepatitis C virus is a single-stranded, positive sense RNA virus. It is the only known member of the hepacivirus genus in the family Flaviviridae. There are six major genotypes of the hepatitis C virus, which are indicated numerically. The hepatitis C virus particle consists of a core of genetic material (RNA), surrounded by an icosahedral protective shell, and further encased in a lipid envelope. Two viral envelope glycoproteins, E1 and E2, are embedded in the lipid envelope. The genome consists of a single open reading frame translated to produce a single protein. This large pre-protein is later cut by cellular and viral proteases into smaller proteins that allow viral replication within the host cell, or assemble into the mature viral particles, e.g., E1, E2, NS2, NS3, NS4, NS4A, NS4B, NS5, NS5A, and NS5B.

HCV leads to inflammation of the liver, and chronic infection leads to cirrhosis. Most people with hepatitis C infection have the chronic form. Diagnosis of HCV can occur via nucleic acid analysis of the 5'-noncoding region. ELISA assay may be performed to detect hepatitis C antibodies and RNA assays to determine viral load. Subjects infected with HCV may exhibit symptoms of abdominal pain, ascites, dark urine, fatigue, generalized itching, jaundice, fever, nausea, pale or clay-colored stools and vomiting.

Therapeutic agents in some cases may suppress the virus for a long period of time. Typical medications are a combination of interferon alpha and ribavirin. Subjects may receive injections of pegylated interferon alpha. Genotypes 1 and 4 are less responsive to interferon-based treatment than are the other genotypes (2, 3, 5 and 6). In certain embodiments, the disclosure relates to treating a subject with HCV by administering a compound disclosed herein to a subject exhibiting symptoms or diagnosed with HCV. In certain embodiments, the compound is administered in combination with interferon alpha and another antiviral agent such as ribavirin, and/or a protease inhibitor such as telaprevir or boceprevir. In certain embodiments, the subject is diagnosed with genotype 2, 3, 5, or 6. In other embodiments, the subject is diagnosed with genotype 1 or 4.

In certain embodiments, the subject is diagnosed to have a virus by nucleic acid detection or viral antigen detection. Cytomegalovirus (CMV) belongs to the Betaherpesvirinae subfamily of Herpesviridae. In humans it is commonly known as HCMV or Human Herpesvirus 5 (HHV-5). Herpesviruses typically share a characteristic ability to remain latent within the body over long periods. HCMV infection may be life threatening for patients who are immunocompromised. In certain embodiments, the disclosure relates to methods of treating a subject diagnosed with cytomegalovirus or preventing a cytomegalovirus infection by administration of a compound disclosed herein. In certain embodiments, the subject is immunocompromised. In typical embodiments, the subject is an organ transplant recipient, undergoing hemodialysis, diagnosed with cancer, receiving an immunosuppressive drug, and/or diagnosed with an HIV-infection. In certain embodiments, the subject may be diagnosed with cytomegalovirus hepatitis, the cause of fulminant liver failure, cytomegalovirus retinitis (inflammation of the retina, may be detected by ophthalmoscopy), cytomegalovirus colitis (inflammation of the large bowel), cytomegalovirus pneumonitis, cytomegalovirus esophagitis, cytomegalovirus mononucleosis, polyradiculopathy, transverse myelitis, and subacute encephalitis. In certain embodiments, a compound disclosed herein is administered in combination with an antiviral agent such as valganciclovir or ganciclovir. In certain embodiments, the subject undergoes regular serological monitoring.

HCMV infections of a pregnant subject may lead to congenital abnormalities. Congenital HCMV infection occurs when the mother suffers a primary infection (or reactivation) during pregnancy. In certain embodiments, the disclosure relates to methods of treating a pregnant subject diagnosed with cytomegalovirus or preventing a cytomegalovirus infection in a subject at risk for, attempting to become, or currently pregnant by administering compound disclosed herein.

Subjects who have been infected with CMV typically develop antibodies to the virus. A number of laboratory tests that detect these antibodies to CMV have been developed. The virus may be cultured from specimens obtained from urine, throat swabs, bronchial lavages and tissue samples to detect active infection. One may monitor the viral load of CMV-infected subjects using PCR. CMV pp65 antigenemia test is an immunoaffinity based assay for identifying the pp65 protein of cytomegalovirus in peripheral blood leukocytes. CMV should be suspected if a patient has symptoms of infectious mononucleosis but has negative test results for mononucleosis and Epstein-Barr virus, or if they show signs of hepatitis, but have negative test results for hepatitis A, B, and C. A virus culture can be performed at any time the subject is symptomatic. Laboratory testing for antibody to CMV can be performed to determine if a subject has already had a CMV infection.

The enzyme-linked immunosorbent assay (or ELISA) is the most commonly available serologic test for measuring antibody to CMV. The result can be used to determine if acute infection, prior infection, or passively acquired maternal antibody in an infant is present. Other tests include various fluorescence assays, indirect hemagglutination, (PCR), and latex agglutination. An ELISA technique for CMV-specific IgM is available.

Hepatitis B virus is a hepadnavirus. The virus particle, (virion) consists of an outer lipid envelope and an icosahedral nucleocapsid core composed of protein. The genome of HBV is made of circular DNA, but the DNA is not fully double-stranded. One end of the strand is linked to the viral DNA polymerase. The virus replicates through an RNA intermediate form by reverse transcription. Replication typically takes place in the liver where it causes inflammation (hepatitis). The virus spreads to the blood where virus-specific proteins and their corresponding antibodies are found in infected people. Blood tests for these proteins and antibodies are used to diagnose the infection.

Hepatitis B virus gains entry into the cell by endocytosis. Because the virus multiplies via RNA made by a host enzyme, the viral genomic DNA has to be transferred to the cell nucleus by host chaperones. The partially double stranded viral DNA is then made fully double stranded and transformed into covalently closed circular DNA (cccDNA) that serves as a template for transcription of viral mRNAs. The virus is divided into four major serotypes (adr, adw, ayr, ayw) based on antigenic epitopes presented on its envelope proteins, and into eight genotypes (A-H) according to overall nucleotide sequence variation of the genome.

The hepatitis B surface antigen (HBsAg) is typically used to screen for the presence of this infection. It is the first detectable viral antigen to appear during infection. However, early in an infection, this antigen may not be present and it may be undetectable later in the infection if it is being cleared by the host. The infectious virion contains an inner "core particle" enclosing viral genome. The icosahedral core particle is made of core protein, alternatively known as hepatitis B core antigen, or HBcAg. IgM antibodies to the hepatitis B core antigen (anti-HBc IgM) may be used as a serological marker. Hepatitis B e antigen (HBeAg) may appear. The presence of HBeAg in the serum of the host is associated with high rates of viral replication. Certain variants of the hepatitis B virus do not produce the 'e' antigen, If the host is able to clear the infection, typically the HBsAg will become undetectable and will be followed by IgG antibodies to the hepatitis B surface antigen and core antigen, (anti-HBs and anti HBc IgG). The time between the removal of the HBsAg and the appearance of anti-HBs is called the window period. A person negative for HBsAg but positive for anti-HBs has either cleared an infection or has been vaccinated previously. Individuals who remain HBsAg positive for at least six months are considered to be hepatitis B carriers. Carriers of the virus may have chronic hepatitis B, which would be reflected by elevated serum alanine aminotransferase levels and inflammation of the liver that may be identified by biopsy. Nucleic acid (PCR) tests have been developed to detect and measure the amount of HBV DNA in clinical specimens.

Acute infection with hepatitis B virus is associated with acute viral hepatitis. Acute viral hepatitis typically begins with symptoms of general ill health, loss of appetite, nausea, vomiting, body aches, mild fever, dark urine, and then progresses to development of jaundice. Chronic infection with hepatitis B virus may be either asymptomatic or may be associated with a chronic inflammation of the liver (chronic hepatitis), possibly leading to cirrhosis. Having chronic hepatitis B infection increases the incidence of hepatocellular carcinoma (liver cancer).

During HBV infection, the host immune response causes both hepatocellular damage and viral clearance. The adaptive immune response, particularly virus-specific cytotoxic T lymphocytes (CTLs), contributes to most of the liver injury associated with HBV infection. By killing infected cells and by producing antiviral cytokines capable of purging HBV from viable hepatocytes, CTLs eliminate the virus. Although liver damage is initiated and mediated by the CTLs, antigen-nonspecific inflammatory cells can worsen CTL-induced immunopathology, and platelets activated at the site of infection may facilitate the accumulation of CTLs in the liver.

Therapeutic agents can stop the virus from replicating, thus minimizing liver damage. In certain embodiments, the disclosure relates to methods of treating a subject diagnosed with HBV by administering a compound disclosed herein disclosed herein. In certain embodiments, the subject is immunocompromised. In certain embodiments, the compound is administered in combination with another antiviral agent such as lamivudine, adefovir, tenofovir, telbivudine, and entecavir, and/or immune system modulators interferon alpha-2a and pegylated interferon alpha-2a (Pegasys). In certain embodiments, the disclosure relates to preventing an HBV infection in an immunocompromised subject at risk of infection by administering a pharmaceutical composition disclosed herein and optionally one or more antiviral agents. In certain embodiments, the subject is at risk of an infection because the sexual partner of the subject is diagnosed with HBV.

Compounds of the present invention can be administered in combination with a second antiviral agent such as abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, sofosbovir, stavudine, telaprevir, tenofovir, tenofovir disoproxil, tipranavir, trifluridine, trizivir, tromantadine, truvada, valaciclovir, valganciclovir, vicriviroc, vidarabine, viramidine zalcitabine, zanamivir, or zidovudine and combinations thereof.

In a particular embodiment, one of the following compounds is administered together with a second antiviral agent mentioned above:

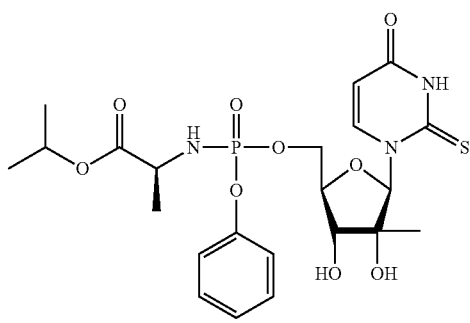

1911

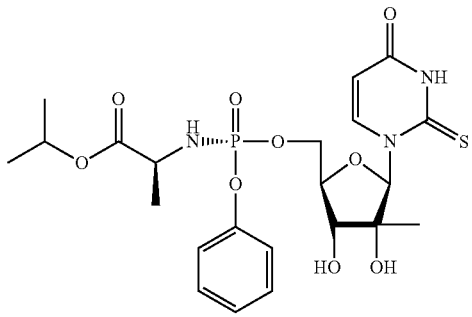

2023

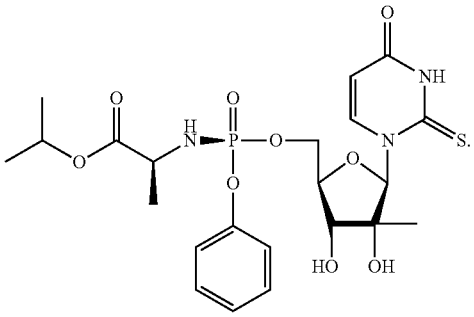

2024

Methods for treating HCV infection in a subject are also provided. The methods comprise administering the compounds of this invention to provide at least two direct acting antiviral agents (DAAs) with or without ribavirin for a duration of no more than twelve weeks, or for another duration as set forth herein. In one embodiment, the duration of the treatment is no more than twelve weeks. In another embodiment, the duration of the treatment is no more than eight weeks. Preferably, the two or more direct acting antiviral agents (DAAs), with or without ribavirin, are administered in amounts effective to provide a sustained virological response (SVR) or achieve another desired measure of effectiveness in a subject. The subject is not administered interferon during the treatment regimen. Put another way, in one embodiment, the methods exclude the administration of interferon to the subject, thereby avoiding the side effects associated with interferon. In some embodiments, the methods further comprise administering an inhibitor of cytochrome P-450 (such as ritonavir) to the subject to improve the pharmacokinetics or bioavailability of one or more of the DAAs.

As another aspect, methods for treating HCV infection in a subject are provided. The methods comprise administering (a) protease inhibitor, (b) at least one polymerase inhibitor, wherein at least one is a polymerase of this invention and combinations thereof, with or without (c) ribavirin and/or (d) an inhibitor or cytochrome P-450 to the subject for a duration of no more than twelve weeks, or for another duration as set forth herein (e.g., the treatment regimen can last a duration of for no more than 8 weeks). Preferably, the compounds are administered in amounts effective to provide high rates of SVR or another measure of effectiveness in the subject. As non-limiting examples, the compounds can be co-formulated and administered once daily, and the treatment regimen preferably lasts for eight weeks or six weeks.

As still another aspect, methods for treating a population of subjects having HCV infection are provided. The methods comprise administering at least two DAAs, wherein one of the DAAs is a compound of this invention, with or without ribavirin, to the subjects for a duration of no more than 12 or 8 or 6 weeks. Preferably, the at least two DAAs are administered to the subjects in amounts effective to result in SVR or another measure of effectiveness in at least about 70% of the population, preferably at least 90% of the population.

In the foregoing methods as well as methods described herein below, the DAAs can be selected from the group consisting of protease inhibitors, nucleoside or nucleotide polymerase inhibitors (one of which is provided herein), non-nucleoside polymerase inhibitors, NS3B inhibitors, NS4A inhibitors, NS5A inhibitors, NS5B inhibitors, cyclophilin inhibitors, and combinations of any of the foregoing. For example, in some embodiments, the DAAs used in the present methods comprise or consist of at least one HCV protease inhibitor and at least one HCV polymerase inhibitor provided herein.

At least one of the HCV polymerase inhibitors is one of the compounds of this invention (described herein). By way of example, compounds of this invention can be administered a total daily dose of from about 100 mg to about 250 mg, or administered once daily at a dose of from about 150 mg to about 250 mg.

In some embodiments, the at least two DAAs comprise at least on HCV polymerase inhibitors of this invention and at least one NS5A inhibitor. By way of example, the polymerase inhibitor of this invention can be administered at a total daily dosage from about 100 mg to about 250 mg, and the NS5A inhibitor can be administered in a total daily dose from about 25 mg to about 200 mg. Ritonavir (or another cytochrome P-450 3A4 inhibitor) can be co-administered with to improve the pharmacokinetics and bioavailability of the compounds.

In the foregoing methods as well as methods described herein, the DAAs with or without ribavirin can be administered in any effective dosing schemes and/or frequencies, for example, they can each be administered daily. Each DAA can be administered either separately or in combination, and each DAA can be administered at lease once a day, at least twice a day, or at least three times a day. Likewise, the ribavirin can be administered at least once a day, at least twice a day, or at least three times a day, either separately or in combination with one of more of the DAAs. In some preferred embodiments, the compounds are administered once daily.

In some aspects, the present technology provides a method for treating HCV infection comprising administering to a subject in need thereof at least two DAAs with or without ribavirin for a duration of no more than twelve or eight or six weeks, wherein the subject is not administered with interferon during said duration. In some aspects, the at least two DAAs with or without ribavirin are administered in an amount effective to result in SVR. Some methods further comprise administering an inhibitor of cytochrome P450 to the subject. In some aspects, the duration is no more than eight weeks.

In yet another aspect, the at least two direct acting antiviral agents comprises a drug combination selected from the group consisting of: a compound of this invention, with one or more of ABT-450 and/or ABT-267, and/or ABT-333; a novel compound of this invention with a compound disclosed in any of US 2010/0144608; U.S. 61/339,964; US 2011/0312973; WO 2009/039127; US 2010/0317568; 2012/151158; US 2012/0172290; WO 2012/092411; WO 2012/087833; WO 2012/083170; WO 2009/039135; US 2012/0115918; WO 2012/051361; WO 2012/009699; WO 2011/156337; US 2011/0207699; WO 2010/075376; U.S. Pat. No. 7,910,595; WO 2010/120935; WO 2010/111437; WO 2010/111436; US 2010/0168384 or US 2004/0167123; a compound of this invention with one or more of Simeprevir, and/or GSK805; a compound of this invention with one or more of Asunaprevir, and/or Daclastavir, and/or BMS-325; a compound of this invention with one or more of GS-9451, and/or Ledisasvir and/or Sofosbuvir, and/or GS-9669; a compound of this invention with one or more of ACH-2684, and/or ACH-3102, and/or ACH-3422; a compound of this invention with one or more of Boceprevir, and/or MK-8742; a compound of this invention with one or more of Faldaprevir and/or Deleobuvir; a compound of this invention with PPI-668; a compound of this invention with one or more of telaprevir and/or VX-135; a compound of this invention with one or more of Samatasvir and/or IDX-437; a compound of this invention with PSI-7977 and/or PSI-938, a compound of this invention with BMS-790052 and/or BMS-650032; a compound of this invention with GS-5885 and/or GS-9451; a compound of this invention with GS-5885, GS-9190 and/or GS-9451; a compound of this invention in combination with BI-201335 and/or BI-27127; a compound of this invention in combination with telaprevir and/or VX-222; a compound of this invention combination with PSI-7977 and/or TMC-435; and a compound of this invention in combination with danoprevir and/or R7128.

In yet another aspect, the at least two direct acting antiviral agents comprises a compound of this invention in a combination of PSI-7977 and/or BMS-790052 (daclatasvir). In yet another aspect, the at least two direct acting antiviral agents comprises a compound of this invention in a combination of PSI-7977 and/or BMS-650032 (asunaprevir). In still another aspect, the at least direct acting antiviral agents comprise a compound of this invention in combination with PSI-7977, BMS-650032 (asunaprevir) and/or BMS-790052 (daclatasvir). The compounds of this invention can be either added to these combinations or used to replace the listed polymerase.

In another aspect, the present technology features a combination of at least two DAAs for use in treating HCV infection, wherein the duration of the treatment regimen is no more than twelve weeks (e.g., the duration being 12 weeks; or the duration being 11, 10, 9, 8, 7, 6, 5. 4, or 3 weeks). The treatment comprises administering the at least two DAAs to a subject infected with HCV. The duration of the treatment can be 12 weeks and also last, for example, no more than eight weeks (e.g., the duration being 8 weeks; or the duration being 7, 6, 5, 4, or 3 weeks). The treatment can include administering ribavirin but does not include administering interferon. The treatment may also include administering ritonavir or another CYP3A4 inhibitor (e.g., cobicistat) if one of the DAAs requires pharmacokinetic enhancement. The at least two DAAs can be administered concurrently or sequentially. For example, one DAA can be administered once daily, and another DAA can be administered twice daily. For another example, the two DAAs are administered once daily. For yet another example, the two DAAs are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV treatment naïve patient, a HCV-treatment experienced patient, an interferon non-responder (e.g., a null responder, a partial responder or a relapser), or not a candidate for interferon treatment.

In another aspect, the present technology features a combination of at least two DAAs for use in treating HCV infection, wherein said combination comprises a compound of this invention in combination with compounds selected from:
a combination of PSI-7977 and/or PSI-938;
a combination of BMS-790052 and/or BMS-650032;
a combination of GS-5885 and/or GS-9451;
a combination of GS-5885, GS-9190 and/or GS-9451;
a combination of BI-201335 and/or BI-27127;
at combination of telaprevir and/or VX-222;
combination of PSI-7977 and/or TMC-435;
a combination of danoprevir and/or R7128;
a combination of ABT-450 and/or ABT-267 and/or ABT-333;
one or more of the following protease inhibitors: ABT450, Simeprevir, Asunaprevir, GS-9451, ACH-2684, Boceprevir, MK-5172, Faldaprevir, and Telaprevir;
one or more of the following NS5A inhibitors: ABT-267, GSK805, Daclastavir, Dedipasvir, GS-5816, ACH-3102, MK-8742, PPI-668, and Samatasvir;
one or more of the following Non-nuc NS5B Inhibitors: ABT-333, TMC055, BMS-325, GS-9669, and Deleobuvir.

In one embodiment, the compound of the present invention used in the combination therapies above is 1911, 2023, or 2024. In a currently preferred embodiment, the novel compound of the present invention used in the combination therapies above is 2023. One or more of 1911, 2033 and 2024 can be combined with one or more of ABT-450, ABT-267 and/or ABT-333 and/or a compound disclosed in US 2010/0144608; U.S. 61/339,964; US 2011/0312973; WO 2009/039127; US 2010/0317568; 2012/151158; US 2012/0172290; WO 2012/092411; WO 2012/087833; WO 2012/083170; WO 2009/039135; US 2012/0115918; WO 2012/051361; WO 2012/009699; WO 2011/156337; US 2011/0207699; WO 2010/075376; U.S. Pat. No. 7,910,595; WO 2010/120935; WO 2010/111437; WO 2010/111436; US 2010/0168384 or US 2004/0167123.

In yet another aspect, the present technology features a combination of at least two DAAs for use in treating HCV infection, wherein said combination comprises a compound of this invention in a combination selected from:
ABT-450, and/or ABT-267 and/or ABT-333 and/or a compound disclosed in US 2010/0144608; U.S. 61/339,964; US 2011/0312973; WO 2009/039127; US 2010/0317568; 2012/151158; US 2012/0172290; WO 2012/092411; WO 2012/087833; WO 2012/083170; WO 2009/039135; US 2012/0115918; WO 2012/051361; WO 2012/009699; WO 2011/156337; US 2011/0207699; WO 2010/075376; U.S. Pat. No. 7,910,595; WO 2010/120935; WO 2010/111437; WO 2010/111436; US 2010/0168384 or US 2004/0167123;
a combination of PSI-797 and/or BMS-790052;
a combination of PSI-7977 and/or BMS-650032;
a combination of PSI-7977, BMS-790052 and/or BMS-650032;
a combination of INX-189 and/or BMS-790052;
combination of INX-189 and/or BMS-650032; or
a combination of INX-189, BMS-790052 and/or BMS-650032.

In still another aspect, the present technology features PSI-7977, or a combination of at least two DAAs, for use in treating HCV infection, wherein said combination comprises a combination of a compound of this invention and a compound selected from:
a combination of mericitabine and/or danoprevir;
a combination of daclatasvir and/or BMS-791325; and
a combination of PSI-7977 and/or GS-5885.

The treatment comprises administering PSI-7977 or the DAA combination to a subject infected with HCV.

In still another aspect, the present technology features a compound of this invention with PSI-7977, or a combination of at least two DAAs, for use in treating HCV infection, wherein said combination comprises a combination selected from:
a combination of mericitabine and/or danoprevir;
combination of INX-189, daclatasvir and/or BMS-791325; and
a combination of PSI-7977 and/or GS-5885.

The treatment comprises administering PSI-7977 or the DAA combination to a subject infected with HCV.

In still another aspect, the present technology features a combination of at least two DAAs, for use in treating HCV infection, wherein said combination comprises a combination selected from a compound of this invention and:
a combination of tegobuvir and/or GS-9256;
a combination of BMS-791325, asunaprevir and/or daclatasvir; and
a combination of TMC-435 and/or daclatasvir.

The treatment comprises administering the DAA combination to a subject infected with HCV.

In yet another aspect, the present technology features a combination of a compound of this invention with PSI-7977 and/or BMS-790052 for use in treating HCV infection. The treatment comprises administering the DAA combination to a subject infected with HCV.

In yet another aspect, the present technology features a combination of a compound of this invention with PSI-7977 and/or TMC-435 for use in treating HCV infection.

In yet another aspect, the present technology features a combination of a compound of this invention with danoprevir and/or mericitabine for use in treating HCV infection.

In yet another aspect, the present technology features a combination of a compound of this invention with daclatasvir and/or BMS-791325 for use in treating HCV infection. The treatment comprises administering the DAA combination to a subject infected with HCV.

In yet another aspect, the present technology features a combination of a compound of this invention with PSI-7977 and/or GS-5885 for use in treating HCV infection. The treatment comprises administering the DAA combination to a subject infected with HCV.

The duration of the treatment regimens is no more than sixteen weeks (e.g., the duration being 16 weeks; or the duration being 14, 12 or 10, 9, 8, 7, 6, 5, 4, 3, 2, or 1 weeks). The treatment includes administering ribavirin but does not include administering interferon. The treatment may include administering ritonavir or another CYP3A4 inhibitor (e.g., cobicistat) if one of the DAAs requires pharmacokinetic enhancement. The two DAAs can be administered concurrently or sequentially. For example, one DAA can be administered once daily, and the other DAA can be administered twice daily. For another example, the two DAAs are administered once daily. For yet another example, the two DAAs are co-formulated in a single composition and administered concurrently (e.g., once daily). As a non-limiting example, the patient being treated can be infected with HCV genotype 1, such as genotype 1a or 1b. As another non-limiting example, the patient can be infected with HCV genotype 2 or 3. As yet another non-limiting example, the patient can be a HCV-treatment naïve patient, a HCV-treatment experienced patient, an interferon non-responded (e.g., a null responder), or not a candidate for interferon treatment.

In yet another embodiment of this aspect of the invention, the at least two DAAs comprise a HCV protease inhibitor and a HCV polymerase inhibitor of this invention. The treatment can last, for example and without limitation, for no more than 12 weeks, such as 8, 9, 10, 11, or 12 weeks. Preferably, the treatment lasts for 12 weeks. The treatment can also last for 8 weeks. The subject being treated can be, for example, a treatment naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In yet another embodiment of this aspect of the invention, the at least two DAAs comprise a compound of this invention with an HCV protease inhibitor and a non-nucleoside or non-nucleotide HCV polymerase inhibitor. The treatment can last, for example, and without limitation, for no more than 12 weeks, such as 8, 9, 10, 11 or 12 weeks. Preferably, the treatment lasts for 12 weeks. The treatment can also last for 8 weeks. The subject being treated can be, for example, a treatment-naïve patient. The subject can also be a treatment-experienced patient, or an interferon non-responder (e.g., a null responder). Preferably, the subject being treated is infected with HCV genotype 1, e.g., HCV genotype 1a. As another non-limiting example, the subject being treatment is infected with HCV genotype 3.

In yet another embodiment of this aspect of the invention, the DAAs comprise a compound of this invention with HCV protease inhibitor and a HCV NS5A inhibitor.

In yet another embodiment of this aspect of the invention, the at least two DAAs comprise a HCV polymerase inhibitor of this invention and a HCV NS5A inhibitor.

In yet another embodiment of this aspect of the invention, the DAAs comprise a compound of this invention and a HCV non-nucleoside or non-nucleotide polymerase inhibitor and a HCV NS5A inhibitor.

In yet another embodiment of this aspect of the invention, the DAAs can comprise a HCV nucleoside or nucleotide polymerase inhibitor of this invention and a HCV NS5A inhibitor.

In yet another embodiment of this aspect of the invention, the at least two DAAs comprise a compound of this invention with PSI-7977 and/or TMC-435.

In yet another embodiment of this aspect of the invention, the DAAs comprise a compound of this invention with PSI-7977 and/or daclatasvir.

In yet another embodiment of this aspect of the invention, the DAAs comprise a compound of this invention with PSI-7977 and/or GS-5885.

In yet another embodiment of this aspect of the invention, the DAAs comprise a compound of this invention with mericitabine and/or danoprevir.

In yet another embodiment of this aspect of the invention, the DAAs comprise a compound of this invention with BMS-790052 and/or BMS-650032.

In yet another embodiment of this aspect of the invention, the DAAs comprise a compound of this invention and INX-189, daclatasvir and/or BMS-791325.

A treatment regimen of the present technology generally constitutes a complete treatment regimen, i.e., no subsequent interferon-containing regimen is intended. Thus, a treatment or use described herein generally does not include any subsequent interferon-containing treatment.

In one aspect of the disclosure, an "infection" or "bacterial infection" refers to an infection caused by *acinetobacter* spp, *bacteroides* spp, *burkholderia* spp, *campylobacter* spp, *chlamydia* spp, *chlamydophila* spp, *clostridium* spp, *enterobacter* spp, *enterococcus* spp, *escherichia* spp, *fusobacterium* spp, *gardnerella* spp, *haemophilus* spp, *helicobacter* spp, *klebsiella* spp, *legionella* spp, *moraxella* spp, *morganella* spp, *mycoplasma* spp, *neisseria* spp, *peptococcus* spp *peptostreptococcus* spp, *proteus* spp, *pseudomonas* spp, *salmonella* spp, *serratia* spp., *staphylococcus* spp, *streptoccocus* spp, *stenotrophomonas* spp, or *ureaplasma* spp.

In one aspect of the disclosure, an "infection" or "bacterial infection" refers to an infection caused by *acinetobacter baumanii, acinetobacter haemolyticus, acinetobacter junii, acinetobacter johnsonii, acinetobacter lwoffi, bacteroides bivius, bacteroides fragilis, burkholderia cepacia, campylobacter jejuni, chlamydia pneumoniae, chlamydia urealyticus, chlamydophila pneumoniae, clostridium difficile, enterobacter aerogenes, enterobacter cloacae, enterococcus faecalis, enterococcus faecium, escherichia coli, gardnerella vaginalis, haemophilus par influenzae, haemophilus influenzae, helicobacter pylori, klebsiella pneumoniae, legionella pneumophila*, methicillin-resistant *staphylococcus aureus*, methicillin-susceptible *staphylococcus aureus, moraxella catarrhalis, morganella morganii, mycoplasma pneumoniae, neisseria gonorrhoeae*, penicillin-resistant *streptococcus pneumoniae*, penicillin-susceptible *streptococcus pneumoniae, peptostreptococcus magnus, peptostreptococcus micros, peptostreptococcus anaerobius, peptostreptococcus asaccharolyticus, peptostreptococcus prevotii, peptostreptococcus tetradius, peptostreptococcus vaginalis, proteus mirabilis, pseudomonas aeruginosa*, quinolone-resistant *staphylococcus aureus*, quinolone-resistant *staphylococcus epidermis, salmonella typhi, salmonella paratyphi, salmonella enteritidis, salmonella typhimurium, serratia marcescens, staphylococcus aureus, staphylococcus epidermidis, staphylococcus saprophyticus, streptoccocus agalactiae, streptococcus pneumoniae, streptococcus pyogenes, stenotrophomonas maltophilia, ureaplasma urealyticum*, vancomycin-resistant *enterococcus faecium*, vancomycin-resistant *enterococcus faecalis*, vancomycin-resistant *staphylococcus aureus*, vancomycin-resistant *staphylococcus epidermis, mycobacterium tuberculosis, clostridium perfringens, klebsiella oxytoca, neisseria miningitidis, proteus vulgaris*, or coagulase-negative *staphylococcus* (including *staphylococcus lugdunensis, staphylococcus capitis, staphylococcus hominis*, or *staphylococcus* saprophytic).

In one aspect of the disclosure "infection" or "bacterial infection" refers to aerobes, obligate anaerobes, facultative anaerobes, gram-positive bacteria, gram-negative bacteria, gram-variable bacteria, or atypical respiratory pathogens.

In some embodiments, the disclosure relates to treating a bacterial infection such as a gynecological infection, a respiratory tract infection (RTI), a sexually transmitted disease, or a urinary tract infection.

In some embodiments, the disclosure relates to treating a bacterial infection such as an infection caused by drug resistant bacteria.

In some embodiments, the disclosure relates to treating a bacterial infection such as community-acquired *pneumoniae*, hospital-acquired *pneumoniae*, skin & skin structure infections, gonococcal cervicitis, gonococcal urethritis, febrile neutropenia, osteomyelitis, endocarditis, urinary tract infections and infections caused by drug resistant bacteria such as penicillin-resistant *streptococcus pneumoniae*, methicillin-resistant *staphylococcus aureus*, methicillin-resistant *staphylococcus epidermidis* and vancomycin-resistant enterococci, syphilis, ventilator-associated pneumonia, intra-abdominal infections, *gonorrhoeae*, meningitis, tetanus, or tuberculosis.

In some embodiments, the disclosure relates to treating a fungal infections such as infections caused by tinea *versi-* color, microsporum, trichophyton, epidermophyton, candidiasis, cryptococcosis, or aspergillosis.

In some embodiments, the disclosure relates to treating an infection caused by protozoa including, but not limited to, malaria, amoebiasis, giardiasis, toxoplasmosis, cryptosporidiosis, trichomoniasis, leishmaniasis, sleeping sickness, or dysentery.

Certain compounds disclosed herein are useful to prevent or treat an infection of a malarial parasite in a subject and/or for preventing, treating and/or alleviating complications and/or symptoms associated therewith and can then be used in the preparation of a medicament for the treatment and/or prevention of such disease. The malaria may be caused by *Plasmodium falciparum, P. vivax, P. ovale,* or *P. malariae.*

In one embodiment, the compound is administered after the subject has been exposed to the malaria parasite. In another embodiment, a compound disclosed herein is administered before the subject travels to a country where malaria is endemic.

The compounds or the above-mentioned pharmaceutical compositions may also be used in combination with one or more other therapeutically useful substances selected from the group comprising antimalarials like quinolines (e.g., quinine, chloroquine, amodiaquine, mefloquine, primaquine, tafenoquine); peroxide antimalarials (e.g., artemisinin, artemether, artesunate); pyrimethamine-sulfadoxine antimalarials (e.g., Fansidar); hydroxynaphtoquinones (e.g., atovaquone); acroline-type antimalarials (e.g., pyronaridine); and antiprotozoal agents such as ethylstibamine, hydroxystilbamidine, pentamidine, stilbamidine, quinapyramine, puromycine, propamidine, nifurtimox, melarsoprol, nimorazole, nifuroxime, aminitrozole and the like.

In an embodiment, compounds disclosed herein can be used in combination one additional drug selected from the group consisting of chloroquine, artemesin, qinghaosu, 8-aminoquinoline, amodiaquine, arteether, artemether, artemisinin, artesunate, artesunic acid, artelinic acid, atovoquone, azithromycine, biguanide, chloroquine phosphate, chlorproguanil, cycloguanil, dapsone, desbutyl halofantrine, desipramine, doxycycline, dihydrofolate reductase inhibitors, dipyridamole, halofantrine, haloperidol, hydroxychloroquine sulfate, imipramine, mefloquine, penfluridol, phospholipid inhibitors, primaquine, proguanil, pyrimethamine, pyronaridine, quinine, quinidine, quinacrineartemisinin, sulfonamides, sulfones, sulfadoxine, sulfalene, tafenoquine, tetracycline, tetrandine, triazine, salts or mixture thereof.

Cancer

In a typical embodiment, the disclosure relates to a method treating cancer comprising administering to a patient a compound disclosed herein. In some embodiments, the disclosure relates to a compound disclosed herein, or a pharmaceutically acceptable salt thereof for uses in treating cancer.

In some embodiments, the disclosure relates to a compound disclosed herein, or a pharmaceutically acceptable salt thereof, as defined herein for use in the treatment of cancer of the breast, colorectum, lung (including small cell lung cancer, non-small cell lung cancer and bronchioalveolar cancer) and prostate.

In some embodiments, the disclosure relates to a compound disclosed herein, or a pharmaceutically acceptable salt thereof, as defined herein for use in the treatment of cancer of the bile duct, bone, bladder, head and neck, kidney, liver, gastrointestinal tissue, oesophagus, ovary, endometrium, pancreas, skin, testes, thyroid, uterus, cervix and vulva, and of leukaemias (including ALL and CML), multiple myeloma and lymphomas.

In some embodiments, the disclosure relates to a compound disclosed herein, or a pharmaceutically acceptable salt thereof, as defined herein for use in the treatment of lung cancer, prostate cancer, melanoma, ovarian cancer, breast cancer, endometrial cancer, kidney cancer, gastric cancer, sarcomas, head and neck cancers, tumors of the central nervous system and their metastases, and also for the treatment of glioblastomas.

In some embodiments, compounds disclosed herein could be used in the clinic either as a single agent by itself or in combination with other clinically relevant agents. This compound could also prevent the potential cancer resistance mechanisms that may arise due to mutations in a set of genes.

The anti-cancer treatment defined herein may be applied as a sole therapy or may involve, in addition to the compound of the disclosure, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon;

(ii) cytostatic agents such as anti-estrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents that inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab), farnesyl transferase inhibitors, tyrosine kinase inhibitors and serine/threonine kinase inhibitors, for example inhibitors of the epidermal growth factor family (for example EGFR family tyrosine kinase inhibitors such as: N-(3-chloro-4-fluorophenyl)-7-methoxy-6-(3-morpholinopropoxy)quinazolin-4-a mine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors or phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (AbI) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies, and approaches using the immunomodulatory drugs thalidomide and lenalidomide [Revlimid®].

Such conjoint treatment may be achieved by way of the simultaneous, sequential or separate dosing of the individual components of the treatment. Such combination products employ the compounds of this disclosure, or pharmaceutically acceptable salts thereof, within the dosage range described hereinbefore and the other pharmaceutically-active agent within its approved dosage range.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound of the disclosure contains a hydrogen-donating heteroatom (e.g., NH), the disclosure also covers salts and/or isomers formed by the transfer of the hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases that form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier that releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as a prodrug are known, for example, in Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It has been shown that ester prodrugs are readily degraded in the body to release the corresponding alcohol. See e.g., Imai, Drug Metab Pharmacokinet. (2006) 21(3):173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, cornstarch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (I-IPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na-CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (PEGylation) to increase the in vivo half-life of circulating therapeutic proteins and decrease the chance of an immune response.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prodrug forms of the nucleoside compounds according to the present invention.

It is appreciated that nucleosides of the present invention have several chiral centers and may exist in and be isolated in optically active and racemic forms. Some compounds may exhibit polymorphism. It is to be understood that the present invention encompasses any racemic, optically active, diastereomeric, polymorphic, or stereoisomeric form, or mixtures thereof, of a compound of the invention, which possess the useful properties described herein. It is well known in the art how to prepare optically active forms (for example, by resolution of the racemic form by recrystallization techniques, by synthesis from optically-active starting materials, by chiral synthesis, or by chromatographic separation using a chiral stationary phase).

Carbons of the nucleoside are chiral, their nonhydrogen substituents (the base and the CHOR groups, respectively) can be either cis (on the same side) or trans (on opposite sides) with respect to the sugar ring system. The four optical isomers therefore are represented by the following configurations (when orienting the sugar moiety in a horizontal plane such that the oxygen atom is in the back): cis (with both groups "up", which corresponds to the configuration of naturally occurring β-D nucleosides), cis (with both groups "down", which is a nonnaturally occurring β-L configuration), trans (with the C2' substituent "up" and the C4' substituent "down"), and trans (with the C2' substituent "down" and the C4' substituent "up"). The "D-nucleosides" are cis nucleosides in a natural configuration and the "L-nucleosides" are cis nucleosides in the nonnaturally occurring configuration.

Likewise, most amino acids are chiral (designated as L or D, wherein the L enantiomer is the naturally occurring configuration) and can exist as separate enantiomers.

Examples of methods to obtain optically active materials are known in the art, and include at least the following. i) physical separation of crystals-a technique whereby macroscopic crystals of the individual enantiomers are manually separated. This technique can be used if crystals of the separate enantiomers exist, i.e., the material is a conglomerate, and the crystals are visually distinct; ii) simultaneous crystallization-a technique whereby the individual enantiomers are separately crystallized from a solution of the racemate, possible only if the latter is a conglomerate in the solid state; iii) enzymatic resolutions-a technique whereby partial or complete separation of a racemate by virtue of differing rates of reaction for the enantiomers with an enzyme; iv) enzymatic asymmetric synthesis-a synthetic technique whereby at least one step of the synthesis uses an enzymatic reaction to obtain an enantiomerically pure or enriched synthetic precursor of the desired enantiomer; v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries; vi) diastereomer separations-a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer; vii) first- and second-order asymmetric transformations-a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer; viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions; ix) enantiospecific synthesis from non-racemic precursors—a synthetic technique whereby the desired enantiomer is obtained from non-chiral starting materials and where the stereochemical integrity is not or is only minimally compromised over the course of the synthesis; x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions; xi) chiral gas chromatography-a technique whereby the racemate is volatilized and enantiomers are separated by virtue of their differing interactions in the gaseous mobile phase with a column containing a fixed non-racemic chiral adsorbent phase; xii) extraction with chiral solvents-a technique whereby the enantiomers are separated by virtue of preferential dissolution of one enantiomer into a particular chiral solvent; xiii) transport across chiral membranes-a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through. Chiral chromatography, including simulated moving bed chromatography, is used in one embodiment. A wide variety of chiral stationary phases are commercially available.

Some of the compounds described herein contain olefinic double bonds and unless otherwise specified, are meant to include both E and Z geometric isomers.

In addition, some of the nucleosides described herein, may exist as tautomers, such as, keto-enol tautomers. The individual tautomers as well as mixtures thereof are intended to be encompassed within the compounds of the present invention.

EXAMPLES

Example 1

Conjugate Preparation

Mono and diphosphate prodrugs have been prepared by several groups. See Jessen et al., Bioreversible Protection of Nucleoside Diphosphates, Angewandte Chemie-International Edition English 2008, 47 (45), 8719-8722, hereby incorporated by reference. In order to prevent rupture of the P—O—P anhydride bond, one utilizes a pendant group that fragments rapidly (e.g. bis-(4-acyloxybenzyl)-nucleoside diphosphates (BAB-NDP) that is deacylated by an endogenous esterase) to generate a negative charge on the second phosphate. See also Routledge et al., Synthesis, Bioactivation and Anti-HIV Activity of 4-Acyloxybenzyl-bis(nucleosid-5'-yl) Phosphates, Nucleosides & Nucleotides 1995, 14 (7), 1545-1558 and Meier et al., Comparative study of bis(benzyl)phosphate triesters of 2',3'-dideoxy-2',3'-didehydrothymidine (d4T) and cycloSal-d4TMP-hydrolysis, mechanistic insights and anti-HIV activity, Antiviral Chemistry and Chemotherapy 2002, 13, 101-114, both hereby incorporated by reference. Once this occurs, the P—O—P anhydride bond is less susceptible to cleavage and the remaining protecting group can then do its final unraveling to produce the nucleoside diphosphate.

Figure 5:
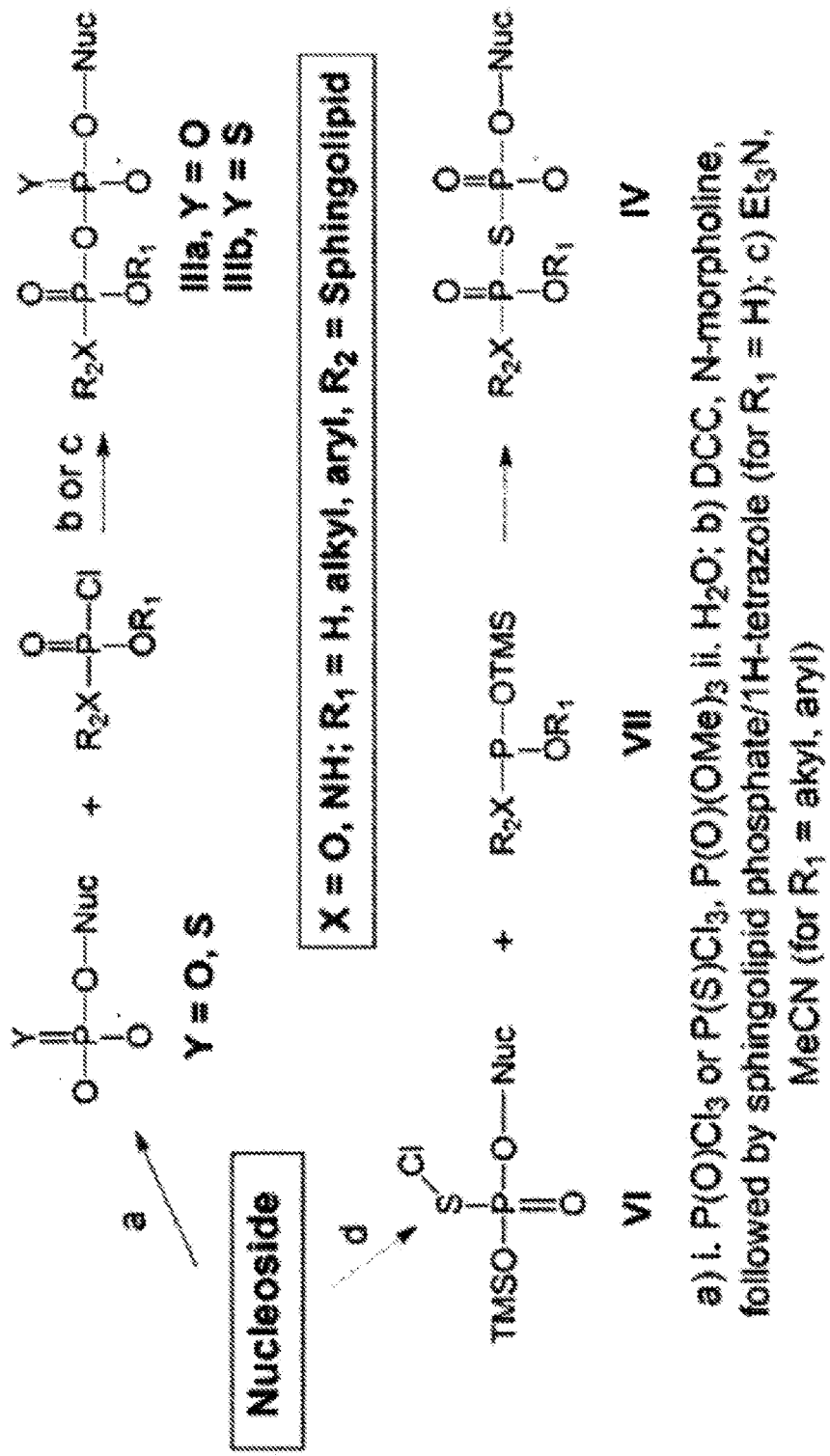
FIG. 5 illustrates schemes for the synthesis of conjugates.
Figure 6:
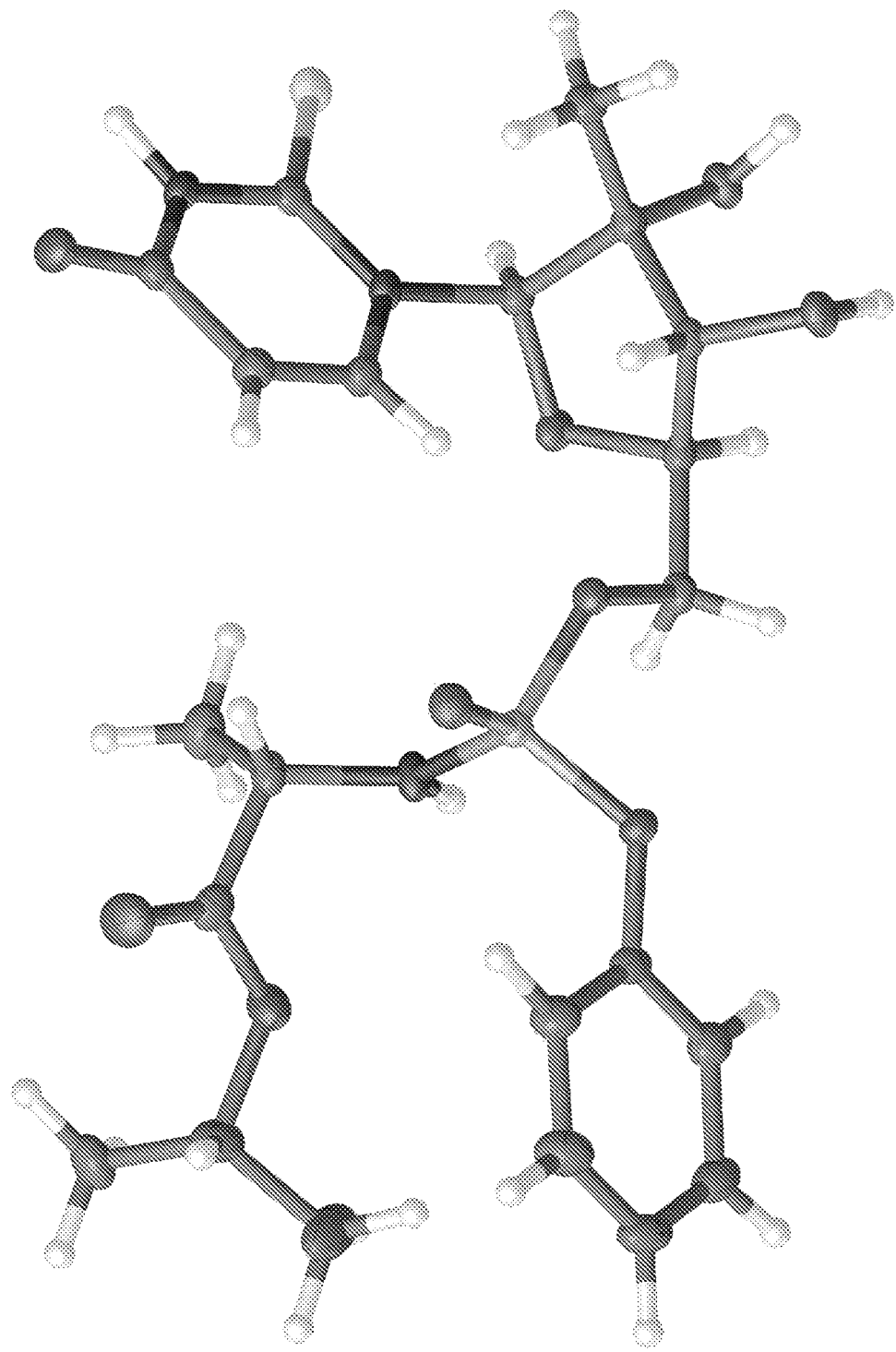
FIG. 6 is the X-ray crystal structure for EIDD-02023.

Other methods to prepare diphosphate and monothiodiphosphate prodrugs are shown in FIG. 5. Standard coupling conditions are used to prepare sphingolipid-nucleoside monophosphate prodrugs. The corresponding diphosphate prodrugs may be prepared according to the protocols shown in FIG. 5 and as provided in Smith et al., Substituted Nucleotide Analogs. U.S. Patent Application 2012/0071434; Skowronska et al., Reaction of Oxophosphorane-Sulfenyl and Oxophosphorane-Selenenyl Chlorides with Dialkyl Trimethylsilyl Phosphites—Novel Synthesis of Compounds Containing a Sulfur or Selenium Bridge Between 2 Phosphoryl Centers, Journal of the Chemical Society-Perkin Transactions 1 1988, 8, 2197-2201; Dembinski et al., An Expedient Synthesis of Symmetrical Tetra-Alkyl Mono-thiopyrophosphates, Tetrahedron Letters 1994, 35 (34), 6331-6334; Skowronska et al., Novel Synthesis of Symmetrical Tetra-Alkyl Monothiophosphates, Tetrahedron Letters 1987, 28 (36), 4209-4210; and Chojnowski et al., Methods of Synthesis of 0,0-Bis Trimethyl-Silyl Phosphorothiolates. Synthesis-Stuttgart 1977, 10, 683-686, all hereby incorporated by reference in their entirety.

Example 2

Activity of 2-Fluoronucleosides

Ribonucleoside analogs when activated to their corresponding triphosphate inhibit RNA-dependent RNA viral replication by acting as competitive substrate inhibitors of the virally encoded RdRp. Compounds in this therapeutic class are useful in the treatment of viruses found in but not limited to the arenaviridae, bunyaviridae, flaviviridae, orthomyxoviridae, paramyxoviridae, and togaviridae viral families. Certain compounds disclosed herein are contemplated to have advantages such as a high genetic barrier for antiviral resistance; broad spectrum activity within viral families; and high oral bioavailability with targeted delivery to sites of infection.

The nucleoside analogs were designed with a 2'-alpha-fluorine substituent to mimic natural ribonucleosides. The C—F bond length (1.35 Å) is similar to the C—O bond length (1.43 Å) and fluorine is a hydrogen-bond acceptor making the fluorine substituent an isopolar and isosteric replacement of a hydroxyl group. Unlike ribonucleoside analogs currently in clinical trials for treating HCV infections, in certain embodiments, the 2', 3'-dideoxy-2'-fluoronucleoside analogs covered by this disclosure lack a 3'-hydroxyl group and are thus obligate chain terminators of viral replication. Once the nucleosides are converted to their triphosphates, they act as competitive substrate inhibitors of the virally encoded RdRp. After incorporation of the chain terminator into nascent RNA, viral replication ceases. One advantage to obligate chain terminators is that they are not mutagenic to the host when treating chronic diseases.

Example 3

NS5B RNA-Dependent RNA Polymerase Reaction Conditions

Compounds were assayed for inhibition of NS5B-δ21 from HCV GT-1b Con-1. Reactions included purified recombinant enzyme, 1 u/μL negative-strand HCV IRES RNA template, and 1 μM NTP substrates including either [$^{32}$P]-CTP or [$^{32}$P]-UTP. Assay plates were incubated at 27° C. for 1 hour before quench. [$^{32}$P] incorporation into macromolecular product was assessed by filter binding.

The table below shows activity of select analog triphosphates against the HCV NS5B polymerase.

| | HCV NS5B pol assay | |
|---|---|---|
| Structure and I.D. | $^{32}$P-CTP | $^{32}$P-UTP |
| 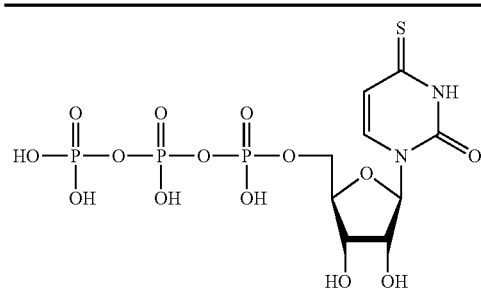ENUC-01824 | IC50 = 80 uM | IC50 = 6 uM |

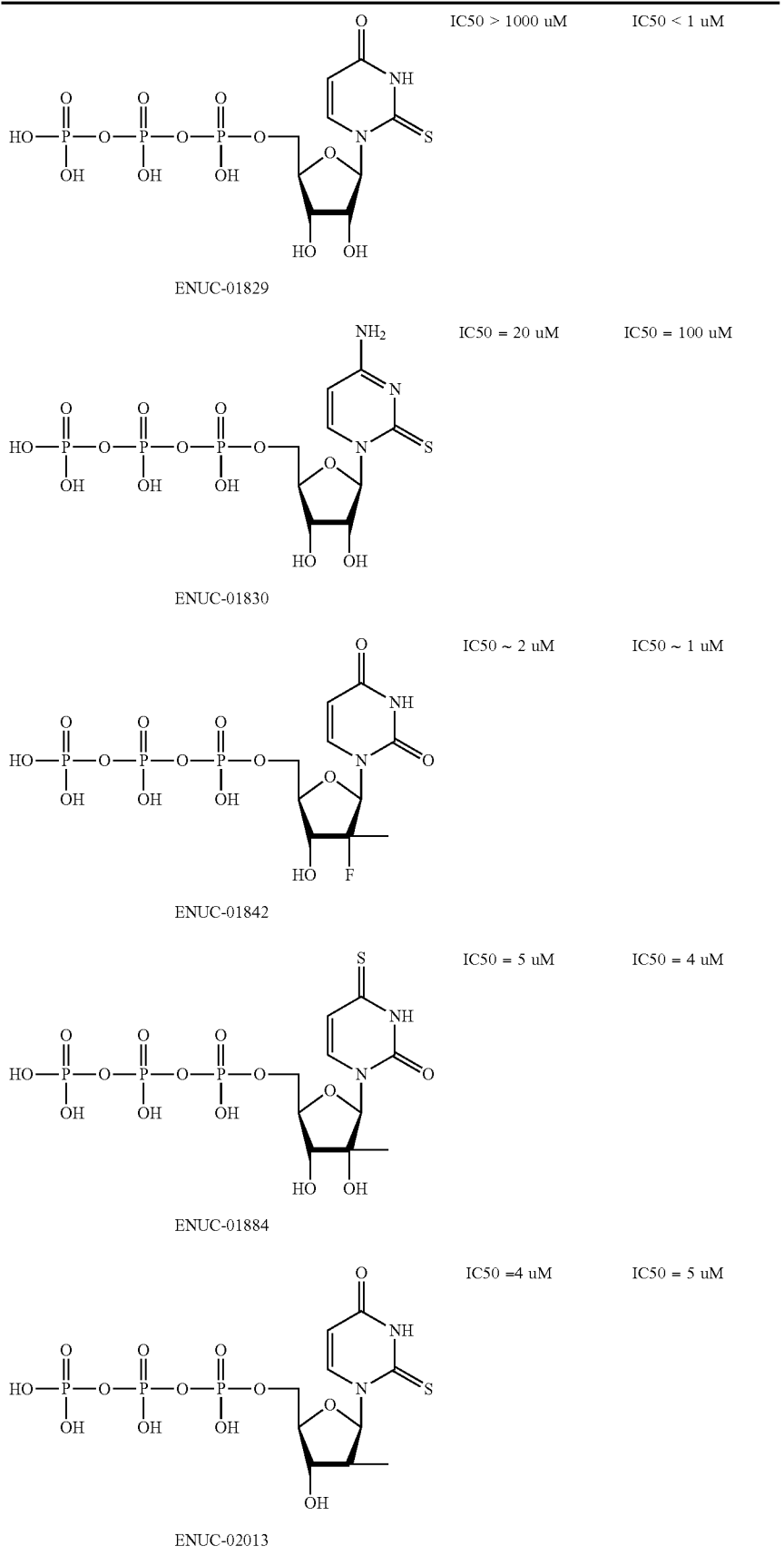

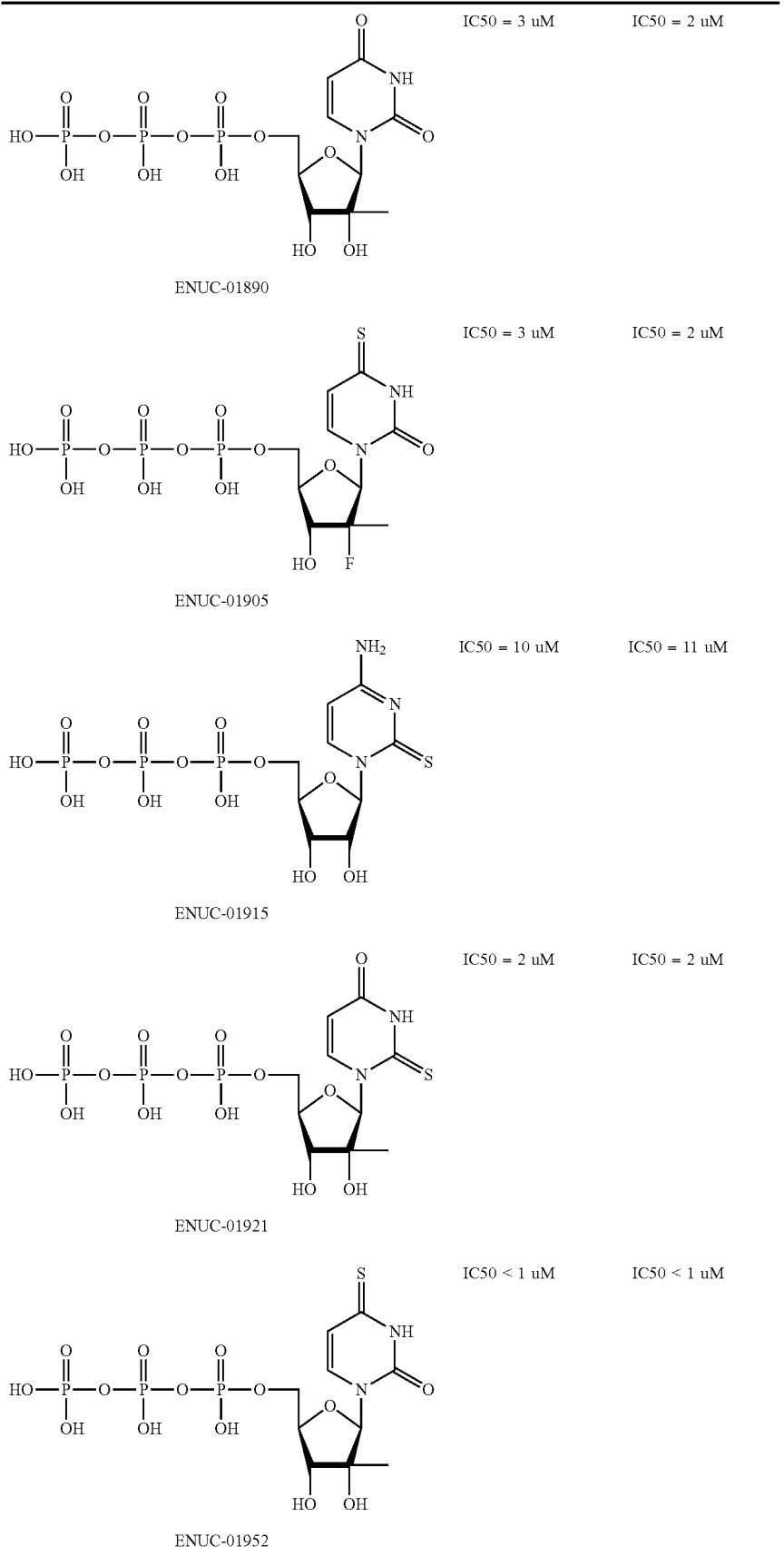

-continued

| Structure and I.D. | HCV NS5B pol assay ($^{32}$P-GTP) | | |
|---|---|---|---|
| | IC25 (uM) | IC50 (uM) | IC95 (uM) |
| ENUC-01842 | 0.52 | 1.24 | 9.91 |
| ENUC-02059 | 6.82 | 50.1 | >100 |

Example 4

| Structure and I.D. | HCV Replicon Assay | Cytotoxicity (CC50 uM) | | | | | |
|---|---|---|---|---|---|---|---|
| | EC50 uM | Huh-7 | HepG2 | BxPC3 | CEM | A204 | IEC-6 H9c |
| ENUC-01893-1 | >100 | 60 | 22.5 | 83 | 2.3 | | |
| ENUC-02071-1 | >100 | 381 | >400 | | 241 | | |

| | | | | | | | |
|---|---|---|---|---|---|---|---|
| 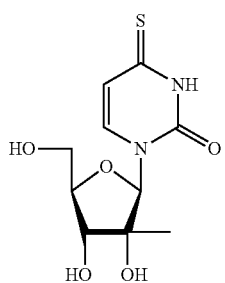<br>ENUC-01916-1 | >100 | >100 | >400 | >100 | >400 | | |
| 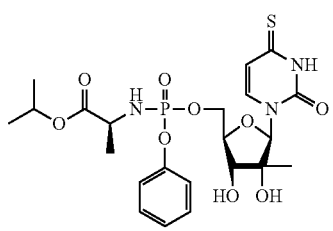<br>ENUC-01920-1 | 7.98 | >400 | >400 | >300 | 169 | >200 | >400 | >200 |
| 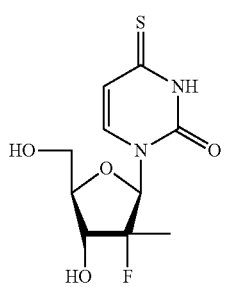<br>ENUC-01946-1 | >100 | >400 | >400 | >400 | | | |
| 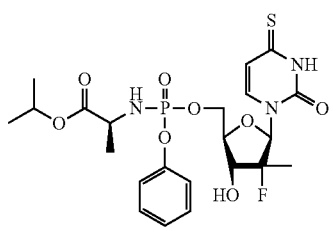<br>ENUC-01943-1 | >100 | >300 | 199 | >300 | 136 | >200 | >400 | >400 |
| 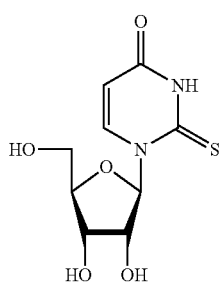<br>ENUC-01894-1 | >100 | 45 | 101 | 147 | 2.7 | | |

-continued
| Structure and I.D. | | | | | | | | |
|---|---|---|---|---|---|---|---|---|
| 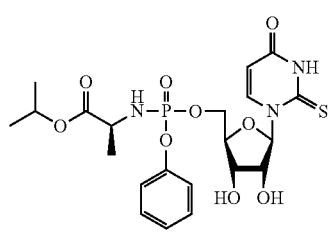 ENUC-02072-1 | 39.2 | >400 | >400 | >400 | | | | |
| 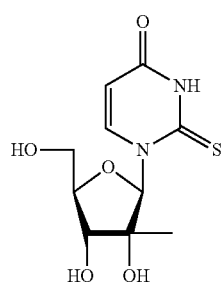 ENUC-01850-1 | >100 | >100 | >400 | >100 | >200 | | | |
| 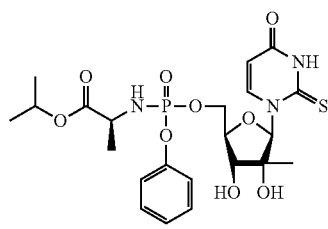 ENUC-01911-1 | 0.187 uM | >400 | >400 | >300 | >300 | 98 | >200 | >200 |
| | HCV Replicon Assay | | Cytotoxicity (CC50 uM) | | | | | | |
|---|---|---|---|---|---|---|---|---|---|
| Structure and I.D. | EC50 uM | EC90 uM | Huh-7 | HepG2 | BxPC3 | CEM | A204 | IEC-6 | H9c |
| 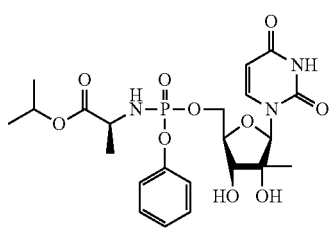 ENUC-01982-1 | 0.0317 | 0.168 | 65 | 159 | 157 | 150 | 124 | 80 | 31 |
| 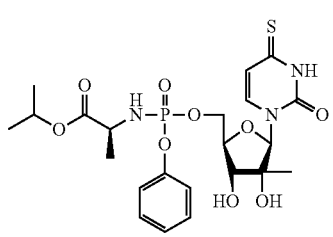 ENUC-01920-1 | 7.98 | 35.7 | >400 | >400 | >300 | 169 | >200 | >400 | >200 |

| Structure | | | | | | | | |
|---|---|---|---|---|---|---|---|---|
| <br>ENUC-01911-2 | 0.152 uM ±<br>0.0239 uM<br>(n = 3) | 0.462 uM ±<br>0.0547 uM<br>(n = 3) | >400 | >400 | >300 | >300 | 98 | >200 >200 |
| 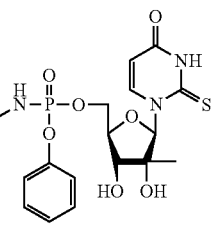<br>ENUC-02058-1 | 3.97 | 43.6 | >100 | >400 | >400 | >400 | | |
| 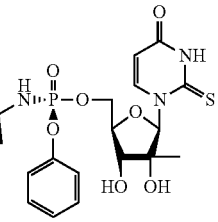<br>ENUC-02023-1 | 0.0441uM ±<br>0.004 uM<br>(n = 2) | 0.176 uM ±<br>0.0318 uM<br>(n = 2) | 252 | >400 | >400 | | | |
| 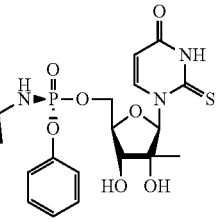<br>ENUC-02024-1 | 0.538 uM ±<br>0.160 uM<br>(n = 2) | 3.33 uM ±<br>1.82 uM<br>(n = 2) | >400 | >400 | >400 | | | |
| 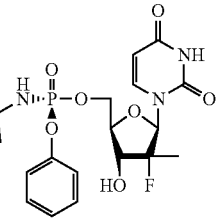<br>ENUC-02025-1 | 0.0199uM | 0.0803uM | 279 | 365 | >400 | | | |
| 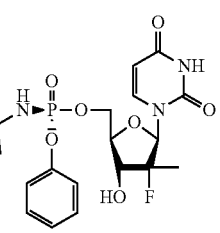<br>ENUC-02026-1 | 0.221 uM | 0.893 uM | >400 | >400 | >400 | | | |

| | | | | | |
|---|---|---|---|---|---|
| 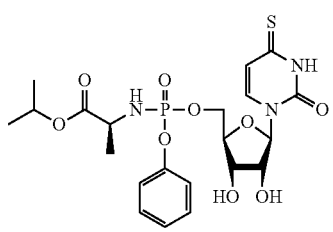
ENUC-02071-1 | >100 | >100 | 369 | >400 | >400 |
| 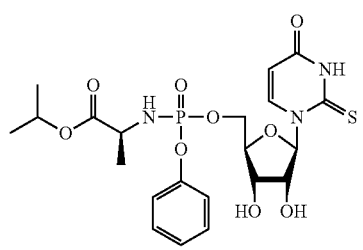
ENUC-02072-2 | 39.2 | >100 | >400 | >400 | >400 |
| 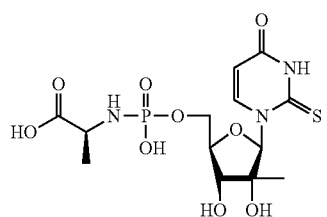
ENUC-01997-1 | >100 | >100 | >400 | >400 | >400 |
| 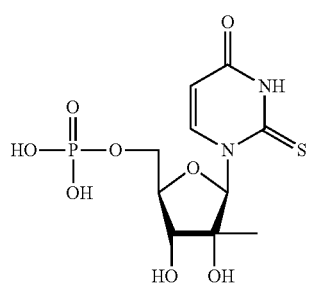
ENUC-01984-1 | 1.35 | >100 | >400 | >400 | >400 |
| 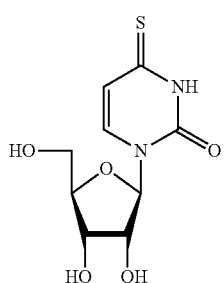
ENUC-01893-1 | >100 | 45.7 | | | |

| Structure and I.D. | HCV Replicon (EC50 uM) | Huh-7 cells (CC50 uM) | Cytotoxicity (CC50 uM) | | |
|---|---|---|---|---|---|
| | | | Huh-7 | HepG2 | CEM |
| 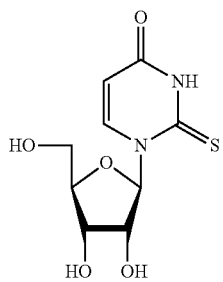 ENUC-01894-2 | >100 | >100 | | | |
| 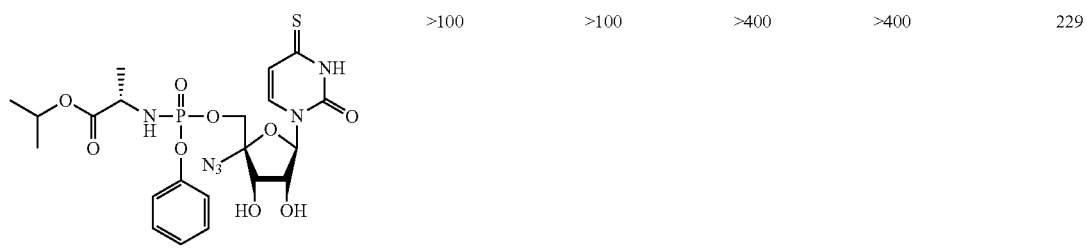 ENUC-02083-1 | >100 | >100 | >400 | >400 | 229 |
Example 5
Human DNA Polymerase Inhibition Data:
| Structure and ID | Human DNA pol α (IC50 uM) | Human DNA pol β (IC50 uM) | Human DNA pol γ (IC50 uM) |
|---|---|---|---|
| 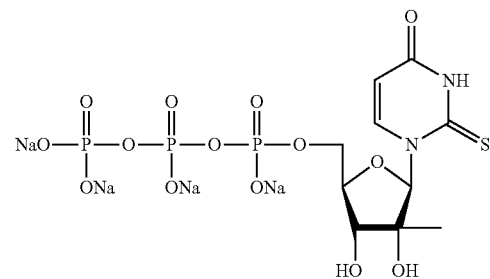 ENUC-01992-1 | >1000 | 588.2 | >1000 |

Example 6

Inhibition of Wild-Type, Mutant, and Chimeric HCV Replicons

| Confidential Compound ID | EC50(μM) | | | | | | | CC50 (μM) GT1b |
|---|---|---|---|---|---|---|---|---|
| | GT1b | GT1a | 2b (GT1b/2b NS5B chimera) | 3a (GT1b/3a NS5B chimera) | 4a (GT1b/4a NS5B chimera) | GT1b-NS5B-S96T | GT1b-NS5B-S282T | |
| ENUC-01911-2 | 0.0946 | 0.0785 | 0.0830 | 0.0882 | 0.0371 | 0.132 | >10 | >10 |
| ENUC-02023-1 | 0.0491 | 0.0265 | 0.0445 | 0.0367 | 0.0254 | 0.0787 | ~7.262 | >10 |
| GS-7977 | 0.0360 | 0.0206 | 0.0199 | 0.0385 | 0.0493 | 0.0702 | 0.287 | >2 |

Example 7

Anti-Dengue Activity:

| Structure and I.D. | Dengue Type 2 Vero Cells (EC50 uM) | Vero Cells (CC50 uM) | Dengue Type 2 Huh-7 Cells (EC50 uM) | Huh-7 Cells (CC50 uM) | Cytotoxicity (CC50 uM) | | | | | | |
|---|---|---|---|---|---|---|---|---|---|---|---|
| | | | | | Huh-7 | HepG2 | BxPC3 | CEM | A204 | IEC-6 | H9c |
| ENUC-01850 | 7.79 | >100 | >100 | >100 | >100 | >400 | >100 | >200 | | | |
| ENUC-01911 | 2.02 | >100 | 5.1 | >100 | >400 | >400 | >300 | >300 | 98 | >200 | >200 |
| ENUC-02023 | 2.35 | >100 | 5.62 | >100 | 252 | >400 | >400 | | | | |
| ENUC-02024 | 56.2 | >100 | 24.9 | >100 | >400 | >400 | >400 | | | | |

-continued

| Structure and I.D. | Dengue Type 2 Huh-7 Cells (EC50 uM) | Huh-7 Cells (CC50 uM) | Cytotoxicity (CC50 uM) | | | | | | |
|---|---|---|---|---|---|---|---|---|---|
| | | | Huh-7 | HepG2 | BxPC3 | CEM | A204 | IEC-6 | H9c |
| ENUC-02069-1 | >100 | >100 | >400 | >400 | | >400 | | | |
| ENUC-02078-1 | 6.07 | >100 | >400 | >400 | | 259 | | | |
| ENUC-02083-1 | 4.82 | >100 | >400 | >400 | | 229 | | | |

Example 8

Pan-Serotype Anti-Dengue Activity

| Structure and I.D. | Cell Line | Dengue Type 1 (EC50 uM) | Dengue Type 3 (EC50 uM) | Dengue Type 4 (EC50 uM) | CC50 uM |
|---|---|---|---|---|---|
| ENUC-02023 | Huh-7 | 1.76 | 7.28 | 14.2 | >100 |

Example 9

Inhibition of DNA Virus Replication

| Structure and I.D. | HBV (EC50 uM) | HepG2 Cells (CC50 uM) | Adenovirus (EC50 uM) | Huh-7 Cells (CC50 uM) | HSV-1 (EC50 uM) | Huh-7 Cells (CC50 uM) |
|---|---|---|---|---|---|---|
| 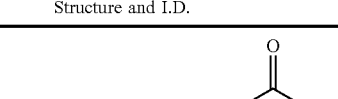 ENUC-01911 | >100 HIV (EC50 uM) >100 | >100 PBM Cells (CC50 uM) >100 | >100 HCMV (EC50 uM) >100 | >100 MRC-5 Cells (CC50 uM) >100 | >100 VZV (EC50 uM) >100 | >100 MRC-5 Cells (CC50 uM) >100 |

Example 10

Antiviral Activity for Cytidine Analogs

| | | Influenza A | | | | | |
|---|---|---|---|---|---|---|---|
| EIDD ID | Structure | H1N1 EC50 | H3N2 EC50 | H5N1 (low path) EC50 | Influenza B EC50 | RSV EC50 | SARS EC50 |
| EFVX-01841 | [structure] | >100 uM | >100 uM | >100 uM | >100 uM | >100 uM | 70 uM CC50 > 89 uM |
| EFVX-01853 | [structure] | >100 uM | >100 uM | >100 uM | >100 uM | >100 uM | >100 uM |

-continued

| EIDD ID | Structure | | | | | | |
|---|---|---|---|---|---|---|---|
| EFVX-01854 | [4-N,N-dimethylamino cytosine, 2'-deoxy-2'-fluoro ribose] | >100 uM | >100 uM | >100 uM | >100 uM | >100 uM | >100 uM |
| EFVX-01855 | [5-methyl cytosine, 2'-deoxy-2'-fluoro ribose] | >100 uM | >100 uM | >100 uM | >100 uM | >100 uM | >100 uM |
| EFVX-01856 | [5-hydroxymethyl cytosine, 2'-deoxy-2'-fluoro ribose] | >100 uM | >100 uM | >100 uM | >100 uM | >100 uM | >100 uM |
| EFVX-01857 | [2-thio cytosine, 2'-deoxy-2'-fluoro ribose] | >100 uM | >100 uM | >100 uM | >100 uM | >100 uM | >87 uM CC50 = 87 uM |

| EIDD ID | Structure | Measles EC50 | CHIK EC50 | Dengue Virus EC50 | RVFV EC50 | Tacaribe Virus EC50 | VEEV EC50 | West Nile Virus EC50 |
|---|---|---|---|---|---|---|---|---|
| EFVX-01853 | [N-methyl cytosine, 2'-deoxy-2'-fluoro ribose] | >100 uM | >100 ug/ml | >100 ug/ml | >100 ug/ml | >100 ug/ml | >100 ug/ml | >100 ug/ml |

| | | | | | | | | |
|---|---|---|---|---|---|---|---|---|
| EFVX-01854 | [structure: N4,N4-dimethyl cytosine with 2'-fluoro sugar] | >100 uM | >100 ug/ml | >100 ug/ml | >100 ug/ml | >100 ug/ml | >100 ug/ml | >100 ug/ml |
| EFVX-01855 | [structure: 5-methyl cytosine with 2'-fluoro sugar] | >100 uM | >100 ug/ml | >100 ug/ml | >100 ug/ml | >100 ug/ml | >100 ug/ml | >100 ug/ml |
| EFVX-01856 | [structure: 5-hydroxymethyl cytosine with 2'-fluoro sugar] | >100 uM | >100 ug/ml | >100 ug/ml | >100 ug/ml | >100 ug/ml | >100 ug/ml | >100 ug/ml |
| EFVX-01857 | [structure: 2-thiocytosine with 2'-fluoro sugar] | >100 uM | >100 ug/ml | >100 ug/ml | >100 ug/ml | >100 ug/ml | >100 ug/ml | >100 ug/ml |

Example 11

Figure 7:
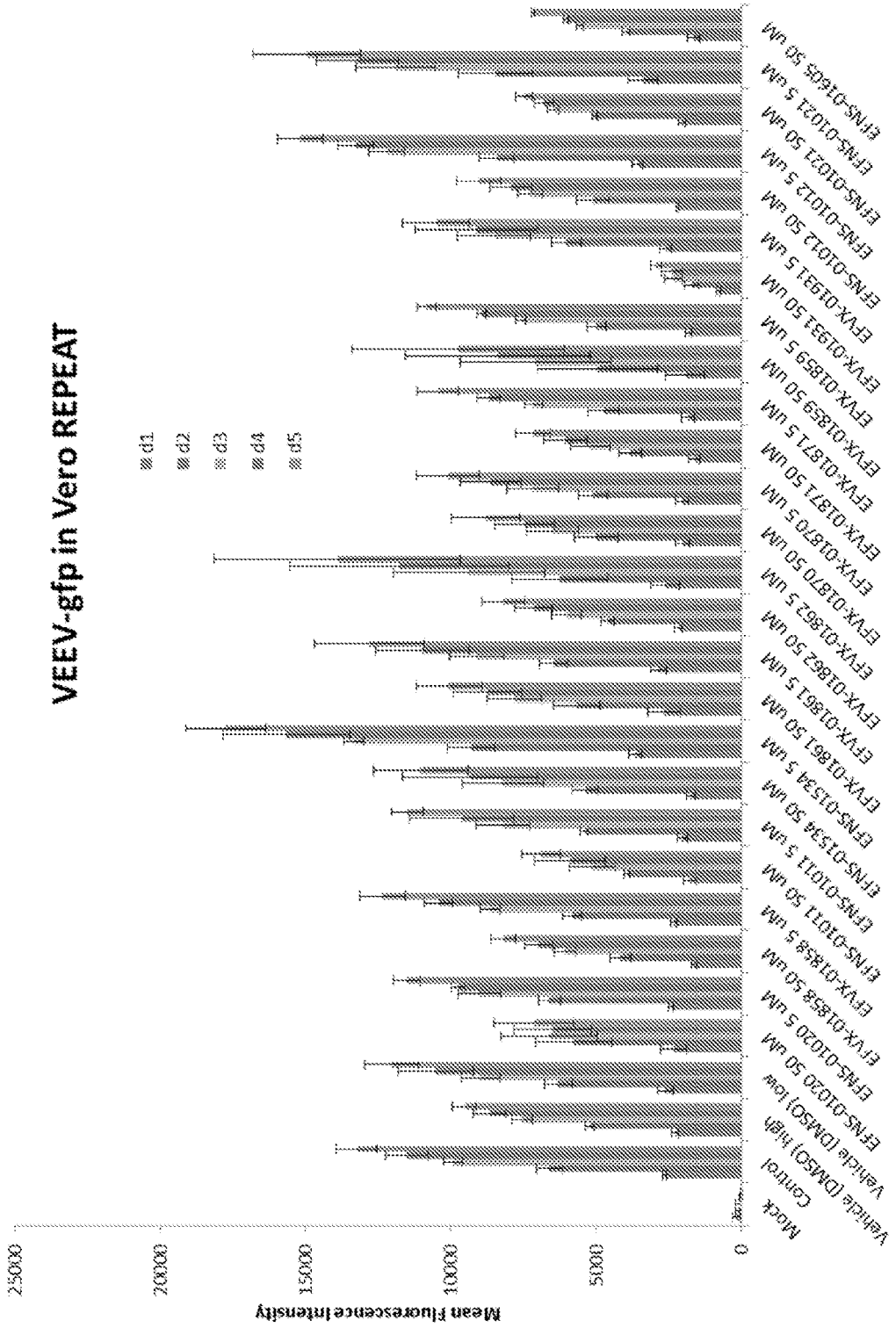
Figure 8:
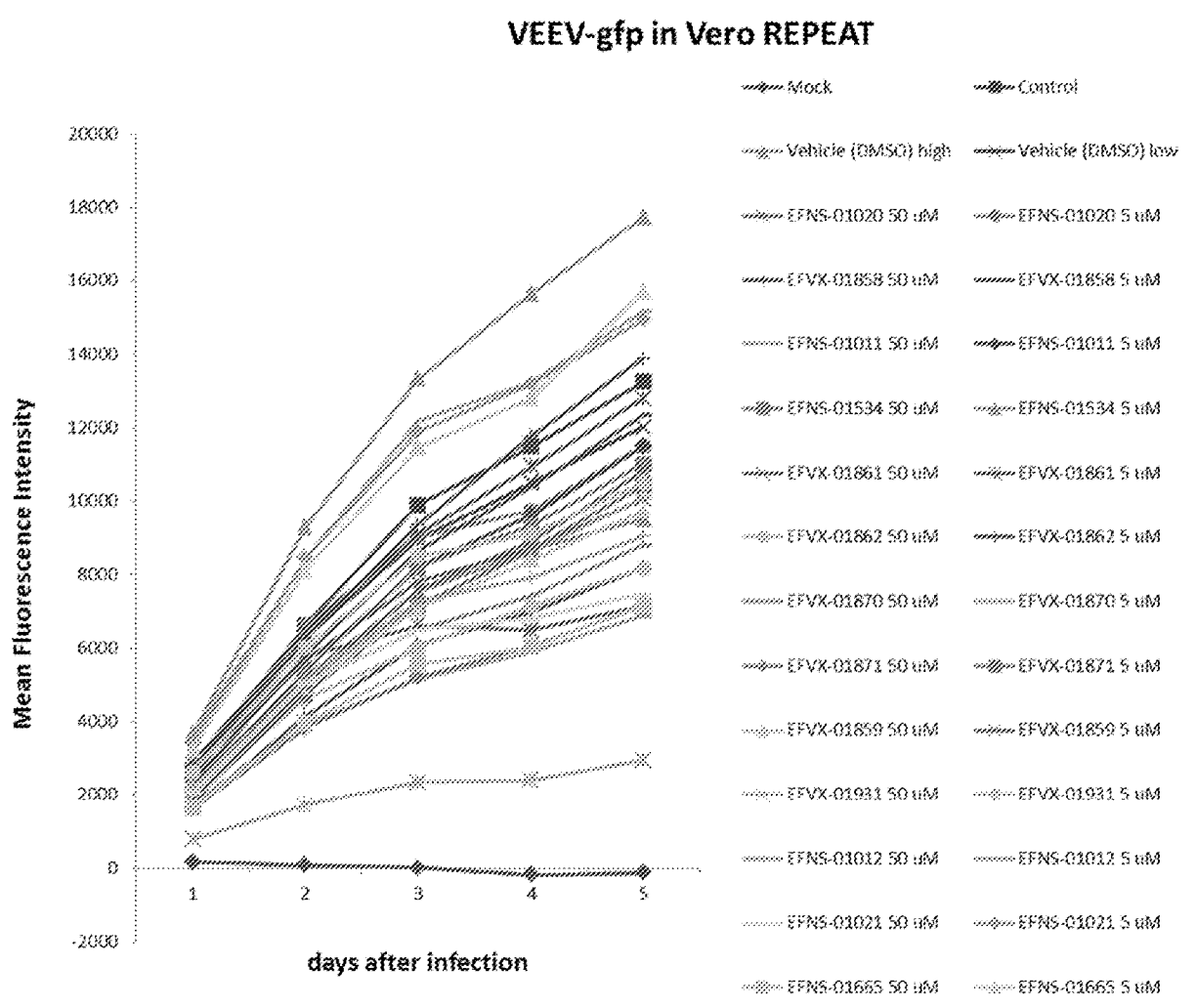

Results from a VEEV Replicon Assay are Shown in FIGS. 7-8.

Compounds Screened:

EFNS-01605

[structure: 6-fluoro-3-hydroxypyrazine-2-carboxamide]

(EFNS-01665 on graph (typo))

EFNS-01020

[structure: 2'-C-methylcytidine]

EFNS-01534
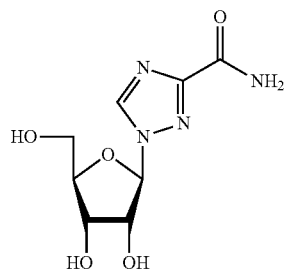
EFNS-01021
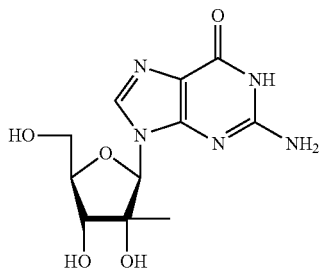
EFNS-01012
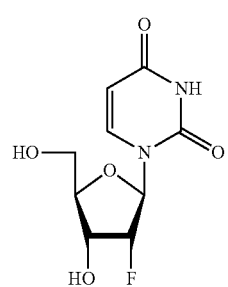
EFVX-01858
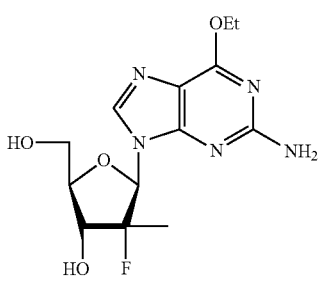
EFNS-01011
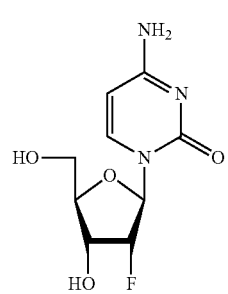
EFVX-01859
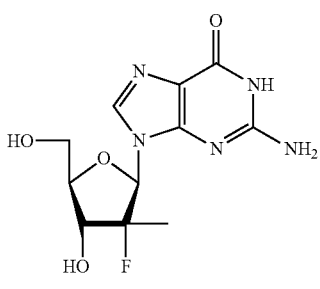
EFVX-01870
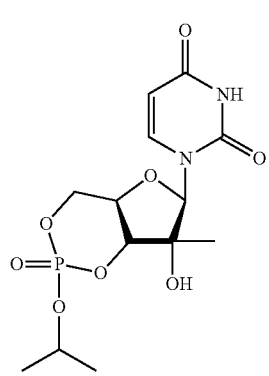
EFVX-01861
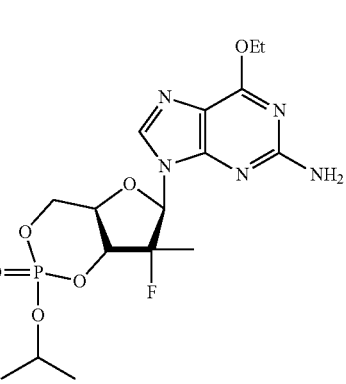
EFVX-01871
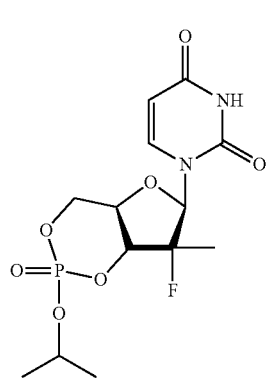
EFVX-01862
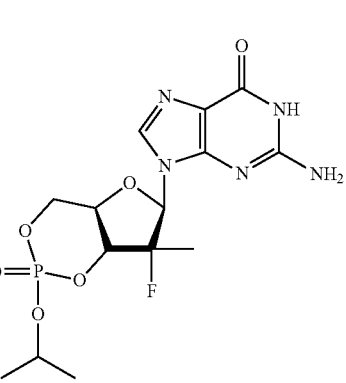

Example 12

Figure 9:
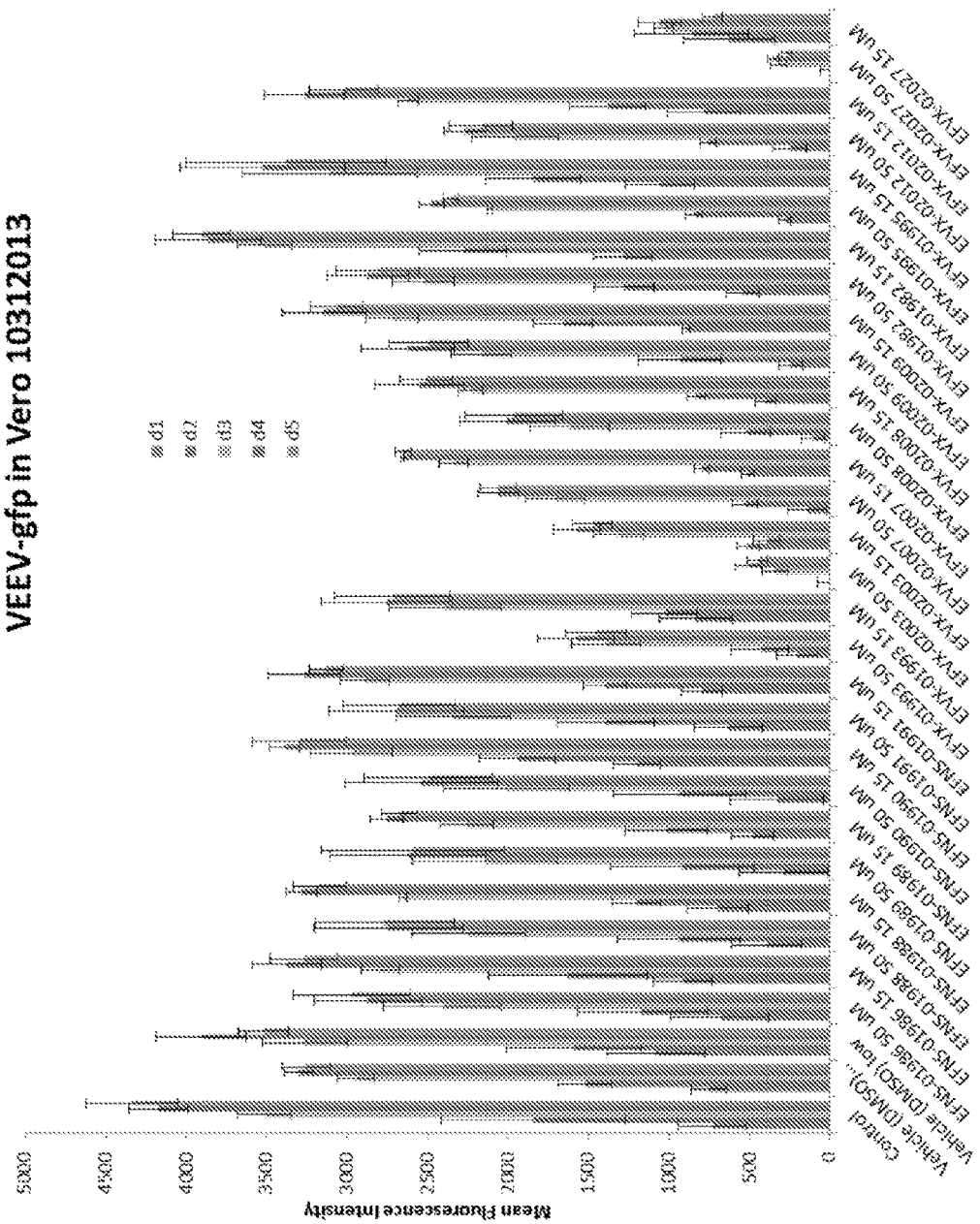
Figure 10:
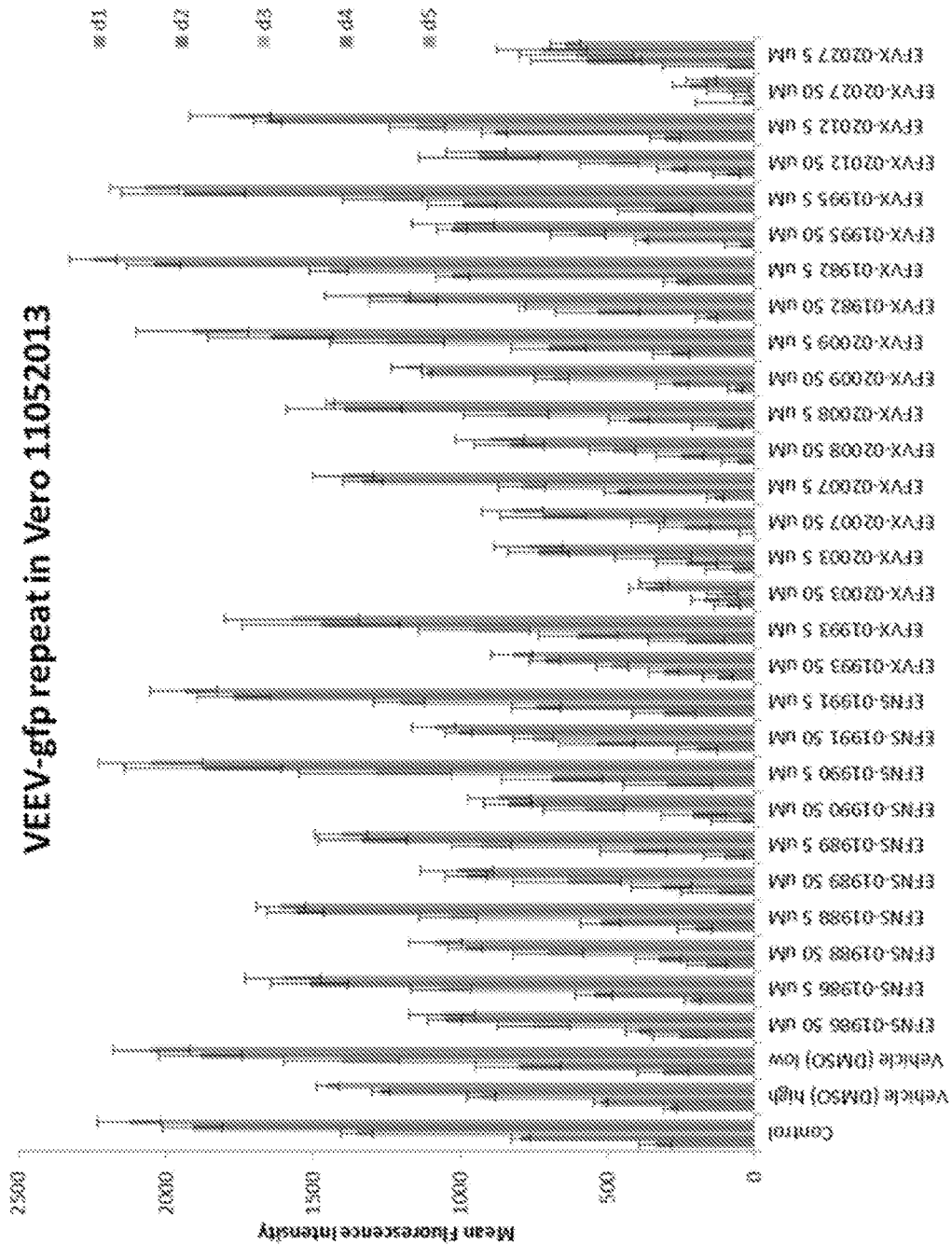

RESULTS from a VEEV replicon assay are shown in FIGS. 9-10.

Compounds Screened:

317
-continued
EFVX-02012
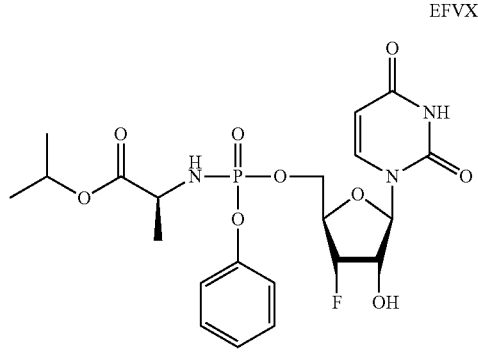
EFVX-02007
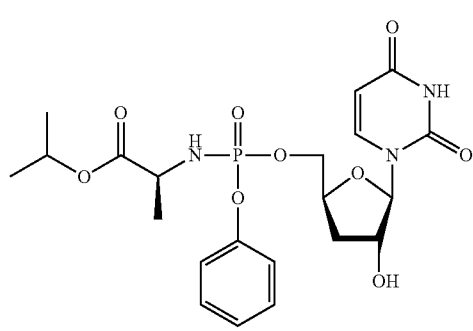
EFVX-02008
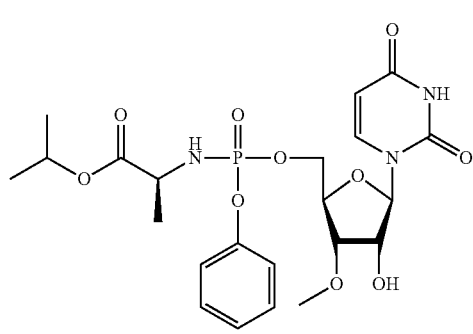
EFVX-01995
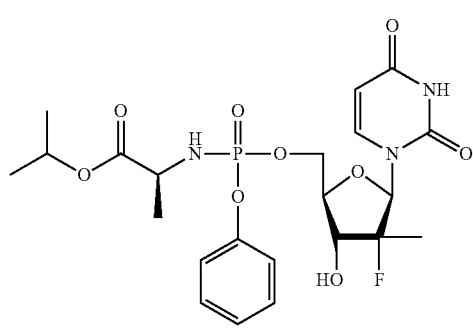
318
-continued
EFVX-01982
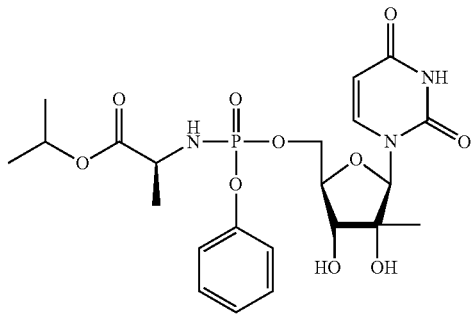
EFVX-02027
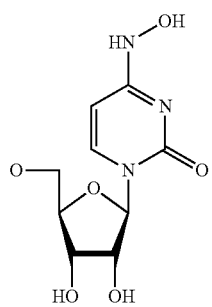
Example 13
Synthesis of Sphingolipids and Derivatives
The preparation of sphingolipids is provided for in PCT/US12/57448 hereby incorporated by reference in its entirety.
Example 14
General Synthesis of 2′, 3′-Dideoxy-2′-β-Substituted-2′-α-Fluoronucleosides
L-Glutamic Acid
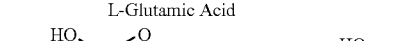

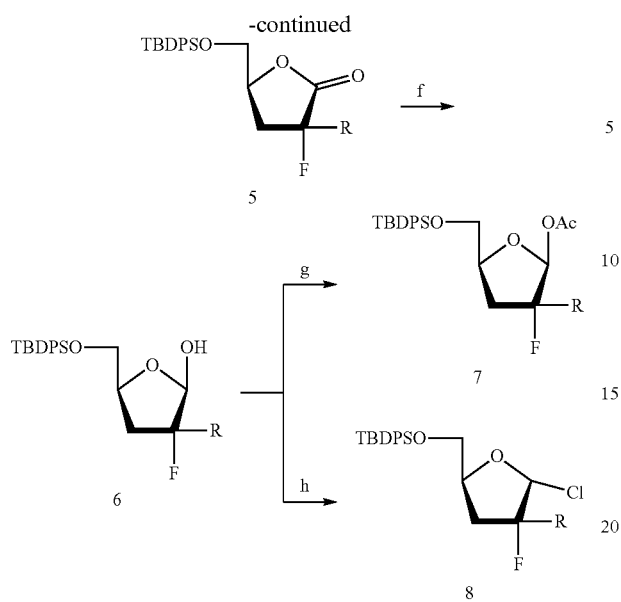
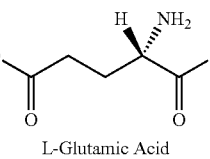
Example 16
Synthesis of 2',3'-Dideoxy-2'-α-Fluoronucleosides
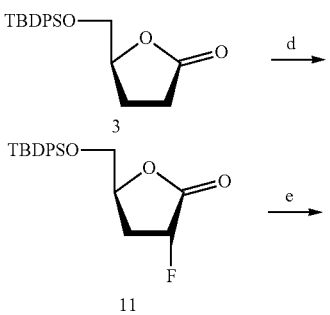
Reagents and conditions: a) NaNO$_2$, HCl$_{(aq)}$; b) BH$_3$•SMe$_2$; c) TBDPSCl, DMAP, pyridine; d) i. LiHMDS, ii. RX (X = Cl, Br, I, etc.); e) i. TBSOTf, Et$_3$N, ii. NFSi; f) DIBAL; g) Ac$_2$O, DMAP; h) HMPT, CCl$_4$
Example 15
Base Coupling and Deprotection
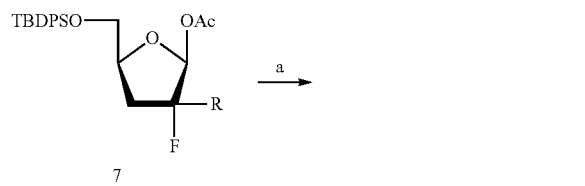
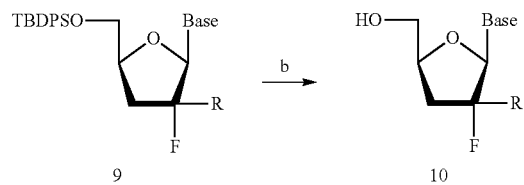
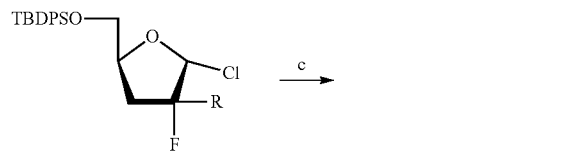
Reagents and conditions: a) silylated base, TMSOTf, DCE; b) TBAF, THF; c) nucleobase, TDA-1, KOH, MeCN

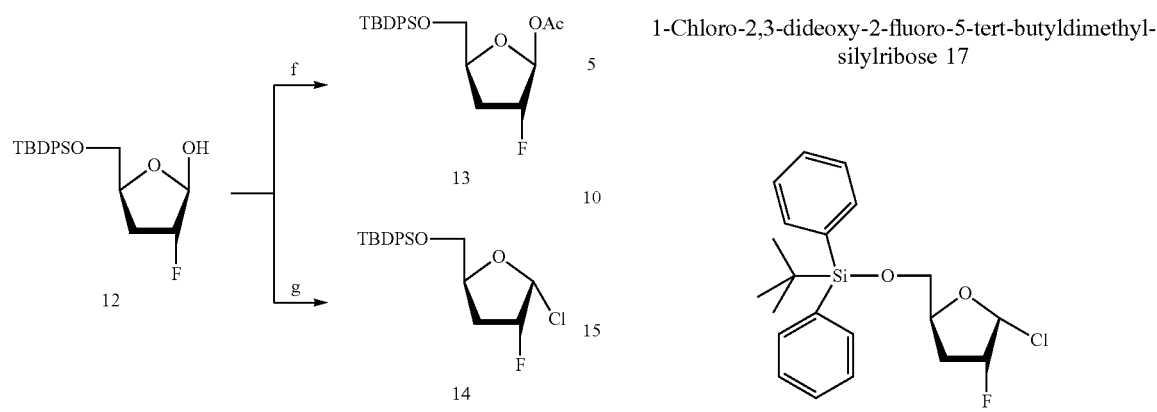

Reagents and conditions: a) NaNO₂, HCl(aq); b) BH₃·SMe₂; c) TBDPSCl, DMAP, pyridine; d) i. LiHMDS, ii. NFSi; e) DIBAL; f) Ac₂O, DMAP; g) HMPT, CCl₄

Example 17

Base Coupling and Deprotection

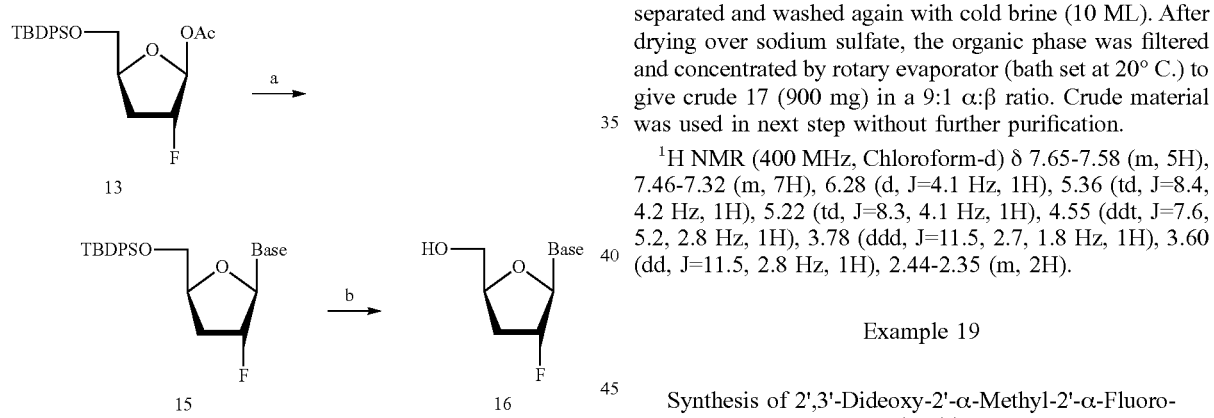

Reagents and conditions: a) silylated base, TMSOTf, DCE; b) TBAF, THF; c) nucleobase, TDA-1, KOH, MeCN Example 18

1-Chloro-2,3-dideoxy-2-fluoro-5-tert-butyldimethyl-silylribose 17

A mixture of 2,3-dideoxy-2-fluoro-5-tert-butyldimethyl-silylribose (840 mg, 2.24 mmol) and carbon tetrachloride (1.55 g, 10.09 mmol) in anhydrous toluene (15 mL) at −50° C. was treated dropwise with a solution of hexamethylphosphorous triamide (440 mg, 2.69 mmol) in toluene (15 mL) over a 35 min period. The mixture was stirred with gradual warming to 0° C. and maintained at this temperature for 3 h. After cooling to −20° C., the mixture was diluted with cold toluene (50 mL) and quenched by dropwise addition of cold brine (5 mL at −10° C.). After 10 min the organic layer was separated and washed again with cold brine (10 ML). After drying over sodium sulfate, the organic phase was filtered and concentrated by rotary evaporator (bath set at 20° C.) to give crude 17 (900 mg) in a 9:1 α:β ratio. Crude material was used in next step without further purification.

$^1$H NMR (400 MHz, Chloroform-d) δ 7.65-7.58 (m, 5H), 7.46-7.32 (m, 7H), 6.28 (d, J=4.1 Hz, 1H), 5.36 (td, J=8.4, 4.2 Hz, 1H), 5.22 (td, J=8.3, 4.1 Hz, 1H), 4.55 (ddt, J=7.6, 5.2, 2.8 Hz, 1H), 3.78 (ddd, J=11.5, 2.7, 1.8 Hz, 1H), 3.60 (dd, J=11.5, 2.8 Hz, 1H), 2.44-2.35 (m, 2H).

Example 19

Synthesis of 2',3'-Dideoxy-2'-α-Methyl-2'-α-Fluoro-nucleosides

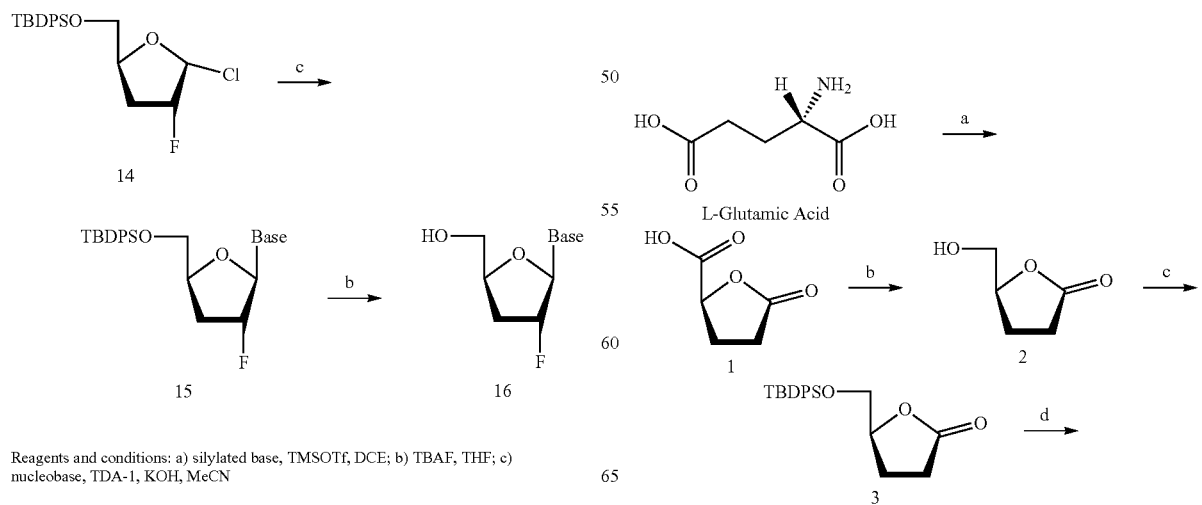

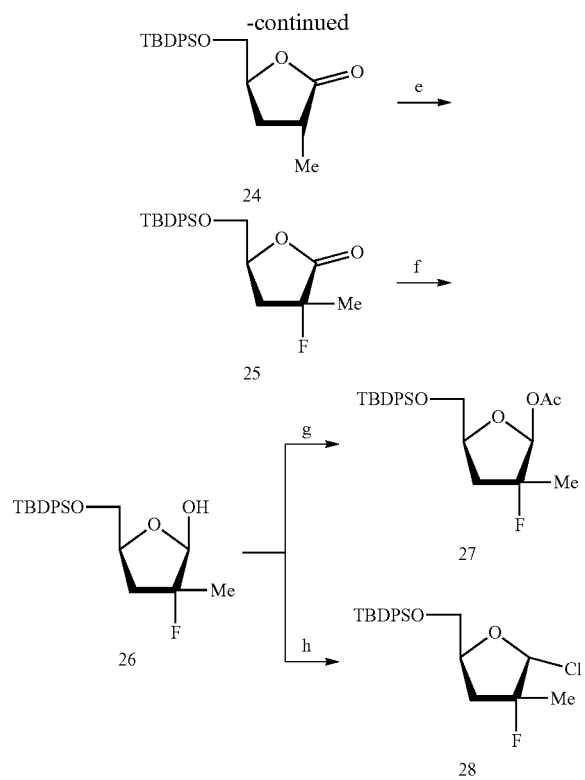

Reagents and conditions: a) NaNO₂, HCl(aq); b) BH₃•SMe₂; c) TBDPSCl, DMAP, pyridine; d) i. LiHMDS, ii. MeI; e) i. TBSOTf, Et₃N, ii. NFSi; f) DIBAL; g) Ac₂O, DMAP; h) HMPT, CCl₄

Example 20

Base Coupling and Deprotection

Reagents and conditions: a) silylated base, TMSOTf, DCE; b) TBAF, THF; c) nucleobase, TDA-1, KOH, MeCN Example 21

(3R,5S)-5-(((tert-butyldiphenylsilyl)oxy)methyl)-3-methyldihydrofuran-2(3H)-one (31)

To a solution of diisopropylamine (2.01 ml, 14.1 mmol) in dry THF (20 ml) at 0° C., under an inert atmosphere, was added n-butyllithium (8.83 ml of a 1.6 M solution in hexane, 14.13 mmol). After 30 minutes of stirring, the solution was cooled to −78° C., and a solution of (4S)-4-tert-butyldiphenylsiloxymethyl-4-butanolide (5.01 g, 14.13 mmol) in dry THF (5 ml) was added drop-wise over a period of 5 minutes. After stirring for a further 30 minutes at −78° C., iodomethane (1.31 ml, 21.0 mmol) was added, and the reaction vessel removed from the ice bath. After 30 minutes at ambient temperature, deionised water (40 ml) was added to the solution, and the organics extracted with ether (3×15 ml). The combined organic layer was washed with 1M HCl (3×20 ml) and once more with brine, before being dried over Mg₂SO₄. The crude product was purified by silica chromatography (product Rf=0.26 in 4:1 hexane:ethyl acetate), eluting with 85:15 hexane:ethyl acetate to afford the final product as a white, crystalline solid. Stereochemistry was established based on comparison of NMR data with reported data.

¹H NMR (400 MHz, CDCl₃): δ 7.67-7.65 (m, 4H), 7.48-7.39 (m, 6H), 4.58-4.53 (m, 1H), 3.86 (dd, J=3.2, 10.8 Hz, 1H), 3.68 (dd, J=3.2, 11.2 Hz, 1H), 2.90-2.81 (m, 1H), 2.45 (ddd, J=3.2, 9.2, 12.8 Hz, 1H), 1.98 (dt, J=8.8, 12.4 Hz, 1H), 1.30 (d, J=7.2 Hz, 3H), 1.06 (s, 9H).

Example 22

(3R,5S)-5-(((tert-butyldiphenylsilyfloxy)methyl)-3-fluoro-3-methyldihydrofuran-2(3H)-one (32)

Compound 31 (0.1000 g, 0.27 mmol) was placed in a dry flask under argon atmosphere and was dissolved in dry DCM (5 mL). Next, TBSOTf (0.075 mL, 0.33 mmol) was added dropwise to the stirring DCM solution of lactone at room temperature followed by the dropwise addition of neat triethylamine (0.057 mL, 0.41 mmol) also at room temp. The reaction mixture was allowed to stir at room temp under nitrogen for 2 hours with monitoring by TLC. Next, NFSi (0.1280 g, 0.41 mmol) was dissolved in 2 mL of dry DCM and was added dropwise to the silyl enol ether at room temp under nitrogen. The reaction mixture turned dark red. The reaction mixture was allowed to stir over night. The reaction mixture was quenched with sat. NH4Cl and was diluted with ether. The organic layer was washed with brine, dried over MgSO4, filtered, and concentrated. The product was purified on silica eluting with 8:1 hexanes/ethyl acetate.

$^1$H NMR (400 MHz, CDCl$_3$): δ 7.67-7.64 (m, 4H), 7.48-7.39 (m, 6H), 4.75-4.70 (m, 1H), 3.96 (dd, J=3.6, 12 Hz, 1H), 3.71 (dd, J=3.6, 11.6 Hz, 1H), 2.53 (ddd, J=6.4, 14.6, 22.8 Hz, 1H), 2.37 (ddd, J=8.8, 14.6, 35.2 Hz, 1H), 1.66 (d, J=22.8 Hz, 3H), 1.05 (s, 9H).

Example 23

(2R,3R,5S)-5-(((tert-butyldiphenylsilyl)oxy)methyl)-3-fluoro-3-methyltetrahydrofuran-2-ol (33)

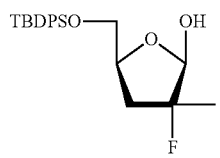

Compound 33 was prepared following the procedure outlined by JOC (1998), 63, 2161-2167.

$^1$H NMR (400 MHz, CDCl$_3$): δ 7.70-7.67 (m, 4H), 7.47-7.39 (m, 6H), 5.10 (t, J=7.2 Hz, 1H), 4.50 (m, 1H), 3.87 (dd, J=2.4, 11.2 Hz, 1H), 3.46 (dd, J=2.4, 11.2 Hz, 1H), 2.27-2.11 (m, 2H), 1.57 (d, J=21.6 Hz, 3H), 1.09 (s, 9H).

Example 24

(2S,3R,5S)-5-(((tert-butyldiphenylsilyl)oxy)methyl)-3-fluoro-3-methyltetrahydrofuran-2-yl Acetate (34)

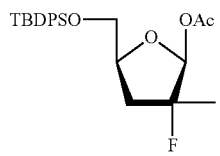

Compound 34 was prepared following the procedure outlined by JOC (1998), 63, 2161-2167.

$^1$H NMR (400 MHz, CDCl$_3$): δ 7.69-7.66 (m, 4H), 7.46-7.37 (m, 6H), 6.13 (d, J=10.4 Hz, 1H), 4.53-4.47 (m, 1H), 3.79 (dd, J=4.4, 10.8 Hz, 1H), 3.72 (dd, J=4.4, 11.6 Hz, 1H), 2.27-2.02 (m, 2H), 1.92 (s, 3H), 1.50 (d, J=21.6 Hz, 3H), 1.07 (s, 9H).

Example 25

General Nucleobase Coupling Conditions

The desired nucleobase (5 equivalents) was transferred to a dry flask under an argon atmosphere and suspended in HMDS (2 mL/mmol nucleobase). Catalytic ammonium sulfate (1-3 mgs) was added to the reaction vessel, and the suspension was allowed to reflux for 1-3 hours. During the course of reaction, the white suspension turned clear. The reaction vessel was allowed to cool to room temperature, and the excess HMDS was removed under reduced pressure. The resulting residue was dissolved in dry DCE (5 mL/mmol compound 34) followed by the addition of compound 34 at room temperature. Finally, neat TMSOTf (5.5 equivalents) was added to the stirring solution. The reaction was quenched with saturated sodium bicarbonate. The organic layer was collected, dried over MgSO$_4$, filtered, and concentrated under reduced pressure. The desired protected nucleoside was purified on silica gel eluting with 9:1 DCM/MeOH.

Example 26

General Deprotection Conditions

A solution of protected nucleoside dissolved in dry THF (10 ml/mmol of protected nucleoside) was treated with tetrabutylammonium fluoride (TBAF, 1 M solution in THF, 1.1 equivalents), and let to stir at room temperature for 3 hours. The crude mixture was concentrated in vacuo, and the resulting residue was purified on silica gel (0-10% methanol in dichloromethane) to give the desired nucleoside.

Example 27

Alternative Route for the Synthesis of 2',3'-Dideoxy-2'-β-Substituted-2'-α-Fluoronucleosides

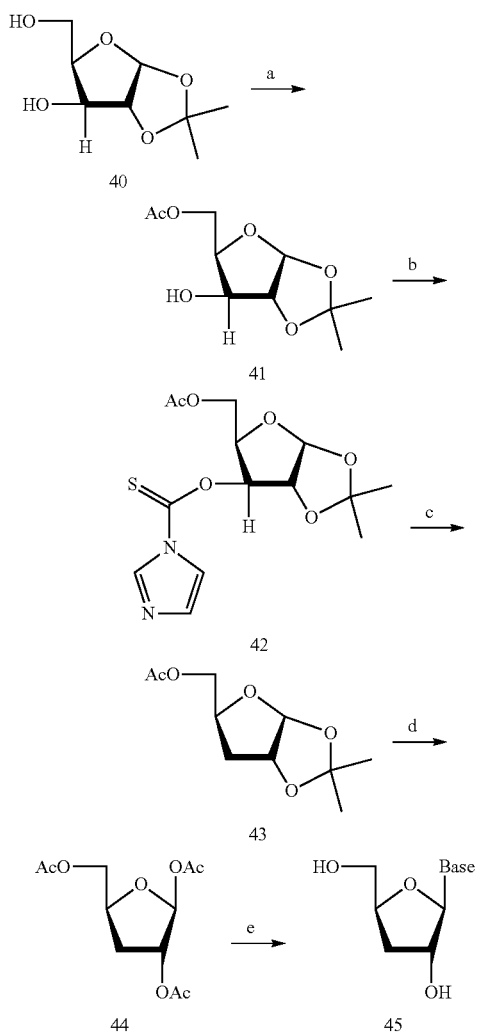

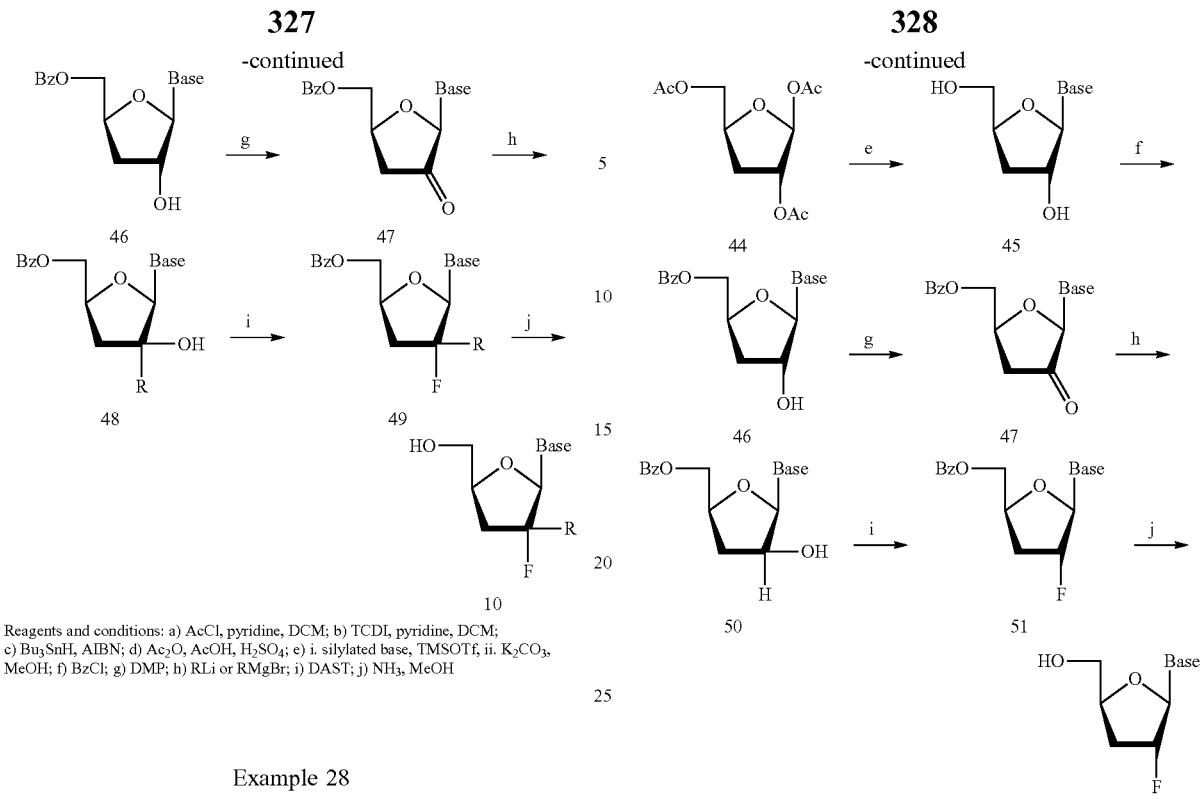

Reagents and conditions: a) AcCl, pyridine, DCM; b) TCDI, pyridine, DCM; c) Bu₃SnH, AIBN; d) Ac₂O, AcOH, H₂SO₄; e) i. silylated base, TMSOTf, ii. K₂CO₃, MeOH; f) BzCl; g) DMP; h) RLi or RMgBr; i) DAST; j) NH₃, MeOH Reagents and conditions: a) AcCl, pyridine, DCM; b) TCDI, pyridine, DCM; c) Bu₃SnH, AIBN; d) Ac₂O, AcOH, H₂SO₄; e) i. silylated base, TMSOTf, ii. K₂CO₃, MeOH; f) BzCl; g) DMP; h) NaBH₄; i) DAST; j) NH₃, MeOH Example 28

Alternative Route to 2',3'-Dideoxy-2'-α-Fluoronucleosides

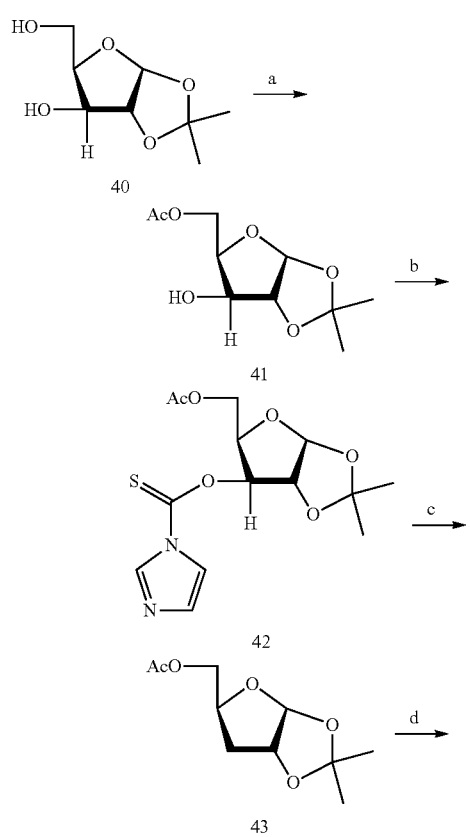

Example 29

2',3'-Dideoxy-2'-β-Ethynyl-2'-α-Fluoronucleosides

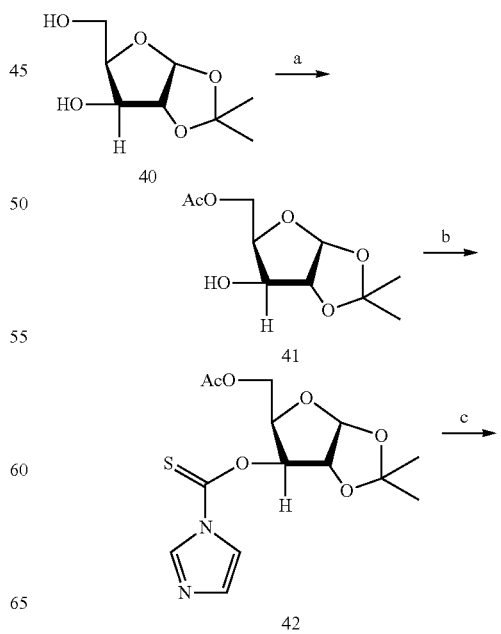

329

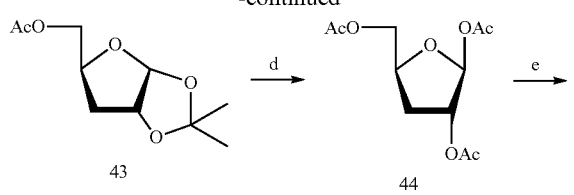

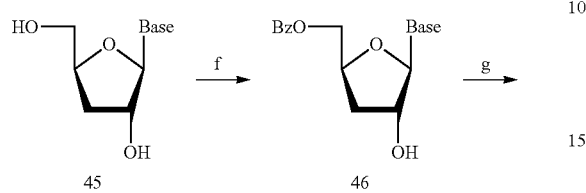

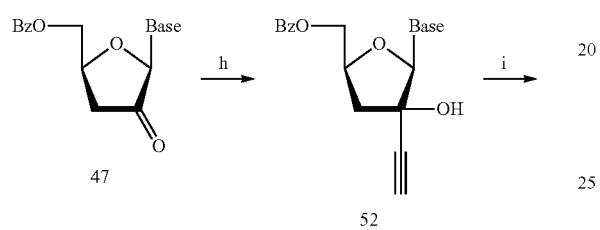

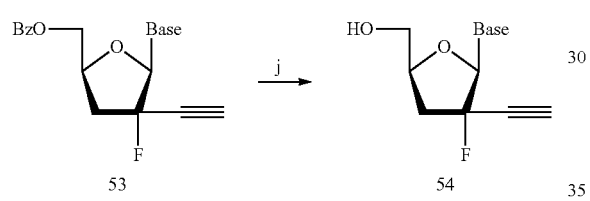

Reagents and conditions: a) AcCl, pyridine, DCM; b) TCDI, pyridine, DCM; c) Bu$_3$SnH, AIBN; d) Ac$_2$O, AcOH, H$_2$SO$_4$; e) i. silylated base, TMSOTf, ii. K$_2$CO$_3$, MeOH; f) BzCl; g) DMP; h) i. trimethylsilylacetylene, BuLi, ii. NH$_4$F, MeOH; i) DAST; j) NH$_3$, MeOH

Example 30

2',3'Dideoxy-2'-β-Fluoromethyl-2'-α-Fluoronucleosides

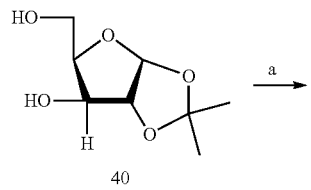

330

Reagents and conditions: a) AcCl, pyridine, DCM; b) TCDI, pyridine, DCM; c) Bu$_3$SnH, AIBN; d) Ac$_2$O, AcOH, H$_2$SO$_4$; e) i. silylated base, TMSOTf, ii. K$_2$CO$_3$, MeOH; f) BzCl; g) DMP; h) Me$_3$S(O)I, NaH; i) KF, 18-crown-6; j) DAST; k) NH$_3$, MeOH

Example 31

2',3'-Dideoxy-2'-β-Difluoromethyl OR Trifluoromethyl-2'-α-Fluoronucleosides

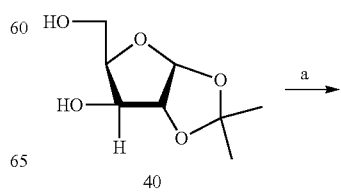

331
-continued
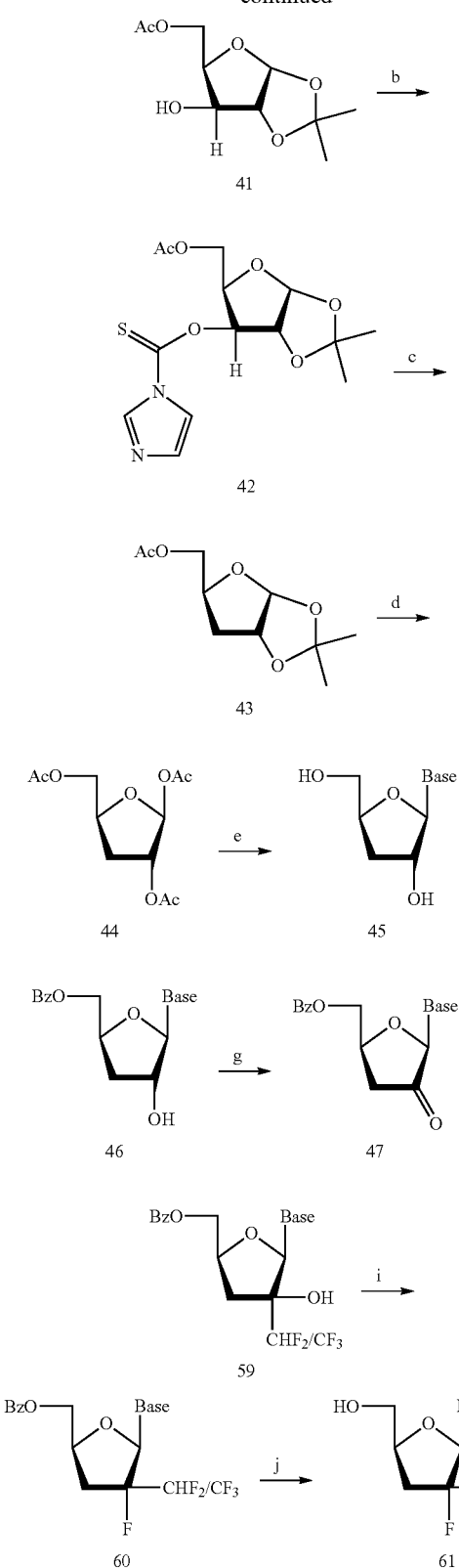
Reagents and conditions: a) AcCl, pyridine, DCM; b) TCDI, pyridine, DCM; c) Bu₃SnH, AIBN; d) Ac₂O, AcOH, H₂SO₄; e) i. silylated base, TMSOTf, ii. K₂CO₃, MeOH; f) BzCl; g) DMP; h) CHF₂: i. PhSO₂CF₂H, LiHMDS, ii. SmI₂ or CF₃: TMSCF₃, TBAF; i) DAST; j) NH₃, MeOH
332
Example 32
Alternative Route to 2',3'-Dideoxy-2'-β-Substituted-2'-α-Fluoronucleosides
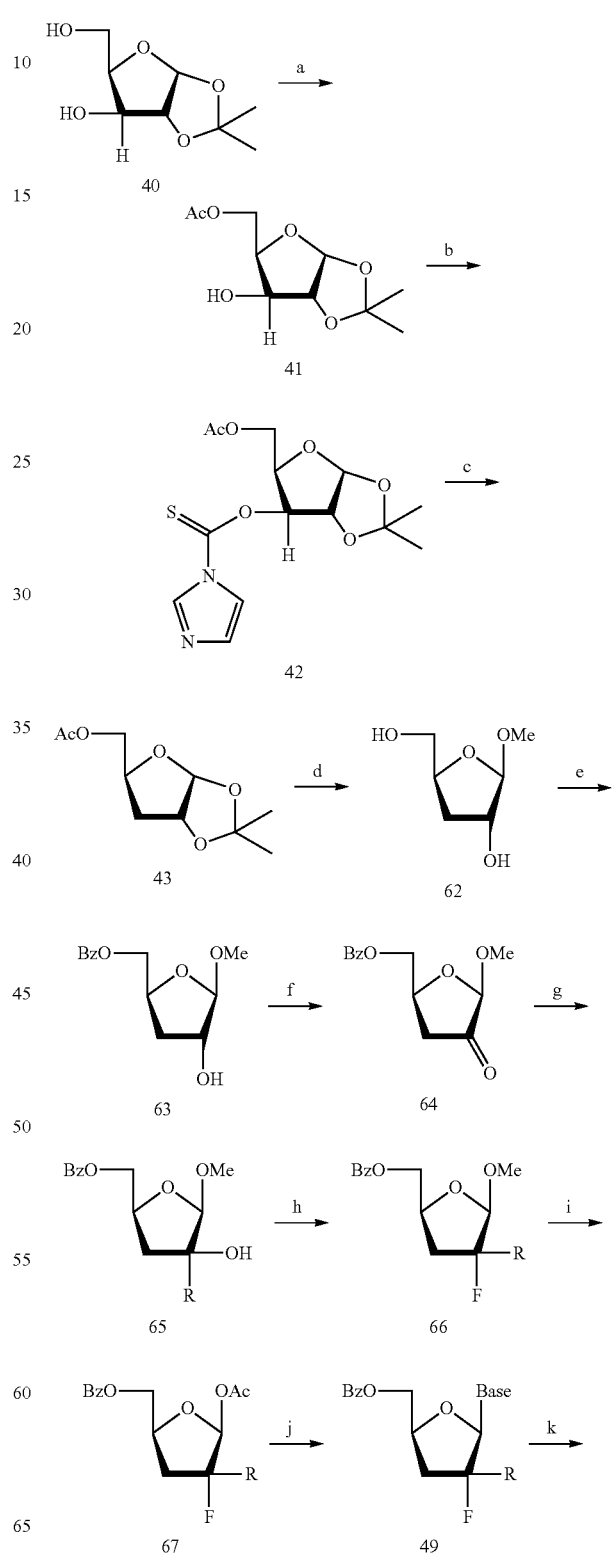

333
-continued

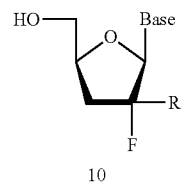
10

Reagents and conditions: a) AcCl, pyridine, DCM; b) TCDI, pyridine, DCM; c) Bu₃SnH, AIBN; d) i. H₂SO₄, MeOH ii. K₂CO₃, MeOH; e) BzCl, pyridine; f) DMP; g) RLi or RMgBr; h) DAST; i) Ac₂O, AcOH, H₂SO₄; j) silylated base, TMSOTf; k) NH₃, MeOH Example 33

Synthesis of 2'-Deoxy-2'-α-Fluororibonucleosides

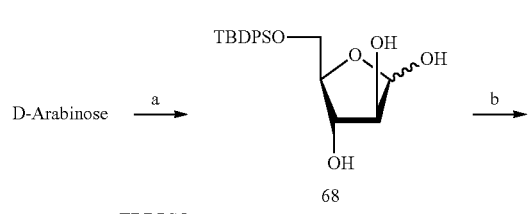

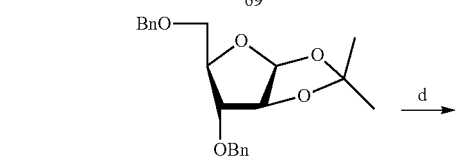

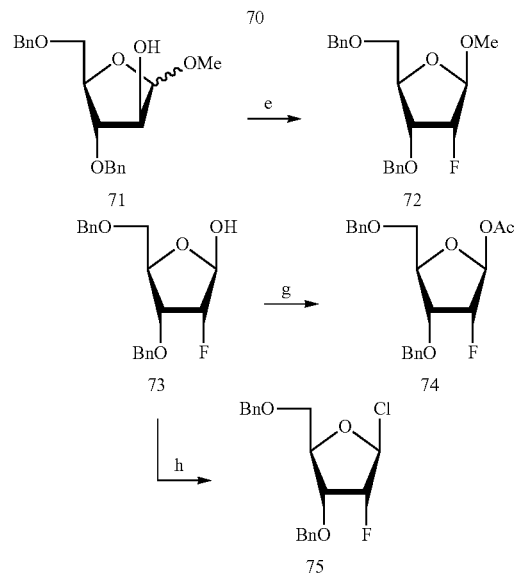

Reagents and conditions: a) TBDPSCl, imidazole; b) acetone, CuSO₄, H₂SO₄; c) KOH, BnCl; d) CSA, MeOH; e) i. Tf₂O, ii. TBAF; f) 90% TFA$_{(aq)}$; g) Ac₂O, DMAP; h) HMPT, CCl₄

334
Example 34

Base Coupling and Deprotection

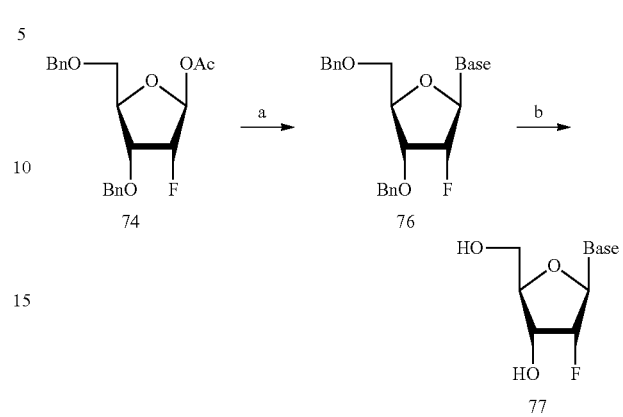

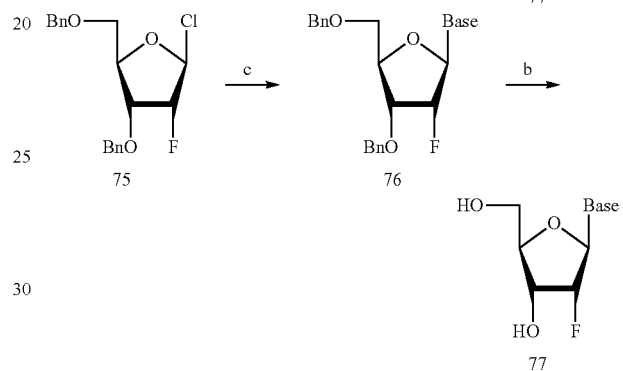

Reagents and conditions: a) silylated base, TMSOTf, DCE; b) BCl₃, DCM; c) nucleobase, TDA-1, KOH, MeCN Example 35

Synthesis of 2'-Deoxy-2'-β-Substituted-2'-α-Fluororibonucleosides

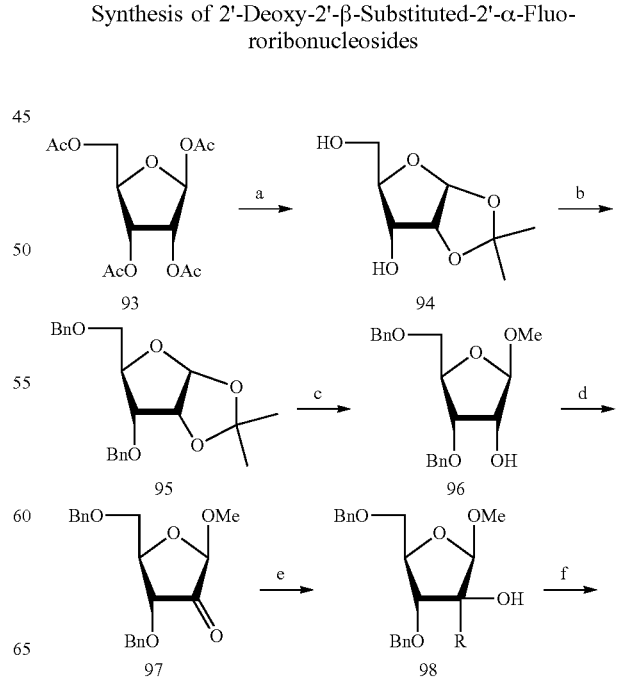

335

-continued

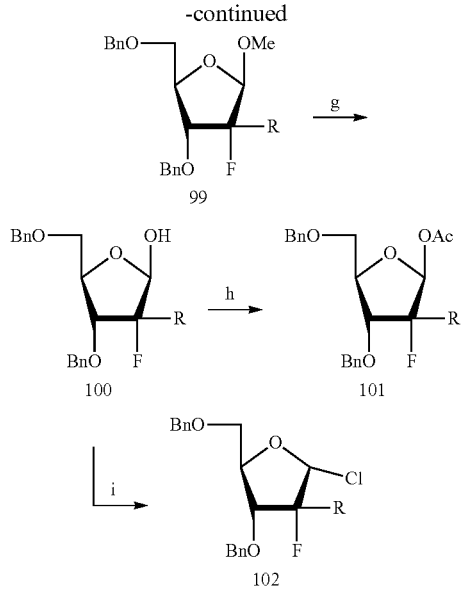

Reagents and conditions: a) i. I₂, acetone, ii. K₂CO₃, MeOH; b) KOH, BnCl; c) H₂SO₄, MeOH; d) DMP; e) RLi or RMgBr; f) DAST; g) H₂SO₄, H₂O; h) Ac₂O, DMAP; i) HMPT, CCl₄

Example 36

Base Coupling and Deprotection

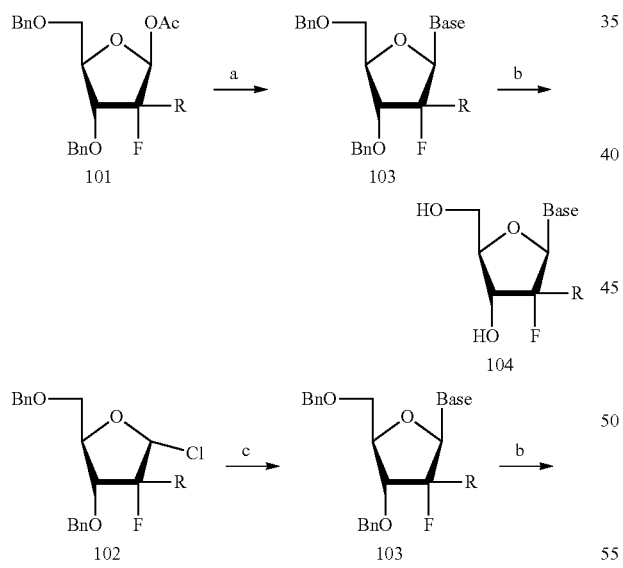

Reagents and conditions: a) silylated base, TMSOTf, DCE; b) BCl₃, DCM; c) nucleobase, TDA-1, KOH, MeCN

336

Example 37

Alternative Synthesis for 2'-Deoxy-2'-α-Fluororibo-nucleosides

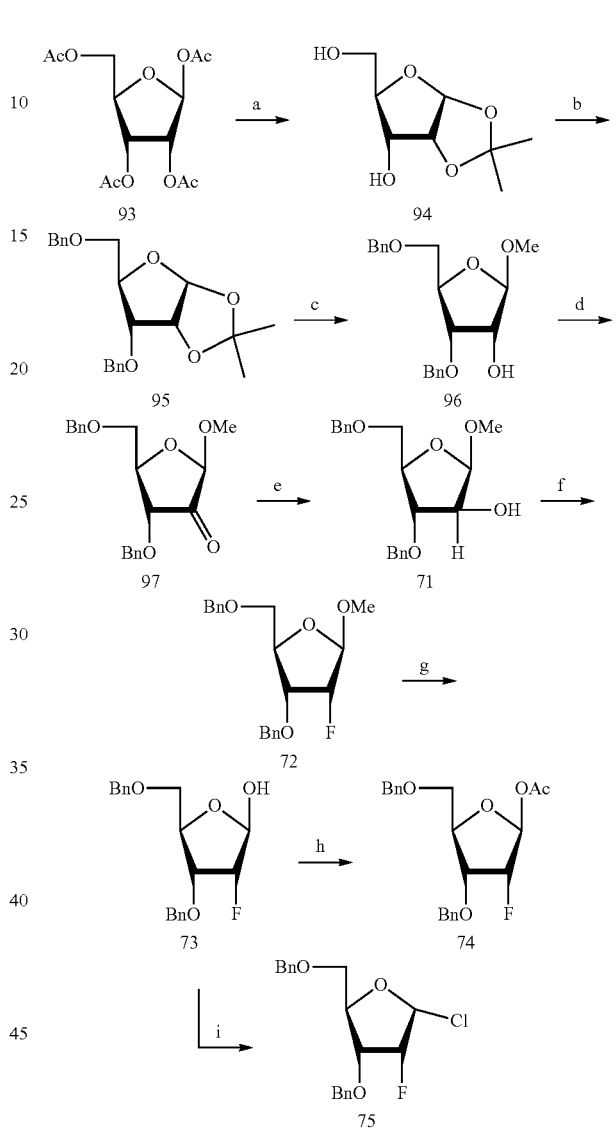

Reagents and conditions: a) i. I₂, acetone, ii. K₂CO₃, MeOH; b) KOH, BnCl; c) H₂SO₄, MeOH; d) DMP; e) NaBH₄; f) DAST; g) H₂SO₄, H₂O; h) Ac₂O, DMAP; i) HMPT, CCl₄

Example 38

Base Coupling and Deprotection

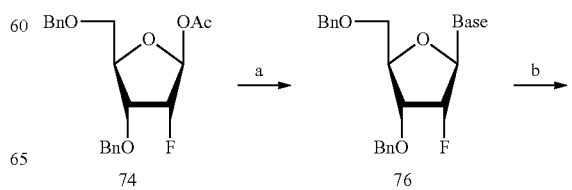

337
-continued

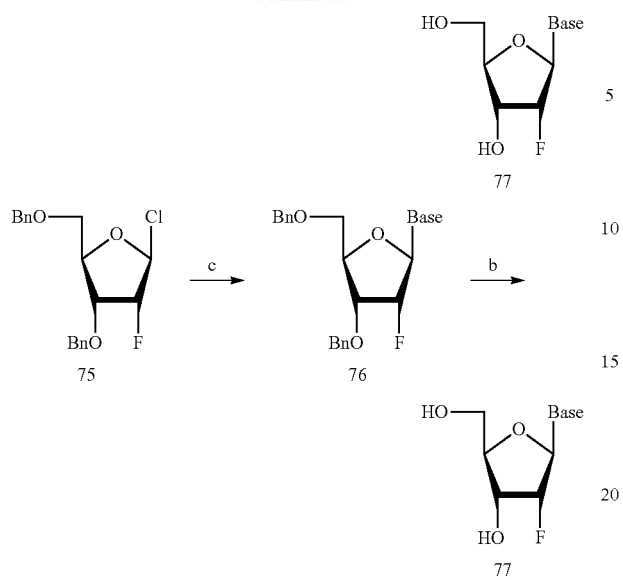

Reagents and conditions: a) silylated base, TMSOTf, DCE; b) BCl₃, DCM; c) nucleobase, TDA-1, KOH, MeCN

Example 39

Synthesis of 2'-Deoxy-2'-β-Fluoromethyl-2'-α-Fluororibonucleosides

338
-continued

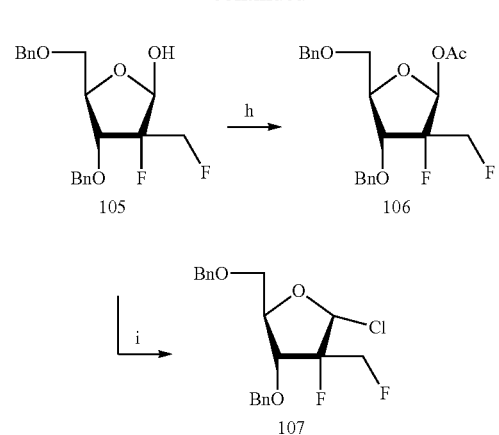

Reagents and conditions: a) i. I₂, acetone, ii. K₂CO₃, MeOH; b) KOH, BnCl; c) H₂SO₄, MeOH; d) DMP; e) i. Me₃S(O)I, NaH, ii. KF, 18-crown-6; f) DAST; g) H₂SO₄, H₂O; h) Ac₂O, DMAP; i) HMPT, CCl₄

Example 40

Base Coupling and Deprotection

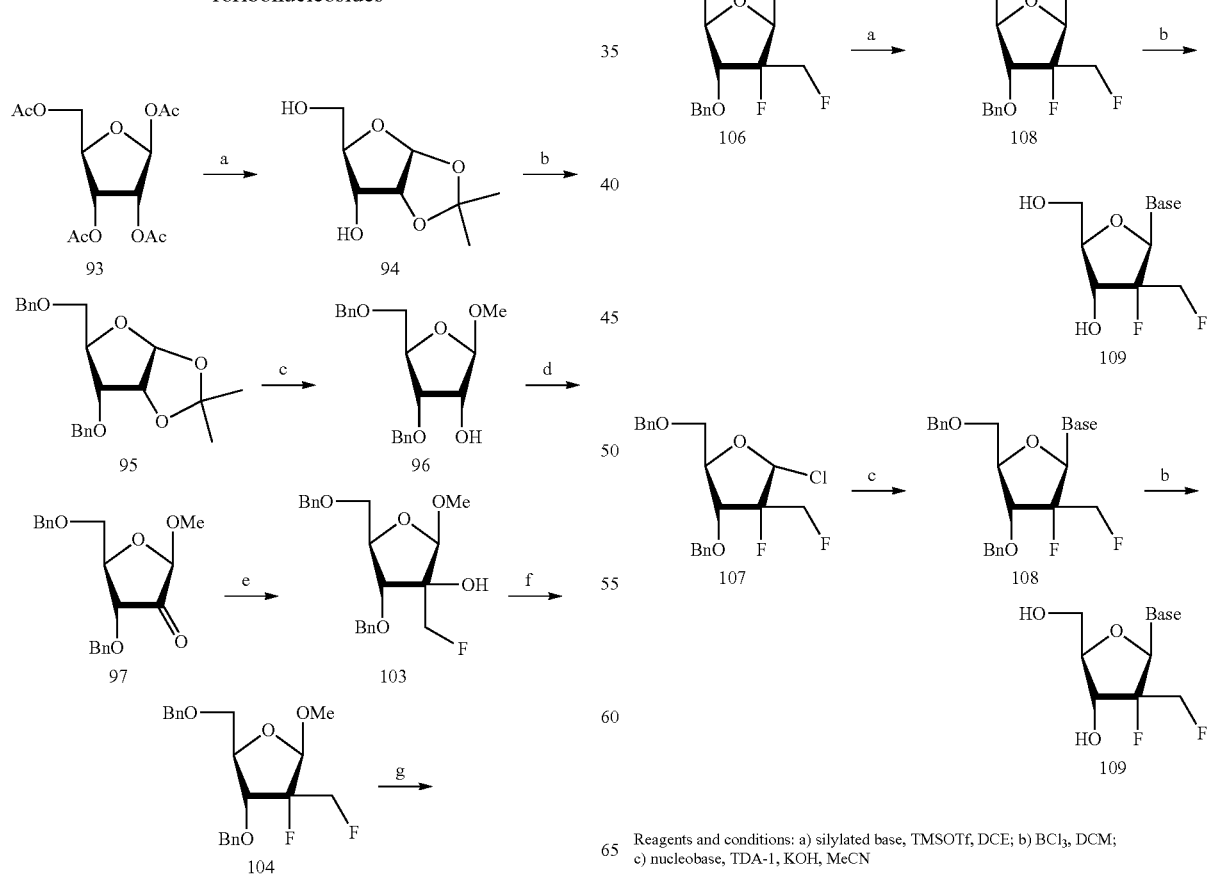

Reagents and conditions: a) silylated base, TMSOTf, DCE; b) BCl₃, DCM; c) nucleobase, TDA-1, KOH, MeCN

Example 41

Synthesis of 2'-Deoxy-2'-β-Difluoromethyl OR Trifluoromethyl-2'-α-Fluororibonucleosides

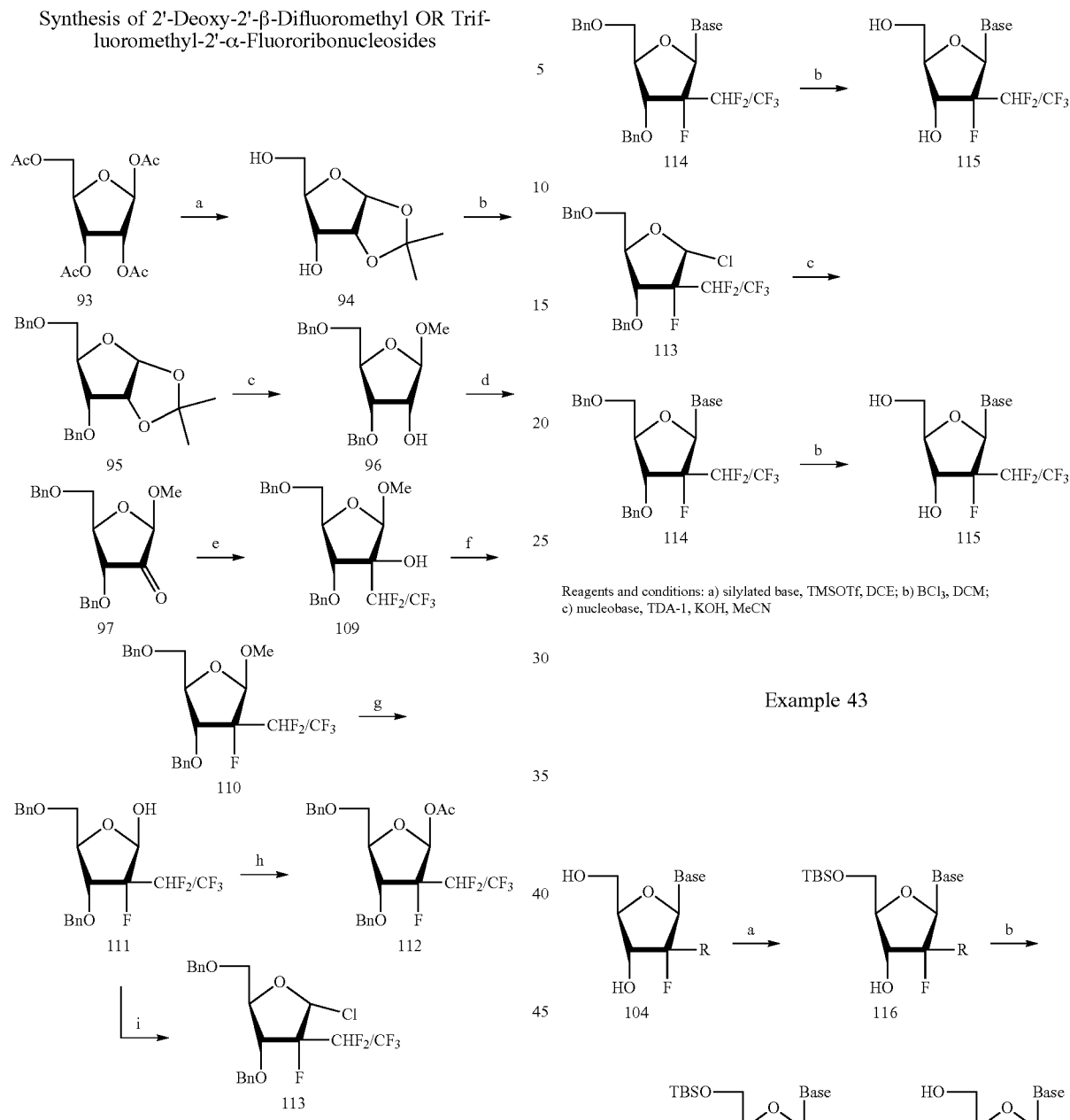

Reagents and conditions: a) i. I₂, acetone, ii. K₂CO₃, MeOH; b) KOH, BnCl; c) H₂SO₄, MeOH; d) DMP; e) CHF₂: i. PhSO₂CF₂H, LiHMDS, ii. SmI₂ or CF₃: TMSCF₃, TBAF; f) DAST; g) H₂SO₄, H₂O; h) Ac₂O, DMAP; i) HMPT, CCl₄

Example 42

Base Coupling and Deprotection

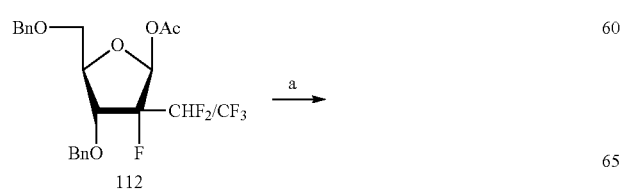

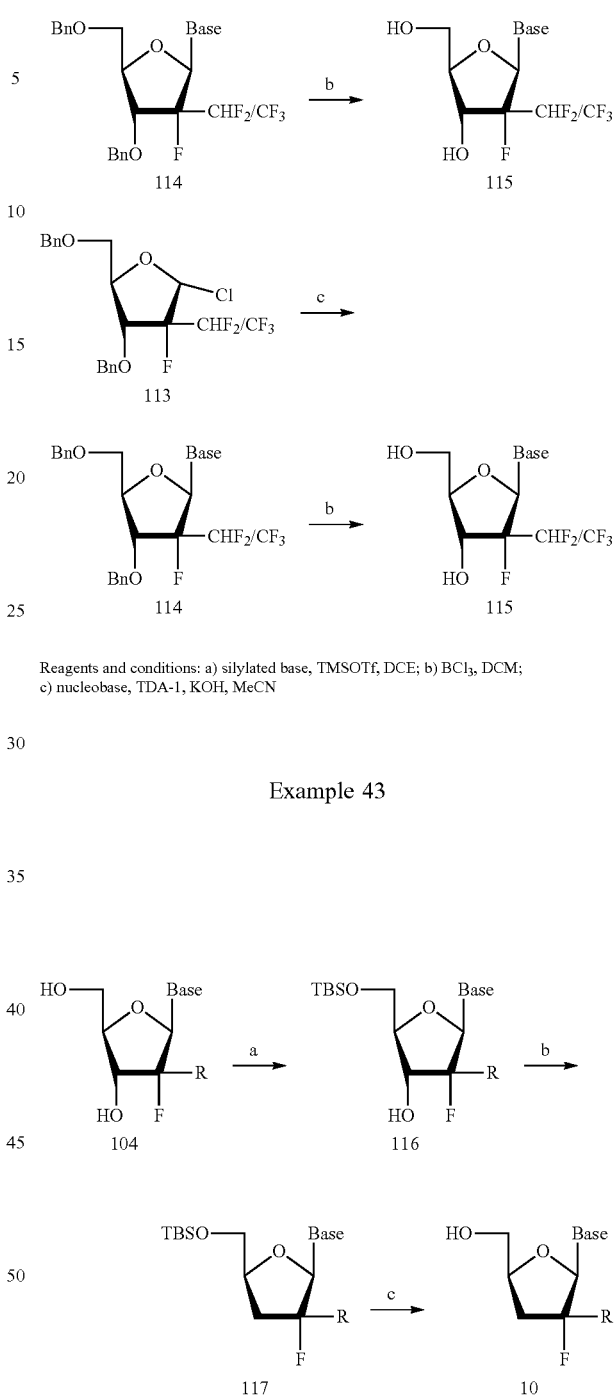

Reagents and conditions: a) silylated base, TMSOTf, DCE; b) BCl₃, DCM; c) nucleobase, TDA-1, KOH, MeCN

Example 43

Reagents and conditions: a) TBSCl, Et₃N, DMAP; b) i. phenylchlorothionoformate, ii. AIBN; c) TBAF

Example 44

Monophosphate and Diphosphate Prodrug Synthesis

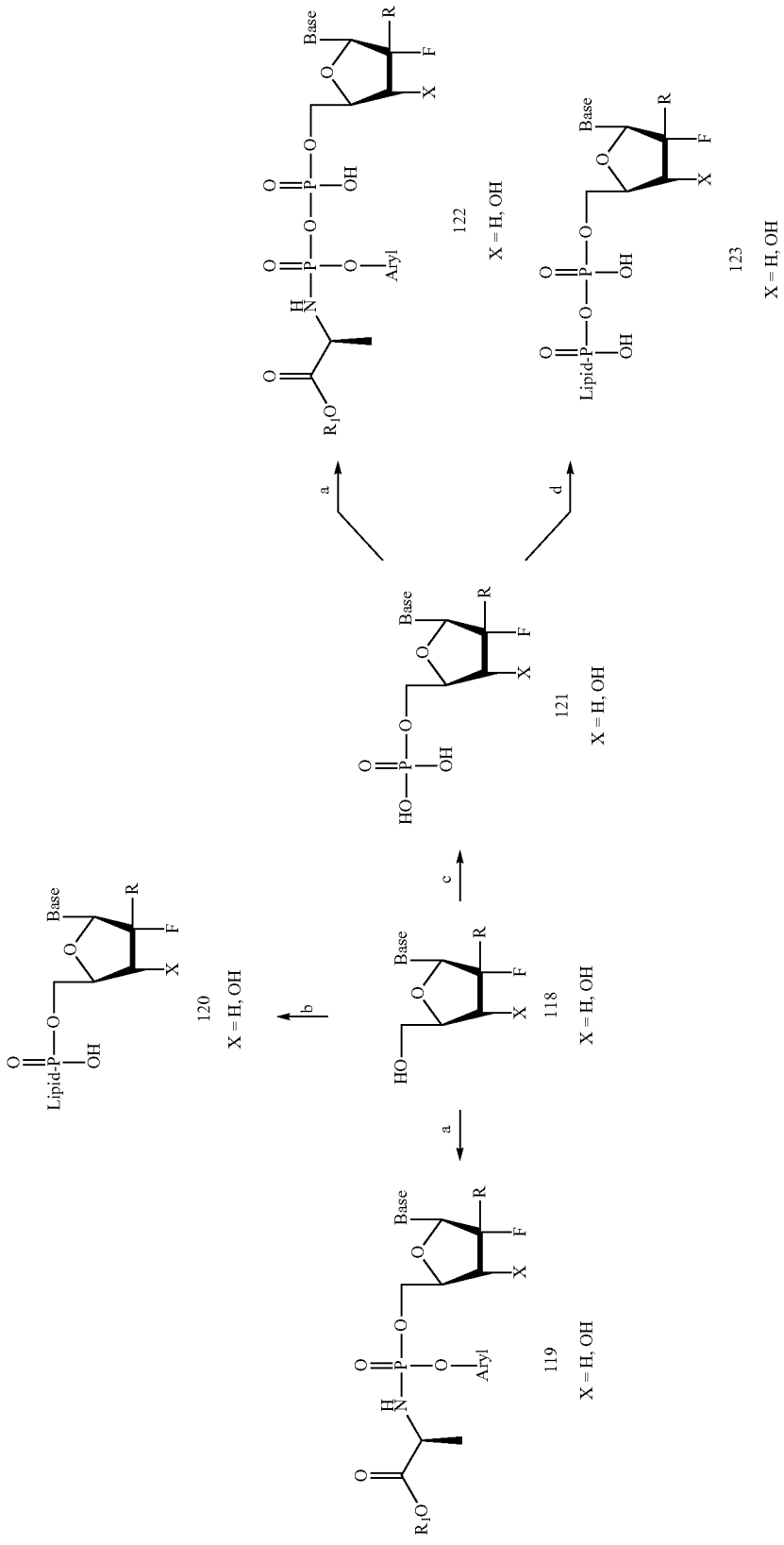
Reagents and conditions: a) chlorophosphoramidate, imidazole; b) DIC, lipid-1-phosphate; c) POCl₃, O=P(OMe)₃; d) i. DIC, morpholine, ii. Sphingoid base-1-phosphate, tetrazole

Example 45

N-tert-Butyloxycarbonyl-sphingosine (124)

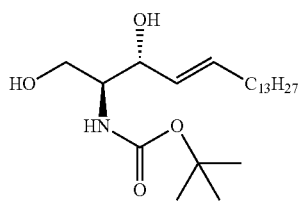

124

Prepared according to Boumendjel, Ahcene and Miller, Stephen *Journal of Lipid Research* 1994, 35, 2305.

A mixture of sphingosine (450 mg, 1.50 mmol) and di-tert-butyl dicarbonate (0.656 g, 3.01 mmol) in methylene chloride (100 mL) at 4° C. was treated dropwise with diisopropylethylamine (0.53 mL, 3.01 mmol). After gradual warming to rt, the mixture was stirred for an additional 12 h and then diluted with methylene chloride (100 mL) followed by a wash with water (30 mL) and brine (30 mL). The organic phase was dried over sodium sulfate, filtered and concentrated to dryness. The crude residue was purified by flash column chromatography over silica gel (19 mm×175 mm) using 50% ethyl acetate in hexanes to give N-tert-butyloxycarbonyl-sphingosine (540 mg, 90%) as a white solid.

$^1$H NMR (300 MHz, Chloroform-d) δ 5.77 (dt, J=15.4, 8.4 Hz, 1H), 5.52 (dd, J=15.4, 8.4 Hz, 1H), 3.93 (dd, J=11.4, 3.7 Hz, 1H), 3.70 (dd, J=11.4, 3.7 Hz, 1H), 3.59 (s, 3H), 2.05 (q, J=7.0 Hz, 2H), 1.52 (s, 9H), 1.25 (s, 22H), 0.87 (t, J=6.5 Hz, 3H).

Example 46

N-tert-Butyloxycarbonyl-sphingosine-1-O-dimethyl-phosphate (125)

125

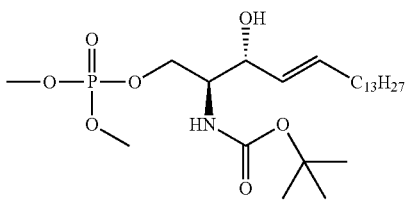

N-tert-Butyloxycarbonyl-sphingosine 124 (540 mg, 1.35 mmol) was rendered anhydrous by co-evaporation with anhydrous pyridine (2×12 mL). The residue was then dissolved in anhydrous pyridine and treated with carbon tetrabromide (622 mg, 1.88 mmol). The mixture was cooled to 0° C. and treated dropwise with a solution of trimethylphosphite (0.25 mL, 2.10 mmol) in anhydrous pyridine (3 mL) over a 30 min period. After an additional 12 h at rt, both LCMS and tlc (5% methanol in methylene chloride) analysis indicated complete conversion. The mixture was quenched with water (2 mL) and then concentrated to dryness. The resulting dark oil was dissolved in ethyl acetate (150 mL) and washed with 3% HCL solution (2×20 mL) followed by saturated sodium bicarbonate solution (30 mL). The organic layer was dried over sodium sulfate, filtered and concentrated. The crude residue was purified by flash column chromatography over silica gel (19 mm×175 mm) using 2% methanol in methylene chloride to give N-tert-butyloxycarbonyl-sphingosine-1-O-dimethylphosphate 125 (350 mg, 51%) as a gum.

$^1$H NMR (400 MHz, Chloroform-d) δ 5.82 (dt, J=15.4, 7.1 Hz, 1H), 5.48 (dd, J=15.4, 7.1 Hz, 1H), 4.99 (d, J=8.9 Hz, 1H), 4.32 (ddd, J=10.7, 8.0, 4.6 Hz, 1H), 4.11 (ddt, J=10.7, 7.4, 3.1 Hz, 2H), 3.77 (dd, J=11.1, 2.1 Hz, 6H), 2.01 (q, J=7.1 Hz, 2H), 1.41 (s, 9H), 1.34 (m, 2H), 1.23 (m, 20H), 0.86 (t, J=6.4 Hz, 3H).

$^{31}$P NMR (162 MHz, Chloroform-d) δ 2.00.

MS C17H25NO4 [M+Na+]; calculated: 330.2, found: 330.2.

Example 47

Sphingosine-1-phosphate (126)

126

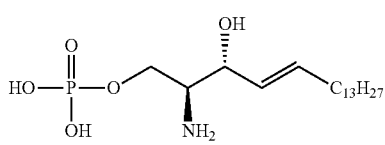

A solution of N-tert-butyloxycarbonyl-sphingosine-1-O-dimethylphosphate 125 (350 mg, 0.689 mmol) in anhydrous methylene chloride (8 mL) was treated dropwise with trimethylsilyl bromide (0.45 mL, 3.45 mmol) at 0° C. After warming to room temperature, the mixture was allowed to stir at rt for 6 h and then concentrated to dryness. The resulting residue was co-evaporated with methylene chloride to remove excess trimethylsilyl bromide and then treated with 66% aqueous THF (6 mL). The resulting precipitate was collected by filtration to give sphingosine-1-phosphate 126 (218 mg, 83%) as a white solid.

$^1$H NMR (400 MHz, Methanol-d$_4$+CD$_3$CO$_2$D) δ 5.84 (dt, J=15.5, 6.7 Hz, 1H), 5.46 (dd, J=15.5, 6.7 Hz, 1H), 4.33 (t, J=6.0 Hz, 1H), 4.13 (ddd, J=11.8, 7.7, 3.6 Hz, 1H), 4.03 (dt, J=11.8, 8.4 Hz, 1H), 3.47 (ddd, J=8.3, 4.8, 3.2 Hz, 1H), 2.10-1.99 (m, 2H), 1.37 (m, 2H), 1.24 (m, 20H), 0.83 (t, J=6.4 Hz, 3H).

$^{31}$P NMR (162 MHz, Chloroform-d) δ 0.69.

MS C$_{18}$H$_{38}$NO$_5$P [M−H$^+$]; calculated: 378.2, found: 378.2.

Example 48

N-Trifluoroacetyl-phytosphingosine (131)

131

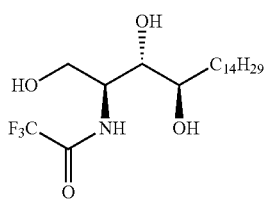

To a slurry of phytosphingosine (4 g, 12.6 mmol) and anhydrous powdered potassium carbonate (5.22 g, 37.8 mmol) in methylene chloride (85 mL) was added trifluoroacetic anhydride (1.96 mL, 13.9 mmol). The mixture was stirred at rt for 18 h and then diluted with methylene chloride (500 mL). The mixture was washed with water (100 mL). Methanol (60 mL) was added to break the emulsion. The organic phase was then dried over sodium sulfate, filtered and concentrated to give 131 (4.9 g, 94%) as a white solid ¹H NMR (400 MHz, DMSO-$d_6$) δ 8.90 (s, 1H), 4.90-4.68 (m, 1H), 4.56 (d, J=6.1 Hz, 1H), 4.43 (s, 1H), 3.97 (d, J=7.6 Hz, 1H), 3.65 (d, J=10.8 Hz, 1H), 3.46 (t, J=10.2 Hz, 1H), 3.32-3.16 (m, 1H), 1.42 (tt, J=15.7, 7.5 Hz, 2H), 1.20 (s, 24H), 0.83 t, J=6.8 Hz, 3H).

Example 49

1-O-tert-Butyldiphenylsilyl-2-N-trifluoroacetyl-phytosphingosine (132)

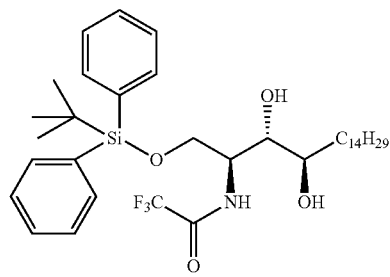

132

N-Trifluoroacetyl-phytosphingosine (131, 1.88 g, 4.5 mmol) in anhydrous pyridine (23 mL) was treated with DMAP (56 mg, 0.45 mmol) and then dropwise with tert-butyldiphenylsilyl chloride (1.38 g, 5.0 mmol). After 18 h concentrated to dryness. The resulting residue was dissolved in ethyl acetate (200 mL) and washed with saturated ammonium chloride (2×50 mL) and then brine (50 mL). The aqueous phases was back-extracted with ethyl acetate (50 mL). Combined organic phases were dried over sodium sulfate and concentrated to give crude 1-O-tert-Butyldiphenylsilyl-2-N-trifluoroacetyl-phytosphingosine 132 (3 g, 100%) as a gum. The material was used in the next step without further purification.

¹H NMR (400 MHz, Chloroform-d) δ 7.62 (m, 2H), 7.60-7.56 (m, 2H), 7.47-7.31 (m, 6H), 7.07 (d, J=8.4 Hz, 1H), 4.23 (dd, J=8.5, 4.1 Hz, 1H, 4.04 (dt, J=11.0, 2.5 Hz, 1H), 3.82 (ddd, J=11.0, 4.3, 1.8 Hz, 1H), 3.64 (dq, J=10.6, 6.0, 4.3 Hz, 2H), 1.45 (m, 2H), 1.39-1.15 (m, 24H), 1.05 (m, 9H), 0.94-0.80 (t, J=6.9 Hz 3H).

Example 50

1-O-tert-Butyldiphenylsilyl-3,4-O-isopropylidene-2-N-trifluoroacetyl-phytosphingosine (133)

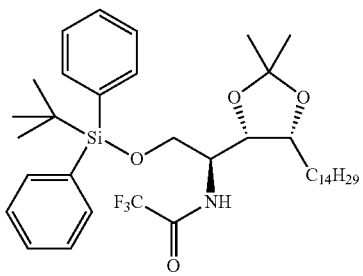

133

A solution of 1-O-tert-Butyldiphenylsilyl-2-N-trifluoroacetyl-phytosphingosine 132 (3 g, 4.5 mmol) in 1/1 (v/v) 2,2-dimethoxypropane/THF was treated with catalytic amount of p-toluenesulfonic acid (87 mg, 0.45 mmol) and allowed to stir for 16 h at rt. The mixture was quenched with saturated sodium bicarbonate (30 mL) and then excess THF/2,2-dimethoxypropane was removed under vacuum. The mixture was extracted with ethyl acetate (200 mL). After washing with brine, the organic layer was dried over sodium sulfate, filtered and concentrated. The crude oil was purified by column chromatography (25 mm×175 mm) over silica gel with a hexanes/ethyl acetate mobile phase to give 133 (2.45 g, 78%).

¹H NMR (400 MHz, Chloroform-d) δ 7.68-7.63 (m, 2H), 7.63-7.57 (m, 2H), 7.39 (m, 6H), 6.54 (d, J=9.4 Hz, 1H), 4.23 (dd, J=8.2, 5.6 Hz, 1H), 4.12 (ddd, J=13.3, 6.9, 3.8 Hz, 2H), 3.96 (dd, J=10.5, 3.9 Hz, 1H), 3.69 (dd, J=10.5, 2.9 Hz, 1H), 1.52-1.36 (m, 2H), 1.33 (s, 3H), 1.31 (s, 3H), 1.24 (m, 24H), 1.03 (s, 9H), 0.86 (t, J=53.7, 6.9 Hz, 3H).

Example 51

3,4-O-Isopropylidene-2-N-Trifluoroacetyl-phytosphingosine (134)

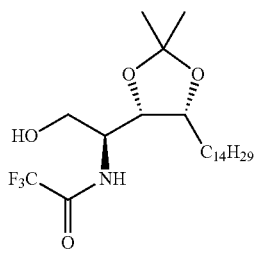

134

A solution of 1-O-tert-Butyldiphenylsilyl-3,4-O-isopropylidene-2-N-trifluoroacetyl-phytosphingosine 133 (2.45 g, 3.54 mmol) in THF (18 mL) was treated with tetrabutylammonium fluoride (4.25 mL of a 1.0 M solution in THF, 4.25 mmol) and stirred at rt for 12 h. The mixture was diluted with ethyl acetate (100 mL) and saturated ammonium chloride (2×50 mL) and then brine (50 mL). The organic phase was dried over sodium sulfate, filtered, and concentrated to give a white solid that was further purified by column chromatography (25 mm×175 mm) over silica gel with a 9:1 hexanes: ethyl acetate mobile phase to afford 134 (1.5 g, 93%) as a white solid.

¹H NMR (300 MHz, Chloroform-d) δ 6.92 (d, J=8.7 Hz, 1H), 4.31-4.16 (m, 2H), 4.11 (dq, J=11.7, 3.7 Hz, 1H), 4.00 (dd, J=11.5, 2.6 Hz, 1H), 3.70 (dd, J=11.5, 3.6 Hz, 1H), 1.48 (s, 3H), 1.35 (s, 3H), 1.25 (m, 26H), 0.88 (t, J=6.9 Hz 3H).

Example 52

3,4-O-Isopropylidene-2-N-trifluoroacetyl-phytosphingosine-1-O-dimethylphosphate (135)

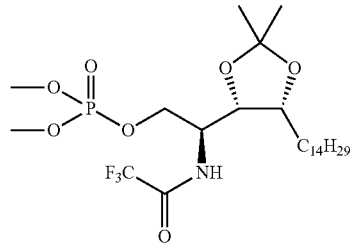

135

A solution of 3,4-O-Isopropylidene-2-N-Trifluoroacetyl-phytosphingosine 134 (630 mg, 1.39 mmol) was rendered anhydrous by co-evaporation with anhydrous pyridine (2×12 mL). The residue was then dissolved in anhydrous pyridine (12 mL) and treated with carbon tetrabromide (533 mg, 1.67 mmol). The mixture was cooled to 0° C. and treated dropwise with a solution of trimethylphosphite (0.23 mL, 1.95 mmol) in anhydrous pyridine (3 mL) over a 30 min period. After an additional 12 h at rt, both LCMS and tlc (5% methanol in methylene chloride) analysis indicated complete conversion. The mixture was quenched with water (2 mL) and then concentrated to dryness. The resulting dark oil was dissolved in ethyl acetate (100 mL) and washed with 3% HCL solution (2×20 mL) followed by saturated sodium bicarbonate solution (30 mL). The organic layer was dried over sodium sulfate, filtered and concentrated. The crude residue was purified by flash column chromatography over silica gel (19 mm×175 mm) using 2% methanol in methylene chloride to give 135 (650 mg, 83%).

$^1$H NMR (300 MHz, Chloroform-d) δ 7.42 (d, J=8.8 Hz, 1H), 4.36 (td, J=10.9, 5.0 Hz, 1H), 4.25 (m, 1H), 4.19 (m, J=6.5, 2.0 Hz, 3H), 3.77 (dd, J=11.2, 7.5 Hz, 6H), 1.44 (s, 3H), 1.33 (s, 3H), 1.25 (m, 26H), 0.87 (t, J=6.6 Hz, 3H).

$^{31}$P NMR (121 MHz, Chloroform-d) δ 1.69.

MS $C_{25}H_{47}F_3NO_7P$ [M–H$^+$]; calculated: 560.3, found: 560.2.

Example 53

3,4-O-Isopropylidene-2-N-trifluoroacetyl-phytosphingosine-1-phosphate (136)

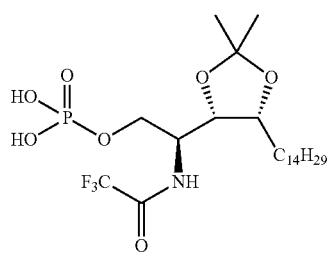

A solution of 3,4-O-Isopropylidene-2-N-trifluoroacetyl-phytosphingosine-1-O-dimethylphosphate 135 (650 mg, 1.16 mmol) in anhydrous methylene chloride (12 mL) was treated dropwise with trimethylsilyl bromide (0.81 mL, 6.23 mmol) at 0° C. After 12 h at rt, the mixture was concentrated to dryness and the resulting residue co-evaporated with methylene chloride (3×50 mL) to remove excess trimethylsilyl bromide. The residue then was dissolved in cold (4° C.) solution of 1% NH$_4$OH while maintaining pH 7-8. After 10 min at rt, the mixture was concentrated to dryness, and the resulting solid triturated with methanol/acetonitrile. The solid was collected by filtration, washed with acetonitrile, and dried under high vacuum to give 136 (500 mg, 75%) as a white solid.

$^1$H NMR (300 MHz, Methanol-d$_4$) δ 4.31 (dd, J=8.7, 5.4 Hz, 1H), 4.09 (m, 4H), 1.42 (s, 3H), 1.36 (s, 3H), 1.31 (m, 26H), 0.89 (t, J=6.4 Hz, 3H).

$^{31}$P NMR (121 MHz, Methanol-d$_4$) δ 1.28.

$^{19}$F NMR (282 MHz, Methanol-d$_4$) 5-77.13.

HRMS $C_{23}H_{42}F_3NO_7P$ [M–H$^+$]; calculated: 532.26565, found: 532.26630.

Example 54

2',3'-dideoxy-2'-fluoro-5'-(N-trifluoroacetyl-3,4-O-isopropylidene-phytosphingosine-1-phospho)-7-deazaguanosine (137)

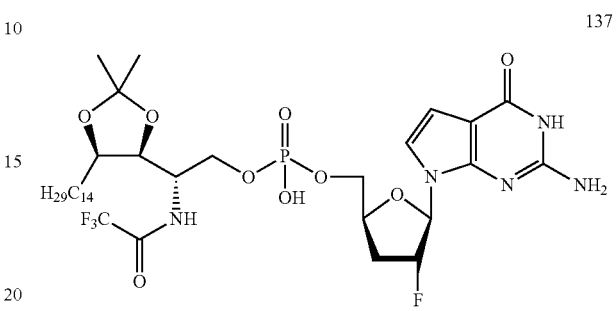

A mixture of N-trifluoroacetyl-phytosphingosine-1-phosphate 136 (200 mg, 0.373 mmol) and 2',3'-dideoxy-2'-fluoro-7-deazaguanine (100 mg, 0.373 mmol) was rendered anhydrous by co-evaporation with anhydrous pyridine (3×10 mL). The resulting residue then was dissolved in anhydrous pyridine (4 mL) and treated with diisopropylcarbodiimide (127 mg, 1.01 mmol) and HOBt (60 mg, 0.447 mmol). After 24 h at 75° C., the reaction mixture was cooled to rt and concentrated to dryness. The crude material was purified by flash column chromatography (19 mm×170 mm) over silica gel using a solvent gradient from 5 to 7.5% methanol in chloroform with 1% (v/v) NH$_4$OH to give 137 (80 mg, 27%) as a white solid.

$^1$H NMR (300 MHz, Methanol-d$_4$) δ 6.88 (d, J=3.8 Hz, 1H), 6.46 (d, J=3.8 Hz, 1H), 6.24 (d, J=19.9 Hz, 1H), 5.34 (dd, J=52.4, 4.6 Hz, 1H), 4.53 (s, 1H), 4.34-3.97 (m, 6H), 2.63-2.17 (m, 2H), 1.40 (s, 3H), 1.30 (s, 3H), 1.27 (m, 26H), 0.89 (t, J=6.6 Hz, 3H).

$^{31}$H NMR (121 MHz, Methanol-d$_4$) δ 12.50.

$^{19}$F NMR (282 MHz, Methanol-d$_4$) δ–77.10, –179.69--180.25 (m).

MS $C_{34}H_{52}2F_4N_5O_9P$ [M–H$^+$]; calculated: 781.3, found: 782.2.

Example 55

Experimental Procedure for Synthesis of Prodrugs

A solution of isopropyl 2-((chloro(phenoxy)phosphoryl)amino)propanoate (0.397 g, 1.300 mmol) in anhydrous THF (5 ml) was added to a –78° C. stirred solution of 2'-deoxy-2'-fluoronucleoside (0.812 mmol) and 1-methyl-1H-imidazole (0.367 ml, 4.63 mmol) in pyridine (10.00 ml). After 15 min the reaction was allowed to warm to room temperature and was stirred for an additional 3 hours. Next, the solvent was removed under reduced pressure. The crude product was dissolved in 120 ml of DCM and was washed with 20 ml 1 N HCl solution followed by 10 ml water. The organic phase was dried over sodium sulfate, filtered and concentrated in vacuo. The residues were separated over silica column (neutralized by TEA) using 5% MeOH in DCM as a mobile phase to yield the respective products as diastereomers.

Example 56

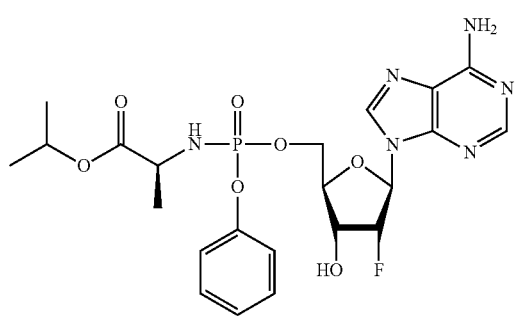

139

$^1$H NMR (400 MHz, CDCl$_3$) δ 1.48-1.06 (m, 9H), 4.04-3.84 (m, 1H), 4.60-4.14 (m, 3H), 4.86-4.64 (m, 1H), 5.11-4.90 (m, 1H), 5.61-5.19 (m, 1H), 6.32-5.94 (m, 3H), 7.44-7.02 (m, 5H), 8.11-7.89 (m, 1H), 8.46-8.20 (m, 1H). LC-MS m/z 589.4 (M+H$^+$).

Example 57

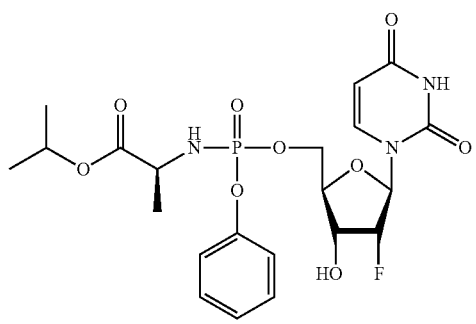

140

$^1$H NMR (400 MHz, CDCl$_3$) δ 1.14-1.29 (m, 6H), 1.31-1.43 (m, 3H), 3.83-4.07 (m, 2H), 4.15-4.54 (m, 3H), 4.91-5.11 (m, 1H), 5.61-5.74 (m, 1H), 5.81-5.97 (m, 1H), 7.14-7.24 (m, 3H), 7.27-7.44 (m, 2H), 7.48-7.51 (m, 1H), 7.80 (t, J=7.96, 7.96 Hz, 0H), 9.30 (s, 1H). LC-MS m/z 516.3 (M+1$^+$)

Example 58

Phosphonate Synthesis

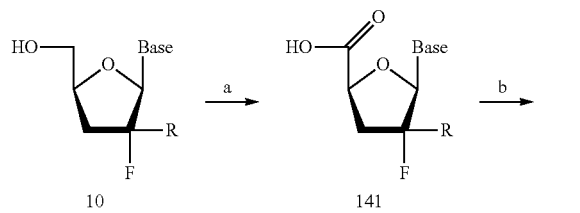

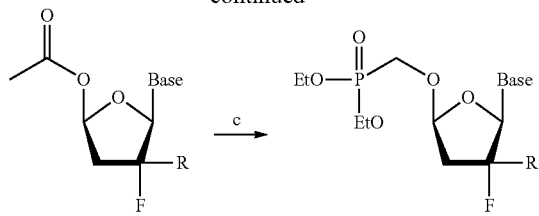

Reagents and condition: a) BAIB, TEMPO; b) Pb(OAc)$_4$; c) (EtO)$_2$POCH$_2$OH, pTSA

Example 59

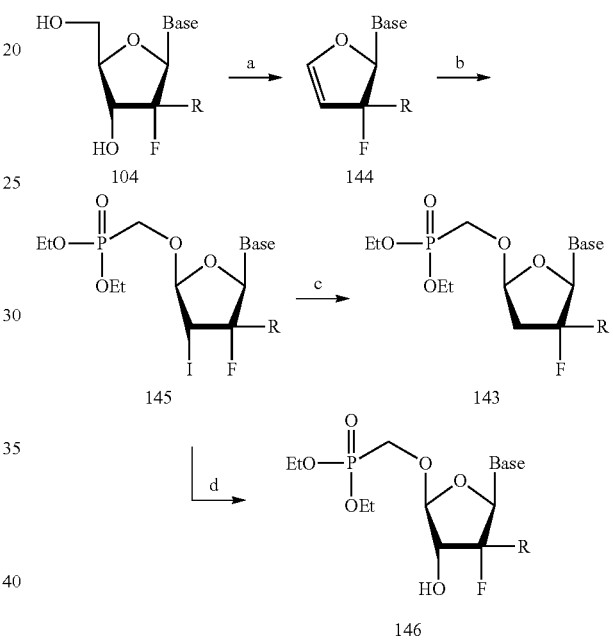

Reagents and condition: a) i). Pt/C, O$_2$, ii. DMF-dineopentyl acetal; b) IBr, (EtO)$_2$POCH$_2$OH; c) AIBN, Bu$_3$SnH; d) i. AgOAc, ii. NaOMe, MeOH, iii. PPh$_3$, DIAD, 4-NO$_2$C$_6$H$_4$COOH, iv. NaOMe, MeOH.

Example 60

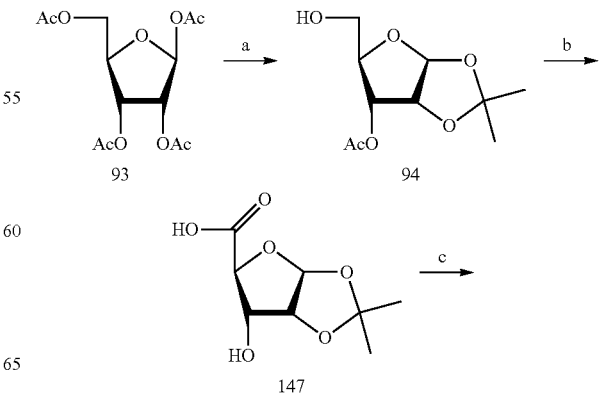

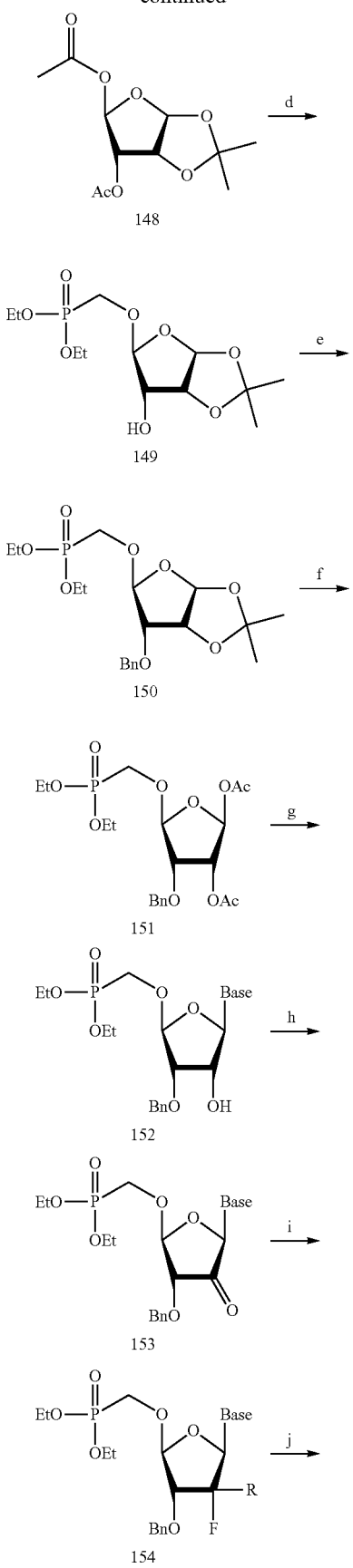
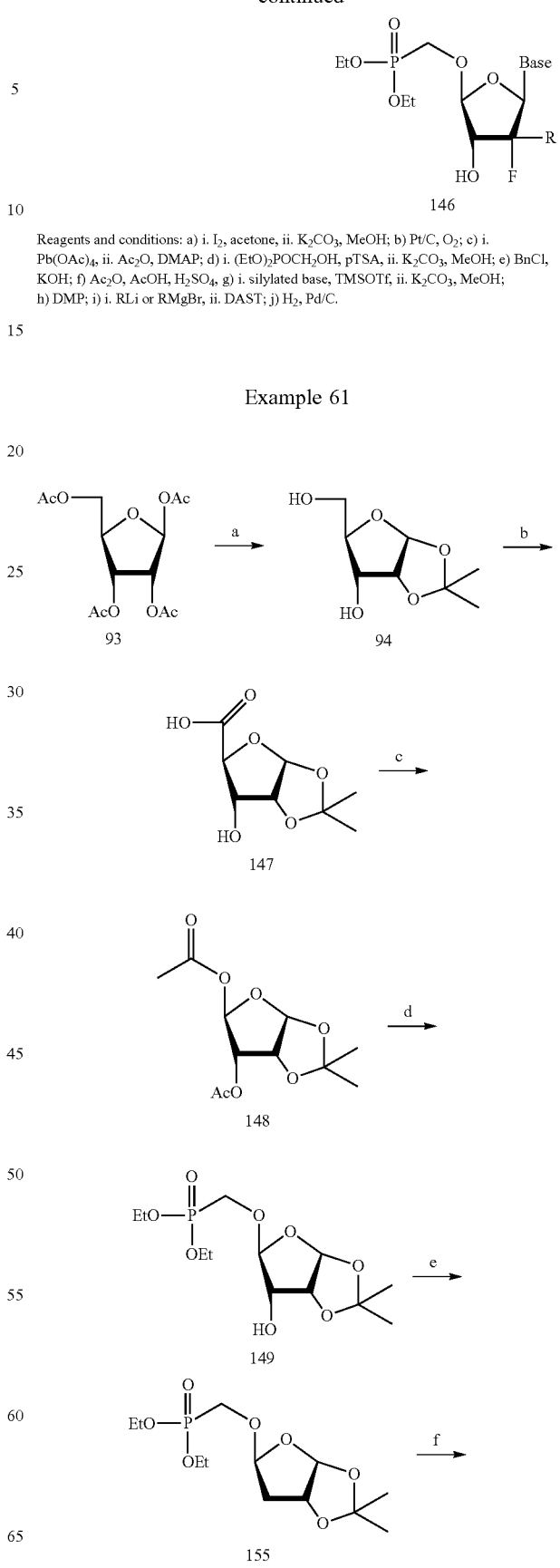
Reagents and conditions: a) i. I$_2$, acetone, ii. K$_2$CO$_3$, MeOH; b) Pt/C, O$_2$; c) i. Pb(OAc)$_4$, ii. Ac$_2$O, DMAP; d) i. (EtO)$_2$POCH$_2$OH, pTSA, ii. K$_2$CO$_3$, MeOH; e) BnCl, KOH; f) Ac$_2$O, AcOH, H$_2$SO$_4$, g) i. silylated base, TMSOTf, ii. K$_2$CO$_3$, MeOH; h) DMP; i) i. RLi or RMgBr, ii. DAST; j) H$_2$, Pd/C.
Example 61

353

-continued

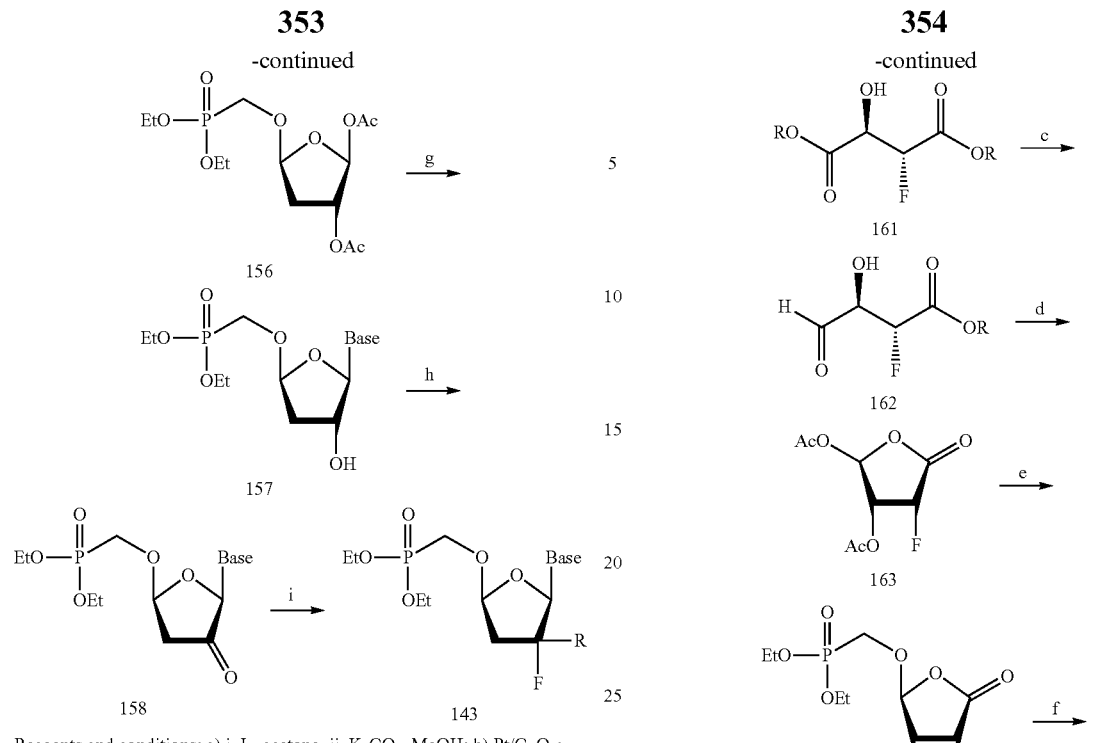

Reagents and conditions: a) i. I₂, acetone, ii. K₂CO₃, MeOH; b) Pt/C, O₂; c) i. Pb(OAc)₄, ii. Ac₂O, DMAP; d) i. (EtO)₂POCH₂OH, pTSA, ii. K₂CO₃, MeOH; e) i. TCDI, pyrdine, ii. Bu₃SnH, AIBN; f) Ac₂O, AcOH, H₂SO₄; g) i. silylated base, TMSOTf, ii. K₂CO₃, MeOH; h) DMP; i) RLi or RMgBr, ii. DAST Example 62

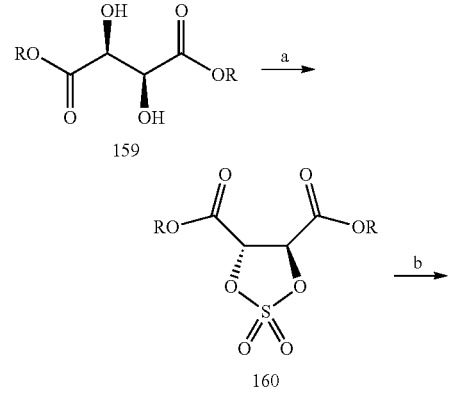

354

-continued

Reagents and conditions: a) i. SOCl₂, ii. NaIO₄, RuCl₃; b) TBAF; c) BF₃·OEt₂, DIBAL; d) Ac₂O, AcOH, H₂SO₄; e) (EtO)₂POCH₂OH, pTSA; f) DIBAL, ii. Ac₂O, Et₃N, DMAP; g) i. silylated base, TMSOTf, ii. K₂CO₃, MeOH Example 63

Phosphonate Prodrug Synthesis

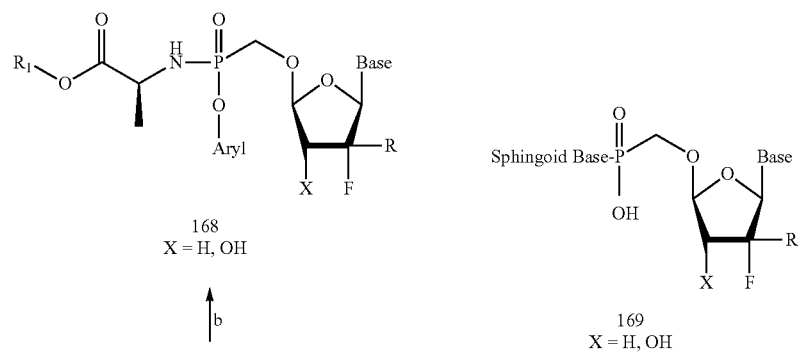

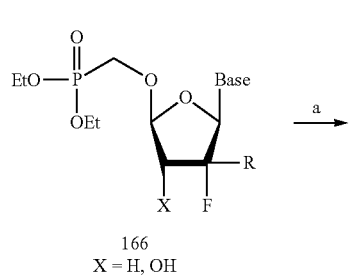
166
X = H, OH

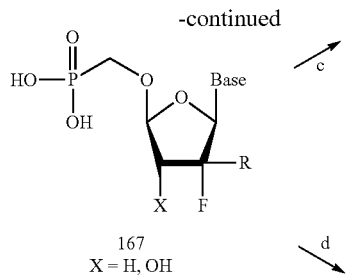
167
X = H, OH

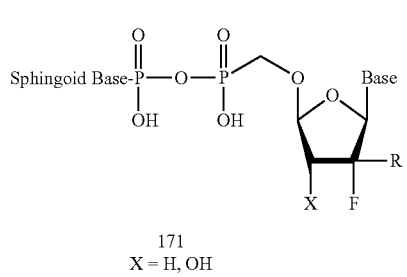
171
X = H, OH

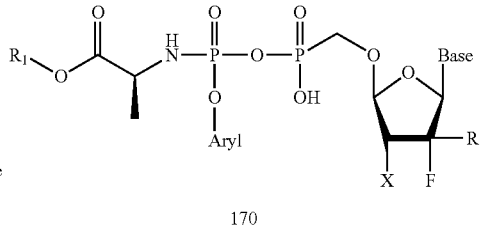
170
X = H, OH

Reagents and conditions: a) TMSBr; b) amino ester, ArOH, Et$_2$N, 2,2′-dithiodipyridine, PPh$_3$; c) i. DIC, shpingoid base, ii. TFA; d) chlorophosphoramidate, Et$_3$N; e) DIC, sphingoid base-1-phosphate

Example 64

N-tert-Butyloxycarbonyl-phytosphingosine (174)

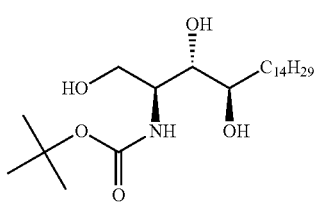
174

A suspension of phytosphingosine (10.6 g, 33.5 mmol) and triethylamine (5.6 ml, 40.2 mmol) in THF (250 mL) was treated dropwise with di-tert-butyl dicarbonate (8.6 mL, 36.9 mmol). After 12 h at rt, the mixture was concentrated to dryness and the resulting white solid was recrystallized from ethyl acetate (80 mL) and then dried under high vacuum at 35° C. for 12 h to give 174 (10.5 g, 75%).

$^1$H NMR (400 MHz, Chloroform-d) δ 5.31 (d, J=8.5 Hz, 1H), 3.89 (d, J=11.1 Hz, 1H), 3.83 (s, 2H), 3.74 (dd, J=11.1, 5.2 Hz, 1H), 3.65 (d, J=8.3 Hz, 1H), 3.61 (d, J=3.9 Hz, 1H), 1.43 (s, 9H), 1.23 (s, 27H), 0.86 (t, J=6.4 Hz, 3H).

Example 65

2-O-tert-Butyldiphenylsilyl-1-N-tert-butyloxycarbonyl-phytosphingosine (175)

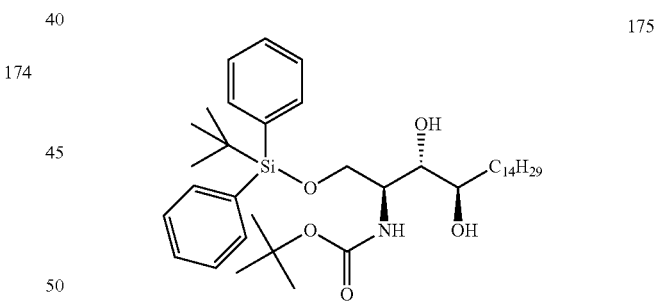
175

A solution of N-tert-Butyloxycarbonyl-phytosphingosine 174 (9.5 g, 22.65 mmol) and triethylamine (3.8 mL, 27.2 mmol) in anhydrous methylene chloride/DMF (120 mL/10 mL) was treated dropwise with tert-butylchlorodiphenylsilane (7 mL, 27.25 mmol). After 18 h at rt, the mixture was diluted with methylene chloride (200 mL) and washed with 0.2N HCl (100 mL) and then brine (100 mL). The organic phase was dried over sodium sulfate, filtered and then concentrated to give 175 (14.9 g) as an oil which was used in the next reaction without further purification.

$^1$H NMR (400 MHz, Chloroform-d) δ 5.31 (d, J=8.5 Hz, 1H), 3.89 (d, J=11.1 Hz, 1H), 3.83 (m, 1H), 3.74 (dd, J=11.1, 5.2 Hz, 1H), 3.65 (d, J=8.3 Hz, 1H), 3.61 (d, J=3.9 Hz, 1H), 1.43 (s, 9H), 1.23 (s, 27H), 0.86 (t, J=6.4 Hz, 3H).

Example 66

2-O-tert-Butyldiphenylsilyl-1-N-tert-butyloxycarbonyl-3,4-O-isopropylidene-phytosphingosine (176)

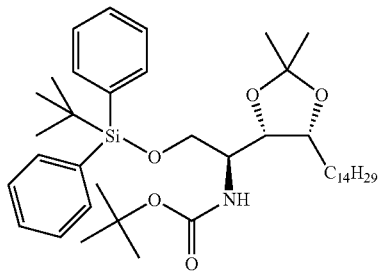

176

A solution of 2-O-tert-Butyldiphenylsilyl-1-N-tert-butyloxycarbonyl-phytosphingosine (175, 14.9 g, 22.65 mmol) in 1/1 (v/v) THF/2,2-dimethoxypropane was treated with catalytic para-toluenesulfonic acid (860 mg, 4.53 mmol). After 24 h, the mixture was quenched with saturated sodium bicarbonate solution (50 mL). The mixture was concentrated and then dissolved in ethyl acetate (200 mL) and washed with brine (2×50 mL). The organic phase was dried over sodium sulfate, filtered and concentrated to give 176 (15.7 g) as a gum which was used in the next step without further purification.

$^1$H NMR (400 MHz, Chloroform-d) δ 7.66 (m, 4H), 7.51-7.27 (m, 6H), 4.78 (d, J=10.0 Hz, 1H), 4.18 (dd, J=9.3, 5.5 Hz, 1H), 3.89 (dd, J=9.9, 3.3 Hz, 1H), 3.80 (d, J=9.9 Hz, 1H), 3.72 (d, J=9.9 Hz, 1H), 1.45 (s, 9H), 1.42 (s, 3H), 1.35 (s, 3H), 1.25 (s, 27H), 1.05 (s, 9H), 0.87 (t, J=6.5 Hz, 3H).

Example 67

1-N-tert-butyloxycarbonyl-3,4-O-isopropylidene-phytosphingosine (177)

177

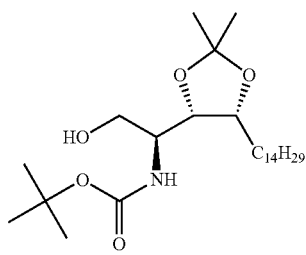

A solution of 2-O-tert-Butyldiphenylsilyl-1-N-tert-butyloxycarbonyl-3,4-O-isopropylidene-phytosphingosine 176 (15.7 g, 22.6 mmol) in THF at 0° C. was treated dropwise with a solution of tetrabutylammonium fluoride (1.0 M in THF, 24.9 mL, 24.9 mmol) over a 20 min period. After 16 h at rt, tlc (3:1 hexanes:ethyl acetate) indicated complete conversion. The mixture was concentrated to dryness and the resulting residue was dissolved in ethyl acetate (300 mL) and washed with water (3×100 mL). The organic phase was dried over sodium sulfate, filtered and concentrated. The resulting oil purified by flash column chromatography (35 mm×180 mm) using a solvent gradient from 25 to 50% ethyl acetate in hexanes to give 177 (7.3 g, 71% over 3 steps) as a white solid.

$^1$H NMR (400 MHz, Chloroform-d) δ 4.93 (d, J=9.1, 1H), 4.16 (q, J=7.1, 6.4 Hz, 1H), 4.07 (t, J=6.5 Hz, 1H), 3.83 (dd, J=11.1, 2.4 Hz, 1H), 3.76 (m, 1H), 3.67 (dd, J=11.2, 3.6 Hz, 1H), 1.43 (s, 3H), 1.42 (s, 9H), 1.32 (s, 3H), 1.23 (s, 27H), 0.86 (t, J=6.9 Hz, 3H).

Example 68

Synthesis of Cyclic Phosphate Prodrugs

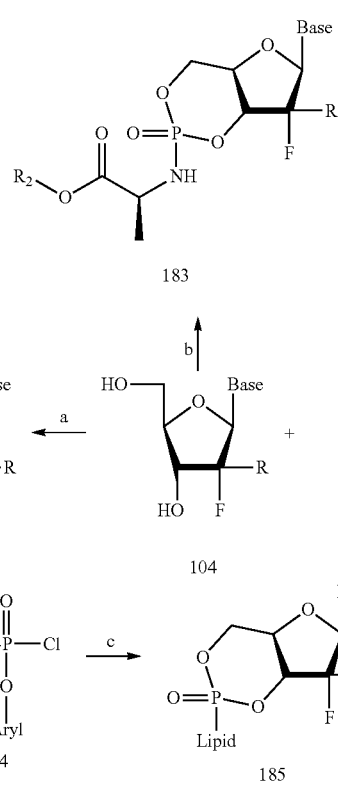

Reagents and conditions: a) i. R$_1$OP(NiPr$_2$)$_2$, DCI, ii. mCPBA; b) i. chlorophosphoramidate, imidazole, ii. t-BuOK; c) i. imidazole, ii. t-BuOK

Example 69

General Method for the Synthesis of 4-Thiouridine Nucleoside Analogs

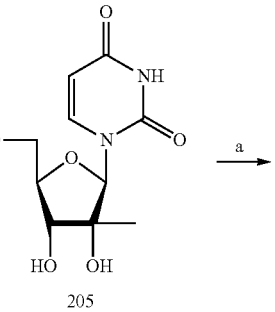

205

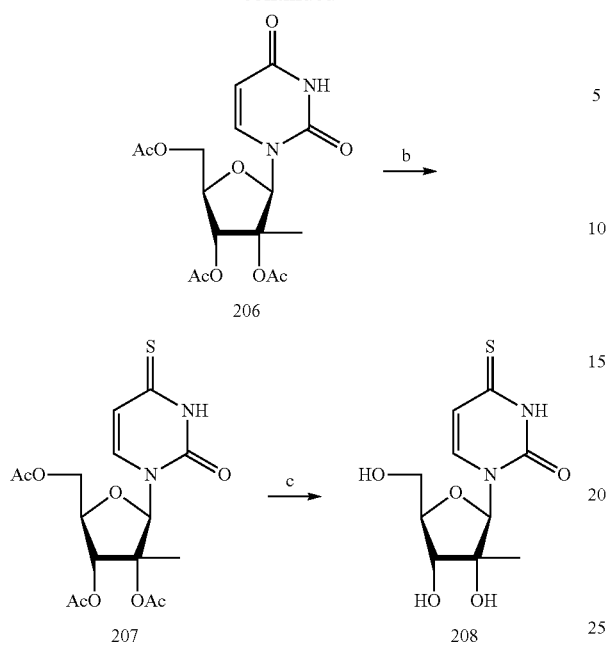

Reagents and conditions: a) Ac₂O, Et₃N, DMAP; b) Lawesson's reagent, dioxane, reflux; c) NH₃, MeOH Example 70

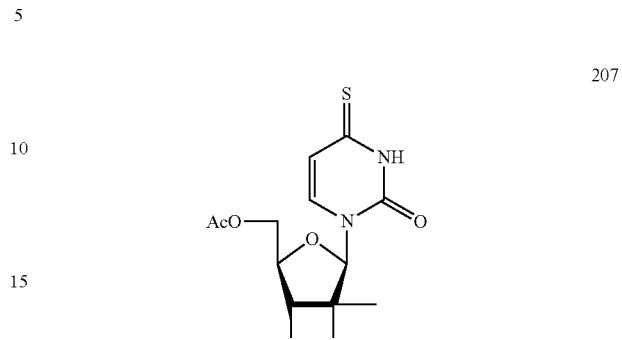

A suspension of 2'-Methyluridine (0.258 g, 0.999 mmol) in Ac₂O (4.00 ml) in the presence of DMAP (0.024 g, 0.200 mmol) and Et₃N (0.139 ml, 0.999 mmol) was stirred at r.t. overnight. The reaction mixture became homogeneous and yellowish upon stirring. The reaction was condensed on rotavap, and co-evaporated with EtOH (15 mL×3). The product was purified via ISCO to give a white solid with a yield of >95%.

Physical data: $^1$H NMR (400 Hz, CDCl₃): δ 1.519 (s, 3H), 2.087 (s, 6H), 2.099 (s, 3H), 4.265 (m, 1), 4.369 (m, 2H), 5.220 (d, 1H, J=6 Hz), 5.756 (d, 1H, J=8 Hz), 6.217 (s, 1H), 7.407 (d, 1H, J=8 Hz), 9.744 (s, 1H); $^{13}$C NMR (100 Hz, CDCl₃): δ 17.773, 20.520, 20.687, 21.461, 62.649, 74.313, 79.284, 84.195, 89.409, 102.364, 140.530, 150.040, 163.071, 169.643, 169.742, 170.318; MS: m/z 273.1 (M-uracil+H); LC-MS 99.6% purity; FIRMS Calc. for C₁₆H₂₁O₉N₂ (M+H): 385.12416, Found: 385.12420.

Example 71

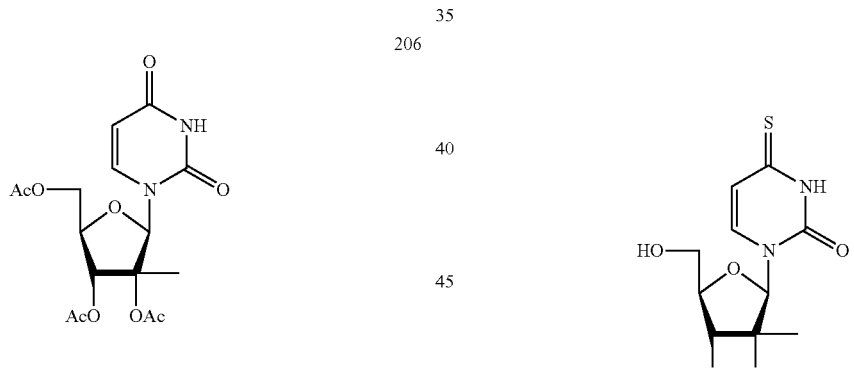

A mixture of per-Ac-2'-methyluridine (0.100 g, 0.260 mmol) and Lawesson's Reagent (0.127 g, 0.315 mmol) in dry Dioxane (1.301 ml) was refluxed under nitrogen for 2 hrs. The reaction was condensed on rotavap and the obtained yellow residue was loaded on ISCO and eluted with 3% MeOH/CH₂Cl₂. The obtained yellow foam was used in next step without further purification, and LC-MS showed 53% purity.

Example 72

A solution of crude per-Ac-5-thio-2'-methyluridine obtained from previous step (0.126 g, 0.315 mmol) in NH₃ in MeOH (7 M, 1.573 ml, 11.01 mmol) was stirred at r.t. in a sealed tube for 4.5 hrs. The yellow solution was condensed on rotavap and loaded on ISCO (4 g column, 8%→15% MeOH/CH₂Cl₂) to give a yellow foam with a 55% yield in two steps.

Physical data: NMR (400 Hz, CD₃OD): δ 1.201 (s, 3H), 3.835 (m, 2H), 3.983 (m, 2H), 5.595 (s, 1H), 6.396 (d, 1H, J=7.6 Hz), 8.006 (d, 1H, J=7.2 Hz); $^{13}$C NMR (100 Hz, CD₃OD): δ 20.983, 61.259, 74.123, 80.862, 84.809, 94.144, 114.863, 137.236, 150.806, 192.972; MS: m/z 275.0 (M+H); LC-MS 95.9% purity; HRMS Calc. for C₁₀H₁₅O₅N₂S (M+H): 275.06962, Found: 275.06967.

Example 73

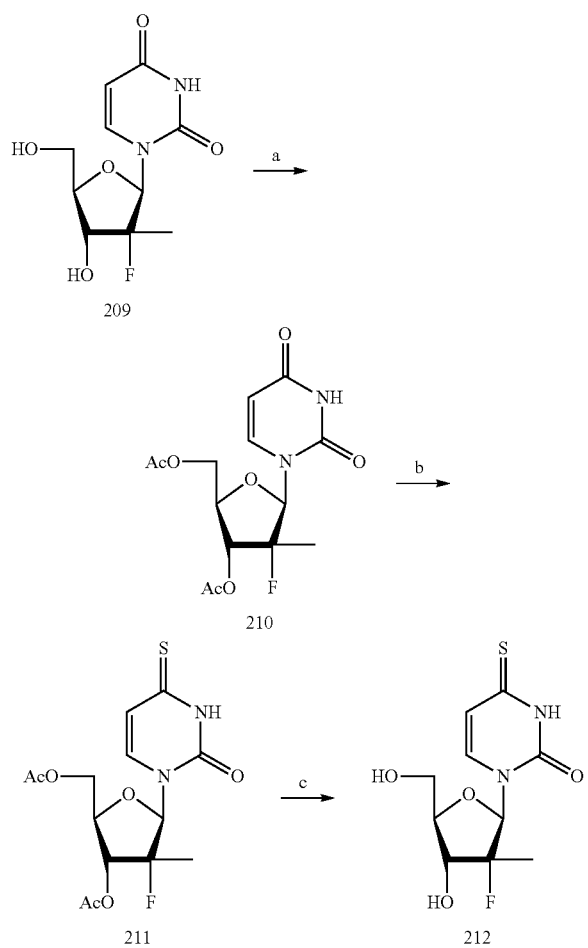

Reagents and conditions: a) Ac₂O, Et₃N, DMAP; b) Lawesson's reagent, dioxane, reflux; c) NH₃, MeOH

Example 74

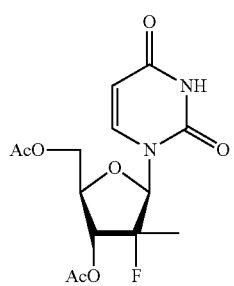
210

A brownish suspension of 2'-F-2'-Methyluracil (0.120 g, 0.461 mmol) in Ac₂O (1.845 ml) in the presence of DMAP (5.63 mg, 0.046 mmol) was stirred at r.t. for 2 hrs. The reaction mixture became homogeneous upon stirring. The reaction was condensed on rotavap, and co-evaporated with MeOH (5 mL×2). The obtained residue was purified via ISCO (12 g column, 40%→80% EtOAc/Hexanes) to give a white solid with 81% yield.

Physical data: $^1$H NMR (400 Hz, CDCl₃): δ 1.398 (d, 3H, J=22 Hz), 2.142 (s, 3H), 2.183 (s, 3H), 4.379 (m, 3H), 5.128 (dd, 1H, J₁=21.2 Hz, J₂=8.8 Hz), 5.788 (d, 1H, J=8.4 Hz), 6.179 (d, 1H, J=18.4 Hz), 7.549 (d, 1H, J=8 Hz), 8.882 (s 1H); $^{13}$C NMR (100 Hz, CDCl₃): δ 17.113, 17.363, 20.490, 20.672, 61.457, 71.498, 71.665, 98.539, 100.390, 103.085, 138.990, 149.911, 162.312, 169.924; MS: m/z 345.0 (M-uracil+H); LC-MS 95% purity; HRMS Calc. for C₁₄H₁₈FO₇N₂ (M+H): 345.10926, Found: 345.10906.

Example 75

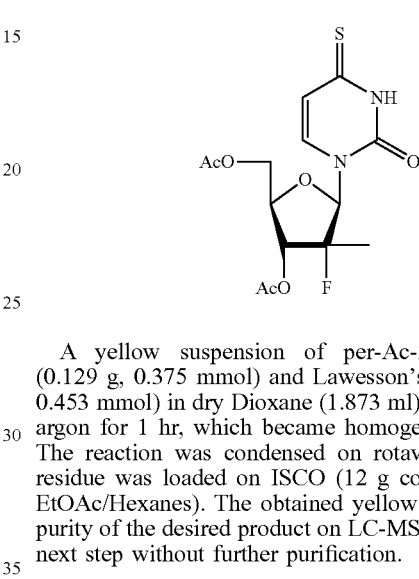
211

A yellow suspension of per-Ac-2'-F-2'-Methyluracil (0.129 g, 0.375 mmol) and Lawesson's Reagent (0.183 g, 0.453 mmol) in dry Dioxane (1.873 ml) was refluxed under argon for 1 hr, which became homogenous upon heating. The reaction was condensed on rotavap and the yellow residue was loaded on ISCO (12 g column, 20%→100% EtOAc/Hexanes). The obtained yellow foam showed 74% purity of the desired product on LC-MS, which was used in next step without further purification.

Example 76

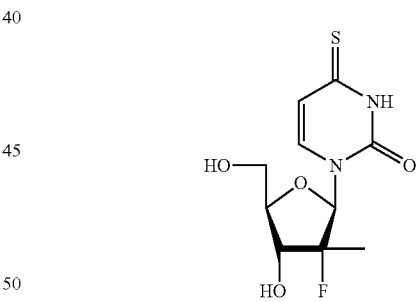
212

A solution of per-Ac-2'-F-2'-methyl-4-thiouracil (0.135 g, 0.375 mmol) in NH₃ in MeOH (7 M, 1.873 ml, 13.11 mmol) was stirred at r.t. in a sealed tube for 4.5 hrs (10:04:05 AM). The yellow solution was condensed on rotavap and loaded on ISCO (4 g column, 5%→12% MeOH/CH₂Cl₂). The obtained product is a yellow foam with a 73% yield in two steps.

Physical data: $^1$H NMR (400 Hz, CD₃OD): δ 1.367 (d, 3H, J=22.4 Hz), 3.794 (dd, 1H, J₁=12.4 Hz, J₂=2.4 Hz), 3.971 (m, 3H), 6.094 (d, 1H, J=18 Hz), 6.368 (d, 1H, J=7.6 Hz), 7.888 (d, 1H, J=7.6 Hz). $^{13}$C NMR (100 Hz, CD₃OD): δ 16.757 (d, J=25 Hz), 59.951, 72.276, 83.395, 90.704 (d, J=34.9 Hz), 101.894 (d, J=179.9 Hz), 114.435, 135.602, 149.733, 192.200; MS: m/z 277.0 (M+H); LC-MS 100% purity; HRMS Calc. for C₁₀H₁₄FO₄N₂S (M+H): 277.06528, Found: 277.06496.

Example 77

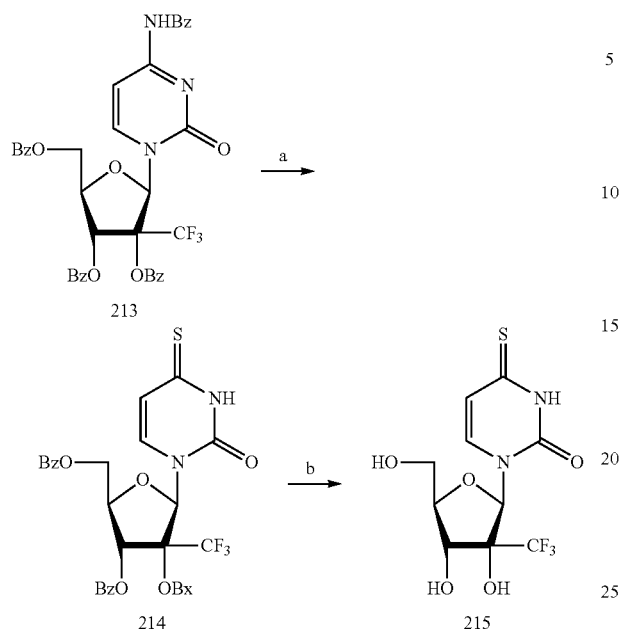

Reagents and conditions: a) dioxane, Lawesson's reagent, reflux; b) NH₃, MeOH

Example 78

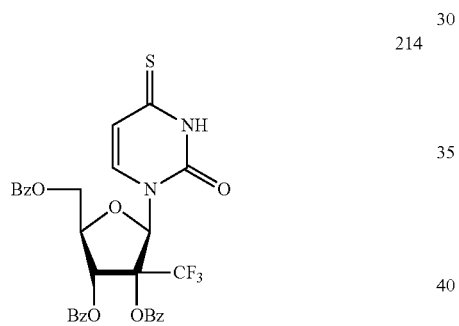

A stirred solution of benzoate (1 g, 1.37 mmol) in dioxane (6.9 mL, 0.2M) was charged with Lawesson's reagent (673 mg, 1.66 mmol) and was heated to reflux, during which time reaction became homogeneous and brown. After 2 h, reaction was concentrated and purified by silica gel chromatography 10-30% ethyl acetate in hexanes to provide 600 mg of thiouridine 68%.

Example 79

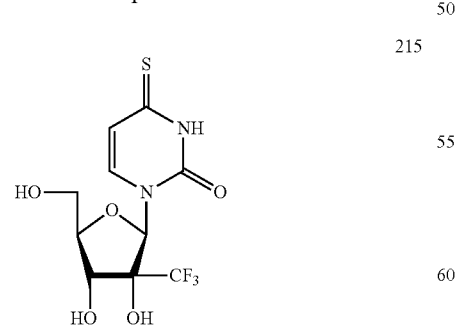

A stirred solution of benzoate (600 mg, 2.08 mmol) in ammonia (9 mL, 7M in methanol) was prepared. After 16H, reaction was concentrated and purified by silica gel chromatography 2-15% methanol in dcm to provide 269 mg of thiourdine 87%.

Example 80

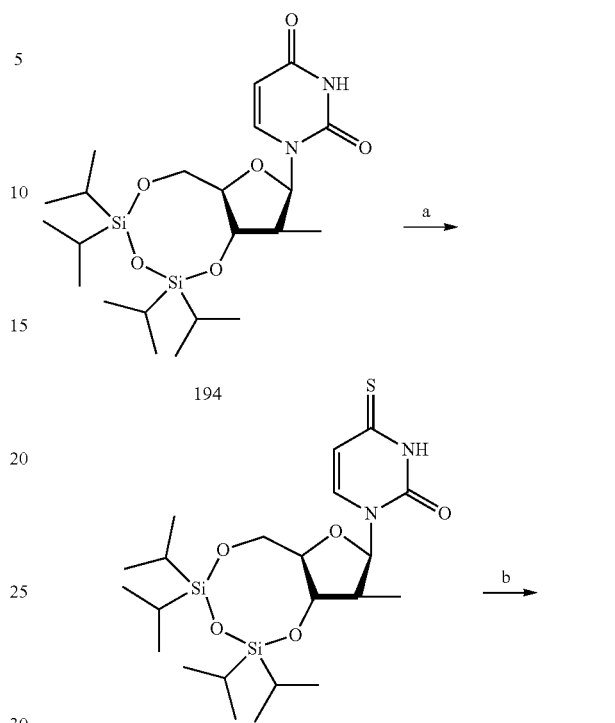

Reagents and conditions: a) dioxane, Lawesson's reagent, reflux; b) TBAF, THF

Example 81

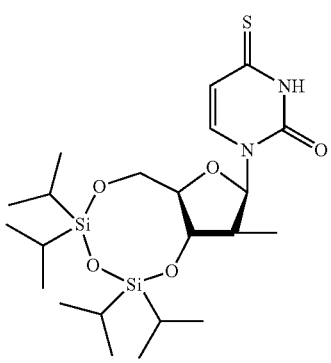

1-((6aR,8R,9S,9aR)-2,2,4,4-tetraisopropyl-9-methyltetrahydro-6H-furo[3,2-f][1,3,5,2,4]trioxadisilocin-8-yl)pyrimidine-2,4(1H,3H)-dione (0.16 g, 0.33 mmol) was heated with Lawesson's reagent (0.17 g, 0.43 mmol) in dry 1,4-dioxane (1.65 mL) under argon for 1 h. Then solvent was removed in vacuo and the crude material was purified by ISCO column chromatography eluting from 10% to 40% EtOAc in hexanes to afford 1-((6aR,8R,9S,9aR)-2,2,4,4-tetraisopropyl-9-methyltetrahydro-6H-furo[3,2-f][1,3,5,2,4]trioxadisilocin-8-yl)-4-thioxo-3,4-dihydropyrimidin-2(1H)-one (0.11 g, 67%) as a yellow solid.

$^1$H NMR (400 MHz, CDCl$_3$) δ 9.33 (bs, 1H), 7.68 (d, J=7.6 Hz, 1H), 6.40 (dd, J=7.6, 1.6 Hz), 6.20 (d, J=7.2 Hz, 1H), 4.18 (d, J=13.6 Hz, 1H), 4.04-3.89 (m, 2H), 3.78 (dd, J=8.8, 2.4 Hz, 1H), 2.71-2.62 (m, 1H), 1.12-0.84 (m, 31H).

Example 82

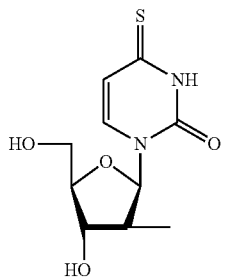

217

1-((6aR,8R,9S,9aR)-2,2,4,4-tetraisopropyl-9-methyltetrahydro-6H-furo[3,2-f][1,3,5,2,4]trioxadisilocin-8-yl)-4-thioxo-3,4-dihydropyrimidin-2(1H)-one (0.11 g, 0.22 mmol) was stirred with TBAF (1.0 M in THF, 0.44 mL, 0.44 mmol) at rt overnight. Then solvent was removed in vacuo and the crude material was purified by SiO2 column chromatography eluting from 100% DCM to 4% MeOH in DCM to afford 1-((2R,3S,4R,5R)-4-hydroxy-5-(hydroxymethyl)-3-methyltetrahydrofuran-2-yl)-4-thioxo-3,4-dihydropyrimidin-2(1H)-one (33 mg, 58%) as a yellow solid.

$^1$H NMR (400 MHz, CD$_3$OD) δ 7.81 (d, J=7.6 Hz 1H), 6.38 (d, J=8.0 Hz, 1H), 6.17 (d, J=7.6 Hz, 1H), 3.96-3.71 (m, 4H), 2.53-2.50 (m, 1H), 0.96 (d, J=7.2 Hz, 3H).

LCMS C$_{10}$H$_{13}$N$_2$O$_4$S [M+H$^+$]; calculated: 257.1, found 256.9.

Example 83

Synthetic Route for the Synthesis of 2'-Fluoro-2-Thiouridine Nucleoside Analogs

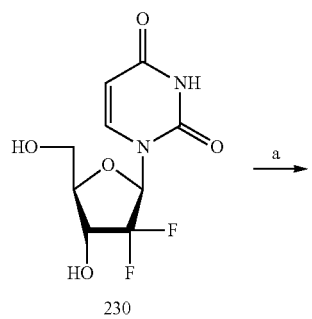

230

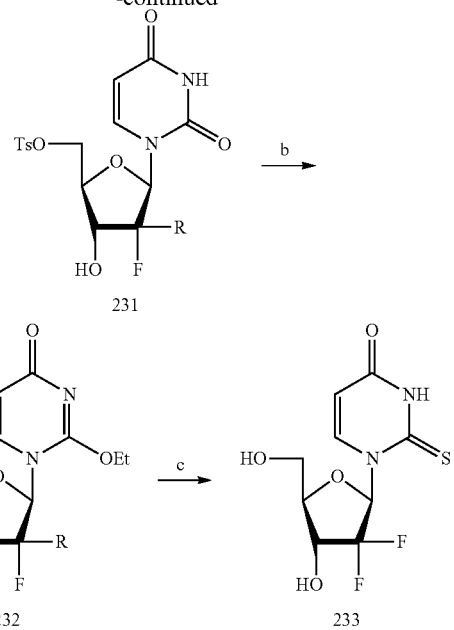

Reagents and conditions: a) tosyl chloride, Et$_3$N, DMAP; b) NaHCO$_3$, ethanol, reflux; c) NaSH, DMF 2'-Fluoro-2-thiouridine nucleoside analogs can be made by treating the parent nucleoside (1 equivalent) with tosyl chloride (1.2 equivalents) dissolved in pyridine:DCM (1:1) under an inert atmosphere. The resulting 5'-tosyl nucleoside analog can then be treated with sodium bicarbonate (5 equivalents) in reflux ethanol to obtain the 2-ethoxy nucleoside. Finally, the desired 2-thionucleoside analog can be obtained by treating the 2-ethoxy intermediate with sodium hydrosulfide (10 equivalents) in a polar solvent such as DMF.

Example 84

Synthetic Route for the Synthesis of 2'-Fluoro-2'-Methyl-2-Thiouridine Nucleoside Analogs

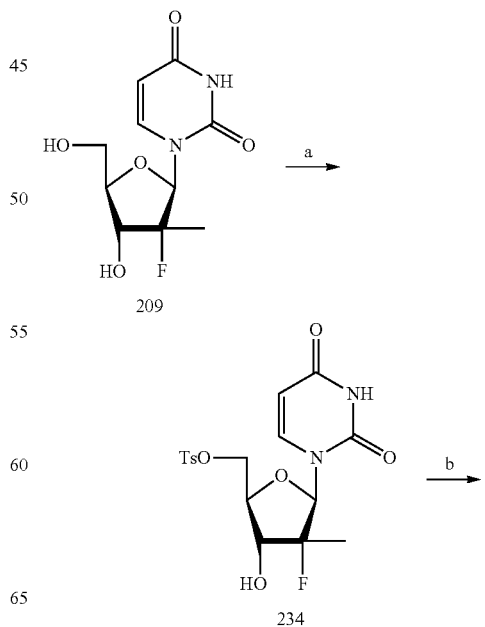

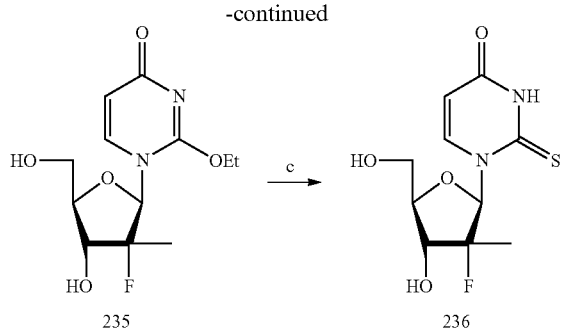

Reagents and conditions: a) tosyl chloride, Et₃N, DMAP; b) NaHCO₃, ethanol, reflux; c) NaSH, DMF 2'-Fluoro-2'-methyl-2-thiouridine nucleoside analogs can be made by treating the parent nucleoside (1 equivalent) with tosyl chloride (1.2 equivalents) dissolved in pyridine:DCM (1:1) under an inert atmosphere. The resulting 5'-tosyl nucleoside analog can then be treated with sodium bicarbonate (5 equivalents) in reflux ethanol to obtain the 2-ethoxy nucleoside. Finally, the desired 2-thionucleoside analog can be obtained by treating the 2-ethoxy intermediate with sodium hydrosulfide (10 equivalents) in a polar solvent such as DMF.

Example 85

Synthetic Route for the Synthesis of 2'-C-Methyl-2-Thiouridine Nucleoside Analogs

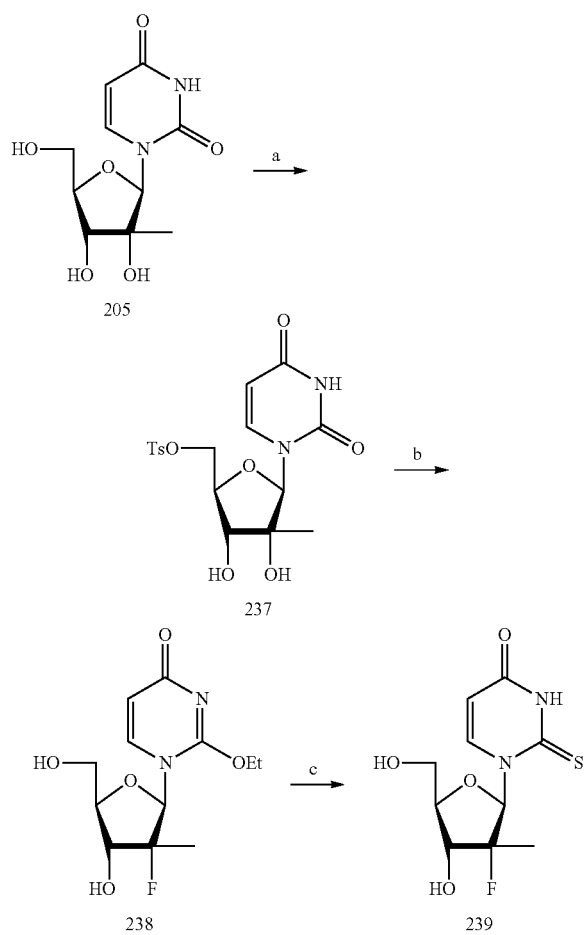

Reagents and conditions: a) tosyl chloride, Et₃N, DMAP; b) NaHCO₃, ethanol, reflux; c) NaSH, DMF 2'-C-methyl-2-thiouridine nucleoside analogs can be made by treating the parent nucleoside (1 equivalent) with tosyl chloride (1.2 equivalents) dissolved in pyridine:DCM (1:1) under an inert atmosphere. The resulting 5'-tosyl nucleoside analog can then be treated with sodium bicarbonate (5 equivalents) in reflux ethanol to obtain the 2-ethoxy nucleoside. Finally, the desired 2-thionucleoside analog can be obtained by treating the 2-ethoxy intermediate with sodium hydrosulfide (10 equivalents) in a polar solvent such as DMF.

Example 86

Alternative Synthetic Route for the Synthesis of 2'-C-Methyl-2-Thiouridine Nucleoside Analogs

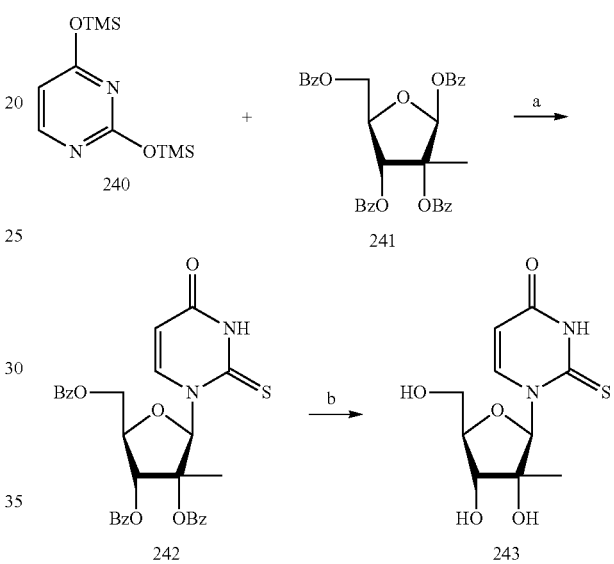

Reagents and conditions: a) SnCl₄, DCE, rt; b) NH₃/MeOH

Example 87

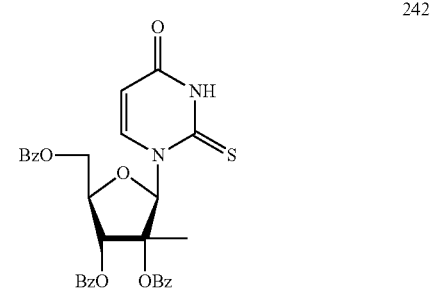

The persilylated 2-thiouracil was prepared in a round bottom flask charged with 2-thiouracil (1.99 g, 15.5 mmol), chlorotrimethylsilane (1.55 mL, 12.21 mmol), and bis(trimethylsilyl)amine (46.5 mL, 222 mmol) under nitrogen. The mixture was refluxed with stirring overnight (16 h) until all solids dissolved and a blue-green solution formed. The mixture was cooled to room temperature and volatiles were removed by rotary evaporation followed by high vacuum to give persilylated 2-thiouracil as a light blue liquid. This compound was used immediately in the next step.

The freshly prepared persilylated 2-thiouracil 240 (4.22 g, 15.50 mmol) was dissolved in 1,2-dichloroethane (50 mL) under nitrogen with stirring at room temperature. A solution of 241 (4.50 g, 7.75 mmol) in 1,2-dichloroethane (50 mL) was added all at once to the stirred mixture.

To this mixture was added SnCl$_4$ (1.36 mL, 3.03 g, 11.63 mmol) dropwise via syringe, and the mixture was stirred at room temperature 6 h until all starting material was consumed. The mixture was cooled to 0° C. and a sat. aq. NaHCO$_3$ solution (125 mL) was added. The mixture was warmed to room temperature and stirred 30 min. The mixture was extracted with EtOAc (2×200 mL) and the combined organic layers were washed with brine (1×100 mL), dried over Na$_2$SO$_4$, filtered, and concentrated by rotary evaporation to give 5.5 g crude product. The crude material was taken up in dichloromethane, immobilized on Celite, and subjected to flash chromatography on the Combiflash (120 g column, 5 to 50% EtOAc in hexanes gradient) to give 242 (2.41 g, 53%) as a clear sticky solid in ~90% purity. This material was used directly in the next step without further purification. $^1$H NMR (400 MHz, CDCl$_3$) δ ppm 9.37 (br s, 1H), 8.10-8.05 (m, 4H), 7.82 (d, J=7.7 Hz, 2H), 7.70 (d, J=8.3 Hz, 1H), 7.66-7.45 (m, 6H), 7.42 (t, J=7.8 Hz, 2H), 7.27-7.21 (m, 2H), 5.88 (d, J=8.2 Hz, 1H), 5.62 (d, J=5.5 Hz, 1H), 4.91-4.83 (m, 2H), 4.77 (dd, J=11.8 Hz, 4.7 Hz, 1H), 1.77 (s 3H).

Example 88

243

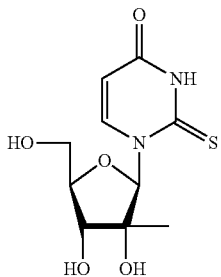

A round bottom flask was charged with 242 (2.41 g, 4.11 mmol) under nitrogen and cooled to 0° C. To this flask was added a ~7.0 N solution of ammonia in methanol (58.7 mL, 411 mmol) and the mixture was gently stirred and allow to warm to room temperature overnight. After 24 h stirring at room temperature, volatiles were removed by rotary evaporation to give 2.5 g of crude material. The crude material was taken up in MeOH, immobilized on Celite, and subjected to flash chromatography on the Combiflash (80 g column, 0 to 10% EtOH in EtOAc gradient) to give 243 (0.873 g, 41% two-step yield from scaffold) as an off-white solid. $^1$H NMR (400 MHz, MeOH-d$_4$) S ppm 8.27 (d, J=8.2 Hz, 1H); 6.95 (s, 1H), 5.95 (d, 1H, J=8.1 Hz), 3.98 (dd, J=12.5 Hz, 2.1 Hz, 1H), 3.93 (dt, J=9.3 Hz, 2.1 Hz, 1H), 3.84 (d, J=9.4 Hz, 1H), 3.78 (dd, J=12.5 Hz, 2.3 Hz), 1.24 (s, 3H).

Example 89

General Procedure for the Preparation of 5'-Phosphoramidate Prodrugs Synthesis of Chlorophosphoramidate:

251

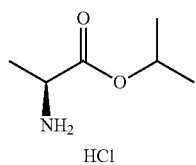

Thionyl chloride (80 g, 49.2 mL, 673 mmol) was added dropwise over a 30 min period to a suspension of L-alanine (50 g, 561 mmol) in isopropanol (500 mL). The mixture was heated to a gentle reflux for 5 h and then concentrated by rotary evaporator (bath set at 60° C.). The resulting thick gum solidified upon trituration with ether (150 ml). The white powder was triturated a second time with ether (150 mL), collected by filtration while under a stream of argon, and then dried under high vacuum for 18 h to give (S)-isopropyl 2-aminopropanoate hydrochloride (88 g, 94%).

$^1$H NMR (400 MHz, DMSO-d$_6$) δ 8.62 (s, 3H), 5.10-4.80 (m, 1H), 3.95 (q, J=7.2 Hz, 1H), 1.38 (d, J=7.2 Hz, 3H), 1.22 (d, J=4.6 Hz, 3H), 1.20 (d, J=4.6 Hz, 3H).

Example 90

252

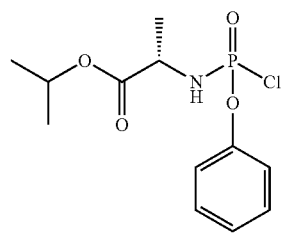

A solution of phenyl dichlorophosphate (30.9 g, 146 mmol) in dichloromethane (450 mL) was cooled to 0° C. then treated with (S)-isopropyl 2-aminopropanoate hydrochloride (24.5 g, 146 mmol). The mixture was further cooled to −78° C. and then treated dropwise with triethylamine (29.6 g, 40.8 mL, 293 mmol) over a 30 min period. The mixture continued to stir at −78° C. for an additional 2 h and then allowed to gradually warm to rt. After 18 h the mixture was concentrated to dryness and the resulting gum dissolved in anhydrous ether (150 mL). The slurry was filtered while under a stream of argon, and the collected solid washed with small portions of anhydrous ether (3×30 mL). Combined filtrates were concentrated to dryness by rotary evaporator to give a 1:1 diastereomeric mixture of phosphochloridate (41.5 g, 93%) as pale yellow oil.

$^1$H NMR (300 MHz, Chloroform-d) δ 7.43-7.14 (m, 5H), 5.06 (m, 1H), 4.55 (dd, J=14.9, 7.0 Hz, 1H), 4.21-4.01 (m, 1H), 1.48 (d, J=7.0 Hz, 2H), 1.27 (d, J=6.2 Hz, 3H), 1.26 (d, J=5.8 Hz, 3H).

$^{31}$P NMR (121 MHz, Chloroform-d) δ 8.18 and 7.87.

Example 91

Synthesis of 2-chloro-4-nitrophenyl Phosphoramidate

253

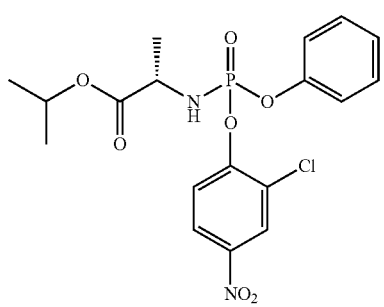

A solution of phenyl dichlorophosphate (60 g, 42.5 mL, 284 mmol) in dichloromethane (300 mL) was cooled to 0° C. and then treated with (S)-isopropyl 2-aminopropanoate hydrochloride (47.7 g, 284 mmol). The mixture was further cooled to −78° C. and treated dropwise with a solution of triethylamine (57.6 g, 79 mL, 569 mmol) in methylene chloride (300 mL) over a 1 h period. The reaction mixture was warmed to 0° C. for 30 min and then treated with a preformed mixture of 2-chloro-4-nitrophenol (46.9 g, 270 mmol) and triethylamine (28.8 g, 39.6 mL, 284 mmol) in dichloromethane (120 mL) over a 20 min period. After 2 h at 0° C., the mixture was filtered through a fitted funnel, and the collected filtrate concentrated to dryness. The crude gum was dissolved MTBE (500 mL) and washed with 0.2 M $K_2CO_3$ (2×100 mL) followed by 10% brine (3×75 mL). The organic phase was dried over sodium sulfate, filtered and concentrated to dryness by rotary evaporator to give a diastereomeric mixture (100 g, 93%) as a pale yellow oil.

$^1$H NMR (400 MHz, Chloroform-d) δ 8.33 (dd, J=2.7, 1.1 Hz, 1H, diastereomer 1), 8.31 (dd, J=2.7, 1.1 Hz, 1H, diastereomer 2), 8.12 (dd, J=9.1, 2.7 Hz, 1H), 7.72 (dt, J=9.1, 1.1 Hz, 1H), 7.40-7.31 (m, 2H), 7.28-7.19 (m, 6H), 5.01 (pd, J=6.3, 5.2 Hz, 1H), 4.22-4.08 (m, 1H), 3.96 (td, J=10.7, 9.1, 3.6 Hz, 1H), 1.43 (dd, J=7.0, 0.6 Hz, 3H), 1.40 (dd, J=7.2, 0.6 Hz, 3H, diastereomer 2), 1.25-1.20 (m, 9H).

Example 92

Separation of Compound 253 Diastereomers:

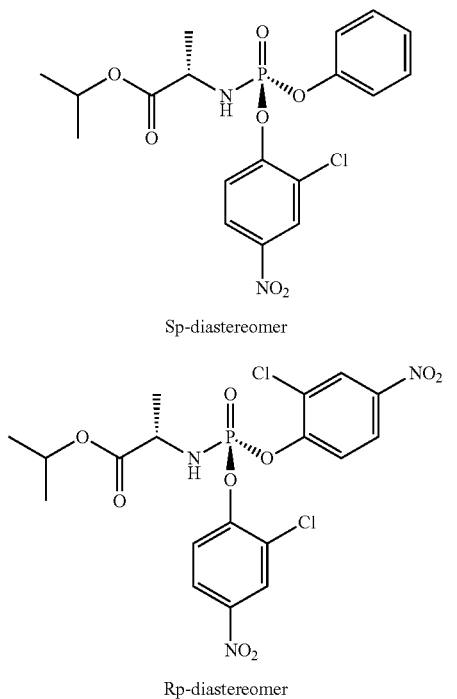

The diastereomeric mixture 253 (28 g, 63.2 mmol) was dissolved in 2:3 ethyl acetate:hexanes (100 mL) and cooled to −20° C. After 16 h, the resulting white solid was collected by filtration and dried under high vacuum to give a 16:1 $S_p:R_p$-diastereomeric mixture (5.5 g, 19.6%). The mother liquor was concentrated and the resulting residue dissolved in 2:3 ethyl acetate:hexanes (50 mL). After 16 h at −10° C., the resulting white solid was collected and dried under high vacuum to give a 1:6 $S_p:R_p$-diastereomeric mixture (4 g, 14%). The 16:1 $S_p:R_p$-diastereomeric mixture (5.5 g, 12.4 mmol) was suspended in hot hexanes (50 mL) and treated slowly with ethyl acetate (approximately 10 mL) until complete dissolution. After cooling to 0° C., the resulting white solid was collected by filtration, washed with hexanes, and dried under high vacuum to give the $S_p$-diastereomer of 254 (4.2 g, 76%) as a single isomer.

$^1$H NMR ($S_p$-diastereomer, 400 MHz, Chloroform-d) δ 8.33 (dd, J=2.7, 1.1 Hz, 1H), 8.12 (dd, J=9.1, 2.7 Hz, 1H), 7.71 (dd, J=9.1, 1.2 Hz, 1H), 7.41-7.30 (m, 2H), 7.29-7.11 (m, 3H), 5.00 (m, 1H), 4.25-4.07 (m, 1H), 3.97 (dd, J=12.7, 9.4 Hz, 1H), 1.43 (d, J=7.0 Hz, 3H), 1.23 (d, J=2.2 Hz, 3H), 1.21 (d, J=2.2 Hz, 3H).

The 1:6 $S_p:R_p$-diastereomeric mixture (4 g, 12.4 mmol) was suspended in hot hexanes (50 mL) and treated slowly with ethyl acetate (approximately 5 mL) until complete dissolution. After cooling to 0° C., the resulting white solid was collected by filtration, washed with hexanes, and dried under high vacuum to give the $R_p$-diastereomer of 255 (3.2 g, 80%) as a single isomer. Absolute stereochemistry was confirmed by X-ray analysis.

$^1$H NMR ($R_p$-diastereomer, 400 MHz, Chloroform-d) δ 8.31 (dd, J=2.7, 1.1 Hz, 1H), 8.11 (dd, J=9.1, 2.7 Hz, 1H), 7.72 (dd, J=9.1, 1.2 Hz, 1H), 7.42-7.30 (m, 2H), 7.31-7.14 (m, 3H), 5.01 (p, J=6.3 Hz, 1H), 4.15 (tq, J=9.0, 7.0 Hz, 1H), 4.08-3.94 (m, 1H), 1.40 (d, J=7.0 Hz, 3H), 1.24 (d, J=3.5 Hz, 3H), 1.22 (d, J=3.5 Hz, 3H).

Example 93

General Procedure for Phosphoramidate Prodrug Formation:

The desired nucleoside (1 equivalent) to be converted into its 5'-phosphoramidate prodrug was dried in a vacuum oven at 50° C. overnight. The dry nucleoside is placed in a dry flask under an inert atmosphere and suspended in either dry THF or dry DCM to achieve a 0.05M solution. The flask was then cooled to 0° C., and the chlorophosphoramidate reagent (5 equivalents) was added to the suspended nucleoside. Next, 1-methylimidazole (8 equivalents) was added to the reaction mixture dropwise. The reaction was allowed to stir at room temperature for 12-72 hours. After the reaction was complete as judged by TLC, the reaction mixture was diluted with ethyl acetate. The diluted reaction mixture was then washed with saturated aqueous ammonium chloride solution. The aqueous layer was re-extracted with ethyl acetate. The combined organic layers were then washed with brine, dried over $MgSO_4$, filtered, and concentrated. The concentrated crude product was then purified on silica eluting with a gradient of DCM to 5% MeOH in DCM.

Example 94

5'-Phosphoramidate Prodrugs Synthesized Utilizing the General Procedure

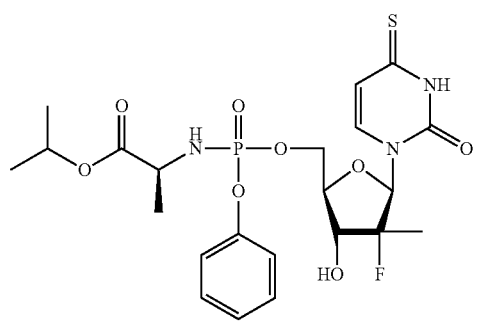

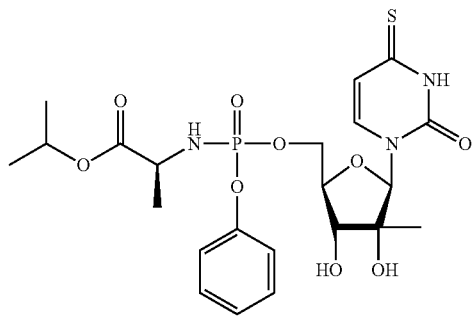

260

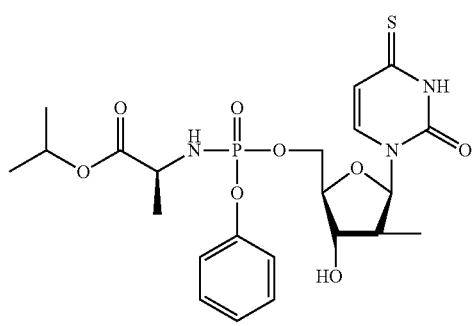

261

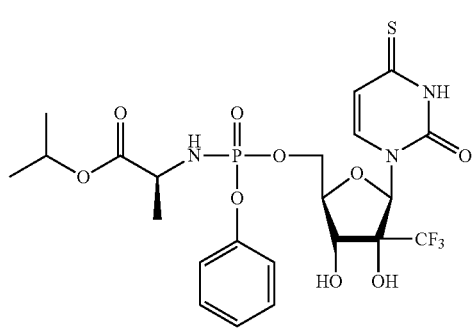

264

Example 95

Procedure for Synthesis of 2'-C-Methyl-2-Thiouridine-5'-Phosphoramidate

275

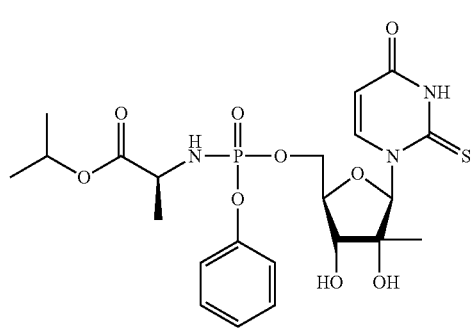

The desired nucleoside (1 equivalent) to be converted into its 5'-phosphoramidate prodrug was dried in a vacuum oven at 50° C. overnight. To a stirred solution of 1-((2R,3R,4R,5R)-3,4-dihydroxy-5-(hydroxymethyl)-3-methyltetrahydrofuran-2-yl)-2-thioxo-2,3-dihydropyrimidin-4(1H)-one (100 mg, 0.365 mmol) in THF (4 ml) at 0° C. under nitrogen, was added (2S)-isopropyl 2-((chloro(phenoxy)phosphoryl)amino)propanoate (334 mg, 1.094 mmol) in THF (2.000 ml) dropwise via syringe. The stirred mixture was treated with 1-methyl-1H-imidazole (0.145 ml, 1.823 mmol) dropwise via syringe over 5 min. The mixture was slowly warmed to rt and stirred overnight. After 20 h stirring, the mixture was concentrated by rotary evaporation and taken up in 2 mL EtOH. A quick column on the Isco (12 g column, 0 to 3% EtOH in EtOAc) removed most baseline impurities to give 220 mg of compound. A second column on the Isco (12 g column, 0 to 3% EtOH in EtOAc) removed the less polar impurities but the more polar ones streaked with the product. 170 mg total were recovered. A third column on the Isco (12 g column, 0 to 10% MeOH in DCM) gave good separation and produced the desired product (93 mg, 0.171 mmol, 46.9% yield).

Example 96

Synthesis of (S,Sp)-diastereomer of Compound 275

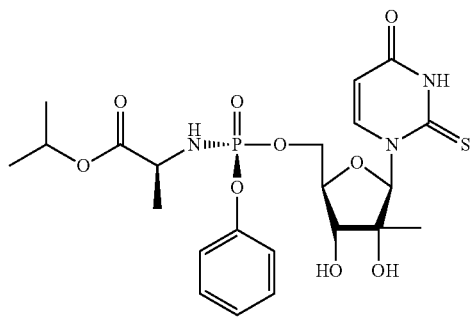

276

To a dry 50 ml flask was added 1-((2R,3R,4R,5R)-3,4-dihydroxy-5-(hydroxymethyl)-3-methyltetrahydrofuran-2-yl)-2-thioxo-2,3-dihydropyrimidin-4(1H)-one (0.5 g, 1.823 mmol) and THF (20 ml) and suspension was cooled in ice bath under nitrogen. tert-butylmagnesium chloride (2.260 ml, 2.260 mmol) was added via syringe and clear solution was formed. The mixture was stirred at ambient temp for 30 minutes and cooled to 0° C. again. A solution of compound 254 in THF (20 ml) was added via syringe over 10 min. period at 0° C. The resulting yellowish color solution was stirred at RT for overnight.

The reaction was quenched with saturated ammonium chloride solution and extracted with ethyl acetate. The organic layer washed with 5% K2CO3 solution, water and brine dried and concentrated under reduced pressure to give crude product. TLC 5% MeOH/DCM: SM Rf=0.25 and product Rf=0.5. The product was purified on 20 g of $SiO_2$ and eluting with 500 ml 3% MeOH in DCM. Desired fractions were combined and concentrated to give TLC single spot product. Small amount was crystallized as a plates by dissolving in toulene and allowing it to stand at RT for few weeks.

$^1$H NMR (400 MHz, Methanol-$d_4$) δ 7.76 (d, J=8.1 Hz, 2H), 7.38 (t, J=7.9 Hz, 2H), 7.34-7.13 (m, 3H), 6.98 (s, 1H), 5.87 (d, J=8.1 Hz, 1H), 5.06-4.89 (m, 1H), 4.53 (ddd, J=11.8, 5.8, 2.0 Hz, 1H), 4.39 (ddd, J=11.9, 5.8, 3.3 Hz, 1H), 4.11 (dp, J=7.9, 2.2 Hz, 1H), 3.92 (dq, J=9.9, 7.0 Hz, 1H), 3.78 (d, J=9.4 Hz, 1H), 1.36 (dd, J=7.2, 1.0 Hz, 3H), 1.24 (s, 3H), 1.23 (d, J=1.5 Hz, 3H), 1.21 (d, J=1.5 Hz, 3H).

MS C$_{22}$H$_{31}$N$_3$O$_9$PS [M+H$^+$]; calculated: 544.1, found: 544.1.

Example 97

Synthesis of (S,Rp)-diastereomer of Compound 275

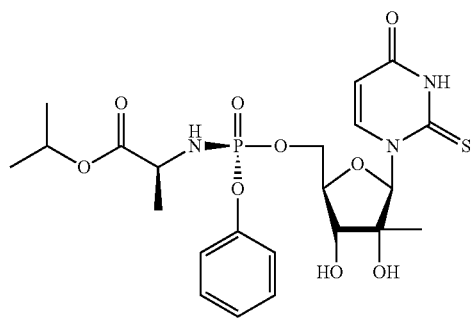

277

To a dry 50 ml flask was added 1-((2R,3R,4R,5R)-3,4-dihydroxy-5-(hydroxymethyl)-3-methyltetrahydrofuran-2-yl)-2-thioxo-2,3-dihydropyrimidin-4(1H)-one (0.5 g, 1.823 mmol) and THF (20 ml) and suspension was cooled in ice bath under nitrogen. tert-butylmagnesium chloride (2.260 ml, 2.260 mmol) was added via syringe and clear solution was formed. The mixture was stirred at ambient temp for 30 minutes and cooled to 0° C. again. A solution of compound 255 in THF (20 ml) was added via syringe over 10 min. period at 0° C. The resulting yellowish color solution was stirred at RT for overnight.

The reaction was quenched with saturated ammonium chloride solution and extracted with ethyl acetate. The organic layer washed with 5% K2CO3 solution, water and brine dried and concentrated under reduced pressure to give crude product. TLC 5% MeOH/DCM: SM Rf=0.25 and product Rf=0.5. The product was purified on 20 g of SiO$_2$ and eluting with 500 ml 3% MeOH in DCM. Desired fractions were combined and conc to give TLC single spot product.

1H NMR (400 MHz, Methanol-d$_4$) δ 7.78 (d, J=8.1 Hz, 1H), 7.38 (t, J=7.9 Hz, 2H), 7.31-7.14 (m, 3H), 6.98 (s, 1H), 5.91 (d, J=8.1 Hz, 1H), 4.99 (mz, 1H), 4.60 (ddd, J=11.9, 4.8, 2.1 Hz, 1H), 4.43 (ddd, J=11.8, 5.3, 2.6 Hz, 1H), 4.18-3.98 (m, 1H), 3.90 (dq, J=9.3, 7.2 Hz, 1H), 3.78 (d, J=9.4 Hz, 1H), 1.32 (dd, J=7.1, 1.3 Hz, 3H), 1.23 (m, 8H).

MS C$_{22}$H$_{31}$N$_3$O$_9$PS [M+H$^+$]; calculated: 544.1, found: 544.1.

Example 98

General Procedure for Preparation of 5'-Triphosphates:

Nucleoside analogue was dried under high vacuum at 50° C. for 18 h and then dissolved in anhydrous trimethylphosphate (0.3 M). After addition of proton-Sponge® (1.5 molar equiv), the mixture was cooled to 0° C. and treated dropwise with phosphoryl chloride (1.3 molar equiv) via microsyringe over a 15 min period. The mixture continued stirring at 0° C. for 4 to 6 h while being monitored by tlc (7:2:1 isopropanol: conc. NH$_4$OH: water). Once greater than 85% conversion to the monophosphate, the reaction mixture was treated with a mixture of bis(tri-n-butylammonium pyrophosphate) (3 molar equiv) and tributylamine (6 molar equiv) in anhydrous DMF (1 mL). After 20 min at 0° C. with monitoring by tlc (11:7:2 NH$_4$OH: isopropanol: water), the mixture was treated with 20 mL of a 100 mM solution of triethylammonium bicarbonate (TEAB), stirred for 1 h at rt and then extracted with ether (3×15 mL). The aqueous phase was then purified by anion-exchange chromatography over DEAE Sephadex® A-25 resin (11×200 mm) using a buffer gradient from 50 mM (400 mL) to 600 mM (400 mL) TEAB. Fractions of 10 mL were analyzed by tlc (11:7:2 NH$_4$OH: isopropanol:water). Triphosphate (eluted @ 500 mM TEAB) containing fractions were combined and concentrated by rotary evaporator (bath <25° C.). The resulting solid was reconstituted in DI water (10 mL) and concentrated by lyophilization.

Example 99

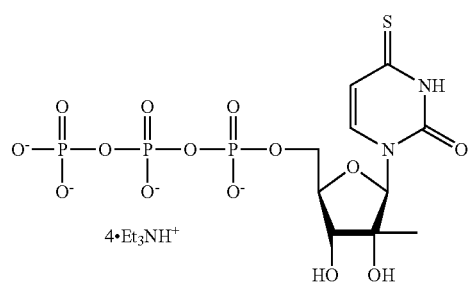

280

Triphosphate was prepared according to the general procedure.

Physical data: $^1$H NMR (400 Hz, D$_2$O): δ 1.226 (s, 3H), 1.280 (t, 36H, J=7.2 Hz), 3.202 (q, 24H, J=7.2 Hz), 4.143 (m, 2H), 4.363 (dq, 2H, J$_1$=12.8 Hz, J$_2$=1.2 Hz), 6.006 (s, 1H), 6.666 (d, 1H, J=7.6 Hz), 7.889 (d, 1H, J=7.2 Hz); MS (negative ion): m/z 512.9 (M−H).

Example 100

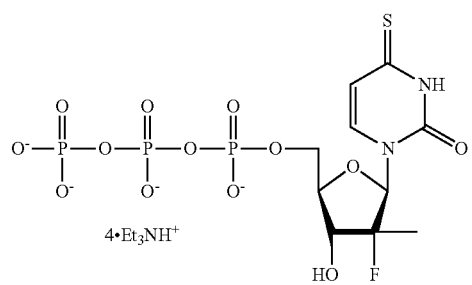

281

Triphosphate was prepared according to the general procedure.

Physical data: $^1$H NMR (400 Hz, D$_2$O): δ 1.402 (d, 3H, J=23.2 Hz), 1.262 (t, 36H, J=7.2 Hz), 3.186 (q, 24H, J=7.2 Hz), 4.314 (m, 4H), 6.212 (d, 1H, J=18.8 Hz), 6.650 (d, 1H, J=7.6 Hz), 7.770 (d, 1H, J=7.6 Hz); MS (negative ion): m/z 514.9 (M−H).

Example 101

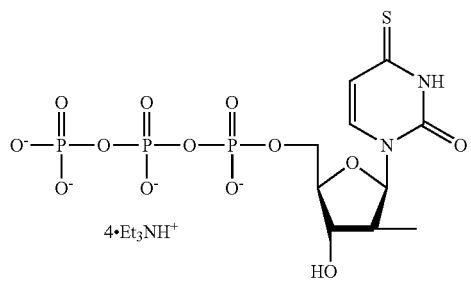

Following the General Procedure for making triphosphate, ((2R,3S,4R,5R)-3-hydroxy-4-methyl-5-(2-oxo-4-thioxo-3,4-dihydropyrimidin-1(2H)-yl)tetrahydrofuran-2-yl)methyl tetrahydrogen triphosphate (4 mg, 3.5%) was obtained as a yellow solid as tetra-triethylammonium salt.

$^1$H NMR (400 MHz, D$_2$O) δ 7.84 (d, J=7.6 Hz, 1H), 6.66 (d, J=7.6 Hz, 1H), 6.29 (d, J=7.6 Hz, 1H), 4.33 (bs, 2H), 4.13 (t, J=8.8, 1H), 4.00 (d, J=7.2 Hz, 1H), 3.21 (q, J=6.8 Hz, 24H), 2.72-2.64 (m, 1H), 1.27 (t, J=7.2 Hz, 36H).

Example 102

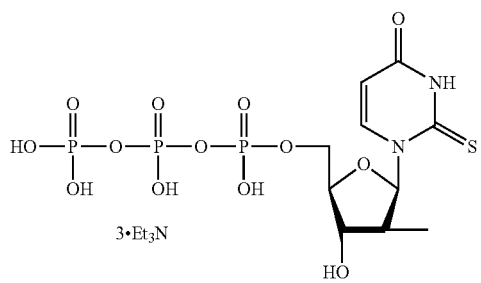

Following the General Procedure for making triphosphates, ((2R,3S,4R,5R)-3-hydroxy-4-methyl-5-(4-oxo-2-thioxo-3,4-dihydropyrimidin-1(2H)-yl)tetrahydrofuran-2-yl)methyl tetrahydrogen triphosphate (69 mg, 44%) was obtained as a white solid as a triple triethylamine salt.

$^1$H NMR (400 MHz, D$_2$O) δ 8.07 (d, J=8.0 Hz, 1H), 7.14 (d, J=8.0 Hz, 1H), 6.24 (d, J=7.2 Hz, 1H), 4.35 (bs, 2H), 4.20 (t, J=8.4 Hz, 1H), 4.03-4.01 (m, 1H), 3.21 (q, J=7.6 Hz, 18H), 2.80-2.73 (m, 1H), 1.28 (t, J=7.6 Hz, 27H), 1.00 (d, J=7.2 Hz, 3H).

$^{31}$P NMR (121 MHz, D$_2$O) δ −6.03 (d, J=21.1 Hz, γP), −10.52 (d, J=20.2 Hz, αP), −21.76 (t, J=20.7 Hz, βP).

HRMS C$_{10}$H$_{16}$N$_2$O$_{13}$P$_3$S [M−H$^+$]; calculated: 496.9664, found 496.9586.

Example 103

Method for the Synthesis of 2'-C-Methyl-2-Thiouridine-5'-Triphosphate

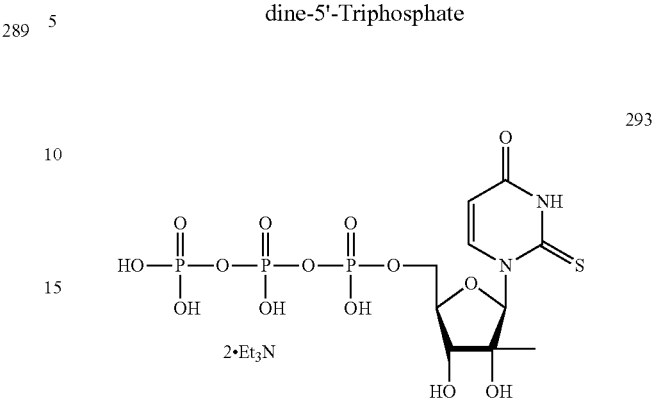

After drying under high vacuum at 50° C. for 18 h, 2'-C-methyl-2-thiouridine (29 mg, 0.106 mmol) was dissolved in anhydrous trimethylphosphate (0.4 mL) and treated with proton-Sponge® (34 mg, 0.159 mmol). The mixture was cooled to 0° C. and treated dropwise with phosphoryl chloride (13 μL, 0.137 mmol, 1.3 equiv) via microsyringe over a 5 min period. After 2 h at 0° C., tlc (7:2:1 isopropanol: conc. NH$_4$OH: water) showed mostly starting material indicating the parent nucleoside was slow to react under standard conditions. The mixture then was treated incrementally (10 μL/hr) with additional phosphoryl chloride (40 μL, 0.137 mmol, 4 equiv.), and after 5 h tlc indicated complete conversion to the monophosphoryl dichloridate intermediate. While still at 0° C., the reaction mixture was treated dropwise with a solution containing bis(tri-n-butylammonium pyrophosphate) (145 mg, 0.264 mmol) and tributylamine (153 μL, 0.634 mmol) in anhydrous DMF (1 mL). After 20 min at 0° C., the mixture was quenched with 20 mL of a 100 mM solution of triethylammonium bicarbonate (TEAB), stirred for 1 h with warming to rt and then extracted with ether (3×15 mL). The aqueous phase was purified by anion-exchange chromatography over DEAE Sephadex® A-25 resin (11×200 mm) using a buffer gradient from 50 mM (400 mL) to 600 mM (400 mL) TEAB. Fractions of 8 mL were first analyzed by tlc (11:7:2 NH$_4$OH: isopropanol: water), and then the triphosphate containing fractions were further analyzed by phosphorus NMR to ensure the product was free of inorganic phosphate (Product mixture contained high concentration of inorganic phosphate because of excess phosphoryl chloride needed to initiate phosphorylation of this unreactive nucleoside analogue). Pure triphosphate (eluted @ 500 mM TEAB) containing fractions were combined and concentrated by rotary evaporator (bath <25° C.). The resulting solid was reconstituted in DI water (10 mL) and concentrated by lyophilization to give 2'-C-methyl-2'-thiouridine-5'-triphosphate (25 mg, 33%) as a bis(triethylammonium salt).

$^1$H NMR (400 MHz, Deuterium Oxide) δ 8.01 (d, J=7.9 Hz, 1H), 7.08 (s, 2H), 6.20 (d, J=7.9 Hz, 2H), 4.36 (m, 2H), 4.14 (m, 2H), 3.19 (q, J=7.3 Hz, 12H), 1.27 (t, J=7.3 Hz, 20H).

$^{31}$P NMR (162 MHz, Deuterium Oxide) δ −8.81 (d, J=20.6 Hz), −13.70 (d, J=19.9 Hz), −24.82 (t, J=20.6 Hz).

HRMS C$_{10}$H$_{17}$N$_2$O$_{14}$P$_3$S [M−H$^+$]; calculated: 512.95287, found: 512.95406.

Example 104

Synthesis of Nucleotide Alaninyl Phosphate

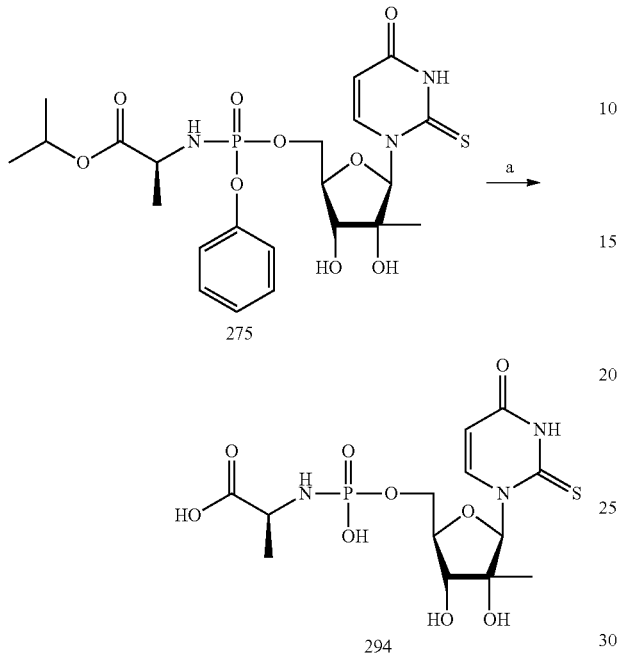

Reagents and conditions: a) Et₃N, H₂O, 37° C.

Example 105

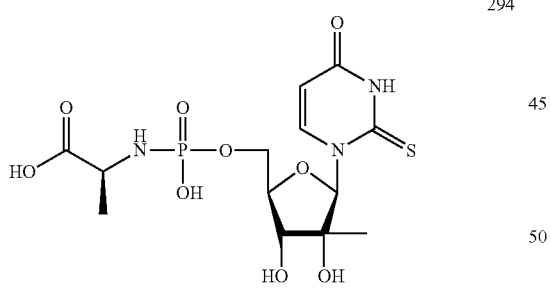

The parent nucleotide 5'-phosphoramidate (0.1 mmol) was suspended in triethylamine (5 mL) and distilled water (5 mL) in a round bottom flask at room temperature. The reaction mixture was stirred at 37° C. for 24 hours, and then the solvents were removed under reduced pressure. The crude residue was purified on silica eluting with 2-propanol, water, ammonia (8:1:1). The fractions containing the desired product were pooled and concentrated under reduced pressure to remove most of the volatiles. The remaining aqueous solution was transferred to a vial, and was then frozen in a dry ice/acetone bath. The material was then freeze-dried to provide the desired product as a white solid.

Example 106

Synthesis of (R)-2,2,2-trifluoro-N-(1-hydroxyoctadecan-2-yl)acetamide

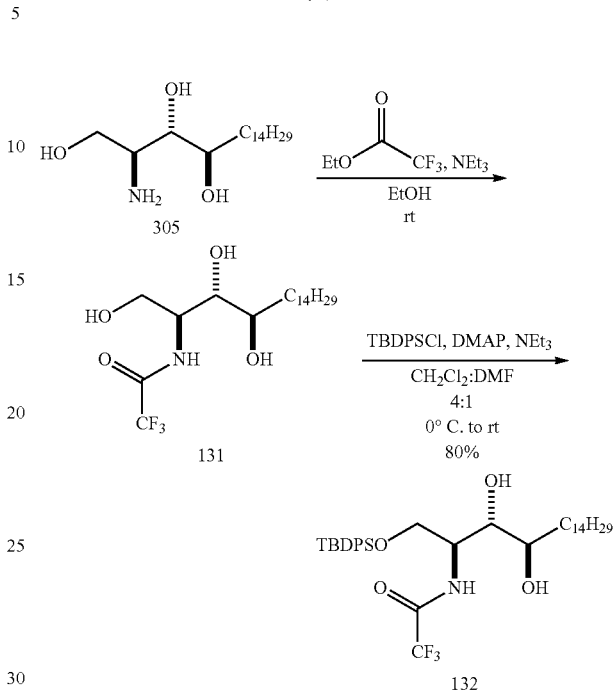

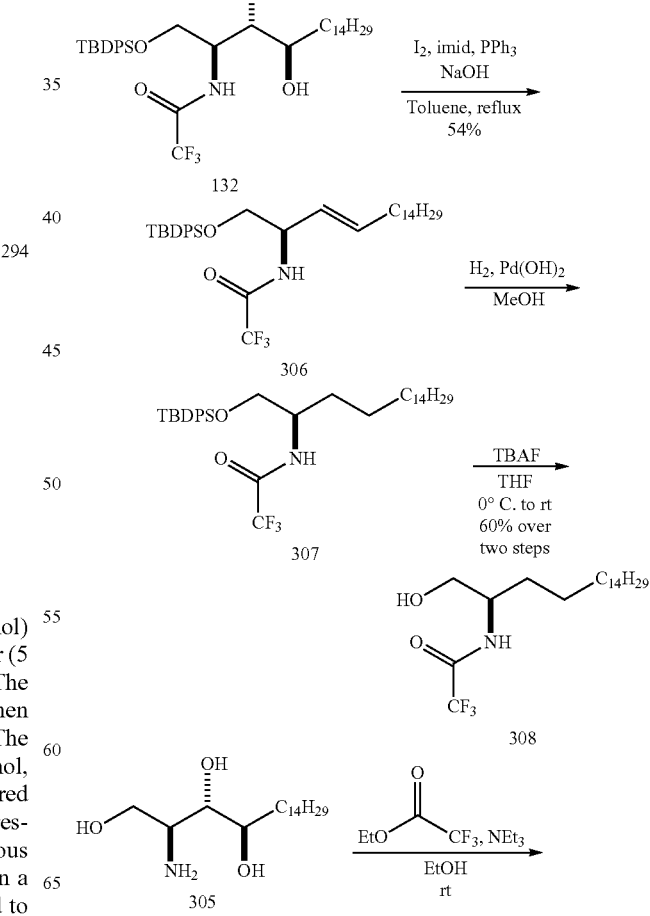

Phytosphingosine (15.75 mmol) was dissolved in EtOH (0.5M) and ethyl trifluoroacetate (15.75 mmol) was added dropwise. NEt$_3$ (24.41 mmol) was added next the reaction mixture stirred overnight. The solvent was removed in vacuo and the residue was taken up in EtOAc and brine, washed, dried and concentrated. The crude material that was a white powder was good enough to use in the next step without further purification. Characterization matched literature: *Synthesis*, 2011, 867.

Example 107

The primary alcohol (15.75 mmol), DMAP (1.575 mmol) and NEt$_3$ (39.4 mmol) were dissolved in CH$_2$Cl$_2$ and DMF (0.18M) mixture and cooled to 0° C. TBDPSCl (19.69 mmol) was added dropwise then the solution was allowed to warm to room temperature and stirred overnight.

NH$_4$Cl solution was added to quench. The reaction mixture was extracted with EtOAc and the combined organic layers were washed with water (×2) to remove DMF. It was then dried and concentrated. A column was run to purify the mixture. 10-20% EtOAc/Hex. Characterization matched literature: *Synthesis*, 2011, 867.

Example 108

The diol (12.58 mmol), triphenylphosphine (50.3 mmol) and imidazole (50.03 mmol) were dissolved in toluene and reheated to reflux. The iodine (37.7 mmol) was then added slowly and the reaction mixture continued to be stirred at reflux. After three hours it was cooled to room temperature and 1 equivalent of iodine (12.58 mmol) was added followed by 8 equivalents of 1.5M NaOH (100.64 mmol). The reaction mixture was stirred until all the solids dissolved. The aqueous layer was removed in a separatory funnel and the organic layer was washed with Na$_2$S$_2$O$_3$ solution then NaHCO$_3$ solution then brine. It was dried and concentrated. A column was run to purify the mixture 0-20% EtOAc/Hex and a mixture of cis and trans was obtained but carried on to the next step.

δ $^1$H NMR (400 MHz, Chloroform-d) δ 7.64 (ddt, J=7.8, 3.8, 1.7 Hz, 4H), 7.51-7.35 (m, 6H), 6.68 (dd, J=16.0, 8.2 Hz, 1H), 5.6-5.40 (m, 2H), 4.57-4.46 (m, 1H), 3.84-3.62 (m, 2H), 2.04 (q, J=7.0 Hz, 1H), 1.28-1.21 (m, 24H), 1.15-0.98 (m, 9H), 0.90 (t, J=6.8 Hz, 3H).

HRMS: 617.38759.

Example 109

The alkene (2.91 mmol) was dissolved in MeOH (0.1M) and Pd(OH)$_2$/C (0.146 mmol) was added. A Parr Hydrogenator was used at 40 psi. The palladium catalyst was carefully filtered off through celite and rinsed with EtOAc. The crude material was used in the next step and provided quantitative yield.

Example 110

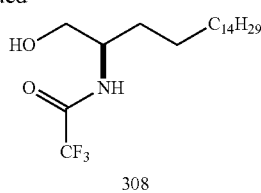

The silyl ether was dissolved in THF and cooled to 0° C. then TBAF was added dropwise. After stirring for 1 hour it was warmed to room temperature. After two hours NH4Cl solution was added and it was extracted with EtOAc, washed with brine and dried and concentrated. A column was run 10-50% EtOAc/Hex.

$^1$H NMR (400 MHz, Chloroform-d) δ 7.60 (tt, J=7.0, 1.5 Hz, 2H), 7.48-7.33 (m, 4H), 3.73-3.61 (m, 1H), 1.24 (d, J=3.5 Hz, 18H), 1.05 (s, 6H), 0.86 (t, J=6.8 Hz, 3H). HRMS: 381.28546.

Example 111

Synthesis of 2-Amino-Octadecyl-FTC-5'-Monophosphate Conjugates

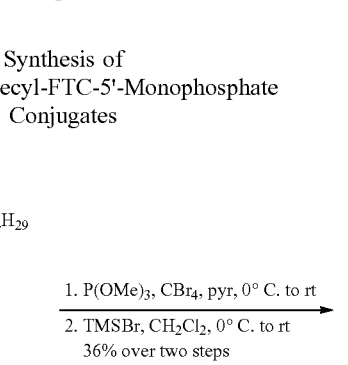

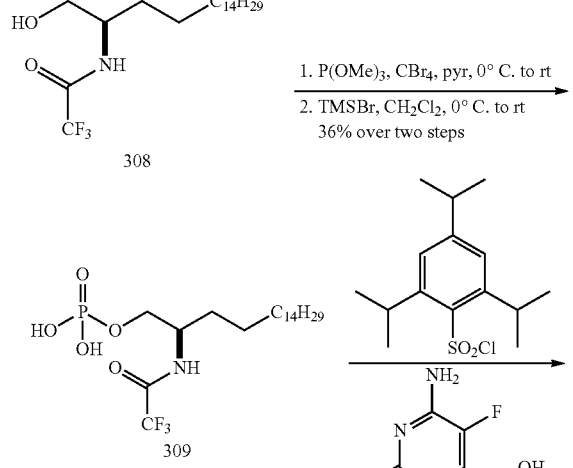

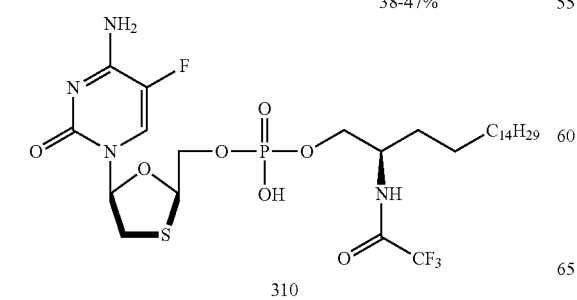

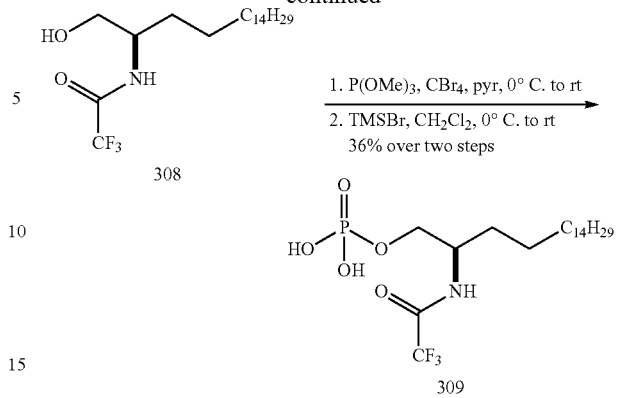

Step 1: The alcohol (0.604 mmol) was dissolved in pyridine (0.1 M) and cooled to 0° C. then CBr$_4$(0.755 mmol) was added followed by dropwise addition of P(OMe)$_3$ (0.845 mmol) over one hour. Once addition was complete the mixture was stirred at 0° C. for one hour then allowed to warm to room temperature. To quench water was added and the solvent was removed in vacuo. The residue was dissolved in EtOAc and washed with 3% HCl (×2) then NaHCO$_3$ solution and then brine. Bad emulsion took place especially after washing with NaHCO$_3$ solution. It was then dried and concentrated. The crude material was taken on to the next step although a column could have been run because some starting material is present because the reaction did not go to completion. Phosphate formation was confirmed by $^{31}$P NMR and $^1$H NMR.

$^1$H NMR (300 MHz, Chloroform-d) δ 7.55 (d, J=8.0 Hz, 1H), 4.10 (dq, J=7.1, 4.4 Hz, 3H), 3.76 (dd, J=11.2, 4.7 Hz, 6H), 1.67-1.56 (m, 2H), 1.23-1.18 (m, 28H), 0.91-0.76 (m, 3H).

HRMS: 489.28309.

Step 2: The dimethyl phosphate (0.291 mmol) was dissolved in dry CH$_2$Cl$_2$ (0.1 M) and cooled to 0° C. with ice-bath and then treated dropwise via syringe pump with TMSBr (1.454 mmol) over a 30 min period. The mixture was allowed to warm to room temperature for one hour. It was concentrated to dryness after 4 hours and then co-evaporated with CH$_2$Cl$_2$ 3x 50 mL. The crude residue was cooled in ice-bath and treated with ice-cold mixture of approx. 1% aqueous NH$_4$OH/THF. The mixture was agitated at 4° C. for 10 min and then concentrated to dryness. The crude material was analyzed by $^1$H NMR and $^{31}$P NMR and then triturated with methanol/ACN and then filtered. The collected off-white solid was washed with dry acetonitrile.

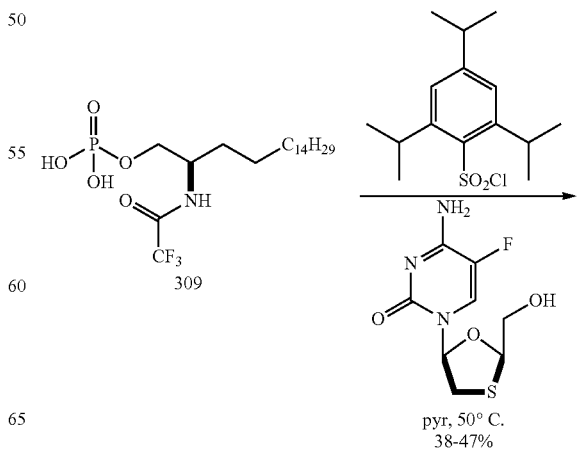

385
-continued

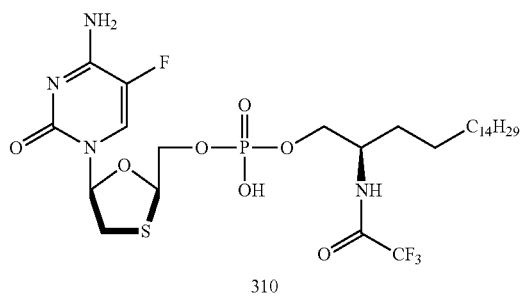
310

FTC (0.155 mmol) and the phosphate (0.155 mmol) were dissolved in pyridine (0.05 M) and trisyl chloride was added. It was stirred at 50° C. overnight. The solvent was removed in vacuo and the crude material was purified by column 5%-50% MeOH/NH$_4$OH/CHCl$_3$.

$^1$H NMR (400 MHz, Methanol-d$_4$) δ 8.15-8.08 (m, 1H), 6.27-6.19 (m, 1H), 5.37 (t, J=4.0 Hz, 1H), 4.19-4.10 (m, 1H), 4.07 (td, J=7.7, 5.5, 3.1 Hz, 1H), 3.96-3.83 (m, 2H), 3.29 (s, 1H), 1.58-1.50 (m, 1H), 1.26-1.18 (m, 28H), 0.92-0.83 (m, 3H).

HRMS: 690.28392.

Example 112

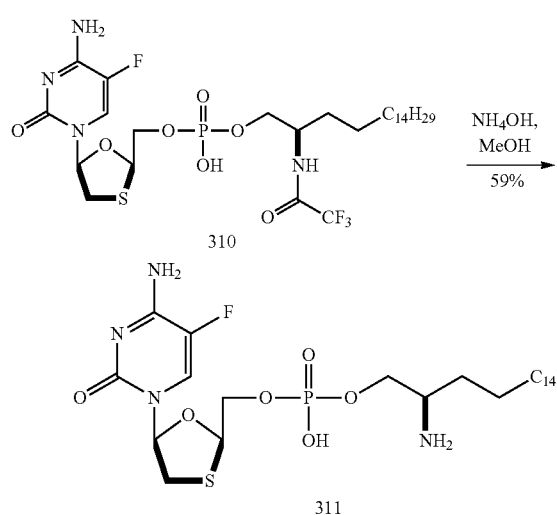

The phosphate was dissolved in MeOH (0.05M) and NH$_4$OH in a pressure tube and stirred at 40° C. overnight. This reaction was very stubborn and on more than one occasion the reaction was not complete after 24 hours. In those cases it was resubjected for another 24 hours.

$^1$H NMR (400 MHz, Methanol-d$_4$) δ 8.10 (t, J=6.0 Hz, 1H), 6.24 (q, J=5.4 Hz, 1H), 5.49-5.42 (m, 1H), 5.38 (dt, J=9.2, 4.1 Hz, 1H), 4.26-4.10 (m, 2H), 4.07 (q, J=5.0, 4.6 Hz, 1H), 3.95-3.82 (m, 1H), 3.48 (dt, J=9.5, 4.6 Hz, 1H), 3.32 (d, J=3.6 Hz, 2H), 3.17 (ddd, J=12.3, 7.7, 4.3 Hz, 1H), 1.61 (dt, J=13.0, 7.2 Hz, 2H), 1.25 (d, J=9.1 Hz, 28H), 0.87 (t, J=5.7, 4.8 Hz, 3H).

HRMS: 594.30162.

386
Example 113

Synthesis of 2-Amino-Octadecyl-Tenofovir-5'-Monophosphate Conjugates

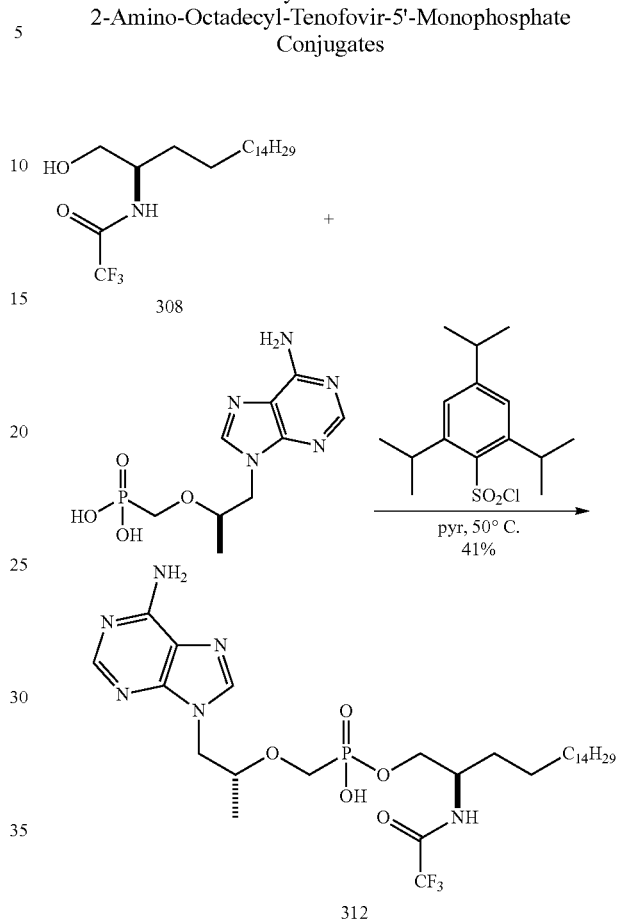

Tenofovir (0.149 mmol) and the alcohol (0.149 mmol) were dissolved in pyridine (0.05 M) and trisyl chloride (0.448 mmol) was added. It was stirred at 50° C. overnight. The solvent was removed in vacuo and the crude material was purified by column using 5%-50% MeOH/NH$_4$OH/CHCl$_3$.

$^1$H NMR (400 MHz, Methanol-d$_4$) δ 8.3 (s, 1H), 8.2 (s, 1H), 4.4-3.2 (m, 8H), 1.6 (m, 2H), 1.4-1.1 (m, 31H), 0.9 (t, 3H). HRMS: 650.35324.

Example 114

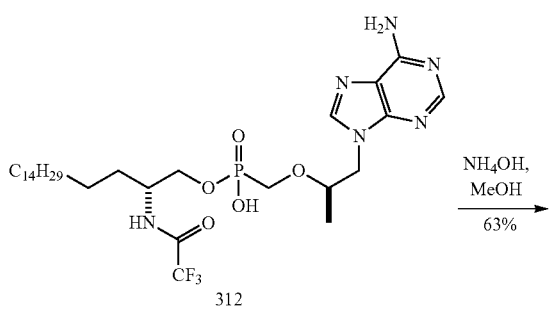

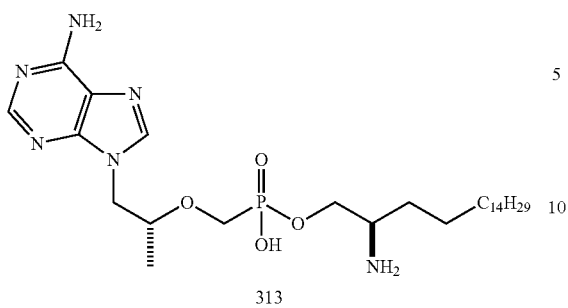

313

The phosphate was dissolved in MeOH (0.05M) and NH$_4$OH in a pressure tube and stirred at 40 t overnight. This reaction was very stubborn and on more than one occasion the reaction was not complete after 24 hours. In those cases it was resubjected for another 24 hours.

$^1$H NMR (300 MHz, Methanol-d$_4$) δ 8.31 (d, J=5.4 Hz, 1H), 8.21 (d, J=5.5 Hz, 1H), 4.5-3.2 (m, 10H), 1.63-1.52 (m, 2H), 1.4-1.0 (m, 31H), 0.87 (t, J=6.3 Hz, 3H).

HRMS: 554.37094.

Example 115

Synthesis of 2'-Fluoro-2'-Methyluridine-5'-HDP-Monophosphate Conjugate

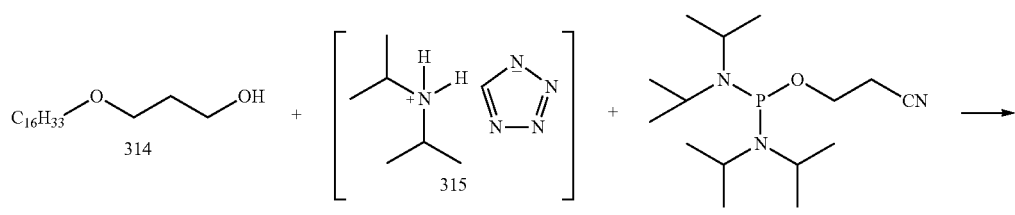

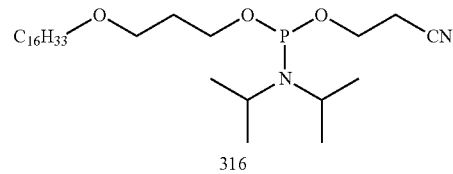

316

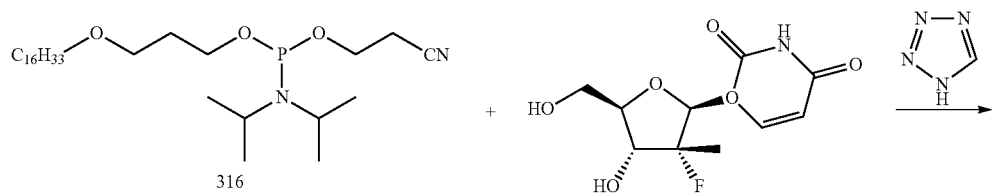

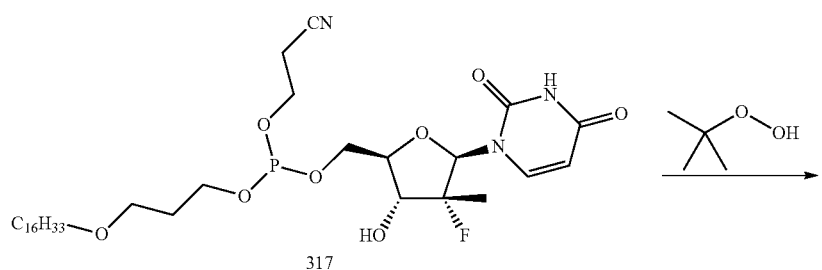

317

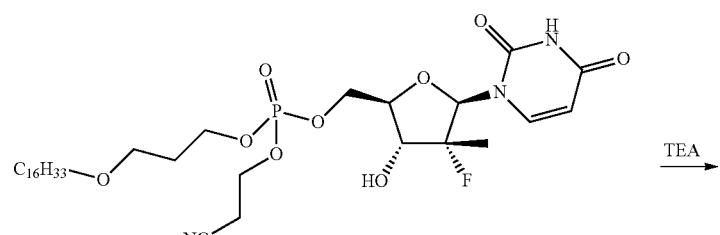

318

-continued

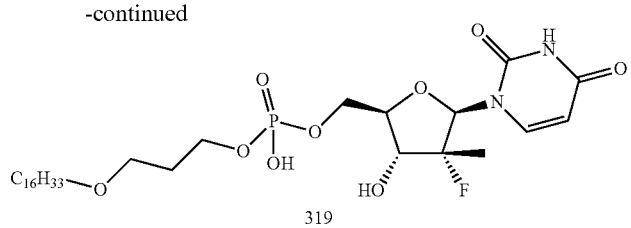
319

Compound 314 was prepared following literature procedure (Bioorganic & Medicinal Chemistry 20 (2012) 3658-3665).

Compound 315: To a solution of I H-tetrazole (0.415 g, 5.92 mmol) in 25 ml ether and 10 ml acetonitrile diisopropylamine (0.93 ml, 0.726 g, 7.03 mmol) was added. The precipitate was filtered off, washed with ether and dried under vacuum to give diisopropylammonium tetrazolide.

Compound 316: 3-(hexadecyloxy)propan-1-ol (0.301 g, 1.00 mmol) and diisopropylammonium tetrazolide (0.115 g, 0.67 mmol) were coevaporated with DCM-AcCN mixture (10:10) 3 times. Dried mixture was dissolved in 7 ml DCM and added 3-((bis(diisopropylamino)phosphino)oxy)propanenitrile (0.673 ml, 2.120 mmol). After 1 hour stirring at room temperature 1 ml methanol was added and stirred for 15 minutes. Then reaction was concentrated under vacuum; diluted with 10% TEA solution in EtOAc (100 ml) and washed with 10% NaHCO₃ solution (2×50 ml) and water (2×50 ml); dried over anhydrous MgSO4; filtered off and evaporated. The crude product was purified with column chromatography using Hexanes:EtOAc:TEA (10:4:0.5).

¹H-NMR: 3.89-3.54 (m, 6H); 3.49 (t, 2H, J=6.4 Hz); 3.39 (t, 2H, J=6.4 Hz); 2.63 (dt, 2H, J=1.6, 6.4 Hz); 1.89-1.83 (m, 1H); 1.57-1.51 (m, 1H); 1.24 (s, 24H); 1.19-1.16 (m, 16H); 0.87 (t, 3H, J=6.4 Hz).

Compound 317 318, 319: The amidophosphite (compound 3) (0.114 g, 0.228 mmol) and 1-((2R,3R,4R,5R)-3-fluoro-4-hydroxy-5-(hydroxymethyl)-3-methyltetrahydrofuran-2-yl)pyrimidine-2,4(1H,3H)-dione (0.065 g, 0.248 mmol) were dried by coevaporating with anhydrous DCM (4×10 ml), dissolved in 4 ml DCM and a solution of 3% 1H-tetrazole in acetonitrile (0.75 ml, 0.320 mmol) was added. After 1 hour stirring at room temperature 5.5 M solution of tert-butyl peroxide (0.25 ml, 1.359 mmol) was added. After 40 minutes the solvents were evaporated and reaction mixture was dissolved in toluene and 1 ml TEA was added. It was stirred for 5 hours. All the solvents were evaporated and coevaporated with toluene (2×2 ml). Crude material was purified with column chromatography starting with CHCl3 and increased the polarity slowly with CHCl3:MeOH:NH₄OH (75:25:5) to give compound 319.

¹H-NMR: (CDCl3-CD3OD, 3:1) 1.024 (t, 3H, 6.4 Hz); 1.35-1.49 (m, 27H); 1.55 (d, 2H, 6.0 Hz); 1.63-1.70 (m, 2H); 2.011-2.067 (m, 2H); 3.47-3.49 (m, 2H); 3.54 (q; 2H, J=4.8 Hz); 3.65-3.70 (m, 2H); 4.07-4.20 (m, 3H); 4.23-4.42 (m, 2H); 5.99 (d, 1H, J=8.4 Hz); 6.32 (dd, 1H, J=19.2, 5.2 Hz); 8.125 (t, 1H, J=8.0 Hz).

³¹P-NMR: (CDCl3-CD3OD, 3:1) 17.95 ppm.

HRMS: 623.34722.

Example 116

Synthesis of 2'-Deoxy-2'-Beta-Methyl-2-Thiouridine

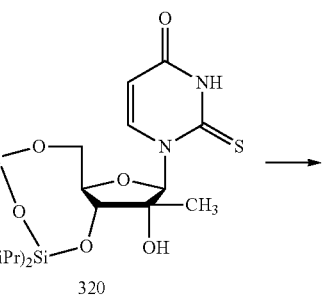
320

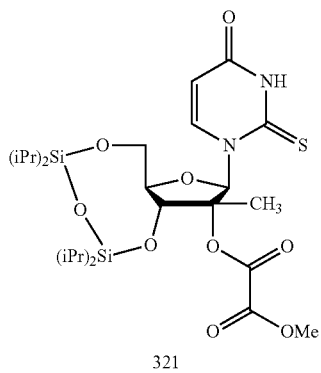
321

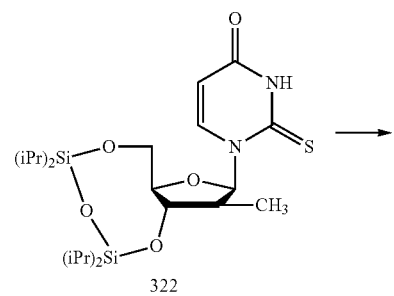
322

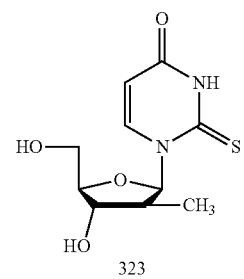
323

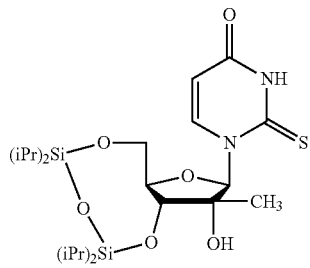

320

The nucleoside (4.15 g, 15.13 mmol) was dried by azeotroping residual water by dissolving in pyridine and removing volatiles by rotary evaporation (3×50 mL). The residue was dissolved in pyridine (200 mL) with stirring under nitrogen at 0° C., and 1,3-dichloro-1,1,3-3-tetraisopropyldisiloxane (5.81 mL, 18.2 mmol) was added dropwise via syringe over 5 min. The mixture was warmed to rt and stirred 16 h. The mixture was then concentrated by rotary evaporation and taken up in CH$_2$Cl$_2$ (500 mL). The solution was washed with sat. aq. NaHCO$_3$ (2×500 mL) and then dried over Na$_2$SO$_4$, filtered, and concentrated by rotary evaporation to give 12 g crude material. The mixture was taken up in CH$_2$Cl$_2$, and flash chromatography on the CombiFlash (120 g column, 5 to 30% EtOAc in hexanes gradient) gave 320 (6.55 g, 84%) as a white powdery solid.

$^1$H NMR (400 MHz, CDCl$_3$) δ 9.29 (br s, 1H), 7.81 (d, J=8.2 Hz, 1H), 6.87 (br s, 1H), 5.97 (d, J=8.1 Hz, 1H), 4.24 (d, J=13.6 Hz, 1H), 4.10 (dd, J=9.1 Hz, 2.6 Hz, 1H), 4.02 (dd, J=13.6 Hz, 2.8 Hz, 1H), 3.99 (d, J=9.1 Hz, 1H), 1.33 (s, 3H), 1.14-1.05 (m, 28H).

Example 117

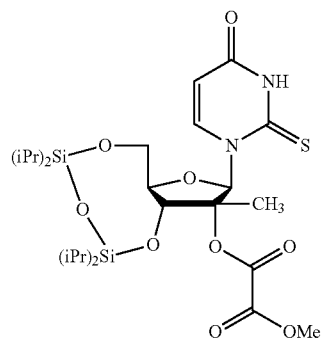

321

To a stirred solution of 320 (6.25 g, 12.09 mmol) and 4-DMAP (2.95 g, 24.19 mmol) in acetonitrile (121 mL) at rt under nitrogen, was added methyl-2-chloro-2-oxoacetate (1.67 mL, 18.14 mmol) dropwise via syringe. The mixture was stirred at rt for 2 h, and was then diluted with EtOAc (600 mL). This organic solution was washed sequentially with sat. aq. NaHCO$_3$, water, and brine (1×120 mL each), dried over MgSO$_4$, filtered, and concentrated by rotary evaporation. The resulting crude was dried under high vacuum overnight to give 321 (7.60 g) as a pale yellow solid. The entirety of the crude product mixture was taken on to the next step without further purification.

$^1$H NMR (400 MHz, CDCl$_3$) δ 7.82 (1H, d, J=8.2 Hz), 7.12 (s, 1H), 5.99 (d, J=8.2 Hz, 1H), 4.25-4.18 (m, 2H), 4.10 (d, J=9.3 Hz, 1H), 4.02 (dd, J=13.7 Hz, 2.8 Hz, 1H), 3.91 (s, 3H), 1.86 (s, 3H), 1.15-0.90 (m, 28H).

Example 118

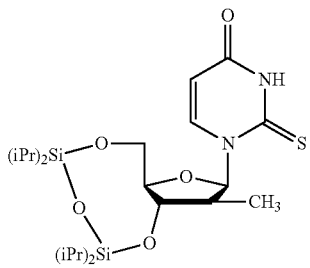

322

To a stirred solution of crude 321 (7.60 g) and tributyltin hydride (4.89 mL, 18.14 mmol) in toluene (216 mL) at reflux under nitrogen, was added solid AIBN (0.397 g, 2.42 mmol) all at once. The mixture was heated at reflux for 2 h and then cooled to rt. Volatiles were removed by rotary evaporation, and the crude residue was taken up in a small amount of PhMe. Flash chromatography on the Combiflash (120 g column, 1 to 30% EtOAc in hexanes gradient) gave 322 (5.30 g, ~79% yield) as a white solid of ~90 purity (remainder tributylstannane residues). NMR analysis showed a 10:1 β:α dr at the C$_2$' position. The entirety of this mostly pure product was taken on to the next step without further purification.

Major isomer $^1$H NMR (400 MHz, CDCl$_3$) δ 9.37 (br s, 1H), 7.87 (d, J=8.2 Hz, 1H), 7.01 (d, J=7.5 Hz, 1H), 5.96 (dd, J=8.0 Hz, 2.1 Hz, 1H), 4.17 (d, J=13.2 Hz, 1H), 4.03 (dd, J=13.5 Hz, 2.8 Hz, 1H), 3.98 (t, J=9.6 Hz, 1H), 3.78 (ddd, J=8.8 Hz, 2.8 Hz, 1.0 Hz, 1H), 2.74 (m, 1H), 1.15-0.95 (m, 31H). Signals for the minor isomer were also seen at $^1$H NMR (400 MHz, CDCl$_3$) δ 8.08 (d, J=8.2 Hz, 1H), 4.38 (dd, J=9.1 Hz, 7.5 Hz, 1H), 4.24 (d, J=12.9 Hz, 1H), 2.53 (m, 1H).

Example 119

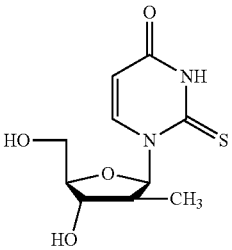

323

To a stirred solution of 322 (5.30 g, 10.58 mmol) in THF (106 mL) under nitrogen at 0° C., was added a solution of TBAF (1.0 M in THF, 21.17 mL) dropwise via syringe. The mixture was brought to rt and stirred 2 h. Volatiles were removed by rotary evaporation to give a crude yellow oil. The material was taken up in EtOAc and flash chromatography on the Combiflash (330 g column, 0 to 5% MeOH in DCM gradient) gave 2.8 g of mostly purified material as a white solid. This material was dissolved in methanol and immobilized on Celite, then loaded on top of a 10% w/w KF/silica column. Flash chromatography (10% MeOH in EtOAc) gave 323 (1.96 g, 63% yield over 3 steps) as a white solid. $^1$H NMR analysis showed a 13:1 β:α dr at the C$_2$'position (integration of methyl doublet).

Major isomer ¹H NMR (400 MHz, MeOH-d₄) δ 8.18 (d, J=8.1 Hz, 1H), 7.04 (d, J=7.6 Hz, 1H), 5.95 (d, J=8.2 Hz, 1H), 3.93 (dd, J=12.2 Hz, 2.1 Hz, 1H), 3.89 (t, J=8.2 Hz, 1H), 2.64 (m, 1H), 0.99 (d, 7.1 Hz, 3H). ES+APCI (70 eV) m/z: [M+HCO₂]⁻ 302.9.

Example 120

Synthesis of 2'-Deoxy-2'-Fluoro-2-Thiouridine

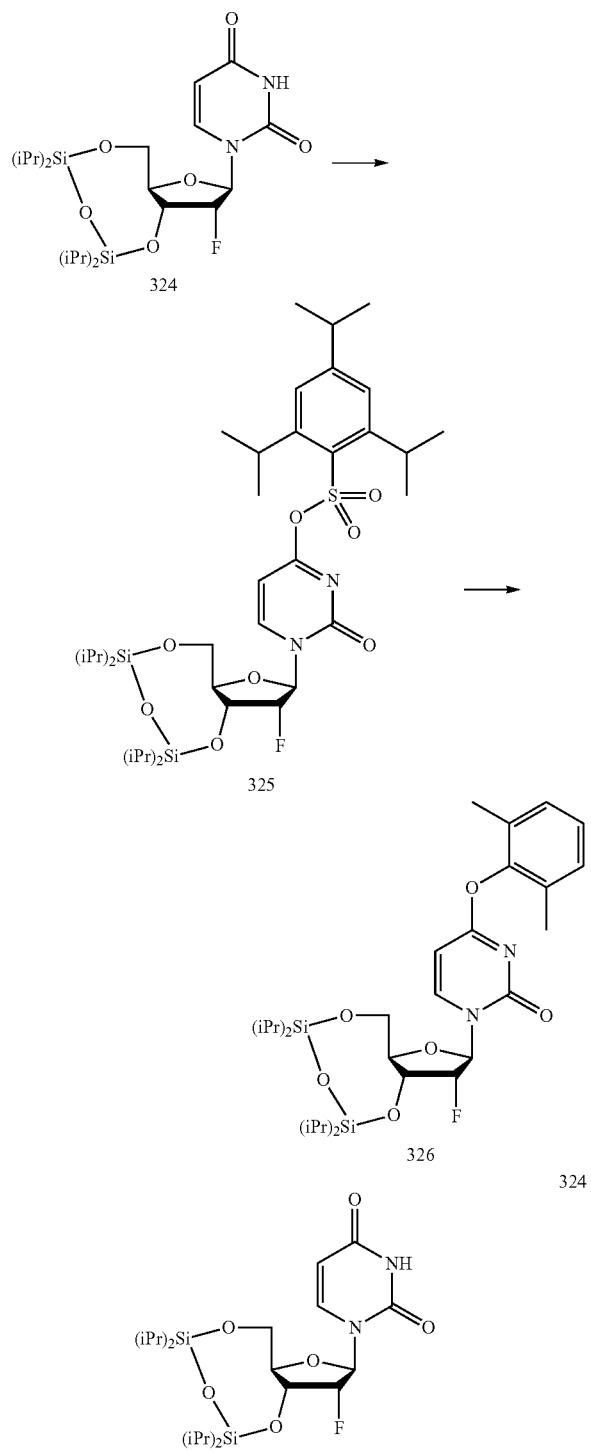

2'-Deoxy-2'-fluorouridine (4.92 g, 20.0 mmol) was dried by azeotroping residual water by dissolving in pyridine and removing volatiles by rotary evaporation (3×50 mL). The residue was dissolved in pyridine (100 mL) with stirring under nitrogen at 0° C., and 1,3-dichloro-1,1,3-3-tetraisopropyldisiloxane (7.68 mL, 24.0 mmol) was added dropwise via syringe over 5 min. The mixture was warmed to rt and stirred 16 h. The mixture was then concentrated by rotary evaporation and taken up in CH₂Cl₂ (500 mL). The solution was washed with sat. aq. NaHCO₃ (2×500 mL) and then dried over Na₂SO₄, filtered, and concentrated by rotary evaporation to give 324 (9.09 g, 93% yield) as a white solid of >95% purity by NMR analysis.

¹H NMR (400 MHz, CDCl₃) δ 8.07 (br s, 1H), 7.81 (d, J=8.2 Hz, 1H), 5.90 (d, J=16.2 Hz, 1H), 5.71 (dd, J=8.2 Hz, 2.3 Hz, 1H), 4.90 (dd, J=53.2 Hz, 3.4 Hz, 1H), 4.30 (ddd, J=28.2 Hz, 9.6 Hz, 3.6 Hz, 1H), 4.29 (d, J=14.3 Hz, 1H), 4.16 (d, J=10.6 Hz, 1H), 4.02 (dd, J=13.6 Hz, 2.5 Hz, 1H), 1.15-1.00 (m, 28H).

Example 121

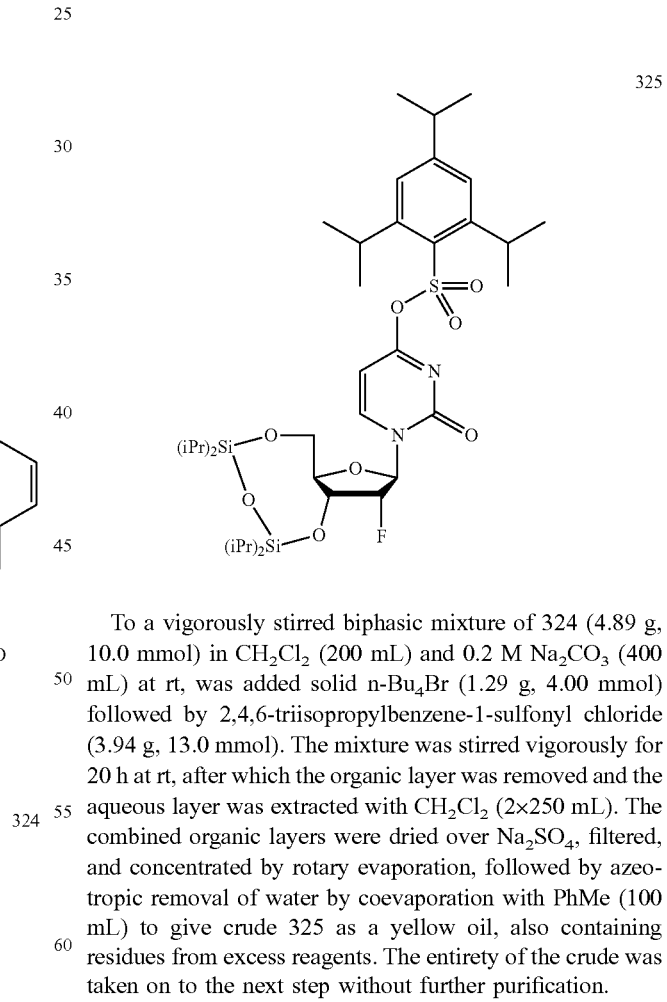

To a vigorously stirred biphasic mixture of 324 (4.89 g, 10.0 mmol) in CH₂Cl₂ (200 mL) and 0.2 M Na₂CO₃ (400 mL) at rt, was added solid n-Bu₄Br (1.29 g, 4.00 mmol) followed by 2,4,6-triisopropylbenzene-1-sulfonyl chloride (3.94 g, 13.0 mmol). The mixture was stirred vigorously for 20 h at rt, after which the organic layer was removed and the aqueous layer was extracted with CH₂Cl₂ (2×250 mL). The combined organic layers were dried over Na₂SO₄, filtered, and concentrated by rotary evaporation, followed by azeotropic removal of water by coevaporation with PhMe (100 mL) to give crude 325 as a yellow oil, also containing residues from excess reagents. The entirety of the crude was taken on to the next step without further purification.

¹H NMR (400 MHz, CDCl₃) δ 8.28 (d, J=7.3 Hz, 1H), 7.23 (s, 2H), 6.04 (d, J=7.4 Hz, 1H), 5.86 (d, J=15.2 Hz, 1H), 4.92 (dd, J=52.4 Hz, 2.9 Hz, 1H), 4.30-4.05 (m, 5H), 3.99 (dd, J=13.7 Hz, 2.3 Hz, 1H), 3.0-2.85 (m, 1H), 1.35-1.25 (m, 18H), 1.15-1.00 (m, 28H).

Example 122

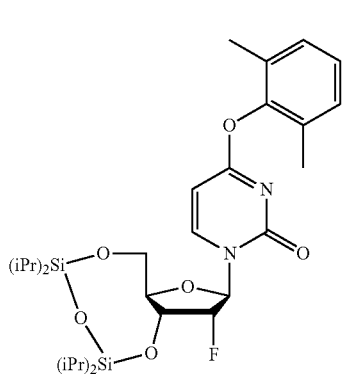

326

To a stirred solution of crude 325 in MeCN (100 mL) under nitrogen at rt, was added dropwise a solution of 2,6-dimethylphenol (1.22 g, 10.0 mmol), triethylamine (4.18 mL, 30.0 mmol), and DABCO (0.112 g, 1.00 mmol) in MeCN over 30 min. The mixture immediately turned deep red at the beginning of addition, and was stirred an additional 90 min after addition was completed. The reaction mixture was concentrated by rotary evaporation, and the residue was redissolved in CHCl$_3$ (300 mL). The solution was washed sequentially with sat. aq. NaHCO$_3$ (1×300 mL) and brine (2×300 mL), dried over Na$_2$SO$_4$, filtered, and concentrated by rotary evaporation to give a crude red oil. Flash chromatography on the Combiflash (330 g column, 5 to 20% EtOAc in hexanes gradient), gave 326 (5.02 g, 85% yield over 2 steps) as an off-white solid foam.

$^1$H NMR (400 MHz, CDCl$_3$) δ 8.20 (d, J=7.4 Hz, 1H), 7.06 (s, 3H), 6.08 (d, J=7.4 Hz, 1H), 5.94 (d, J=15.9 Hz, 1H), 5.02 (dd, J=52.1 Hz, 3.1 Hz, 1H), 4.31 (d, J=13.8 Hz, 1H), 4.32-4.18 (m, 2H), 4.03 (dd, J=13.6 Hz, 2.0 Hz, 1H), 2.13 (s, 6H), 1.15-0.97 (m, 28H).

Example 123

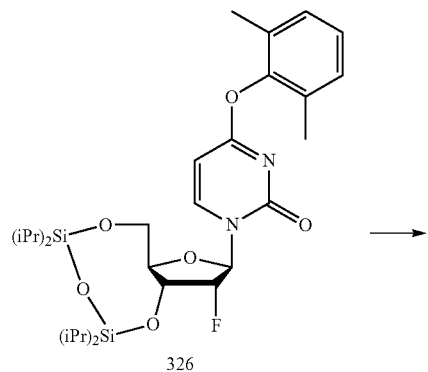

326

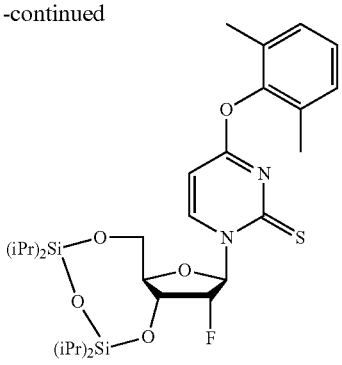

327

To a solution of 326 (4.50 g, 7.59 mmol) in PhMe (76 mL) under nitrogen with stirring was added Lawesson's reagent (4.61 g, 11.39 mmol) all at once as a solid. The mixture was refluxing with stirring under nitrogen for 2 h and was then cooled to rt. The mixture was filtered through Celite and the pad was rinsed with PhMe (2×30 mL). The combined filtrates were concentrated by rotary evaporation, the crude residue was taken up in CH$_2$Cl$_2$, and flash chromatography on the CombiFlash (120 g column, 1 to 15% EtOAc in hexanes gradient) gave 327 (2.80 g, 55% yield) as a fluffy yellow solid in approximate 90% purity as determined by $^1$H NMR analysis.

$^1$H NMR (400 MHz, CDCl$_3$) δ 8.46 (d, J=7.5 Hz, 1H), 7.08 (s, 3H), 6.57 (d, J=14.6 Hz, 1H), 6.26 (d, J=7.5 Hz, 1H), 5.23 (dd, J=51.3 Hz, 3.4 Hz, 1H), 4.35-4.25 (m, 2H), 4.16 (ddd, J=29.4 Hz, 10.3 Hz, 3.9 Hz, 1H), 4.03 (dd, J=13.8 Hz, 2.5 Hz, 1H), 2.14 (s, 6H), 1.15-0.95 (m, 28H).

Example 124

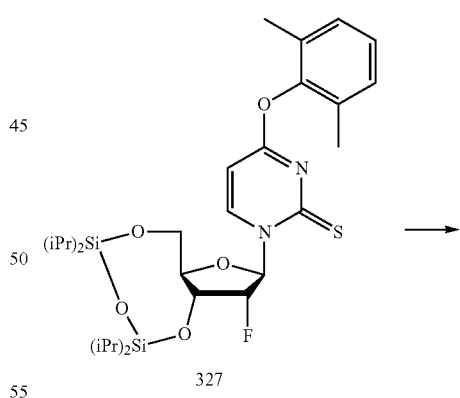

327

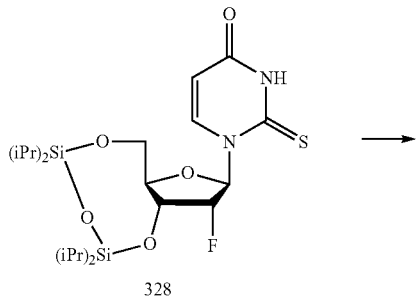

328

-continued

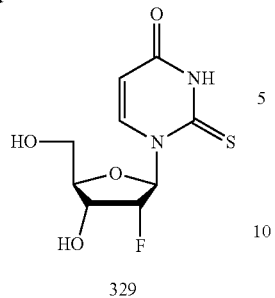

329

To a stirred solution of 327 (2.70 g, 4.43 mmol) in MeCN (44 mL) at rt under nitrogen, was added a solution of 1,1,3,3-tetramethylguanidine (1.67 mL, 13.3 mmol) and (Z)-2-nitrobenzaldehyde oxime (2.21 g, 13.3 mmol) in MeCN (44 mL) dropwise via syringe over 5 min. The mixture was stirred for 20 h, then diluted with CHCl$_3$ (450 mL). The solution was washed with sat. aq. NaHCO$_3$ (1×450 mL) and brine (1×450 mL), dried over Na$_2$SO$_4$, filtered, and concentrated by rotary evaporation. Flash chromatography on the CombiFlash (40 g column, 1 to 25% EtOAc in hexanes gradient) gave an inseparable mixture of 328 and nitrobenzaldehyde oxime (~5:3 mole ratio by NMR) as a yellow oil. The entirety of this product was taken on to the next step without further purification.

$^1$H NMR (400 MHz, CDCl$_3$) δ 9.72 (br s, 1H), 8.02 (d, J=8.2 Hz, 1H), 6.47 (d, J=14.6 Hz, 1H), 5.98 (d, J=8.4 Hz, 1H), 5.03 (dd, J=51.8 Hz, 3.4 Hz, 1H), 4.32 (d, J=13.7 Hz, 1H), 4.24 (dt, J=9.8 Hz, 1.8 Hz, 1H), 4.16 (ddd, J=28.0 Hz, 9.7 Hz, 3.3 Hz, 1H), 4.02 (dd, J=13.7 Hz, 2.3 Hz, 1H), 1.15-0.95 (m, 28H).

To a stirred solution of 328 in THF (44 mL) at 0° C. under nitrogen, was added a solution of TBAF (8.86 mL, 1.0 M in THF, 8.86 mmol) dropwise via syringe over 5 min. The mixture was warmed to rt and was stirred for 1 h. The mixture was concentrated by rotary evaporation, the crude residue was taken up in EtOAc, and flash chromatography on the CombiFlash (80 g column, 10% MeOH in EtOAc) removed bulk impurities to give 1.8 g impure product. The mixture was redissolved in MeOH and immobilized on Celite. A second flash chromatography column on the Combiflash (80 g, 1 to 10% MeOH in EtOAc gradient) gave 329 (0.940 g, 81% yield over 2 steps) as a white solid.

$^1$H NMR (400 MHz, MeOH-d$_4$) δ 8.36 (d, J=8.1 Hz, 1H), 6.68 (d, J=15.6 Hz, 1H), 5.94 (d, J=8.2 Hz, 1H), 5.03 (dd, J=52.0 Hz, 4.0 Hz, 1H), 4.24 (ddd, J=24.2 Hz, 9.0 Hz, 4.1 Hz, 1H), 4.08 (d, J=8.9 Hz, 1H), 4.03 (d, J=12.7 Hz, 1H), 3.81 (dd, J=12.6 Hz, 2.2 Hz, 1H).

ES+APCI (70 eV) m/z: [M+H]$^+$ 263.0.

Example 125

Synthesis of α-Boranotriphosphate Analogs

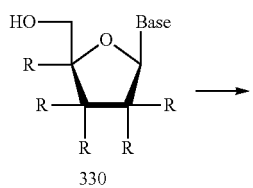

330

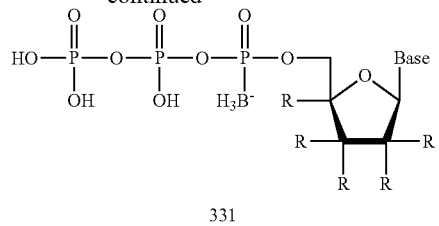

331

The nucleoside for conversion was dried overnight in a vacuum oven at 60° C. The dried nucleoside was suspended in dry THF in a dry flask under an argon atmosphere. The suspension was then treated with 2-chloro-4H-1,2,3-benzodioxaphosporin-4-one and tributylamine. After consumption of starting material, a 0.5M tributylammonium pyrophosphate solution in DMF and tributylamine was added. Next, a 2.0M dimethylsulfide borane complex in THF was added. The reaction mixture was quenched with a triethylamine/water (3:2) mixture. The desired product was purified on a DEAE column eluting with triethylammonium bicarbonate solution.

Example 126

Synthesis of Nucleotide Amino Acid Boranophosphoramidate Analogs

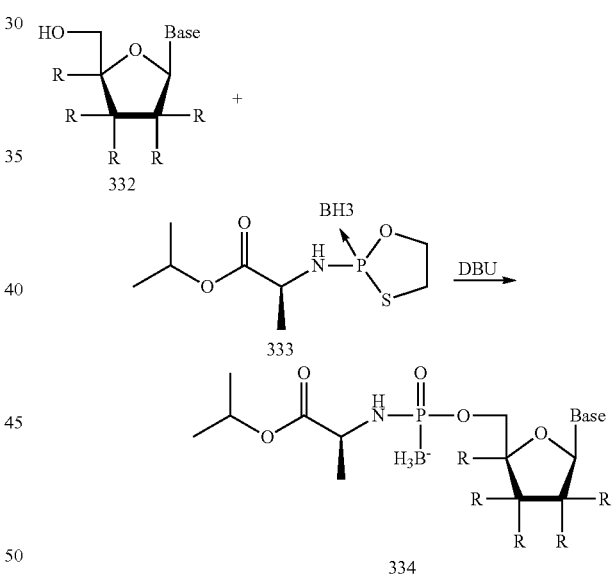

L-alanine isopropyl ester hydrochloride (0.5 mmol) was suspended in dry DCM in a dry flask under an argon atmosphere and was treated with DIPEA (1 mmol). After a clear solution formed, 2-chloro-1,3,2-oxathiaphospholane 333 (0.55 mmol) was added. After 30 minutes of stirring at room temperature, borane-dimethyl sulfide complex (2.5 mmol) was added. The reaction was allowed to stir for an additional 30 minutes. Next, the nucleoside (0.4 mmol) and DBU (1.5-5 equivalents) in dry acetonitrile was added to the reaction. The reaction was quenched with triethylamine/water (1:1 v/v) with stirring for 15 minutes. Solvents were then reduced under reduced pressure. The residue was then coevaporated with ethanol (3×15 mL). The desired product was purified on silica eluting with methanol (3-15%) in DCM containing 0.5% triethylamine.

Example 127
Synthesis of 3'-Fluoro-2'-Substituted Ribonucleoside Analogs
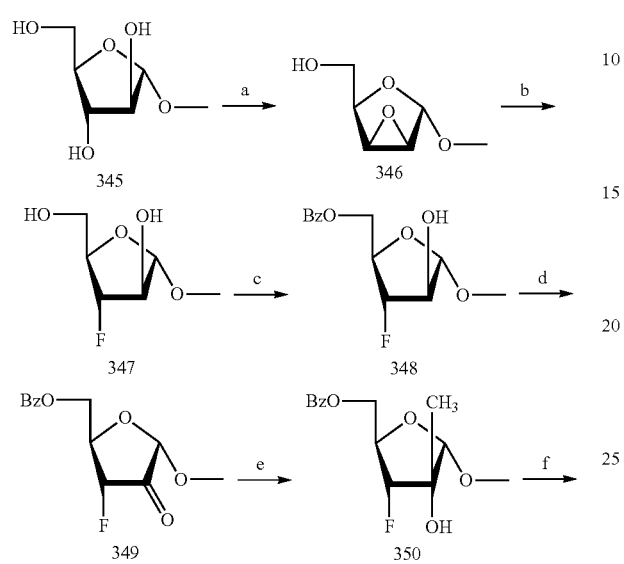
Example 128
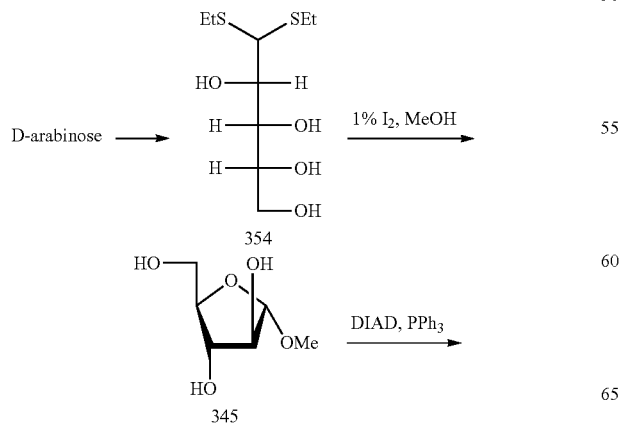
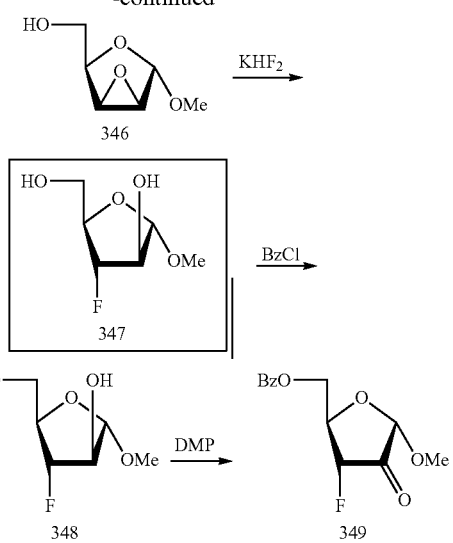
Example 129
Synthesis of 3'-Substituted Ribonucleoside Analogs
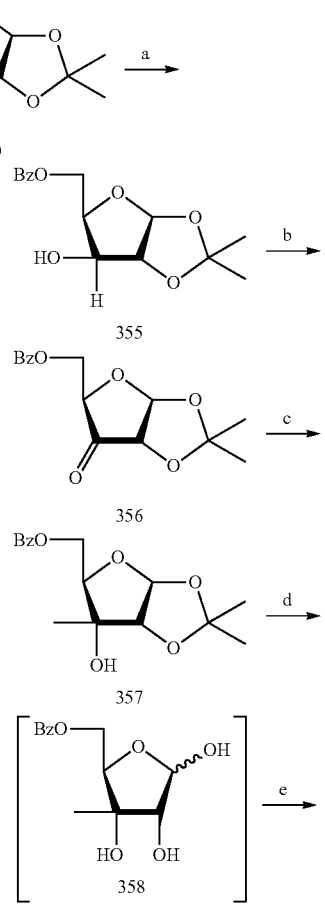

401
-continued

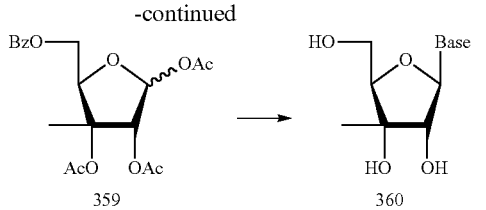

Example 130

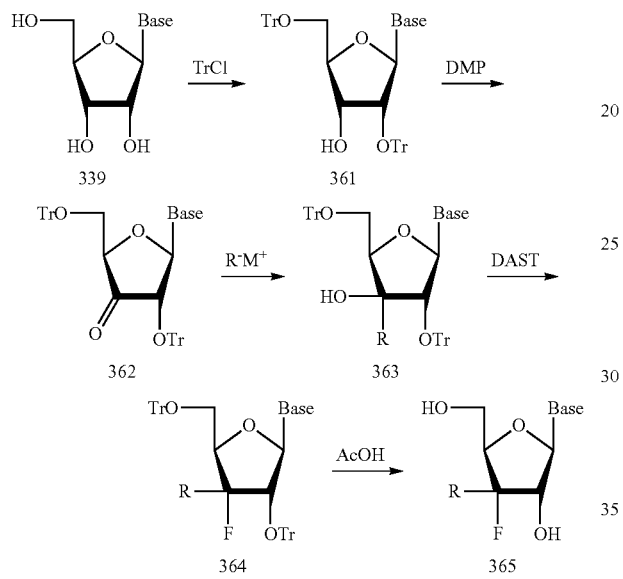

Example 131

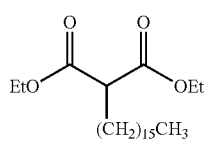
380

To 33.4 g sodium ethoxide solution (21% wt) in ethanol, diethyl malonate (15 g) and then 1-bromohexadecane (31.5 g) were added dropwise. After reflux for 8 hrs, ethanol was evaporated in vacuo. The remaining suspension was mixed with ice-water (200 ml) and extracted with diethyl ether (3×200 ml). The combined organic layers were dried over MgSO4, filtered and the filtrate was evaporated in vacuo to yield a viscous oil residue. This residue was purified by column chromatography (silica: 500 g) using hexane/diethyl ether (12:1) as mobile phase to yield the main compound.

402
Example 132

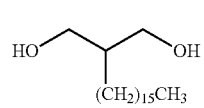
381

In a 250 mL round-bottomed flask was aluminum lithium hydride (2.503 g, 66.0 mmol) in Diethyl ether (90 ml) to give a suspension. To this suspension was added diethyl 2-hexadecylmalonate (18.12 g, 47.1 mmol) dropwise and the reaction was refluxed for 6 h. The reaction was followed up by TLC using PMA and H2SO4 as drying agents. The excess lithium aluminium hydride was destroyed by 200 ml of ice-water. 150 ml of 10% H2SO4 was added to dissolve aluminium hydrate. The reaction mixture was extracted by diethyl ether (100 ml×3). The organic layer including undissolved product was filtered. The collect solids were washed with ethyl acetate. The filtrate was dried over MgSO4, filtered and concentrated under reduced pressure. The product was purified on silica (100 g) column eluting with Hexane:EtOAc (3:1) to (1:1).

Example 133

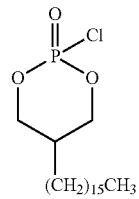
382

To a solution of 2-hexadecylpropane-1,3-diol (7.04 g, 23.43 mmol) in 100 ml of DCM was added dropwise phosphorous trichloride (3.59 g, 23.43 mmol) dissolved in 20 ml of DCM followed by triethylamine (6.53 ml, 46.9 mmol). The reaction was refluxed for one hour. TLC analysis showed that the starting material was consumed and two new spots formed. The mixture was concentrated to dryness, dissolved in dry diethyl ether and filtered. The filtrate was concentrated to yield the crude product (8.85 g) that was used in the next step without further purification.

Example 134

Synthesis of 5'-Deuterated Nucleoside Analogs

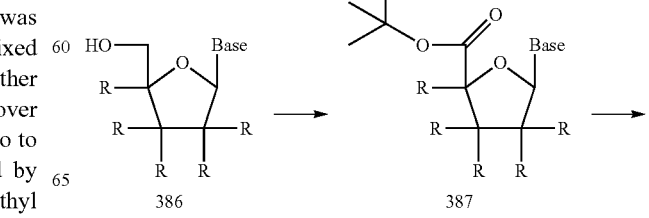

403
-continued

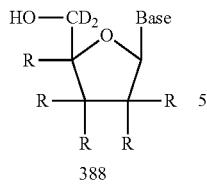
388

The nucleoside was suspended in methylene chloride (40 mL, partially soluble). After stirring at rt for 30 min the mixture was treated sequentially with PDC, acetic anhydride and then tert-butanol. The mixture continued to stir at room temperature. TLC (5% methanol in DCM) and LCMS indicated only a small amount of remaining starting material at 4 hours. The mixture was filtered through a pad of silica gel that was loaded into a 150 mL fritted funnel. The silica was eluted with ethyl acetate. The collected filtrate was concentrated by under reduced pressure. The crude dark oil was purified by chromatography over silica gel (25 mm×175 mm) with 2:1 hexanes:ethyl acetate to ethyl acetate gradient. The pure fractions were collected and concentrated to give of a white gum. The material was placed under high vacuum for 2 days and was used in the next step without further purification.

The 5'-protected nucleoside was dissolved in 200 proof ethanol and was then treated with solid sodium borodeuteride. The mixture became homogeneous and was then heated to 80° C. After 12 h, a white/pale yellow precipitate formed. The mixture was allowed to cool to rt. TLC (5% methanol in methylene chloride) indicates complete conversion of starting material. The mixture was cooled to 0° C. with an ice-bath and then slowly quenched with acetic acid (approximately 1 mL). The clear solution was warmed to rt and then partitioned between ethyl acetate (30 mL) and brine (3 mL). The organic phase was concentrated and then purified by chromatography over silica gel (19 mm×180 mm) using a mobile phase of 5% methanol in methylene chloride.

Example 135

Synthesis of 1'-Deuterated Nucleoside Analogs

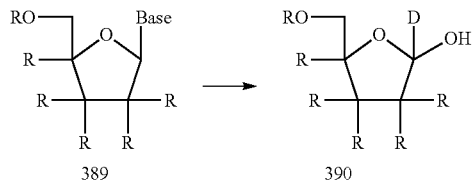

The lactone (0.0325 mol) was added to a dry flask under an argon atmosphere and was then dissolved in dry THF (250 mL). The solution as then cooled to −78° C. and a DIBAL-D solution in toluene (0.065 mol) was dropwise. The reaction was allowed to stir at −78° C. for 3-4 hours. The reaction was then quenched with the slow addition of water (3 mL). The reaction was then allowed to stir while warming to room temperature. The mixture was then diluted with two volumes of diethyl ether and was then poured into an equal volume of saturated sodium potassium tartrate solution. The organic layer was separated, dried over MgSO$_4$, filtered, and concentrated under reduced pressure. The residue was purified on silica eluting with hexanes/ethyl acetate.

404

Example 136

Synthesis of 4'-Substituted Nucleoside Analogs

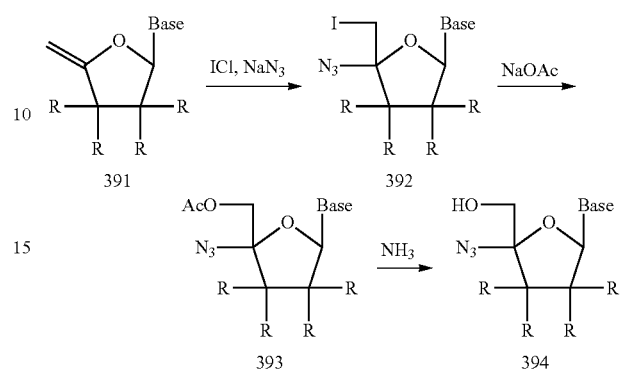

Example 137

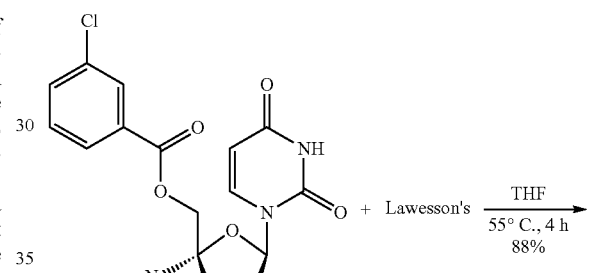

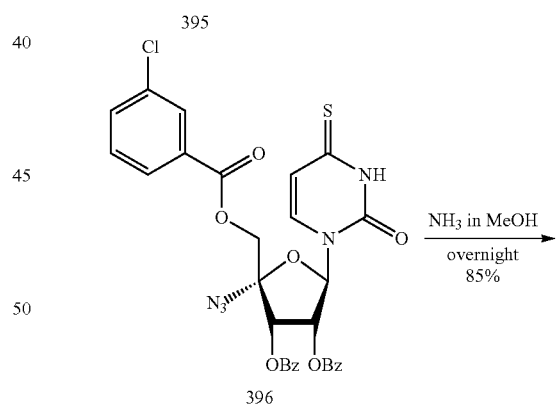

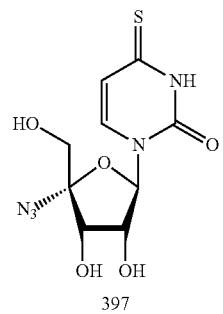
397

1-(4'-Azido-5'-O-(3-chloro)benzoyl-2',3'-O-dibenzoyl-β-D-ribofuranosyl)4-thiouracil (396)

A pear-shaped flask was charged under nitrogen atmosphere with 1-(4'-azido-5'-O-(3-chloro)benzoyl-2',3'-O-dibenzoyl-β-D-ribofuranosyl)uracil (1.08 g, 1.709 mmol), Lawesson's reagent (0.76 g, 1.88 mmol), THF (40 mL), and placed into a 55° C. oil bath. The reaction, monitored by TLC, was completed after ~4 h. Then the mixture was concentrated by rotary evaporation to give an oil which was purified by silica gel chromatography 20-25% EtOAc in hexanes to provide 1-(4'-azido-5'-O-(3-chloro)benzoyl-2',3'-O-dibenzoyl-β-D-ribofuranosyl)4-thiouracil (1.04 g, 94%) as a yellow solid. $^1$H NMR (400 MHz, CDCl$_3$); δ 9.51 (br s, 1H), 8.04-7.91 (m, 5H), 7.59-7.51 (m, 3H), 7.41-7.30 (m, 6H), 7.06 (d, J=7.6 Hz, 1H), 6.40 (d, J=7.6 Hz, 1H), 6.25 (d, J=7.6 Hz, 1H), 5.97 (dd, J=2.4, 7.6 Hz, 1H), 5.86 (d, J=2.4 Hz, 1H), 4.82 (d, J=12.0 Hz, 1H), 4.77 (d, J=12.0 Hz, 1H).

1-(4'-Azido-β-D-ribofuranosyl)4-thiouracil (397)

To a stirred solution of 1-(4'-azido-5'-O-(3-chloro)benzoyl-2',3'-O-dibenzoyl-β-D-ribofuranosyl)4-thiouracil (1.04 g, 1.605 mmol) in methanol (32 ml) at 0° C., was added methanolic ammonia (7 mL, 7 M in MeOH). The mixture was allowed to warm to room temperature and stirred at room temperature for overnight. The solvent was evaporated under reduced pressure and the residue was purified by silica gel column chromatography [eluent: stepwise gradient of methanol (5-8%) in methylene chloride] to give pure 1-(4'-azido-β-D-ribofuranosyl)4-thiouracil (410 mg, 85%) as yellow solid. $^1$H NMR (400 MHz, CD$_3$OD); δ 7.71 (d, J=8.0 Hz, 1H), 6.37 (d, J=8.0 Hz, 1H), 6.13 (d, J=5.2 Hz, 1H), 4.38 (t, J=5.2 Hz, 1H), 4.30 (d, J=5.2 Hz, 1H), 3.67 (d, J=12.0 Hz, 1H), 3.58 (d, J=12.0 Hz, 1H). $^{13}$C NMR (100 MHz, CD$_3$OD); δ 192.4, 149.8, 136.6, 114.7, 100.8, 92.1, 74.6, 73.3, 64.9. HRMS (ESI) Calcd. for C$_9$H$_{11}$O$_5$N$_5$NaS [M+Na]$^+$: 324.0373. Found: 324.0372.

Example 138

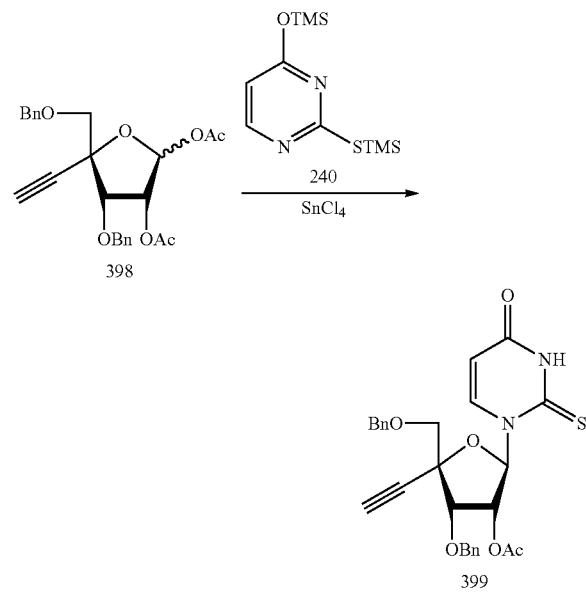

A round bottom flask was charged with 2-thiouracil (1.28 g, 10.0 mmol), (NH$_4$)$_2$SO$_4$ (66 mg, 0.50 mmol), and bis(trimethylsilyl)amine (21 mL, 100 mmol) under nitrogen. The mixture was refluxed with stirring overnight (16 h) until a blue-green solution formed. The mixture was cooled to room temperature and volatiles were removed by rotary evaporation, followed by high vacuum, to give persilylated 2-thiouracil as a light blue liquid. Quantitative yield was assumed, and this compound was used immediately in the next step. A solution of 398 (2.19 g, 5.00 mmol) in 1,2-dichloroethane (50 mL) was added to the freshly prepared 240 under nitrogen, and the resulting cloudy mixture was cooled to 0° C. with stirring. Tin (IV) chloride (1.17 mL, 10.0 mmol) was added to the stirred mixture via syringe over one minute, and the mixture was allowed to warm to room temperature. After stirring for 20 h, the mixture was diluted with 75 mL DCM, and solid NaHCO$_3$ and Celite (2.0 g each) were carefully added to the vigorously stirred reaction mixture. The mixture was cooled to 0° C., and sat. aq. NaHCO$_3$ (1.2 mL) was added dropwise to the vigorously stirred mixture. The mixture was warmed to room temperature and stirred 2 h. The mixture was filtered through a Celite pad, which was rinsed with DCM (30 mL). The combined filtrates were concentrated by rotary evaporation to yield ~5 g of a crude orange oil. The crude was taken up in DCM, and automated flash chromatography on a Combiflash (80 g column, 5 to 50% EtOAc in hexanes gradient) yielded 399 (2.21 g, 83%) as a white flaky solid in 95% purity. $^1$H NMR (400 MHz, CDCl$_3$) δ 9.17 (br s, 1H), 7.96 (d, 1H), 7.40-7.30 (m, 8H), 7.14-7.06 (m, 2H), 6.75 (d, J=1.9 Hz, 1H), 5.45 (dd, J=5.4 Hz, 2.0 Hz, 1H), 5.27 (dd, J=8.3 Hz, 2.5 Hz, 1H), 4.76 (d, J=12.4 Hz, 1H), 4.50 (d, J=12.4 Hz, 1H), 4.33 (d, J=10.6 Hz, 1H), 4.25-4.20 (m, 2H), 3.92 (d, J=10.7 Hz, 1H), 3.61 (d, J=10.7 Hz, 1H), 2.72 (s, 1H), 2.20 (s, 3H). ESI-MS: m/z 379.1 ([M−thiouridine]$^+$).

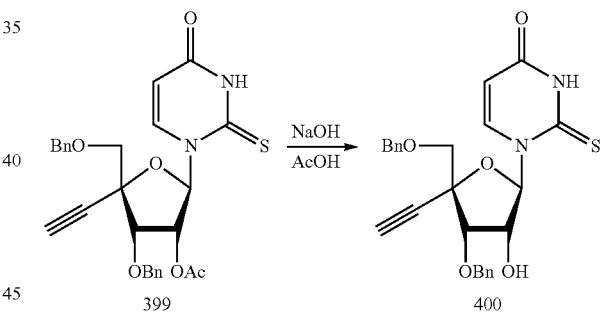

To a stirred solution of 399 (2.21 g, 4.36 mmol) in 1,4-dioxane (227 mL) and water (38 mL) at room temperature, was added 1.0 M aqueous NaOH (38 mL, 38 mmol) all at once. The mixture was stirred at room temperature for 16 h, and was neutralized by dropwise addition of AcOH (2.17 mL, 38 mmol). The mixture was stirred for 30 min and was then concentrated by rotary evaporation. The residue was partitioned between EtOAc and water (100 mL each). The organic layer was removed and the aqueous layer was extracted with EtOAc (1×100 mL). The combined organic layers were dried over Na$_2$SO$_4$, filtered, and concentrated by rotary evaporation to give 2.5 g of crude material. The crude was taken up in DCM, and automated flash chromatography on a Combiflash (80 g column, 5 to 50% EtOAc in hexanes gradient) provided 400 (1.57 g, 77%) as a white solid. $^1$H NMR (400 MHz, CDCl$_3$) δ 9.21 (br s, 1H), 7.91 (d, J=8.2 Hz, 1H), 7.45-7.30 (m, 8H), 7.20-7.15 (m, 2H), 6.72 (d, J=2.5 Hz, 1H), 5.37 (dd, J=8.2 Hz, 2.3 Hz, 1H), 4.79 (d, J=11.9 Hz, 1H), 4.70 (d, J=11.9 Hz, 1H), 4.45 (d, J=10.8 Hz, 1H), 4.41 (d, J=10.8 Hz, 1H), 4.28 (td, J=5.6 Hz, 2.6 Hz, 1H), 4.21 (d, J=5.6 Hz, 1H), 3.95 (d, J=10.6 Hz, 1H), 3.71

(d, J=10.7 Hz, 1H), 3.08 (d, J=5.7 Hz, 1H), 2.77 (s, 1H). ESI-MS: m/z 465.1 ([M+H]$^+$).

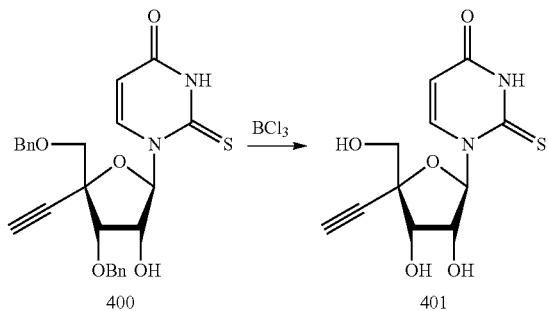

To a stirred solution of 400 (1.57 g, 3.38 mmol) in DCM (68 mL) under nitrogen at −78° C., was added dropwise via syringe a 1.0 M solution of BCl$_3$ in DCM (16.9 mL, 16.9 mmol). The mixture was stirred at −78° C. for 3 h, then quenched by slow dropwise addition of a 7:10 v/v pyridine/MeOH mixture (68 mL). The mixture was warmed to room temperature with stirring, and concentrated by rotary evaporation to give 11 g of crude oil. The crude was taken up in 9:1 DCM:MeOH, and automated flash chromatography on a Combiflash (120 g column, 10 to 25% MeOH in DCM gradient) removed bulk impurities. Fractions containing the desired product were collected and concentrated to give 2 g of semipure product. This crude was taken up in MeOH and immobilized on Celite. A second automated flash chromatography on a Combiflash (40 g column, 2.5 to 25% MeOH in DCM gradient) provided 401 (0.622 g, 65%) as a powdery white solid. $^1$H NMR (400 MHz, CD$_3$OD) δ 8.19 (d, J=8.1 Hz, 1H), 6.88 (d, J=3.3 Hz, 1H), 5.95 (d, J=8.1 Hz, 1H), 4.26 (d, J=6.0 Hz, 1H), 4.23 (dd, J=5.9 Hz, 3.4 Hz, 1H), 3.85 (d, J=12.2 Hz, 1H), 3.77 (d, J=12.2 Hz, 1H), 3.08 (s, 1H). $^{13}$C NMR (100 MHz, CD$_3$OD) δ 178.2, 162.3, 142.7, 106.9, 94.7, 85.6, 80.6, 79.2, 76.4, 71.0, 65.8. ESI-MS: m/z 285.0 ([M+H]$^+$).

Example 139

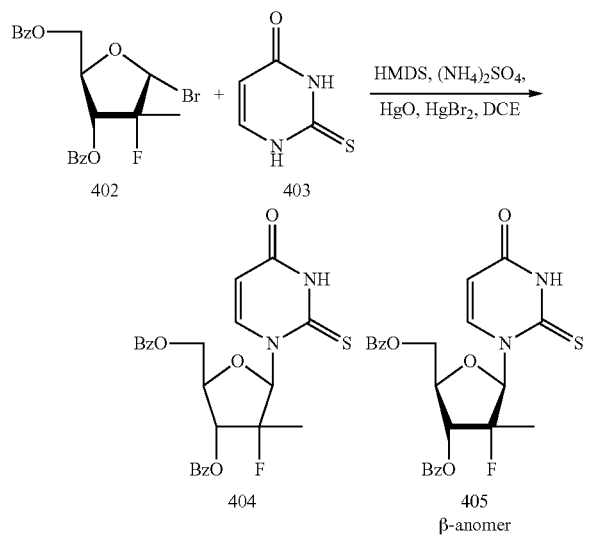

A stirred suspension of thiouracil (3.48 g, 27.2 mmol, 2.2 eq) in HMDS (25.9 mL, 1M) with 10 mg of ammonium sulfate was heated to reflux under argon. After 2 h the clear solution that resulted was cooled and concentrated to a white paste. A solution of bromosugar (5.4 g, 12.35 mmol, 1 eq) in DCE (40 mL) was then added to the thiouracil flask via cannula with 2×10 mL DCE washes. The reaction was charged with mercury oxide (3.48 g, 16 mmol, 1.3 eq), mercury bromide (3.56 g, 9.88 mmol, 0.8 eq) was added and the reaction was fitted with a reflux condenser and refluxed. After 16 h was cooled, and quenched with 100 mL of a 3:1 mix of methanol and water. After 30 min of stirring reaction was diluted in 300 mL water and extracted with dichloromethane (3×100 mL). The combined organics were dried with sodium sulfate, filtered and concentrated in vacuo. Crude reaction was purified by silica gel chromatography (2-10% methanol in dichloromethane) to provide 2.5 g of nucleoside as a mixture of two compounds bearing the correct mass. Further silica gel chromatography (20-70% ethyl acetate in hexanes) afforded 785 mg of compound 404 (13%) and 805 mg of compound 405 (13%).

Compound 404 $^1$H NMR (400 MHz, Chloroform-d) δ 8.03 (dd, J=34.2, 7.8 Hz, 4H), 7.86 (d, J=6.6 Hz, 1H), 7.61 (d, J=7.5 Hz, 1H), 7.57-7.32 (m, 4H), 6.48 (d, J=21.7 Hz, 1H), 6.30 (d, J=6.6 Hz, 1H), 5.50 (dd, J=16.6, 8.1 Hz, 1H), 4.87-4.48 (m, 4H), 1.71 (d, J=21.5 Hz, 3H).

Compound 405 $^1$H NMR (400 MHz, Chloroform-d) δ 8.06 (dd, J=26.3, 8.0 Hz, 5H), 7.86 (d, J=6.7 Hz, 1H), 7.71-7.33 (m, 7H), 6.43 (d, J=17.5 Hz, 1H), 6.29 (d, J=6.7 Hz, 1H), 5.69 (dd, J=21.8, 8.5 Hz, 1H), 4.94-4.35 (m, 5H), 1.66 (d, J=22.1 Hz, 3H).

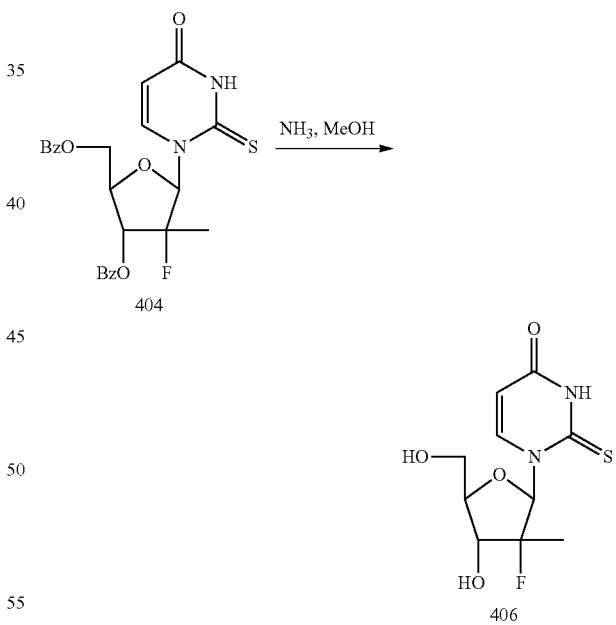

A suspension of the compound 404 (785 mg, 1.62 mmol) in 7M ammonia in methanol (16 mL, 0.1M) was prepared. After 16 h, reaction was concentrated and purified by silica gel chromatography (5-20% methanol in dcm) provided 220 mg of diol (49%). $^1$H NMR (400 MHz, Methanol-d$_4$) δ 7.85 (d, J=6.6 Hz, 1H), 6.38 (d, J=28.2 Hz, 1H), 6.19 (t, J=5.4 Hz, 1H), 4.13-3.91 (m, 2H), 3.85 (dd, J=12.6, 1.9 Hz, 1H), 3.64 (dd, J=12.5, 3.7 Hz, 1H), 1.62-1.42 (m, 3H). LCMS calculated for C$_{10}$H$_{13}$FN$_2$O$_4$S 276.06 found 277.00 M+1; 274.90 M−1

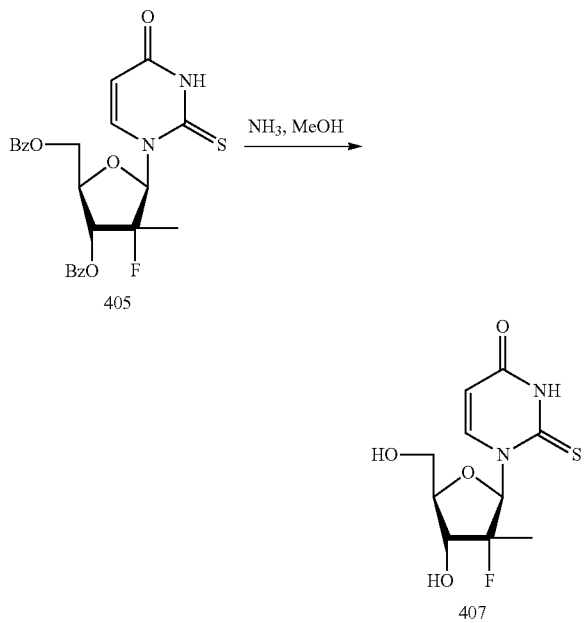

A suspension of the compound 405 (805 mg, 1.62 mmol) in 7M ammonia in methanol (16 mL, 0.1M) was prepared. After 16 h, reaction was concentrated and purified by silica gel chromatography (5-20% methanol in dcm) provided 210 mg of diol (46%). $^1$H NMR (400 MHz, Methanol-$d_4$) δ 7.89 (d, J=6.6 Hz, 1H), 6.43 (d, J=18.3 Hz, 1H), 6.19 (d, J=6.6 Hz, 1H), 4.02-3.88 (m, 1H), 3.81 (dd, J=12.5, 2.1 Hz, 1H), 3.72-3.53 (m, 1H), 3.39-3.23 (m, 1H), 1.56 (d, J=22.3 Hz, 3H). LCMS calculated for $C_{10}H_{13}FN_2O_4S$ 276.06 found 274.90 M−1. The phosphoramidate prodrug of compound 236 can be synthesized using the general procedure in Example 93, and the triphosphate of compound 236 can be synthesized using the general procedure in Example 98.

Example 140

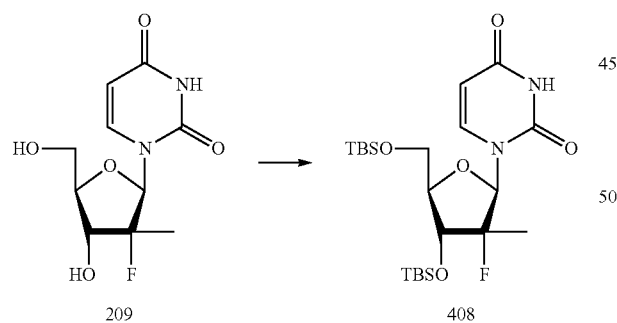

A stirred suspension of nucleoside (190 mg, 0.73 mmol) in dichloromethane (14.6 mL, 0.05M) was charged sequentially with DMAP (89 mg, 0.73 mmol), imidazole (124 mg, 1.83 mmol), and TBSCl (242 mg, 1.61 mmol) and was stirred overnight. After 18 h reaction was concentrated, diluted in ether and filtered. The liqueur was concentrated and purified by silica gel chromatography 5-50% ethyl acetate in hexanes to provide 200 mg (57%) of desired bis TBS nucleoside. $^1$H NMR (400 MHz, Chloroform-d) δ 7.89 (d, J=8.1 Hz, 1H), 6.18 (d, J=17.8 Hz, 1H), 5.70 (d, J=8.1 Hz, 1H), 4.17-3.90 (m, 3H), 3.87-3.64 (m, 1H), 1.31 (d, J=21.7 Hz, 3H), 0.90 (d, J=10.2 Hz, 18H), 0.10 (s, 12H).

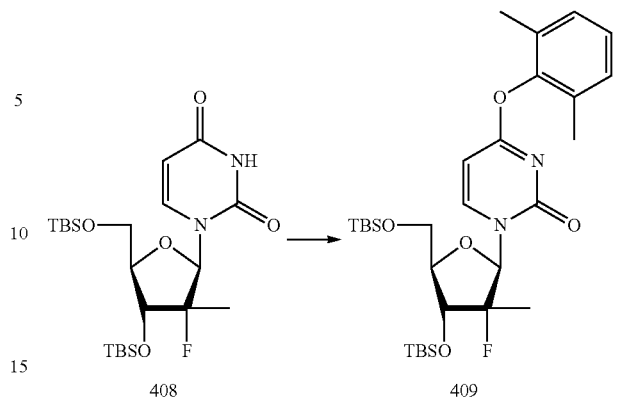

A stirred solution of 408 (200 mg, 0.409 mmol) in DCM (4 mL) was charged with DMAP (100 mg, 0.818 mmol) and triethylamine (120 μl, 0.859 mmol). The clear solution was cooled to 0° C. and then charged with 2,4,6-triisopropyl-benzene-1-sulfonyl chloride (248 mg, 0.818 mmol). Reaction was stirred 18 h then cooled back to 0° C. A 0° C. solution 2,6-dimethylphenol (150 mg, 1.228 mmol), DABCO (9.18 mg, 0.082 mmol) and triethylamine (171 μl, 1.228 mmol) in DCM (4 mL) was prepared and added to the reaction dropwise. Reaction was stirred 3 h then was quenched with cold 50 mL sat $NaHCO_3$ and 100 mL DCM. The separated organic layer was washed with once with brine, dried ($MgSO_4$), filtered and concentrated in vacuo. Resulting oil was purified 5-50% EtOAc in hexanes to provide 234 mg of phenol ether as a glass. $^1$H NMR (400 MHz, Chloroform-d) δ 8.33 (d, J=7.4 Hz, 1H), 7.04 (s, 3H), 6.33 (d, J=17.8 Hz, 1H), 6.08 (d, J=7.4 Hz, 1H), 4.30-3.94 (m, 3H), 3.84 (d, J=12.0 Hz, 1H), 2.13 (s, 6H), 1.32 (d, J=21.8 Hz, 3H), 0.95 (d, J=27.3 Hz, 18H), 0.15 (d, J=15.3 Hz, 12H).

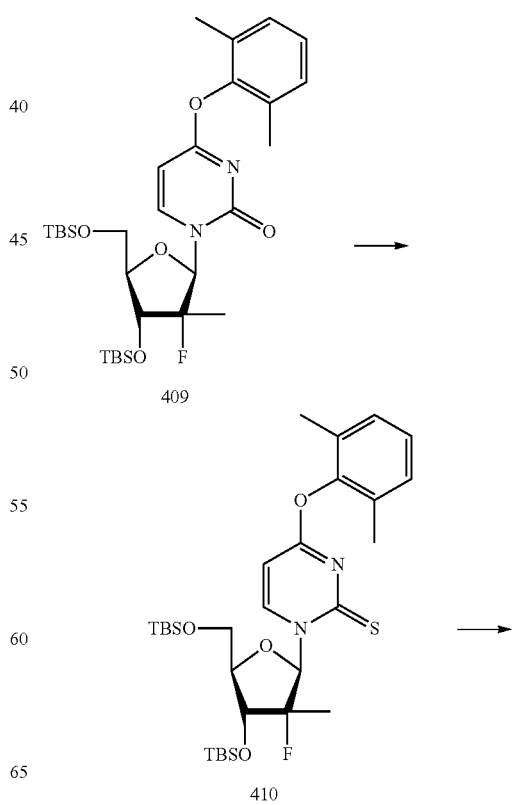

411
-continued

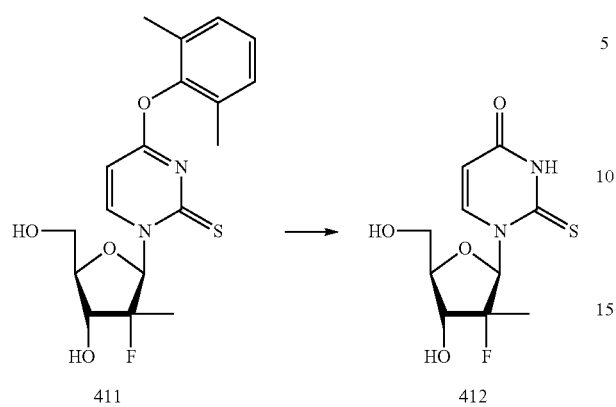

A stirred solution of 409 (200 mg, 0.338 mmol) in toluene (6.6 mL, 0.05M) was charged with lawesson's reagent (204 mg, 0.506 mmol) and heated to 110° C. After 3 h, the reaction was cooled, concentrated onto 1 g of celite, and was purified by silica gel chromatography 1-20% EtOAc/hexanes to provide a total of 200 mg of material containing a minor amount of phosphorus impurity which was carried on. $^1$H NMR (400 MHz, Chloroform-d) δ 8.42 (d, J=7.4 Hz, 1H), 7.41 (d, J=18.2 Hz, 1H), 7.03 (s, 3H), 6.28 (d, J=7.4 Hz, 1H), 4.34-3.95 (m, 4H), 2.11 (s, 6H), 1.44 (d, J=21.6 Hz, 3H), 1.06-0.82 (m, 18H), 0.14 (dd, J=9.0, 1.1 Hz, 12H).

A stirred solution of 410 (200 mg, ~0.338 mmol) in THF (6.6 mL, 0.5M) was charged TBAF (821 uL 1M in THF, 0.821 mmol). The reaction was stirred for 18 h, was concentrated on 1 g of celite, and then was purified via silica gel chromatography 2-7% methanol in DCM to provide 100 mg (~80% 2 steps) of material containing a minor amount of tetrabutylammonium salt. $^1$H NMR (400 MHz, Methanol-d$_4$) δ 8.75 (dd, J=7.5, 1.7 Hz, 1H), 7.35 (dd, J=18.2, 1.7 Hz, 1H), 7.22-6.96 (m, 3H), 6.60-6.41 (m, 1H), 4.13-3.91 (m, 3H), 3.91-3.73 (m, 2H), 2.11 (s, 6H), 1.42 (dd, J=22.2, 1.6 Hz, 3H).

A solution of syn-o-nitrobenzaldoxime (131 mg, 0.789 mmol) in acetonitrile (2.6 mL) was charged with 1,1,3,3-tetramethylguanidine (99 μl, 0.789 mmol) to give an orange solution. After 15 minutes, the resulting solution was added dropwise to a stirred solution of 411 (100 mg, 0.63 mmol) in acetonitrile (2.6 mL). After 3 h, the reaction was concentrated onto 500 mg of celite and was purified by silica gel chromatography 2-20% methanol in DCM to provide 45 mg of 412 62%. $^1$H NMR (400 MHz, Methanol-d$_4$) δ 8.17 (d, J=8.1 Hz, 1H), 7.16 (d, J=18.7 Hz, 1H), 5.98 (d, J=8.1 Hz, 1H), 4.09-3.87 (m, 3H), 3.80 (dd, J=12.5, 1.9 Hz, 1H), 1.43 (d, J=22.2 Hz, 3H). MS C$_{10}$H$_{13}$FN$_2$O$_4$S [M−H$^+$]; calculated: 277.1, found: 277.0.

The triphosphate of compound 412 has activity against dengue virus infection.

Example 141

5′-Phosphoramidate Prodrugs Synthesized Utilizing the General Procedure

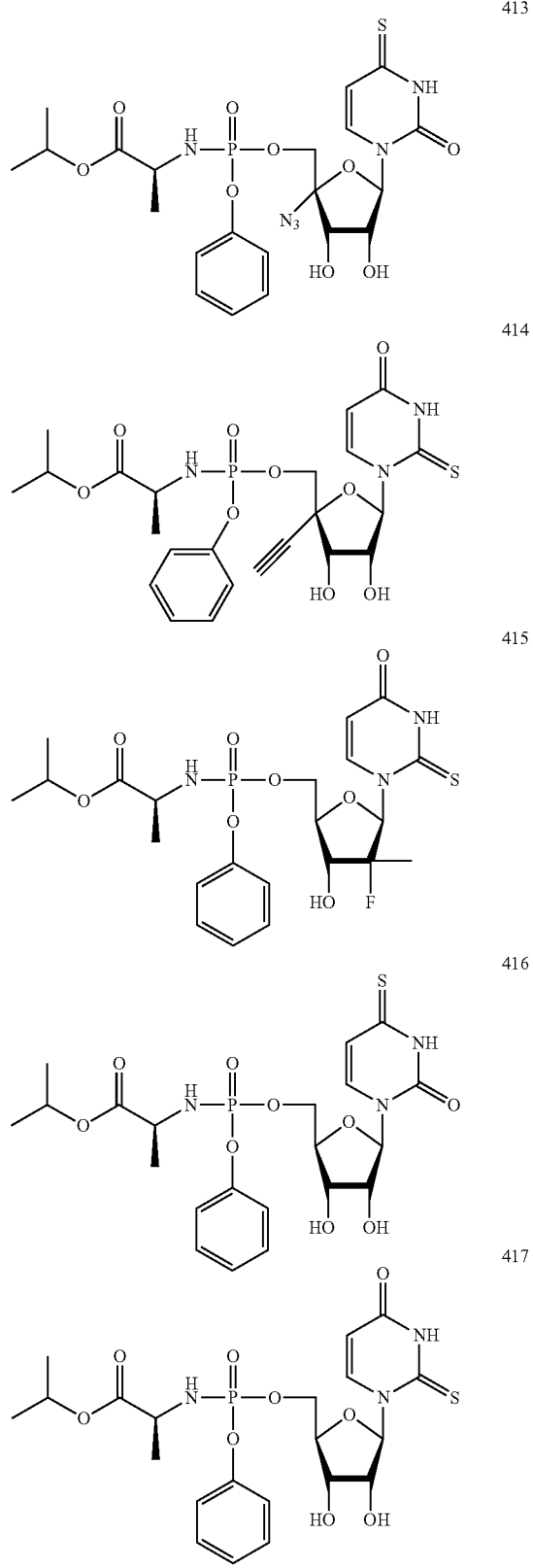

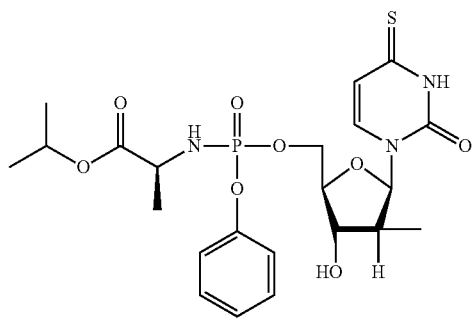

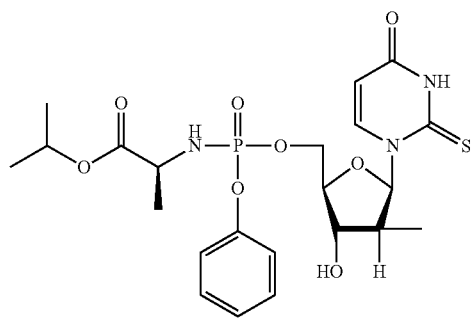

Example 142

Synthesis of 2'-methyl-2-selenouridine

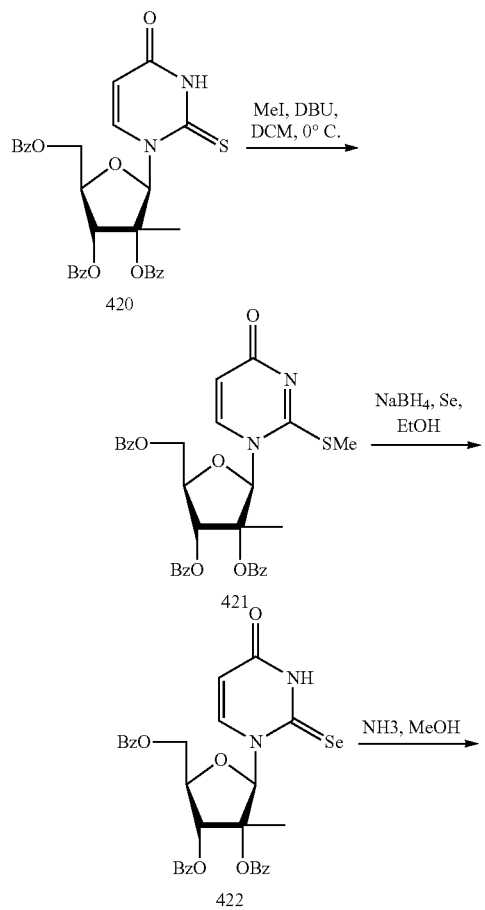

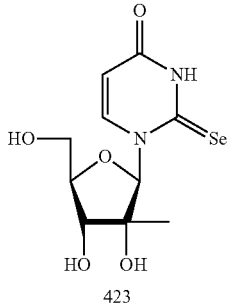

Synthesis of 421.

To a stirred solution of (2R,3R,5R)-5-((benzoyloxy)methyl)-3-methyl-2-(4-oxo-2-thioxo-3,4-dihydropyrimidin-1(2H)-yl)tetrahydrofuran-3,4-diyldibenzoate 420 (2.899 g, 4.94 mmol) in anhydrous $CH_2Cl_2$ (35 ml) was added iodomethane (3.08 ml, 49.4 mmol) and cooled to 0° C. DBU (1.106 ml, 7.41 mmol) was then added dropwise and stirred at 0° C. for 1 h. The reaction was quenched by the addition of 15 mL of water and extracted with $CH_2Cl_2$. The aqueous layer was separated and organic layer was washed with water (2×15 mL) and the aqueous layer was back extracted with $CH_2Cl_2$ (25 mL). The combined organic layers were dried ($Na_2SO_4$), filtered and concentrated to give an oil, which was purified over silica gel column chromatography using linear gradient of 0-50% EtOAC in Hexanes to get pure 421 as a white solid (2.678 g, 90% yield). $^1H$ NMR (400 MHz, Chloroform-d) δ 8.11-7.98 (m, 4H), 7.83-7.79 (m, 2H), 7.67 (d, J=7.9 Hz, 1H), 7.65-7.53 (m, 2H), 7.53-7.32 (m, 5H), 7.32-7.16 (m, 2H), 6.63 (s, 1H), 5.95 (dd, J=7.8, 0.6 Hz, 1H), 5.64 (d, J=6.0 Hz, 1H), 5.00-4.63 (m, 3H), 2.63 (s, 3H), 1.68 (s, 3H). 13C NMR (100 MHz, $CDCl_3$) δ 167.7, 166.2, 165.5, 165.3, 162.9, 138.5, 134.0, 133.9, 130.1, 129.9, 129.8, 129.6, 129.4, 129.3, 128.9, 128.8, 128.6, 128.4, 109.6, 91.21, 85.5, 80.5, 77.5, 77.2, 76.9, 74.7, 62.6, 19.4, 15.4.

Synthesis of 422.

Anhydrous Ethanol (10 ml) was cooled at 0° C. and deoxygenated by passing argon for 15 min and this solution was added to a mixture of gray powder selenium (0.263 g, 3.33 mmol) and sodium tetrahydroborate (0.132 g, 3.50 mmol) cooled in an ice bath. After being stirred for 30 min, this solution was carefully added to deoxygenated neat solid of 421 (1.000 g, 1.665 mmol) at 0° C. and stirred for 10 min at 0° C., then allowed to warm to RT overnight. TLC (5% MeOH: $CH_2Cl_2$) showed product $R_f$=0.71. The mixture was bubbled with argon to remove $H_2Se$ for an hour, diluted with EtOAC (30 mL) and washed with water (15 mL) followed by brine (15 mL). The aqueous layer was reextracted with EtOAC (30 mL). Combined organic layers were dried ($Na_2SO_4$), filtered and concentrated to get crude solid which was purified by silica column chromatography using 0-10% linear gradient of methanol in dichloromathane to obtain 422 as a pale yellow solid. The solid was repurified by column chromatography using EtOAC and hexanes to remove minor impurities and obtained pure 422 in 99% yield. $^1H$ NMR (300 MHz, Chloroform-d) δ 10.25 (s, 1H), 8.07 (t, J=8.4 Hz, 4H), 7.81 (d, J=6.0 Hz, 2H), 7.77 (s, 1H), 7.71 (d, J=6.0 Hz, 1H), 7.67-7.36 (m, 7H), 7.30-7.19 (m, 2H), 5.96 (d, J=8.3 Hz, 1H), 5.61 (d, J=6.0 Hz, 1H), 5.01-4.59 (m, 3H), 1.77 (s, 3H).

Synthesis of 423.

A solution of 422 (0.950 g, 1.500 mmol) in 7 N $NH_3$ in methanol (10 mL) was heated in a sealed tube at 40° C. overnight. TLC (10% $MeOH:CH_2Cl_2$) showed complete conversion with product $R_f$=0.2, while starting material $R_f$=0.7. The reaction mixture was concentrated and the resulting crude mixture was purified by silica gel column chromatography and eluted with 0-20% linear gradient of methanol in $CH_2Cl_2$ to obtain 423 as a pale yellow solid (0.350 g, 72.7% yield). $^1$H NMR (300 MHz, Methanol-d4) δ 8.29 (d, J=8.1 Hz, 1H), 7.10 (s, 1H), 6.08 (d, J=8.1 Hz, 1H), 4.62 (s, 1H), 4.08-3.69 (m, 4H), 1.28 (s, 3H); $^{13}$C NMR (150 MHz, DMSO): 179.3, 161.76, 143.8, 111.1, 100.5, 85.4, 81.8, 74.5, 61.4, 23.5; HRMS [M+Na]$^+$ for $C_{10}H_{14}N_2O_5NaSe$ cacld:344.99601, observed:344.99632.

Example 143

5'-Phosphoramidate Prodrugs Synthesized Utilizing the General Procedure

424

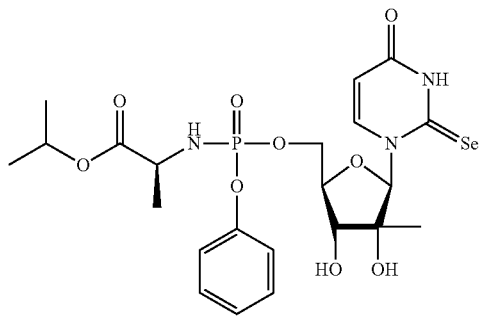

Example 144

5'-Triphosphates Synthesized Utilizing the General Procedure

425

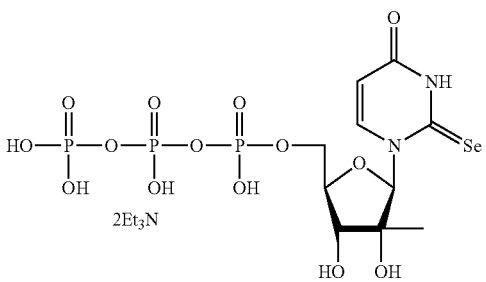

426

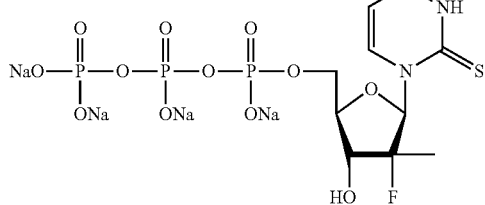

Example 145

Synthesis of 2'-methyl-4-thiouridine-5'-monophosphate

427

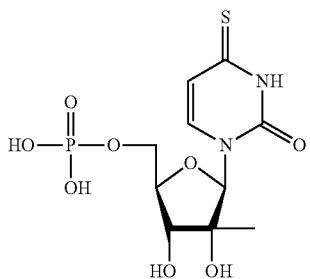

To a 10 mL flame-dried pear-shaped flas charged with 1-((2R,3R,4R,5R)-3,4-dihydroxy-5-(hydroxymethyl)-3-methyltetrahydrofuran-2-yl)-4-thioxo-3,4-dihydropyrimidin-2(1H)-one (0.205 g, 0.747 mmol) was added PO(OMe)$_3$ (1.868 ml) to give a bright yellow solution. This was cooled to 0° C. and then POCl$_3$ (0.139 ml, 1.495 mmol) was added dropwise to give still a bright yellow solution. After stirring at 0° C. for 4.5 h, TLC showed no SM. The crude mixture was poured into 30 mL cold DI water. After stirring for 5 min, it was transferred to a separation funnel and CHCl$_3$ (30 mL) was added. The aqueous layer was washed with CHCl$_3$ (30 mL) once again. Then the aqueous layer was neutralized to about pH=7.2 by adding concentrated NH$_4$OH dropwise. The mixture was re-extracted with CHCl$_3$ (30 mL) once. The aqueous layer was concentrated in vacuo to give a light yellow solid. The solids were stirred with MeOH (60 mL) for 1 h and then it was filtered through a sinsterted glass. The filtrate was treated with celite and concentrated in vacuo. The crude material was purified by SiO$_2$ column chromatography eluting from 100% DCM to 100% IPA to IPA/NH$_4$OH/H$_2$O=8/1/1 to 7/2/1 to afford the product and some other inorganics (white). Then the material was diluted with MeOH and celite was added. The crude material was concentrated in vacuo and was purified by 100% IPA to IPA/NH$_4$OH/H$_2$O=9/1/1 to 8/1/1 to 7/2/1. The fractions containing product was pulled together and concentrated in vacuo and co-evaporated with MeOH to afford an yellow oil, which was dissolved in water and lyophilized overnight to afford 427 (25 mg) as an yellow solid.

$^1$H NMR (400 MHz, CD$_3$OD); δ 7.99 (d, J=8.0 Hz, 1H), 6.51 (d, J=7.6 Hz, 1H), 5.93 (s, 1H), 4.29-4.25 (m, 1H), 4.14-4.09 (m, 1H), 4.03-3.94 (m, 2H), 1.18 (s, 3H). $^{13}$C NMR (100 MHz, CD$_3$OD); δ 192.3, 150.2, 136.7, 114.8, 93.2, 83.1, 80.3, 73.0, 63.3, 20.3. $^{31}$P NMR (400 MHz, CD$_3$OD); δ 1.27. HRMS (ESI) Calcd. for $C_{10}H_{14}O_8N_2PS$ [M−H]$^+$: 353.0214. Found: 353.0213.

Example 146

Synthesis of 2'-methyl-4-thiouridine-5'-diphosphate

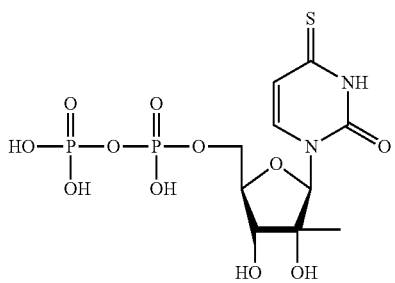

428

A stirred solution of 427 (39 mg, 110 umol) in DMF (1.1 mL, 0.1M) was charged with tributyl amine (262 uL, 1.1 mmol). Reaction was stirred for 25 min then concentrated in vacuo. Resultant paste was redisolved in DMF (1.1 mL, 0.1M) and charged with carbonyl diimidazole (89 mg, 550 umol) to give a clear solution. After stirring 24 h methanol (150 uL, 1.4 mmol) wad added dropwise. After 2 h reaction was charged with tributylammonium phosphate (12 mL, 0.5M in DMF, 2.2 mmol) to give a cloudy solution. Reaction was stirred 2d, solvent was then removed and crude paste was loaded onto a DEAE column eluting from 50-450 mM TEAB to provide triethyl ammonium salt of diphosphate. Diphosphate was transformed to sodium salt eluting through a column of Na+Dowex at 0° C. to afford 28 mg 51% yield of sodium salt of diphosphate.

$^1$H NMR (400 MHz, D$_2$O) δ7.73 (d, J=7.6 Hz, 1H), 6.53 (d, J=7.5 Hz, 1H), 5.87 (s, 1H), 4.24-4.11 (m, 2H), 4.00 (d, J=2.1 Hz, 2H), 1.08 (s, 3H). $^{32}$P NMR (162 MHz, D$_2$O) −6.55 (d, J=23.0 Hz), −11.02 (d, J=22.9 Hz). HRMS C$_{10}$H$_{16}$N$_2$O$_{11}$P$_2$S [M$^-$]; calculated:432.995, found: 432.988.

Example 147

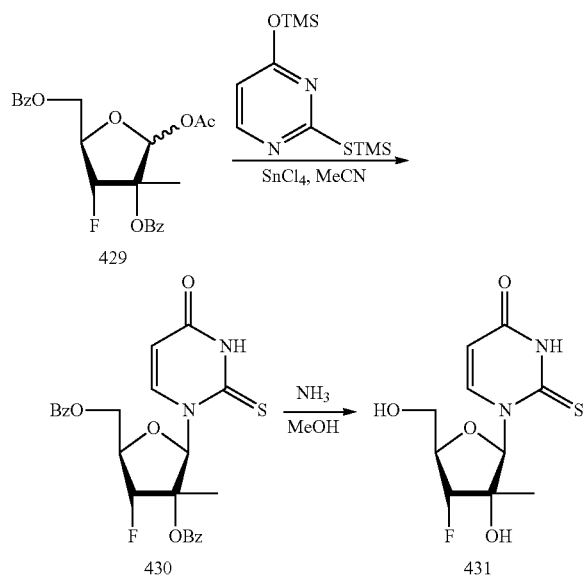

2-Thiouracil (1.025 g, 8.0 mmol) was persilylated by mixing with ammonium sulfate (0.053 g, 0.400 mmol) in hexamethyldisilazane (16.77 mL, 80.0 mmol) and heating the mixture to reflux for 16 h. The resulting light blue solution was cooled to room temperature, and volatiles were removed by rotary evaporation followed by high vacuum to give persilylated 2-thiouracil as a light blue liquid, which was >95% pure by $^1$H NMR analysis. The entirety of this material was used immediately in the next step.

To a stirred solution of the crude, freshly prepared persilyl-2-thiouracil (8.0 mmol) in 1,2-dichloroethane (20.0 mL) under nitrogen at room temperature, was added a solution of 429 (1.666 g, 4.00 mmol) in 1,2-dichloroethane all at once. The stirred solution was cooled to 0° C., and SnCl$_4$ (0.94 mL, 8.00 mmol) was added dropwise via syringe. The mixture was warmed to rt and stirred overnight for 16 h. The mixture was then recooled to 0° C. and quenched carefully with sat. aq. NaHCO$_3$ (40 mL). The mixture was warmed to rt and vigorously stirred 1 h. The mixture was extracted with EtOAc (2×150 mL), and the combined organic layers were dried over Na$_2$SO$_4$, filtered, and concentrated by rotary evaporation to give 3.5 g crude residue. The crude residue was taken up in DCM, and automated flash chromatography on a Combiflash (80 g column, 5 to 50% EtOAc gradient in hexanes) gave 430 (0.708 g, 1.46 mmol, 37% yield) as a white flaky solid. $^1$H NMR analysis showed ~95% purity; the entirety of the compound was used directly in the next step. $^1$H NMR (400 MHz, CDCl$_3$) δ 9.52 (br s, 1H), 8.18 (d, J=7.0 Hz, 2H), 8.06 (d, J=7.0 Hz, 2H), 7.67-7.57 (m, 2H), 7.59 (d, J=8.3 Hz, 1H), 7.55-7.45 (m, 5H), 5.96 (dd, J=8.3 Hz, 2.1 Hz, 1H), 5.33 (dd, J=52.0 Hz, 2.4 Hz, 1H), 4.84-4.68 (m, 3H), 1.65 (d, J=2.0 Hz, 3H).

A sealable pressure tube was charged with a stir bar, 430 (0.708 g, 1.461 mmol) and a 7 N ammonia solution in MeOH (20 mL, 140 mmol) at 0° C. The tube was sealed, warmed to room temperature, and stirred for 3 days at rt. The tube was then heated at 45° C. for 5 h, recooled to rt, and concentrated by rotary evaporation to give 700 mg crude. The crude was dissolved in MeOH and immobilized on Celite. Automated flash chromatography on a Combiflash (24 g column, 0 to 10% MeOH gradient in DCM) gave approximately 450 mg of a partially deprotected 2'-monobenzoate product. This compound was placed into a sealable pressure tube with a stir bar and a 7 N ammonia solution in MeOH (20 mL, 140 mmol). The mixture was heated with stirring, gradually increasing heat, until the reaction was complete: 24 h at 45° C., 24 h at 55° C., and finally 24 h at 75° C. The mixture was cooled to rt and concentrated by rotary evaporation to give 500 mg of a brown oil. The crude was dissolved in MeOH and immobilized on Celite. Automated flash chromatography on a Combiflash (24 g column, 0 to 10% MeOH gradient in DCM) gave 160 mg of a mostly pure compound. This was again taken up in MeOH and immobilized on Celite. A second automated flash column on the Combiflash (12 g column, 0 to 7% MeOH gradient in DCM) gave 115 mg of a white solid with some solvent occluded. The solid was dissolved in water, frozen in a dry ice/acetone bath, and lyophilized to give 431 (0.102 g, 0.369 mmol, 9.2% yield over 2 steps) as a white solid. $^1$H NMR (400 MHz, DMSO-d$_6$) δ 12.70 (s, 1H), 8.03 (d, J=8.2 Hz, 1H), 6.85 (d, J=2.5 Hz, 1H), 6.02 (d, J=8.2 Hz, 1H), 5.86 (s, 1H), 5.47 (t, J=4.9 Hz, 1H), 4.76 (dd, J=52.9 Hz, 8.7 Hz, 1H), 4.20-4.10 (br m, 1H), 3.85 (ddd, J=13.1 Hz, 5.4 Hz, 2.1 Hz, 1H), 3.66 (ddd, J=12.8 Hz, 4.9 Hz, 2.5 Hz, 1H), 1.20 (s, 3H); $^1$H NMR (400 MHz, D$_2$O) δ 7.94 (d, J=8.2 Hz, 1H), 6.98 (d, J=2.1 Hz, 1H), 6.17 (d, J=8.2 Hz, 1H), 4.81 (dd, J=52.4, 8.1 Hz, 1H), 4.38-4.27 (m, 1H), 4.04 (dd, J=13.2 Hz, 2.7 Hz, 1H), 3.90 (dd, J=13.2 Hz, 3.6 Hz, 1H), 1.34 (s, 3H); $^{13}$C NMR (100 MHz, D$_2$O) δ 176.5, 162.2, 141.8, 106.9, 94.2 (d, J=3.8 Hz), 91.3 (d, J=190.6 Hz), 79.9 (d, J=24.3 Hz), 78.6 (d, J=14.2 Hz), 59.0, 19.5; $^{19}$F NMR (376 MHz, D$_2$O) δ−212.37 (dd, J=52.3 Hz, 14.3 Hz); HRMS calcd. for C$_{10}$H$_{13}$FN$_2$O$_4$SNa [M+Na]$^+$: 299.04723, found: 299.04743.

Example 148

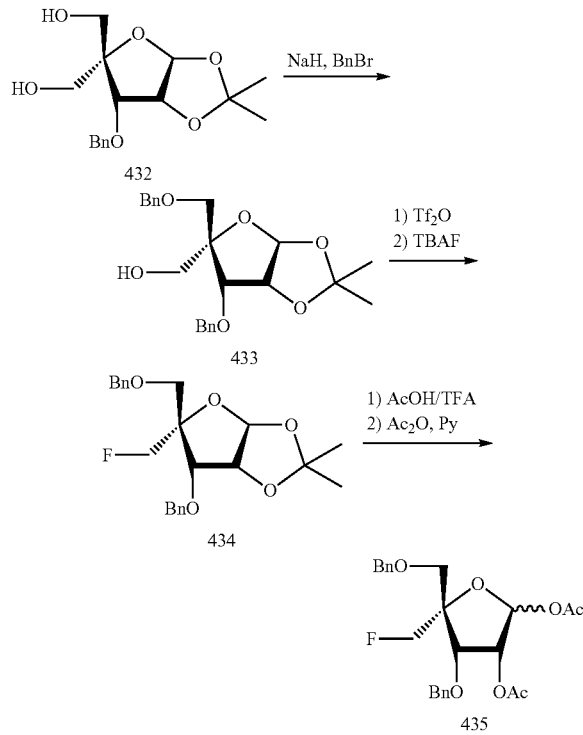

3,5-Di-O-benzyl-4-C-hydroxymethyl-1,2-O-isopropylidene-α-D-ribofuranose

To a solution of 3-O-benzyl-4-C-hydroxymethyl-1,2-O-isopropylidene-α-D-ribofuranose (10.0 g, 32.2 mmol) in anhydrous DMF (50 mL) at −5° C. was added a suspension of NaH (60% in mineral oil (w/w), two portions during 30 main, total 1.48 g, 37.1 mmol). Benzyl bromide (4.4 mL, 37.1 mmol) was added dropwise and stirring at room temperature was continued for 3 h whereupon ice-cold water (50 mL) was added. The mixture was extracted with EtOAc (4×50 mL) and the combined organic phase was dried (Na$_2$SO$_4$). After evaporation, the residue was purified by silica gel column chromatography eluting with 15-20% EtOAc in Hexanes (v/v) to yield the product, 433 (8.84 g, 69%) as colorless liquid. $^1$H NMR (400 MHz, CDCl$_3$); δ 7.37-7.25 (m, 10H), 5.79 (d, J=4.0 Hz, 1H), 4.79 (d, J=12.0 Hz, 1H), 4.65 (t, J=4.8 Hz, 1H), 4.54 (d, J=12.0 Hz, 1H), 4.51 (d, J=12.0 Hz, 1H), 4.46 (d, J=12.0 Hz, 1H), 4.27 (d, J=4.8 Hz, 1H), 3.93 (d, J=12.0 Hz, 1H), 3.83 (d, J=12.0 Hz, 1H), 3.61 (d, J=12.0 Hz, 1H), 3.54 (d, J=12.0 Hz, 1H), 2.26 (br s, 1H), 1.64 (s, 3H), 1.35 (s, 3H).

3,5-Di-O-benzyl-4-C-fluoromethyl-1,2-O-isopropylidene-α-D-ribofuranose

To a stirred solution of 433 (7.87 g, 19.65 mmol) in CH$_2$Cl$_2$ (190 mL) was added successively pyridine (2.37 mL, 29.5 mmol) and trifluoromethanesulfonic anhydride (3.64 mL, 21.62 mmol) at 0° C. The reaction mixture was stirred at 0° C. for −45 min. and then TLC indicated completion of reaction to a single, faster moving compound. After which, the mixture was washed with water and brine. The combined aqueous layers were back extracted with CH$_2$Cl$_2$. The combined organic phase was dried (Na$_2$SO$_4$), concentrated under reduced pressure to give a light brown solid.

The solid obtained from previous step was dissolved in acetonitrile (100 ml). A 1M solution of tetrabutylammonium fluoride in THF (78 mL, 78.0 mmol) was added and the reaction mixture was stirred at −50° C. for overnight. Removal of the solvent under reduced pressure and silica gel chromatography of the dark oily residue [10-15% EtOAc in Hexanes] gave 434 (4.3 g, 55%) as a colorless oil. $^1$H NMR (400 MHz, CDCl$_3$); δ 7.34-7.26 (m, 10H), 5.77 (d, J=3.6 Hz, 1H), 4.87 (dd, J=10.0, 48.8 Hz, 1H), 4.73 (d, J=10 Hz, 1H), 4.63-4.47 (m, 5H), 4.26 (dd, J=1.6, 4.8 Hz, 1H), 3.61 (dd, J=1.6, 10.4 Hz, 1H), 3.55 (dd, J=1.6, 10.4 Hz, 1H), 1.63 (s, 3H), 1.35 (s, 3H). $^{19}$F NMR (400 MHz, CDCl$_3$); δ−28.46 (t, J=48.8 Hz).

1,2-Di-O-acetyl-3,5-di-O-benzyl-4-C-fluoromethyl-D-ribofuranose

A stirred solution of 434 in 70% acetic acid (73 mL) was charged with TFA (7.3 mL), and heated to 40° C. After 4 h reaction was concentrated and coevaporated with toluene. Paste was then dissolved in pyridine (27 mL) and charged with acetic anhydride (10.57 mL, 112 mmol). After stirring overnight reaction was concentrated and pulled up in ethyl acetate and was washed with water. The dried (Na$_2$SO$_4$) was filtered and concentrated to an oil which was purified by silica gel chromatography 5-20% ethyl acetate in hexanes to provide 435 (3.54 g, 71%) as colorless liquid. $^1$H NMR (400 MHz, CDCl$_3$); δ 7.35-7.25 (m, 10H), 6.18 (s, 1H), 5.35 (d, J=5.2 Hz, 1H), 4.73-4.66 (m, 1H), 4.60-4.48 (m, 5H), 4.43 (d, J=4.8 Hz, 1H), 3.68 (dd, J=1.6, 10.4 Hz, 1H), 3.51 (dd, J=1.6, 10.4 Hz, 1H), 2.11 (s, 3H), 1.90 (s, 3H).

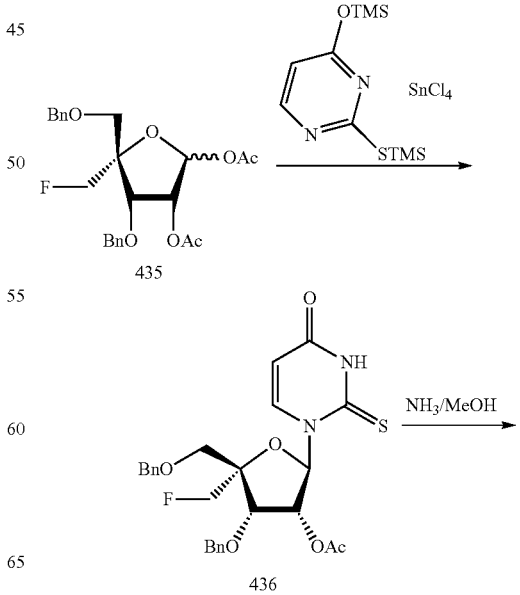

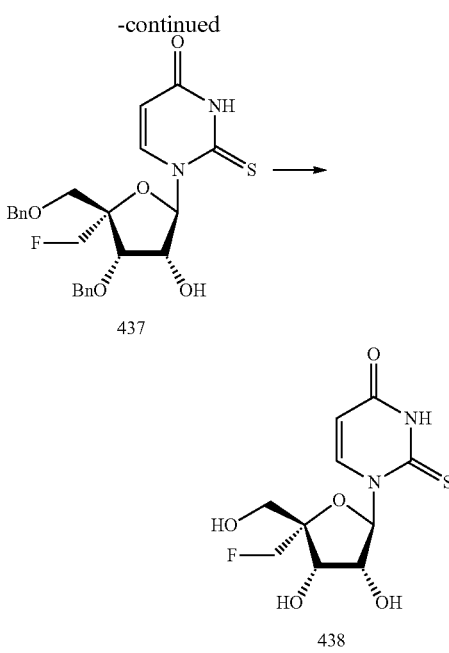

437

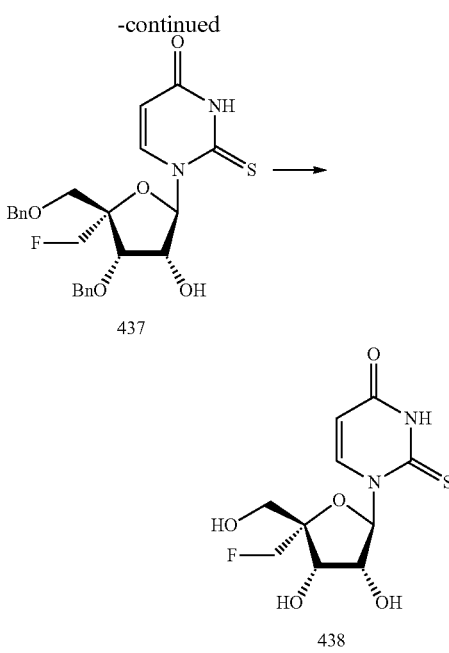

438

1-(2'-O-Acetyl-3',5'-di-O-benzyl-4'-C-fluoromethyl-β-D-ribofuranosyl)2-thiouracil A stirred mixture of 2-thiouracil (600 mg, 4.68 mmol) and ammonium sulfate (30 mg, 0.23 mmol) in hexamethyldisilazane (4.9 mL, 23.41 mmol) and chlorobenzene (10 mL) was heated to reflux under nitrogen 3-4 h. until all solids dissolved and a light blue solution was formed. The mixture was cooled to rt and concentrated by rotary evaporation, followed by hi-vac, to give a blue liquid with some white solid in it. The entirety of the crude was taken on to the next step immediately.

To a stirred cloudy solution of 435 (950 mg, 2.13 mmol) and bis-silylated 2-thiouracil in 1,2-DCE (10.0 ml) at 0° C. under nitrogen, was added tin(IV) chloride (0.5 ml, 4.26 mmol). The mixture immediately turned yellow, and the mixture became less cloudy. The mixture was warmed to rt and stirred overnight. After stirring 15 h at rt, the mixture was diluted with 25 mL DCM, and 1.0 g each of solid NaHCO$_3$ and Celite were carefully added to the vigorously stirred reaction mixture. The mixture was cooled to 0° C., and sat. aq. NaHCO$_3$ (2 mL) was added dropwise with vigorous stirring. The mixture was warmed to rt and stirred 2 h. The mixture was filtered through a small Celite pad which was then rinsed with DCM (20 mL). The combined filtrates were concentrated to an oil which was purified by silica gel chromatography 30-35% ethyl acetate in hexanes to provide 436 (890 mg, 81%) as colorless foamy solid. $^1$H NMR (400 MHz, CDCl$_3$); δ 10.11 (br s, 1H), 8.05 (d, J=8.0 Hz, 1H), 7.40-7.19 (m, 10H), 6.81 (d, J=2.8 Hz, 1H), 5.49 (dd, J=3.2, 4.8 Hz, 1H), 5.38 (d, J=8.0 Hz, 1H), 4.73-4.59 (m, 3H), 4.50-4.35 (m, 4H), 3.95 (d, J=10.0 Hz, 1H), 3.57 (d, J=10.4 Hz, 1H), 2.15 (s, 3H). $^{19}$F NMR (400 MHz, CDCl$_3$); δ−28.22 (t, J=50.8 Hz).

1-(3',5'-Di-O-benzyl-4'-C-fluoromethyl-β-D-ribofuranosyl)2-thiouracil

To a stirred solution of 436 (890 mg, 1.73 mmol) in methanol (29 ml) at 0° C., was added methanolic ammonia (6.2 mL, 7 M in MeOH). The mixture was allowed to warm 40° C. and stirred for overnight. The solvent was evaporated under reduced pressure and then purified by silica gel chromatography 25-30% ethyl acetate in hexanes to provide 437 (800 mg, 89%) as colorless foamy solid.

1-(4'-C-Fluoromethyl-β-D-ribopentofuranosyl)2-thiouracil

In a 50 mL pear-shaped flask charged with 437 (800 mg, 1.693 mmol) was added dry DCM (20.0 mL) under N$_2$. This was cooled to −78° C. and then BCl$_3$ (11.8 mL, 11.8 mmol, 1.0M in DCM) was added dropwise. The reaction was allowed to stir at −78° C. for 15 min, and then warm up slowly to −40° C., TLC showed no SM, then MeOH (5 mL) was added dropwise and stirred at −40° C. for. After which, solvent was removed in vacuo and the crude material was purified by SiO$_2$ column chromatography eluting 5-7% MeOH in DCM to provide 438 (340 mg, 69%) as white solid. $^1$H NMR (400 MHz, CD$_3$OD); δ 8.21 (d, J=8.0 Hz, 1H), 6.96 (d, J=5.6 Hz, 1H), 5.98 (d, J=8.0 Hz, 1H), 4.67 (d, J=0.8 Hz, 1H), 4.56 (d, J=2.0 Hz, 1H), 4.34-4.30 (m, 2H), 3.81-3.78 (m, 2H). $^{13}$C NMR (100 MHz, CD$_3$OD); δ 178.9, 162.4, 143.0, 107.3, 93.3, 88.9, 88.8, 85.3, 83.6, 76.7, 72.3, 63.5. $^{19}$F NMR (400 MHz, CDCl$_3$); δ−30.18 (t, J=50.8 Hz). HRMS (ESI) Calcd. for C$_{10}$H$_{13}$O$_5$N$_2$FNaS [M+Na]$^+$: 315.0421. Found: 315.0424.

Example 149

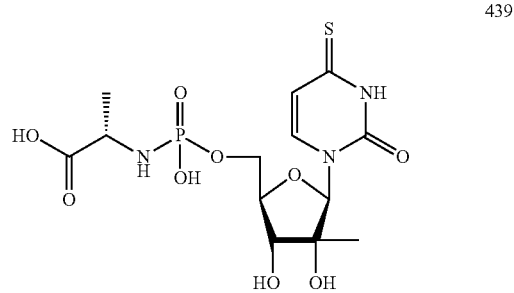

439

To a 100 mL pear-shaped flask charged with 260 (300 mg, 0.552 mmol) was added H$_2$O (8.00 ml) and Et$_3$N (8 ml). This was heated to 35° C. (oil-bath temp). Start at 4:50 μm and stop at 9 am. After overnight stirring, TLC showed no SM. Then solvent was removed in vacuo and then Celite was added and the mixture was concentrated in vacuo. The crude material was purified by SiO$_2$ column chromatography eluting from iPrOH (3CV) to iPrOH/NH$_4$OH/H2O=8/1/1 to afford 439 (0.18 g, 77% yield) as a yellow solid.

$^1$H NMR (400 MHz, D$_2$O); δ 7.91 (d, J=7.6 Hz, 1H), 6.66 (d, J=7.6 Hz, 1H), 5.98 (s, 1H), 4.23-4.11 (m, 2H), 4.03-3.96 (m, 2H), 3.62-3.55 (m, 1H), 1.29 (d, J=6.8 Hz, 3H), 1.21 (s, 3H). $^{13}$C NMR (100 MHz, D$_2$O); δ 190.4, 180.4, 149.0, 136.2, 113.7, 91.7, 80.7, 79.0, 71.6, 61.9, 51.0, 20.4, 18.8. $^{31}$P NMR (400 MHz, D20); δ 7.67. HRMS (ESI) Calcd. for C$_{13}$H$_{19}$O$_9$N$_3$PS [M−H]$^+$: 424.0585. Found: 424.0584.

Example 150

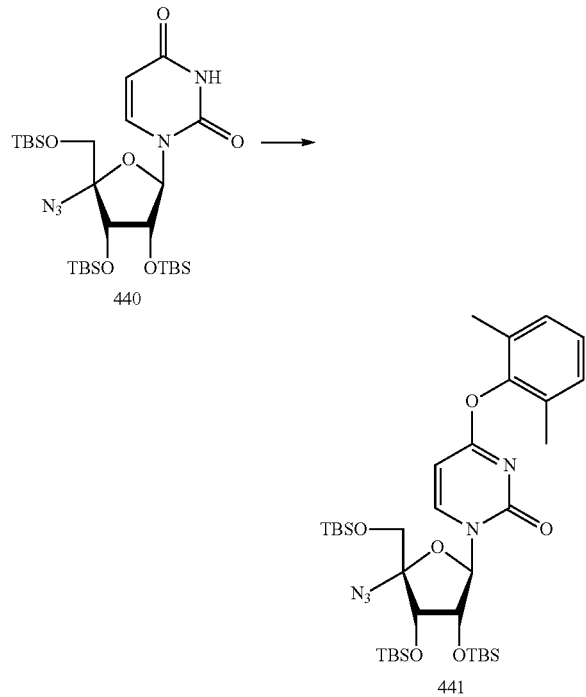

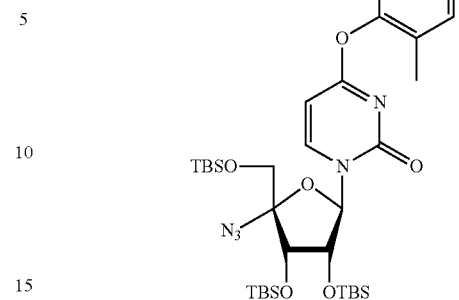

To a 250 mL pear-shaped flask charged with 1-((2R,3R,4S,5R)-5-azido-3,4-bis((tert-butyldimethylsilyl)oxy)-5-(((tert-butyldimethylsilyl)oxy)methyl)tetrahydrofuran-2-yl)pyrimidine-2,4(1H,3H)-dione (6.4 g, 10.19 mmol) was added dry DCM (85 ml) to give a colorless solution under argon. This was treated with N,N-dimethylpyridin-4-amine (2.490 g, 20.38 mmol) and triethylamine (2.98 ml, 21.40 mmol) to give a still colorless solution. The flask was cooled to 0° C. and then 2,4,6-triisopropylbenzene-1-sulfonyl chloride (6.17 g, 20.38 mmol) was added. After 1 h, ice-water bath was removed. After stirring for 17 h, the reaction became a brownish solution. It was cooled to 0° C. and then a dry DCM (21.23 ml) solution of 2,6-dimethylphenol (3.73 g, 30.6 mmol), DABCO (0.229 g, 2.038 mmol) and triethylamine (4.26 ml, 30.6 mmol) was added dropwisely. After addition, ice-water bath was removed. After stirring for 5 h, it was quenched with 50 mL NaHCO$_3$, the organic layer was separated, washed again with 50 mL water once, 50 mL brine once, dried (Na2SO4), filtered and concentrated in vacuo. The crude material was dissolved in DCM and was purified by ISCO column chromatography (120 g, 50 mL each) eluting from 100% to 20% EtOAc in hexanes in 30 min (product came out ~4.5% EtOAc in hexanes) to afford the product, which was triturated with hexanes to afford 441 (4.7 g, 6.42 mmol, 63.0% yield) as a white solid.

$^1$H NMR (400 MHz, CDCl$_3$) δ 8.28 (d, J=7.4 Hz, 1H), 7.04 (d, J=1.6 Hz, 3H), 6.14 (d, J=3.7 Hz, 1H), 6.10 (d, J=7.4 Hz, 1H), 4.37-4.29 (m, 1H), 4.26 (d, J=4.7 Hz, 1H), 3.86 (d, J=11.3 Hz, 1H), 3.64 (d, J=11.3 Hz, 1H), 2.14 (s, 6H), 0.99 (s, 8H), 0.96 (s, 8H), 0.92 (s, 8H), 0.18 (d, J=7.1 Hz, 6H), 0.14 (d, J=3.1 Hz, 6H), 0.08 (d, J=0.5 Hz, 5H).

To a 500 mL rbf charged with 441 (12.7 g, 17.35 mmol) was added dry toluene (173 ml) under argon. Then 2,4-bis (4-methoxyphenyl)-1,3,2,4-dithiadiphosphetane 2,4-disulfide (10.52 g, 26.0 mmol) was added. This mixture was heated to 110° C. for 5 hours, the crude material was concentrated in vacuo and the crude material was purified by SiO$_2$ column chromatography eluting from 100% hexanes to 5% EtOAc in hexanes to 10% EtOAc in hexanes to afford 442 (10 g, 13.37 mmol, 77% yield) as a glassy solid, which contains some impurity but used for the next step directly.

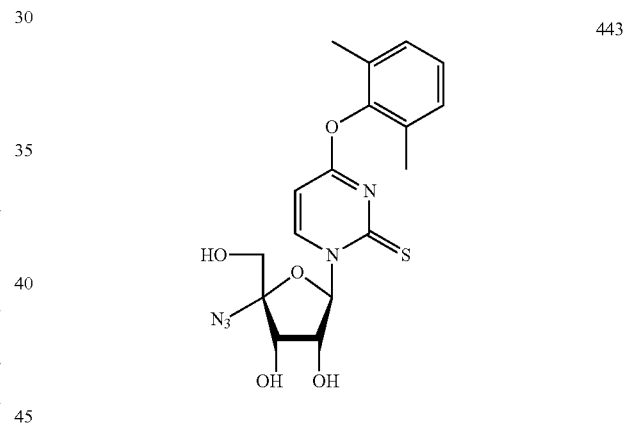

To a 200 mL pear-shaped flask charged with 442 (0.14 g, 0.187 mmol) (yellow solid) was added dry THF (1.871 ml) to give a yellow solution. This was vacuumed and charged with argon. The flask was cooled to 0° C. and then TBAF (0.599 ml, 0.599 mmol) was added dropwisely, followed by glacial AcOH (0.034 ml, 0.599 mmol). After 3 min, ice-water bath was removed. After 1.5 h, TLC showed no SM. Then the crude mixture was diluted with CHCl$_3$, which was poured into a separation funnel. Then sat NaHCO$_3$ was added. The aqueous layer was re-extracted with CHCl3 once, the combined organic layer was washed with brine once. Again, the aqueous layer was re-extracted with DCM. The combined organic layer was dried (Na$_2$SO$_4$), filtered and concentrated in vacuo. The crude material was purified by SiO$_2$ column chromatography eluting from 100% DCM (75 mL, 3CV) to 1% MeOH in DCM (100 mL) to 2% MeOH in DCM (200 mL) to afford 443 (70 mg, 0.173 mmol, 92% yield) as an off-white solid.

$^1$H NMR (400 MHz, CDCl$_3$) δ 8.54 (d, J=7.2 Hz, 1H), 7.9 (s, 3H), 6.60 (s, 1H), 6.39 (d, J=7.6 Hz, 1H), 4.39-4.26 (m, 3H), 4.05-3.90 (m, 2H), 3.16 (d, J=8.8 Hz, 1H), 2.14 (s, 6H).

425

444

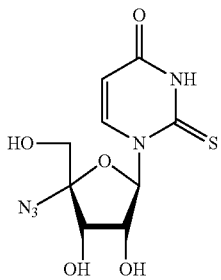

To a 10 mL pear-shaped flask charged with 443 (70 mg, 0.173 mmol) was added dry $CH_3CN$ (1.7 mL) to give a light yellow solution. Then to another 10 mL flask charged with syn-o-nitrobenzaldoxime (86 mg, 0.518 mmol) was added dry $CH_3CN$ (1.7 mL), followed by 1,1,3,3-tetramethylguanidine (0.065 mL, 0.518 mmol) to give an orange solution. This was added dropwise to the previous flask to give an orange solution at the end. After stirring at rt for 2 h, TLC showed no SM. Then silica gel was added and the crude material was concentrated in vacuo. The crude material was purified by $SiO_2$ column chromatography eluting from 5% MeOH in DCM to 7.5% MeOH in DCM to afford 444 (38 mg, 73% yield) as an off-white solid.

$^1$H NMR (400 MHz, $CD_3OD$) δ 8.20 (d, J=8.0 Hz, 1H), 7.06 (d, J=4.0 Hz, 1H), 5.97 (d, J=8.4 Hz, 1H), 4.34-4.27 (m, 2H), 3.68 (dd, J=38.4, 12.0 Hz, 2H). $^{13}$C NMR (100 MHz, $CD_3OD$); δ 178.5, 162.4, 142.4, 107.3, 101.1, 95.2, 75.8, 72.4, 64.2. HRMS (ESI) Calcd. for $C_9H_{11}O_5N_5NaS$ [M+Na]$^+$: 324.0373. Found: 324.0370.

Example 151

5'-Phosphoramidate Prodrugs Synthesized Utilizing the General Procedure

445

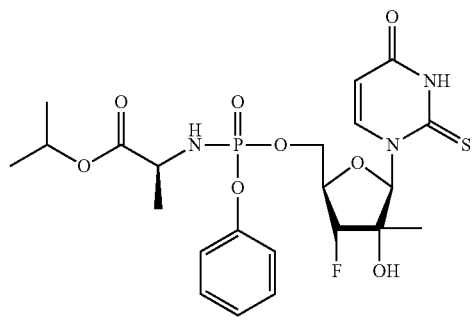

446

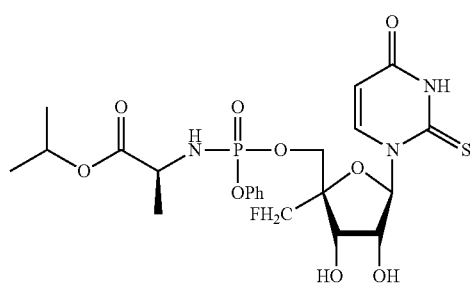

426

-continued

447

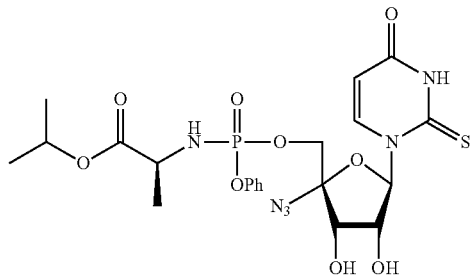

Example 152

Assay Protocols
(1) Screening Assays for DENV, JEV, POWV, WNV, YFV, PTV, RVFV, CHIKV, EEEV, VEEV, WEEV, TCRV, PCV, JUNV, MPRLV Primary Cytopathic Effect (CPE) Reduction Assay Four-concentration CPE inhibition assays are performed. Confluent or near-confluent cell culture monolayers in 96-well disposable microplates are prepared. Cells are maintained in MEM or DMEM supplemented with FBS as required for each cell line. For antiviral assays the same medium is used but with FBS reduced to 2% or less and supplemented with 50 μg/ml gentamicin. The test compound is prepared at four $log_{10}$ final concentrations, usually 0.1, 1.0, 10, and 100 μg/ml or μM. The virus control and cell control wells are on every microplate. In parallel, a known active drug is tested as a positive control drug using the same method as is applied for test compounds. The positive control is tested with each test run. The assay is set up by first removing growth media from the 96-well plates of cells. Then the test compound is applied in 0.1 ml volume to wells at 2× concentration. Virus, normally at <100 50% cell culture infectious doses ($CCID_{50}$) in 0.1 ml volume, is placed in those wells designated for virus infection. Medium devoid of virus is placed in toxicity control wells and cell control wells. Virus control wells are treated similarly with virus. Plates are incubated at 37° C. with 5% $CO_2$ until maximum CPE is observed in virus control wells. The plates are then stained with 0.011% neutral red for approximately two hours at 37° C. in a 5% $CO_2$ incubator. The neutral red medium is removed by complete aspiration, and the cells may be rinsed 1× with phosphate buffered solution (PBS) to remove residual dye. The PBS is completely removed and the incorporated neutral red is eluted with 50% Sorensen's citrate buffer/50% ethanol (pH 4.2) for at least 30 minutes. Neutral red dye penetrates into living cells, thus, the more intense the red color, the larger the number of viable cells present in the wells. The dye content in each well is quantified using a 96-well spectrophotometer at 540 nm wavelength. The dye content in each set of wells is converted to a percentage of dye present in untreated control wells using a Microsoft Excel computer-based spreadsheet. The 50% effective ($EC_{50}$, virus-inhibitory) concentrations and 50% cytotoxic ($CC_{50}$, cell-inhibitory) concentrations are then calculated by linear regression analysis. The quotient of $CC_{50}$ divided by $EC_{50}$ gives the selectivity index (SI) value.

Secondary CPE/Virus Yield Reduction (VYR) Assay.

This assay involves similar methodology to what is described in the previous paragraphs using 96-well microplates of cells. The differences are noted in this section. Eight half-$log_{10}$ concentrations of inhibitor are tested for antiviral activity and cytotoxicity. After sufficient virus replication occurs, a sample of supernatant is taken from each infected well (three replicate wells are pooled) and held for the VYR portion of this test, if needed. Alternately, a separate plate may be prepared and the plate may be frozen for the VYR assay. After maximum CPE is observed, the viable plates are stained with neutral red dye. The incorporated dye content is quantified as described above. The data generated from this portion of the test are neutral red $EC_{50}$, $CC_{50}$, and SI values. Compounds observed to be active above are further evaluated by VYR assay. The VYR test is a direct determination of how much the test compound inhibits virus replication. Virus that was replicated in the presence of test compound is titrated and compared to virus from untreated, infected controls. Titration of pooled viral samples (collected as described above) is performed by endpoint dilution. This is accomplished by titrating $log_{10}$ dilutions of virus using 3 or 4 microwells per dilution on fresh monolayers of cells by endpoint dilution. Wells are scored for presence or absence of virus after distinct CPE (measured by neutral red uptake) is observed. Plotting the $log_{10}$ of the inhibitor concentration versus $log_{10}$ of virus produced at each concentration allows calculation of the 90% (one $log_{10}$) effective concentration by linear regression. Dividing $EC_{90}$ by the $CC_{50}$ obtained in part 1 of the assay gives the SI value for this test.

Example 153

(2) Screening Assays for Lassa Fever Virus (LASV)
Primary Lassa Fever Virus Assay.
Confluent or near-confluent cell culture monolayers in 12-well disposable cell culture plates are prepared. Cells are maintained in DMEM supplemented with 10% FBS. For antiviral assays the same medium is used but with FBS reduced to 2% or less and supplemented with 1% penicillin/streptomycin. The test compound is prepared at four $log_{10}$ final concentrations, usually 0.1, 1.0, 10, and 100 µg/ml or µM. The virus control and cell control will be run in parallel with each tested compound. Further, a known active drug is tested as a positive control drug using the same experimental set-up as described for the virus and cell control. The positive control is tested with each test run. The assay is set up by first removing growth media from the 12-well plates of cells, and infecting cells with 0.01 MOI of LASV strain Josiah. Cells will be incubated for 90 min: 500 µI inoculum/M12 well, at 37° C., 5% CO2 with constant gentle rocking. The inoculums will be removed and cells will be washed 2× with medium. Then the test compound is applied in 1 ml of total volume of media. Tissue culture supernatant (TCS) will be collected at appropriate time points. TCS will then be used to determine the compounds inhibitory effect on virus replication. Virus that was replicated in the presence of test compound is titrated and compared to virus from untreated, infected controls. For titration of TCS, serial ten-fold dilutions will be prepared and used to infect fresh monolayers of cells. Cells will be overlaid with 1% agarose mixed 1:1 with 2× MEM supplemented with 10% FBS and 1% penicillin, and the number of plaques determined. Plotting the $log_{10}$ of the inhibitor concentration versus $log_{10}$ of virus produced at each concentration allows calculation of the 90% (one $log_{10}$) effective concentration by linear regression.
Secondary Lassa Fever Virus Assay.
The secondary assay involves similar methodology to what is described in the previous paragraphs using 12-well plates of cells. The differences are noted in this section. Cells are being infected as described above but this time overlaid with 1% agarose diluted 1:1 with 2× MEM and supplemented with 2% FBS and 1% penicillin/streptomycin and supplemented with the corresponding drug concentration. Cells will be incubated at 37° C. with 5% CO2 for 6 days. The overlay is then removed and plates stained with 0.05% crystal violet in 10% buffered formalin for approximately twenty minutes at room temperature. The plates are then washed, dried and the number of plaques counted. The number of plaques is in each set of compound dilution is converted to a percentage relative to the untreated virus control. The 50% effective (EC50, virus-inhibitory) concentrations are then calculated by linear regression analysis.

Example 154

(3) Screening Assays for Ebola Virus (EBOV) and Nipah Virus (NIV)
Primary Ebola/Nipah Virus Assay.
Four-concentration plaque reduction assays are performed. Confluent or near-confluent cell culture monolayers in 12-well disposable cell culture plates are prepared. Cells are maintained in DMEM supplemented with 10% FBS. For antiviral assays the same medium is used but with FBS reduced to 2% or less and supplemented with 1% penicillin/streptomycin. The test compound is prepared at four $log_{10}$, final concentrations, usually 0.1, 1.0, 10, and 100 µg/ml or µM. The virus control and cell control will be run in parallel with each tested compound. Further, a known active drug is tested as a positive control drug using the same experimental set-up as described for the virus and cell control. The positive control is tested with each test run. The assay is set up by first removing growth media from the 12-well plates of cells. Then the test compound is applied in 0.1 ml volume to wells at 2× concentration. Virus, normally at approximately 200 plaque-forming units in 0.1 ml volume, is placed in those wells designated for virus infection. Medium devoid of virus is placed in toxicity control wells and cell control wells. Virus control wells are treated similarly with virus. Plates are incubated at 37° C. with 5% $CO_2$ for one hour. Virus-compound inoculums will be removed, cells washed and overlaid with 1.6% tragacanth diluted 1:1 with 2× MEM and supplemented with 2% FBS and 1% penicillin/streptomycin and supplemented with the corresponding drug concentration. Cells will be incubated at 37° C. with 5% $CO_2$ for 10 days. The overlay is then removed and plates stained with 0.05% crystal violet in 10% buffered formalin for approximately twenty minutes at room temperature. The plates are then washed, dried and the number of plaques counted. The number of plaques is in each set of compound dilution is converted to a percentage relative to the untreated virus control. The 50% effective ($EC_{50}$, virus-inhibitory) concentrations are then calculated by linear regression analysis.
Secondary Ebola/NIpah Virus Assay with VYR Component.
The secondary assay involves similar methodology to what is described in the previous paragraphs using 12-well plates of cells. The differences are noted in this section. Eight half-$log_{10}$ concentrations of inhibitor are tested for antiviral activity. One positive control drug is tested per batch of compounds evaluated. For this assay, cells are infected with virus. Cells are being infected as described above but this time incubated with DMEM supplemented with 2% FBS and 1% penicillin/streptomycin and supplemented with the corresponding drug concentration. Cells will be incubated for 10 days at 37° C. with 5% $CO_2$, daily observed under microscope for the number of green fluorescent cells. Aliquots of supernatant from infected cells will be taken daily and the three replicate wells are pooled. The pooled supernatants are then used to determine the compounds inhibitory effect on virus replication. Virus that was replicated in the presence of test compound is titrated and compared to virus from untreated, infected controls. For titration of pooled viral samples, serial ten-fold dilutions will be prepared and used to infect fresh monolayers of cells. Cells are overlaid with tragacanth and the number of plaques determined. Plotting the $\log_{10}$ of the inhibitor concentration versus $\log_{10}$ of virus produced at each concentration allows calculation of the 90% (one $\log_{10}$) effective concentration by linear regression.

Example 155

Anti-Dengue Virus Cytoprotection Assay:

Cell Preparation-BHK21 cells (Syrian golden hamster kidney cells, ATCC catalog # CCL-I 0), Vero cells (African green monkey kidney cells, ATCC catalog# CCL-81), or Huh-7 cells (human hepatocyte carcinoma) were passaged in DMEM supplemented with 10% FBS, 2 mM L-glutamine, 100 U/mL penicillin, and 100 µg/mL streptomycin in T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at $3 \times 10^3$ ($5 \times 10^5$ for Vero cells and Huh-7 cells) cells per well in tissue culture medium and added to flat bottom microtiter plates in a volume of 100 µL. The plates were incubated at 37° C./5% $CO_2$ overnight to allow for cell adherence. Monolayers were observed to be approximately 70% confluent.

Virus Preparation—The Dengue virus type 2 New Guinea C strain was obtained from ATCC (catalog# VR-1584) and was grown in LLC-MK2 (Rhesus monkey kidney cells; catalog #CCL-7.1) cells for the production of stock virus pools. An aliquot of virus pretitered in BHK21 cells was removed from the freezer (−80° C.) and allowed to thaw slowly to room temperature in a biological safety cabinet. Virus was resuspended and diluted into assay medium (DMEM supplemented with 2% heat-inactivated FBS, 2 mM L-glutamine, 100 U/mL penicillin, and 100 µg/mL streptomycin) such that the amount of virus added to each well in a volume of 100 µL was the amount determined to yield 85 to 95% cell killing at 6 days post-infection.

Plate Format—Each plate contains cell control wells (cells only), virus control wells (cells plus virus), triplicate drug toxicity wells per compound (cells plus drug only), as well as triplicate experimental wells (drug plus cells plus virus).

Efficacy and Toxicity XTT-Following incubation at 37° C. in a 5% $CO_2$ incubator, the test plates were stained with the tetrazolium dye XTT (2,3-bis(2-methoxy-4-nitro-5-sulfophenyl)-5-[(phenylamino)carbonyl]-2H-tetrazolium hydroxide). XTT-tetrazolium was metabolized by the mitochondrial enzymes of metabolically active cells to a soluble formazan product, allowing rapid quantitative analysis of the inhibition of virus-induced cell killing by antiviral test substances. XTT solution was prepared daily as a stock of 1 mg/mL in RPMI 1640. Phenazine methosulfate (PMS) solution was prepared at 0.15 mg/mL in PBS and stored in the dark at −20° C. XTT/PMS stock was prepared immediately before use by adding 40 µL of PMS per ml of XTT solution. Fifty microliters of XTT/PMS was added to each well of the plate and the plate was reincubated for 4 hours at 37° C. Plates were sealed with adhesive plate sealers and shaken gently or inverted several times to mix the soluble formazan product and the plate was read spectrophotometrically at 450/650 nm with a Molecular Devices Vmax plate reader.

Data Analysis—Raw data was collected from the Softmax Pro 4.6 software and imported into a Microsoft Excel spreadsheet for analysis. The percent reduction in viral cytopathic effect compared to the untreated virus controls was calculated for each compound. The percent cell control value was calculated for each compound comparing the drug treated uninfected cells to the uninfected cells in medium alone.

Example 156

Anti-RSV Cytoprotection Assay:

Cell Preparation-HEp2 cells (human epithelial cells, A TCC catalog# CCL-23) were passaged in DMEM supplemented with 10% FBS, 2 mM L-glutamine, 100 U/mL penicillin, 100 µg/mL streptomycin 1 mM sodium pyruvate, and 0.1 mM NEAA, T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at $1 \times 10^4$ cells per well in tissue culture medium and added to flat bottom microtiter plates in a volume of 100 µL. The plates were incubated at 37° C./5% $CO_2$ overnight to allow for cell adherence. Virus Preparation—The RSV strain Long and RSV strain 9320 were obtained from ATCC (catalog# VR-26 and catalog #VR-955, respectively) and were grown in HEp2 cells for the production of stock virus pools. A pretitered aliquot of virus was removed from the freezer (−80° C.) and allowed to thaw slowly to room temperature in a biological safety cabinet. Virus was resuspended and diluted into assay medium (DMEM supplemented with 2% heat-inactivated FBS, 2 mM L-glutamine, 100 U/mL penicillin, 100 µg/mL streptomycin, 1 mM sodium pyruvate, and 0.1 mM NEAA) such that the amount of virus added to each well in a volume of 100 µL was the amount determined to yield 85 to 95% cell killing at 6 days post-infection. Efficacy and Toxicity XTT-Plates were stained and analyzed as previously described for the Dengue cytoprotection assay.

Example 157

Anti-Influenza Virus Cytoprotection Assay:

Cell Preparation-MOCK cells (canine kidney cells, ATCC catalog# CCL-34) were passaged in DMEM supplemented with 10% FBS, 2 mM L-glutamine, 100 U/mL penicillin, 100 µg/mL streptomycin 1 mM sodium pyruvate, and 0.1 mM NEAA, T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at $1 \times 10^4$ cells per well in tissue culture medium and added to flat bottom microtiter plates in a volume of 100 µL. The plates were incubated at 37° C./5% $CO_2$ overnight to allow for cell adherence.

Virus Preparation—The influenza A/PR/8/34 (A TCC #VR-95), A/CA/05/09 (CDC), A/NY/18/09 (CDC) and A/NWS/33 (ATCC #VR-219) strains were obtained from ATCC or from the Center of Disease Control and were grown in MDCK cells for the production of stock virus pools. A pretitered aliquot of virus was removed from the freezer (−80° C.) and allowed to thaw slowly to room temperature in a biological safety cabinet. Virus was resuspended and diluted into assay medium (DMEM supplemented with 0.5% BSA, 2 mM L-glutamine, 100 U/mL penicillin, 100 µg/mL streptomycin, 1 mM sodium pyruvate, 0.1 mM NEAA, and 1 µg/ml TPCK-treated trypsin) such that the amount of virus added to each well in a volume of 100 µL was the amount determined to yield 85 to 95% cell killing at 4 days post-infection. Efficacy and Toxicity XTT-Plates were stained and analyzed as previously described for the Dengue cytoprotection assay.

Example 158

Anti-Hepatitis C Virus Assay:

Cell Culture—The reporter cell line Huh-luc/neo-ET was obtained from Dr. Ralf Bartenschlager (Department of Molecular Virology, Hygiene Institute, University of Heidelberg, Germany) by ImQuest BioSciences through a specific licensing agreement. This cell line harbors the persistently replicating $I_{389}$luc-ubi-neo/NS3-3'/ET replicon containing the firefly luciferase gene-ubiquitin-neomycin phosphotransferase fusion protein and EMCV IRES driven NS3-5B HCV coding sequences containing the ET tissue culture adaptive mutations (E1202G, T12081, and K1846T). A stock culture of the Huh-luc/neo-ET was expanded by culture in DMEM supplemented with I 0% FCS, 2 mM glutamine, penicillin (100 µU/mL)/streptomycin (100 µg/mL) and I X nonessential amino acids plus 1 mg/mL G418. The cells were split 1:4 and cultured for two passages in the same media plus 250 µg/mL G418. The cells were treated with trypsin and enumerated by staining with trypan blue and seeded into 96-well tissue culture plates at a cell culture density $7.5 \times 10^3$ cells per well and incubated at 3° C. 5% $CO_2$ for 24 hours. Following the 24 hour incubation, media was removed and replaced with the same media minus the G418 plus the test compounds in triplicate. Six wells in each plate received media alone as a no-treatment control. The cells were incubated an additional 72 hours at 3TC 5% $CO_2$ then anti-HCV activity was measured by luciferase endpoint. Duplicate plates were treated and incubated in parallel for assessment of cellular toxicity by XTT staining.

Cellular Viability—The cell culture monolayers from treated cells were stained with the tetrazolium dye XTT to evaluate the cellular viability of the Huh-luc/neo-ET reporter cell line in the presence of the compounds.

Measurement of Virus Replication—HCV replication from the replicon assay system was measured by luciferase activity using the britelite plus luminescence reporter gene kit according to the manufacturer's instructions (Perkin Elmer, Shelton, Conn.). Briefly, one vial of britelite plus lyophilized substrate was solubilized in 10 mL of britelite reconstitution buffer and mixed gently by inversion. After a 5 minute incubation at room temperature, the britelite plus reagent was added to the 96 well plates at 100 µL per well. The plates were sealed with adhesive film and incubated at room temperature for approximately 10 minutes to lyse the cells. The well contents were transferred to a white 96-well plate and luminescence was measured within 15 minutes using the Wallac 1450Microbeta Trilux liquid scintillation counter. The data were imported into a customized Microsoft Excel 2007 spreadsheet for determination of the 50% virus inhibition concentration ($EC_{50}$).

Example 159

Anti-Parainfluenza-3 Cytoprotection Assay

Cell Preparation—HEp2 cells (human epithelial cells, ATCC catalog# CCL-23) were passaged in DMEM supplemented with 10% FBS, 2 mM L-glutamine, 100 U/mL penicillin, 100 µg/mL streptomycin 1 mM sodium pyruvate, and 0.1 mM NEAA, T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at $1 \times 10^4$ cells per well in tissue culture medium and added to flat bottom microtiter plates in a volume of 100 µL. The plates were incubated at 37° C./5% $CO_2$ overnight to allow for cell adherence.

Virus Preparation—The Parainfluenza virus type 3 SF4 strain was obtained from ATCC (catalog# VR-281) and was grown in HEp2 cells for the production of stock virus pools. A pretitered aliquot of virus was removed from the freezer (−80° C.) and allowed to thaw slowly to room temperature in a biological safety cabinet. Virus was resuspended and diluted into assay medium (DMEM supplemented with 2% heat-inactivated FBS, 2 mM L-glutamine, 100 U/mL penicillin, and 100 µg/mL streptomycin) such that the amount of virus added to each well in a volume of 1004 was the amount determined to yield 85 to 95% cell killing at 6 days post-infection.

Plate Format—Each plate contains cell control wells (cells only), virus control wells (cells plus virus), triplicate drug toxicity wells per compound (cells plus drug only), as well a triplicate experimental wells (drug plus cells plus virus). Efficacy and Toxicity XTT-Following incubation at 37° C. in a 5% $CO_2$ incubator, the test plates were stained with the tetrazolium dye XTT (2,3-bis(2-methoxy-4-nitro-5-sulfophenyl)-5-[(phenylamino)carbonyl]-2H-tetrazol hydroxide). XTT-tetrazolium was metabolized by the mitochondrial enzymes of metabolically active cells to a soluble formazan product, allowing rapid quantitative analysis of the inhibition of virus-induced cell killing by antiviral test substances. XTT solution was prepared daily as a stock of 1 mg/mL in RPMI1640. Phenazine methosulfate (PMS) solution was prepared at 0.15 mg/mL in PBS and stored in the dark at −20° C. XTT/PMS stock was prepared immediately before use by adding 404 of PMS per ml of XTT solution. Fifty microliters of XTT/PMS was added to each well of the plate and the plate was reincubated for 4 hours at 3 7° C. Plates were sealed with adhesive plate sealers and shaken gently or inverted several times to mix the soluble fomlazan product and the plate was read spectrophotometrically at 450/650 nm with a Molecular Devices Vmax plate reader.

Data Analysis—Raw data was collected from the Softmax Pro 4.6 software and imported into a Microsoft Excel spreadsheet for analysis. The percent reduction in viral cytopathic effect compared to the untreated virus controls was calculated for each compound. The percent cell control value was calculated for each compound comparing the drug treated uninfected cells to the uninfected cells in medium alone.

Example 160

Influenza Polymerase Inhibition Assay:

Virus Preparation—Purified influenza virus A/PR/8/34 (1 ml) was obtained from Advanced Biotechnologies, Inc. (Columbia, Md.), thawed and dispensed into five aliquots for storage at −80° C. until use. On the day of assay set up, 20 µL of 2.5% Triton N-101 was added to 180 µL of purified virus. The disrupted virus was diluted 1:2 in a solution containing 0.25% Triton and PBS. Disruption provided the source of influenza ribonucleoprotein (RNP) containing the influenza RNA-dependent RNA polymerase and template RNA. Samples were stored on ice until use in the assay.

Polymerase reaction—Each 50 µL, polymerase reaction contained the following: 5 µL of the disrupted RNP, 100 mM Tris-HCl (pH 8.0), 100 mM KCl, 5 mM MgCl$_2$. 1 mM dithiothreitol, 0.25% Triton N-101, 5 µCi of [α-$^{32}$P] GTP, 100 µM ATP, 50 µM each (CTP, UTP), 1 µM GTP, and 200 µM adenyl (3'-5') guanosine. For testing the inhibitor, the reactions contained the inhibitor and the same was done for reactions containing the positive control (2'-Deoxy-2'-fluoroguanosine-5'-triphosphate). Other controls included RNP+ reaction mixture, and RNP+I % DMSO. The reaction mixture without the ApG primer and NTPs was incubated at 30° C. for 20 minutes. Once the ApG and NTPs were added to the reaction mixture, the samples were incubated at 30° C. for 1 hour then immediately followed by the transfer of the reaction onto glass-fiber filter plates and subsequent precipitation with 10% trichloroacetic acid (TCA). The plate was then washed five times with 5% TCA followed by one wash with 95% ethanol. Once the filter had dried, incorporation of [α-$^{32}$P] GTP was measured using a liquid scintillation counter (Micro beta).

Plate Format—Each test plate contained triplicate samples of the three compounds (6 concentrations) in addition to triplicate samples of RNP+reaction mixture (RNP alone), RNP+1% DMSO, and reaction mixture alone (no RNP).

Data Analysis—Raw data was collected from the Micro Beta scintillation counter. The incorporation of radioactive GTP directly correlates with the levels of polymerase activity.

The "percent inhibition values" were obtained by dividing the mean value of each test compound by the RNP+1% DMSO control. The mean obtained at each concentration of 2DFGTP was compared to the RNP+reaction control. The data was then imported into Microsoft Excel spreadsheet to calculate the IC$_{50}$ values by linear regression analysis.

Example 161

HCV Polymerase Inhibition Assay:

Activity of compounds for inhibition of HCV polymerase was evaluated using methods previously described (Lam et al. 2010. Antimicrobial Agents and Chemotherapy 54(8): 3187-3196). HCV NS5B polymerase assays were performed in 20 µL volumes in 96 well reaction plates. Each reaction contained 40 ng/µL purified recombinant NS5BΔ22 genotype-1b polymerase, 20 ng/µL of HCV genotype-1b complimentary IRES template, 1 µM of each of the four natural ribonucleotides, 1 U/mL Optizyme RNAse inhibitor (Promega, Madison, Wis.), 1 mM MgCl$_2$, 0.75 mM MnCl$_2$, and 2 mM dithiothreitol (DTT) in 50 mM HEPES buffer (pH 7.5). Reaction mixtures were assembled on ice in two steps. Step 1 consisted of combining all reaction components except the natural nucleotides and labeled UTP in a polymerase reaction mixture. Ten microliters (10 µL) of the polymerase mixture was dispensed into individual wells of the 96 well reaction plate on ice. Polymerase reaction mixtures without NS5B polymerase were included as no enzyme controls. Serial half-logarithmic dilutions of test and control compounds, 2'-O-Methyl-CTP and 2'-O-Methyl-GTP (Trilink, San Diego, Calif.), were prepared in water and 5 µL of the serial diluted compounds or water alone (no compound control) were added to the wells containing the polymerase mixture. Five microliters of nucleotide mix (natural nucleotides and labeled UTP) was then added to the reaction plate wells and the plate was incubated at 27° C. for 30 minutes. The reactions were quenched with the addition of 80 µL stop solution (12.5 mM EDTA, 2.25 M NaCl, and 225 mM sodium citrate) and the RNA products were applied to a Hybond-N+membrane (GE Healthcare, Piscataway, N.J.) under vacuum pressure using a dot blot apparatus. The membrane was removed from the dot blot apparatus and washed four times with 4× SSC (0.6 M NaCl, and 60 mM sodium citrate), and then rinsed one time with water and once with 100% ethanol. The membrane was air dried and exposed to a phosphoimaging screen and the image captured using a Typhoon 8600 Phospho imager. Following capture of the image, the membrane was placed into a Micro beta cassette along with scintillation fluid and the CPM in each reaction was counted on a Micro beta 1450. CPM data were imported into a custom Excel spreadsheet for determination of compound IC$_{50}$s.

Example 162

NS5B RNA-Dependent RNA Polymerase Reaction Conditions

Compounds were assayed for inhibition of NS5B-621 from HCV GT-1b Con-1. Reactions included purified recombinant enzyme, 1 u/µL negative-strand HCV IRES RNA template, and 1 µM NTP substrates including either [$^{32}$P]-CTP or [$^{32}$P]-UTP. Assay plates were incubated at 27° C. for 1 hour before quench. [$^{32}$P] incorporation into macromolecular product was assessed by filter binding.

Example 163

Human DNA Polymerase Inhibition Assay:

The human DNA polymerase alpha (catalog#1075), beta (catalog#1077), and gamma (catalog#1076) were purchased from CHIMERx (Madison, Wis.). Inhibition of beta and gamma DNA polymerase activity was assayed in microtiter plates in a 50 uL reaction mixture containing 50 mM Tris-HCl (pH 8.7), KCl (10 mM for beta and 100 mM for gamma), 10 mM MgCl$_2$, 0.4 mg/mL BSA, 1 mM DTT, 15% glycerol, 0.05 mM of dCTP, dTTP, and dATP, 10 uCi [$^{32}$P]-alpha-dGTP (800 Ci/mmol), 20 ug activated calf thymus DNA and the test compound at indicated concentrations. The alpha DNA polymerase reaction mixture was as follows in a 50 uL volume per sample: 20 mM Tris-HCl (pH 8), 5 mM magnesium acetate, 0.3 mg/mL BSA, 1 mM DTT, 0.1 mM spermine, 0.05 mM of dCTP, dTTP, and dATP, 10 uCi [$^{32}$P]-alpha-dGTP (800 Ci/mmol), 20 ug activated calf thymus DNA and the test compound at the indicated concentrations. For each assay, the enzyme reactions were allowed to proceed for 30 minutes at 3TC followed by the transfer onto glass-fiber filter plates and subsequent precipitation with 10% trichloroacetic acid (TCA). The plate was then washed with 5% TCA followed by one wash with 95% ethanol. Once the filter had dried, incorporation of radioactivity was measured using a liquid scintillation counter (Microbeta).

Example 164

HIV Infected PBMC Assay:

Fresh human peripheral blood mononuclear cells (PBMCs) were obtained from a commercial source (Biological Specialty) and were determined to be seronegative for HIV and HBV. Depending on the volume of donor blood received, the leukophoresed blood cells were washed several times with PBS. After washing, the leukophoresed blood was diluted 1:1 with Dulbecco's phosphate buffered saline (PBS) and layered over 15 mL of Ficoll-Hypaque density gradient in a 50 ml conical centrifuge tube. These tubes were centrifuged for 30 min at 600 g. Banded PBMCs were gently aspirated from the resulting interface and washed three times with PBS. After the final wash, cell number was determined by Trypan Blue dye exclusion and cells were re-suspended at 1×10^6 cells/mL in RPMI 1640 with 15% Fetal Bovine Serum (FBS), 2 mmol/L L-glutamine, 2 ug/mL PHA-P, 100 U/mL penicillin and 100 ug/mL streptomycin and allowed to incubate for 48-72 hours at 3TC. After incubation, PBMCs were centrifuged and resuspended in tissue culture medium. The cultures were maintained until use by half-volume culture changes with fresh IL-2 containing tissue culture medium every 3 days. Assays were initiated with PBMCs at 72 hours post PHA-P stimulation.

To minimize effects due to donor variability, PBMCs employed in the assay were a mixture of cells derived from 3 donors. Immediately prior to use, target cells were resuspended in fresh tissue culture medium at 1×10^6 cells/mL and plated in the interior wells of a 96-well round bottom microtiter plate at 50 uL/well. Then, 100 uL of 2× concentrations of compound-containing medium was transferred to the 96-well plate containing cells in 50 uL of the medium. AZT was employed as an internal assay standard.

Following addition of test compound to the wells, 50 uL of a predetermined dilution of HIV virus (prepared from 4× of final desired in-well concentration) was added, and mixed well. For infection, 50-150 $TCID_{50}$ of each virus was added per well (final MOI approximately 0.002). PBMCs were exposed in triplicate to virus and cultured in the presence or absence of the test material at varying concentrations as described above in the 96-well microtiter plates. After 7 days in culture, HIV-1 replication was quantified in the tissue culture supernatant by measurement of reverse transcriptase (RT) activity. Wells with cells and virus only served as virus controls. Separate plates were identically prepared without virus for drug cytotoxicity studies.

Reverse Transcriptase Activity Assay—Reverse transcriptase activity was measured in cell-free supernatants using a standard radioactive incorporation polymerization assay. Tritiated thymidine triphosphate (TTP; New England Nuclear) was purchased at 1 Ci/mL and 1 uL was used per enzyme reaction. A rAdT stock solution was prepared by mixing 0.5 mg/mL poly rA and 1.7 U/mL oligo dT in distilled water and was stored at −20° C. The RT reaction buffer was prepared fresh daily and consists of 125 uL of 1 mol/L EGTA, 125 uL of $dH_2O$, 125 uL of 20% Triton X-100, 50 uL of 1 mol/L Tris (pH 7.4), 50 uL of 1 mol/L DTT, and 40 uL of 1 mol/L $MgCl_2$. For each reaction, 1 uL of TTP, 4 uL of $dH_2O$, 2.5 uL of rAdT, and 2.5 uL of reaction buffer were mixed. Ten microliters of this reaction mixture was placed in a round bottom microtiter plate and 15 uL of virus-containing supernatant was added and mixed. The plate was incubated at 3TC in a humidified incubator for 90 minutes. Following incubation, 10 uL of the reaction volume was spotted onto a DEAE filter mat in the appropriate plate format, washed 5 times (5 minutes each) in a 5% sodium phosphate buffer, 2 times (1 minute each) in distilled water, 2 times (1 minute each) in 70% ethanol, and then air dried. The dried filtermat was placed in a plastic sleeve and 4 mL of Opti-Fluor O was added to the sleeve. Incorporated radioactivity was quantified utilizing a Wallac 1450 Microbeta Trilux liquid scintillation counter.

Example 165

HBV:

HepG2.2.15 cells (100 µL) in RPMI1640 medium with 10% fetal bovine serum was added to all wells of a 96-well plate at a density of 1×10^4 cells per well and the plate was incubated at 37° C. in an environment of 5% $CO_2$ for 24 hours. Following incubation, six ten-fold serial dilutions of test compound prepared in RPMI1640 medium with 10% fetal bovine serum were added to individual wells of the plate in triplicate. Six wells in the plate received medium alone as a virus only control. The plate was incubated for 6 days at 37° C. in an environment of 5% $CO_2$. The culture medium was changed on day 3 with medium containing the indicated concentration of each compound. One hundred microliters of supernatant was collected from each well for analysis of viral DNA by qPCR and cytotoxicity was evaluated by XTT staining of the cell culture monolayer on the sixth day.

Ten microliters of cell culture supernatant collected on the sixth day was diluted in qPCR dilution buffer (40 µg/mL sheared salmon sperm DNA) and boiled for 15 minutes. Quantitative real time PCR was performed in 386 well plates using an Applied Biosystems 7900HT Sequence Detection System and the supporting SDS 2.4 software. Five microliters (5 µL) of boiled DNA for each sample and serial 10-fold dilutions of a quantitative DNA standard were subjected to real time Q-PCR using Platinum Quantitative PCR SuperMix-UDG (Invitrogen) and specific DNA oligonucleotide primers (IDT, Coralville, Id.) HBV-AD38-qF1 (5'-CCG TCT GTG CCT TCT CAT CTG-3'), HBV-AD38-qR1 (5'-AGT CCA AGA GTY CTC TTA TRY AAG ACC TT-3'), and HBV-AD38-qP1 (5'-FAM CCG TGT GCA/ZEN/CTT CGC TTC ACC TCT GC-3'BHQ1) at a final concentration of 0.2 µM for each primer in a total reaction volume of 15 µL. The HBV DNA copy number in each sample was interpolated from the standard curve by the SDS.24 software and the data were imported into an Excel spreadsheet for analysis.

The 50% cytotoxic concentration for the test materials are derived by measuring the reduction of the tetrazolium dye XTT in the treated tissue culture plates. XTT is metabolized by the mitochondrial enzyme NADPH oxidase to a soluble formazan product in metabolically active cells. XTT solution was prepared daily as a stock of 1 mg/mL in PBS. Phenazine methosulfate (PMS) stock solution was prepared at 0.15 mg/mL in PBS and stored in the dark at −20° C. XTT/PMS solution was prepared immediately before use by adding 40 µL of PMS per 1 mL of XTT solution. Fifty microliters of XTT/PMS was added to each well of the plate and the plate incubated for 2-4 hours at 37° C. The 2-4 hour incubation has been empirically determined to be within linear response range for XTT dye reduction with the indicated numbers of cells for each assay. Adhesive plate sealers were used in place of the lids, the sealed plate was inverted several times to mix the soluble formazan product and the plate was read at 450 nm (650 nm reference wavelength) with a Molecular Devices SpectraMax Plus 384 spectrophotometer. Data were collected by Softmax 4.6 software and imported into an Excel spreadsheet for analysis.

Example 166

Dengue RNA-Dependent RNA Polymerase Reaction Conditions

RNA polymerase assay was performed at 30° C. using 100 µl reaction mix in 1.5 ml tube. Final reaction conditions were 50 mM Hepes (pH 7.0), 2 mM DTT, 1 mM MnCl$_2$, 10 mM KCl, 100 nM UTR-Poly A (self-annealing primer), 10 µM UTP, 26 nM RdRp enzyme. The reaction mix with different compounds (inhibitors) was incubated at 30° C. for 1 hour. To assess amount of pyrophosphate generated during polymerase reaction, 30 µl of polymerase reaction mix was mixed with a luciferase coupled-enzyme reaction mix (70 µl). Final reaction conditions of luciferase reaction were 5 mM MgCl$_2$, 50 mM Tris-HCl (pH 7.5), 150 mM NaCl, 200 µU ATP sulfurylase, 5 µM APS, 10 nM Luciferase, 100 µM D-luciferin. White plates containing the reaction samples (100 µl) were immediately transferred to the luminometer Veritas (Turner Biosystems, CA) for detection of the light signal.

The invention claimed is:

1. A compound (β-D or β-L) of the following formula:

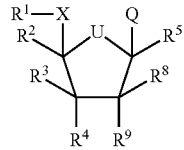

Formula If or a pharmaceutically acceptable salt thereof, wherein
U is O;
X is CH$_2$;
Q is a pyrimidine with at least one thione, thiol or thioether at the 2 and/or 4-position of said pyrimidine;
R$^5$ is H;
R$^2$, R$^3$, R$^4$, R$^8$ and R$^9$ are each independently H, CH$_3$, CD$_3$, CF$_3$, CF$_2$H, CFH$_2$, OH, SH, NH$_2$, N$_3$, CHO, CN, Cl, Br, F or I;
R$^1$ is one of the formula:

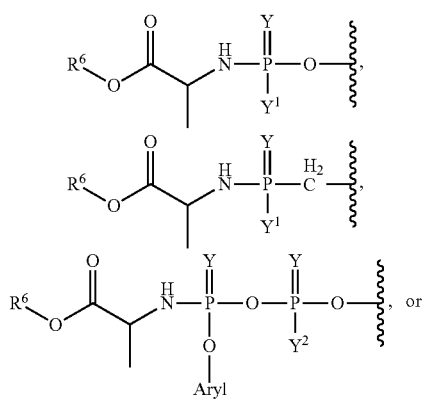

-continued

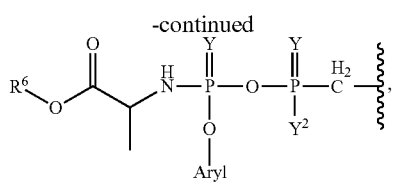

Y is O or S;
Y$^1$ is OAryl or BH$_3^-$M$^+$;
Y$^2$ is OH or BH$_3^-$M$^+$;
Aryl is phenyl, 1-naphthyl, 2-naphthyl, aromatic, heteroaromatic, 4-substituted phenyl, 4-chlorophenyl, or 4-bromophenyl;
R$^6$ is alkyl, halogen, nitro, cyano, hydroxyl, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein each R$^6$ is optionally substituted with one or more, the same or different, R$^{10}$; and
each R$^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl.

2. A compound of one of the following formulae:

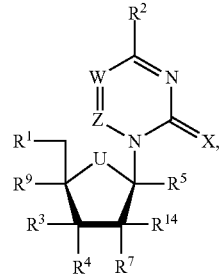

Formula Ig

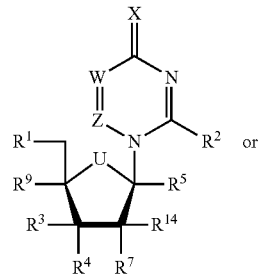

Formula Ih

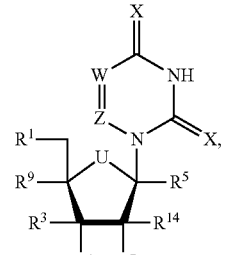

Formula Ii or a pharmaceutically acceptable salt thereof wherein,
U is O or S;
R$^5$ is H or D;

$R^1$ is one of the formula:

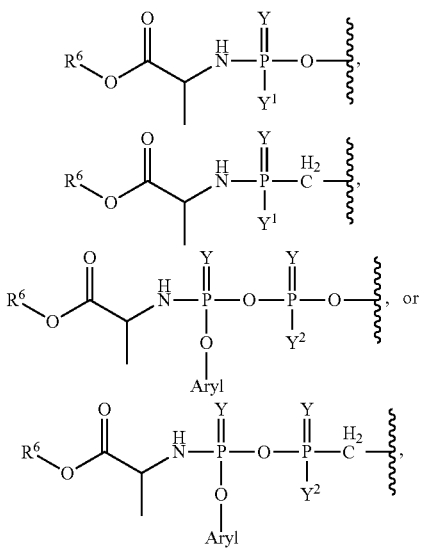

Y is O or S;
$Y^1$ is OAryl or $BH_3^-M^+$
$Y^2$ is OH or $BH_3^-M^+$
each X is independently O, S, NH, $NR^8$, NHOH, $NR^8OH$, $NHOR^8$, or $NR^8OR^8$;
$R^2$ is OH, SH, $NH_2$, $OR^8$, $SR^8$, $NHR^8$, NHOH, $NR^8OH$, $NHOR^8$, or $NR^8OR^8$;
  wherein in Formula Ig and Ih, one of X is S or $R^2$ is $SR^8$, or both X is S and $R^2$ is $SR^8$;
  wherein in Formula Ii, at least one X is S;
W is CH, N, or $CR^8$;
Z is CH, N, or $CR^8$;
$R^3$, $R^4$, $R^7$, $R^9$ and $R^{14}$ are each independently H, $C_{1-22}$ alkyl, $C_{2-22}$ alkenyl, $C_{2-22}$ alkynyl, allyl, ethynyl, vinyl, $C_{1-22}$ alkoxy, OH, SH, $NH_2$, $N_3$, CHO, CN, Cl, Br, F, I, or $C_{1-22}$ alkyl optionally substituted with one or more, the same or different, $R^{10}$;
each $R^{10}$ is independently selected from alkyl, deutero, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl;
Aryl is phenyl, 1-naphthyl, 2-naphthyl, aromatic, heteroaromatic, 4-substituted phenyl, 4-chlorophenyl, or 4-bromophenyl;
$R^8$ is methyl, alkenyl, alkynyl, vinyl, allyl, halogen, halogentated alkyl, hydroxyl alkyl, acyl, lipid, geranyl, or $C_{1-22}$ alkyl optionally substituted with one or more, the same or different, $R^{10}$;
$R^6$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein each $R^6$ is optionally substituted with one or more, the same or different, $R^{10}$.

3. The compound of claim 2, or a pharmaceutically acceptable salt thereof, wherein
U is O;
W and Z are CH;
$R^5$ is H;

$R^1$ is

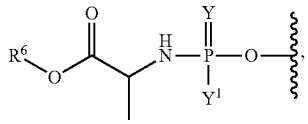

wherein Y is O and $Y^1$ is phenoxy; and
$R^6$ is alkyl.

4. The compound of claim 2, or a pharmaceutically acceptable salt thereof, wherein $R^3$, $R^4$, $R^7$, $R^9$ and $R^{14}$ are each independently H, $CH_3$, $CD_3$, $CF_3$, $CF_2H$, $CFH_2$, OH, SH, $NH_2$, $N_3$, CHO, CN, Cl, Br, F or I.

5. The compound of claim 4, or a pharmaceutically acceptable salt thereof, wherein one X is O and the other X is S.

6. The compound of claim 5, or a pharmaceutically acceptable salt thereof, wherein $R^6$ is iso-propyl.

7. The compound of claim 2, or a pharmaceutically acceptable salt thereof, wherein $R^5$ is H, $R^3$ is H, $R^4$ is hydroxyl, $R^7$ is hyroxyl, $R^{14}$ is methyl, $R^1$ is

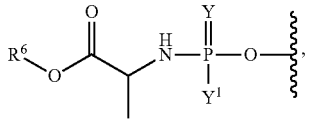

Y is O, $Y^1$ is phenoxy, and $R^6$ is iso-propyl.

8. A compound having one of the following structures:

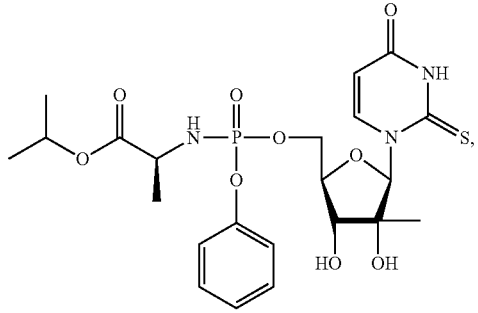

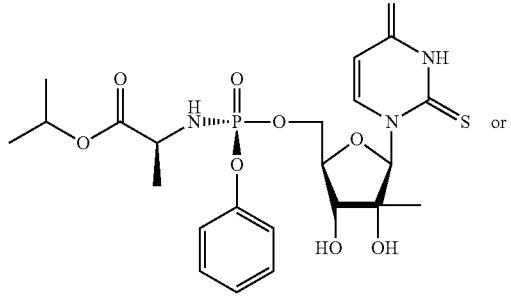

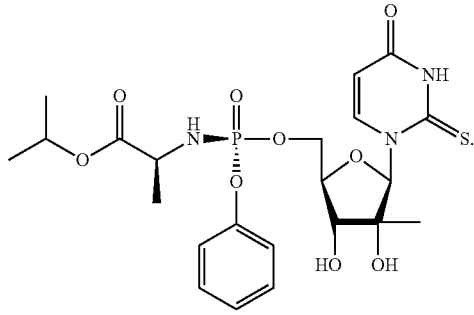

9. A liposomal composition comprising a compound of claim 1, or its pharmaceutically acceptable salt, and a pharmaceutically acceptable carrier.

10. A liposomal composition comprising a compound of claim 2, or its pharmaceutically acceptable salt, and a pharmaceutically acceptable carrier.

11. A liposomal composition comprising a compound of claim 8, or its pharmaceutically acceptable salt, and a pharmaceutically acceptable carrier.

12. A pharmaceutical composition comprising a compound of claim 1, or its pharmaceutically acceptable salt, and a pharmaceutically acceptable carrier.

13. A pharmaceutical composition comprising a compound of claim 2, or its pharmaceutically acceptable salt, and a pharmaceutically acceptable carrier.

14. A pharmaceutical composition comprising a compound of claim 8, or its pharmaceutically acceptable salt, and a pharmaceutically acceptable carrier.

\* \* \* \* \*

UNITED STATES PATENT AND TRADEMARK OFFICE
CERTIFICATE OF CORRECTION

PATENT NO. : 10,149,859 B2
APPLICATION NO. : 14/917681
DATED : December 11, 2018
INVENTOR(S) : Dennis C. Liotta et al.

Page 1 of 1

It is certified that error appears in the above-identified patent and that said Letters Patent is hereby corrected as shown below:

In Column 1, Line 15, insert:
--STATEMENT REGARDING FEDERALLY SPONSORED RESEARCH
This invention was made with government support under Contract No. HDTA1-13-C-0072 awarded by the Department of Defense (DTRA). The government has certain rights in the invention.--

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*